US012678512B2

(12) United States Patent
Ishizaki et al.

(10) Patent No.: US 12,678,512 B2
(45) Date of Patent: Jul. 14, 2026

(54) ANTI-EGFR ANTIBODY-DRUG CONJUGATE WITH A CYCLIC DINUCLEOTIDE DERIVATIVE

(71) Applicant: DAIICHI SANKYO COMPANY, LIMITED, Tokyo (JP)

(72) Inventors: Masayuki Ishizaki, Tokyo (JP); Osamu Suzuki, Tokyo (JP); Mariko Kyutoku, Tokyo (JP); Hiroshi Yukiura, Tokyo (JP); Kyoko Hara, Tokyo (JP); Masataka Chihara, Tokyo (JP); Takafumi Otsuka, Tokyo (JP); Teiji Wada, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 876 days.

(21) Appl. No.: 17/908,381

(22) PCT Filed: Mar. 5, 2021

(86) PCT No.: PCT/JP2021/008635
§ 371 (c)(1),
(2) Date: Aug. 31, 2022

(87) PCT Pub. No.: WO2021/177438
PCT Pub. Date: Sep. 10, 2021

(65) Prior Publication Data

US 2023/0330248 A1 Oct. 19, 2023

(30) Foreign Application Priority Data

Mar. 6, 2020 (JP) ................................ 2020-038983

(51) Int. Cl.
*A61K 47/68* (2017.01)
*A61P 35/00* (2006.01)

(52) U.S. Cl.
CPC ...... *A61K 47/6809* (2017.08); *A61K 47/6849* (2017.08); *A61K 47/6889* (2017.08); *A61P 35/00* (2018.01)

(58) Field of Classification Search
CPC ............ A61K 47/6849; A61K 47/6889; A61K 31/7084; A61P 35/00
See application file for complete search history.

(56) References Cited

U.S. PATENT DOCUMENTS 6,235,883 B1 5/2001 Jakobovits et al.
7,662,387 B2 2/2010 Law et al.
10,980,825 B2 4/2021 Yoshikawa et al.
11,453,697 B1 9/2022 Altman et al.
2002/0173629 A1 11/2002 Jakobovits et al.
2005/0100546 A1 5/2005 Jakobovits et al.
2006/0183887 A1 8/2006 Jakobovits et al.
2006/0233794 A1 10/2006 Law et al.
2008/0025989 A1 1/2008 Law et al.
2009/0148942 A1 6/2009 Mcdonagh et al.
2010/0150925 A1 6/2010 Law et al.
2010/0158910 A1 6/2010 Law et al.
2010/0183636 A1 7/2010 Law et al.
2010/0305307 A1 12/2010 Jakobovits et al.
2011/0150908 A1 6/2011 Law et al.
2012/0045436 A1 2/2012 Mcdonagh et al.
2012/0251559 A1 10/2012 Law et al.
2012/0288512 A1 11/2012 Law et al.
2014/0178936 A1 6/2014 Mcdonagh et al.
2016/0082119 A1 3/2016 Gonzalez et al.
2016/0129128 A1 5/2016 Cuevas Marchante et al.
2017/0022282 A1 1/2017 Mcdonagh et al.
2017/0044206 A1 2/2017 Altman et al.
2017/0342157 A1 11/2017 Mcdonagh et al.
2018/0230178 A1 8/2018 Altman et al.
2018/0237469 A1 8/2018 Altman et al.
2018/0244712 A1 8/2018 Altman et al.
2018/0312536 A1 11/2018 Sakamuri et al.
2019/0062365 A1 2/2019 Katibah et al.
2019/0185511 A1 6/2019 Kanne et al.
2019/0192549 A1 6/2019 Yoshikawa et al.
2019/0374560 A1 12/2019 Gonzalez et al.
2020/0063100 A1 2/2020 Terrett et al.
2020/0199169 A1 6/2020 Leong et al.
2020/0291096 A1 9/2020 Keen et al.
(Continued)

FOREIGN PATENT DOCUMENTS

CN 108137641 A 6/2018
CN 108430503 A 8/2018
(Continued)

OTHER PUBLICATIONS

Office Action issued in corresponding Australian Patent Application No. 2021230226 dated Mar. 7, 2025.
Office Action issued in corresponding Russian Patent Application No. 2022122372 dated Aug. 23, 2024 (16 pages).
Abe et al., "Cytosolic-DNA-Mediated, STING-Dependent Proinflammatory Gene Induction Necessitates Canonical NF-κB Activation through TBK1," Journal of Virology, vol. 88, Issue 10, May 15, 2014, pp. 5328-5341.
Challa et al., "Pharmacodynamic and preclinical studies of SB 11285, a highly potent, and systematically bioavailable STING agonist as a novel immuno-therapeutic agent", AACR Tumor Immunology and Immunotherapy, 2017, Poster#A25.
(Continued)

*Primary Examiner* — Elly-Gerald Stoica
(74) *Attorney, Agent, or Firm* — Foley & Lardner LLP

(57) ABSTRACT

[Problem] It is desired to develop an antibody-drug conjugate capable of being systemically administered and delivering a STING agonist specifically to a target cells or organ (for example, a tumor lesion), and a therapeutic agent and/or therapeutic method using the antibody-drug conjugate for diseases related to STING agonist activity, for example, diseases (for example, cancers) to which immunostimulation therapy can be applied. [Solution] The present invention provides a novel antibody-CDN derivative conjugate which can be systemically administered and exhibits an antitumor effect against an antigen-expressing tumor.

49 Claims, 15 Drawing Sheets

Specification includes a Sequence Listing.

(56) References Cited

U.S. PATENT DOCUMENTS

| | | | |
|---|---|---|---|
| 2020/0376013 | A1 | 12/2020 | Gonzalez et al. |
| 2021/0002380 | A1 | 1/2021 | Mcdonagh et al. |
| 2021/0060072 | A1 | 3/2021 | Terrett et al. |
| 2021/0106607 | A1 | 4/2021 | Yoshikawa et al. |
| 2021/0246425 | A1 | 8/2021 | Terrett et al. |
| 2021/0261919 | A1 | 8/2021 | Terrett et al. |
| 2021/0353652 | A1 | 11/2021 | Vincent et al. |
| 2022/0008549 | A1 | 1/2022 | Tsuda et al. |
| 2022/0168436 | A1 | 6/2022 | Cuevas Marchante et al. |
| 2024/0066047 | A1 | 2/2024 | Yoshikawa et al. |
| 2024/0150390 | A1 | 5/2024 | Ogura et al. |
| 2024/0190981 | A1 | 6/2024 | Mcdonagh et al. |
| 2024/0293567 | A1 | 9/2024 | Tsuda et al. |
| 2025/0205270 | A1 | 6/2025 | Yoshikawa et al. |
| 2025/0257320 | A1 | 8/2025 | Terrett et al. |

FOREIGN PATENT DOCUMENTS

| | | | |
|---|---|---|---|
| CO | 2021/0004032 | | 4/2021 |
| EA | 201991315 | A1 | 12/2019 |
| EP | 3 512 861 | A2 | 7/2019 |
| EP | 3 848 054 | A1 | 7/2021 |
| EP | 4 286 393 | A1 | 12/2023 |
| JP | 2001-523973 | A | 11/2001 |
| JP | 2006-518753 | A | 8/2006 |
| JP | 2020-504085 | A | 2/2020 |
| JP | 7254818 | B2 | 4/2023 |
| RU | 2809547 | C2 | 12/2023 |
| WO | WO-98/50433 | A2 | 11/1998 |
| WO | WO-2004/073656 | A3 | 9/2004 |
| WO | WO-2014/093936 | A1 | 6/2014 |
| WO | WO-2014/099824 | A1 | 6/2014 |
| WO | WO-2014/176284 | A1 | 10/2014 |
| WO | WO-2014/179335 | A1 | 11/2014 |
| WO | WO-2014/189805 | A1 | 11/2014 |
| WO | WO-2014/189806 | A1 | 11/2014 |
| WO | WO-2014/191578 | A1 | 12/2014 |
| WO | WO-2015/074145 | A1 | 5/2015 |
| WO | WO-2015/098099 | A1 | 7/2015 |
| WO | WO-2015/185565 | A1 | 12/2015 |
| WO | WO-2016/012305 | A1 | 1/2016 |
| WO | WO-2016/096714 | A1 | 6/2016 |
| WO | WO-2016/145102 | A1 | 9/2016 |
| WO | WO-2017/027645 | A1 | 2/2017 |
| WO | WO-2017/027646 | A1 | 2/2017 |
| WO | WO-2017/075477 | A1 | 5/2017 |
| WO | WO-2017/093933 | A1 | 6/2017 |
| WO | WO-2017/100305 | A1 | 6/2017 |
| WO | WO-2017/123669 | A1 | 7/2017 |
| WO | WO-2017/161349 | A1 | 9/2017 |
| WO | WO-2017/175147 | A1 | 10/2017 |
| WO | WO-2017/175156 | A1 | 10/2017 |
| WO | WO-2018/009466 | A1 | 1/2018 |
| WO | WO-2018/009648 | A1 | 1/2018 |
| WO | WO-2018/045204 | A1 | 3/2018 |
| WO | WO-2018/060323 | A1 | 4/2018 |
| WO | WO-2018/065360 | A1 | 4/2018 |
| WO | WO-2018/067423 | A1 | 4/2018 |
| WO | WO-2018/100558 | A2 | 6/2018 |
| WO | WO-2018/198076 | A1 | 11/2018 |
| WO | WO-2018/200812 | A1 | 11/2018 |
| WO | WO-2018/227023 | A1 | 12/2018 |
| WO | WO-2019/034866 | A1 | 2/2019 |
| WO | WO-2019/215500 | A1 | 11/2019 |
| WO | WO-2019/236567 | A2 | 12/2019 |
| WO | WO-2020/050406 | A1 | 3/2020 |
| WO | WO-2022/163846 | A1 | 8/2022 |

OTHER PUBLICATIONS

Conlon et al., "Mouse, but not Human STING, Binds and Signals in Response to the Vascular Disrupting Agent 5,6-Dimethylxanthenone-4-Acetic Acid," The Journal of Immunology, vol. 190, Issue 10, May 15, 2013, pp. 5216-5225.

Corrales et al., "Direct Activation of STING in the Tumor Microenvironment Leads to Potent and Systemic Tumor Regression and Immunity," Cell Rep., vol. 11, Issue 7, May 19, 2015, pp. 1018-1030.

Deng et al., "STING-Dependent Cytosolic DNA Sensing Promotes Radiation-Induced Type I Interferon-Dependent Antitumor Immunity in Immunogenic Tumors," Immunity, vol. 41, Issue 5, Nov. 20, 2014, pp. 843-852.

Ishikawa et al., "STING an Endoplasmic Reticulum Adaptor that Facilitates Innate Immune Signaling," Nature, vol. 455, Issue 7213, Oct. 2, 2008, pp. 674-678.

Kranzusch et al., "Ancient Origin of cGAS-STING Reveals Mechanism of Universal 2',3' cGAMP Signaling," Mol Cell., vol. 59, Issue 6, Sep. 17, 2015, pp. 891-903.

Lara Jr et al., "Randomized Phase III Placebo-Controlled Trial of Carboplatin and Paclitaxel With or Without the Vascular Disrupting Agent Vadimezan (ASA404) in Advanced Non-Small-Cell Lung Cancer," Journal of Clinical Oncology, vol. 29, Issue 22, Aug. 1, 2011, pp. 2965-2971.

Li et al., "Antitumor Activity of cGAMP via Stimulation of cGAS-cGAMP-STING-IRF3 Mediated Innate Immune Response," Scientific Reports, vol. 6, Article No. 19049, 2016, pp. 1-14.

Liu et al., "CD47 blockade triggers T cell-mediated destruction of immunogenic tumors," Nat. Med. Vol. 21, Issue 10, Oct. 2015, pp. 1209-1215.

Liu et al., "Phosphorylation of innate immune adaptor proteins Mavs, Sting, and TRIF induces IRF3 activation," Science, vol. 347, Issue 6227, Jan. 29, 2015, aaa2630.

Perera et al., "Activation of LPS-inducible genes by the antitumor agent 5,6-dimethylxanthenone-4-acetic acid in primary murine macrophages. Dissection of signaling pathways leading to gene induction and tyrosine phosphorylation," The Journal of Immunology, vol. 153, Issue 10, Nov. 15, 1994, pp. 4684-4693.

Woo et al., "STING-Dependent Cytosolic DNA Sensing Mediates Innate Immune Recognition of Immunogenic Tumors," Immunity, vol. 41, Issue 5, Nov. 20, 2014, pp. 830-842.

Zhang et al., Cyclic GMP-AMP Containing Mixed Phosphodiester Linkages Is an Endogenous High-Affinity Ligand for STING, Molecular Cell, vol. 51, Issue 2, Jul. 25, 2013, pp. 226-235.

International Searching Authority, "International Search Report," issued in connection with International Patent Application No. PCT/JP2021/008635, dated Apr. 13, 2021.

International Searching Authority, "Written Opinion," issued in connection with International Patent Application No. PCT/JP2021/008635, dated Apr. 13, 2021.

Office Action issued in corresponding Singaporean Patent Application No. 11202251601A dated Aug. 19, 2025.

Office Action issued in corresponding Vietnamese Patent Application No. 1-2022-06355 dated Jun. 13, 2025.

Office Action issued in corresponding Japanese Patent Application No. 2022-504474 dated Mar. 5, 2024 (5 pages).

European Extended Search Report issued in corresponding European Patent Application No. 21765256.9 dated Sep. 26, 2024.

Li et al., "The Cyclopeptide Astin C Specifically Inhibits the Innate Immune CDN Sensor STING", Cell Reports, vol. 25, No. 12, Dec. 18, 2018, pp. 3405-3421.

Office Action issued in corresponding Chinese Patent Application No. 202180019047.0 dated Feb. 6, 2024 (15 pages).

Office Action issued in corresponding Taiwanese Patent Application No. 110108019 dated Dec. 22, 2023 (8 pages).

Office Action issued in corresponding Philippine Patent Application No. 1-2022-551961 dated Jan. 4, 2026.

Office Action issued in corresponding New Zealand Patent Application No. 791969 dated Oct. 6, 2025.

Office Action issued in corresponding Colombian Patent Application No. NC2022/0013971 dated Nov. 20, 2025.

[Figure 1]
A
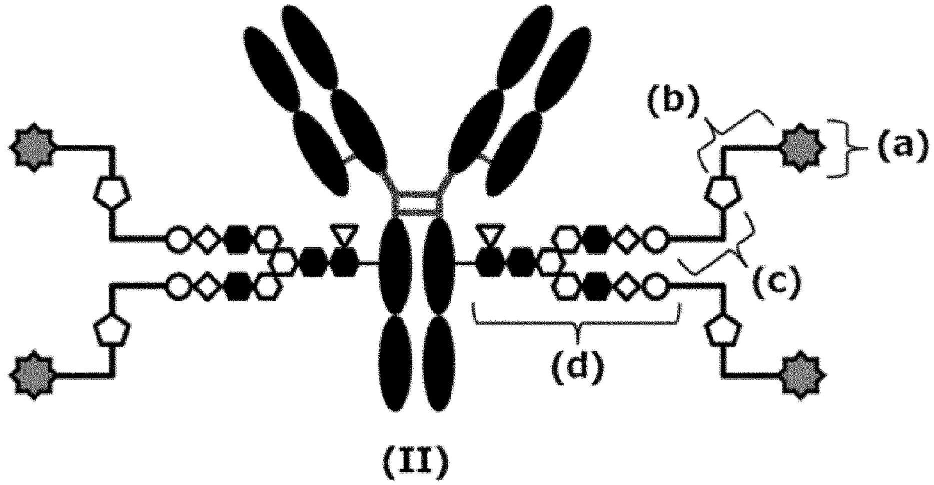
B
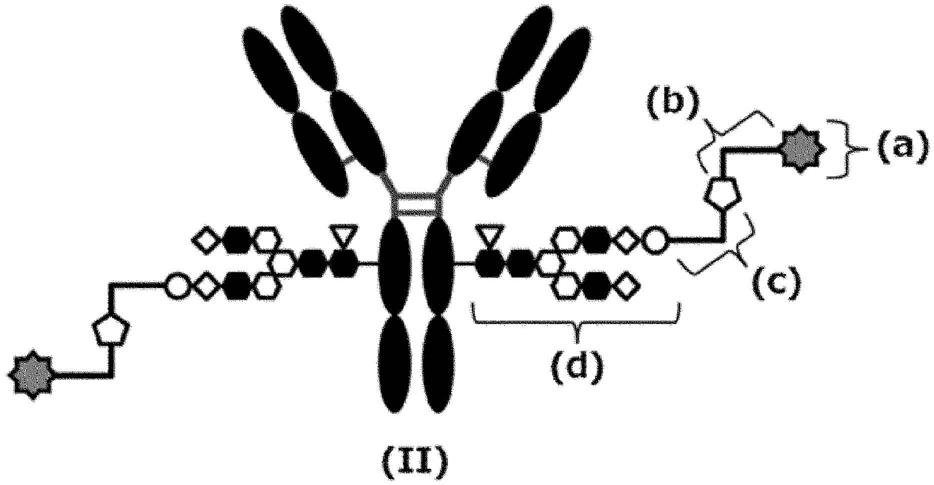

[Figure 2]
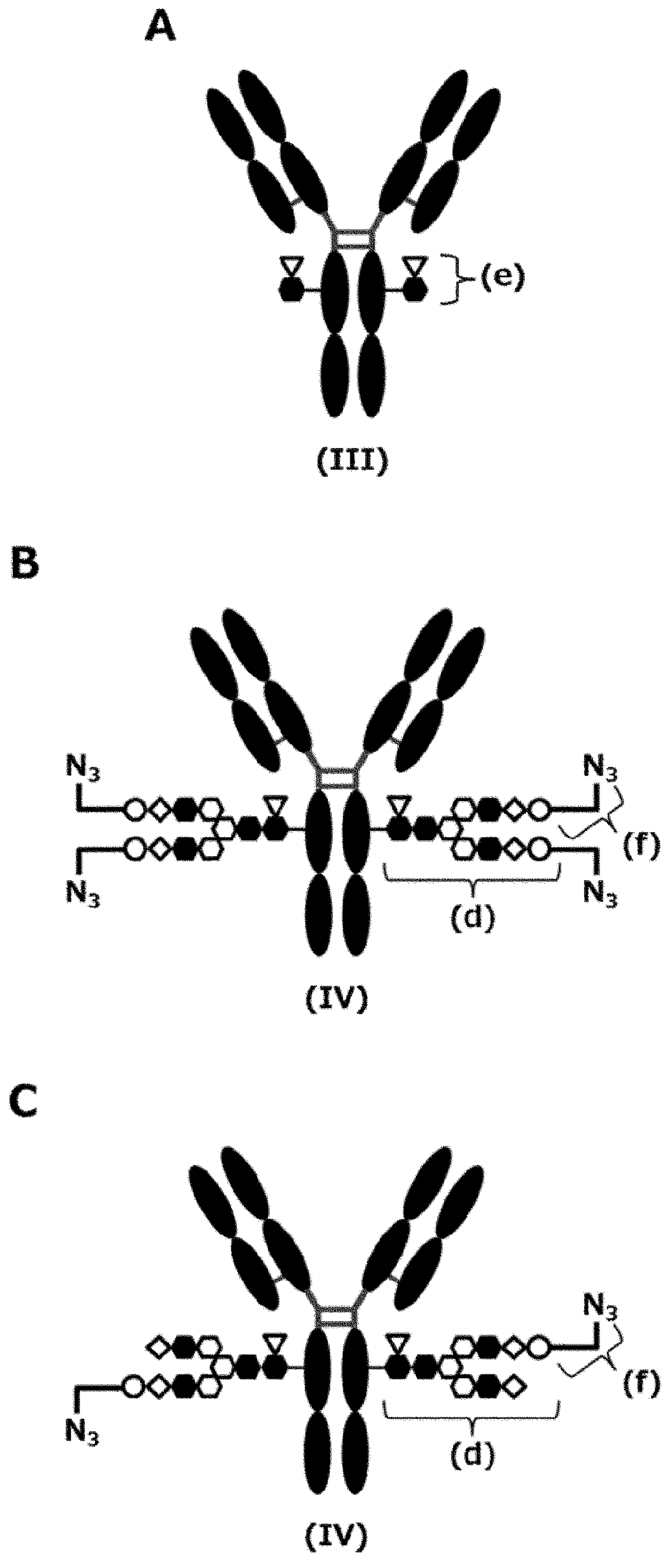

[Figure 3]
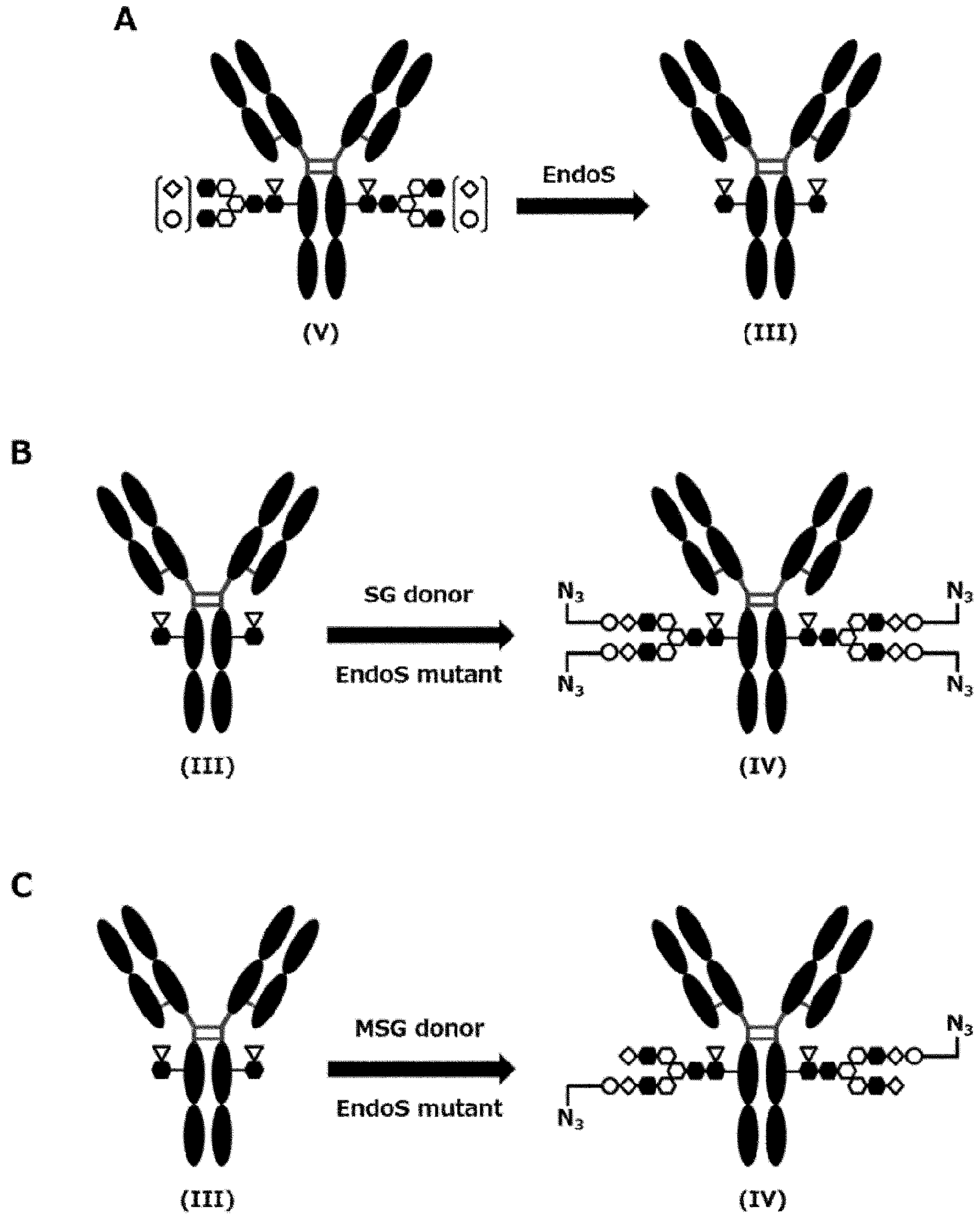

[Figure 4]

The amino acid sequence of the light chain of anti-CD70 antibody 1 (SEQ ID NO: 1)

DIVMTQSPDSLAVSLGERATINCRASKSVSTSGYSFMHWYQQKPGQPPKLLIYLASNLES
GVPDRFSGSGSGTDFTLTISSLQAEDVAVYYCQHSREVPWTFGQGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

The amino acid sequence of the heavy chain of anti-CD70 antibody 1 (SEQ ID NO: 2)

QVQLVQSGAEVKKPGASVKVSCKASGYTFTNYGMNWVRQAPGQGLKWMGWINTYTGEPTY
ADAFKGRVTMTRDTSISTAYMELSRLRSDDTAVYYCARDYGDYGMDYWGQGTTVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPEAAGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK (The LALA mutation site is underlined.)

[Figure 5]

The amino acid sequence of the light chain of anti-CD70 antibody 2 (SEQ ID NO: 3)

EIVLTQSPATLSLSPGERATLSCRASQSVSSYLAWYQQKPGQAPRLLIYDASNRATGIPA
RFSGSGSGTDFTLTISSLEPEDFAVYYCQQRTNWPLTFGGGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

The amino acid sequence of the heavy chain of anti-CD70 antibody 2 (SEQ ID NO: 4)

QVQLVESGGGVVQPGRSLRLSCAASGFTFSSYIMHWVRQAPGKGLEWVAVISYDGRNKYY
ADSVKGRFTISRDNSKNTLYLQMNSLRAEDTAVYYCARDTDGYDFDYWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPEAAGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK (The LALA mutation site is underlined.)

[Figure 6]

The amino acid sequence of the light chain of anti-TROP2 antibody 1 (SEQ ID NO: 5)

DIQMTQSPSSLSASVGDRVTITCKASQDVSTAVAWYQQKPGKAPKLLIYSASYRYTGVPS
RFSGSGSGTDFTLTISSLQPEDFAVYYCQQHYITPLTFGQGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

The amino acid sequence of the heavy chain of anti-TROP2 antibody 1 (SEQ ID NO: 6)

QVQLVQSGAEVKKPGASVKVSCKASGYTFTTAGMQWVRQAPGQGLEWMGWINTHSGVPKY
AEDFKGRVTISADTSTSTAYLQLSSLKSEDTAVYYCARSGFGSSYWYFDVWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK

[Figure 7]

The amino acid sequence of the light chain of anti-TROP2 antibody 2 (SEQ ID NO: 7)

DIQMTQSPSSLSASVGDRVTITCKASQDVSTAVAWYQQKPGKAPKLLIYSASYRYTGVPS
RFSGSGSGTDFTLTISSLQPEDFAVYYCQQHYITPLTFGQGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

The amino acid sequence of the heavy chain of anti-TROP2 antibody 2 (SEQ ID NO: 8)

QVQLVQSGAEVKKPGASVKVSCKASGYTFTTAGMQWVRQAPGQGLEWMGWINTHSGVPKY
AEDFKGRVTISADTSTSTAYLQLSSLKSEDTAVYYCARSGFGSSYWYFDVWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDKS
RWQQGNVFSCSVMHEALHNHYTQKSLSLSPGK (The LALA mutation site is underlined.)

[Figure 8]

The amino acid sequence of the light chain of anti-EGFR antibody 1 (SEQ ID NO: 9)

DIQMTQSPSSLSASVGDRVTITCQASQDISNYLNWYQQKPGKAPKLLIYDASNLETGVPS
RFSGSGSGTDFTFTISSLQPEDIATYFCQHFDHLPLAFGGGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

The amino acid sequence of the heavy chain of anti-EGFR antibody 1 (SEQ ID NO: 10)

QVQLQESGPGLVKPSETLSLTCTVSGGSVSSGDYYWTWIRQSPGKGLEWIGHIYYSGNTN
YNPSLKSRLTISIDTSKTQFSLKLSSVTAADTAIYYCVRDRVTGAFDIWGQGTMVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPE<u>AA</u>GG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (The LALA mutation site is underlined.)

[Figure 9]

The amino acid sequence of the light chain of anti-EGFR antibody 2 (SEQ ID NO: 11)

DILMTQSPSSMSVSLGDTVSITCHSSQDINSNIGWLQQRPGKSFKGLIYHGTNLDDEVPS
RFSGSGSGADYSLTISSLESEDFADYYCVQYAQFPWTFGGGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

The amino acid sequence of the heavy chain of anti-EGFR antibody 2 (SEQ ID NO: 12)

DVQLQESGPSLVKPSQSLSLTCTVTGYSITSDFAWNWIRQFPGNKLEWMGYISYSGNTRY
NPSLKSRISITRDTSKNQFFLQLNSVTIEDTATYYCVTAGRGFPYWGQGTLVTVSAASTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPE<u>AA</u>GGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK (The LALA mutation site is underlined.)

[Figure 10]

(a) The amino acid sequence of human wild-type STING (SEQ ID NO: 13)

MPHSSLHPSIPCPRGHGAQKAALVLLSACLVTLWGLGEPPEHTLRYLVLHLASLQLGLLL
NGVCSLAEELRHIHSRYRGSYWRTVRACLGCPLRRGALLLLSIYFYYSLPNAVGPPFTWM
LALLGLSQALNILLGLKGLAPAEISAVCEKGNFNVAHGLAWSYYIGYLRLILPELQARIR
TYNQHYNNLLRGAVSQRLYILLPLDCGVPDNLSMADPNIRFLDKLPQQTGDRAGIKDRVY
SNSIYELLENGQRAGTCVLEYATPLQTLFAMSQYSQAGFSREDRLEQAKLFCRTLEDILA
DAPESQNNCRLIAYQEPADDSSFSLSQEVLRHLRQEEKEEVTVGSLKTSAVPSTSTMSQE
PELLISGMEKPLPLRTDFS (b) The amino acid sequence of human STING REF mutant (R232H) (SEQ ID NO: 15)

MPHSSLHPSIPCPRGHGAQKAALVLLSACLVTLWGLGEPPEHTLRYLVLHLASLQLGLLL
NGVCSLAEELRHIHSRYRGSYWRTVRACLGCPLRRGALLLLSIYFYYSLPNAVGPPFTWM
LALLGLSQALNILLGLKGLAPAEISAVCEKGNFNVAHGLAWSYYIGYLRLILPELQARIR
TYNQHYNNLLRGAVSQRLYILLPLDCGVPDNLSMADPNIRFLDKLPQQTGDHAGIKDRV
YSNSIYELLENGQRAGTCVLEYATPLQTLFAMSQYSQAGFSREDRLEQAKLFCRTLEDIL
ADAPESQNNCRLIAYQEPADDSSFSLSQEVLRHLRQEEKEEVTVGSLKTSAVPSTSTMSQ
EPELLISGMEKPLPLRTDFS (The site of R232H mutation is underlined.)

(c) The amino acid sequence of human STING HAQ mutant (R71H, G230A, R293Q) (SEQ ID NO: 17)

MPHSSLHPSIPCPRGHGAQKAALVLLSACLVTLWGLGEPPEHTLRYLVLHLASLQLGLLL
NGVCSLAEELHHIHSRYRGSYWRTVRACLGCPLRRGALLLLSIYFYYSLPNAVGPPFTW
MLALLGLSQALNILLGLKGLAPAEISAVCEKGNFNVAHGLAWSYYIGYLRLILPELQARI
RTYNQHYNNLLRGAVSQRLYILLPLDCGVPDNLSMADPNIRFLDKLPQQTADRAGIKDR
VYSNSIYELLENGQRAGTCVLEYATPLQTLFAMSQYSQAGFSREDRLEQAKLFCQTLED
ILADAPESQNNCRLIAYQEPADDSSFSLSQEVLRHLRQEEKEEVTVGSLKTSAVPSTSTM
SQEPELLISGMEKPLPLRTDFS (The three underlines indicate the sites of R71H, G230A, and R293Q mutations, respectively.)

[Figure 11]
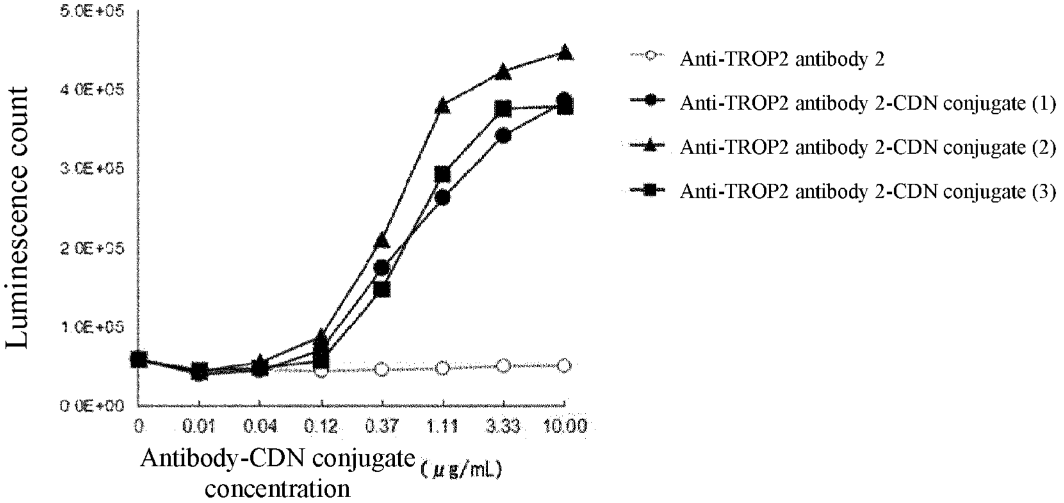
[Figure 12]
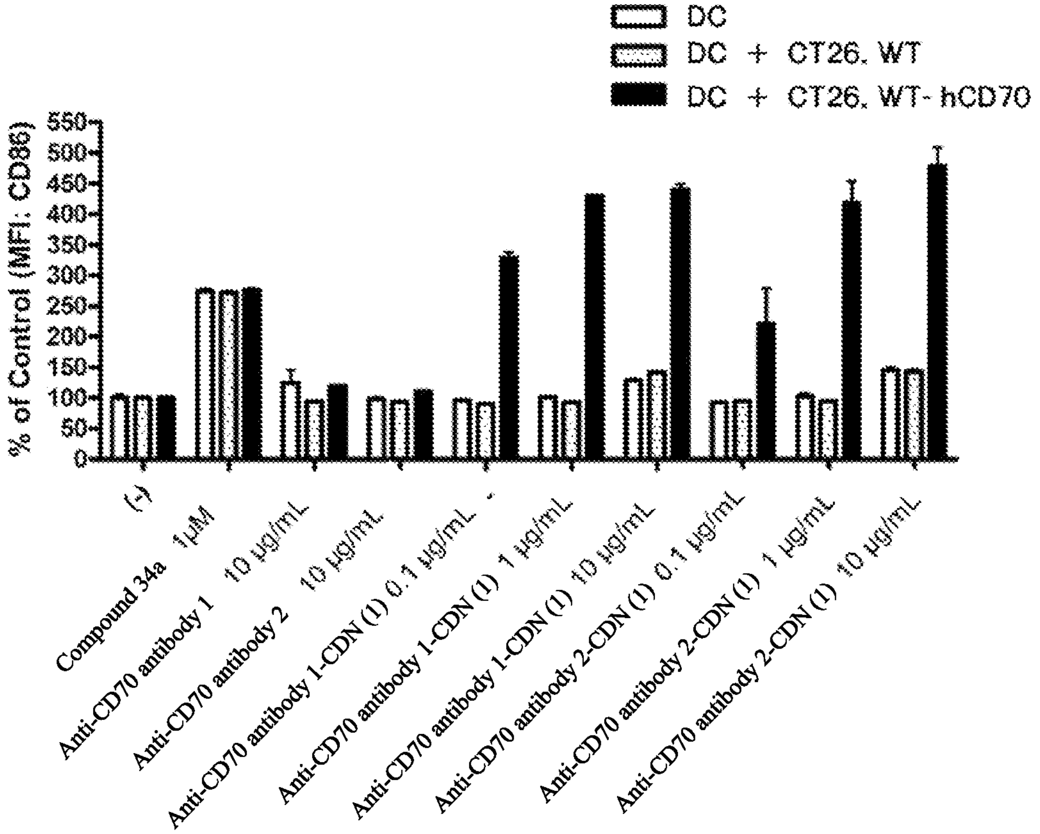

[Figure 13]
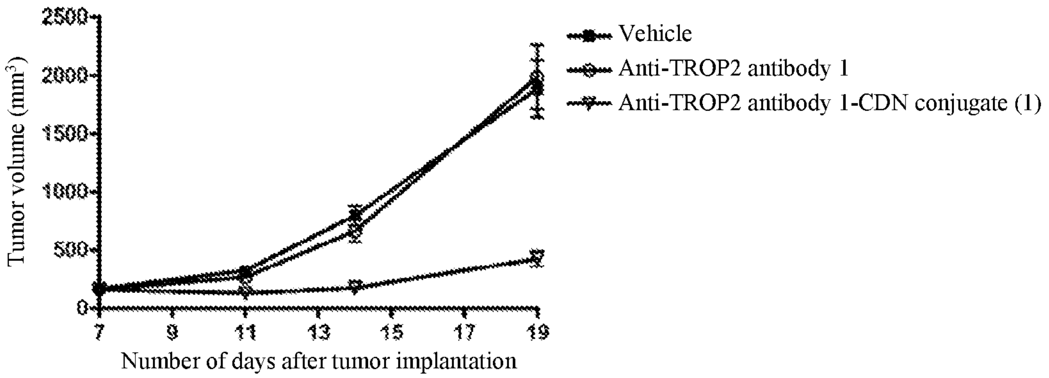
[Figure 14]
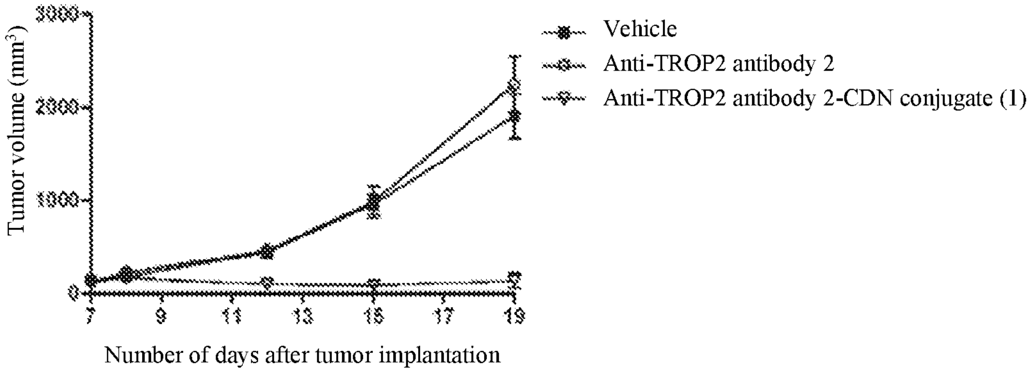
[Figure 15]
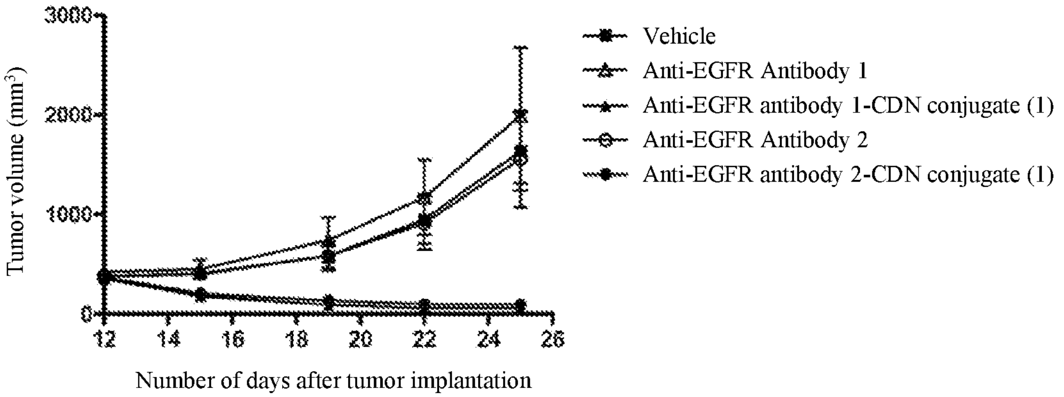

[Figure 16]

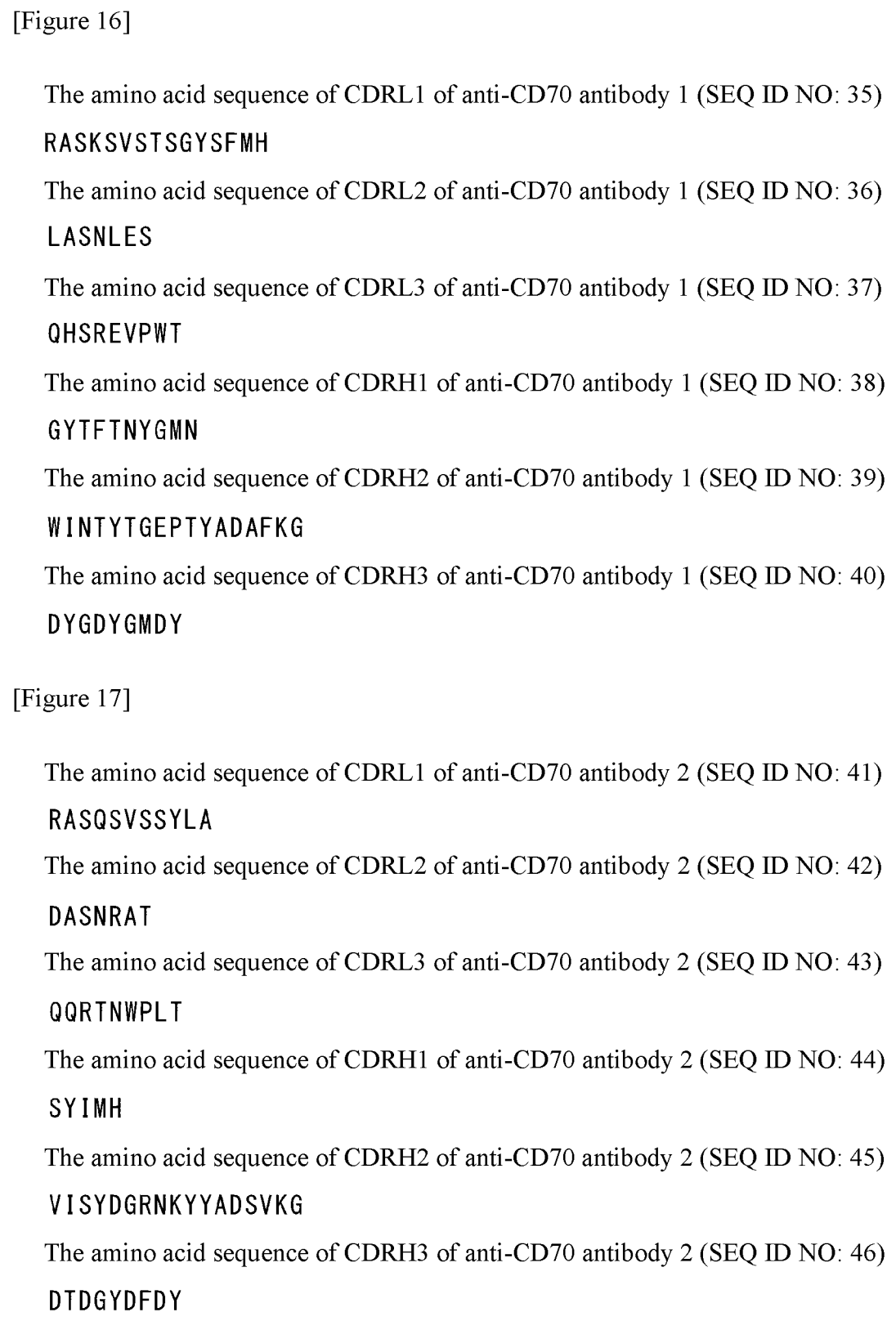

The amino acid sequence of CDRL1 of anti-CD70 antibody 1 (SEQ ID NO: 35)

RASKSVSTSGYSFMH

The amino acid sequence of CDRL2 of anti-CD70 antibody 1 (SEQ ID NO: 36)

LASNLES

The amino acid sequence of CDRL3 of anti-CD70 antibody 1 (SEQ ID NO: 37)

QHSREVPWT

The amino acid sequence of CDRH1 of anti-CD70 antibody 1 (SEQ ID NO: 38)

GYTFTNYGMN

The amino acid sequence of CDRH2 of anti-CD70 antibody 1 (SEQ ID NO: 39)

WINTYTGEPTYADAFKG

The amino acid sequence of CDRH3 of anti-CD70 antibody 1 (SEQ ID NO: 40)

DYGDYGMDY

[Figure 17]

The amino acid sequence of CDRL1 of anti-CD70 antibody 2 (SEQ ID NO: 41)

RASQSVSSYLA

The amino acid sequence of CDRL2 of anti-CD70 antibody 2 (SEQ ID NO: 42)

DASNRAT

The amino acid sequence of CDRL3 of anti-CD70 antibody 2 (SEQ ID NO: 43)

QQRTNWPLT

The amino acid sequence of CDRH1 of anti-CD70 antibody 2 (SEQ ID NO: 44)

SYIMH

The amino acid sequence of CDRH2 of anti-CD70 antibody 2 (SEQ ID NO: 45)

VISYDGRNKYYADSVKG

The amino acid sequence of CDRH3 of anti-CD70 antibody 2 (SEQ ID NO: 46)

DTDGYDFDY

[Figure 18]

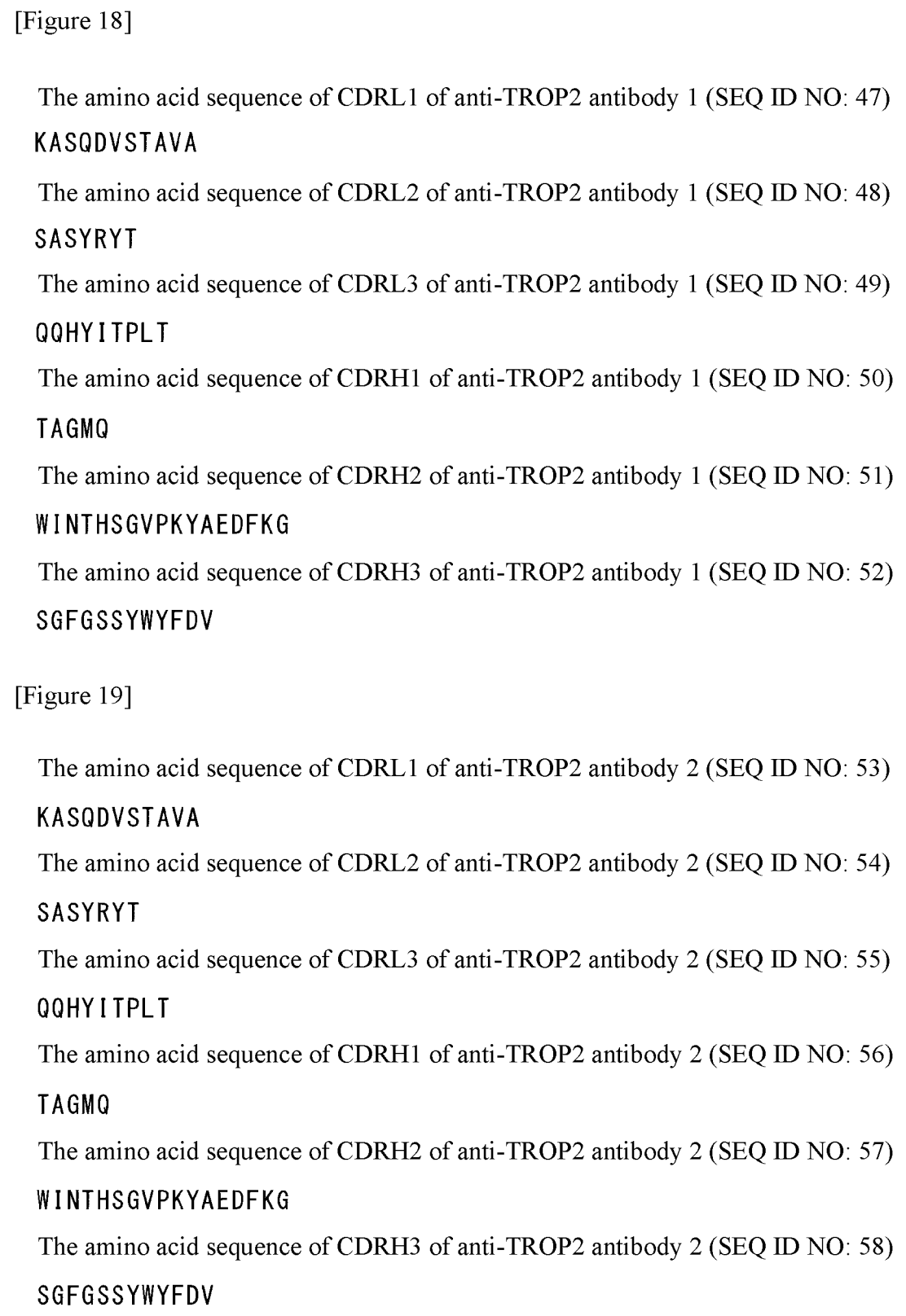

The amino acid sequence of CDRL1 of anti-TROP2 antibody 1 (SEQ ID NO: 47)

KASQDVSTAVA

The amino acid sequence of CDRL2 of anti-TROP2 antibody 1 (SEQ ID NO: 48)

SASYRYT

The amino acid sequence of CDRL3 of anti-TROP2 antibody 1 (SEQ ID NO: 49)

QQHYITPLT

The amino acid sequence of CDRH1 of anti-TROP2 antibody 1 (SEQ ID NO: 50)

TAGMQ

The amino acid sequence of CDRH2 of anti-TROP2 antibody 1 (SEQ ID NO: 51)

WINTHSGVPKYAEDFKG

The amino acid sequence of CDRH3 of anti-TROP2 antibody 1 (SEQ ID NO: 52)

SGFGSSYWYFDV

[Figure 19]

The amino acid sequence of CDRL1 of anti-TROP2 antibody 2 (SEQ ID NO: 53)

KASQDVSTAVA

The amino acid sequence of CDRL2 of anti-TROP2 antibody 2 (SEQ ID NO: 54)

SASYRYT

The amino acid sequence of CDRL3 of anti-TROP2 antibody 2 (SEQ ID NO: 55)

QQHYITPLT

The amino acid sequence of CDRH1 of anti-TROP2 antibody 2 (SEQ ID NO: 56)

TAGMQ

The amino acid sequence of CDRH2 of anti-TROP2 antibody 2 (SEQ ID NO: 57)

WINTHSGVPKYAEDFKG

The amino acid sequence of CDRH3 of anti-TROP2 antibody 2 (SEQ ID NO: 58)

SGFGSSYWYFDV

[Figure 20]

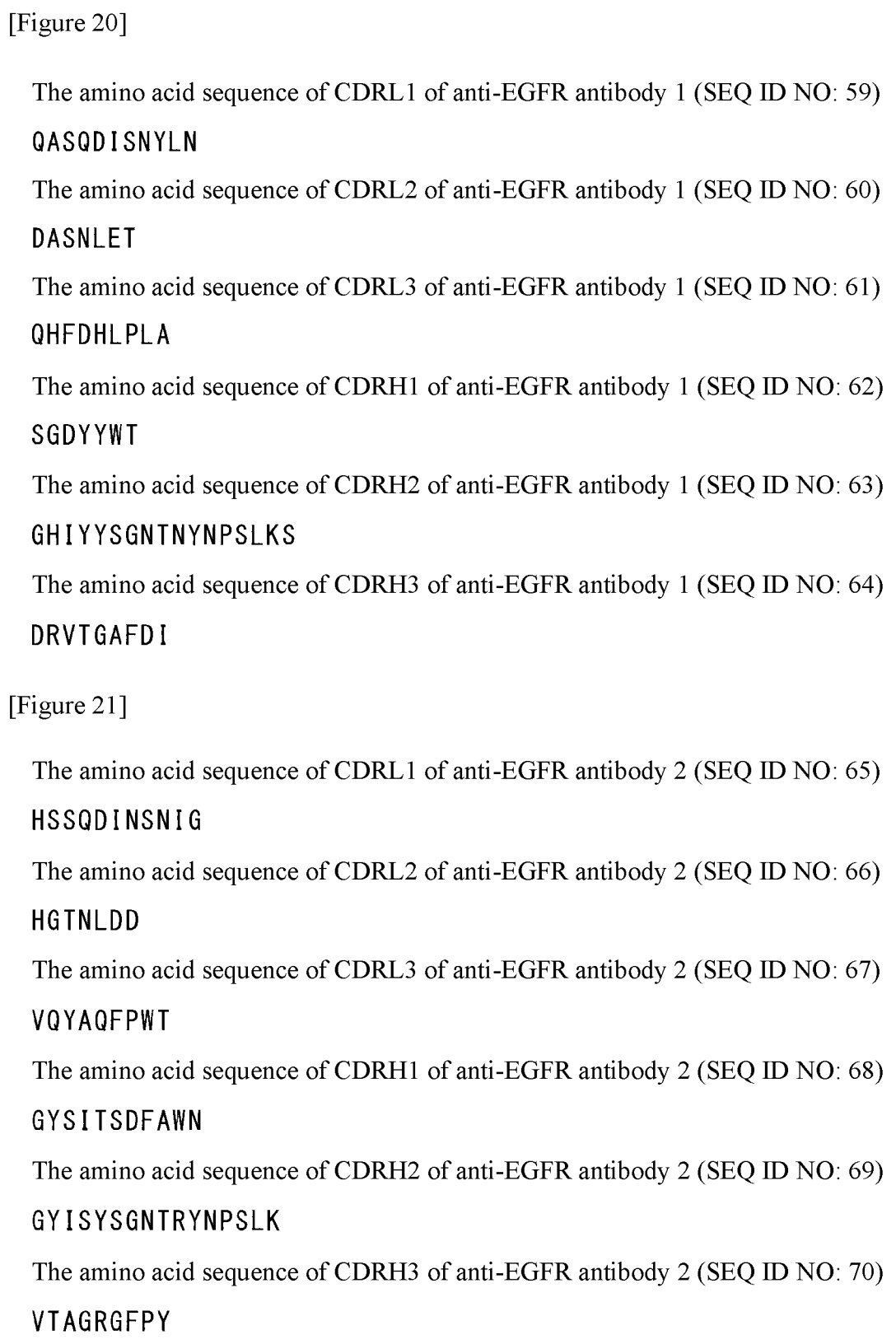

The amino acid sequence of CDRL1 of anti-EGFR antibody 1 (SEQ ID NO: 59)

QASQDISNYLN

The amino acid sequence of CDRL2 of anti-EGFR antibody 1 (SEQ ID NO: 60)

DASNLET

The amino acid sequence of CDRL3 of anti-EGFR antibody 1 (SEQ ID NO: 61)

QHFDHLPLA

The amino acid sequence of CDRH1 of anti-EGFR antibody 1 (SEQ ID NO: 62)

SGDYYWT

The amino acid sequence of CDRH2 of anti-EGFR antibody 1 (SEQ ID NO: 63)

GHIYYSGNTNYNPSLKS

The amino acid sequence of CDRH3 of anti-EGFR antibody 1 (SEQ ID NO: 64)

DRVTGAFDI

[Figure 21]

The amino acid sequence of CDRL1 of anti-EGFR antibody 2 (SEQ ID NO: 65)

HSSQDINSNIG

The amino acid sequence of CDRL2 of anti-EGFR antibody 2 (SEQ ID NO: 66)

HGTNLDD

The amino acid sequence of CDRL3 of anti-EGFR antibody 2 (SEQ ID NO: 67)

VQYAQFPWT

The amino acid sequence of CDRH1 of anti-EGFR antibody 2 (SEQ ID NO: 68)

GYSITSDFAWN

The amino acid sequence of CDRH2 of anti-EGFR antibody 2 (SEQ ID NO: 69)

GYISYSGNTRYNPSLK

The amino acid sequence of CDRH3 of anti-EGFR antibody 2 (SEQ ID NO: 70)

VTAGRGFPY

[Figure 22]
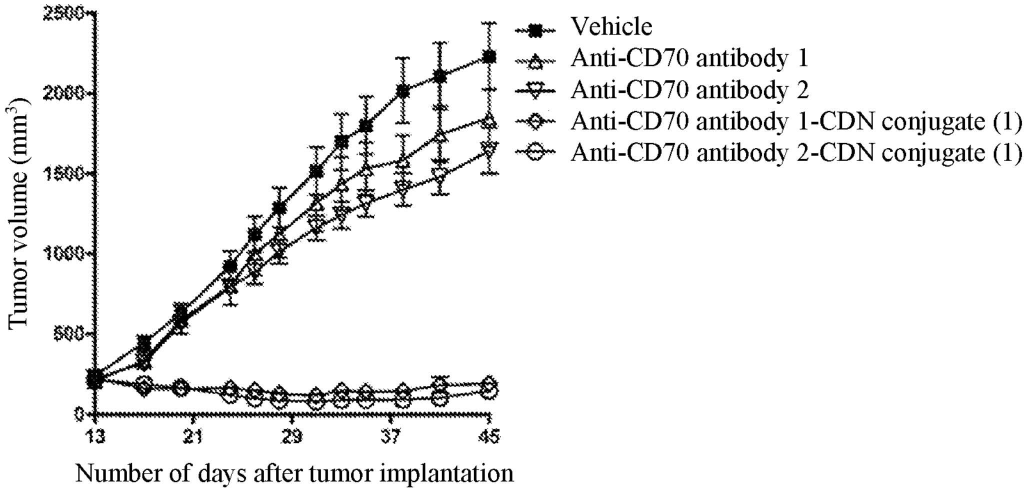
[Figure 23]
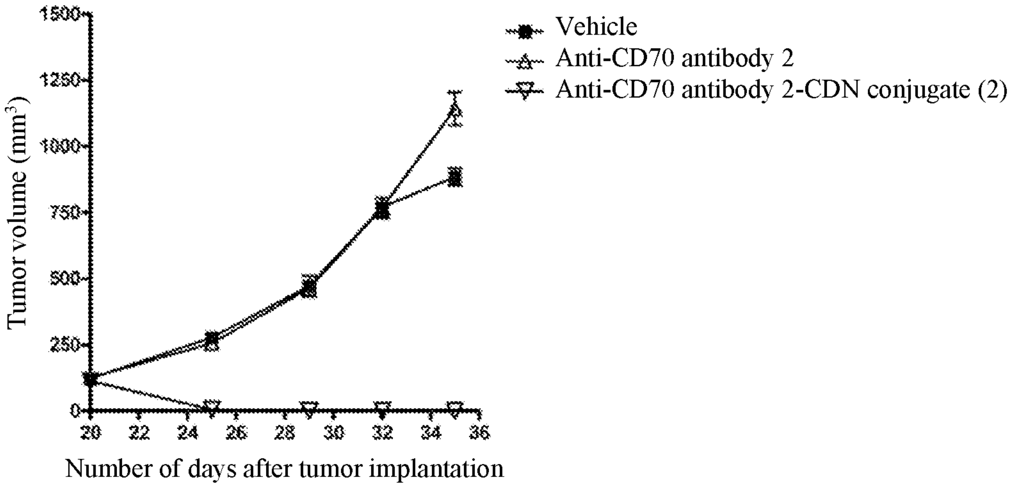
[Figure 24]
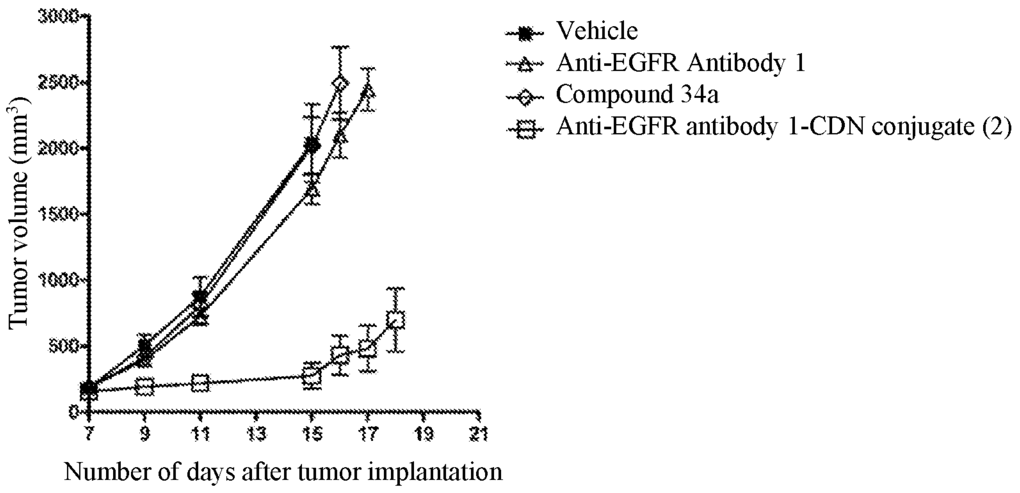

SEQUENCE LISTING

<160> NUMBER OF SEQ ID NOS: 70

<210> SEQ ID NO 1
<211> LENGTH: 218
<212> TYPE: PRT
<213> ORGANISM: Homo sapiens

<400> SEQUENCE: 1

Asp Ile Val Met Thr Gln Ser Pro Asp Ser Leu Ala Val Ser Leu Gly
1 5 10 15

Glu Arg Ala Thr Ile Asn Cys Arg Ala Ser Lys Ser Val Ser Thr Ser
20 25 30

Gly Tyr Ser Phe Met His Trp Tyr Gln Gln Lys Pro Gly Gln Pro Pro
35 40 45

Lys Leu Leu Ile Tyr Leu Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln His Ser Arg
85 90 95

Glu Val Pro Trp Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 2
<211> LENGTH: 448
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Gln Gly Leu Lys Trp Met
35 40 45

Gly Trp Ile Asn Thr Tyr Thr Gly Glu Pro Thr Tyr Ala Asp Ala Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Tyr Gly Asp Tyr Gly Met Asp Tyr Trp Gly Gln Gly Thr 100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 3
<211> LENGTH: 214
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 448
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 5
<211> LENGTH: 214
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Val Tyr Tyr Cys Gln Gln His Tyr Ile Thr Pro Leu
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 6
<211> LENGTH: 451
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Thr His Ser Gly Val Pro Lys Tyr Ala Glu Asp Phe
    50                  55                  60

Lys Gly Arg Val Thr Ile Ser Ala Asp Thr Ser Thr Ser Thr Ala Tyr
65                  70                  75                  80

Leu Gln Leu Ser Ser Leu Lys Ser Glu Asp Thr Ala Val Tyr Tyr Cys
                85                  90                  95

Ala Arg Ser Gly Phe Gly Ser Ser Tyr Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 7
<211> LENGTH: 214
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 8
<211> LENGTH: 451
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Thr His Ser Gly Val Pro Lys Tyr Ala Glu Asp Phe
    50                  55                  60

Lys Gly Arg Val Thr Ile Ser Ala Asp Thr Ser Thr Ser Thr Ala Tyr
65                  70                  75                  80

Leu Gln Leu Ser Ser Leu Lys Ser Glu Asp Thr Ala Val Tyr Tyr Cys
                85                  90                  95

Ala Arg Ser Gly Phe Gly Ser Ser Tyr Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 9
<211> LENGTH: 214
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 10
<211> LENGTH: 449
<212> TYPE: PRT
<213> ORGANISM: Homo sapiens

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 11
<211> LENGTH: 214
<212> TYPE: PRT
<213> ORGANISM: Homo sapiens

<400> SEQUENCE: 11

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 446
<212> TYPE: PRT
<213> ORGANISM: Homo sapiens

<400> SEQUENCE: 12

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60
```

-continued

```
Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 13
<211> LENGTH: 379
<212> TYPE: PRT
<213> ORGANISM: Homo sapiens

<400> SEQUENCE: 13

-continued

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

<210> SEQ ID NO 14
<211> LENGTH: 1140
<212> TYPE: DNA
<213> ORGANISM: Homo sapiens

<400> SEQUENCE: 14
atgccccact ccagcctgca tccatccatc ccgtgtccca ggggtcacgg ggcccagaag 60
gcagccttgg ttctgctgag tgcctgcctg gtgacccttt gggggctagg agagccacca 120
gagcacactc tccggtacct ggtgctccac ctagcctccc tgcagctggg actgctgtta 180
aacggggtct gcagcctggc tgaggagctg cgccacatcc actccaggta ccggggcagc 240
tactggagga ctgtgcgggc ctgcctgggc tgcccccctcc gccgtggggc cctgttgctg 300
ctgtccatct atttctacta ctccctccca aatgcggtcg gcccgccctt cacttggatg 360
cttgccctcc tgggcctctc gcaggcactg aacatcctcc tgggcctcaa gggcctggcc 420
ccagctgaga tctctgcagt gtgtgaaaaa gggaatttca acgtggccca tgggctggca 480
tggtcatatt acatcggata tctgcggctg atcctgccag agctccaggc ccggattcga 540
acttacaatc agcattacaa caacctgcta cggggtgcag tgagccagcg gctgtatatt 600
ctcctcccat tggactgtgg ggtgcctgat aacctgagta tggctgaccc caacattcgc 660
ttcctggata aactgcccca gcagaccggt gaccatgctg gcatcaagga tcgggtttac 720
agcaacagca tctatgagct tctggagaac gggcagcggg cgggcacctg tgtcctggag 780
tacgccaccc ccttgcagac tttgtttgcc atgtcacaat acagtcaagc tggctttagc 840
cgggaggata ggcttgagca ggccaaactc ttctgccgga cacttgagga catcctggca 900
gatgcccctg agtctcagaa caactgccgc ctcattgcct accaggaacc tgcagatgac 960
agcagcttct cgctgtccca ggaggttctc cggcacctgc ggcaggagga aaaggaagag 1020
gttactgtgg gcagcttgaa gacctcagcg gtgcccagta cctccacgat gtcccaagag 1080
cctgagctcc tcatcagtgg aatggaaaag cccctccctc tccgcacgga tttctcttag 1140

<210> SEQ ID NO 15
<211> LENGTH: 379
<212> TYPE: PRT
<213> ORGANISM: Homo sapiens

<400> SEQUENCE: 15

Met Pro His Ser Ser Leu His Pro Ser Ile Pro Cys Pro Arg Gly His
1 5 10 15

Gly Ala Gln Lys Ala Ala Leu Val Leu Leu Ser Ala Cys Leu Val Thr
20 25 30

Leu Trp Gly Leu Gly Glu Pro Pro Glu His Thr Leu Arg Tyr Leu Val
35 40 45

Leu His Leu Ala Ser Leu Gln Leu Gly Leu Leu Leu Asn Gly Val Cys
50 55 60

Ser Leu Ala Glu Glu Leu Arg His Ile His Ser Arg Tyr Arg Gly Ser
65 70 75 80

Tyr Trp Arg Thr Val Arg Ala Cys Leu Gly Cys Pro Leu Arg Arg Gly
85 90 95

Ala Leu Leu Leu Leu Ser Ile Tyr Phe Tyr Tyr Ser Leu Pro Asn Ala
100 105 110

Val Gly Pro Pro Phe Thr Trp Met Leu Ala Leu Leu Gly Leu Ser Gln
115 120 125

Ala Leu Asn Ile Leu Leu Gly Leu Lys Gly Leu Ala Pro Ala Glu Ile
130 135 140

Ser Ala Val Cys Glu Lys Gly Asn Phe Asn Val Ala His Gly Leu Ala
145 150 155 160

Trp Ser Tyr Tyr Ile Gly Tyr Leu Arg Leu Ile Leu Pro Glu Leu Gln

-continued

```
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375
```

<210> SEQ ID NO 16
<211> LENGTH: 1140
<212> TYPE: DNA
<213> ORGANISM: Homo sapiens

<400> SEQUENCE: 16

```
atgccccact ccagcctgca tccatccatc ccgtgtccca ggggtcacgg ggcccagaag     60

gcagccttgg ttctgctgag tgcctgcctg gtgacccttt gggggctagg agagccacca    120

gagcacactc tccggtacct ggtgctccac ctagcctccc tgcagctggg actgctgtta    180

aacggggtct gcagcctggc tgaggagctg cgccacatcc actccaggta ccggggcagc    240

tactggagga ctgtgcgggc ctgcctgggc tgcccctcc gccgtggggc cctgttgctg    300

ctgtccatct atttctacta ctccctccca aatgcggtcg gcccgccctt cacttggatg    360

cttgccctcc tgggcctctc gcaggcactg aacatcctcc tgggcctcaa gggcctggcc    420

ccagctgaga tctctgcagt gtgtgaaaaa gggaatttca acgtggccca tgggctggca    480

tggtcatatt acatcggata tctgcggctg atcctgccag agctccaggc ccggattcga    540

acttacaatc agcattacaa caacctgcta cggggtgcag tgagccagcg gctgtatatt    600

ctcctcccat tggactgtgg ggtgcctgat aacctgagta tggctgaccc caacattcgc    660

ttcctggata aactgcccca gcagaccggt gaccgtgctg gcatcaagga tcgggtttac    720

agcaacagca tctatgagct tctggagaac gggcagcggg cgggcacctg tgtcctggag    780

tacgccaccc ccttgcagac tttgtttgcc atgtcacaat acagtcaagc tggctttagc    840

cgggaggata ggcttgagca ggccaaactc ttctgccgga cacttgagga catcctggca    900
```

```
gatgcccctg agtctcagaa caactgccgc ctcattgcct accaggaacc tgcagatgac    960

agcagcttct cgctgtccca ggaggttctc cggcacctgc ggcaggagga aaaggaagag   1020

gttactgtgg gcagcttgaa gacctcagcg gtgcccagta cctccacgat gtcccaagag   1080

cctgagctcc tcatcagtgg aatggaaaag cccctccctc tccgcacgga tttctcttag   1140
```

<210> SEQ ID NO 17
<211> LENGTH: 379
<212> TYPE: PRT
<213> ORGANISM: Homo sapiens

<400> SEQUENCE: 17

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335
```

```
Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 18
<211> LENGTH: 1140
<212> TYPE: DNA
<213> ORGANISM: Homo sapiens

<400> SEQUENCE: 18

atgccccact ccagcctgca tccatccatc ccgtgtccca ggggtcacgg ggcccagaag     60

gcagccttgg ttctgctgag tgcctgcctg gtgacccttt gggggctagg agagccacca    120

gagcacactc tccggtacct ggtgctccac ctagcctccc tgcagctggg actgctgtta    180

aacggggtct gcagcctggc tgaggagctg caccacatcc actccaggta ccggggcagc    240

tactggagga ctgtgcgggc ctgcctgggc tgcccctcc gccgtggggc cctgttgctg    300

ctgtccatct atttctacta ctccctccca aatgcggtcg gcccgccctt cacttggatg    360

cttgccctcc tgggcctctc gcaggcactg aacatcctcc tgggcctcaa gggcctggcc    420

ccagctgaga tctctgcagt gtgtgaaaaa gggaatttca acgtggccca tgggctggca    480

tggtcatatt acatcggata tctgcggctg atcctgccag agctccaggc ccggattcga    540

acttacaatc agcattacaa caacctgcta cggggtgcag tgagccagcg gctgtatatt    600

ctcctcccat tggactgtgg ggtgcctgat aacctgagta tggctgaccc caacattcgc    660

ttcctggata aactgcccca gcagaccgct gaccgtgctg gcatcaagga tcgggtttac    720

agcaacagca tctatgagct tctggagaac gggcagcggg cgggcacctg tgtcctggag    780

tacgccaccc ccttgcagac tttgtttgcc atgtcacaat acagtcaagc tggctttagc    840

cgggaggata ggcttgagca ggccaaactc ttctgccaga cacttgagga catcctggca    900

gatgcccctg agtctcagaa caactgccgc ctcattgcct accaggaacc tgcagatgac    960

agcagcttct cgctgtccca ggaggttctc cggcacctgc ggcaggagga aaaggaagag   1020

gttactgtgg gcagcttgaa gacctcagcg gtgcccagta cctccacgat gtcccaagag   1080

cctgagctcc tcatcagtgg aatggaaaag cccctccctc tccgcacgga tttctcttag   1140


<210> SEQ ID NO 19
<211> LENGTH: 378
<212> TYPE: PRT
<213> ORGANISM: Mus musculus

<400> SEQUENCE: 19

Met Pro Tyr Ser Asn Leu His Pro Ala Ile Pro Arg Pro Arg Gly His
1               5                   10                  15

Arg Ser Lys Tyr Val Ala Leu Ile Phe Leu Val Ala Ser Leu Met Ile
            20                  25                  30

Leu Trp Val Ala Lys Asp Pro Pro Asn His Thr Leu Lys Tyr Leu Ala
        35                  40                  45

Leu His Leu Ala Ser His Glu Leu Gly Leu Leu Leu Lys Asn Leu Cys
    50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Leu Gly Cys Pro Ile His Cys Met
```

```
                85                  90                  95

Ala Met Ile Leu Leu Ser Ser Tyr Phe Tyr Phe Leu Gln Asn Thr Ala
            100                 105                 110

Asp Ile Tyr Leu Ser Trp Met Phe Gly Leu Leu Val Leu Tyr Lys Ser
        115                 120                 125

Leu Ser Met Leu Leu Gly Leu Gln Ser Leu Thr Pro Ala Glu Val Ser
    130                 135                 140

Ala Val Cys Glu Glu Lys Lys Leu Asn Val Ala His Gly Leu Ala Trp
145                 150                 155                 160

Ser Tyr Tyr Ile Gly Tyr Leu Arg Leu Ile Leu Pro Gly Leu Gln Ala
                165                 170                 175

Arg Ile Arg Met Phe Asn Gln Leu His Asn Asn Met Leu Ser Gly Ala
            180                 185                 190

Gly Ser Arg Arg Leu Tyr Ile Leu Phe Pro Leu Asp Cys Gly Val Pro
        195                 200                 205

Asp Asn Leu Ser Val Val Asp Pro Asn Ile Arg Phe Arg Asp Met Leu
    210                 215                 220

Pro Gln Gln Asn Ile Asp Arg Ala Gly Ile Lys Asn Arg Val Tyr Ser
225                 230                 235                 240

Asn Ser Val Tyr Glu Ile Leu Glu Asn Gly Gln Pro Ala Gly Val Cys
                245                 250                 255

Ile Leu Glu Tyr Ala Thr Pro Leu Gln Thr Leu Phe Ala Met Ser Gln
            260                 265                 270

Asp Ala Lys Ala Gly Phe Ser Arg Glu Asp Arg Leu Glu Gln Ala Lys
        275                 280                 285

Leu Phe Cys Arg Thr Leu Glu Glu Ile Leu Glu Asp Val Pro Glu Ser
    290                 295                 300

Arg Asn Asn Cys Arg Leu Ile Val Tyr Gln Glu Pro Thr Asp Gly Asn
305                 310                 315                 320

Ser Phe Ser Leu Ser Gln Glu Val Leu Arg His Ile Arg Gln Glu Glu
                325                 330                 335

Lys Glu Glu Val Thr Met Asn Ala Pro Met Thr Ser Val Ala Pro Pro
            340                 345                 350

Pro Ser Val Leu Ser Gln Glu Pro Arg Leu Leu Ile Ser Gly Met Asp
        355                 360                 365

Gln Pro Leu Pro Leu Arg Thr Asp Leu Ile
    370                 375
```

<210> SEQ ID NO 20
<211> LENGTH: 1137
<212> TYPE: DNA
<213> ORGANISM: Mus musculus

<400> SEQUENCE: 20

```
atgccatact ccaacctgca tccagccatc ccacggccca gaggtcaccg ctccaaatat      60

gtagccctca tctttctggt ggccagcctg atgatccttt gggtggcaaa ggatccacca     120

aatcacactc tgaagtacct agcacttcac ctagcctcgc acgaacttgg actactgttg     180

aaaaacctct gctgtctggc tgaagagctg tgccatgtcc agtccaggta ccagggcagc     240

tactggaagg ctgtgcgcgc ctgcctggga tgccccatcc actgtatggc tatgattcta     300

ctatcgtctt atttctattt cctccaaaac actgctgaca tatacctcag ttggatgttt     360

ggccttctgg tcctctataa gtccctaagc atgctcctgg gccttcagag cttgactcca     420

gcggaagtct ctgcagtctg tgaagaaaag aagttaaatg ttgcccacgg gctggcctgg     480
```

```
tcatactaca ttgggtactt gcggttgatc ttaccagggc tccaggcccg gatccgaatg    540

ttcaatcagc tacataacaa catgctcagt ggtgcaggga gccgaagact gtacatcctc    600

tttccattgg actgtggggt gcctgacaac ctgagtgtag ttgaccccaa cattcgattc    660

cgagatatgc tgccccagca aaacatcgac cgtgctggca tcaagaatcg ggtttattcc    720

aacagcgtct acgagattct ggagaacgga cagccagcag gcgtctgtat cctggagtac    780

gccacccccct tgcagaccct gtttgccatg tcacaggatg ccaaagctgg cttcagtcgg    840

gaggatcggc ttgagcaggc taaactcttc tgccggacac ttgaggaaat cctggaagat    900

gtccccgagt ctcgaaataa ctgccgcctc attgtctacc aagaacccac agacggaaac    960

agtttctcac tgtctcagga ggtgctccgg cacattcgtc aggaagaaaa ggaggaggtt   1020

accatgaatg cccccatgac ctcagtggca cctcctccct ccgtactgtc ccaagagcca   1080

agactcctca tcagtggtat ggatcagcct ctcccactcc gcactgacct catctga      1137
```

```
<210> SEQ ID NO 21
<211> LENGTH: 243
<212> TYPE: PRT
<213> ORGANISM: Homo sapiens

<400> SEQUENCE: 21

Met Gly Ser Ser His His His His His His Ser Ser Gly Ser Gly Leu
1               5                   10                  15

Asn Asp Ile Phe Glu Ala Gln Lys Ile Glu Trp His Glu Gly Gly Ser
            20                  25                  30

Glu Asn Leu Tyr Phe Gln Gly Leu Ala Pro Ala Glu Ile Ser Ala Val
        35                  40                  45

Cys Glu Lys Gly Asn Phe Asn Val Ala His Gly Leu Ala Trp Ser Tyr
    50                  55                  60

Tyr Ile Gly Tyr Leu Arg Leu Ile Leu Pro Glu Leu Gln Ala Arg Ile
65                  70                  75                  80

Arg Thr Tyr Asn Gln His Tyr Asn Asn Leu Leu Arg Gly Ala Val Ser
                85                  90                  95

Gln Arg Leu Tyr Ile Leu Leu Pro Leu Asp Cys Gly Val Pro Asp Asn
            100                 105                 110

Leu Ser Met Ala Asp Pro Asn Ile Arg Phe Leu Asp Lys Leu Pro Gln
        115                 120                 125

Gln Thr Gly Asp Arg Ala Gly Ile Lys Asp Arg Val Tyr Ser Asn Ser
    130                 135                 140

Ile Tyr Glu Leu Leu Glu Asn Gly Gln Arg Ala Gly Thr Cys Val Leu
145                 150                 155                 160

Glu Tyr Ala Thr Pro Leu Gln Thr Leu Phe Ala Met Ser Gln Tyr Ser
                165                 170                 175

Gln Ala Gly Phe Ser Arg Glu Asp Arg Leu Glu Gln Ala Lys Leu Phe
            180                 185                 190

Cys Arg Thr Leu Glu Asp Ile Leu Ala Asp Ala Pro Glu Ser Gln Asn
        195                 200                 205

Asn Cys Arg Leu Ile Ala Tyr Gln Glu Pro Ala Asp Asp Ser Ser Phe
    210                 215                 220

Ser Leu Ser Gln Glu Val Leu Arg His Leu Arg Gln Glu Glu Lys Glu
225                 230                 235                 240

Glu Val Thr
```

<210> SEQ ID NO 22
<211> LENGTH: 243
<212> TYPE: PRT
<213> ORGANISM: Homo sapiens

<400> SEQUENCE: 22

```
Met Gly Ser Ser His His His His His His Ser Ser Gly Ser Gly Leu
1               5                   10                  15

Asn Asp Ile Phe Glu Ala Gln Lys Ile Glu Trp His Glu Gly Gly Ser
            20                  25                  30

Glu Asn Leu Tyr Phe Gln Gly Leu Ala Pro Ala Glu Ile Ser Ala Val
        35                  40                  45

Cys Glu Lys Gly Asn Phe Asn Val Ala His Gly Leu Ala Trp Ser Tyr
    50                  55                  60

Tyr Ile Gly Tyr Leu Arg Leu Ile Leu Pro Glu Leu Gln Ala Arg Ile
65                  70                  75                  80

Arg Thr Tyr Asn Gln His Tyr Asn Asn Leu Leu Arg Gly Ala Val Ser
                85                  90                  95

Gln Arg Leu Tyr Ile Leu Leu Pro Leu Asp Cys Gly Val Pro Asp Asn
            100                 105                 110

Leu Ser Met Ala Asp Pro Asn Ile Arg Phe Leu Asp Lys Leu Pro Gln
        115                 120                 125

Gln Thr Gly Asp His Ala Gly Ile Lys Asp Arg Val Tyr Ser Asn Ser
    130                 135                 140

Ile Tyr Glu Leu Leu Glu Asn Gly Gln Arg Ala Gly Thr Cys Val Leu
145                 150                 155                 160

Glu Tyr Ala Thr Pro Leu Gln Thr Leu Phe Ala Met Ser Gln Tyr Ser
                165                 170                 175

Gln Ala Gly Phe Ser Arg Glu Asp Arg Leu Glu Gln Ala Lys Leu Phe
            180                 185                 190

Cys Arg Thr Leu Glu Asp Ile Leu Ala Asp Ala Pro Glu Ser Gln Asn
        195                 200                 205

Asn Cys Arg Leu Ile Ala Tyr Gln Glu Pro Ala Asp Asp Ser Ser Phe
    210                 215                 220

Ser Leu Ser Gln Glu Val Leu Arg His Leu Arg Gln Glu Glu Lys Glu
225                 230                 235                 240

Glu Val Thr
```

<210> SEQ ID NO 23
<211> LENGTH: 243
<212> TYPE: PRT
<213> ORGANISM: Homo sapiens

<400> SEQUENCE: 23

```
Met Gly Ser Ser His His His His His His Ser Ser Gly Ser Gly Leu
1               5                   10                  15

Asn Asp Ile Phe Glu Ala Gln Lys Ile Glu Trp His Glu Gly Gly Ser
            20                  25                  30

Glu Asn Leu Tyr Phe Gln Gly Leu Ala Pro Ala Glu Ile Ser Ala Val
        35                  40                  45

Cys Glu Lys Gly Asn Phe Asn Val Ala His Gly Leu Ala Trp Ser Tyr
    50                  55                  60

Tyr Ile Gly Tyr Leu Arg Leu Ile Leu Pro Glu Leu Gln Ala Arg Ile
65                  70                  75                  80

Arg Thr Tyr Asn Gln His Tyr Asn Asn Leu Leu Arg Gly Ala Val Ser
                85                  90                  95
```

Gln Arg Leu Tyr Ile Leu Leu Pro Leu Asp Cys Gly Val Pro Asp Asn
100 105 110

Leu Ser Met Ala Asp Pro Asn Ile Arg Phe Leu Asp Lys Leu Pro Gln
115 120 125

Gln Thr Ala Asp Arg Ala Gly Ile Lys Asp Arg Val Tyr Ser Asn Ser
130 135 140

Ile Tyr Glu Leu Leu Glu Asn Gly Gln Arg Ala Gly Thr Cys Val Leu
145 150 155 160

Glu Tyr Ala Thr Pro Leu Gln Thr Leu Phe Ala Met Ser Gln Tyr Ser
165 170 175

Gln Ala Gly Phe Ser Arg Glu Asp Arg Leu Glu Gln Ala Lys Leu Phe
180 185 190

Cys Gln Thr Leu Glu Asp Ile Leu Ala Asp Ala Pro Glu Ser Gln Asn
195 200 205

Asn Cys Arg Leu Ile Ala Tyr Gln Glu Pro Ala Asp Asp Ser Ser Phe
210 215 220

Ser Leu Ser Gln Glu Val Leu Arg His Leu Arg Gln Glu Glu Lys Glu
225 230 235 240

Glu Val Thr

<210> SEQ ID NO 24
<211> LENGTH: 243
<212> TYPE: PRT
<213> ORGANISM: Homo sapiens

<400> SEQUENCE: 24

Met Gly Ser Ser His His His His His His Ser Ser Gly Ser Gly Leu
1 5 10 15

Asn Asp Ile Phe Glu Ala Gln Lys Ile Glu Trp His Glu Gly Gly Ser
20 25 30

Glu Asn Leu Tyr Phe Gln Gly Leu Thr Pro Ala Glu Val Ser Ala Val
35 40 45

Cys Glu Glu Lys Lys Leu Asn Val Ala His Gly Leu Ala Trp Ser Tyr
50 55 60

Tyr Ile Gly Tyr Leu Arg Leu Ile Leu Pro Gly Leu Gln Ala Arg Ile
65 70 75 80

Arg Met Phe Asn Gln Leu His Asn Asn Met Leu Ser Gly Ala Gly Ser
85 90 95

Arg Arg Leu Tyr Ile Leu Phe Pro Leu Asp Cys Gly Val Pro Asp Asn
100 105 110

Leu Ser Val Val Asp Pro Asn Ile Arg Phe Arg Asp Met Leu Pro Gln
115 120 125

Gln Asn Ile Asp Arg Ala Gly Ile Lys Asn Arg Val Tyr Ser Asn Ser
130 135 140

Val Tyr Glu Ile Leu Glu Asn Gly Gln Pro Ala Gly Val Cys Ile Leu
145 150 155 160

Glu Tyr Ala Thr Pro Leu Gln Thr Leu Phe Ala Met Ser Gln Asp Ala
165 170 175

Lys Ala Gly Phe Ser Arg Glu Asp Arg Leu Glu Gln Ala Lys Leu Phe
180 185 190

Cys Arg Thr Leu Glu Glu Ile Leu Glu Asp Val Pro Glu Ser Arg Asn
195 200 205

Asn Cys Arg Leu Ile Val Tyr Gln Glu Pro Thr Asp Gly Asn Ser Phe
210 215 220

-continued

Ser Leu Ser Gln Glu Val Leu Arg His Ile Arg Gln Glu Glu Lys Glu
225 230 235 240

Glu Val Thr

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
cgtgctggca tcaaggatcg ggtttac 27

<210> SEQ ID NO 26
<211> LENGTH: 27
<212> TYPE: DNA
<213> ORGANISM: Artificial Sequence
<220> FEATURE:
<223> OTHER INFORMATION: primer

<400> SEQUENCE: 26
gtcaccggtc tgctggggca gtttatc 27

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
gctgaccgtg ctggcatcaa ggatcgggtt tac 33

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
ggtctgctgg ggcagtttat ccagg 25

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
caccacatcc actccaggta ccgg 24

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
cagctcctca gccaggctgc agac 24

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
cagacacttg aggacatcct ggcag 25

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
gcagaagagt ttggcctgct caa 23

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
acctgtattt tcagggcctg gccccagctg agatctctg 39

<210> SEQ ID NO 34
<211> LENGTH: 44
<212> TYPE: DNA
<213> ORGANISM: Artificial Sequence
<220> FEATURE:
<223> OTHER INFORMATION: primer

<400> SEQUENCE: 34
cagaattcgc aagcttttaa gtaacctctt ccttttcctc ctgc 44

<210> SEQ ID NO 35
<211> LENGTH: 15
<212> TYPE: PRT
<213> ORGANISM: Homo sapiens

<400> SEQUENCE: 35

Arg Ala Ser Lys Ser Val Ser Thr Ser Gly Tyr Ser Phe Met His
1 5 10 15

<210> SEQ ID NO 36
<211> LENGTH: 7
<212> TYPE: PRT
<213> ORGANISM: Homo sapiens

<400> SEQUENCE: 36

Leu Ala Ser Asn Leu Glu Ser
1 5

<210> SEQ ID NO 37
<211> LENGTH: 9
<212> TYPE: PRT
<213> ORGANISM: Homo sapiens

<400> SEQUENCE: 37

Gln His Ser Arg Glu Val Pro Trp Thr
1 5

<210> SEQ ID NO 38
<211> LENGTH: 10
<212> TYPE: PRT
<213> ORGANISM: Homo sapiens

<400> SEQUENCE: 38

Gly Tyr Thr Phe Thr Asn Tyr Gly Met Asn
1               5                   10

<210> SEQ ID NO 39
<211> LENGTH: 17
<212> TYPE: PRT
<213> ORGANISM: Homo sapiens

<400> SEQUENCE: 39

Trp Ile Asn Thr Tyr Thr Gly Glu Pro Thr Tyr Ala Asp Ala Phe Lys
1               5                   10                  15

Gly

<210> SEQ ID NO 40
<211> LENGTH: 9
<212> TYPE: PRT
<213> ORGANISM: Homo sapiens

<400> SEQUENCE: 40

Asp Tyr Gly Asp Tyr Gly Met Asp Tyr
1               5

<210> SEQ ID NO 41
<211> LENGTH: 11
<212> TYPE: PRT
<213> ORGANISM: Homo sapiens

<400> SEQUENCE: 41

Arg Ala Ser Gln Ser Val Ser Ser Tyr Leu Ala
1               5                   10

<210> SEQ ID NO 42
<211> LENGTH: 7
<212> TYPE: PRT
<213> ORGANISM: Homo sapiens

<400> SEQUENCE: 42

Asp Ala Ser Asn Arg Ala Thr
1               5

<210> SEQ ID NO 43
<211> LENGTH: 9
<212> TYPE: PRT
<213> ORGANISM: Homo sapiens

<400> SEQUENCE: 43

Gln Gln Arg Thr Asn Trp Pro Leu Thr
1               5

<210> SEQ ID NO 44
<211> LENGTH: 5
<212> TYPE: PRT
<213> ORGANISM: Homo sapiens

<400> SEQUENCE: 44

Ser Tyr Ile Met His
1               5

<210> SEQ ID NO 45
<211> LENGTH: 17
<212> TYPE: PRT
<213> ORGANISM: Homo sapiens

<400> SEQUENCE: 45

Val Ile Ser Tyr Asp Gly Arg Asn Lys Tyr Tyr Ala Asp Ser Val Lys
1 5 10 15

Gly

<210> SEQ ID NO 46
<211> LENGTH: 9
<212> TYPE: PRT
<213> ORGANISM: Homo sapiens

<400> SEQUENCE: 46

Asp Thr Asp Gly Tyr Asp Phe Asp Tyr
1 5

<210> SEQ ID NO 47
<211> LENGTH: 11
<212> TYPE: PRT
<213> ORGANISM: Homo sapiens

<400> SEQUENCE: 47

Lys Ala Ser Gln Asp Val Ser Thr Ala Val Ala
1 5 10

<210> SEQ ID NO 48
<211> LENGTH: 7
<212> TYPE: PRT
<213> ORGANISM: Homo sapiens

<400> SEQUENCE: 48

Ser Ala Ser Tyr Arg Tyr Thr
1 5

<210> SEQ ID NO 49
<211> LENGTH: 9
<212> TYPE: PRT
<213> ORGANISM: Homo sapiens

<400> SEQUENCE: 49

Gln Gln His Tyr Ile Thr Pro Leu Thr
1 5

<210> SEQ ID NO 50
<211> LENGTH: 5
<212> TYPE: PRT
<213> ORGANISM: Homo sapiens

<400> SEQUENCE: 50

Thr Ala Gly Met Gln
1 5

<210> SEQ ID NO 51
<211> LENGTH: 17
<212> TYPE: PRT
<213> ORGANISM: Homo sapiens

<400> SEQUENCE: 51

Trp Ile Asn Thr His Ser Gly Val Pro Lys Tyr Ala Glu Asp Phe Lys
1 5 10 15

Gly

<210> SEQ ID NO 52
<211> LENGTH: 12
<212> TYPE: PRT
<213> ORGANISM: Homo sapiens

<400> SEQUENCE: 52

Ser Gly Phe Gly Ser Ser Tyr Trp Tyr Phe Asp Val
1               5                   10

<210> SEQ ID NO 53
<211> LENGTH: 11
<212> TYPE: PRT
<213> ORGANISM: Homo sapiens

<400> SEQUENCE: 53

Lys Ala Ser Gln Asp Val Ser Thr Ala Val Ala
1               5                   10

<210> SEQ ID NO 54
<211> LENGTH: 7
<212> TYPE: PRT
<213> ORGANISM: Homo sapiens

<400> SEQUENCE: 54

Ser Ala Ser Tyr Arg Tyr Thr
1               5

<210> SEQ ID NO 55
<211> LENGTH: 9
<212> TYPE: PRT
<213> ORGANISM: Homo sapiens

<400> SEQUENCE: 55

Gln Gln His Tyr Ile Thr Pro Leu Thr
1               5

<210> SEQ ID NO 56
<211> LENGTH: 5
<212> TYPE: PRT
<213> ORGANISM: Homo sapiens

<400> SEQUENCE: 56

Thr Ala Gly Met Gln
1               5

<210> SEQ ID NO 57
<211> LENGTH: 17
<212> TYPE: PRT
<213> ORGANISM: Homo sapiens

<400> SEQUENCE: 57

Trp Ile Asn Thr His Ser Gly Val Pro Lys Tyr Ala Glu Asp Phe Lys
1               5                   10                  15

Gly

<210> SEQ ID NO 58
<211> LENGTH: 12
<212> TYPE: PRT
<213> ORGANISM: Homo sapiens

<400> SEQUENCE: 58

Ser Gly Phe Gly Ser Ser Tyr Trp Tyr Phe Asp Val
1 5 10

<210> SEQ ID NO 59
<211> LENGTH: 11
<212> TYPE: PRT
<213> ORGANISM: Homo sapiens

<400> SEQUENCE: 59

Gln Ala Ser Gln Asp Ile Ser Asn Tyr Leu Asn
1 5 10

<210> SEQ ID NO 60
<211> LENGTH: 7
<212> TYPE: PRT
<213> ORGANISM: Homo sapiens

<400> SEQUENCE: 60

Asp Ala Ser Asn Leu Glu Thr
1 5

<210> SEQ ID NO 61
<211> LENGTH: 9
<212> TYPE: PRT
<213> ORGANISM: Homo sapiens

<400> SEQUENCE: 61

Gln His Phe Asp His Leu Pro Leu Ala
1 5

<210> SEQ ID NO 62
<211> LENGTH: 7
<212> TYPE: PRT
<213> ORGANISM: Homo sapiens

<400> SEQUENCE: 62

Ser Gly Asp Tyr Tyr Trp Thr
1 5

<210> SEQ ID NO 63
<211> LENGTH: 17
<212> TYPE: PRT
<213> ORGANISM: Homo sapiens

<400> SEQUENCE: 63

Gly His Ile Tyr Tyr Ser Gly Asn Thr Asn Tyr Asn Pro Ser Leu Lys
1 5 10 15

Ser

<210> SEQ ID NO 64
<211> LENGTH: 9
<212> TYPE: PRT
<213> ORGANISM: Homo sapiens

<400> SEQUENCE: 64

Asp Arg Val Thr Gly Ala Phe Asp Ile
1 5

<210> SEQ ID NO 65
<211> LENGTH: 11
<212> TYPE: PRT
<213> ORGANISM: Homo sapiens

<400> SEQUENCE: 65

-continued

```
His Ser Ser Gln Asp Ile Asn Ser Asn Ile Gly
1               5                   10


<210> SEQ ID NO 66
<211> LENGTH: 7
<212> TYPE: PRT
<213> ORGANISM: Homo sapiens

<400> SEQUENCE: 66

His Gly Thr Asn Leu Asp Asp
1               5


<210> SEQ ID NO 67
<211> LENGTH: 9
<212> TYPE: PRT
<213> ORGANISM: Homo sapiens

<400> SEQUENCE: 67

Val Gln Tyr Ala Gln Phe Pro Trp Thr
1               5


<210> SEQ ID NO 68
<211> LENGTH: 11
<212> TYPE: PRT
<213> ORGANISM: Homo sapiens

<400> SEQUENCE: 68

Gly Tyr Ser Ile Thr Ser Asp Phe Ala Trp Asn
1               5                   10


<210> SEQ ID NO 69
<211> LENGTH: 16
<212> TYPE: PRT
<213> ORGANISM: Homo sapiens

<400> SEQUENCE: 69

Gly Tyr Ile Ser Tyr Ser Gly Asn Thr Arg Tyr Asn Pro Ser Leu Lys
1               5                   10                  15


<210> SEQ ID NO 70
<211> LENGTH: 9
<212> TYPE: PRT
<213> ORGANISM: Homo sapiens

<400> SEQUENCE: 70

Val Thr Ala Gly Arg Gly Phe Pro Tyr
1               5
```

ANTI-EGFR ANTIBODY-DRUG CONJUGATE WITH A CYCLIC DINUCLEOTIDE DERIVATIVE

CROSS-REFERENCE TO RELATED APPLICATIONS

The present application claims priority under 35 U.S.C. § 371 to International Patent Application No. PCT/JP2021/008635, filed Mar. 5, 2021, which claims priority to and the benefit of Japanese Patent Application No. 2020-038983, filed on Mar. 6, 2020. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122763-0110_SL.txt and is 69 kb in size.

TECHNICAL FIELD

The present invention relates to an antibody-drug conjugate in which a cyclic dinucleotide derivative with a novel structure having STING agonist activity is conjugated with an antibody against a target cell via a linker, a pharmaceutical composition comprising the antibody-drug conjugate, and so on.

BACKGROUND ART

STING (Stimulator of Interferon Genes) is a transmembrane adaptor protein localized in endoplasmic reticulum (Non-Patent Literature 1). STING functions as a central molecule for the activation of innate immunity in mammals, and is at the forefront of defense against the entry of pathogens such as bacteria and viruses. The activation of STING is known to be triggered by a signal(s) from multiple cytoplasmic DNA sensors at the time of detecting exogenous or endogenous DNA. Among the cytoplasmic DNA sensors, cGAS (Cyclic GMP-AMP Synthase) is considered to be an important DNA sensor. When cGAS senses DNA, a cyclic dinucleotide (2',3'-cGAMP) is produced, and this 2',3'-cGAMP binds directly to STING and activates STING (Non-Patent Literature 2). Activated STING translocates to the Golgi apparatus, where autophosphorylation of TBK1 (Tank-binding kinase 1) is promoted. Autophosphorylated and activated TBK1 activates both the IRF3 (Interferon regulatory factor 3) transcriptional pathway (Non-Patent Literature 3) and the NFκB transcriptional pathway (Non-Patent Literature 4), and increases the production of inflammatory proteins called interferons and cytokines (type I IFN (Interferon), IL-6 (Interleukin-6), TNF-α (Tumor Necrosis Factor-α)). These proteins trigger the adaptive immune system including T cells, which destroy pathogens and cancer cells through a complex cascade.

Recent studies have shown that STING promotes not only host defense against microbes but also anti-tumor immunity. For example, when immunogenic tumor cells are transplanted into STING-deficient mice, the tumor grows more rapidly than in wild-type mice or in TRIF (Toll/Interleukin-1 (IL-1) receptor domain containing adaptor-inducing interferon-β)-deficient mice. In addition, unlike TLR (Toll-like receptor), MyD88 (Myeloid differentiation primary response 88), or MAVS (Mitochondrial antiviral-signaling protein)-deficient mice, spontaneous priming of $CD8^+$ T cells to tumors was also lost in the STING-deficient mice. These results suggest that the STING pathway, which is initiated by detecting cytoplasmic DNA, is involved in the regulation of tumor growth (Non-Patent Literature 5). Other studies have also shown that STING is necessary for the anti-tumor effects of radiation therapy (Non-Patent Literature 6) and for anti-CD47 antibody therapy (Non-Patent Literature 7). DNA derived from dead tumor cells after treatment with radiation or anti-CD47 antibody translocates to the cytoplasm of dendritic cells, activates the cGAS-STING pathway, and induces IFN production to activate adaptive immunity through the innate immunity. These studies suggest that dendritic cell-mediated cross-priming activated by the STING pathway is critical for triggering adaptive immunity against tumors. DMXAA, a flavonoid-based small molecule compound known as a vascular disrupting agent, induces type I IFN in macrophages and has been shown to have potent anti-tumor activity in a mouse tumor model (Non-Patent Literature 8). DMXAA was expected to be an immunotherapeutic drug for non-small cell lung carcinoma due to its excellent anti-tumor effect in preclinical studies, but failed in clinical trials (Non-Patent Literature 9). Recent studies have revealed that DMXAA is a mouse STING-specific agonist and cannot bind to human STING due to lack of cross-species reactivity (Non-Patent Literature 10). Although DMXAA was ineffective in humans, studies in the mouse model suggest that small molecule drugs can effectively prime CD8+ T cells and enhance anti-tumor immunity via STING.

Another small molecule compound, cyclic dinucleotide (CDN), has been shown to enhance a STING-mediated anti-tumor immune response, markedly inhibit tumor growth, and improve the survival rate in tumor-bearing mice (Non-Patent Literature 11). CDNs are grouped into bacterial CDN with two canonical 3'-5' phosphate bonds (cyclic-di-GMP, cyclic-di-AMP, 3',3'-cGAMP), and a mixed-linkage CDN with two non-canonical 2'-5' phosphate bonds and produced by mammalian cGAS (2',3'-cGAMP). Recent studies have demonstrated that mixed-linkage CDNs are more capable of universally activating a variety of STINGs than canonical CDNs (Non-Patent Literature 12).

Naturally occurring CDNs, like most nucleic acid molecules, are rapidly degraded by nucleases in blood, and cannot thus be administered as they are. In view of this, synthetic small molecule compounds with in vivo STING agonist activity have been developed (e.g., Patent Literatures 1 to 26).

The STING agonist MIW-815 (also called ADU-S100, ML RR-S2 CDA, or ML-RR-CDA-$2Na^+$), which is currently undergoing a clinical trial as an anti-tumor agent, is administered directly into a tumor. In the method for directly administering a STING agonist to a tumor, the drug can only be delivered to a limited area in the tumor. In addition, it is difficult to directly administer the drug to all distant metastatic tumors. Unfortunately, this limits the type of tumors that can be treated. Non-Patent Literature 13 describes the anti-tumor effect upon administration of ML RR-S2 CDA, but only by intratumor administration, not by systemic administration (e.g., intravenous administration). Non-Patent Literature 14 discloses that intravenous administration of SB 11285, a STING agonist, to a mouse tumor model elicited anti-tumor effects. However, what kind of specific structure the compound SB11285 has is not indicated. Patent Literature 14 describes a conjugate containing an immunostimulant, an antibody construct, and a linker. However, no specific examples of the conjugate using a STING agonist as the immunostimulant have been disclosed. Patent Literature 26 describes a conjugate in which a CDN with a specific structure is conjugated via a linker to an antibody. However, there are no examples of in vivo administration of the conjugate. Besides, no anti-tumor effects of the conjugate have been demonstrated.

CITATION LIST

Patent Literature

Patent Literature 1: International Publication No. WO 2014/099824
Patent Literature 2: International Publication No. WO 2014/179335
Patent Literature 3: International Publication No. WO 2014/189805
Patent Literature 4: International Publication No. WO 2014/189806
Patent Literature 5: International Publication No. WO 2015/074145
Patent Literature 6: International Publication No. WO 2015/185565
Patent Literature 7: International Publication No. WO 2016/096714
Patent Literature 8: International Publication No. WO 2016/012305
Patent Literature 9: International Publication No. WO 2016/145102
Patent Literature 10: International Publication No. WO 2017/027646
Patent Literature 11: International Publication No. WO 2017/027645
Patent Literature 12: International Publication No. WO 2017/075477
Patent Literature 13: International Publication No. WO 2017/093933
Patent Literature 14: International Publication No. WO 2017/100305
Patent Literature 15: International Publication No. WO 2017/123669
Patent Literature 16: International Publication No. WO 2017/161349
Patent Literature 17: International Publication No. WO 2017/175147
Patent Literature 18: International Publication No. WO 2017/175156
Patent Literature 19: International Publication No. WO 2018/009466
Patent Literature 20: International Publication No. WO 2018/045204
Patent Literature 21: International Publication No. WO 2018/060323
Patent Literature 22: International Publication No. WO 2018/067423
Patent Literature 23: International Publication No. WO 2018/065360
Patent Literature 24: International Publication No. WO 2014/093936
Patent Literature 25: International Publication No. WO 2018/009648
Patent Literature 26: International Publication No. WO 2018/100558

Non Patent Literature

Non-Patent Literature 1: Nature 2008, 455, 674-678
Non-Patent Literature 2: Mol. Cell, 2013, 51, 226-235
Non-Patent Literature 3: Science 2015a, 347, aaa2630
Non-Patent Literature 4: J. Virol. 2014, 88, 5328-5341
Non-Patent Literature 5: Immunity 2014, 41, 830-842
Non-Patent Literature 6: Immunity 2014, 41, 843-852
Non-Patent Literature 7: Nat. Med. 2015, 21, 1209-1215
Non-Patent Literature 8: J. Immunol. 1994, 153, 4684-4693
Non-Patent Literature 9: J. Clin. Oncol. 2011, 29, 2965-2971
Non-Patent Literature 10: J. Immunol. 2013, 190, 5216-5225
Non-Patent Literature 11: Sci. Rep. 2016, 6, 19049
Non-Patent Literature 12: Mol. Cell, 2015, 59, 891-903
Non-Patent Literature 13: Cell Rep. 2015, 11, 1018-1030
Non-Patent Literature 14: AACR Tumor Immunology and Immunotherapy, 2017, Poster #A25

SUMMARY OF INVENTION

Problem to be Resolved by the Invention

The following should be developed, including an antibody-drug conjugate that can be systemically administered and can specifically deliver a STING agonist to a target cell(s) or organ(s) (e.g., a tumor site), and a therapeutic agent and/or method for treating a STING agonist-related disease (e.g., a disease (e.g., cancer) that can be treated by immunostimulants) by using the antibody-drug conjugate.

Means of Solving the Problem

The present inventors have addressed the above problem, and have discovered an antibody-drug conjugate obtained by conjugating a novel CDN derivative, which is characterized by the presence of a fused tricyclic substituent, and a specific antibody via a linker. It has been also found that systemic administration of the antibody-drug conjugate elicits anti-tumor effects in an antigen-expressing tumor. Then, the present invention has been completed.

Specifically, the invention of the present application relates to the following, but is not limited to them.

[1] An antibody-drug conjugate represented by the following formula (II):

[Formula 1]

$$Ab\text{—}[L\text{—}D]_{m^1} \qquad (II)$$

wherein $m^1$ ranges from 1 to 10;

Ab represents an antibody or a functional fragment of the antibody, wherein the antibody optionally has a remodeled glycan, wherein the antibody is any antibody selected from the group consisting of an anti-CD70 antibody, an anti-TROP2 antibody, and an anti-EGFR antibody;

L represents a linker linking Ab and D, wherein

Ab may directly bond to L from an amino acid residue of Ab or may bond to L through the glycan or remodeled glycan of Ab;

D represents a compound represented by the following formula (I):

[Formula 2]

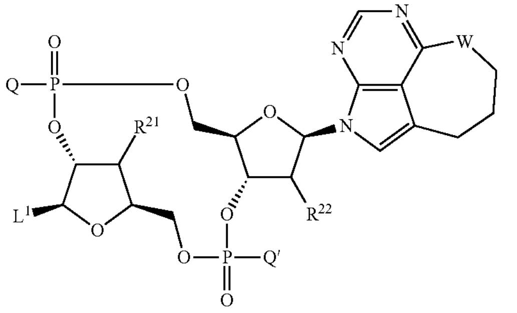

(I)

wherein

L bonds to any —$NH_2$ or a hydroxy group included in $L^1$, $L^1$ represents any one group of the following three formulas:

[Formula 3]

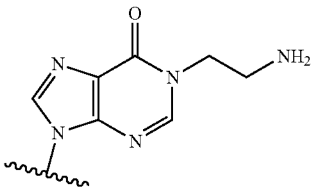

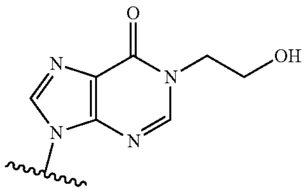 and

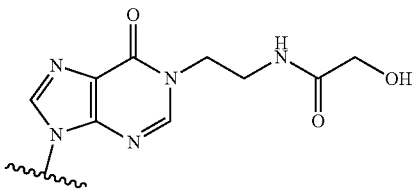

wherein the wavy line represents a position of substitution,

Q and Q', each independently, represent a hydroxy group or a thiol group, $R^{21}$ and $R^{22}$, each independently, represent a hydroxy group or a fluorine atom, and W represents —NH— or a sulfur atom.

[2] The antibody-drug conjugate according to [1], wherein D is represented by any one of the following two formulas:

[Formula 4]

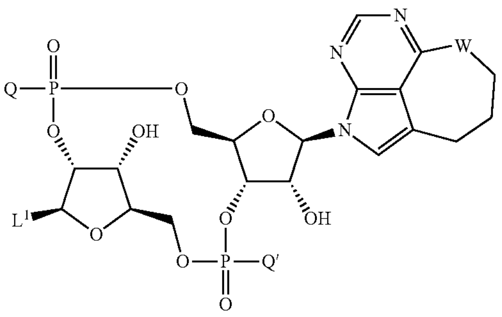 or

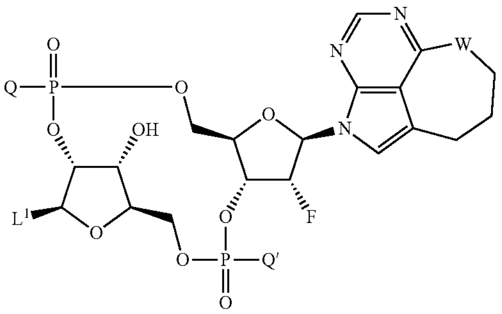

wherein $L^1$, Q, Q', and W are as defined above.

[3] The antibody-drug conjugate according to [1] or [2], wherein D is represented by any one of the following four formulas:

[Formula 5]

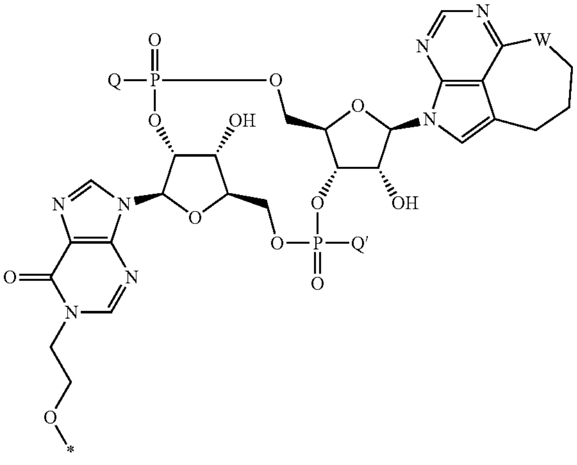

-continued
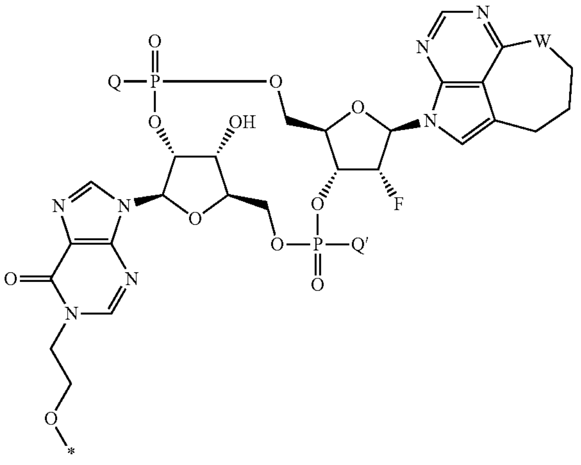
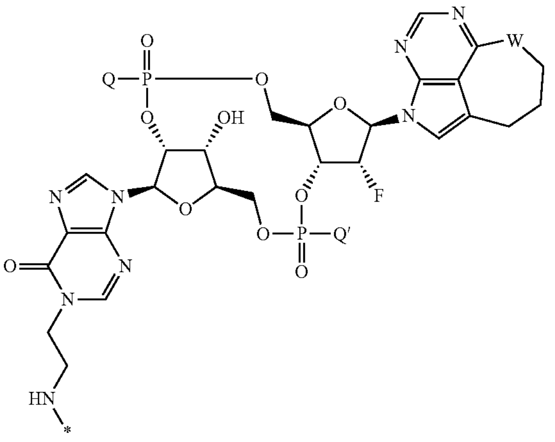
or
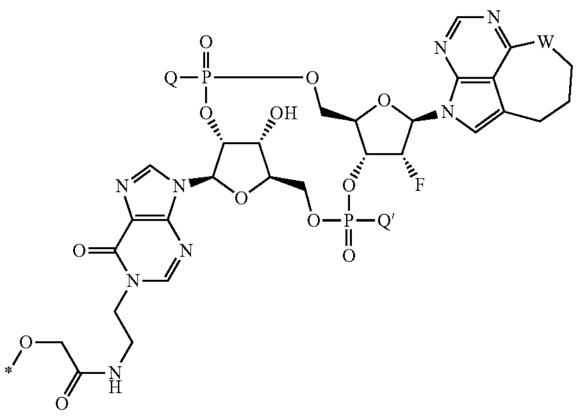
wherein the asterisk represents bonding to L, and Q, Q', and W are as defined above.
[4] The antibody-drug conjugate according to any one of [1] to [3], wherein D is represented by any one of the following three formulas:
[Formula 6]
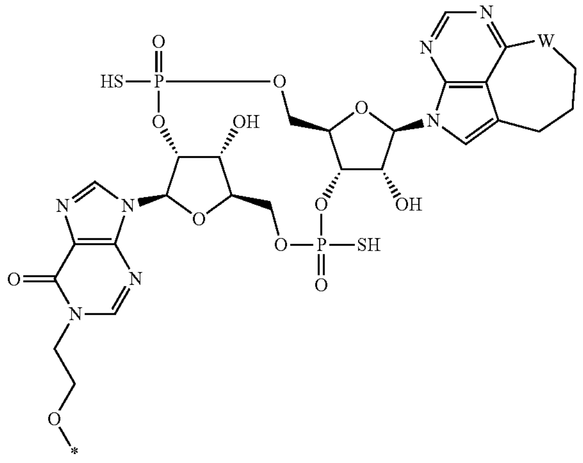
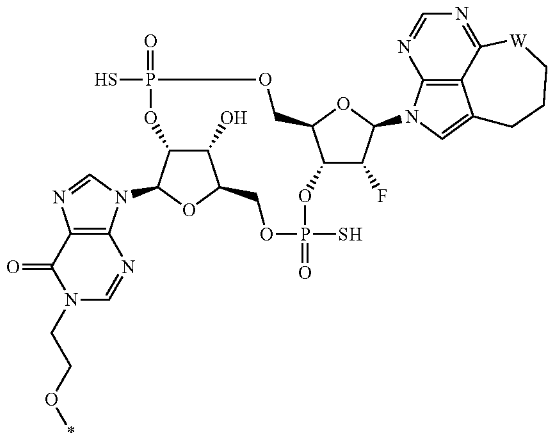
or
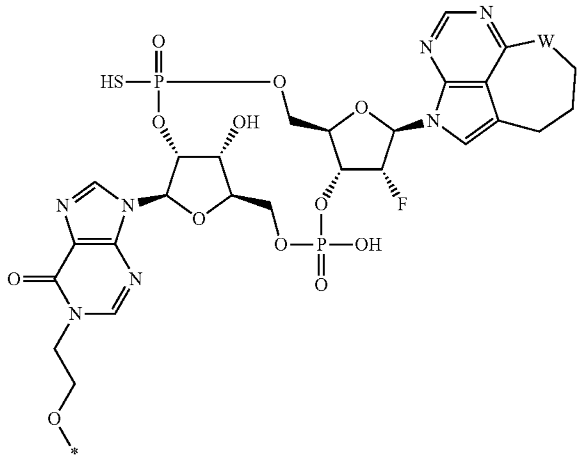
wherein the asterisk represents bonding to L, and W is as defined above.

[5] The antibody-drug conjugate according to any one of [1] to [4], wherein D is represented by any one of the following three formulas:
[Formula 7]
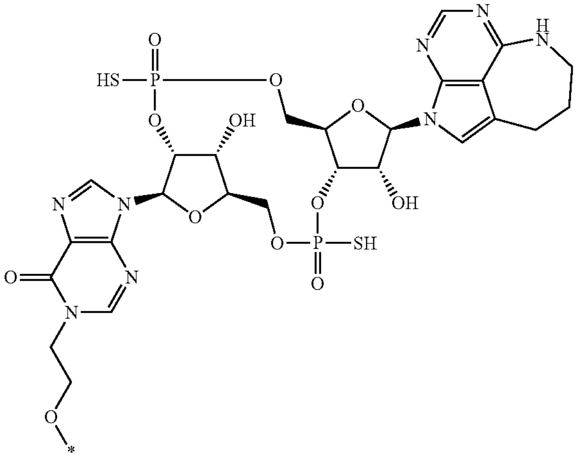
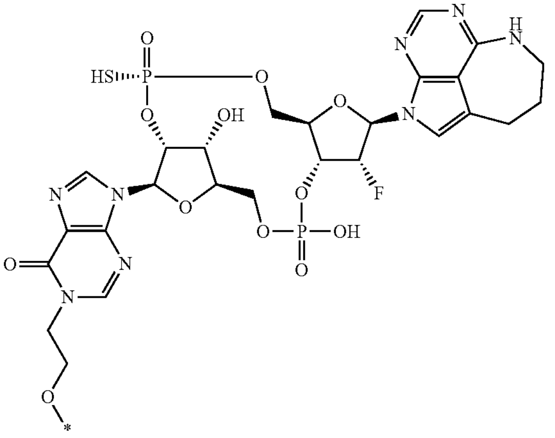
or
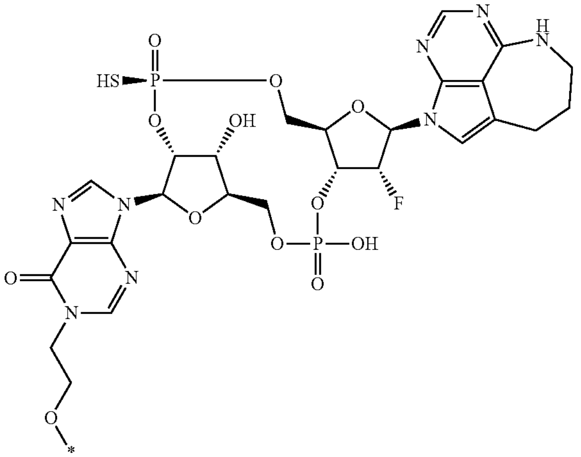
wherein the asterisk represents bonding to L.
[6] The antibody-drug conjugate according to any one of [1] to [4], wherein D is represented by any one of the following four formulas:
[Formula 8]
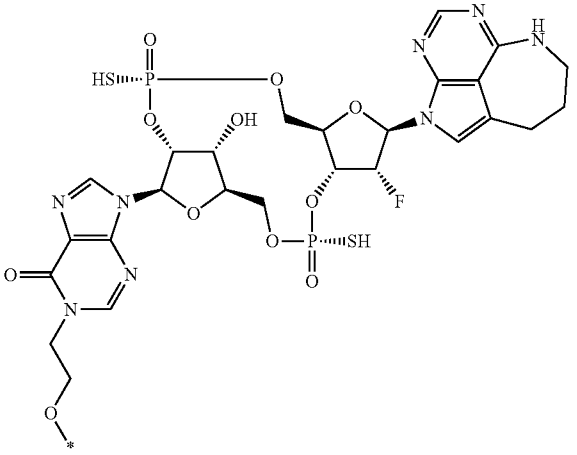
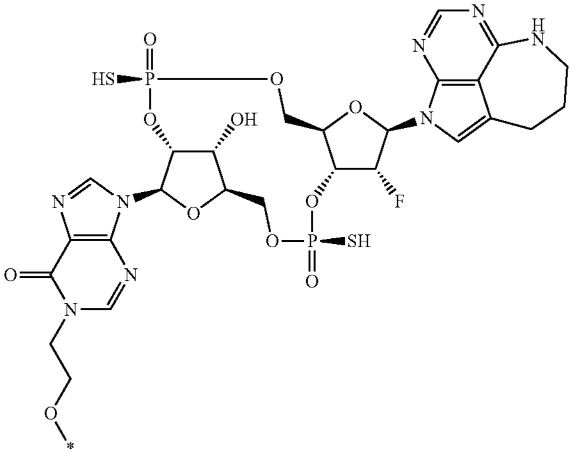 [SMILES: *OCCn1cnc2c(ncn2[C@@H]2O[C@@H]3CO[P@@](=O)(S)O[C@H]4[C@@H](F)[C@H](n5cc6c7c(ncnc75)NCCC6)O[C@@H]4CO[P@](=O)(S)O[C@@H]2[C@@H]3O)c1=O]
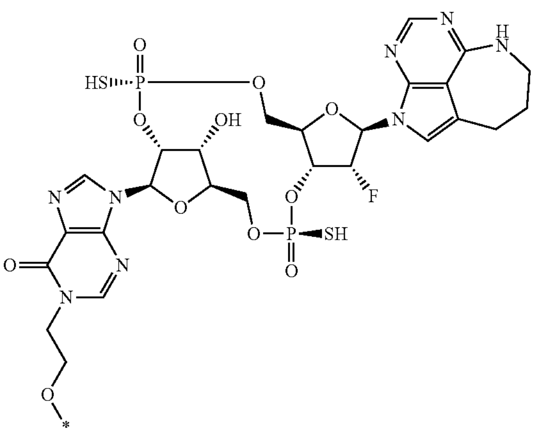
or -continued

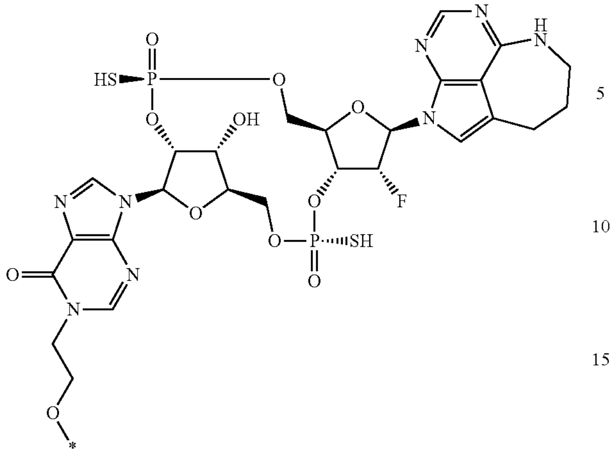

wherein the asterisk represents bonding to L.

[7] The antibody-drug conjugate according to any one of [1] to [4] and [6], wherein D is represented by the following formula:

[Formula 9]

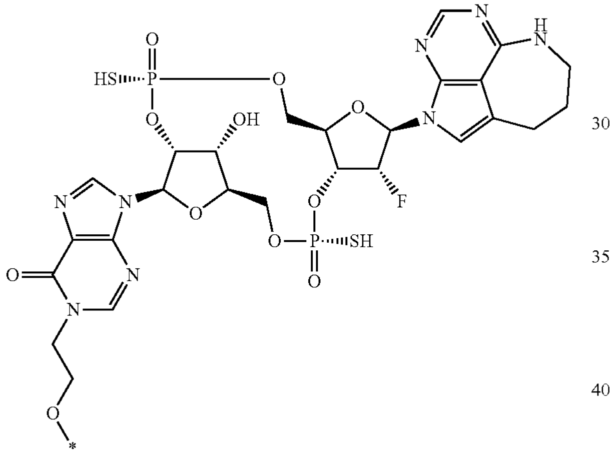

wherein the asterisk represents bonding to L.

[8] The antibody-drug conjugate according to any one of [1] to [3], wherein D is represented by any one of the following two formulas:

[Formula 10]

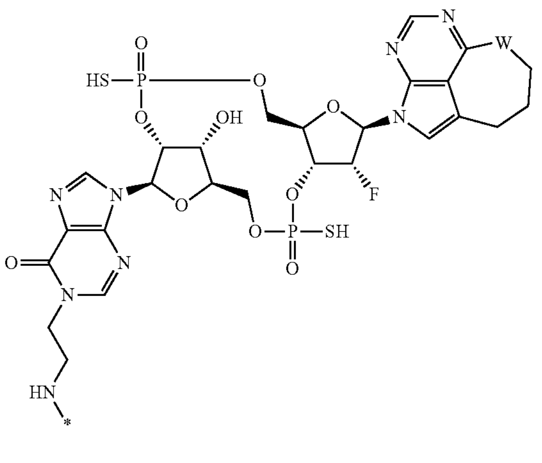

or

-continued

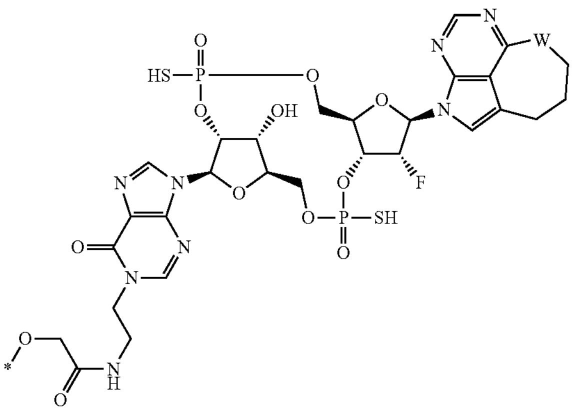

wherein the asterisk represents bonding to L, and W is as defined above.

[9] The antibody-drug conjugate according to any one of [1] to [3] and [8], wherein D is represented by any one of the following four formulas:

[Formula 11]

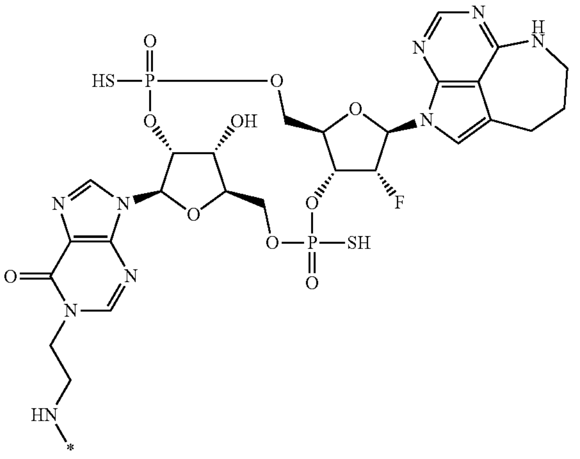

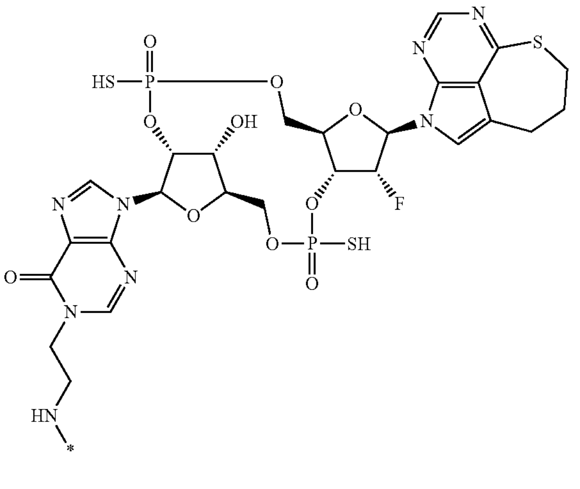

-continued

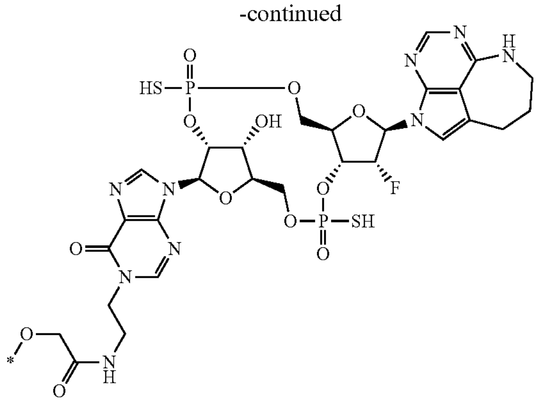

or

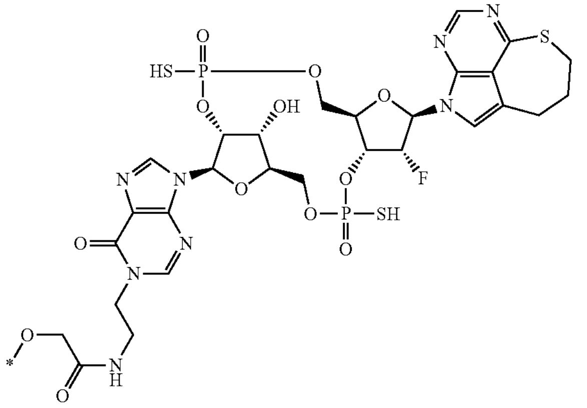

wherein the asterisk represents bonding to L.

[10] The antibody-drug conjugate according to any one of [1] to [9], wherein the linker L is represented by -Lb-La-Lp-Lc-* wherein the asterisk represents bonding to the drug D;

Lp represents a linker consisting of an amino acid sequence cleavable in a target cell or is absent;

La represents any one selected from the group consisting of the following.

—C(═O)—$(CH_2CH_2)n^2$—C(═O)—,
—C(═O)—$(CH_2CH_2)n^2$—$CH_2$—C(═O)—,
—C(═O)—$(CH_2CH_2)n^2$—C(═O)—NH—$(CH_2CH_2)n^3$—C(═O)—,
—C(═O)—$(CH_2CH_2)n^2$—C(═O)—NH—$(CH_2CH_2)n^3$—$CH_2$—C(═O)—,
—C(═O)—$(CH_2CH_2)n^2$—C(═O)—NH—$(CH_2CH_2O)n^3$—$CH_2$—C(═O)—,
$(CH_2)n^4$—O—C(═O)—, and
$(CH_2)n^9$—C(═O)—, where $n^2$ represents an integer of 1 to 3, $n^3$ represents an integer of 1 to 5, $n^4$ represents an integer of 0 to 2, and $n^9$ represents an integer of 2 to 7;

Lb represents a spacer for bonding La to the glycan or remodeled glycan of Ab or a spacer for bonding La to a cysteine residue of Ab; and Lc represents —NH—$CH_2$—, —NH-phenyl-$CH_2$—O(C═O)—, or —NH-heteroaryl-$CH_2$—O(C═O)—, or is absent.

[11] The antibody-drug conjugate according to [10], wherein Lc is —NH—$CH_2$—.

[12] The antibody-drug conjugate according to [10] or [11], wherein Lp is any one of -GGFG-, -GGPI-, -GGVA-, -GGFM-, -GGVCit-, -GGFCit-, -GGICit-, -GGPL-, -GGAQ-, or -GGPP-.

[13] The antibody-drug conjugate according to [12], wherein Lp is -GGFG- or -GGPI-.

[14] The antibody-drug conjugate according to any one of [10] to [13], wherein La represents any one selected from the group consisting of the following:

—C(═O)—$CH_2CH_2$—C(═O)—,
—C(═O)—$CH_2CH_2$—C(═O)—NH—$(CH_2CH_2O)_3$—$CH_2$—C(═O)—,
—C(═O)—$CH_2CH_2$—C(═O)—NH—$(CH_2CH_2O)_4$—$CH_2$—C(═O)—, and
—$(CH_2)_5$—C(═O)—.

[15] The antibody-drug conjugate according to any one of [10] to [14], wherein Lb is represented by any one of the following formula:

[Formula 12]

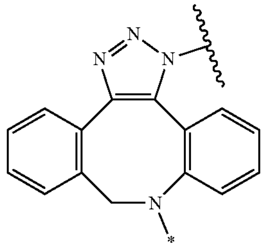

or

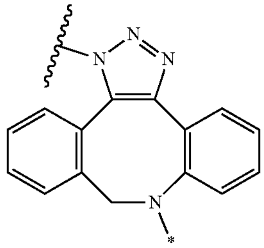

or

[Formula 13]

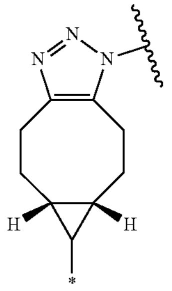

or

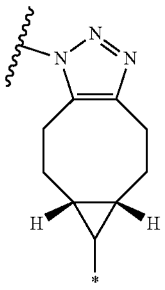

wherein, in the structural formula of Lb shown above, the asterisk represents bonding to La, and the wavy line represents bonding to the glycan or remodeled glycan of Ab.

[16] The antibody-drug conjugate according to any one of [10] to [14], wherein Lb represents -(succinimid-3-yl-N)-, wherein -(succinimid-3-yl-N)- is represented by the following structural formula:

[Formula 14]

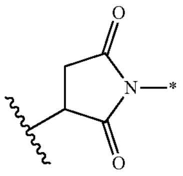

wherein the asterisk represents bonding to La, and the wavy line represents bonding to a side chain of a cysteine residue of the antibody by forming a thioether.

[17] The antibody-drug conjugate according to any one of [10] to [15], wherein the linker L is represented by -Lb-La-Lp-Lc-* wherein the asterisk represents bonding to the drug D;

Lp is -GGFG- or -GGPI-;

La represents —C(=O)—$CH_2CH_2$—C(=O)—;

Lb represents the following formula:

[Formula 15]

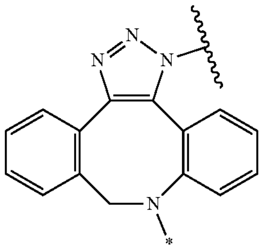

or

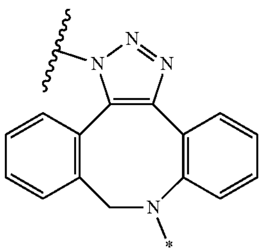

Wherein, in the structural formula of Lb shown above, the asterisk represents bonding to La, and the wavy line represents bonding to the glycan or remodeled glycan of Ab; and Lc represents —NH—$CH_2$-.

[18] The antibody-drug conjugate according to any one of [1] to [17], wherein the average number of the conjugated drug molecules per antibody molecule in the antibody-drug conjugate ranges from 1 to 10.

[19] The antibody-drug conjugate according to [18], wherein the average number of the conjugated drug molecules per antibody molecule in the antibody-drug conjugate ranges from 1 to 5.

[20] The antibody-drug conjugate according to [19], wherein the average number of the conjugated drug molecules per antibody molecule in the antibody-drug conjugate ranges from 3 to 5.

[21] The antibody-drug conjugate according to any one of [1] to [20], wherein the antibody bonds via a glycan bonding to Asn297 of the antibody (N297glycan) to L.

[22] The antibody-drug conjugate according to [21], wherein the N297 glycan is a remodeled glycan.

[23] The antibody-drug conjugate according to [21] or [22], wherein the N297 glycan is N297-(Fuc)MSG1 or N297-(Fuc)SG having a structure represented by the following formula:

[Formula 16]

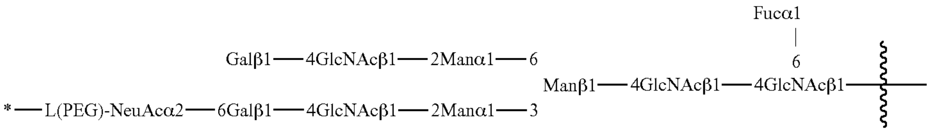

[N297-(Fuc)MSG1]

wherein the wavy line represents bonding to Asn297 of the antibody,

L(PEG) represents —($CH_2$—$CH_2O$)$n^5$—$CH_2$—$CH_2$—NH—, wherein the amino group at the right end of the L(PEG) is bound via an amide bond to a carboxyl group at the 2- position on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ is an integer of 2 to 5;

[Formula 17]

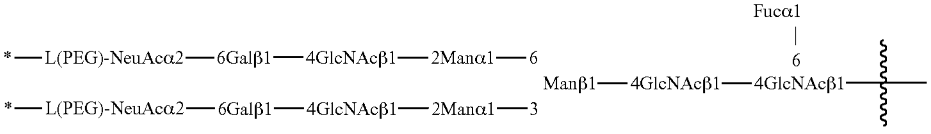

[N297-(Fuc)SG]

wherein the wavy line represents bonding to Asn297 of the antibody,

L(PEG) represents $—(CH_2—CH_2O)n^5—CH_2—CH_2—NH—$, wherein the amino group at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, and $n^5$ is an integer of 2 to 5.

[24] The antibody-drug conjugate according to any one of [21] to [23], wherein the antibody-drug conjugate is represented by the following formula:

[Formula 18]

$$Ab\left[(N297\ glycan)\left[L—D\right]_{m2}\right]_2$$

wherein $m^2$ represents an integer of 1 or 2,

L is a linker linking N297 glycan of Ab and D, as defined previously,

Ab represents an anti-CD70 antibody, an anti-TROP2 antibody, or an anti-EGFR antibody, or a functional fragment thereof, N297 glycan of Ab is represented by N297-(Fuc)MSG1 or N297-(Fuc)SG having a structure represented by the following formula:

[Formula 19]

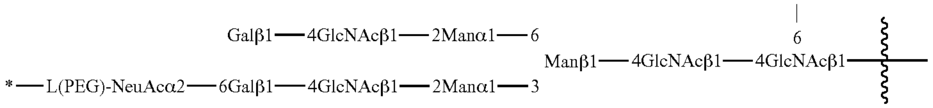

[N297-(Fuc)MSG1]

wherein the wavy line represents bonding to Asn297 of the antibody,

L(PEG) represents $—(CH_2—CH_2O)n^5—CH_2—CH_2—NH—$, wherein the amino group at the right end of the L(PEG) is bound via an amide bond to a carboxyl group at the 2-posiion on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ represents an integer of 2 to 5;

[Formula 20]

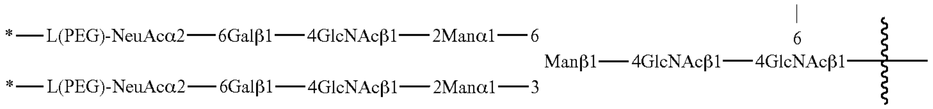

[N297-(Fuc)SG]

wherein the wavy line represents bonding to Asn297 of the antibody,

L(PEG) represents $—(CH_2—CH_2—O)n^5—CH_2—CH_2—NH—$, wherein the amino group at the right end of the L(PEG) is bound via an amide bond to a carboxyl group at the 2-posiion on a sialic acid at the non-reducing terminal on each of 1-3 and 1-6 branched chains of 1-Man in the N297 glycan, the asterisk represents bonding to a nitrogen atom at 1- or 3-position on 1,2,3-triazole ring of Lb in the linker L, and $n^5$ represents an integer of 2 to 5, D is represented by any one of the following four formulas:

[Formula 21]
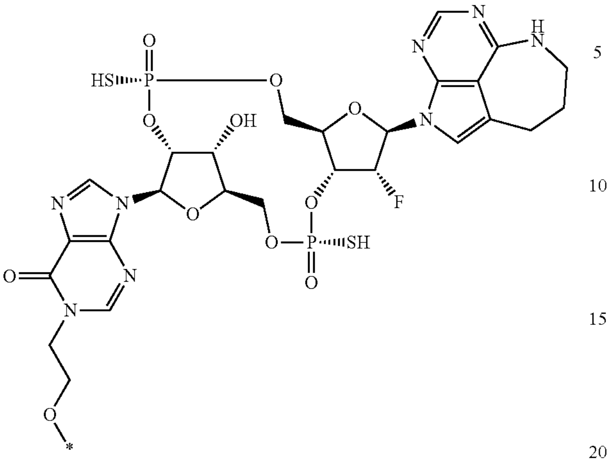
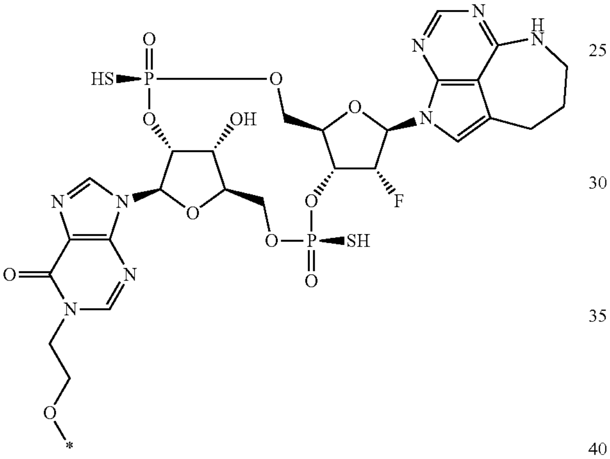
-continued
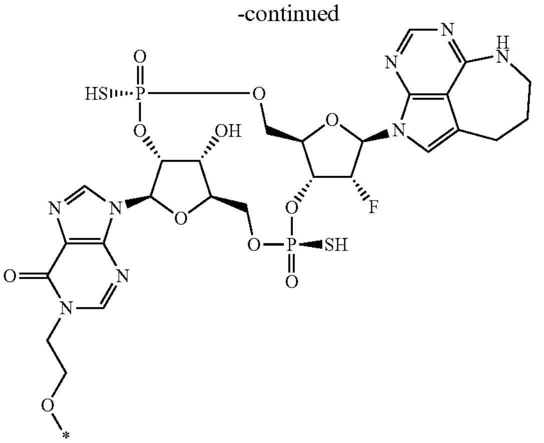
or
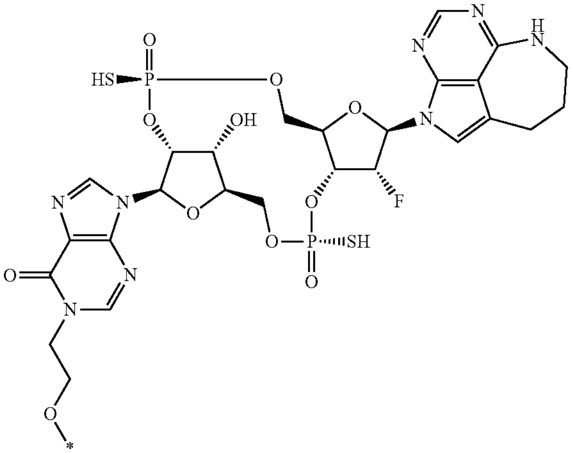 [SMILES: *OCCn1cnc2c(ncn2[C@@H]2O[C@@H]3CO[P@@](=O)(S)O[C@H]4[C@@H](F)[C@H](n5cc6c7c(ncnc75)NCCC6)O[C@@H]4CO[P@](=O)(S)O[C@@H]2[C@@H]3O)c1=O]
wherein the asterisk represents bonding to L.
[25] The antibody-drug conjugate according to [24], wherein the antibody-drug conjugate is represented by the following formulas selected from
[Formula 22]
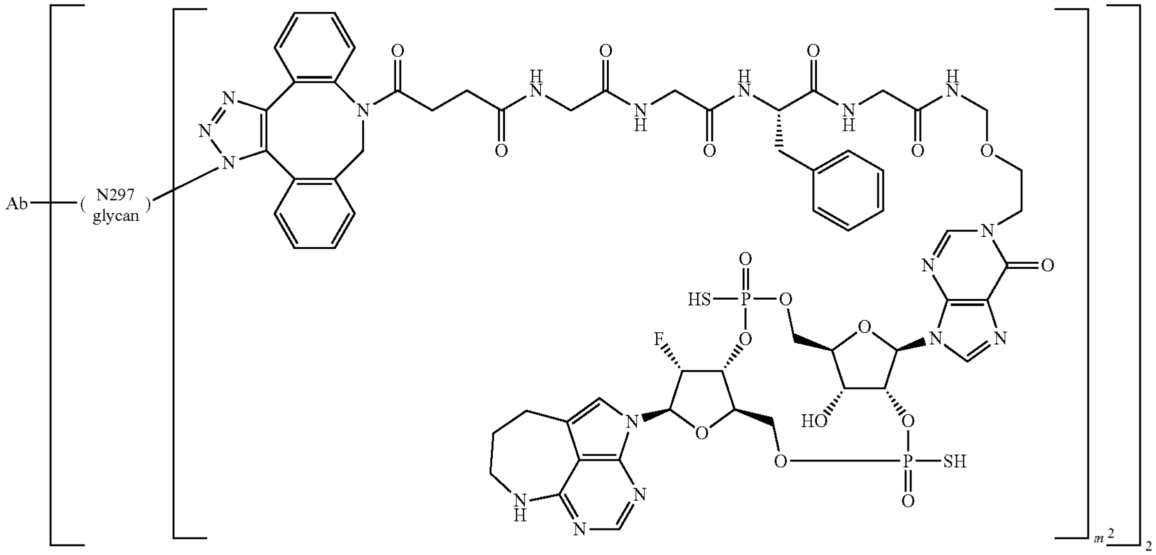
or -continued

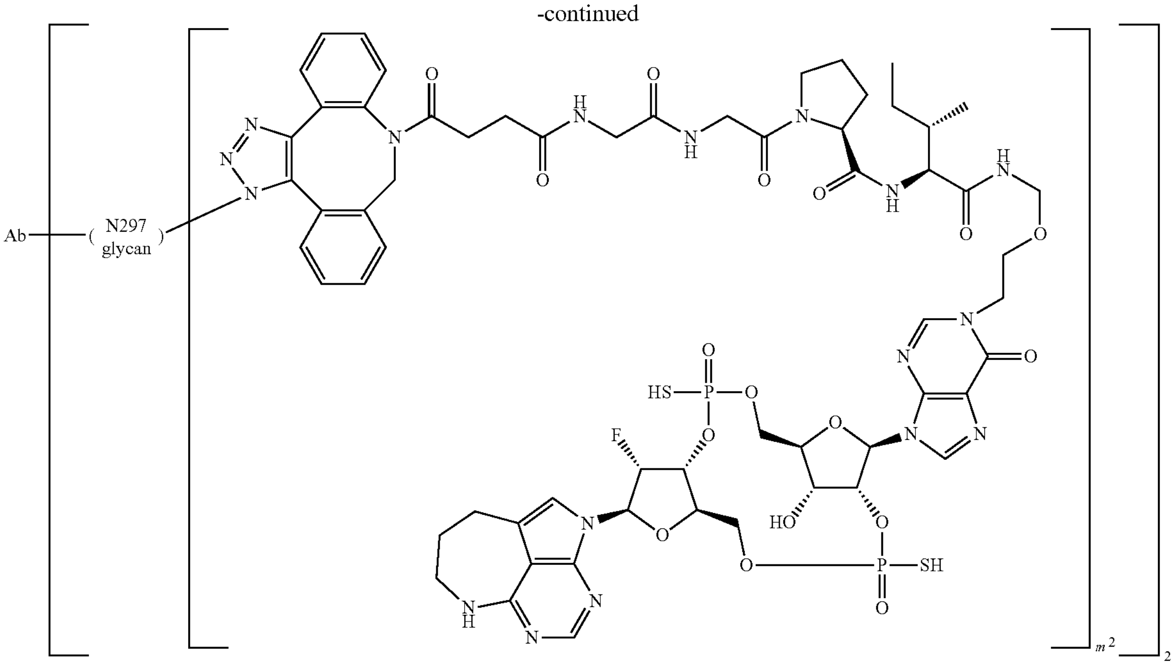

wherein, in each the structural formula shown above, $m^2$ is an integer of 1 or 2, Ab represents an anti-CD70 antibody, an anti-TROP2 antibody, or an anti-EGFR antibody, or a functional fragment thereof, N297 glycan of Ab is represented by any one of N297-(Fuc)MSG1 or N297-(Fuc)SG having a structure represented by the following formula:

[Formula 23]

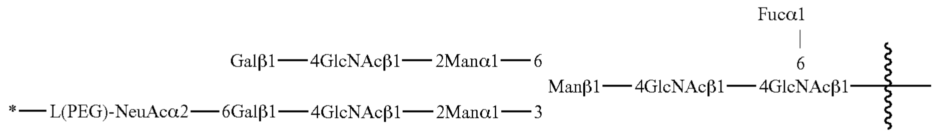

[N297-(Fuc)MSG1]

wherein the wavy line represents bonding to Asn297 of the antibody,

L(PEG) represents —$(CH_2—CH_2O)n^5$—$CH_2$—$CH_2$—NH—, wherein the amino group at the right end of the L(PEG) is bound via an amide bond to a carboxyl group at the 2-posiion on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ represents an integer of 2 to 5; or

[Formula 24]

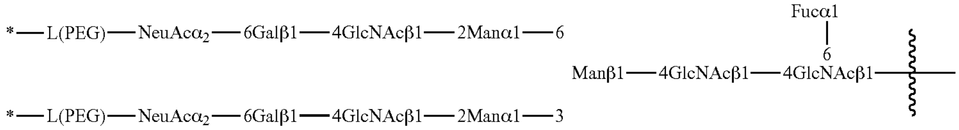

[N297—(Fuc)SG]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, and $n^5$ represents an integer of 2 to 5.

[26] The antibody-drug conjugate according to [25], wherein the antibody-drug conjugate is represented by the following formulas selected from

[Formula 25]

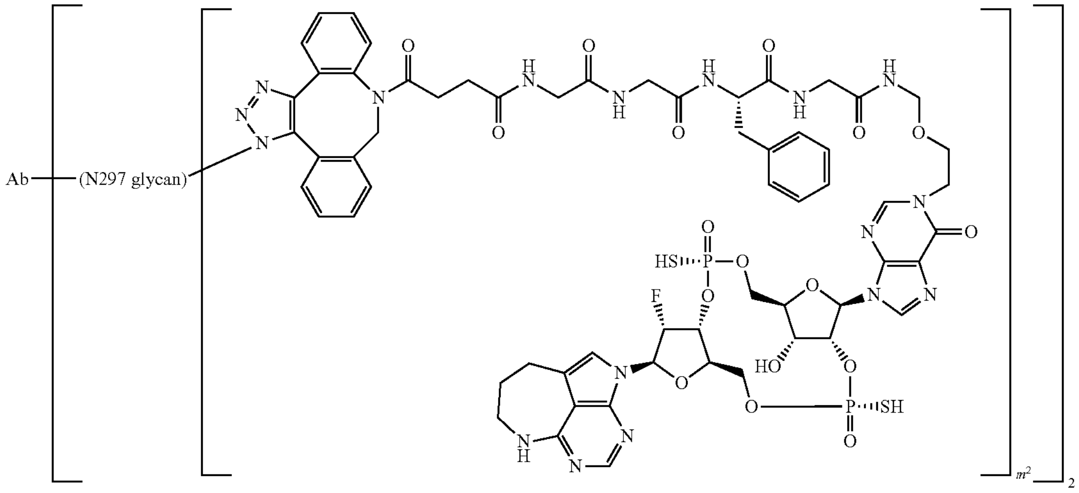

or

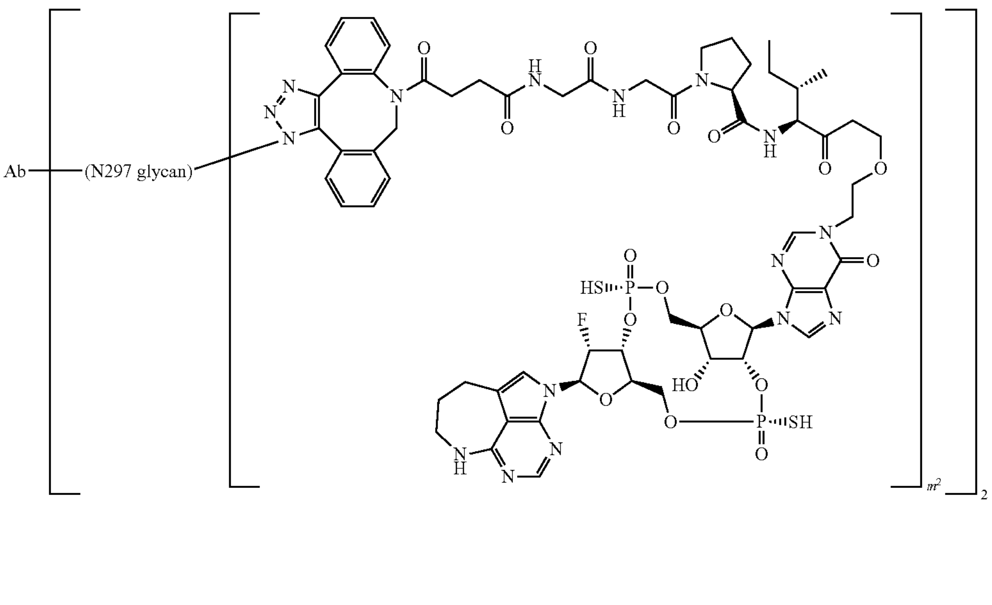

wherein, in each the structural formula shown above, $m^2$ is an integer of 1 or 2, Ab represents an anti-CD70 antibody, an anti-TROP2 antibody, or an anti-EGFR antibody, or a functional fragment thereof, N297 glycan of Ab is represented by any one of N297-(Fuc)MSG1 or N297-(Fuc)SG having a structure represented by the following formula:

[Formula 26]

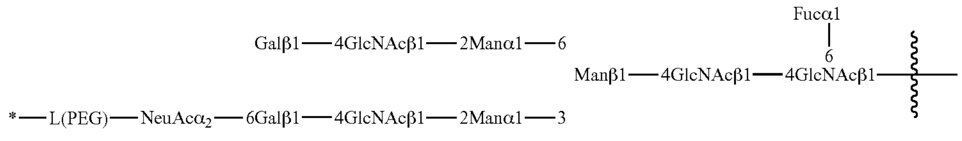

[N297—(Fuc)MSG1]

wherein the wavy line represents bonding to Asn297 of the antibody,

L(PEG) represents $—(CH_2—CH_2—O)n^5—CH_2—CH_2—NH—$, wherein the amino group at the right end of the L(PEG) is bound via an amide bond to a carboxyl group at the 2-posiion on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ represents an integer of 2 to 5;

[Formula 27]

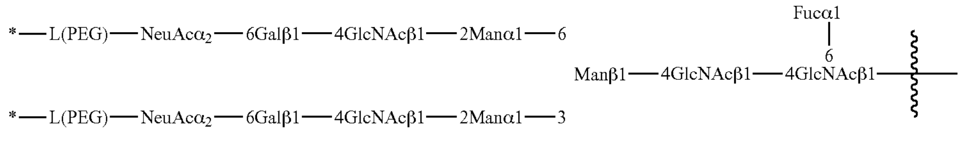

[N297—(Fuc)SG]

wherein the wavy line represents bonding to Asn297 of the antibody,

L(PEG) represents $—(CH_2—CH_2O)n^5—CH_2—CH_2—NH—$, wherein the amino group at the right end of the L(PEG) is bound via an amide bond to a carboxyl group at the 2-posiion on a sialic acid at the non-reducing terminal on each of 1-3 and 1-6 branched chains of j-Man in the N297 glycan, the asterisk represents bonding to a nitrogen atom at 1- or 3-position on 1,2,3-triazole ring of Lb in the linker L, and $n^5$ represents an integer of 2 to 5.

[27] The antibody-drug conjugate according to any one of [1] to [26], wherein the antibody is an anti-CD70 antibody.

[28] The antibody-drug conjugate according to any one of [1] to [26], wherein the antibody is an anti-TROP2 antibody.

[29] The antibody-drug conjugate according to any one of [1] to [26], wherein the antibody is an anti-EGFR antibody.

[30] The antibody-drug conjugate according to [27], wherein the antibody is an antibody comprising a light chain consisting of an amino acid sequence set forth in SEQ ID NO: 1 and a heavy chain consisting of an amino acid sequence set forth in SEQ ID NO: 2 or an antibody comprising a light chain consisting of an amino acid sequence set forth in SEQ ID NO: 3 and a heavy chain consisting of an amino acid sequence set forth in SEQ ID NO: 4.

[31] The antibody-drug conjugate according to [28], wherein the antibody is an antibody comprising a light chain consisting of an amino acid sequence set forth in SEQ ID NO: 5 and a heavy chain consisting of an amino acid sequence set forth in SEQ ID NO: 6 or an antibody comprising a light chain consisting of an amino acid sequence set forth in SEQ ID NO: 7 and a heavy chain consisting of an amino acid sequence set forth in SEQ ID NO: 8.

[32] The antibody-drug conjugate according to [29], wherein the antibody is an antibody comprising a light chain consisting of an amino acid sequence set forth in SEQ ID NO: 9 and a heavy chain consisting of an amino acid sequence set forth in SEQ ID NO: 10 or an antibody comprising a light chain consisting of an amino acid sequence set forth in SEQ ID NO: 11 and a heavy chain consisting of an amino acid sequence set forth in SEQ ID NO: 12.

[33] The antibody-drug conjugate according to [27], wherein the antibody is an antibody comprising a light chain comprising a light chain variable region consisting of amino acid residues 1 to 112 of SEQ ID NO: 1 and a heavy chain comprising a heavy chain variable region consisting of amino acid residues 1 to 118 of SEQ ID NO: 2 or an antibody comprising a light chain comprising a light chain variable region consisting of amino acid residues 1 to 108 of SEQ ID NO: 3 and a heavy chain comprising a heavy chain variable region consisting of amino acid residues 1 to 118 of SEQ ID NO: 4.

[34] The antibody-drug conjugate according to [28], wherein the antibody is an antibody comprising a light chain comprising a light chain variable region consisting of amino acid residues 1 to 108 of SEQ ID NO: 5 and a heavy chain comprising a heavy chain variable region consisting of amino acid residues 1 to 121 of SEQ ID NO: 6 or an antibody comprising a light chain comprising a light chain variable region consisting of amino acid residues 1 to 108 of SEQ ID NO: 7 and a heavy chain comprising a heavy chain variable region consisting of amino acid residues 1 to 121 of SEQ ID NO: 8.

[35] The antibody-drug conjugate according to [29], wherein the antibody is an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10 or an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

[36] The antibody-drug conjugate according to [27], wherein the antibody is an antibody comprising a light chain comprising CDRL1 consisting of an amino acid sequence set forth in SEQ ID NO: 35, CDRL2 consisting of an amino acid sequence set forth in SEQ ID NO: 36, and CDRL3 consisting of an amino acid sequence set forth in SEQ ID NO: 37 and a heavy chain comprising CDRH1 consisting of an amino acid sequence set forth in SEQ ID NO: 38, CDRH2 consisting of an amino acid sequence set forth in SEQ ID NO: 39, and CDRH3 consisting of an amino acid sequence set forth in SEQ ID NO: 40 or an antibody comprising a light chain comprising CDRL1 consisting of an amino acid sequence set forth in SEQ ID NO: 41, CDRL2 consisting of an amino acid sequence set forth in SEQ ID NO: 42, and CDRL3 consisting of an amino acid sequence set forth in SEQ ID NO: 43 and a heavy chain comprising CDRH1 consisting of an amino acid sequence set forth in SEQ ID NO: 44, CDRH2 consisting of an amino acid sequence set forth in SEQ ID NO: 45, and CDRH3 consisting of an amino acid sequence set forth in SEQ ID NO: 46.

[37] The antibody-drug conjugate according to [28], wherein the antibody is an antibody comprising a light chain comprising CDRL1 consisting of an amino acid sequence set forth in SEQ ID NO: 47, CDRL2 consisting of an amino acid sequence set forth in SEQ ID NO: 48, and CDRL3 consisting of an amino acid sequence set forth in SEQ ID NO: 49 and a heavy chain comprising CDRH1 consisting of an amino acid sequence set forth in SEQ ID NO: 50, CDRH2 consisting of an amino acid sequence set forth in SEQ ID NO: 51, and CDRH3 consisting of an amino acid sequence set forth in SEQ ID NO: 52 or an antibody comprising a light chain comprising CDRL1 consisting of an amino acid sequence set forth in SEQ ID NO: 53, CDRL2 consisting of an amino acid sequence set forth in SEQ ID NO: 54, and CDRL3 consisting of an amino acid sequence set forth in SEQ ID NO: 55 and a heavy chain comprising CDRH1 consisting of an amino acid sequence set forth in SEQ ID NO: 56, CDRH2 consisting of an amino acid sequence set forth in SEQ ID NO: 57, and CDRH3 consisting of an amino acid sequence set forth in SEQ ID NO: 58.

[38] The antibody-drug conjugate according to [29], wherein the antibody is an antibody comprising a light chain comprising CDRL1 consisting of an amino acid sequence set forth in SEQ ID NO: 59, CDRL2 consisting of an amino acid sequence set forth in SEQ ID NO: 60, and CDRL3 consisting of an amino acid sequence set forth in SEQ ID NO: 61 and a heavy chain comprising CDRH1 consisting of an amino acid sequence set forth in SEQ ID NO: 62, CDRH2 consisting of an amino acid sequence set forth in SEQ ID NO: 63, and CDRH3 consisting of an amino acid sequence set forth in SEQ ID NO: 64 or an antibody comprising a light chain comprising CDRL1 consisting of an amino acid sequence set forth in SEQ ID NO: 65, CDRL2 consisting of an amino acid sequence set forth in SEQ ID NO: 66, and CDRL3 consisting of an amino acid sequence set forth in SEQ ID NO: 67 and a heavy chain comprising CDRH1 consisting of an amino acid sequence set forth in SEQ ID NO: 68, CDRH2 consisting of an amino acid sequence set forth in SEQ ID NO: 69, and CDRH3 consisting of an amino acid sequence set forth in SEQ ID NO: 70.

[39] An antibody-drug conjugate represented by the following formula:

[Formula 28]

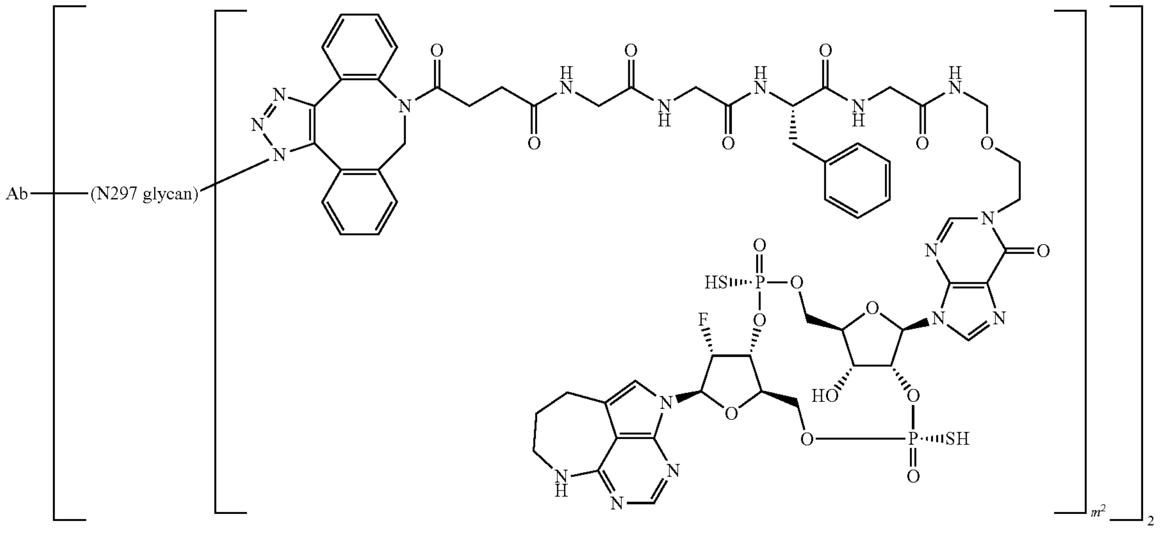

wherein Ab represents any one selected from the group consisting of the following:

an antibody comprising a light chain consisting of an amino acid sequence set forth in SEQ ID NO: 1 and a heavy chain consisting of an amino acid sequence set forth in SEQ ID NO: 2, an antibody comprising a light chain consisting of an amino acid sequence set forth in SEQ ID NO: 3 and a heavy chain consisting of an amino acid sequence set forth in SEQ ID NO: 4, an antibody comprising a light chain consisting of an amino acid sequence set forth in SEQ ID NO: 5 and a heavy chain consisting of an amino acid sequence set forth in SEQ ID NO: 6, an antibody comprising a light chain consisting of an amino acid sequence set forth in SEQ ID NO: 7 and a heavy chain consisting of an amino acid sequence set forth in SEQ ID NO: 8, an antibody comprising a light chain consisting of an amino acid sequence set forth in SEQ ID NO: 9 and a heavy chain consisting of an amino acid sequence set forth in SEQ ID NO: 10, and an antibody comprising a light chain consisting of an amino acid sequence set forth in SEQ ID NO: 11 and a heavy chain consisting of an amino acid sequence set forth in SEQ ID NO: 12, wherein N297 glycan of Ab is represented by the following formula:

[Formula 29]

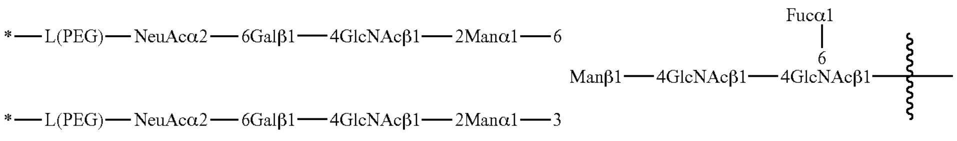

[N297-(Fuc)SG]

wherein the wavy line represents bonding to Asn297 of the antibody,

L(PEG) represents $-(CH_2-CH_2O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, $n^5$ is 3, and $m^2$ is 2.

[40] An antibody-drug conjugate represented by the following formula:

[Formula 30]

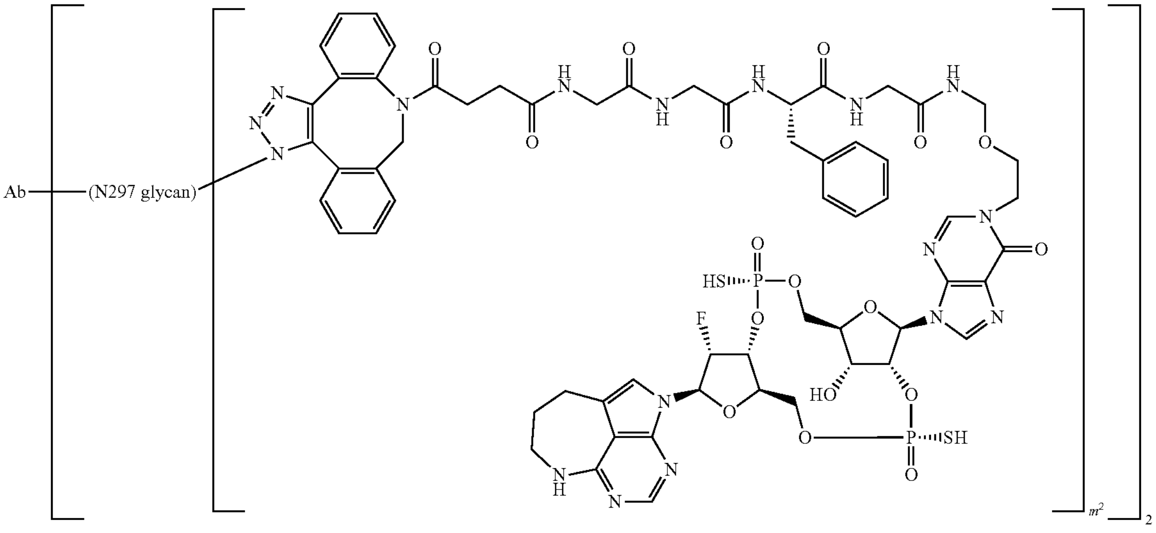

wherein Ab represents any one selected from the group consisting of the following:

an antibody comprising a light chain comprising a light chain variable region consisting of amino acid residues 1 to 112 of SEQ ID NO: 1 and a heavy chain comprising a heavy chain variable region consisting of amino acid residues 1 to 118 of SEQ ID NO: 2, an antibody comprising a light chain comprising a light chain variable region consisting of amino acid residues 1 to 108 of SEQ ID NO: 3 and a heavy chain comprising a heavy chain variable region consisting of amino acid residues 1 to 118 of SEQ ID NO: 4, an antibody comprising a light chain comprising a light chain variable region consisting of amino acid residues 1 to 108 of SEQ ID NO: 5 and a heavy chain comprising a heavy chain variable region consisting of amino acid residues 1 to 121 of SEQ ID NO: 6, an antibody comprising a light chain comprising a light chain variable region consisting of amino acid residues 1 to 108 of SEQ ID NO: 7 and a heavy chain comprising a heavy chain variable region consisting of amino acid residues 1 to 121 of SEQ ID NO: 8, an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10, and an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12, wherein N297 glycan of Ab is represented by the following formula:

[Formula 31]

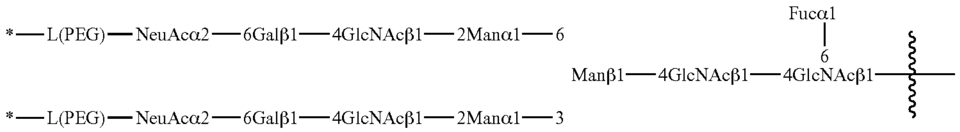

[N297-(Fuc)SG]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, $n^5$ is 3, and $m^2$ is 2.

[41] An antibody-drug conjugate represented by the following formula:

[Formula 32]

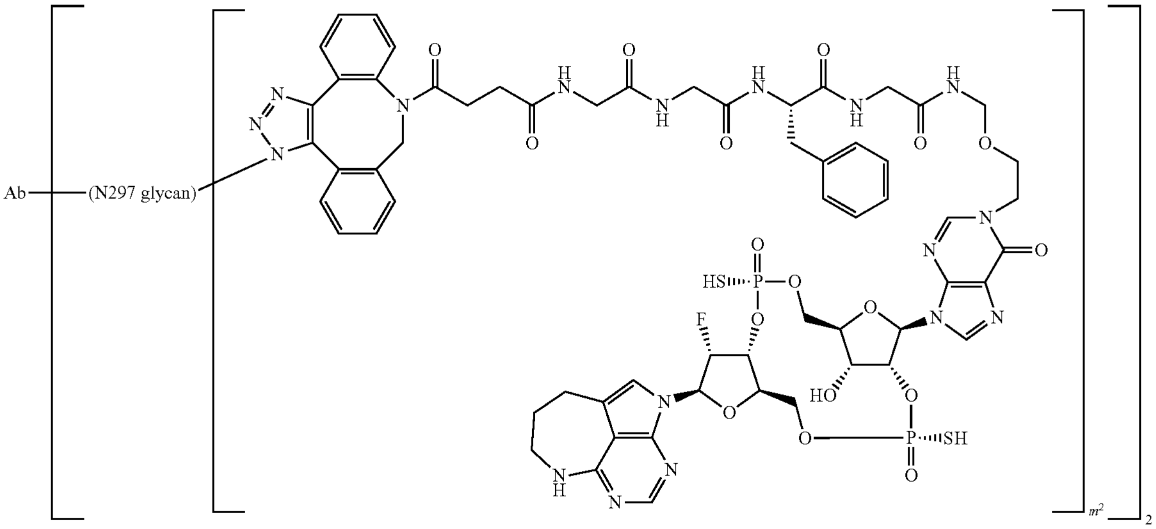

wherein Ab represents any one selected from the group consisting of the following:

an antibody comprising a light chain comprising CDRL1 consisting of an amino acid sequence set forth in SEQ ID NO: 35, CDRL2 consisting of an amino acid sequence set forth in SEQ ID NO: 36, and CDRL3 consisting of an amino acid sequence set forth in SEQ ID NO: 37 and a heavy chain comprising CDRH1 consisting of an amino acid sequence set forth in SEQ ID NO: 38, CDRH2 consisting of an amino acid sequence set forth in SEQ ID NO: 39, and CDRH3 consisting of an amino acid sequence set forth in SEQ ID NO: 40, an antibody comprising a light chain comprising CDRL1 consisting of an amino acid sequence set forth in SEQ ID NO: 41, CDRL2 consisting of an amino acid sequence set forth in SEQ ID NO: 42, and CDRL3 consisting of an amino acid sequence set forth in SEQ ID NO: 43 and a heavy chain comprising CDRH1 consisting of an amino acid sequence set forth in SEQ ID NO: 44, CDRH2 consisting of an amino acid sequence set forth in SEQ ID NO: 45, and CDRH3 consisting of an amino acid sequence set forth in SEQ ID NO: 46, an antibody comprising a light chain comprising CDRL1 consisting of an amino acid sequence set forth in SEQ ID NO: 47, CDRL2 consisting of an amino acid sequence set forth in SEQ ID NO: 48, and CDRL3 consisting of an amino acid sequence set forth in SEQ ID NO: 49 and a heavy chain comprising CDRH1 consisting of an amino acid sequence set forth in SEQ ID NO: 50, CDRH2 consisting of an amino acid sequence set forth in SEQ ID NO: 51, and CDRH3 consisting of an amino acid sequence set forth in SEQ ID NO: 52, an antibody comprising a light chain comprising CDRL1 consisting of an amino acid sequence set forth in SEQ ID NO: 53, CDRL2 consisting of an amino acid sequence set forth in SEQ ID NO: 54, and CDRL3 consisting of an amino acid sequence set forth in SEQ ID NO: 55 and a heavy chain comprising CDRH1 consisting of an amino acid sequence set forth in SEQ ID NO: 56, CDRH2 consisting of an amino acid sequence set forth in SEQ ID NO: 57, and CDRH3 consisting of an amino acid sequence set forth in SEQ ID NO: 58, an antibody comprising a light chain comprising CDRL1 consisting of an amino acid sequence set forth in SEQ ID NO: 59, CDRL2 consisting of an amino acid sequence set forth in SEQ ID NO: 60, and CDRL3 consisting of an amino acid sequence set forth in SEQ ID NO: 61 and a heavy chain comprising CDRH1 consisting of an amino acid sequence set forth in SEQ ID NO: 62, CDRH2 consisting of an amino acid sequence set forth in SEQ ID NO: 63, and CDRH3 consisting of an amino acid sequence set forth in SEQ ID NO: 64, and an antibody comprising a light chain comprising CDRL1 consisting of an amino acid sequence set forth in SEQ ID NO: 65, CDRL2 consisting of an amino acid sequence set forth in SEQ ID NO: 66, and CDRL3 consisting of an amino acid sequence set forth in SEQ ID NO: 67 and a heavy chain comprising CDRH1 consisting of an amino acid sequence set forth in SEQ ID NO: 68, CDRH2 consisting of an amino acid sequence set forth in SEQ ID NO: 69, and CDRH3 consisting of an amino acid sequence set forth in SEQ ID NO: 70, wherein N297 glycan of Ab is represented by the following formula:

[Formula 33]

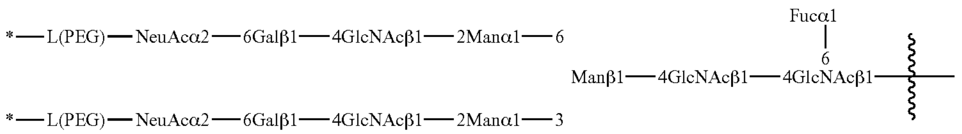

[N297-(Fuc)SG]

wherein the wavy line represents bonding to Asn297 of the antibody,

L(PEG) represents $—(CH_2—CH_2—O)n^5—CH_2—CH_2—NH—$, wherein the amino group at the right end of the L(PEG) is bound via an amide bond to a carboxyl group at the 2-posiion on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, $n^5$ is 3, and $m^2$ is 2.

[42] An antibody-drug conjugate represented by the following formula:

[Formula 34]

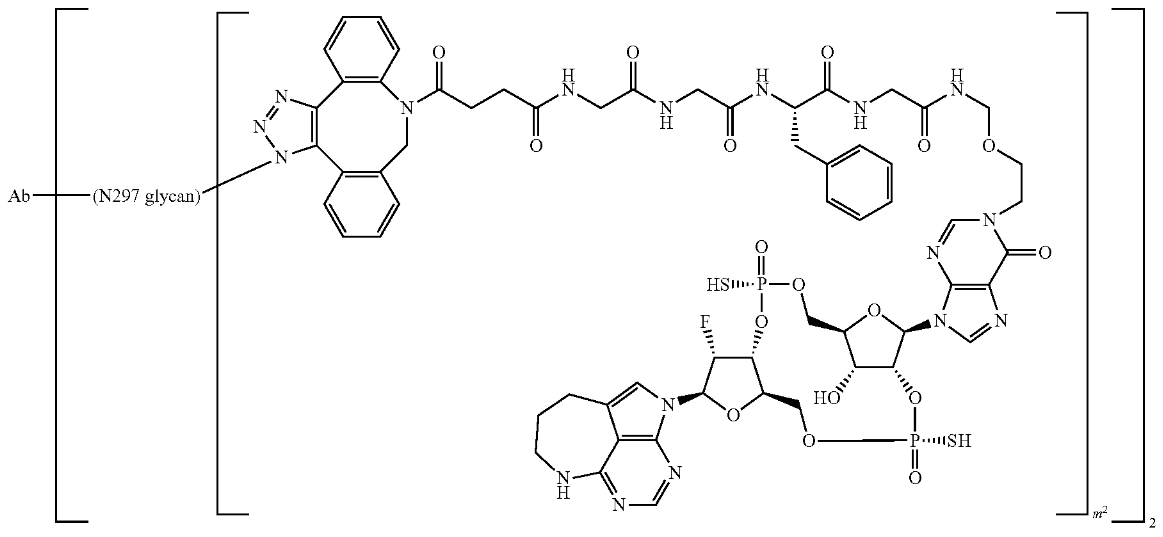

wherein Ab represents any one selected from the group consisting of the following:

an antibody comprising a light chain consisting of an amino acid sequence set forth in SEQ ID NO: 1 and a heavy chain consisting of an amino acid sequence set forth in SEQ ID NO: 2, an antibody comprising a light chain consisting of an amino acid sequence set forth in SEQ ID NO: 3 and a heavy chain consisting of an amino acid sequence set forth in SEQ ID NO: 4, an antibody comprising a light chain consisting of an amino acid sequence set forth in SEQ ID NO: 5 and a heavy chain consisting of an amino acid sequence set forth in SEQ ID NO: 6, an antibody comprising a light chain consisting of an amino acid sequence set forth in SEQ ID NO: 7 and a heavy chain consisting of an amino acid sequence set forth in SEQ ID NO: 8, an antibody comprising a light chain consisting of an amino acid sequence set forth in SEQ ID NO: 9 and a heavy chain consisting of an amino acid sequence set forth in SEQ ID NO: 10, and an antibody comprising a light chain consisting of an amino acid sequence set forth in SEQ ID NO: 11 and a heavy chain consisting of an amino acid sequence set forth in SEQ ID NO: 12, wherein N297 glycan of Ab is represented by the following formula:

[Formula 35]

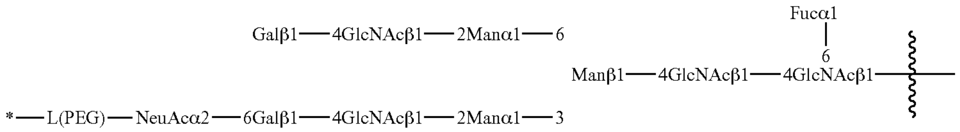

[N297-(Fuc)$MSG_1$]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of j-Man in the N297 glycan, the asterisk represents bonding to a nitrogen atom at 1- or 3-position on 1,2,3-triazole ring of Lb in the linker L, $n^5$ is 3, and $m^2$ is 1.

[43] An antibody-drug conjugate represented by the following formula:

[Formula 36]

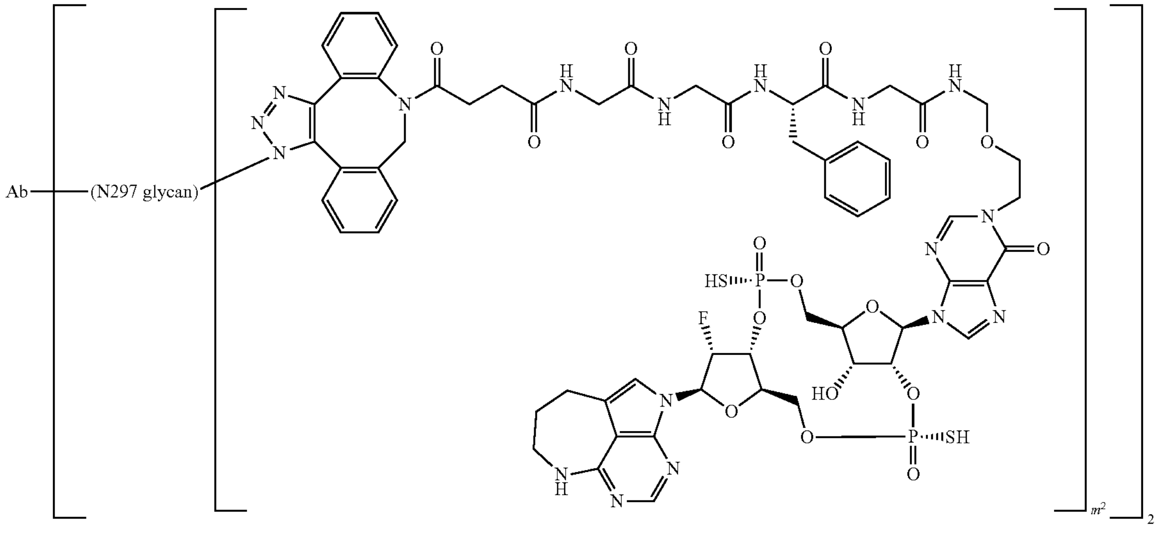

wherein Ab represents any one selected from the group consisting of the following:

an antibody comprising a light chain comprising a light chain variable region consisting of amino acid residues 1 to 112 of SEQ ID NO: 1 and a heavy chain comprising a heavy chain variable region consisting of amino acid residues 1 to 118 of SEQ ID NO: 2, an antibody comprising a light chain comprising a light chain variable region consisting of amino acid residues 1 to 108 of SEQ ID NO: 3 and a heavy chain comprising a heavy chain variable region consisting of amino acid residues 1 to 119 of SEQ ID NO: 10, and an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12, wherein N297 glycan of Ab is represented by the following formula:

[Formula 37]

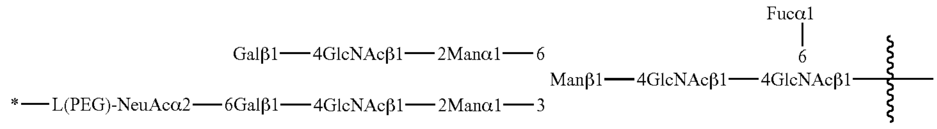

[N297-(Fuc)MSG1]

prising a heavy chain variable region consisting of amino acid residues 1 to 118 of SEQ ID NO: 4, an antibody comprising a light chain comprising a light chain variable region consisting of amino acid residues 1 to 108 of SEQ ID NO: 5 and a heavy chain comprising a heavy chain variable region consisting of amino acid residues 1 to 121 of SEQ ID NO: 6, an antibody comprising a light chain comprising a light chain variable region consisting of amino acid residues 1 to 108 of SEQ ID NO: 7 and a heavy chain comprising a heavy chain variable region consisting of amino acid residues 1 to 121 of SEQ ID NO: 8, an antibody comprising a light chain comprising a light chain variable region consisting of amino acid residues 1 to 108 of SEQ ID NO: 9 and a heavy chain comwherein the wavy line represents bonding to Asn297 of the antibody, L(PEG) represents $-(CH_2-CH_2-O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, $n^5$ is 3, and $m^2$ is 1.

[44] An antibody-drug conjugate represented by the following formula:

[Formula 38]

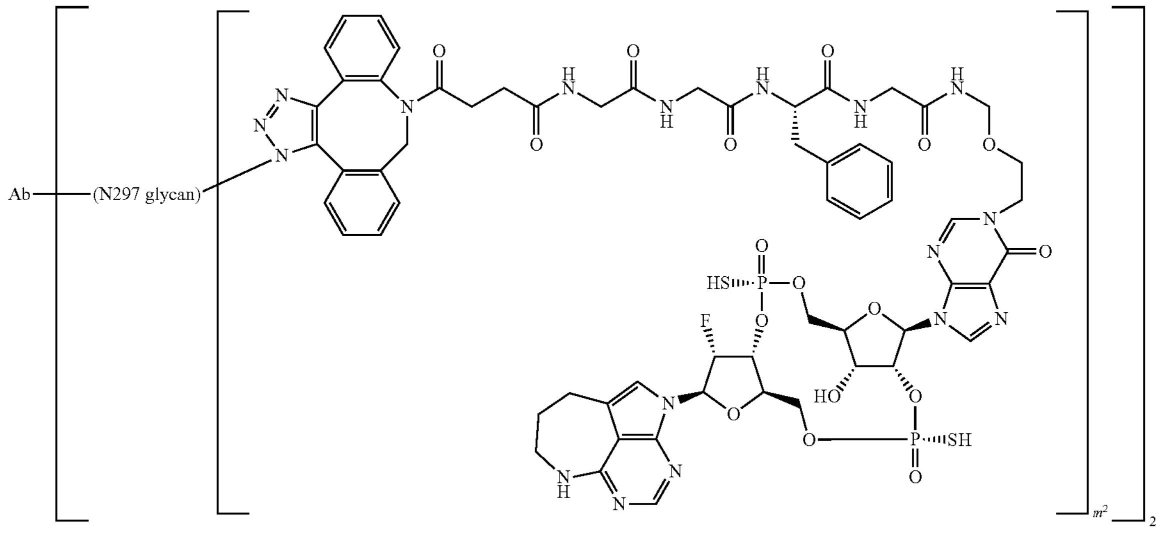

wherein Ab represents any one selected from the group consisting of the following:

an antibody comprising a light chain comprising CDRL1 consisting of an amino acid sequence set forth in SEQ ID NO: 35, CDRL2 consisting of an amino acid sequence set forth in SEQ ID NO: 36, and CDRL3 consisting of an amino acid sequence set forth in SEQ ID NO: 37 and a heavy chain comprising CDRH1 consisting of an amino acid sequence set forth in SEQ ID NO: 38, CDRH2 consisting of an amino acid sequence set forth in SEQ ID NO: 39, and CDRH3 consisting of an amino acid sequence set forth in SEQ ID NO: 40, an antibody comprising a light chain comprising CDRL1 consisting of an amino acid sequence set forth in SEQ ID NO: 41, CDRL2 consisting of an amino acid sequence set forth in SEQ ID NO: 42, and CDRL3 consisting of an amino acid sequence set forth in SEQ ID NO: 43 and a heavy chain comprising CDRH1 consisting of an amino acid sequence set forth in SEQ ID NO: 44, CDRH2 consisting of an amino acid sequence set forth in SEQ ID NO: 45, and CDRH3 consisting of an amino acid sequence set forth in SEQ ID NO: 46, an antibody comprising a light chain comprising CDRL1 consisting of an amino acid sequence set forth in SEQ ID NO: 47, CDRL2 consisting of an amino acid sequence set forth in SEQ ID NO: 48, and CDRL3 consisting of an amino acid sequence set forth in SEQ ID NO: 49 and a heavy chain comprising CDRH1 consisting of an amino acid sequence set forth in SEQ ID NO: 50, CDRH2 consisting of an amino acid sequence set forth in SEQ ID NO: 51, and CDRH3 consisting of an amino acid sequence set forth in SEQ ID NO: 52, an antibody comprising a light chain comprising CDRL1 consisting of an amino acid sequence set forth in SEQ ID NO: 53, CDRL2 consisting of an amino acid sequence set forth in SEQ ID NO: 54, and CDRL3 consisting of an amino acid sequence set forth in SEQ ID NO: 55 and a heavy chain comprising CDRH1 consisting of an amino acid sequence set forth in SEQ ID NO: 56, CDRH2 consisting of an amino acid sequence set forth in SEQ ID NO: 57, and CDRH3 consisting of an amino acid sequence set forth in SEQ ID NO: 58, an antibody comprising a light chain comprising CDRL1 consisting of an amino acid sequence set forth in SEQ ID NO: 59, CDRL2 consisting of an amino acid sequence set forth in SEQ ID NO: 60, and CDRL3 consisting of an amino acid sequence set forth in SEQ ID NO: 61 and a heavy chain comprising CDRH1 consisting of an amino acid sequence set forth in SEQ ID NO: 62, CDRH2 consisting of an amino acid sequence set forth in SEQ ID NO: 63, and CDRH3 consisting of an amino acid sequence set forth in SEQ ID NO: 64, and an antibody comprising a light chain comprising CDRL1 consisting of an amino acid sequence set forth in SEQ ID NO: 65, CDRL2 consisting of an amino acid sequence set forth in SEQ ID NO: 66, and CDRL3 consisting of an amino acid sequence set forth in SEQ ID NO: 67 and a heavy chain comprising CDRH1 consisting of an amino acid sequence set forth in SEQ ID NO: 68, CDRH2 consisting of an amino acid sequence set forth in SEQ ID NO: 69, and CDRH3 consisting of an amino acid sequence set forth in SEQ ID NO: 70, wherein N297 glycan of Ab is represented by the following formula:

[Formula 39]

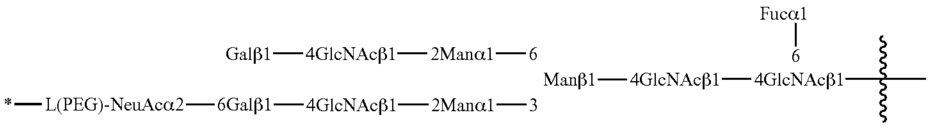

[N297-(Fuc)MSG1]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-posiion on a sialic acid at the non-reducing terminal on each of 1-3 and 1-6 branched chains of j-Man in the N297 glycan, the asterisk represents bonding to a nitrogen atom at 1- or 3-position on 1,2,3-triazole ring of Lb in the linker L, $n^5$ is 3, and $m^2$ is 1.

[45]A STING agonist comprising the antibody-drug conjugate according to any one of [1] to [44].

[46]A pharmaceutical composition comprising the antibody-drug conjugate according to any one of [1] to [44].

[47] An anti-tumor agent comprising the antibody-drug conjugate according to any one of [1] to [44].

[48] The anti-tumor agent according to [47], wherein the tumor is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, esophageal cancer, endometrial cancer, testicular cancer, cervical cancer, placental choriocarcinoma, brain tumor, head and neck cancer, thyroid cancer, mesothelioma, gastrointestinal stromal tumor (GIST), gall bladder cancer, bile duct cancer, adrenal cancer, squamous-cell carcinoma, pharyngeal cancer, tongue cancer, auditory organ cancer, thymus cancer, small intestine cancer, leukemia, malignant lymphoma, plasmacytoma, myeloma, or sarcoma.

[49]A method for treating cancer, comprising administering any one selected from the group consisting of the antibody-drug conjugate according to any one of [1] to [44], the STING agonist according to [45], the pharmaceutical composition according to [46], and the anti-tumor agent according to [47] or [48].

[50] The method according to [49], wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, esophageal cancer, endometrial cancer, testicular cancer, cervical cancer, placental choriocarcinoma, brain tumor, head and neck cancer, thyroid cancer, mesothelioma, gastrointestinal stromal tumor (GIST), gall bladder cancer, bile duct cancer, adrenal cancer, squamous-cell carcinoma, pharyngeal cancer, tongue cancer, auditory organ cancer, thymus cancer, small intestine cancer, leukemia, malignant lymphoma, plasmacytoma, myeloma, or sarcoma.

[51] The antibody-drug conjugate according to any one of [27], [30], [33], and [36], wherein the antibody-drug conjugate exerts an antibody target-dependent anti-tumor effect in BALB/c-nu mouse subcutaneously transplanted with Caki-1 cells, a human kidney cancer cell line.

[52] The antibody-drug conjugate according to any one of [42] to [44], wherein the antibody-drug conjugate exerts a more potent anti-tumor effect than the antibody included in the antibody-drug conjugate in an animal of the following (i) or (ii):

(i) BALB/c mouse subcutaneously transplanted with CT26.WT (CRL2638), a mouse colorectal cancer cell line transfected with a gene encoding a human-mouse chimeric antigen, in which an epitope site on the antigen of the antibody included in the antibody-drug conjugate is replaced by a human type counterpart; or (ii) BALB/c-nu mouse subcutaneously transplanted with A-498 (HTB-44) cells, a human kidney cancer cell line.

Advantageous Effects of Invention

The present invention provides a novel antibody-CDN derivative conjugate that can be systemically administered and elicits anti-tumor effects in an antigen-expressing tumor.

BRIEF DESCRIPTION OF DRAWINGS

FIG. 1 is a schematic diagram of antibody-drug conjugates (the molecules of (II)) of the present invention, namely an antibody-drug conjugate (the molecule of (II) in FIG. 1A) obtained from an SG-type glycan-remodeled antibody and an antibody-drug conjugate (a molecule (II) in FIG. 1B) obtained from an MSG-type glycan-remodeled antibody. Here, (a) denotes a drug D, (b) denotes a linker L, (c) denotes a PEG linker (L(PEG)), and (d) denotes N297 glycan (where white circle is NeuAc(Sia), white hexagon is Man, black hexagon is GlcNAc, white diamond is Gal, and white inverted triangle is Fuc), respectively. The white pentagon denotes a triazole ring formed by the reaction of the linker L-derived alkyne with the PEG linker-derived azide group. The Y-shaped diagram represents an antibody Ab. The PEG linker bonds via an amide bond to the carboxyl group at 2-position of the sialic acid located at the non-reducing end. Unless otherwise stated, such a manner of illustration is applied throughout the specification.

FIG. 2 is a schematic diagrams illustrating the structures of each production intermediate of an antibody-drug conjugate of the present invention, namely a (Fucα1, 6)GlcNAc-antibody (the molecule of (III) in A of FIG. 2), a SG-type glycan-remodeled antibody (the molecule of (IV) in B of FIG. 2), and an MSG-type glycan-remodeled antibody (the molecule of (IV) in C of FIG. 2). In all of the diagrams, the Y-shaped diagram represents antibody Ab as in FIG. 1. In A in FIG. 2, (e) denotes N297 glycan consisting of a disaccharide in which GlcNAc at 6-position is connected to 1-position of Fuc via α-glycoside bond. In B and C in FIG. 2, (d) denotes the same N297 glycan as in FIG. 1, and (f) denotes a PEG linker having an azide group, an azide group to be bonded to linker L at the end. The bonding mode of the PEG linker having an azide group is the same as to the PEG linker in FIG. 1.

FIG. 3 is a schematic diagram for the step of producing an SG-type glycan-remodeled antibody or an MSG-type glycan-remodeled antibody from an antibody produced in animal cells. Molecules (III) and (IV) in the Figure represent, as in FIG. 2, a (Fucα1, 6)GlcNAc-antibody and a SG-type glycan-remodeled antibody or an MSG-type glycan-remodeled antibody, respectively. Molecule (V) is an antibody produced in animal cells, and is a mixture of molecules with heterogeneous N297 glycan molecules. FIG. 3A illustrates the step of producing homogeneous (Fucα1, 6)GlcNAc-antibody (III) by treating heterogeneous N297 glycan molecules of (V) with hydrolase such as EndoS. FIG. 3B illustrates the step of producing the SG-type glycan-remodeled antibody of (IV) by subjecting GlcNAc of the N297 glycan in antibody (III) to transglycosidase such as EndoS D233Q/Q303L variant to transglycosylate an SG-type glycan donor molecule. FIG. 3C illustrates the step, as in FIG. 3B, of producing the MSG-type glycan-remodeled antibody of (IV) by subjecting antibody (III) to transglycosylate an MSG-type glycan donor molecule. Each of SG- and MSG-type glycan donor molecules used here has a sialic acid at each non-reducing terminal modified with a PEG linker having an azide group. Thus, resulting SG- and MSG-type N-297 glycan-remodeled antibodies also have a sialic acid at the non-reducing terminal modified in the same manner as described for FIGS. 2B and 2C.

FIG. 4 shows the light chain amino acid sequence (SEQ ID NO: 1) and the heavy chain amino acid sequence (SEQ ID NO: 2) of anti-CD70 antibody 1 (as used herein, the term “anti-CD70 antibody 1” is also referred to as “modified anti-CD70 antibody 1”).

FIG. 5 shows the light chain amino acid sequence (SEQ ID NO: 3) and the heavy chain amino acid sequence (SEQ ID NO: 4) of anti-CD70 antibody 2 (as used herein, the term “anti-CD70 antibody 2” is also referred to as “modified anti-CD70 antibody 2”).

FIG. 6 shows the light chain amino acid sequence (SEQ ID NO: 5) and the heavy chain amino acid sequence (SEQ ID NO: 6) of anti-TROP2 antibody 1.

FIG. 7 shows the light chain amino acid sequence (SEQ ID NO: 7) and the heavy chain amino acid sequence (SEQ ID NO: 8) of anti-TROP2 antibody 2 (as used herein, the term “anti-TROP2 antibody 2” is also referred to as “modified anti-TROP2 antibody”).

FIG. 8 shows the light chain amino acid sequence (SEQ ID NO: 9) and the heavy chain amino acid sequence (SEQ ID NO: 10) of anti-EGFR antibody 1 (as used herein, the term “anti-EGFR antibody 1” is also referred to as “modified anti-EGFR antibody 1”).

FIG. 9 shows the light chain amino acid sequence (SEQ ID NO: 11) and the heavy chain amino acid sequence (SEQ ID NO: 12) of anti-EGFR antibody 2 (as used herein, the term “anti-EGFR antibody 2” is also referred to as “modified anti-EGFR antibody 2”).

FIG. 10(*a*) shows the amino acid sequence of human wild-type STING (SEQ ID NO: 13), FIG. 10(*b*) shows the amino acid sequence of human STING REF mutant (R232H) (SEQ ID NO: 15), and FIG. 10(*c*) shows the amino acid sequence of human STING HAQ mutant (R71H, G230A, R293Q) (SEQ ID NO: 17).

FIG. 11 shows how the anti-TROP2 antibody 2, the anti-TROP2 antibody 2-CDN conjugate (1), the anti-TROP2 antibody 2-CDN conjugate (2), and the anti-TROP2 antibody 2-CDN conjugate (3) exerted the STING agonist activity in TROP2-expressing cells.

FIG. 12 shows how the compound 34a, the anti-CD70 antibody 1, the anti-CD70 antibody 2, the anti-CD70 antibody 1-CDN conjugate (1), and the anti-CD70 antibody 2-CDN conjugate (1) exerted the activity in a co-culture assay system with mouse bone marrow-derived dendritic cells and a CT26.WT or CT26.WT-hCD70 cell line.

FIG. 13 shows the anti-tumor effects of intravenously administered anti-TROP2 antibody 1 and anti-TROP2 antibody 1-CDN conjugate (1). In the graph, the line (black squares) denotes the vehicle group; the line (inverted white triangles) denotes the anti-TROP2 antibody 1-CDN conjugate (1) administration group, the conjugate obtained by conjugating the anti-TROP2 antibody 1 produced in Reference Example 5 with compound 6b in Example 1; and the line (white circles) denotes the anti-TROP2 antibody 1 administration group. The vertical axis represents the tumor volume ($mm^3$) and the horizonal axis represents the number of days after tumor implantation.

FIG. 14 shows the anti-tumor effects of intravenously administered anti-TROP2 antibody 2 and anti-TROP2 antibody 2-CDN conjugate (1). In the graph, the line (black squares) denotes the vehicle group; the line (inverted white triangles) denotes the anti-TROP2 antibody 2-CDN conjugate (1) administration group, the conjugate obtained by conjugating the anti-TROP2 antibody 2 produced in Reference Example 6 with compound 34a in Example 2; and the line (white circles) denotes the anti-TROP2 antibody 2 administration group. The vertical axis represents the tumor volume ($mm^3$) and the horizonal axis represents the number of days after tumor implantation.

FIG. 15 shows the anti-tumor effects of intravenously administered anti-EGFR antibody 1, anti-EGFR antibody 2, or anti-EGFR antibody-CDN conjugate. The anti-tumor effects have been demonstrated by intravenously administering the anti-EGFR antibody 1-CDN conjugate (1) obtained by conjugating the anti-EGFR antibody 1 produced in Reference Example 7 with the compound 34a in Example 2 and the anti-EGFR antibody 2-CDN conjugate (1) obtained by conjugating the anti-EGFR antibody 2 produced in Reference Example 8 with the compound 34a in Example 2. In the graph, the line (black squares) denotes the vehicle group; the line (white triangles) denotes the anti-EGFR antibody 1 administration group; the line (black triangles) denotes the anti-EGFR antibody 1-CDN conjugate (1) administration group; the line (white circles) denotes the anti-EGFR antibody 2 administration group; and the line (black circles) denotes the anti-EGFR antibody 2-CDN conjugate (1) administration group. The vertical axis represents the tumor volume ($mm^3$) and the horizonal axis represents the number of days after tumor implantation.

FIG. 16 shows the amino acid sequence of CDRL1 (SEQ ID NO: 35), the amino acid sequence of CDRL2 (SEQ ID NO: 36), the amino acid sequence of CDRL3 (SEQ ID NO: 37), the amino acid sequence of CDRH1 (SEQ ID NO: 38), the amino acid sequence of CDRH2 (SEQ ID NO: 39), and the amino acid sequence of CDRH3 (SEQ ID NO: 40) of anti-CD70 antibody 1.

FIG. 17 shows the amino acid sequence of CDRL1 (SEQ ID NO: 41), the amino acid sequence of CDRL2 (SEQ ID NO: 42), the amino acid sequence of CDRL3 (SEQ ID NO: 43), the amino acid sequence of CDRH1 (SEQ ID NO: 44), the amino acid sequence of CDRH2 (SEQ ID NO: 45), and the amino acid sequence of CDRH3 (SEQ ID NO: 46) of anti-CD70 antibody 2.

FIG. 18 shows the amino acid sequence of CDRL1 (SEQ ID NO: 47), the amino acid sequence of CDRL2 (SEQ ID NO: 48), the amino acid sequence of CDRL3 (SEQ ID NO: 49), the amino acid sequence of CDRH1 (SEQ ID NO: 50), the amino acid sequence of CDRH2 (SEQ ID NO: 51), and the amino acid sequence of CDRH3 (SEQ ID NO: 52) of anti-TROP2 antibody 1.

FIG. 19 shows the amino acid sequence of CDRL1 (SEQ ID NO: 53), the amino acid sequence of CDRL2 (SEQ ID NO: 54), the amino acid sequence of CDRL3 (SEQ ID NO: 55), the amino acid sequence of CDRH1 (SEQ ID NO: 56), the amino acid sequence of CDRH2 (SEQ ID NO: 57), and the amino acid sequence of CDRH3 (SEQ ID NO: 58) of anti-TROP2 antibody 2.

FIG. 20 shows the amino acid sequence of CDRL1 (SEQ ID NO: 59), the amino acid sequence of CDRL2 (SEQ ID NO: 60), the amino acid sequence of CDRL3 (SEQ ID NO: 61), the amino acid sequence of CDRH1 (SEQ ID NO: 62), the amino acid sequence of CDRH2 (SEQ ID NO: 63), and the amino acid sequence of CDRH3 (SEQ ID NO: 64) of anti-EGFR antibody 1.

FIG. 21 shows the amino acid sequence of CDRL1 (SEQ ID NO: 65), the amino acid sequence of CDRL2 (SEQ ID NO: 66), the amino acid sequence of CDRL3 (SEQ ID NO: 67), the amino acid sequence of CDRH1 (SEQ ID NO: 68), the amino acid sequence of CDRH2 (SEQ ID NO: 69), and the amino acid sequence of CDRH3 (SEQ ID NO: 70) of anti-EGFR antibody 2.

FIG. 22 shows the anti-tumor effects of intravenously administered anti-CD70 antibody 1, anti-CD70 antibody 1-CDN conjugate (1), anti-CD70 antibody 2, and anti-CD70 antibody 2-CDN conjugate (1). In the graph, the line (black squares) denotes the vehicle group; the line (white triangles) denotes the anti-CD70 antibody 1 administration group; the line (inverted white triangles) denotes the anti-CD70 antibody 2 administration group; the line (white diamonds) denotes the anti-CD70 antibody 1-CDN conjugate (1) administration group; and the line (white circles) denotes the anti-CD70 antibody 2-CDN conjugate (1) administration group. The vertical axis represents the tumor volume ($mm^3$) and the horizonal axis represents the number of days after tumor implantation.

FIG. 23 shows the anti-tumor effects of intravenously administered anti-CD70 antibody 2 and anti-CD70 antibody 2-CDN conjugate (2). In the graph, the line (black squares) denotes the vehicle group; the line (white triangles) denotes the anti-CD70 antibody 2 administration group; and the line (inverted white triangles) denotes the anti-CD70 antibody 2-CDN conjugate (2) administration group. The vertical axis represents the tumor volume ($mm^3$) and the horizonal axis represents the number of days after tumor implantation.

FIG. 24 shows the anti-tumor effects of intravenously administered anti-EGFR antibody 1, compound 34a, and anti-EGFR antibody 1-CDN conjugate (2). In the graph, the line (black squares) denotes the vehicle group; the line (white triangles) denotes the anti-EGFR antibody 1 administration group; the line (white diamonds) denotes the compound 34a administration group; and the line (white rectangles) denotes the anti-EGFR antibody 1-CDN conjugate (2) administration group. The vertical axis represents the tumor volume ($mm^3$) and the horizonal axis represents the number of days after tumor implantation.

DESCRIPTION OF EMBODIMENTS

The present invention pertains to an antibody-drug conjugate containing a novel CDN derivative with STING agonist activity and use thereof. The novel CDN derivative has STING agonist activity, stimulates immune cells and then induces the production of interferons and/or cytokines. In addition, the novel CDN derivative exerts the anti-tumor effects by stimulating the relevant immune cells. The antibody-drug conjugate of the present invention is produced by conjugating the CDN derivative to an antibody capable of recognizing and binding to a target cell (e.g., a tumor cell or immune cell) via a given linker, and can be administered systemically. Specific examples of the systemic administration include an intradermal, intramuscular, intraperitoneal, intravenous, and subcutaneous route.

STING (Stimulator of Interferon Genes) is a transmembrane adaptor protein localized in the endoplasmic reticulum. STING is known to have a high frequency of congenital polymorphisms (PLoS One, 2013 Oct, 21, 8(10), e77846). Examples of the STING mutant include a R232H mutant in which the amino acid at 232-position is mutated from arginine (R) to histidine (H), or a HAQ mutant in which the arginine (R) at 71-position is mutated to histidine (H), the glycine (G) at 230-position is mutated to alanine (A), and the arginine (R) at 293-position is mutated to glutamine (Q). Such STING polymorphisms are known to cause a difference in the strength of responses, such as the level of cytokine production induced by STING agonist stimulation (Genes and Immunity, 2011, 12, 263-269). Therefore, in order to make STING agonists stably effective in humans, the STING agonists should elicit activity against each type of STING.

Herein, "cancer", "carcinoma", and "tumor" are used interchangeably.

In the present invention, "immunostimulation" means to induce activation of immune cells that participate in anti-tumor immunity, such as monocytes, macrophages, dendritic cells, T cells, B cells, NK cells, and neutrophils in any way. For example, the term refers to inducing the production of cytokines and chemokines, increased expression of immune-activation markers, decreased expression of immune-suppression markers, changes in phosphorylation and the like of intracellular signaling pathways, changes in gene expression, and any other changes in the structure and function of immune cells. In addition, the term includes causing changes in tumor cells that induce anti-tumor immunity. For example, the term refers to inducing the production of cytokines and chemokines that stimulate immune cells or induce migration, or increased sensitivity to immune cells.

In the present invention, "anti-tumor effects" refers to induction of a decrease or regression of tumor while a drug exerts a direct or indirect effect on the tumor cells. For example, a drug can cause direct damage to tumor cells; the tumor cells stimulate anti-tumor immunity by drug stimulation; and the drug delivered to the tumor cells is released into an extracellular space, stimulating the anti-tumor immunity around the tumor cells. This, for instance, can cause a decrease in the number of tumor cells and damage the tumor or cause regression of the tumor. This is called anti-tumor effects.

In the present invention, "cellular cytotoxic activity" refers to causing pathological change to cells in any way, which includes causing, not only direct injuries, but also all types of damage in the structure and function of cells such as cleavage of DNA, formation of a base dimer, cleavage of a chromosome, damage of the mitotic apparatus, and lowered activity of various enzymes.

In the present invention, "cells" includes cells in individual animals and cultured cells.

[0022]<1. Novel CDN Derivative>

A novel CDN derivative has a structure represented by the following formula (I):

[Formula 40]

(I)

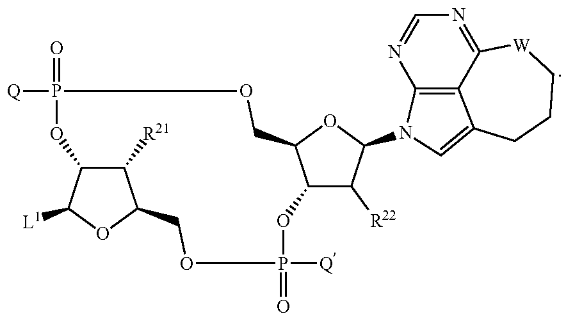

$L^1$ is a group represented by any one of the following three formulas:

[Formula 41]

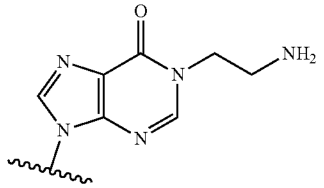

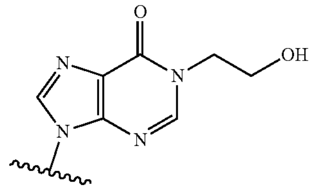

or

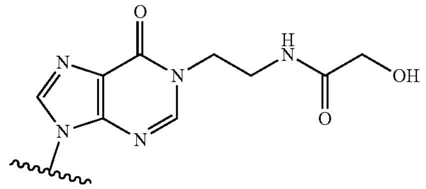

Q and Q', each independently, represent a hydroxy group or a thiol group. Preferably, Q and Q' are each a thiol group.

$R^{21}$ and $R^{22}$, each independently, represent a hydroxy group or a fluorine atom. $R^{21}$ is preferably a hydroxy group. $R^{22}$ is preferably a fluorine atom.

W is —NH— or a sulfur atom. W is preferably —NH—.

Methods for producing the novel CDN derivative will be described in the below-described section <3. Production Methods>.

[0029]<2. Antibody-Drug Conjugate>

It is possible to systemically administer an antibody-drug conjugate of the present invention as produced by conjugating the above-described novel CDN derivative to an antibody capable of recognizing and binding to a target cell (e.g., a tumor cell or immune cell) via a given linker.

An antibody-drug conjugate of the present invention is represented by the following formula (II):

[Formula 42]

$$Ab\text{—}[L\text{—}D]_{m^1}. \quad \text{(II)}$$

Here, $m^1$ ranges from 1 to 10, and indicates the number of conjugated drug molecules per antibody molecule in the antibody-drug conjugate. Ab represents an antibody or a functional fragment thereof; L represents a linker that links Ab and D; and D represents the above-described novel CDN derivative (simply herein referred to as a "drug" when the novel CDN derivative is used as a part of the antibody-drug conjugate).

The drug D is a compound that has immune cell-stimulating activity, specifically, STING agonist activity. When part or all of the linker is cleaved in a target cell(s) (e.g., a tumor cell(s) or immune cell(s)), the drug D is released in its original structure and exerts its immunostimulatory effects. The desired functions can be elicited by increasing the sensitivity of target cells to immune cells or by stimulating immune cells through target cells. The functions of interest are not particularly limited if the functions involve STING agonist activity. However, they preferably involve anti-tumor activity. Specifically, the drug D conjugated, via a given linker, to a tumor-targeting antibody (e.g., anti-CD70 antibody, anti-TROP2 antibody, anti-EGFR antibody) is delivered to a target cell(s) or tissue(s); the linker is partially or completely cleaved; and anti-tumor effects can be exerted through the enhancement of the sensitivity of target cells to immune cells or the target cell-mediated stimulation of immune cells (e.g., production of interferons and/or cytokines).

The drug D conjugated in an antibody-drug conjugate of the present invention is represented by the following formula (I):

[Formula 43]

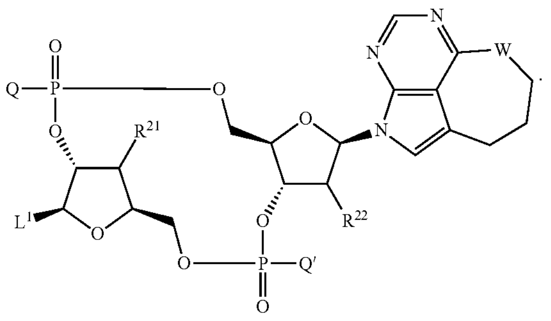

(I)

wherein $L^1$, Q, Q', $R^{21}$, $R^{22}$, and W are as specified above in the section <1. Novel CDN Derivative>.

In addition, the drug D used in an antibody-drug conjugate of the present invention is preferably represented by any one of the following two formulas:

[Formula 44]

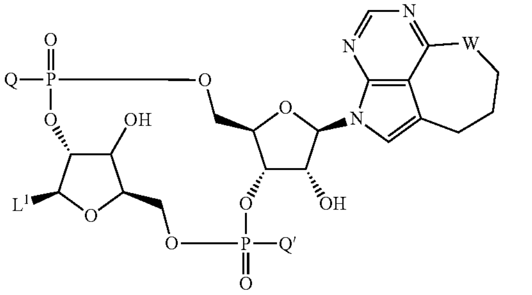

or

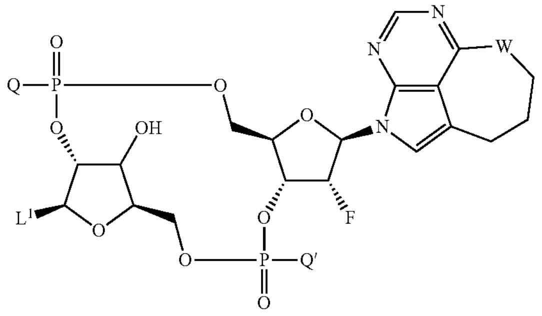

wherein $L^1$, Q, Q', and W are as specified in the above section <1. Novel CDN Derivative>.

Further, the drug D used in an antibody-drug conjugate of the present invention is preferably represented by any one of the following four formulas:

[Formula 45]

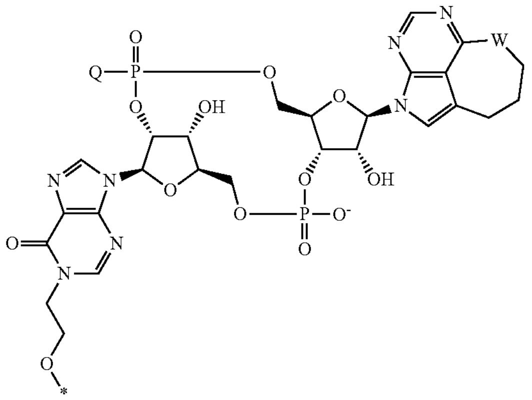

-continued

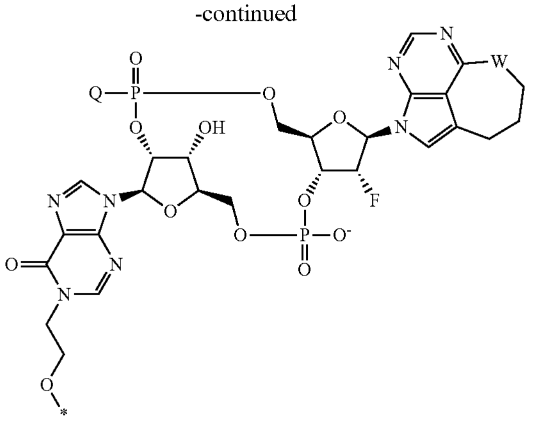

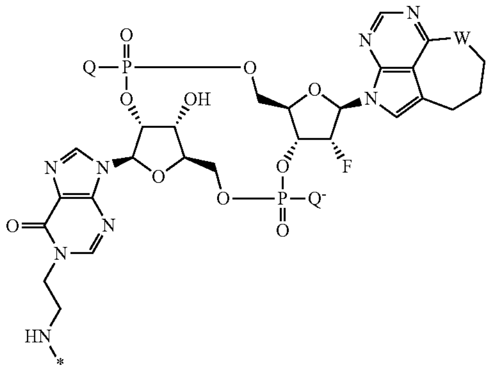

or

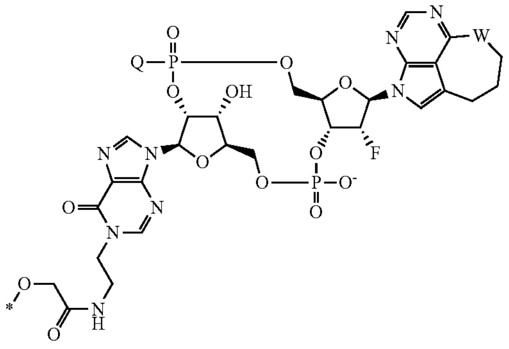

wherein the asterisk represents bonding to L, and Q, Q', and W are as specified in the above section <1. Novel CDN Derivative>.

Furthermore, the drug D used in an antibody-drug conjugate of the present invention is preferably represented by any of the following three formulas:

[Formula 46]

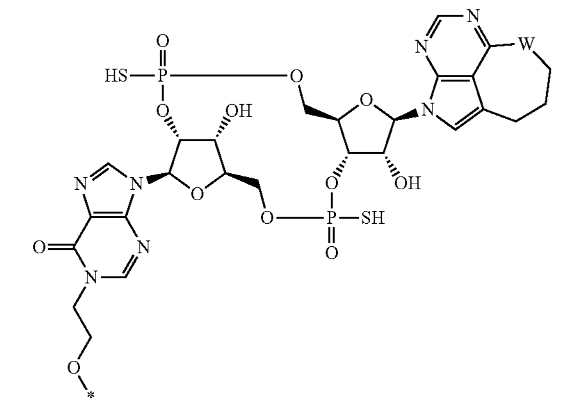

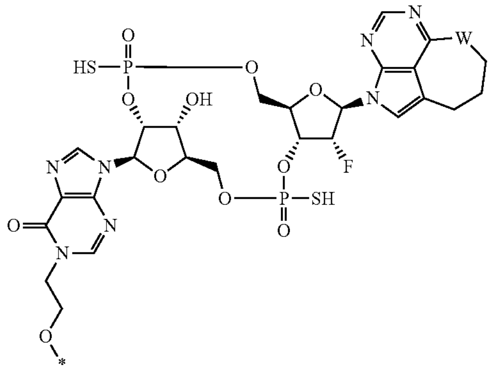

or

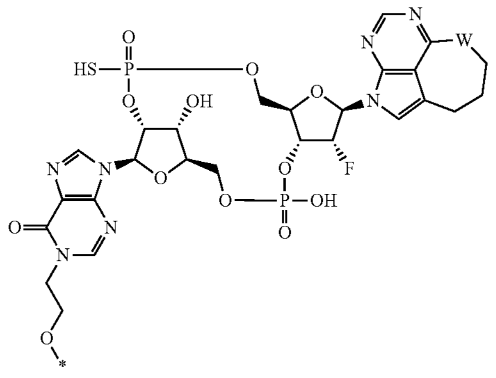

wherein the asterisk represents bonding to L, and W is as specified in the above section <1. Novel CDN Derivative>.

Furthermore, the drug D used in an antibody-drug conjugate of the present invention is preferably represented by any of the following three formulas.

[Formula 47]

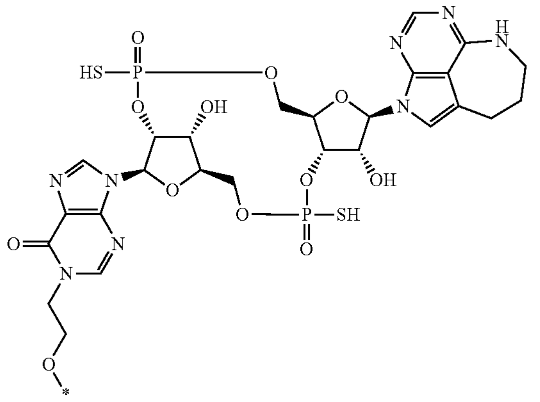

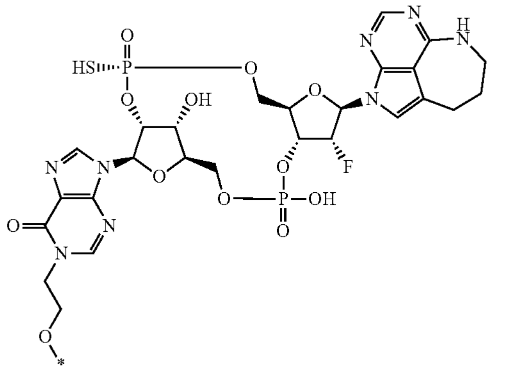

or

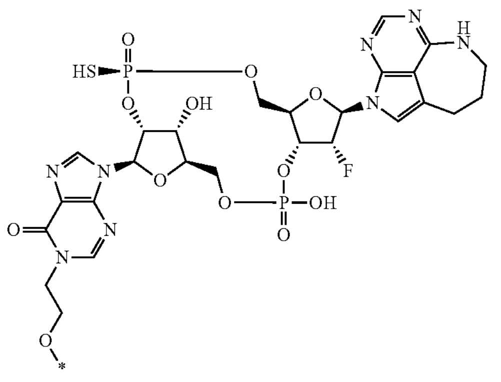

wherein the asterisk represents bonding to L.

Furthermore, the drug D used in an antibody-drug conjugate of the present invention is preferably represented by anyone of the following four formulas.

[Formula 48]

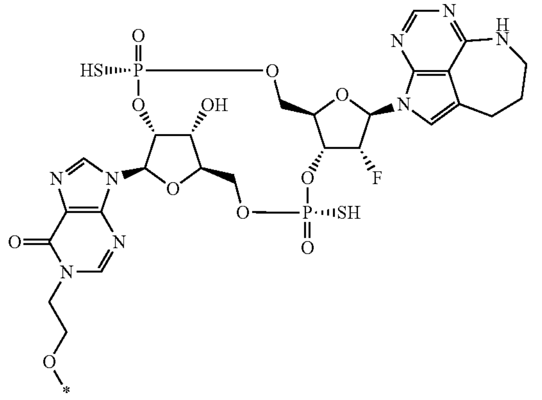

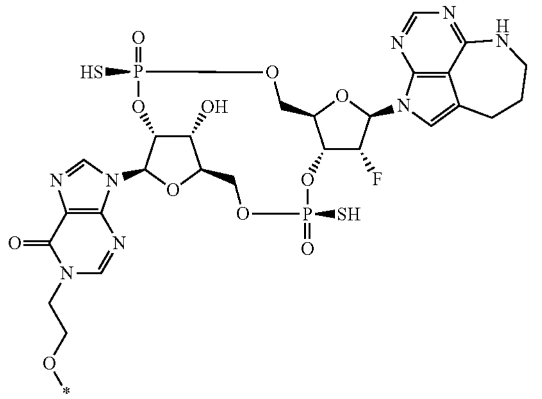

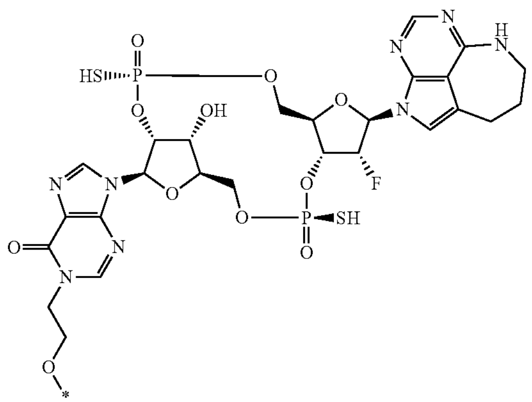

or

-continued

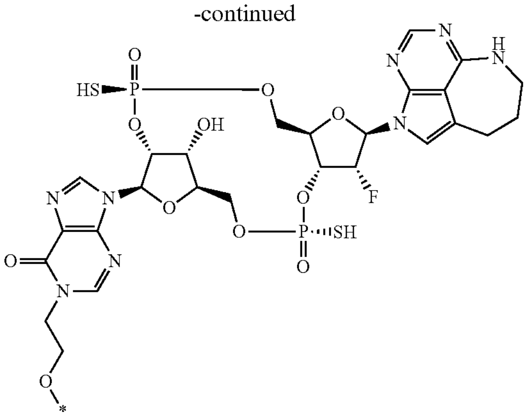

wherein the asterisk represents bonding to L.

Meanwhile, the drug D used in an antibody-drug conjugate of the present invention is more preferably represented by the following formula:

[Formula 49]

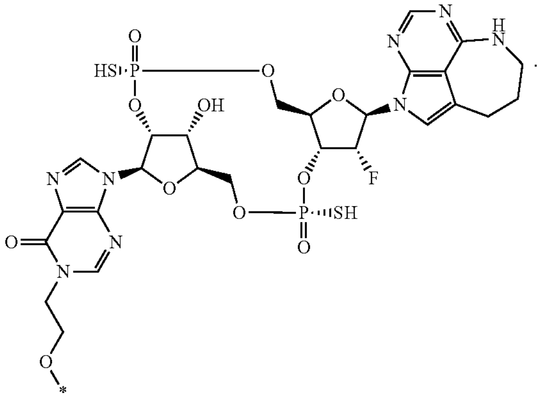

Also, the drug D used in an antibody-drug conjugate of the present invention is preferably represented by the following formula:

[Formula 50]

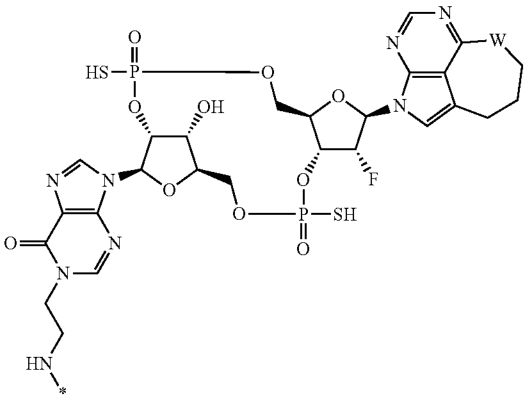

wherein the asterisk represents bonding to L, and W is as specified in the above section <1. Novel CDN Derivative>.

In addition, the drug D used in an antibody-drug conjugate of the present invention is preferably represented by any of the following two formulas:

[Formula 51]

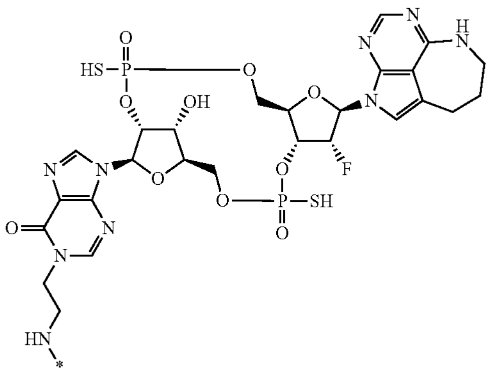

or

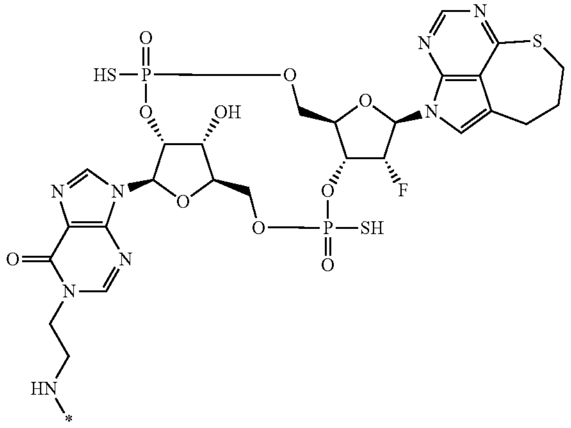

wherein the asterisk represents bonding to L.

Further, the drug D used in an antibody-drug conjugate of the present invention is preferably represented by the following formula:

[Formula 52]

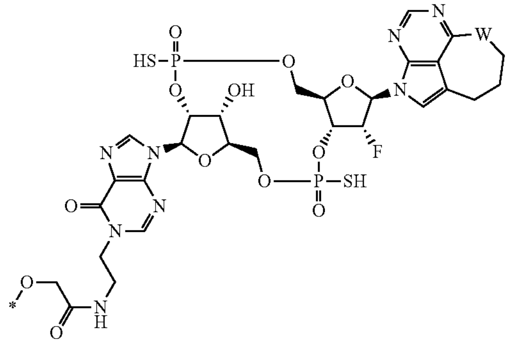

wherein the asterisk represents bonding to L, and W is as specified in the above section <1. Novel CDN Derivative>.

Furthermore, the drug D used in an antibody-drug conjugate of the present invention is preferably represented by any of the following two formulas:

[Formula 53]

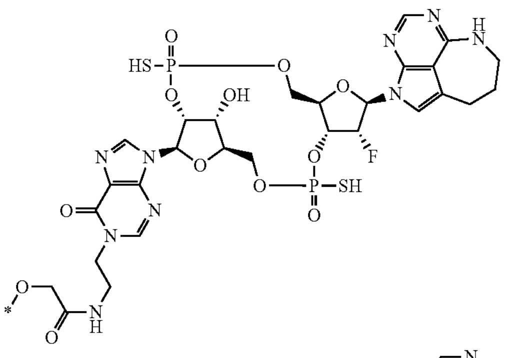

or

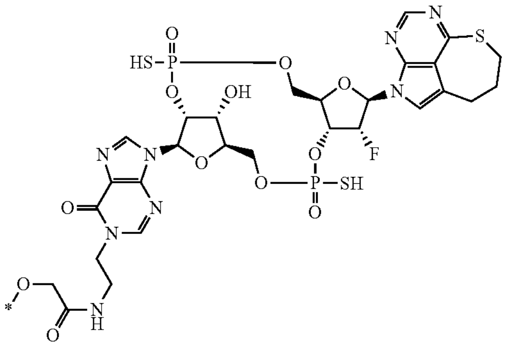

wherein the asterisk represents bonding to L.

<2.1. Linker Structure>

The following describes the structure of a linker used to conjugate a drug to an antibody in an antibody-drug conjugate of the present invention. The linker used in the antibody-drug conjugate of the present invention is not particularly limited if the linker is understandable by those skilled in the art as a linker that conjugates the antibody to the drug. Examples of the linker used in the antibody-drug conjugate of the present invention include, but are not limited to, those described in Protein Cell, 2018, 9(1): 33-46, Pharm Res, 2015, 32: 3526-3540, or Int. J. Mol. Sci, 2016, 17, 561. The linker can be a linker that is cleaved in vivo or a linker that is not cleaved in vivo, but preferably a linker that is cleaved in vivo.

Examples of the linker used in the antibody-drug conjugate of the present invention include, but are not limited to, a linker that conjugates the drug to a glycan or remodeled glycan of the Fc portion of the antibody (sometimes herein referred to as "glycan conjugation") (e.g., as described in WO2018/003983), or a linker that conjugates the drug to a given amino acid residue of the antibody (e.g., a cysteine or lysine residue) (e.g., described in WO2014/057687). The linker that conjugates the drug to a given amino acid residue of the antibody preferably involves the case of thioether bonding to the sulfhydryl group (SH group) of a cysteine of Ab (sometimes herein referred to as "cysteine conjugation") and the case of amide bonding to the amino group ($NH_2$ group) of a lysine of Ab (sometimes herein referred to as "lysine conjugation"). Preferred is cysteine conjugation.

The linker L used in an antibody-drug conjugate of the present invention is preferably represented by the following formula:

L*b*-La-L*p*-L*c*-* wherein the asterisk represents bonding to a drug D.

First, Lp will be described. Lp represents a linker consisting of an amino acid sequence that can be cleaved in vivo or in a target cell (sometimes herein referred to as a peptide linker), or is absent.

Lp can be cleaved, for example, by the action of enzyme such as a peptidase or esterase. Lp is a peptide containing 2 to 7 amino acids (preferably 2 to 4 amino acids). At its N-terminus, Lp forms an amide bond with the right end of the carbonyl group of La described below, and at its C-terminus, Lp forms an amide bond with the amino group (—NH—) of Lc. The amide bond on the C-terminal side of Lp is cleavable by enzyme such as a peptidase.

The amino acids constituting Lp are not particularly limited, but can be, for example, L- or D-amino acids, preferably L-amino acids. The structure of each amino acid may involve the structure of α-amino acid as well as β-alanine, ε-aminocaproic acid, or γ-aminobutyric acid. Further, each amino acid may be a non-natural amino acid such as an N-methylated amino acid. The amino acid sequence of Lp consists of the amino acids which include but are not particularly limited to, for instance, glycine (Gly; G), valine (Val; V), alanine (Ala; A), phenylalanine (Phe; F), glutamic acid (Glu; E), isoleucine (Ile; I), proline (Pro; P), citrulline (Cit), leucine(Leu; L), methionine (Met; M), serine (Ser; S), lysine (Lys; K), and aspartic acid (Asp; D). Among them, preferred are glycine (Gly; G), valine (Val; V), alanine (Ala; A), phenylalanine (Phe; F), citrulline (Cit), isoleucine (Ile; I), and proline (Pro; P). Any of these amino acids may appear multiple times, and Lp has an amino acid sequence including arbitrarily selected amino acids. Drug release pattern may be controlled via amino acid type.

Specific examples of Lp include -GGFG-, -GGPI-, -GGVA-, -GGFM-, -GGVCit-, -GGFCit-, -GGICit-, -GGPL-, -GGAQ-, and -GGPP-. The linker Lp is preferably -GGFG- or -GGPI-, and more preferably -GGFG-.

Next, La will be described. La is represented by any one selected from the following group consisting of:

$—C(=O)—(CH_2CH_2)n^2—C(=O)—$,
$—C(=O)—(CH_2CH_2)n^2—CH_2—C(=O)—$,
$—C(=O)—(CH_2CH_2)n^2—C(=O)—NH—(CH_2CH_2)n^3—C(=O)—$,
$—C(=O)—(CH_2CH_2)n^2—C(=O)—NH—(CH_2CH_2)n^3—CH_2—C(=O)—$,
$—C(=O)—(CH_2CH_2)n^2—C(=O)—NH—(CH_2CH_2O)n^3—CH_2—C(=O)—$,
$—(CH_2)n^4—O—C(=O)—$, and
$—(CH_2)n^9—C(=O)—$, wherein $n^2$ represents an integer from 1 to 3 (preferably, 1 or 2), $n^3$ represents an integer from 1 to 5 (preferably, an integer from 2 to 5, more preferably, 3 or 4), $n^4$ represents an integer from 0 to 2 (preferably, 0 or 1), and $n^9$ represents an integer from 2 to 7 (preferably, an integer from 2 to 5, and more preferably 2, 3, or 5).

La is preferably represented by any one selected from the following group consisting of:

$—C(=O)—CH_2CH_2—C(=O)—$,
$—C(=O)—CH_2CH_2—C(=O)—NH—(CH_2CH_2O)_3—CH_2—C(=O)—$,
$—C(=O)—CH_2CH_2—C(=O)—NH—(CH_2CH_2O)_4—CH_2—C(=O)—$,
$—C(=O)—(CH_2CH_2)_2—C(=O)—$,
$—C(=O)—CH_2CH_2—C(=O)—NH—(CH_2CH_2)_2—C(=O)—$,
$—C(=O)—CH_2CH_2—C(=O)—NH—(CH_2CH_2)_2—CH_2—C(=O)—$,
$—CH_2—OC(=O)—$,
$—OC(=O)—$, and
$—(CH_2)_5—C(=O)—$.

La is more preferably $—C(=O)—CH_2CH_2—C(=O)—$,
$—C(=O)—CH_2CH_2—C(=O)—NH—(CH_2CH_2O)_3—CH_2—C(=O)—$,
$—C(=O)—CH_2CH_2—C(=O)—NH—(CH_2CH_2O)_4—CH_2—C(=O)—$, or
$—(CH_2)_5—C(=O)—$.

La is further preferably $—C(=O)—CH_2CH_2—C(=O)—$.

Next, Lb will be described. Lb represents a spacer used in the linker for glycan conjugation (also herein referred to as a "spacer of linker for glycan conjugation"), or a spacer used in the linker for cysteine conjugation (also herein referred to as a "spacer of linker for cysteine conjugation").

<Case Where Lb Is "Spacer of Linker for Glycan Conjugation">

In the case where Lb is a "spacer of linker for glycan conjugation", examples of Lb include, but are not particularly limited to, each spacer represented by the following formulas:

[Formula 54]

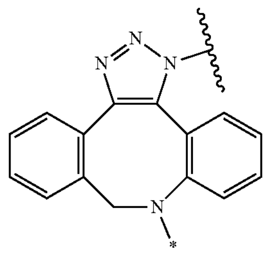

or

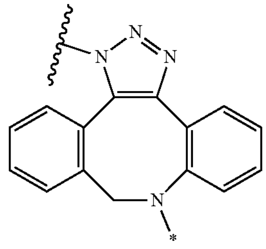

or (Lb-1)

[Formula 55]

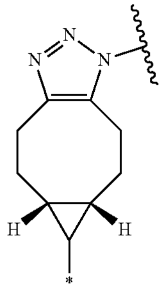

or

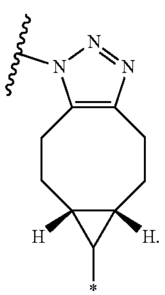

(Lb-3)

In each structural formula shown above, the asterisk represents bonding to the left end of —(C=O)—, $—CH_2—$, or —OC(=O)—. Each wavy line represents bonding to a glycan or remodeled glycan of Ab.

In the case where Lb-1 or Lb-3 is selected as Lb, the triazole ring site provides structures of geometric isomers and contains any one of the two structures or a mixture of both of them in one Lb. The antibody-drug conjugate of the present invention allows multiple drugs to be conjugated to a single antibody molecule. When multiple drugs are conjugated to a single antibody molecule, a plurality of Lb portions are also present (e.g., see the scheme (1e) of the antibody-drug conjugate as shown in Method E of <3. Production Methods>described later). When Lb is selected from Lb-1 or Lb-3 and there are multiple Lb molecules for one antibody molecule (e.g., when $m^2$ is 1 or 2 as described below), the triazole ring site has a geometric isomer structure in each Lb, and contains either one of the two structures or a mixture of them in one Lb.

<Case Where Lb Is "Spacer of Linker for Cysteine Conjugation">

In the case where Lb is a "spacer of linker for cysteine conjugation", examples of Lb include, but are not particularly limited to, -(succinimid-3-yl-N)-. In the present invention, "-(succinimid-3-yl-N)-" has the structure represented by the following formula:

[Formula 56]

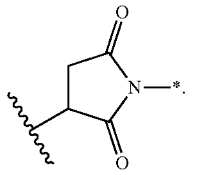

In the structural formula shown above, the asterisk represents bonding to La. The wavy line represents bonding, through thioether formation, to a side chain of cysteine residue of an antibody.

Next, Lc will be described. Lc represents $-NH-CH_2-$, $-NH\text{-phenyl-}CH_2-O(C{=}O)-$, or $-NH\text{-heteroaryl-}CH_2-O(C{=}O)-$, or is absent. Here, the phenyl group is preferably a 1,4-phenyl group. The heteroaryl group is preferably a 2,5-pyridyl group, a 3,6-pyridyl group, a 2,5-pyrimidyl group, or a 2,5-thienyl group. Lc is preferably $-NH-CH_2-$, or is absent.

In the case where the form of antibody-drug conjugation is "glycan conjugation", a more preferred linker L used in the antibody-drug conjugate of the present invention is $-Z^{L1}-C(=O)-CH_2CH_2-C(=O)$-GGFG-,
$-Z^{L1}-C(=O)-CH_2CH_2-C(=O)$-GGVA-,
$-Z^{L1}-C(=O)-CH_2CH_2-C(=O)$-GGVCit-,
$-Z^{L1}-C(=O)-CH_2CH_2-C(=O)$-GGFCit-,
$-Z^{L1}-C(=O)-CH_2CH_2-C(=O)$-GGICit-,
$-Z^{L1}-C(=O)-CH_2CH_2-C(=O)$-GGFM-,
$-Z^{L1}-C(=O)-CH_2CH_2-C(=O)$-GGPI-,
$-Z^{L1}-C(=O)-CH_2CH_2-C(=O)$-GGLM-,
$-Z^{L1}-C(=O)-CH_2CH_2-C(=O)$-FG-,
$-Z^{L1}-C(=O)-CH_2CH_2-C(=O)$-VA-,
$-Z^{L1}-C(=O)-CH_2CH_2-C(=O)$-GGFG-$NH-CH_2-$,
$-Z^{L1}-C(=O)-CH_2CH_2-C(=O)$-GGVA-$NH-CH_2-$,
$-Z^{L1}-C(=O)-CH_2CH_2-C(=O)$-GGVCit-$NH-CH_2-$,
$-Z^{L1}-C(=O)-CH_2CH_2-C(=O)$-GGFCit-$NH-CH_2-$,
$-Z^{L1}-C(=O)-CH_2CH_2-C(=O)-NH-(CH_2CH_2O)_3-CH_2-C(=O)-$, or
$-Z^{L1}-C(=O)-CH_2CH_2-C(=O)-NH-(CH_2CH_2O)_4-CH_2-C(=O)-$, where $Z^{L1}$ represents the following structural formula as described for Lb.

[Formula 57]

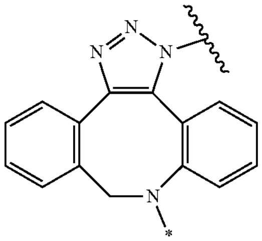

or

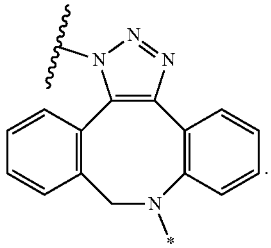

Alternatively, in the case where the form of the drug-antibody conjugation is "cysteine conjugation", the linker L is $-Z^{L2}-(CH_2)_5-C(=O)$-GGFG-,
$-Z^{L2}-(CH_2)_5-C(=O)$-GGVA-,
$-Z^{L2}-(CH_2)_5-C(=O)$-GGVCit-,
$-Z^{L2}-(CH_2)_5-C(=O)$-GGFCit-,
$-Z^{L2}-(CH_2)_5-C(=O)$-GGICit-,
$-Z^{L2}-(CH_2)_5-C(=O)$-GGFM-,
$-Z^{L2}-(CH_2)_5-C(=O)$-GGPI-,
$-Z^{L2}-(CH_2)_5-C(=O)$-GGLM-,
$-Z^{L2}-(CH_2)_5-C(=O)$-FG-,
$-Z^{L2}-(CH_2)_5-C(=O)$-VA-,
$-Z^{L2}-(CH_2)_5-C(=O)$-GGFG-$NH-CH_2-$,
$-Z^{L2}-(CH_2)_5-C(=O)$-GGVA-$NH-CH_2-$,
$-Z^{L2}-(CH_2)_5-C(=O)$-GGVCit-$NH-CH_2-$,
$-Z^{L2}-(CH_2)_5-C(=O)$-GGFCit-$NH-CH_2-$,
$-Z^{L2}-(CH_2)_5-C(=O)-NH-(CH_2CH_2O)_3-CH_2-C(=O)-$, or
$-Z^{L2}-(CH_2)_5-C(=O)-NH-(CH_2CH_2O)_4-CH_2-C(=O)-$, where $Z^{L2}$ represents -(succinimid-3-yl-N)- represented by the following structural formula as described for Lb.

[Formula 58]

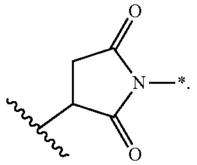

While the form of antibody-drug conjugation is "glycan conjugation", a more preferred linker L used in the antibody-drug conjugate of the present invention is $-Z^{L1}-C(=O)-CH_2CH_2-C(=O)$-GGFG-$NH-CH_2-$, or
$-Z^{L1}-C(=O)-CH_2CH_2-C(=O)$-GGPI-$NH-CH_2-$, where $Z^{L1}$ represents the following structural formula as described for Lb:

[Formula 59]

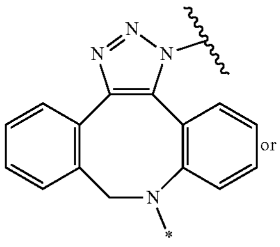

or

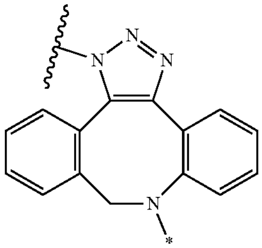

.

[Formula 60]

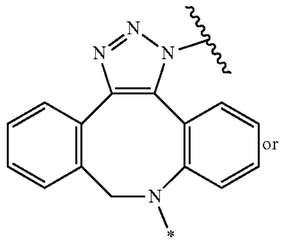

or

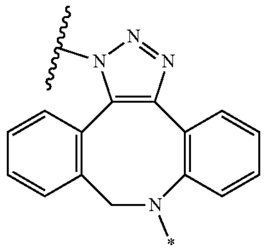

.

While the form of antibody-drug conjugation is "glycan conjugation", a further more preferred linker L used in the antibody-drug conjugate of the present invention is

-$Z^{L1}$-C(=O)—$CH_2CH_2$—C(=O)-GGFG-NH—$CH_2$—, where $Z^{L}$1 represents the following structural formula as described for Lb:

The right end of the above "preferred linker L", "more preferred linker L", "further preferred linker L", or "further more preferred linker L" is linked to the drug D.

A "linker L-drug D" used in an antibody-drug conjugate of the present invention is preferably represented by the following two formulas:

[Formula 61]

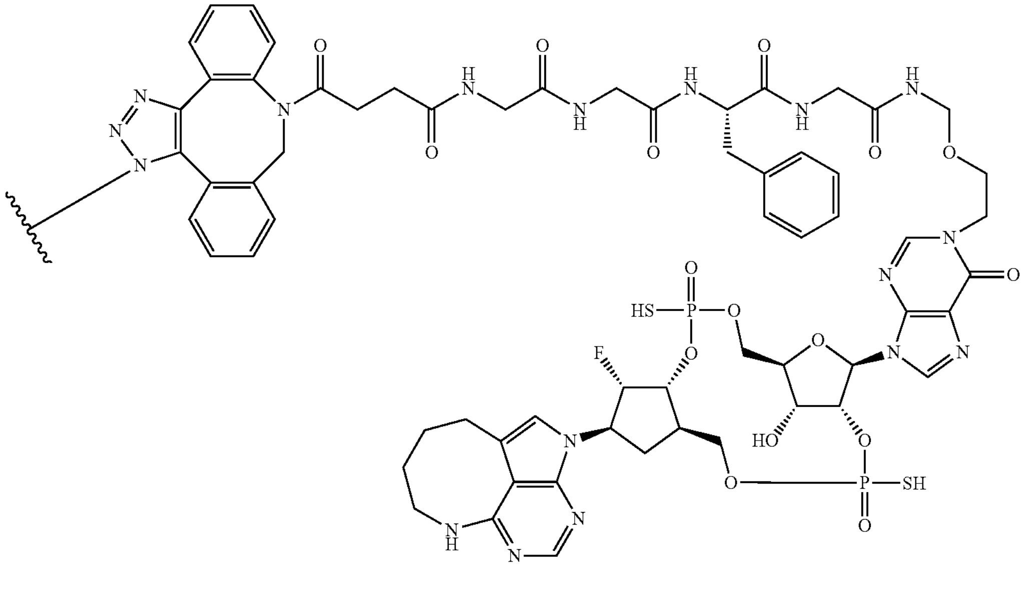

or

-continued
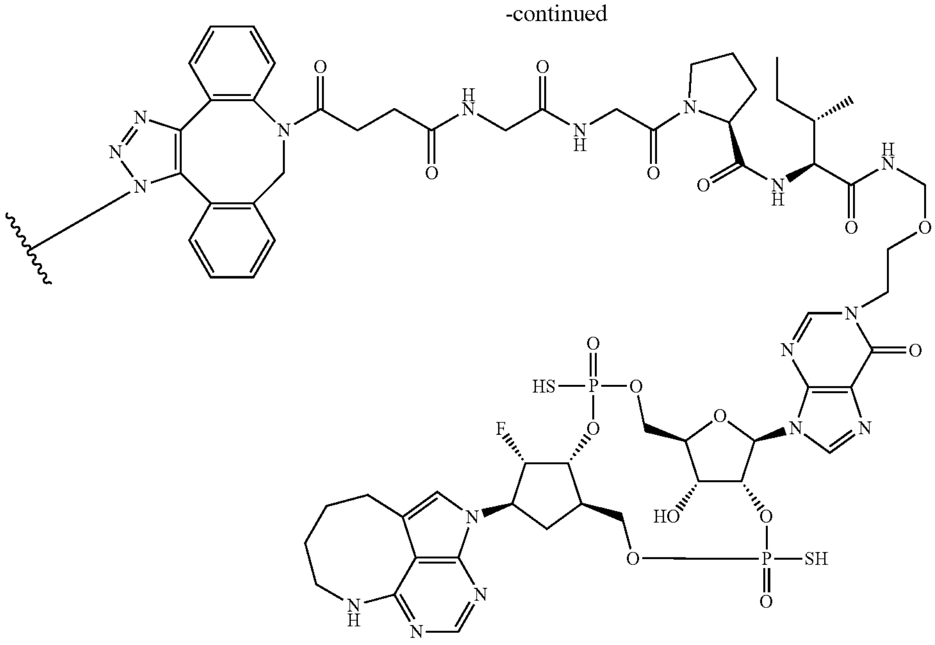
wherein the wavy line represents bonding to a glycan or remodeled glycan of Ab.
The "linker L-drug D" used in an antibody-drug conjugate of the present invention is more preferably represented by the following two formulas:
[Formula 62]
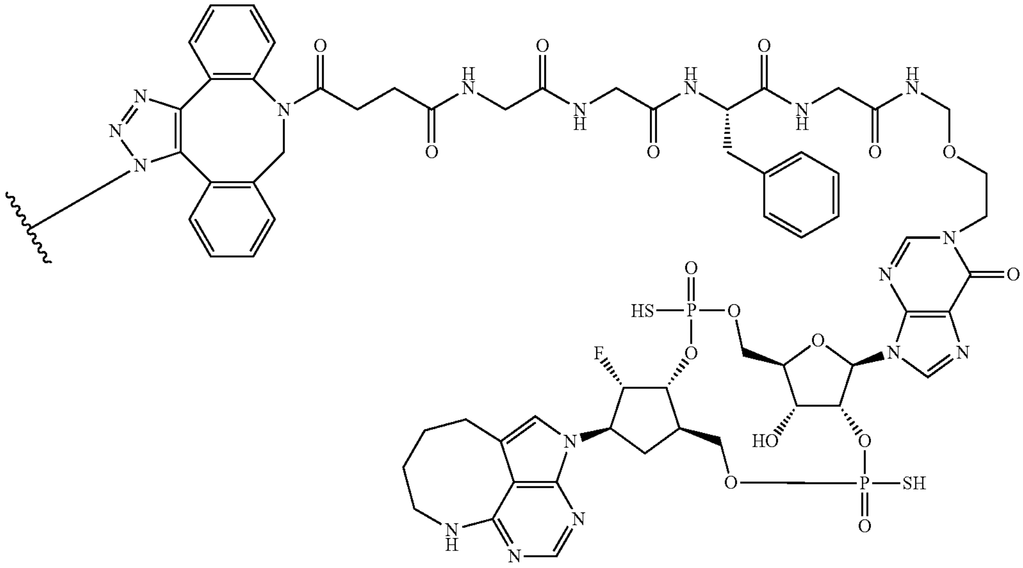
or -continued

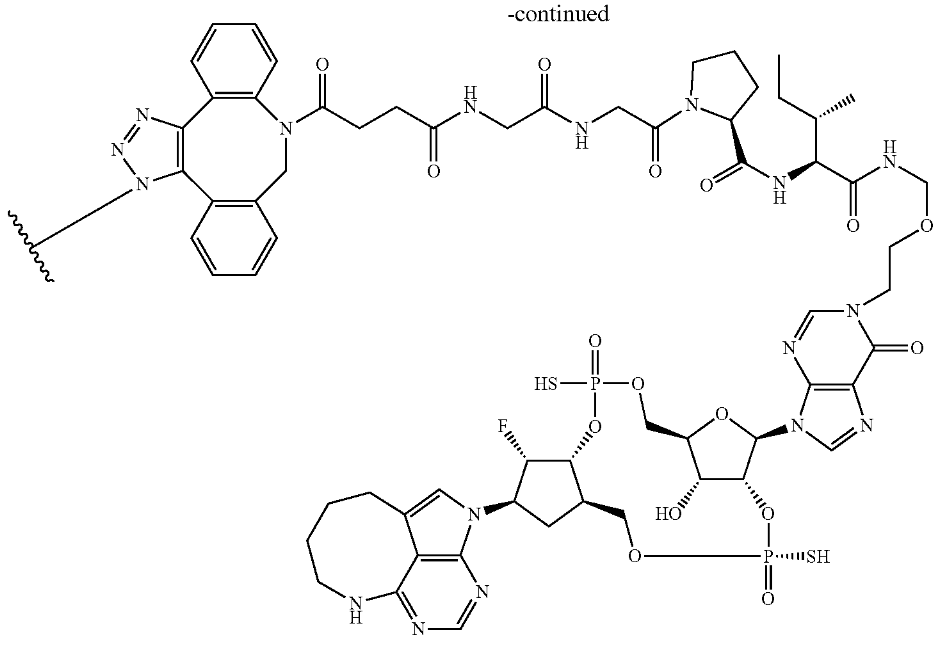

wherein the wavy line represents bonding to a glycan or remodeled glycan of Ab.

The “linker L-drug D” used in an antibody-drug conjugate of the present invention is further preferably represented by the following formula:

[Forrmula 63]

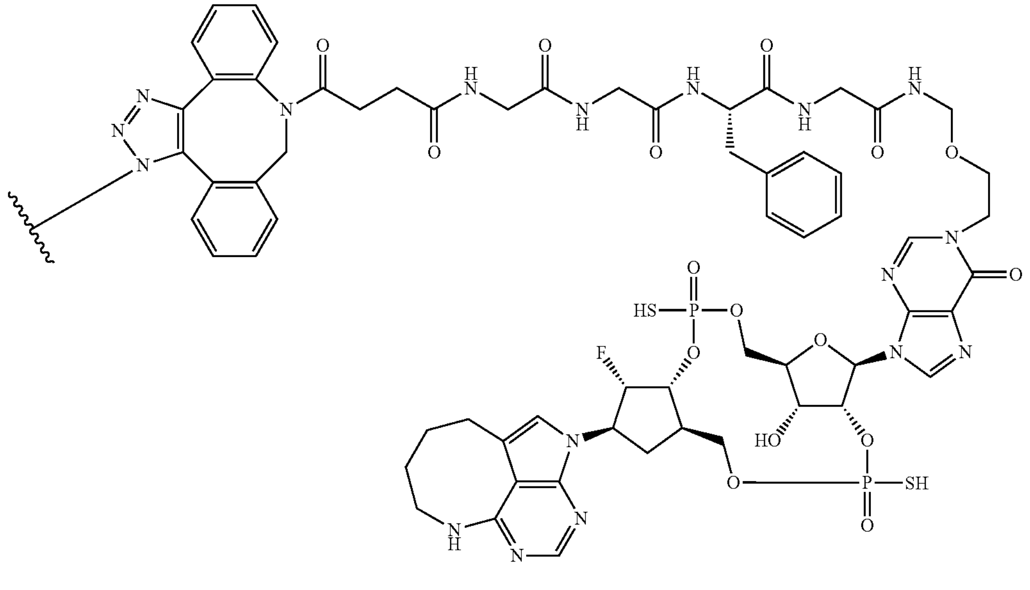

wherein the wavy line represents bonding to a glycan or remodeled glycan of Ab.

[0087]<2.2. Antibody and Its Glycosylation>

<2.2.1 Antibody>

Herein, a “gene” refers to nucleotides or a nucleotide sequence including a nucleotide sequence encoding amino acids of protein or a complementary strand thereof. The meaning of a “gene” encompasses, for example, a polynucleotide, an oligonucleotide, DNA, mRNA, cDNA, and RNA as a nucleotide sequence including a nucleotide sequence encoding amino acids of protein or a complementary strand thereof.

Herein, “nucleotides”, “polynucleotide”, and “nucleotide sequence” have the same meaning as that of “nucleic acids”, and the meaning of “nucleotides” and “nucleotide sequence” encompasses, for example, DNA, RNA, a probe, an oligonucleotide, a polynucleotide, and a primer.

Herein, “polypeptide”, “peptide”, and “protein” are used interchangeably.

Herein, the "functional fragment of antibody" is sometimes called a "antigen-binding fragment of antibody", and means a partial fragment of antibody having antigen-binding activity. Examples thereof include Fab, $F(ab')_2$, Fv, scFv, diabody, linear antibody or multispecific antibody formed using an antibody fragment(s), etc. Fab', which is a monovalent fragment of a variable region of antibody, obtained by treating $F(ab')_2$ under reducing conditions, is also included in the antigen-binding fragment of antibody. Provided that the fragment is not limited to these molecules as long as having an ability to bind to an antigen. In addition, these antigen-binding fragments include not only those obtained by treating a full-length molecule of antibody protein with appropriate enzyme, but also proteins produced in appropriate host cells by using a gene which is modified by genetic engineering.

The antibody functional fragment used in an antibody-drug conjugate of the present invention include a functional fragment having asparagine (Asn297) and amino acids around the asparagine, which asparagine is modified by N-linked glycan which is well-conserved in the Fc region of IgG heavy chain, wherein the functional fragment has an ability to bind to an antigen.

The antibody used in the antibody-drug conjugate of the present invention means an immunoglobulin, which is a molecule containing an antigen-binding site where an antigen can be immunospecifically bound. The antibody used in the antibody-drug conjugate of the present invention may be any of class IgG, IgE, IgM, IgD, IgA, or IgY, and preferred is IgG. In addition, its subclass may be any of IgG1, IgG2, IgG3, IgG4, IgAQ1, or IgA2, and preferred is IgG1, IgG2, or IgG4 (including an antibody with a mutation affecting the ADCC and/or ADCP activities in an Fc region of IgG heavy chain).

In the case where IgG1 is used as the isotype of antibody used in the antibody-drug conjugate of the present invention, the effector function may be adjusted by substituting a part of amino acid residues in the constant region (see WO88/07089, WO94/28027, WO94/29351). Examples of variants of IgG1 include IgG1 LALA mutant (IgG1-L234A, L235A). The L234A, L235A represents substitution of leucine with alanine at the 234- and 235-positions specified by EU-index numbering (Proceedings of the National Academy of Sciences of the United States of America, Vol. 63, No. 1 (May 15, 1969), pp. 78-85).

The constant region of antibody is known to have multiple allotypes. Examples of IgG1 heavy chain include G1ml7, Glm3, G1 ml, and Glm2. Preferable examples of the constant region of antibody used in the present invention include, but are not particularly limited to, G1m17 or G1m3.

It is known that each of heavy chains and light chains of an antibody molecule has three complementarity determining regions (CDRs). CDRs, which are also called a hypervariable region, are located in variable regions of heavy chains and light chains of an antibody and is a site with particularly high variation of the primary structure. Three CDRs are separately located in the primary structure of the polypeptide chain of heavy chains and light chains. Regarding CDRs of antibodies, herein, CDRs of a heavy chain refer to CDRH1, CDRH2, and CDRH3 from the amino terminal side of the heavy chain amino acid sequence, and CDRs of a light chain refer to CDRL1, CDRL2, and CDRL3 from the amino terminal side of the light chain amino acid sequence. These sites are located in the proximity of each other in the three-dimensional structure, determining specificity to an antibody to bind.

The antibody may be derived from any species. Preferable examples include a human, a rat, a mouse, or a rabbit. In the case where the antibody is derived from a species other than human, it is preferable to chimerize or humanize the antibody using well-known techniques. The antibody of the present invention may be a polyclonal or monoclonal antibody, and is preferably a monoclonal antibody. Examples of the monoclonal antibody include each monoclonal antibody derived from a non-human animal (e.g., a rat, a mouse, and a rabbit antibodies), a chimeric antibody, a humanized antibody, a human antibody, or a functional fragment thereof, or a modified antibody thereof.

The antibody is preferably an antibody targeting a tumor cell or an immune cell, but is not limited thereto. The antibody is more preferably an antibody against a tumor cell as a target.

The antibody may be used against a tumor cell as a target. In this case, it is preferable that the antibody should have one or more of the following characteristics: the ability to recognize tumor cells, the ability to bind to tumor cells, the ability to be taken-up and internalized by tumor cells, and the ability to damage tumor cells. The drug used in an antibody-drug conjugate of the present invention has STING agonist activity. The drug induces interferons by activating the signaling of interferon regulatory factor-3 (IRF3). Accordingly, the antibody against tumor cells as a target may be used in the antibody-drug conjugate of the present invention. In this case, the antibody-drug conjugate is administered into the body, delivered to the tumor site, and taken up by the tumor cells; and the linker portion is then cleaved by, for instance, peptidase to release the drug moiety. The released drug moiety is thought to increase the sensitivity of the tumor cell to immune cells through STING agonist activity and to stimulate anti-tumor immunity, thereby exerting an anti-tumor effect. Alternatively, even if the antibody-drug conjugate accumulated on the tumor cells is not internalized, the tumor cells and/or the antibody-drug conjugate are/is taken up by the immune cells by phagocytosis. Then, anti-tumor immunity is stimulated through STING agonist activity, and an anti-tumor effect may be exerted.

The binding activity of the antibody against tumor cells can be confirmed using flow cytometry. The incorporation of the antibody into tumor cells can be checked using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may also be used.

In the case where an antibody against tumor cells is used in an antibody-drug conjugate of the present invention, it is desirable, but not essential, that the antibody itself has an anti-tumor effect.

The anti-tumor activity of the drug and the antibody-drug conjugate refers to cytotoxic activity on tumor cells, anti-cellular effects, and regression of the tumor volume. The anti-tumor activity can be checked by using a known in vitro or in vivo evaluation system.

The action and immunostimulatory activity of the drug and the antibody-drug conjugate refer to the increased sensitivity of tumor cells to immune cells or the activation of immune cells via tumor cells. Known in vitro or in vivo evaluation systems can be used to check the action and immunostimulatory activity of the drug and the antibody-drug conjugate.

Examples of the in vitro or in vivo evaluation system that can be used in the present invention can include, but are not limited to, a co-culture assay system, described in Test Example 4, using CT26.WT and CT26.WT-hCD70 cell lines and mouse bone marrow-derived dendritic cells; a BALB/c mouse system, described in Test Example 5, using subcutaneously implanted CT26.WT-hTROP2 cells in which the human TROP2 gene has been introduced into a mouse colon cancer cell line CT26.WT; a BALB/c mouse system, described in Test Example 6, using subcutaneously implanted CT26.WT-hEGFR cells in which the human EGFR gene has been introduced into a mouse colon cancer cell line CT26.WT; a BALB/c-nu mouse system, described in Test Example 7, using subcutaneously transplanted cells of a human renal cancer cell line Caki-1; a BALB/c-nu mouse system, described in Test Example 8, using subcutaneously transplanted cells of a human renal cancer cell line A-498 (HTB-44); and a BALB/c mouse system, described in Test Example 9, using a subcutaneously transplanted mouse colon cancer cell line CT26.WT (CRL2638) with a human-mouse chimeric antigen gene in which an epitope site on an antigen bound by the antibody included in the antibody-drug conjugate is replaced by a human counterpart.

Examples of the antibody used in the present invention include an anti-CD70 antibody, anti-TROP2 antibody, or anti-EGFR antibody.

The antibody used in the present invention can be obtained by immunizing an animal with a polypeptide that serves as an antigen, and collecting and purifying the antibody produced in vivo, while using the methods routinely implemented in the art. The origin of the antigen is not limited to a human, and each animal can also be immunized with the antigen derived from a non-human animal (e.g., a mouse, a rat). In this case, any antibody applicable to human diseases can be selected by testing the cross-reactivity between the obtained antibody that can bind to a heterologous antigen and the corresponding human antigen.

Alternatively, antibody-producing cells which produce antibodies against the antigen are fused with myeloma cells according to the method known in the art (e.g., Kohler and Milstein, Nature (1975) 256, p.495-497; Kennett, R. ed., Monoclonal Antibodies, p.365-367, Plenum Press, N.Y. (1980)) to establish hybridomas, from which monoclonal antibodies can in turn be obtained.

Note that the antigen can be obtained by genetically engineering a host cell to produce an antigen protein encoded by a gene of interest.

The antibody used in the antibody-drug conjugate of the present invention can be obtained according to the known methods (e.g., Proc. Natl. Acad. Sci. U.S.A., 81, 6851-6855, (1984); Nature (1986) 321, p.522-525, WO90/07861).

For example, an anti-CD70 antibody (e.g., WO2004/073656, WO2007/038637), anti-TROP2 antibody (e.g., WO2015/098099), and anti-EGFR antibody (e.g., WO1998/050433, WO2002/092771) can be obtained by known procedures.

The anti-CD70 antibody used in the present invention is not particularly limited, and should have, for example, the following characteristics.

(1) An anti-CD70 antibody capable of specifically binding to CD70.

(2) The antibody described in (1), wherein the antibody can bind to an extracellular domain of human CD70.

(3) The antibody described in (1) or (2), wherein the antibody is a monoclonal antibody.

(4) The antibody described in any of (1) to (3), wherein the antibody has antibody-dependent cell-mediated cytotoxicity (ADCC) and/or complement-dependent cytotoxicity (CDC).

(5) The antibody described in any of (1) to (4), wherein the antibody is a mouse monoclonal antibody, a chimeric monoclonal antibody, a human monoclonal antibody, or a humanized monoclonal antibody.

(6) The antibody described in any of (1) to (3), wherein a heavy chain constant region thereof is a heavy chain constant region of human IgG1 and includes a mutation which cause a decrease in ADCC and ADCP activities.

(7) The antibody described in (5), wherein a heavy chain constant region thereof is a heavy chain constant region of human IgG1 and leucine residues at the 234- and 235-positions specified by EU Index numbering are substituted with alanine residues.

(8) The antibody described in (7), wherein the antibody is a humanized monoclonal antibody comprising a heavy chain consisting of the amino acid sequence set forth in SEQ ID NO: 2 and a light chain consisting of the amino acid sequence set forth in SEQ ID NO: 1.

(9) The antibody described in (7), wherein the antibody is a humanized monoclonal antibody comprising a heavy chain consisting of the amino acid sequence set forth in SEQ ID NO: 4 and a light chain consisting of the amino acid sequence set forth in SEQ ID NO: 3.

(10) The antibody described in (7), wherein the antibody is a humanized monoclonal antibody comprising: a light chain comprising CDRL1 consisting of the amino acid sequence set forth in SEQ ID NO: 35, CDRL2 consisting of the amino acid sequence set forth in SEQ ID NO: 36, and CDRL3 consisting of the amino acid sequence set forth in SEQ ID NO: 37; and a heavy chain comprising CDRH1 consisting of the amino acid sequence set forth in SEQ ID NO: 38, CDRH2 consisting of the amino acid sequence set forth in SEQ ID NO: 39, and CDRH3 consisting of the amino acid sequence set forth in SEQ ID NO: 40.

(11) The antibody described in (7), wherein the antibody is a humanized monoclonal antibody comprising: a light chain comprising CDRL1 consisting of the amino acid sequence set forth in SEQ ID NO: 41, CDRL2 consisting of the amino acid sequence set forth in SEQ ID NO: 42, and CDRL3 consisting of the amino acid sequence set forth in SEQ ID NO: 43; and a heavy chain comprising CDRH1 consisting of the amino acid sequence set forth in SEQ ID NO: 44, CDRH2 consisting of the amino acid sequence set forth in SEQ ID NO: 45, and CDRH3 consisting of the amino acid sequence set forth in SEQ ID NO: 46.

(12) The antibody described in any of (1) to (11), wherein one or two amino acids are deleted at a heavy chain carboxyl terminus.

(13) An antibody obtained by a method for producing the antibody, the method comprising the steps of culturing a host cell transfected with an expression vector containing a polynucleotide encoding the antibody described in any of (1) to (12), and collecting the antibody of interest from the resulting culture obtained in the former step.

Examples of the anti-CD70 antibody can include vorsetuzumab, MDX-1115, and cusatuzumab. Preferable examples include vorsetuzumab or MDX-1115.

The anti-TROP2 antibody used in the present invention is not particularly limited, and should have, for example, the following characteristics.

(1) An anti-TROP2 antibody capable of specifically binding to TROP2.

(2) The antibody described in (1), wherein the antibody can bind to an extracellular domain of human TROP2.

(3) The antibody described in (1) or (2), wherein the antibody is a monoclonal antibody.

(4) The antibody described in any of (1) to (3), wherein the antibody has antibody-dependent cell-mediated cytotoxicity (ADCC) activity and/or complement-dependent cytotoxicity (CDC) activity.

(5) The antibody described in any of (1) to (4), wherein the antibody is a mouse monoclonal antibody, a chimeric monoclonal antibody, a human monoclonal antibody, or a humanized monoclonal antibody.

(6) The antibody described in any of (1) to (3), wherein a heavy chain constant region thereof is a heavy chain constant region of human IgG1 and includes a mutation which cause a decrease in ADCC and ADCP activities.

(7) The antibody described in any of (1) to (4), wherein the antibody is a humanized monoclonal antibody comprising a heavy chain consisting of the amino acid sequence set forth in SEQ ID NO: 6 and a light chain consisting of the amino acid sequence set forth in SEQ ID NO: 5.

(8) The antibody described in (5), wherein a heavy chain constant region thereof is a heavy chain constant region of human IgG1 and leucine at the 234- and 235-positions specified by EU Index numbering are substituted with alanine.

(9) The antibody described in (8), wherein the antibody is a humanized monoclonal antibody comprising a heavy chain consisting of the amino acid sequence set forth in SEQ ID NO: 8 and a light chain consisting of the amino acid sequence set forth in SEQ ID NO: 7.

(10) The antibody described in (8), wherein the antibody is a humanized monoclonal antibody comprising: a light chain comprising CDRL1 consisting of the amino acid sequence set forth in SEQ ID NO: 47, CDRL2 consisting of the amino acid sequence set forth in SEQ ID NO: 48, and CDRL3 consisting of the amino acid sequence set forth in SEQ ID NO: 49; and a heavy chain comprising CDRH1 consisting of the amino acid sequence set forth in SEQ ID NO: 50, CDRH2 consisting of the amino acid sequence set forth in SEQ ID NO: 51, and CDRH3 consisting of the amino acid sequence set forth in SEQ ID NO: 52.

(11) The antibody described in (8), wherein the antibody is a humanized monoclonal antibody comprising: a light chain comprising CDRL1 consisting of the amino acid sequence set forth in SEQ ID NO: 53, CDRL2 consisting of the amino acid sequence set forth in SEQ ID NO: 54, and CDRL3 consisting of the amino acid sequence set forth in SEQ ID NO: 55; and a heavy chain comprising CDRH1 consisting of the amino acid sequence set forth in SEQ ID NO: 56, CDRH2 consisting of the amino acid sequence set forth in SEQ ID NO: 57, and CDRH3 consisting of the amino acid sequence set forth in SEQ ID NO: 58.

(12) The antibody described in any of (1) to (11), wherein one or two amino acids are deleted at a heavy chain carboxyl terminus.

(13) An antibody obtained by a method for producing the antibody, the method comprising the steps of culturing a host cell transfected with an expression vector containing a polynucleotide encoding the antibody described in any of (1) to (12), and collecting the antibody of interest from the resulting culture obtained in the former step.

The anti-EGFR antibody used in the present invention is not particularly limited, and should have, for example, the following characteristics.

(1) An anti-EGFR antibody capable of specifically binding to EGFR.

(2) The antibody described in (1), wherein the antibody can bind to an extracellular domain of human EGFR.

(3) The antibody described in (1) or (2), wherein the antibody is a monoclonal antibody.

(4) The antibody described in any of (1) to (3), wherein the antibody has antibody-dependent cell-mediated cytotoxicity (ADCC) and/or complement-dependent cytotoxicity (CDC).

(5) The antibody described in any of (1) to (4), wherein the antibody is a mouse monoclonal antibody, a chimeric monoclonal antibody, a human monoclonal antibody, or a humanized monoclonal antibody.

(6) The antibody described in any of (1) to (3), wherein a heavy chain constant region thereof is a heavy chain constant region of human IgG1 and includes a mutation which cause a decrease in ADCC and ADCP activities.

(7) The antibody described in (5), wherein a heavy chain constant region thereof is a heavy chain constant region of human IgG1 and leucine residues at the 234- and 235-positions specified by EU Index numbering are substituted with alanine residues.

(8) The antibody described in (7), wherein the antibody is a humanized monoclonal antibody comprising a heavy chain consisting of the amino acid sequence set forth in SEQ ID NO: 10 and a light chain consisting of the amino acid sequence set forth in SEQ ID NO: 9.

(9) The antibody described in (7), wherein the antibody is a humanized monoclonal antibody comprising a heavy chain consisting of the amino acid sequence set forth in SEQ ID NO: 12 and a light chain consisting of the amino acid sequence set forth in SEQ ID NO: 11.

(10) The antibody described in (7), wherein the antibody is a humanized monoclonal antibody comprising: a light chain comprising CDRL1 consisting of the amino acid sequence set forth in SEQ ID NO: 59, CDRL2 consisting of the amino acid sequence set forth in SEQ ID NO: 60, and CDRL3 consisting of the amino acid sequence set forth in SEQ ID NO: 61; and a heavy chain comprising CDRH1 consisting of the amino acid sequence set forth in SEQ ID NO: 62, CDRH2 consisting of the amino acid sequence set forth in SEQ ID NO: 63, and CDRH3 consisting of the amino acid sequence set forth in SEQ ID NO: 64.

(11) The antibody described in (7), wherein the antibody is a humanized monoclonal antibody comprising: a light chain comprising CDRL1 consisting of the amino acid sequence set forth in SEQ ID NO: 65, CDRL2 consisting of the amino acid sequence set forth in SEQ ID NO: 66, and CDRL3 consisting of the amino acid sequence set forth in SEQ ID NO: 67; and a heavy chain comprising CDRH1 consisting of the amino acid sequence set forth in SEQ ID NO: 68, CDRH2 consisting of the amino acid sequence set forth in SEQ ID NO: 69, and CDRH3 consisting of the amino acid sequence set forth in SEQ ID NO: 70.

(12) The antibody described in any of (1) to (11), wherein one or two amino acids are deleted at a heavy chain carboxyl terminus.

(13) An antibody obtained by a method for producing the antibody, the method comprising the steps of culturing a host cell transfected with an expression vector containing a polynucleotide encoding the antibody described in any of (1) to (12), and collecting the antibody of interest from the resulting culture obtained in the former step.

Examples of the anti-EGFR antibody can include panitumumab, nimotuzumab, cetuximab, ametumumab (SY-101), SYN-004, SCT-200, tomuzotuximab, GC-1118, GR-1401, or depatuxizumab (ABT-806). Preferable examples can include panitumumab and ABT-806.

The antibody used in the present invention may be an antibody with 80% to 99% amino acid identity compared to the heavy and/or light chains of each of the above antibodies. Here, the term "identity" has the general definition used in the art. The % identity refers to the percentage of identical amino acids per total number of amino acids (including gaps) when two amino acid sequences are aligned to maximize the amino acid identity. Such identity is generally greater than or equal to 80% identity, preferably greater than or equal to 90, 91, 92, 93 or 94% identity, more preferably greater than or equal to 95, 96, 97 or 98% identity, and further preferably greater than or equal to 99% identity. It is also possible to select an antibody with various effects equivalent to those of the above antibodies by combining amino acid sequences in which one or several amino acid residues are substituted, deleted, and/or added to the amino acid sequence of the heavy chain and/or light chain. The number of amino acid residues to be substituted, deleted and/or added is generally 10 amino acid residues or less, preferably 5 to 6 amino acid residues or less, more preferably 2 to 3 amino acid residues or less, and further preferably 1 amino acid residue.

<2.2.2 Glycan Remodeling of Antibody>

It has recently been reported that the heterogeneous glycans of antibodies is remodeled by enzymatic reactions so as to introduce functionalized glycans uniformly (ACS Chem. Biol. 2012, 7, 110-122, ACS Med. Chem. Lett. 2016, 7, 1005-1008). Using this glycan remodeling technology, attempts have been made to synthesize a homogeneous ADC by introducing a drug(s) in a site-specific manner (Bioconjugate Chem. 2015, 26, 2233-2242; Angew. Chem. Int. Ed. 2016, 55, 2361-2367, US2016361436).

In the glycan remodeling, heterogeneous glycans added to a protein (e.g., an antibody) are cleaved off, using hydrolase, to leave only GlcNAc at each terminus thereby producing a homogenous protein moiety with GlcNAc (hereinafter, referred to as an "acceptor"). Subsequently, a given glycan separately prepared (hereinafter, referred to as a "donor") is provided, and the acceptor and the donor are linked together by using transglycosidase. Thereby, a homogeneous glycoprotein with a given glycan structure can be synthesized.

In the present invention, a "glycan" refers to a structural unit of two or more monosaccharides bonded together via glycosidic bonds. Specific monosaccharides and glycans are occasionally abbreviated, for example, as "GlcNAc-", "SG-", and so on. In the case where any of these abbreviations is used in a structural formula, the abbreviation is shown with an intention that an oxygen atom or nitrogen atom involved in a glycosidic bond at the reducing terminal to another structural unit is not included in the abbreviation indicating the glycan, unless specifically defined.

In the present invention, a monosaccharide as a basic unit of a glycan is indicated for convenience so that in the ring structure, the position of a carbon atom bonding to an oxygen atom constituting the ring and directly bonding to a hydroxy group (or an oxygen atom involved in a glycosidic bond) is defined as the 1-position (the 2-position only for sialic acids), unless otherwise specified. The names of compounds in Examples are each provided in view of the chemical structure as a whole, and that rule is not necessarily applied.

In the case where a glycan is indicated as a sign (e.g., SG, MSG, GlcNAc) in the present invention, the sign is intended, unless otherwise defined, to include carbon atoms ranging to the reducing terminal and not to include N or O involved in an N- or O-glycosidic bond.

An antibody-drug conjugate of the present invention is represented by the following formula:

[Formula 64]

$$Ab-\!\!\left[L-D\right]_{m^1}$$

wherein an antibody Ab or a functional fragment thereof is bound to L directly through a side chain of its amino acid residue (e.g., cysteine, lysine) or is bound to L through a glycan or remodeled glycan of Ab.

Glycans in Ab of the present invention are N-linked glycans or O-linked glycans, and preferably N-linked glycans.

N-linked glycans and O-linked glycans each bond to an amino acid side chain of an antibody via an N-glycosidic bond and an O-glycosidic bond, respectively.

The Ab in the present invention is IgG, preferably IgG1, IgG2 or IgG4.

IgG has a well-conserved N-linked glycan (hereinafter, referred to as "Asn297 glycan or N297 glycan") on an asparagine residue (hereinafter, referred to as "Asn297 or N297") at the 297-position of the Fc region of the heavy chain, and the N-linked glycan is known to contribute to the activity and kinetics of the antibody molecule (Eon-Duval, A. et al, Biotechnol. Prog. 2012, 28, 608-622; Sanglier-Cianferani, S., Anal. Chem. 2013, 85, 715-736).

The amino acid sequence in the constant region of IgG is well-conserved, and each amino acid is specified by EU Index numbering in Edelman et al. (Proc. Natl. Acad. Sci. U.S.A., 63, 78-85, (1969)). For example, Asn297, to which an N-linked glycan is added in the Fc region, corresponds to 297- position in the EU numbering, and even if the actual amino acid position has varied through fragmentation or loss of the region of the molecule, the amino acid can be uniquely identified by using the EU numbering.

The diagram below shows the case where an antibody-drug conjugate of the present invention bonds via the antibody or the N297 glycan of its functional fragment to L.

[Formula 65]

$$Ab-\!\!\left[(N297\ glycan)-\!\!\left[L-D\right]_{m^2}\right]_2$$

Note that an antibody having a remodeled glycan is called a glycan-remodeled antibody.

SGP ((2,6-SGP), an abbreviation for sialyl glycopeptide, is a representative N-linked glycopeptide. SGP can be separated/purified from the yolk of a hen egg, for example, by using a method described in WO 2011/027868. Purified products of SGP are commercially available from Tokyo Chemical Industry Co., Ltd., or FUSHIMI Pharmaceutical Co., Ltd. Herein, the glycan moiety of SGP is represented as SG, and the glycan deleting one GlcNAc at the reducing terminal of SG is represented as SG(10). SG(10) can be prepared by enzymatic hydrolysis of SGP (see the report by Umekawa et al. (Biochim. Biophys. Acta 2010, 1800, 1203-1209). SG(10) can also be purchased from Tokyo Chemical Industry Co., Ltd., or FUSHIMI Pharmaceutical Co., Ltd.

Herein, a glycan structure formed by deleting a sialic acid at a non-reducing terminal only in either one of the branched chains of β-Man in SG(10) is called as MSG(9), and a structure having sialic acid only in 1-3 glycan of the branched chains is called as MSG1, and a structure having a sialic acid only in the 1-6 glycan of the branched chains is called as MSG2.

The remodeled glycan used in an antibody-drug conjugate of the present invention is N297-(Fuc)SG, N297-(Fuc)MSG1, N297-(Fuc)MSG2, or a mixture of N297-(Fuc)MSG1 and N297-(Fuc)MSG2, preferably N297-(Fuc)SG, N297-(Fuc)MSG1, or N297-(Fuc)MSG2, and more preferably N297-(Fuc)SG or N297-(Fuc)MSG1.

N297-(Fuc)SG is represented by the following structural formula or sequence formula.

In the above formulas, the wavy line represents bonding to Asn297 of the antibody; L(PEG) represents $-(CH_2-CH_2-O)n^5-CH_2-CH_2-NH-$ and the amino group at the right end of the L(PEG) represents bonding via an amide bond to a carboxyl group at the 2-position of a sialic acid at the non-reducing terminal of each on both the 1-3 and 1-6 glycan sides of the branched chains of β-Man in the N297 glycan; and the asterisk represents bonding to the nitrogen atom at the 1- or 3-position on 1,2,3-triazole ring of the linker L, in particular, Lb in the above linker L, where $n^5$ is an integer from 2 to 10, preferably from 2 to 5.

N297-(Fuc)MSG1 is represented by the following structural formula or sequence formula.

[Formula 66]

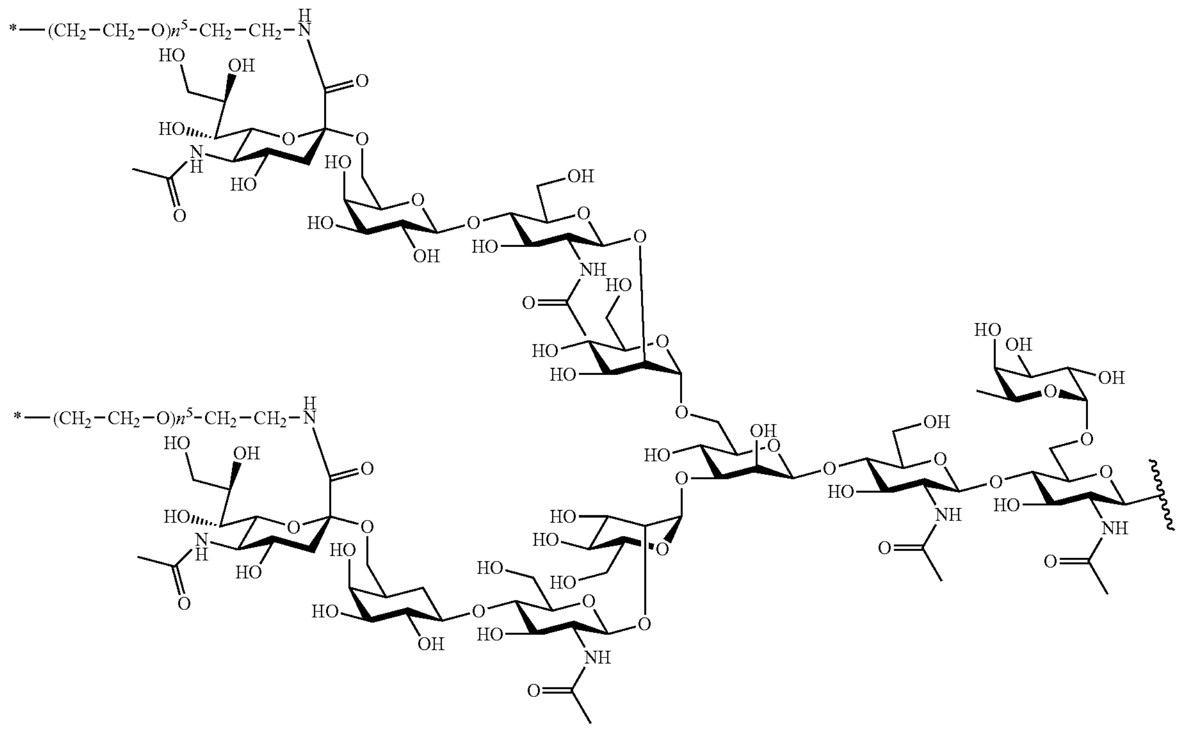

[Formula 67]

Fucα1
|
6

*—L(PEG)—NeuAcα2—6Galβ1—4GlcNAcβ1—2Manα1—6

Manβ1—4GlcNAcβ1—4GlcNAcβ1—

*—L(PEG)—NeuAcα2—6Galβ1—4GlcNAcβ1—2Manα1—3

[N297—(Fuc)SG]

[Formula 68]

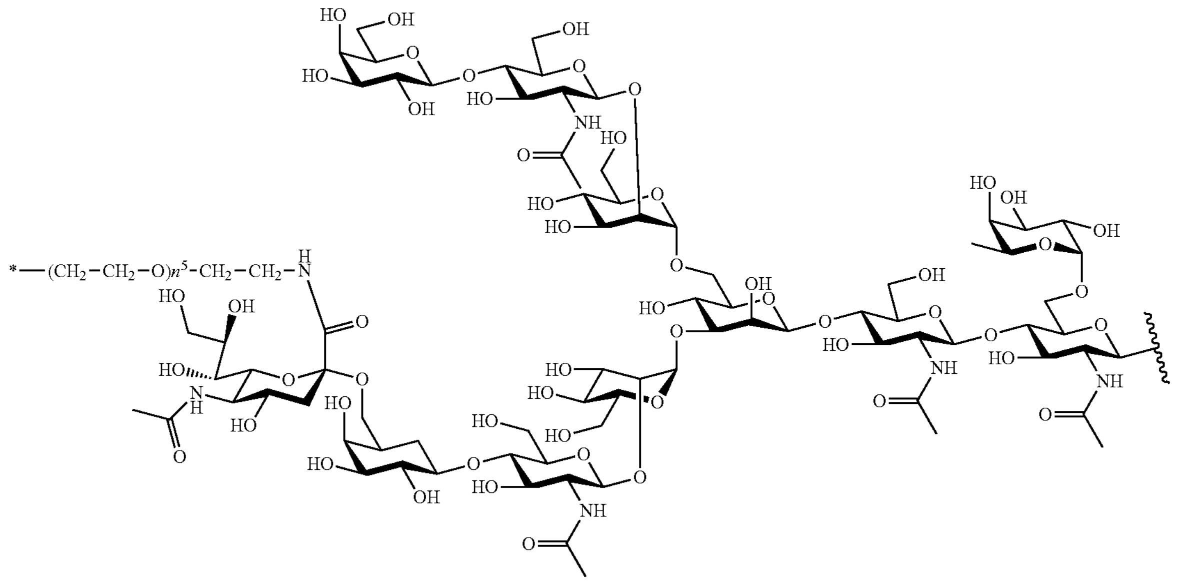

[Formula 69]

Fucα1
|
6
Galβ1—4GlcNAcβ1—2Manα1—6
Manβ1—4GlcNAcβ1—4GlcNAcβ1—
*—L(PEG)—NeuAcα2—6Galβ1—4GlcNAcβ1—2Manα1—3

[N297—(Fuc)MSG1]

In the above formulas, the wavy line represents bonding to Asn297 of the antibody;

L(PEG) represents $-(CH_2-CH_2-O)n^5-CH_2-CH_2-NH-$ and the amino group at the right end of the L(PEG) represents bonding via an amide bond to a carboxyl group at the 2-position of a sialic acid at the non-reducing terminal on the 1-3 glycan side of the branched chains of β-Man in the N297 glycan; and the asterisk represents bonding to the nitrogen atom at the 1- or 3-position on 1,2,3-triazole ring of the linker L, in particular, Lb in the above linker L, where $n^5$ is an integer from 2 to 10, preferably from 2 to 5.

N297-(Fuc)MSG2 is represented by the following structural formula or sequence formula.

[Formula 70]

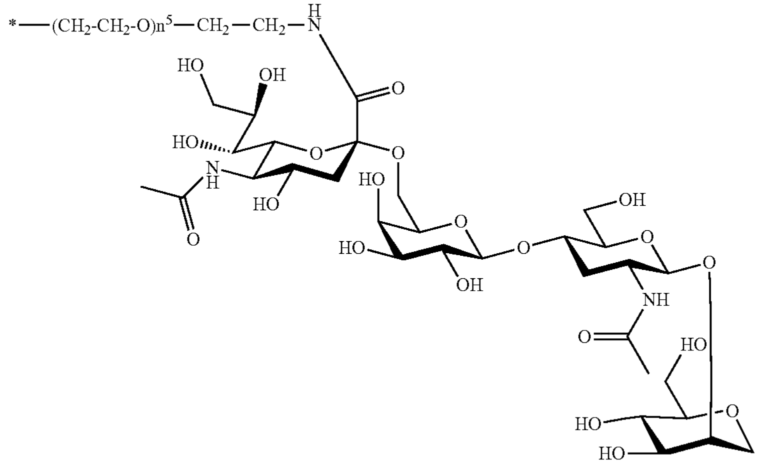

-continued

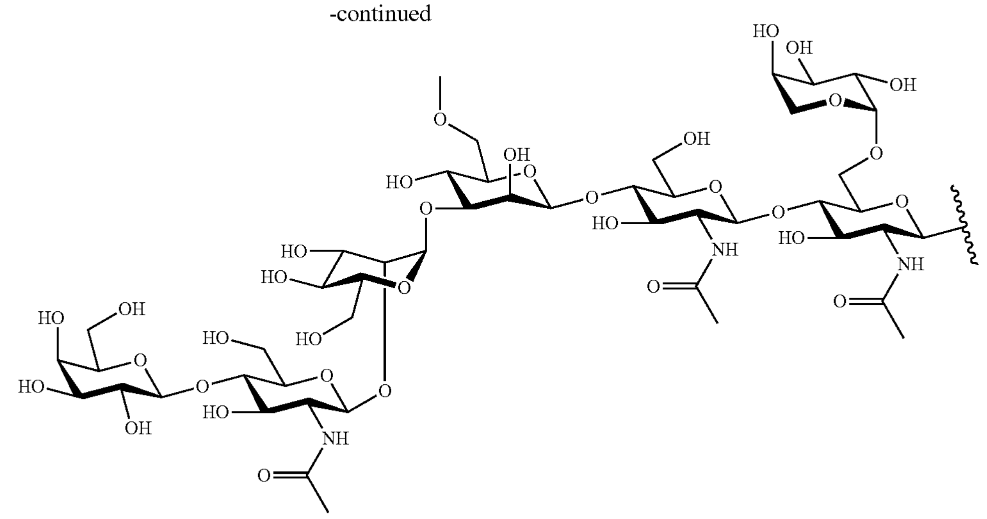

[Formula 71]

Fucα1
|
6

*—L(PEG)-NeuAcα2—6Galβ1—4GlcNAcβ1—2Manα1—6

Manβ1—4GlcNAcβ1—4GlcNAcβ1—

Galβ1—4GlcNAcβ1—2Man$_{\alpha}$1—3

[N297-(Fuc)MSG2]

In the above formulas, the wavy line represents bonding to Asn297 of the antibody; L(PEG) represents —($CH_2$—$CH_2$—O)n[5]—$CH_2$—$CH_2$—NH- and the amino group at the right end of the L(PEG) represents bonding via an amide bond to a carboxyl group at the 2-position of a sialic acid at the non-reducing terminal on the 1-6 glycan side of the branched chains of β-Man in the N297 glycan; and the asterisk represents bonding to the nitrogen atom at the 1- or 3-position on 1,2,3-triazole ring of the linker L, in particular, Lb in the above linker L, where $n^5$ is an integer from 2 to 10, preferably from 2 to 5.

The N297 glycan of the antibody in the antibody-drug conjugate of the present invention may be N297-(Fuc)SG. In this case, since the antibody is a dimer, the antibody-drug conjugate is a molecule in which four linkers L and four drugs D are linked ($m^2$=2).

The N297 glycan of the antibody in the antibody-drug conjugate of the present invention may be N297-(Fuc) MSG1 or N297-(Fuc)MSG2, or a mixture thereof. In this case, since the antibody is a dimer, the antibody-drug conjugate is a molecule in which two linkers L and two drugs D are linked ($m^2$=1) (see FIG. 1).

The N297 glycan is preferably N297-(Fuc)SG or N297-(Fuc)MSG1 or N297-(Fuc)MSG2, more preferably N297-(Fuc)SG or N297-(Fuc)MSG1, and still more preferably N297-(Fuc)SG.

The N297 glycan of the antibody in the antibody-drug conjugate of the present invention may be N297-(Fuc)SG or N297-(Fuc)MSG1 or N297-(Fuc)MSG2. In this case, a highly homogeneous ADC may be obtained.

<3. Production Methods>

The following describes representative methods for producing a novel-CDN-derivative-containing antibody-drug conjugate according to the present invention or a production intermediate thereof. Note that hereinafter, the compound numbers designated in each reaction scheme are used to indicate each compound. Specifically, for instance, "compound of formula (1)" or "compound (1)" is used. Also, the same applies to compounds with numbers other than the above.

In the following Methods A to E, the substituent $L^1$ has the same meaning as above. The substituent $L^2$ represents a substituent selected from the following (i) or (ii):

(i) when bonded to L, $L^2$ represents —NHR', a hydroxy C1-C6 alkyl group, or an amino C1-C6 alkyl group, where R' is a hydrogen atom, a C1-C6 alkyl group, a C2-C6 alkenyl group, a C2-C6 alkynyl group, or a C3-C6 cycloalkyl group, wherein the C1-C6 alkyl group, C2-C6 alkenyl group, or C2-C6 alkynyl group is optionally substituted with 1 to 6 halogen atoms; or (ii) when not bonded to L, $L^2$ represents a hydrogen atom or a halogen atom.

The substituent $W^1$ represents —NH— or a sulfur atom. The substituent $W^2$ represents -CH═. The substituents $Z^1$ to $Z^3$ together represent —$CH_2$—$CH_2$—$CH_2$—. The substituents $R^1$ to $R^3$, each independently, represent a hydrogen atom, a halogen atom, -OR', —OC(═O)R', —$N_3$, —NHR', -NR'R", or —NHC(═O)R', where R' is as defined above and R" represents a C1-C6 alkyl group, a C2-C6 alkenyl group, a C2-C6 alkynyl group, or a C3-C6 cycloalkyl group. The substituent $R^4$ represents a hydrogen atom. When $W^1$ is a nitrogen atom, the substituent $R^5$ represents a hydrogen atom; when $W^1$ is an oxygen atom, $R^5$ is absent. The substituents $R^a$, $R^c$, $R^e$, and $R^g$ each represent a side chain of naturally occurring α-amino acid. Examples include a methyl group, an isopropyl group, a sec-butyl group, an isobutyl group, or a benzyl group. $PRO^1$ represents a primary alcohol protecting group, and is preferably a 4,4'-dimethoxytrityl group, a 4-methoxytrityl group, and the like. $PRO^2$, $PRO^3$, $PRO^7$, and $PRO^1$ each denote a secondary alcohol protecting group. Preferable examples include a tert-butyldimethylsilyl group, triisopropylsilyloxymethyl group, benzoyl group, 2-nitrobenzyl group, and 4-methoxytetrahydropyran-4-yl group. $PRO^6$ represents a carboxylic acid protecting group, and is preferably a tert-butyl group, a benzyl group, and the like. $PRO^5$ and $PRO^9$ each denote an amine protecting group. $PRO^1$ is preferably a tert-butyloxycarbonyl group, a 9-fluorenylmethyloxycarbonyl group, an allyloxycarbonyl group, a 2,2,2-trichloroethoxycarbonyl group, a benzyloxycarbonyl group, and the like. $PRO^9$ is preferably a 9-fluorenylmethyloxycarbonyl group or a 2-(trimethylsilyl)ethoxycarbonyl group. $PRO^4$ represents an alcohol or amine protecting group, and is preferably a tert-butyldimethylsilyl group, a benzoyl group, and the like in the case of alcohol and preferably a 2-(trimethylsilyl)ethoxycarbonyl group, an allyloxycarbonyl group, a tert-butyloxycarbonyl group, and the like in the case of amine. $Q^a$ represents an oxygen or sulfur atom, and $Q^b$ represents a hydroxy or thiol group. $Q^{a'}$ and $Q^{b'}$ each independently represent a negatively charged oxygen (O—) or sulfur (S—) atom. $R^x$ and $R^y$ each independently represent a halogen atom or —O—$PRO^2$. n represents an integer from 1 to 3.

Method A

A CDN derivative represented by (1) as used in an antibody-drug conjugate of the present invention can be produced according to Method A described below.

[Formula 72]

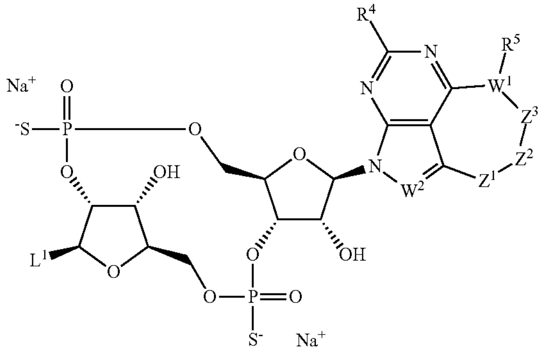

(1)

This synthetic scheme is a method for producing a compound represented by general formula (1). One-pot synthesis can be implemented from steps A-1 to A-5 in this production method according to the report of Gaffney and colleagues (Org. Lett. 2010, 12, 3269-3271).

[Formula 73]

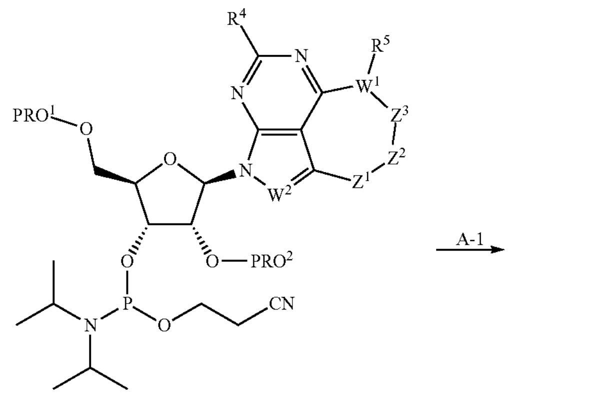

(1a)

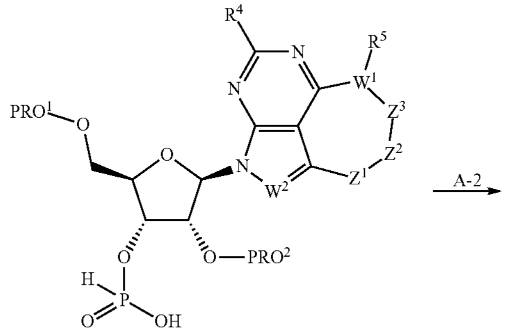

(2a)

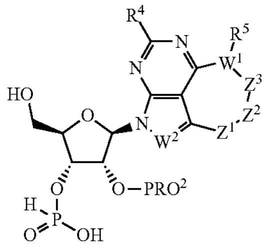

(3a)

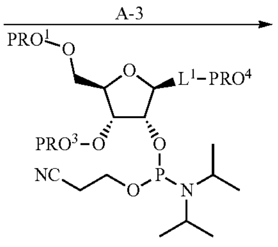

(4a)

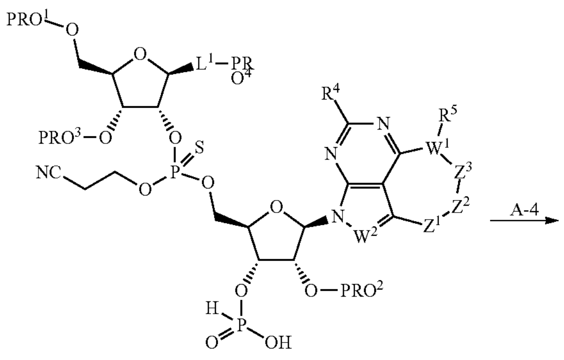

(5a)

-continued

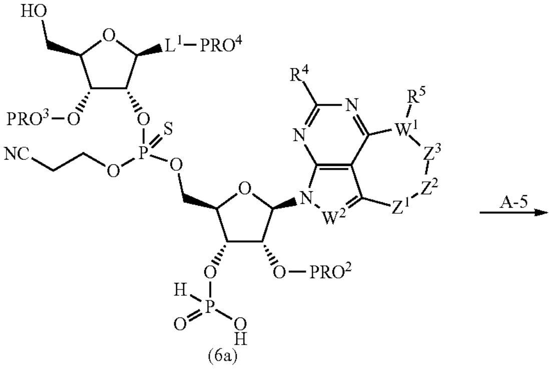

(6a)

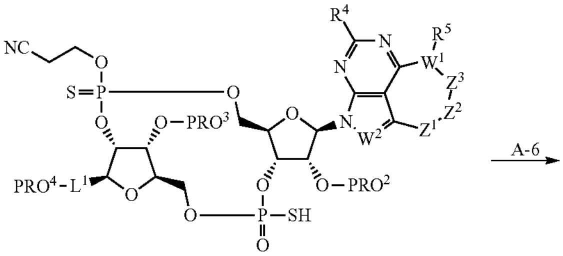

(7a)

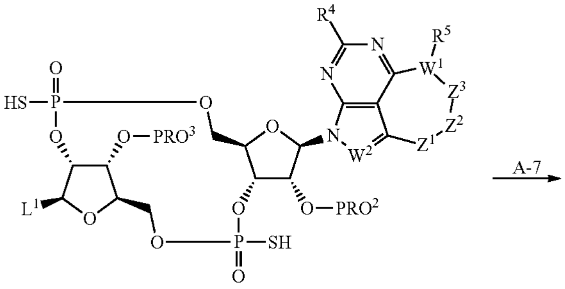

(8a)

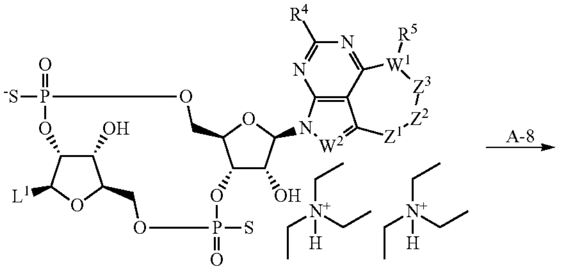

(9a)

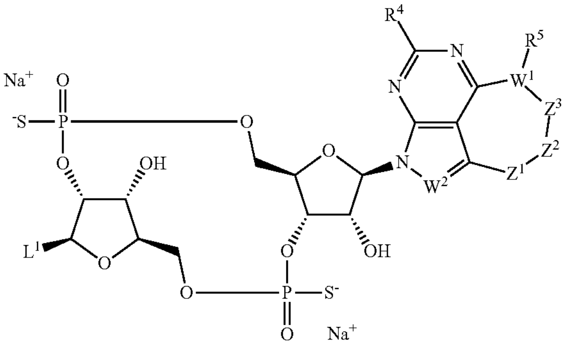

(1)

(Step A-1)

This step is a step of producing a compound of formula (2a) by using a known organic chemistry-based technique to subject a compound of formula (1a) to hydrolysis and cyanoethyl group removal sequentially. The compound (1a) was hydrolyzed while treated with water and an acid (e.g., pyridine trifluoroacetate, 4,5-dicyanoimidazole, 1H-tetrazole) in a solvent (acetonitrile, tetrahydrofuran, N,N-dimethylformamide or a mixture of these solvents) at a temperature of −10° C. to the boiling point of the solvent used for the reaction, preferably from 15° C. to 35° C. For each mole of compound (1a), 2 to excess moles and preferably 2 to 10 moles of water was used, and 1 mole to excess moles and preferably 1 mole to 5 moles of the acid was used. The reaction time is from 1 min to 3 h and preferably from 5 min to 30 min. Next, the cyanoethyl group was removed by adding a base (e.g., tert-butylamine) to the reaction mixture. For each mole of compound (1a), excess moles and preferably 30 to 50 moles of the base was used. The reaction time is from 5 min to 6 h and preferably from 15 min to 1 h. The reaction mixture was concentrated under reduced pressure to give a crude compound (2a). The crude compound (2a) can be sent to the next step without purification.

(Step A-2)

This step is a step of producing a compound of formula (3a) by using a known organic chemistry-based technique to remove a hydroxy group-protecting group from the compound of formula (2a). Before the start of the reaction in this step, the crude form of formula (2a) was dried while azeotroped once to three times with acetonitrile, if necessary. In the case where $PRO^1$ is a 4,4'- dimethoxytrityl group, the compound (2a) was placed in a solvent (e.g., dichloromethane, chloroform, dichloroethane) at a temperature of −10° C. to the boiling point of the solvent used for the reaction, preferably from 15° C. to 35° C., and treated with water and an acid (e.g., trifluoroacetic acid) to remove the 4,4-dimethoxytrityl group. For each mole of compound (2a), excess moles and preferably 10 to 20 moles of water was used; and the acid was diluted with the solvent used in the reaction to 1% to 50% (v/v) and preferably 5% to 10% (v/v), and excess moles and preferably 5 moles to 15 moles of the diluted solution was used. The reaction time is from 1 min to 3 h and preferably from 5 min to 30 min. Pyridine was added to the reaction mixture to stop the reaction. The amount of pyridine was an amount at which the acid can be sufficiently neutralized, and 2 moles to 10 moles of pyridine per mole of acid was preferably used. The reaction mixture was concentrated under reduced pressure to give a crude compound (3a). The crude compound (3a) was azeotroped three to five times using dehydrated acetonitrile. At the last azeotropic distillation, acetonitrile was left to prepare 0.01 M to 1 M compound (3a)-containing acetonitrile solution. The resulting acetonitrile solution was used directly in the next step.

(Step A-3)

This step is a step of producing a compound of formula (5a) by using a known organic chemistry-based technique to subject the compound of formula (3a) to a coupling reaction with a compound of formula (4a) and then subject the resulting coupling product to sulfidation in a sequential manner. Before the start of the reaction in this step, the compound (4a) was azeotroped three to five times using dehydrated acetonitrile. At the last azeotropic distillation, acetonitrile was left to prepare 0.01 M to 1 M compound (4a)-containing acetonitrile solution. A drying agent (Molecular Sieves 3A or Molecular Sieves 4A in a powder or pellet form) was added to the solution, and the resulting solution was stored under a nitrogen or argon atmosphere until use. The coupling reaction was carried out by adding the compound (4a)-containing acetonitrile solution, which had been dried by azeotropic distillation, to the compound (3a)-containing acetonitrile solution at a temperature of 5° C. to 35° C. The reaction time is from 1 min to 24 h and preferably from 5 min to 6 h. Next, the reaction mixture was mixed with a sulfurizing agent (e.g., N,N-dimethyl-N'-(3-sulfaniliden-3H-1,2,4-dithiazol-5-yl)methane imidamide, 3H-1,2-benzodithiol-3-one). In this way, the sulfidation was carried out. For each mole of compound (3a), 1 to 5 moles and preferably 1 to 2 moles of the sulfurizing agent was used. The reaction time is from 5 min to 24 h and preferably from 30 min to 6 h. The reaction mixture was concentrated under reduced pressure to give a crude compound (5a). The resulting crude compound (5a) was used directly in the next step.

(Step A-4)

This step is a step of producing a compound of formula (6a) by using a known organic chemistry-based technique to remove a hydroxy group-protecting group from the compound of formula (5a). In the case where $PRO^1$ is a 4,4'-dimethoxytrityl group, the 4,4-dimethoxytrityl group was removed by treating the compound (5a) with water and an acid (e.g., dichloroacetic acid, trifluoroacetic acid) in a solvent (e.g., dichloromethane, chloroform, dichloroethane) at a temperature of −10° C. to the boiling point of the solvent used for the reaction, preferably from 15° C. to 35° C. For each mole of compound (5a), excess moles and preferably 10 to 20 moles of water was used; and the acid was diluted with the solvent used in the reaction to 1% to 50% (v/v) and preferably 5% to 10% (v/v), and excess moles and preferably 5 moles to 15 moles of the diluted solution was used. The reaction time is from 1 min to 3 h and preferably from 5 min to 30 min. Pyridine was added to the reaction mixture to stop the reaction. The amount of pyridine was an amount at which the acid can be sufficiently neutralized, and 10 moles to 200 moles of pyridine per mole of acid was preferably used. The reaction mixture was concentrated under reduced pressure to give a crude compound (6a). The resulting crude compound (6a) was used directly in the next step.

(Step A-5)

This step is a step of producing a compound of formula (7a) by using a known organic chemistry-based technique to subject the compound of formula (6a) to cyclization and sulfurization sequentially. The compound (6a) was dissolved in pyridine and then concentrated under reduced pressure to prepare a 0.01 M to 0.5 M pyridine solution. The cyclization was carried out by adding a dehydration condensation agent (e.g., 2-chloro-5,5-dimethyl-1,3,2$\lambda^5$-dioxaphosphinan-2-one) to the pyridine solution at a temperature of 5° C. to 35° C. For each mole of compound (6a), 1 to excess moles and preferably 3 moles to 5 moles of the dehydration condensation agent was used. The reaction time is from 1 min to 6 h and preferably from 5 min to 1 h. Next, water and a sulfurizing agent (e.g., 3H-1,2-benzodithiol-3-one, N,N-dimethyl-N'-(3-sulfaniliden-3H-1,2,4-dithiazol-5-yl)methane imidamide) were added to the reaction mixture to carry out the sulfidation. For each mole of compound (6a), excess moles and preferably 30 to 50 moles of water was used, and 1 mole to 5 moles and preferably 1 mole to 2 moles of the sulfurizing agent was used. The reaction time is from 5 min to 12 h and preferably from 30 min to 3 h. After the reaction mixture was added to aqueous sodium bicarbonate (0.1 M to 1 M), the mixture was stirred for 15 min to 24 h and the reaction was then stopped. The reaction mixture was extracted with an organic solvent (ethyl acetate, diethyl ether, toluene, or a mixture of these solvents) one to five times. After that, the extracts were combined, and dried over an anhydrous salt (anhydrous sodium sulfate or anhydrous magnesium sulfate). The drying agent was filtered off, and the filtrate was concentrated under reduced pressure. The resulting residue was purified by silica gel column chromatography [e.g., dichloromethane/methanol, ethyl acetate/methanol, hexane/ethyl acetate], C18 silica gel column chromatography [buffer solution/acetonitrile], or a combination of these procedures to yield a compound (7a) as a mixture of two or more diastereomers or as two or more pure diastereomers. In this step, two diastereomers are frequently obtained. However, depending on the starting material (1a) and (4a), additional one or two diastereomers may be obtained. Even if the resulting compound (7a) is a mixture of multiple diastereomers, the compound can be sent to the next step without further purification.

(Step A-6)

This step is a step of producing a compound of formula (8a) by using a known organic chemistry-based technique to simultaneously remove a cyanoethyl group and all the acyl-based protecting groups from the compound of formula (7a). This step was carried out in an autoclave or in a shielded tube, if necessary. In the case where $PRO^4$ was a benzoyl group, the cyanoethyl and benzoyl groups were removed by treating the compound (7a) with 28% (v/v) ammonia water in a solvent (methanol, ethanol, tetrahydrofuran, or a mixture of these solvents) at a temperature of 5° C. to the boiling point of the solvent used in the reaction. For each mole of compound (7a), excess moles and preferably 300 moles to 3000 moles of ammonia was used. The reaction time is from 30 min to 96 h and preferably from 2 h to 48 h. The reaction mixture was optionally concentrated. The residue was purified by preparative HPLC [e.g., buffer solution/acetonitrile, buffer solution/methanol], C18 silica gel column chromatography [e.g., buffer solution/acetonitrile, buffer solution/methanol], or a combination of these procedures to obtain the compound (8a). Even if the resulting compound (8a) is a mixture of diastereomers, the compound can be sent to the next step without further purification. Meanwhile, the compound may be sent directly to the next step without purification in this step.

(Step A-7)

This step is a step of producing a compound of formula (9a) by using a known organic chemistry-based technique to simultaneously remove all the silyl-based protecting groups from the compound of formula (8a). In the case where $PRO^2$ and $PRO^3$ are tert-butyldimethylsilyl groups, the tert-butyldimethylsilyl groups were removed by directly treating the compound (8a) with triethylamine trihydrofluoride at a temperature of 5° C. to 100° C., preferably from 35° C. to 60° C. For each mole of compound (8a), excess moles and preferably 100 to 200 moles of triethylamine trihydrofluoride was used. The reaction time is from 30 min to 24 h and preferably from 2 h to 12 h. The reaction mixture was cooled to room temperature. Then, an ice-cooled mixture of 1 M aqueous triethylammonium bicarbonate and triethylamine at 3:1 to 10:1 (v/v) was gradually poured into the reaction mixture to stop the reaction. If necessary, the reaction mixture may be poured into an ice-cold mixture of 1 M aqueous triethylammonium bicarbonate and triethylamine. In this case, the reaction vessel was washed with acetonitrile and water. Triethylamine should be used in quantity sufficient to change the reaction mixture property to be weak basic. Preferably, for each mole of triethylamine trihydrofluoride, about 2 moles of triethylamine may be used. The organic solvent component of the reaction mixture was distilled off under reduced pressure. The residual aqueous solution was subjected to purification by preparative HPLC [e.g., buffer solution/acetonitrile, buffer solution/methanol], C18 silica gel column chromatography [e.g., buffer solution/acetonitrile, buffer solution/methanol], or a combination of these procedures to obtain the compound (9a) as a single diastereomer.

(Step A-8)

This step is a step of producing a compound of formula (1) by using a known organic chemistry-based technique to subject the compound of formula (9a) to ion exchange. Cation exchange resin (BT AG (registered trademark); 50W-X2 resin; 100-200 mesh; hydrogen type) was suspended in pure water and packed into an empty column cartridge. The amount of the cation exchange resin used was 10 to 50 times the amount of compound (9a) by weight. After pure water in excess was allowed to flow down, three column volumes of 1M aqueous sodium hydroxide was allowed to flow down, followed by six column volumes of pure water. The compound (9a) was dissolved in about three column volumes of pure water and charged to the column. If the compound is not readily soluble in pure water, a mixture with a small amount of organic solvent (e.g., acetonitrile, methanol) may be used. The solution allowed to flow down was fractionated. Then, additional six column volumes of pure water or the like was used for elution, and the corresponding fractions were collected. Fractions containing the target product were combined and lyophilized to give the compound (1) as a single diastereomer.

Method A'

A CDN derivative represented by (1') as used in an antibody-drug conjugate of the present invention can be produced according to Method A' described below.

[Formula 74]

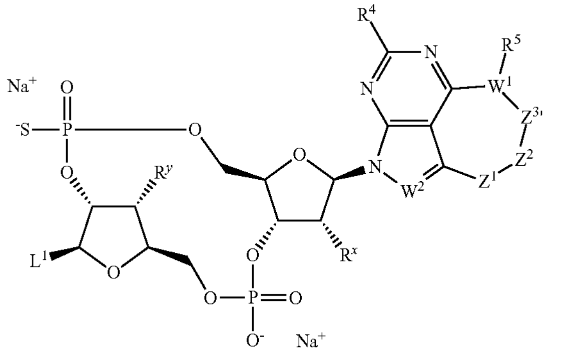

(1)

This synthetic scheme is a method for producing a compound represented by general formula (1') while part of Method A is modified. Specifically, the compound of general formula (1') can be produced by changing step A-5 of Method A to step A'-5 specified below. Meanwhile, if the substituents $R^x$ and $R^y$ are each a halogen atom, step A-7 may be omitted.

[Formula 75]

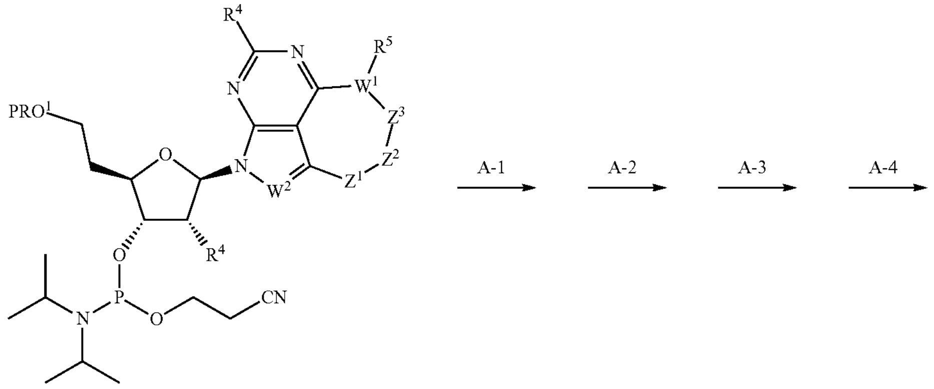

(1a')

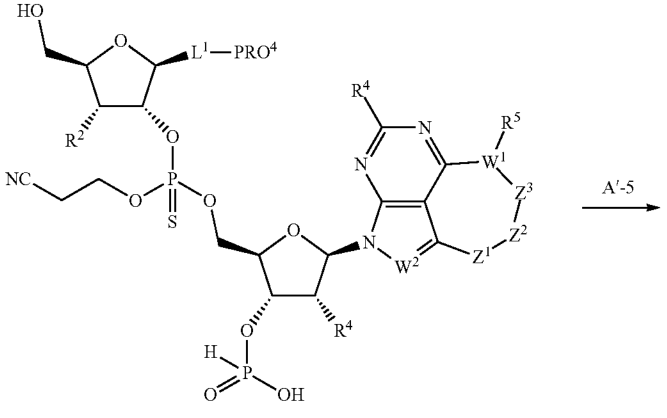

(6a')

-continued

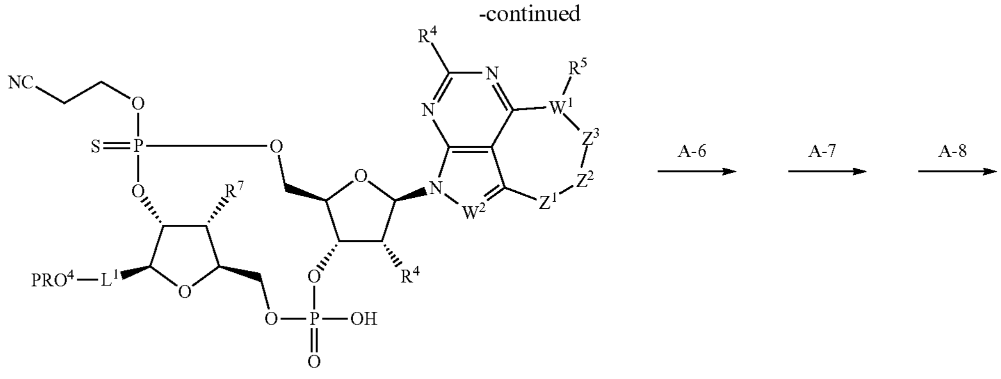

(7a')

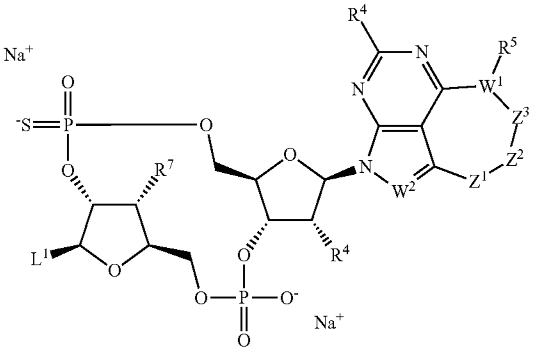

(1')

(Step A'-5)

This step is a step of producing a compound of formula (7a') by using a known organic chemistry-based technique to subject the compound of formula (6a') to cyclization and oxidation sequentially. The compound (6a') was dissolved in pyridine and then concentrated under reduced pressure to prepare a 0.01 M to 0.5 M pyri dine solution. The cyclization was carried out by adding a dehydration condensation agent (e.g., 2-chloro-5,5-dimethyl-1,3,2λ$^5$-dioxaphosphinan-2-one) to the pyridine solution at a temperature of 5° C. to 35° C. For each mole of compound (6a'), 1 mole to excess moles and preferably 3 moles to 5 moles of the dehydration condensation agent was used. The reaction time is from 1 min to 6 h and preferably from 5 min to 1 h. Next, the oxidation was carried out by adding water and an oxidizing agent (e.g., iodine) to the reaction mixture. For each mole of compound (6a'), 0 mole to excess moles and preferably 30 moles to 50 moles of water was used, and 2 moles to 10 moles and preferably 3 moles to 5 moles of the oxidizing agent was used. The reaction time is from 5 min to 12 h and preferably from 30 min to 3 h. After the reaction mixture was added to aqueous sodium bicarbonate (0.1 M to 1 M), the mixture was stirred for 15 min to 24 h and the reaction was then stopped. The reaction mixture was extracted with an organic solvent (ethyl acetate, diethyl ether, toluene, or a mixture of these solvents) one to five times. After that, the extracts were combined, and dried over an anhydrous salt (anhydrous sodium sulfate or anhydrous magnesium sulfate). The drying agent was filtered off, and the filtrate was concentrated under reduced pressure. The resulting residue was purified by silica gel column chromatography [e.g., dichloromethane/methanol, ethyl acetate/methanol, hexane/ethyl acetate], C18 silica gel column chromatography [buffer solution/acetonitrile], or a combination of these procedures to give a compound (7a')

Method A''

A CDN derivative represented by (1'') as used in an antibody-drug conjugate of the present invention can be produced according to Method A'' described below.

[Formula 76]

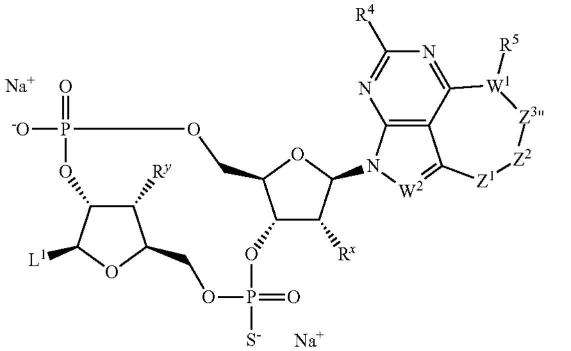

(1)

This synthetic scheme is a method for producing a compound represented by general formula (1'') while part of Method A is modified. Specifically, the compound of general formula (1'') can be produced by changing step A-3 of Method A to step A''-3 specified below. Meanwhile, if the substituents $R^x$ and $R^y$ are each a halogen atom, step A-7 may be omitted.

[Formula 77]
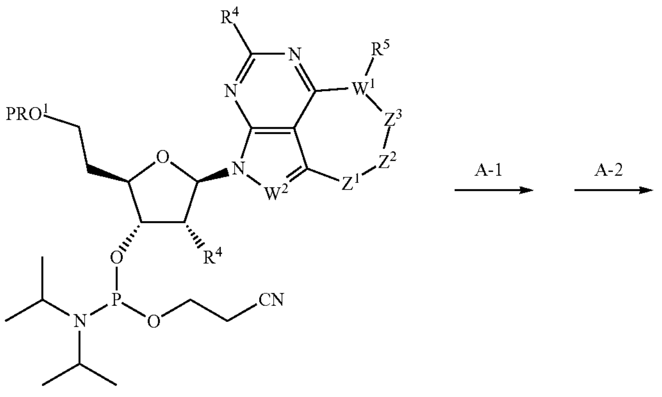
(1a′)
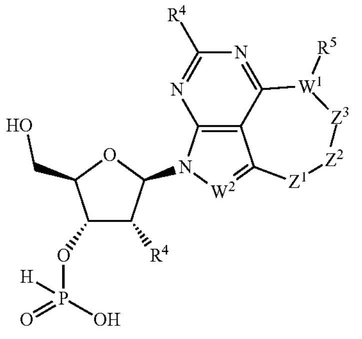
(3a″)
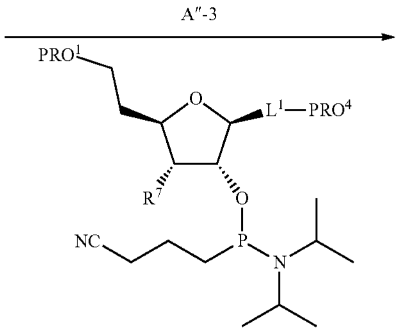
(4a″)
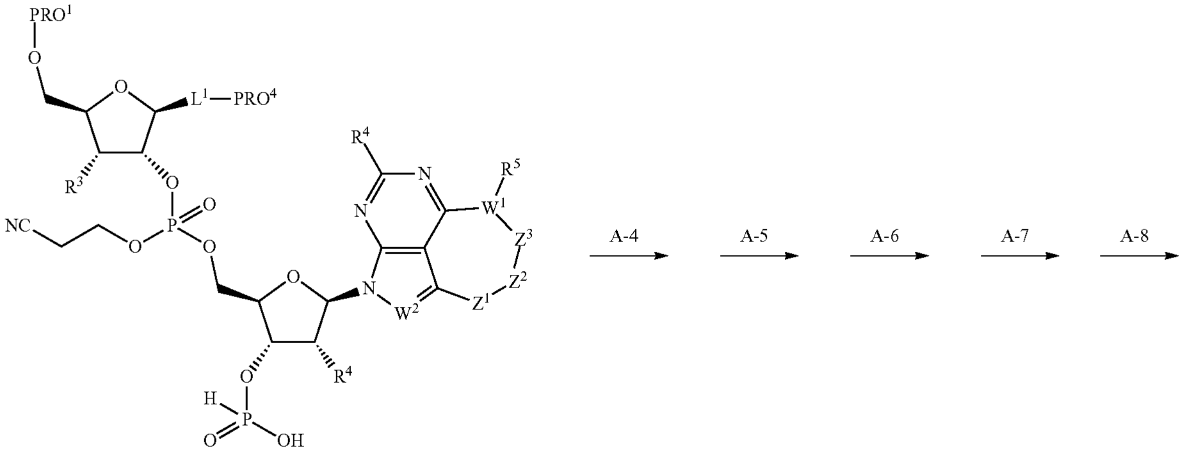
(5a″)

-continued

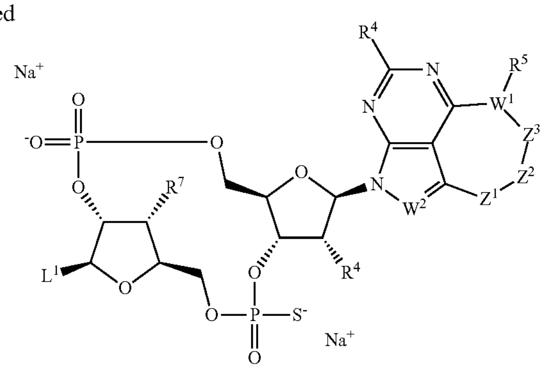

(1'')

(Step A''-3)

This step is a step of producing a compound of formula (5a'') by using a known organic chemistry-based technique to subject the compound of formula (3a'') to a coupling reaction with a compound of formula (4a'') and then subject the resulting coupling product to oxidation in a sequential manner. Before the start of the reaction in this step, the compound (4a'') was azeotroped three to five times using dehydrated acetonitrile. At the last azeotropic distillation, acetonitrile was left to prepare 0.01 M to 1 M compound (4a'')-containing acetonitrile solution. A drying agent (Molecular Sieves 3A or Molecular Sieves 4A in a powder or pellet form) was added to the solution, and the resulting solution was stored under a nitrogen or argon atmosphere until use. The coupling reaction was carried out by adding the compound (4a'')-containing acetonitrile solution, which had been dried by azeotropic distillation, to the compound (3a'')-containing acetonitrile solution at a temperature of 5° C. to 35° C. The reaction time is from 1 min to 24 h and preferably from 5 min to 6 h. Next, the oxidation was carried out by adding an oxidizing agent (e.g., tert-butyl hydroperoxide) to the reaction mixture. For each mole of compound (3a''), 1 mole to 5 moles and preferably 2 moles to 3 moles of the oxidizing agent was used. The reaction time is from 5 min to 24 h and preferably from 30 min to 6 h. Saturated aqueous sodium thiosulfate was added to the reaction mixture, the mixture was stirred for 10 min to 12 h, and the reaction was then stopped. The reaction mixture was extracted with an organic solvent (e.g., a mixed solvent of dichloromethane and methanol) one to five times. After that, the extracts were combined, and dried over an anhydrous salt (anhydrous sodium sulfate or anhydrous magnesium sulfate). The drying agent was filtered off, and the reaction mixture was concentrated under reduced pressure to give a crude compound (5a''). The resulting crude compound (5a'') was used directly in the next step.

Method A'''

A CDN derivative represented by (1''') as used in an antibody-drug conjugate of the present invention can be produced according to Method A''' described below.

[Formula 78]

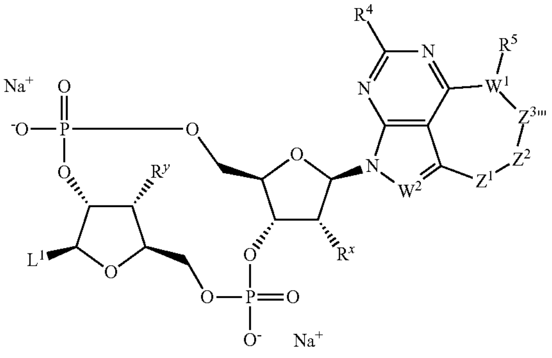

(1)

This synthetic scheme is a method for producing a compound represented by general formula (1''') while part of Method A is modified. Specifically, the compound of general formula (1''') can be produced by changing step A-3 of Method A to step A''-3 and step A-5 of Method A to step A'-5. Meanwhile, if the substituents $R^x$ and $R^y$ are each a halogen atom, step A-7 may be omitted.

[Formula 79]
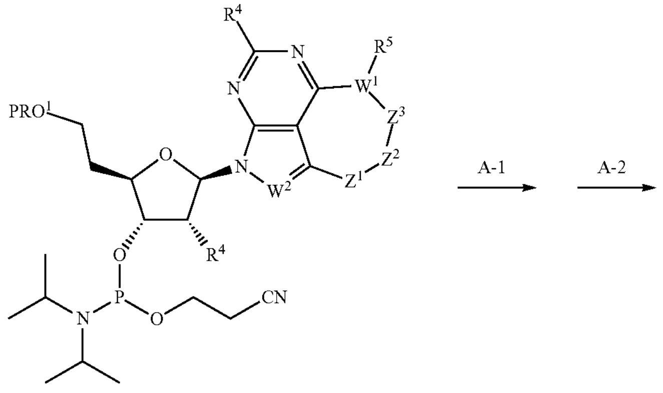
(1a')
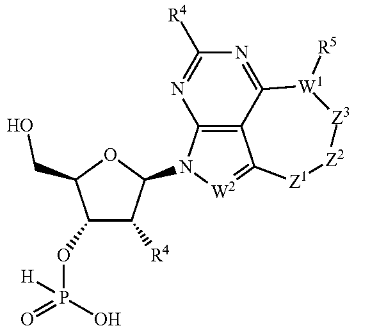
(3a")
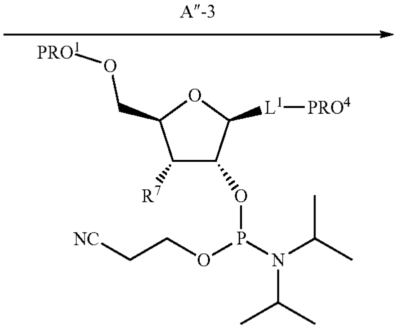
(4a")
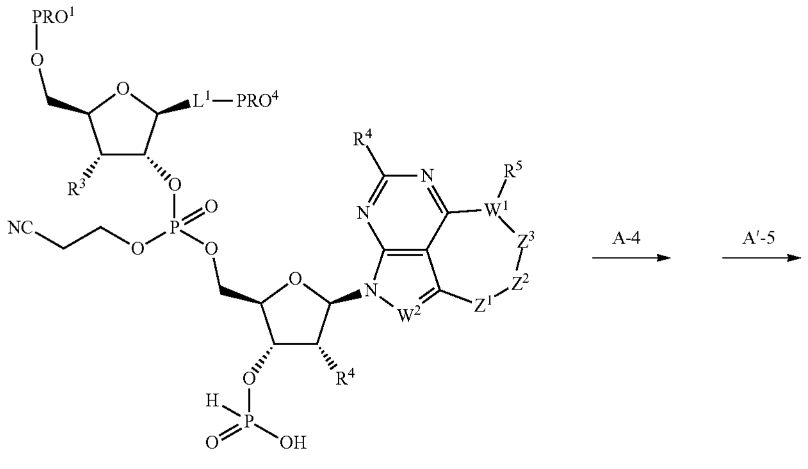
(5a")

-continued
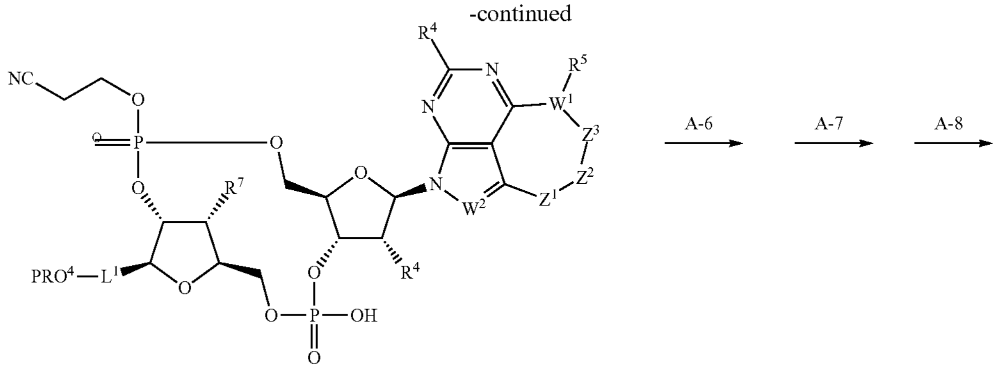
(7a''')
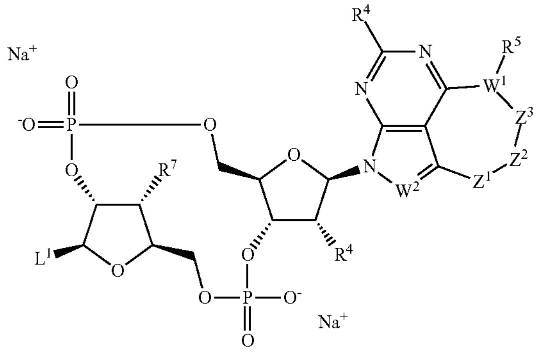
(1'')
Method B: Conjugation Precursor (Glycan Conjugation)
A conjugation precursor represented by (2) as used in an antibody-drug conjugate of the present invention can be produced according to Method B described below.
[Formula 80]
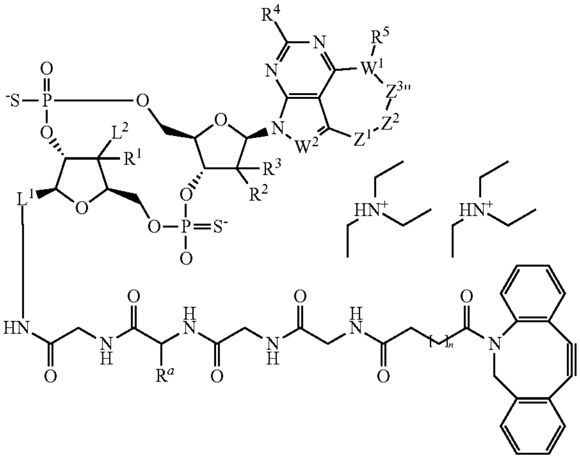
(2)

This synthetic scheme is a method for producing a conjugation precursor (2) in the case where —$NH_2$ is substituted at a given position of $L^1$.
[Formula 81]
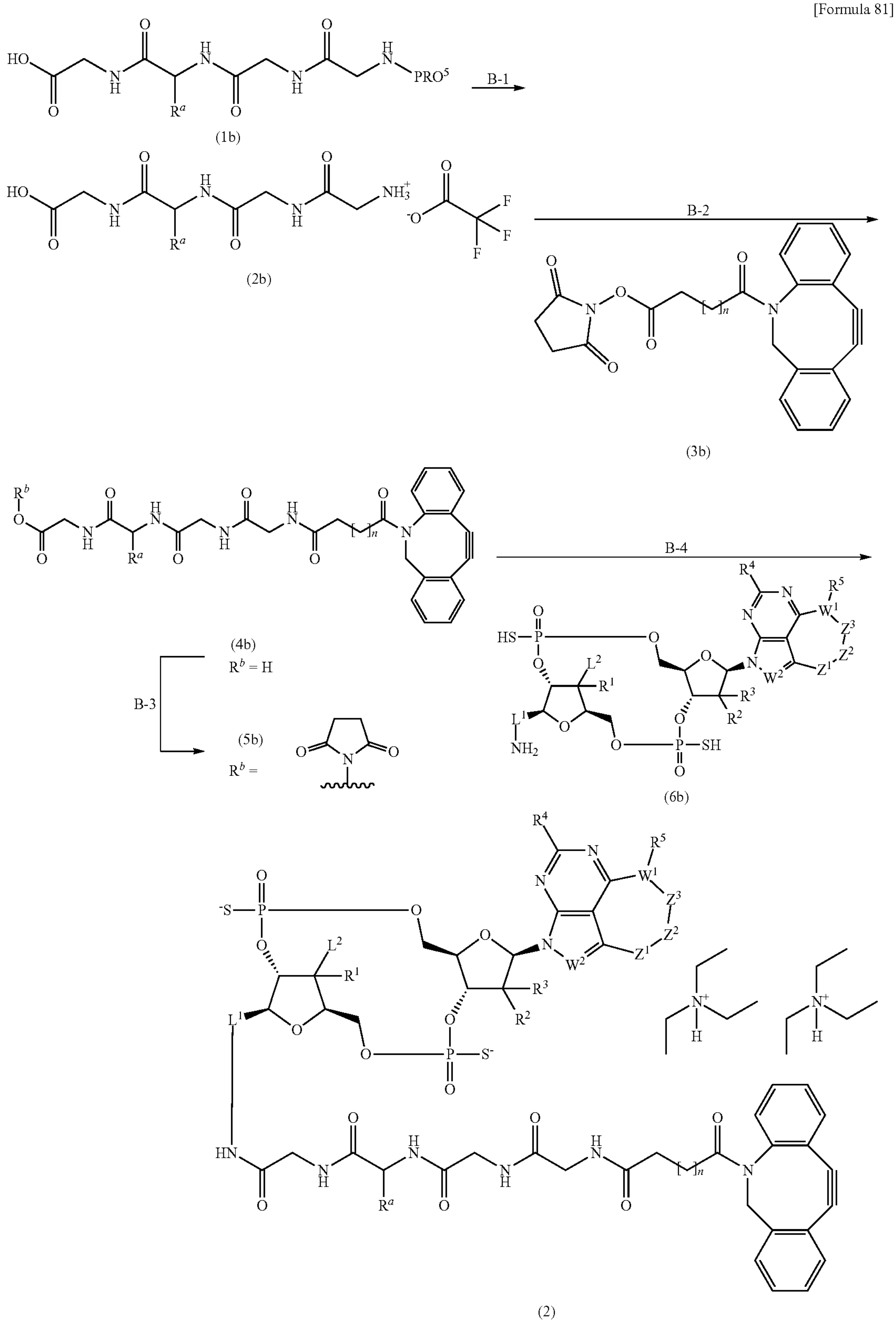
(1b)
(2b)
(3b)
(4b)
$R^b$ = H
(5b)
$R^b$ =
(6b)
(2)

(Step B-1)

This step is a step of producing a compound of formula (2b) by using a known organic chemistry-based technique to remove a protecting group from a compound of formula (1b). In the case where $PRO^1$ was a tert-butyloxycarbonyl group, the protecting group was removed by treating the compound (1b) with trifluoroacetic acid in a solvent (dichloromethane, dioxane, acetonitrile, ethyl acetate, tetrahydrofuran, or a mixture of these solvents) at a temperature of −10° C. to the boiling point of the solvent used in the reaction, preferably from 15° C. to 35° C. For each mole of compound (1b), excess moles and preferably 20 moles to 50 moles of trifluoroacetic acid was used. The reaction time is from 5 min to 24 h and preferably from 30 min to 6 h. The reaction mixture was concentrated under reduced pressure, suspended in toluene, and then re-concentrated under reduced pressure. This procedure was repeated two to five times. A solvent (diethyl ether, diisopropyl ether, hexane, dichloromethane, ethyl acetate, or a mixture of these solvents) was added to form a slurry. The resulting solid was then filtered off to give a crude compound (2b). The crude compound (2b) was sent to the next step without further purification.

(Step B-2) This step is a step of producing a compound of formula (4b) by using a known organic chemistry-based technique to subject the compound of formula (2b) to amidation with a compound of formula (3b). The amidation was carried out by reacting the compound (2b) with a base (e.g., triethylamine, N,N-diisopropylethylamine) and the compound (3b) in a solvent (e.g., N,N-dimethylformamide, N-methylpyrrolidone, N,N-dimethylacetamide, acetonitrile) at a temperature of 5° C. to 35° C. For each mole of compound (2b), 1 mole to 5 moles of the base was used; and 0.5 mole to 1.5 moles of the compound (3b) was used. The reaction time is from 10 min to 72 h and preferably from 1 h to 24 h. The reaction mixture was poured into a two-layer mixture: an organic solvent (dichloromethane, chloroform, ethyl acetate, methanol, or a mixture of these solvents) and water or acidic aqueous solution (e.g., 0.1 to 1 M hydrochloric acid, aqueous citric acid solution), and extracted with the organic solvent one to five times. The resulting extracts were combined, washed with brine, and dried over an anhydrous salt (anhydrous sodium sulfate or anhydrous magnesium sulfate). The drying agent was filtered off, and the filtrate was concentrated under reduced pressure. Note that the above liquid separation procedure may be omitted, and the reaction mixture can be concentrated as it is under reduced pressure and sent to the next silica gel column purification. The resulting residue was purified by silica gel column chromatography [e.g., dichloromethane/methanol, ethyl acetate/methanol] to yield a compound (4b). If necessary, the resulting compound (4b) may be dissolved in a good solvent (ethyl acetate, acetonitrile, dichloromethane, methanol, or a mixture of these solvents); a poor solvent (e.g., diethyl ether, diisopropyl ether, hexane) may then be added to re-precipitate the compound; and the resulting solid may be filtered to increase the purity.

(Step B-3)

This step is a step of producing a compound of formula (5b) by using a known organic chemistry-based technique to subject the compound of formula (4b) to esterification. The esterification was carried out by reacting the compound (4b) with N-hydroxysuccinimide and a condensing agent (e.g., 1-ethyl-3-(3-dimethylaminopropyl)carbodiimide hydrochloride) in a solvent (e.g., N,N-dimethylformamide, N,N-dimethylacetamide, N-methylpyrrolidone, acetonitrile) at a temperature of 5° C. to 35° C. For each mole of compound (4b), 1 mole to 3 moles of each of N-hydroxysuccinimide and the condensing agent was used. The reaction time is from 30 min to 72 h and preferably from 2 h to 24 h. The reaction mixture was diluted with an organic solvent (dichloromethane, chloroform, ethyl acetate, or a mixture of these solvents) and washed three to five times with ice water. The resulting organic layer was dried over an anhydrous salt (anhydrous sodium sulfate or anhydrous magnesium sulfate). The drying agent was filtered off, and the filtrate was concentrated under reduced pressure to give a crude compound (5b). If necessary, the resulting compound (5b) may be purified by C18 silica gel column chromatography [acetonitrile only]. Also, the resulting compound (5b) may be dissolved in a good solvent (ethyl acetate, acetonitrile, dichloromethane, or a mixture of these solvents); a poor solvent (e.g., diethyl ether, diisopropyl ether, hexane) may then be added to re-precipitate the compound; and the resulting solid may be filtered to increase the purity.

(Step B-4)

This step is a step of producing a compound of formula (2) by using a known organic chemistry-based technique to subject the compound of formula (5b) to condensation with a compound of formula (6b). The condensation was carried out by reacting the compound (6b) with a base (e.g., triethylamine, N,N-diisopropylethylamine) and the compound (5b) in a solvent (e.g., N,N-dimethylformamide, N,N-dimethylacetamide, N-methylpyrrolidone, acetonitrile) at a temperature of −10° C. to 100° C., preferably from 15° C. to 35° C. For each mole of compound (6b), 2 moles to 5 moles of the base was used; and 1 mole to 2 moles of the compound (5b) was used. The reaction time is from 5 min to 24 h and preferably from 1 h to 6 h. Benzylamine was added to the reaction mixture to stop the reaction. For each mole of compound (6b), 4 moles to 10 moles of benzylamine was used. If necessary, the reaction mixture was partially concentrated under reduced pressure. The residual solution was subjected to purification by preparative HPLC [e.g., buffer solution/acetonitrile, buffer solution/methanol], C18 silica gel column chromatography [e.g., buffer solution/acetonitrile, buffer solution/methanol], or a combination of these procedures to obtain the compound (2).

Method B': Conjugation Precursor (Cysteine Conjugation)

A conjugation precursor represented by (2') as used in an antibody-drug conjugate of the present invention can be produced according to Method B' described below.

[Formula 82]
(2')
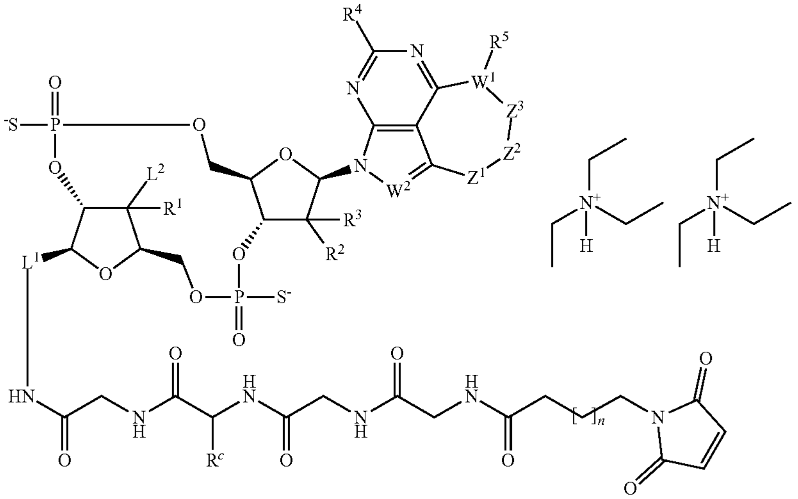
This synthetic scheme is a method for producing a conjugation precursor (2') in the case where $-NH_2$ is substituted at a given position of $L^1$.
[Formula 83]
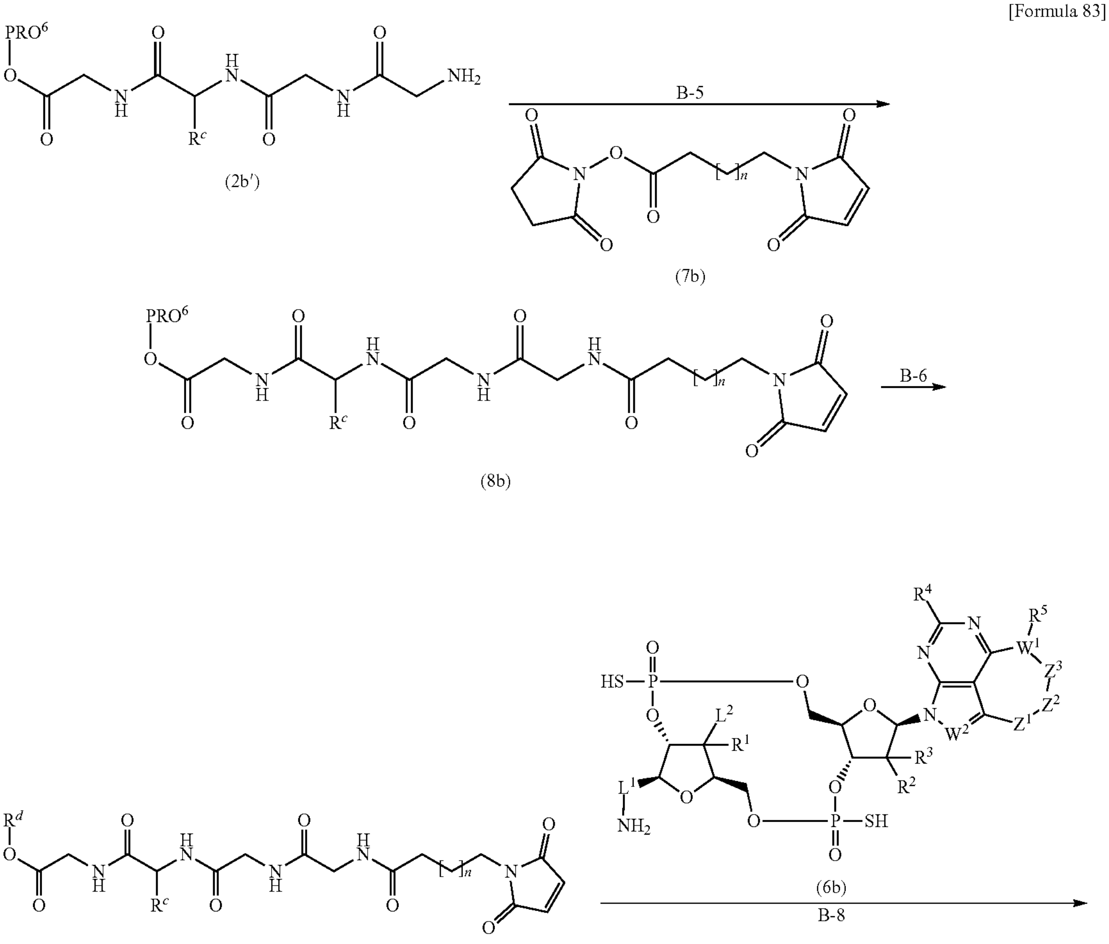
(2b')
(7b)
(8b)
(6b)
(9b)

-continued

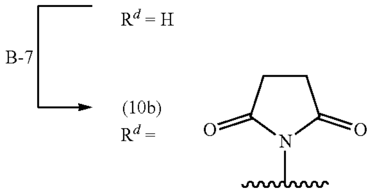

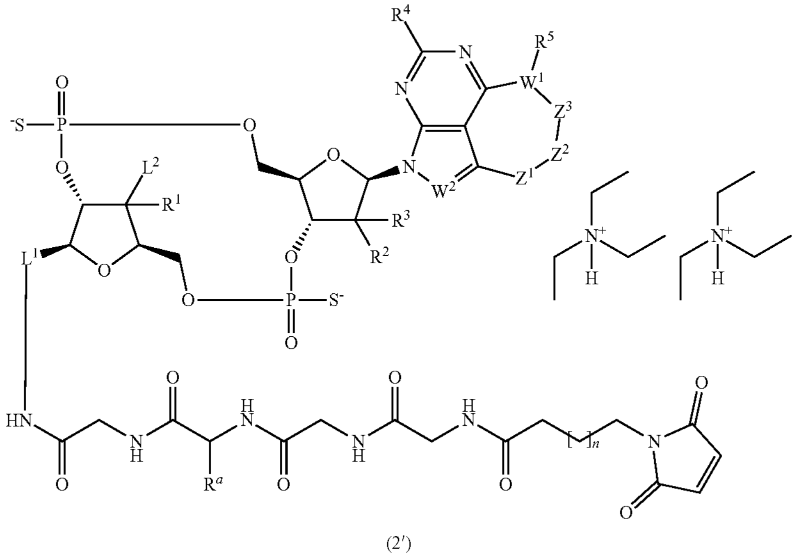

(2')

(Step B-5)

This step is a step of producing a compound of formula (8b) by using a known organic chemistry-based technique to subject the compound of formula (2b') to amidation with a compound of formula (7b). The compound (8b) was obtained according to the procedure described in step B-2 of Method B, except that no base was used.

(Step B-6)

This step is a step of producing a compound of formula (9b) by using a known organic chemistry-based technique to remove a protecting group from the compound of formula (8b). In the case where $PRO^6$ is a tert-butyl group, the compound (9b) was obtained according to the procedure described in step B-1 of Method B, except that silica gel column chromatography [dichloromethane/methanol] was used for purification.

(Step B-7)

This step is a step of producing a compound of formula (10b) by using a known organic chemistry-based technique to subject the compound of formula (9b) to esterification. The compound (10b) was obtained according to the procedure described in step B-3 of Method B.

(Step B-8) This step is a step of producing a compound of formula (2') by using a known organic chemistry-based technique to subject the compound of formula (6b) to condensation with a compound of formula (10b). The compound (2') was obtained according to the procedure described in step B-4 of Method B.

Method C

A conjugation precursor represented by (3) as used in an antibody-drug conjugate of the present invention can be produced according to Method C described below.

[Formula 84]
(3)
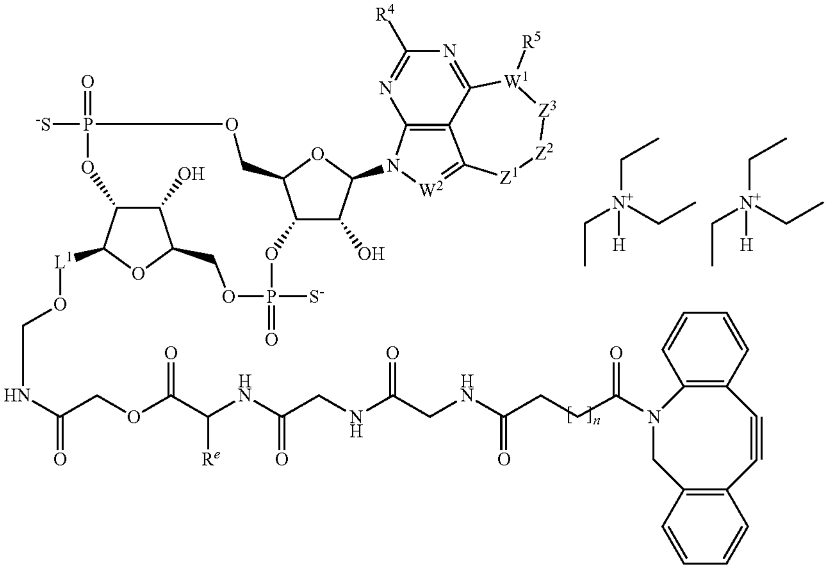
This synthetic scheme is a method for producing a conjugation precursor (3) in the case where a hydroxy group is substituted at a given position of $L^1$.
[Formula 85]
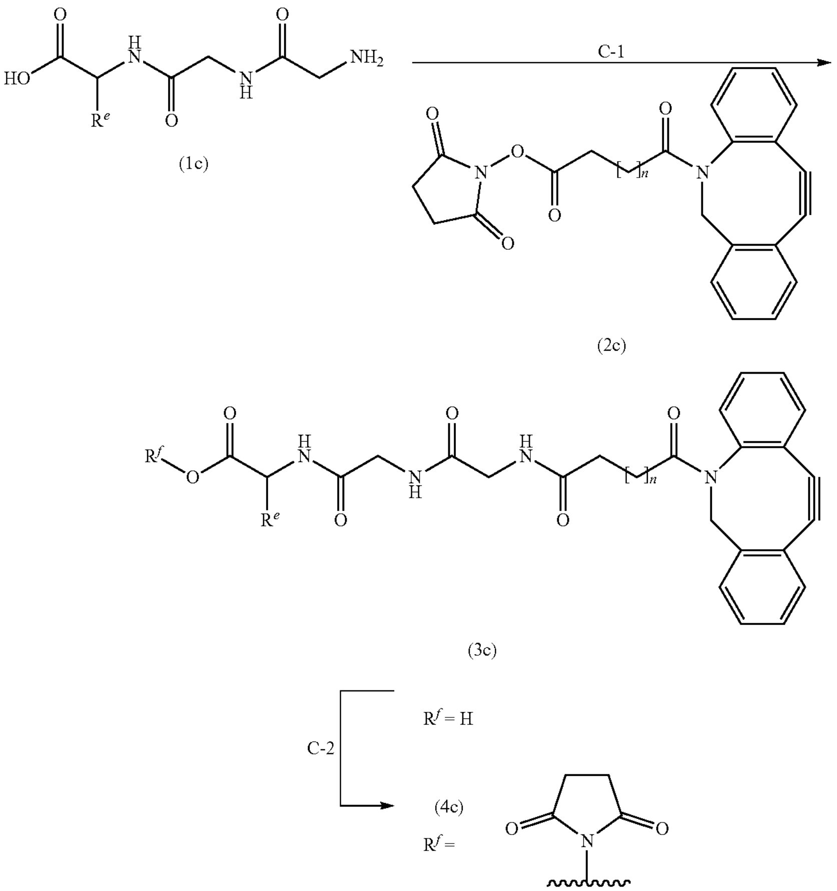
(1c)
(2c)
(3c)
(4c)

-continued
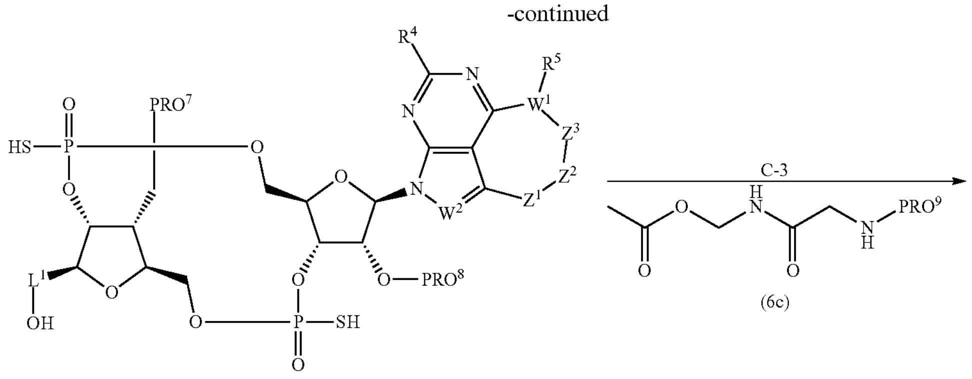
(6c)
(5c)
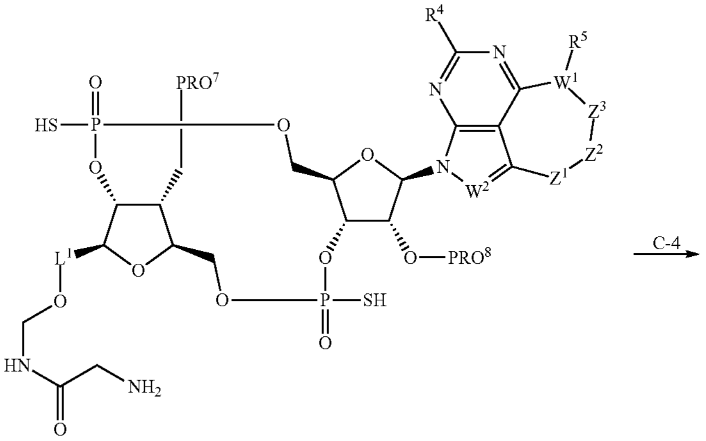
(7c)
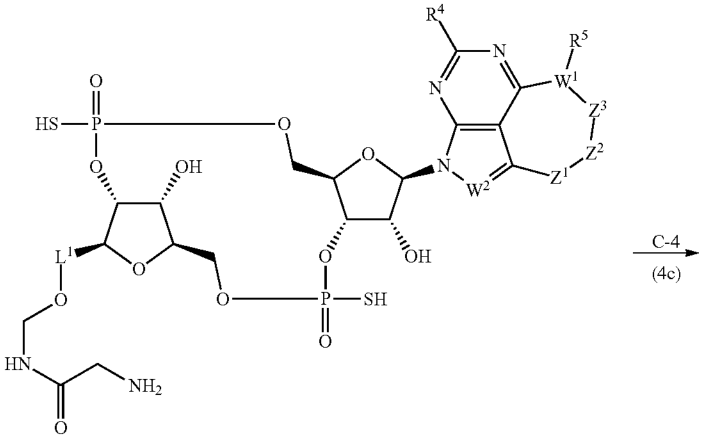
(8c)

-continued

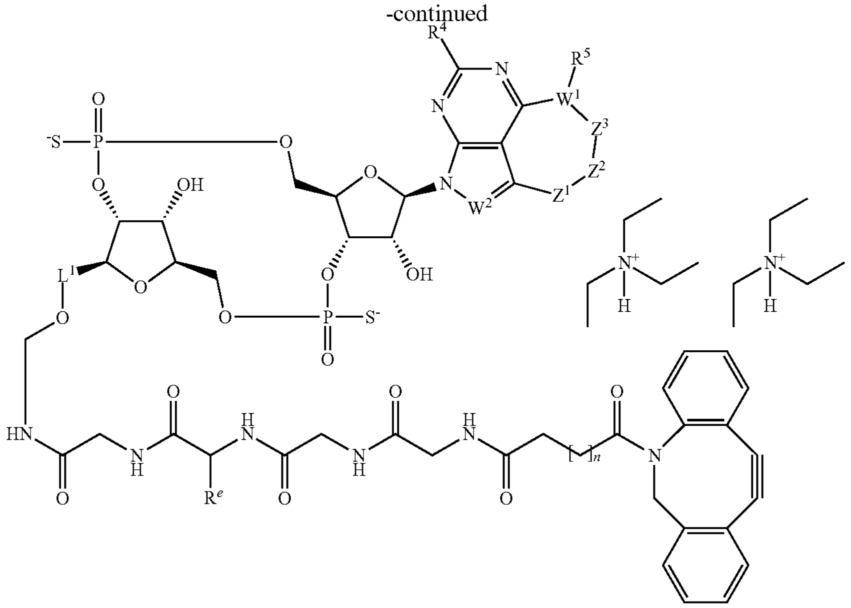

(3)

(Step C-1)

This step is a step of producing a compound of formula (3c) by using a known organic chemistry-based technique to subject a compound of formula (1c) to amidation with a compound of formula (2c). The compound (3c) was obtained according to the procedure described in step B-2 of Method B.

(Step C-2)

This step is a step of producing a compound of formula (4c) by using a known organic chemistry-based technique to subject the compound of formula (3c) to esterification. The compound (4c) was obtained according to the procedure described in step B-3 of Method B.

(Step C-3)

This step is a step of producing a compound of formula (7c) by using a known organic chemistry-based technique to subject a compound of formula (5c) to a coupling reaction (aminomethylenation) with a compound of formula (6c) and then subject the resulting coupling product to deprotection in a sequential manner. In the case where $PRO^9$ was a 9-fluorenylmethyloxycarbonyl group, the aminomethylenation was carried out by reacting the compound (5c) with the compound (6c) and an acid (e.g., p-toluenesulfonic acid) in tetrahydrofuran at a temperature of 5° C. to 35° C. For each mole of compound (5c), 1 mole to 20 moles and preferably 2 moles to 10 moles of the compound (6c) was used, and 0.05 mole to excess moles and preferably 0.1 mole to 3 moles of the acid was used. The reaction time is from 30 min to 72 h and preferably from 2 h to 24 h. Next, a base (e.g., 1,8-diazabicyclo[5.4.0]-7-undecene) was added to the reaction mixture, and deprotection was thus carried out. In the case where the reaction mixture is suspended, a solvent (e.g., N,N-dimethylformamide) may be added and dissolved if necessary, and then the reaction can be carried out. For each mole of compound (5c), excess moles and preferably 5 moles to 20 moles of the base was used. The reaction time is from 10 min to 24 h and preferably from 2 h to 12 h. Water was added to the reaction mixture and the mixture was subjected directly to purification by C18 silica gel column chromatography [e.g., buffer solution/acetonitrile] to give a compound (7c).

(Step C-4)

This step is a step of producing a compound of formula (8c) by using a known organic chemistry-based technique to remove a protecting group from the compound of formula (7c). In the case where $PRO^7$ and $PRO^1$ are each a tert-butyldimethylsilyl group, the compound (8c) was obtained according to the procedure described in step A-7 of Method A.

(Step C-5)

This step is a step of producing a compound of formula (3) by using a known organic chemistry-based technique to subject the compound of formula (8c) to condensation with the compound of formula (4c). The compound (3) was obtained according to the procedure described in step B-4 of Method B.

Method C'

A conjugation precursor represented by (3') as used in an antibody-drug conjugate of the present invention can be produced according to Method C' described below.

[Formula 86]
(3')
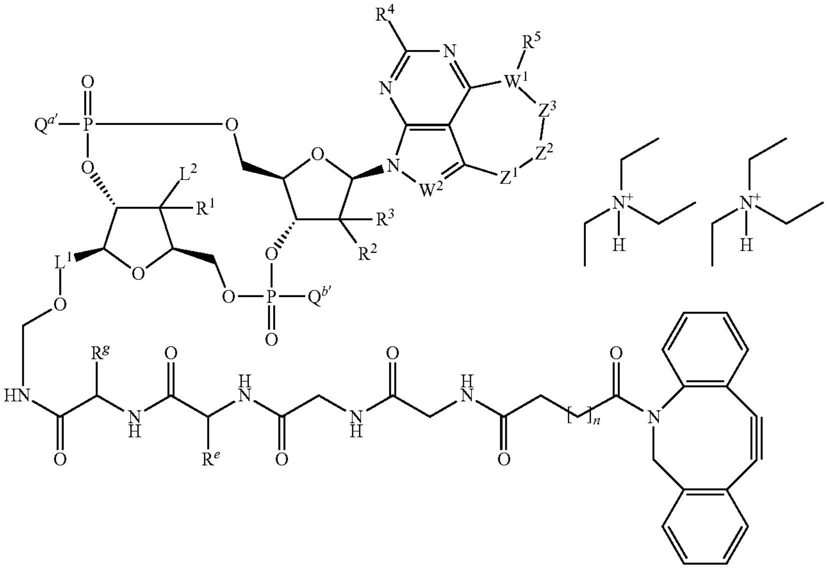
This synthetic scheme is a method for producing a conjugation precursor (3') in the case where a hydroxy group is substituted at a given position of $L^1$.
[Formula 87]
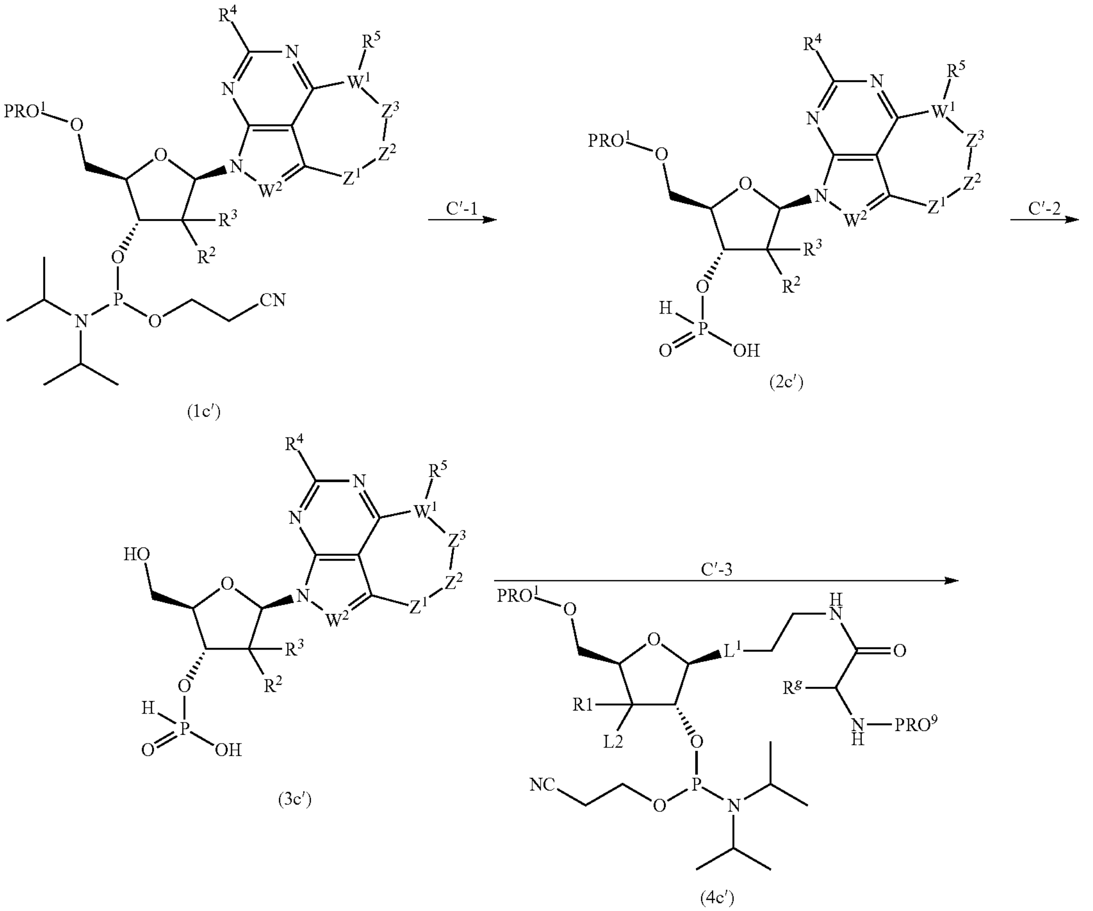
(1c')
(2c')
(3c')
(4c')

-continued
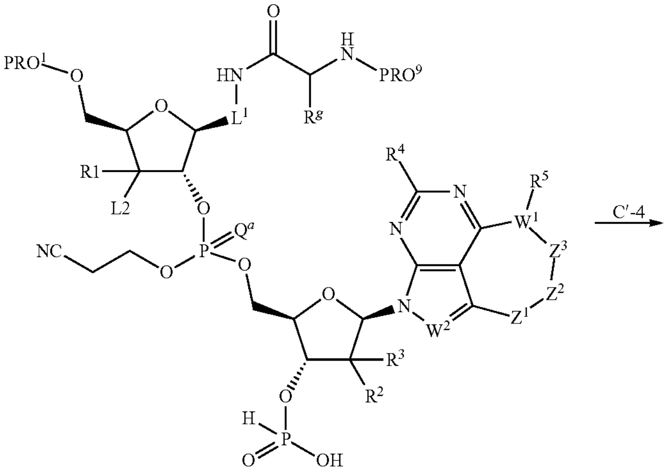
(5c')
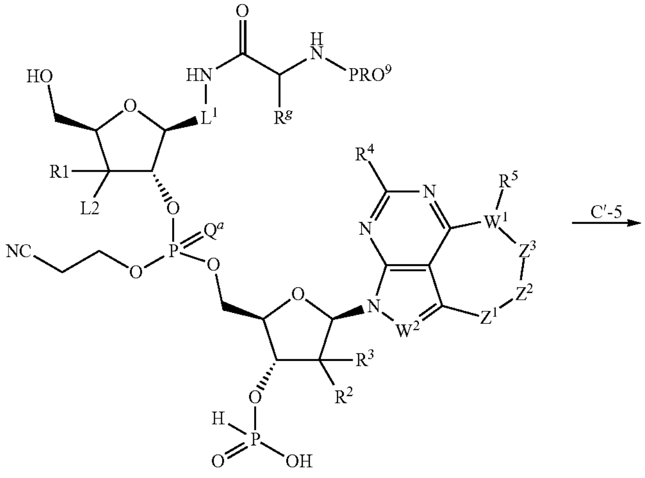
(6c')
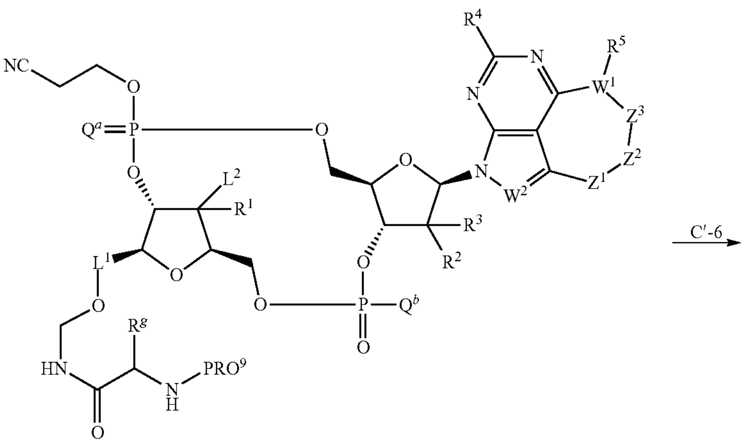
(7c')

-continued
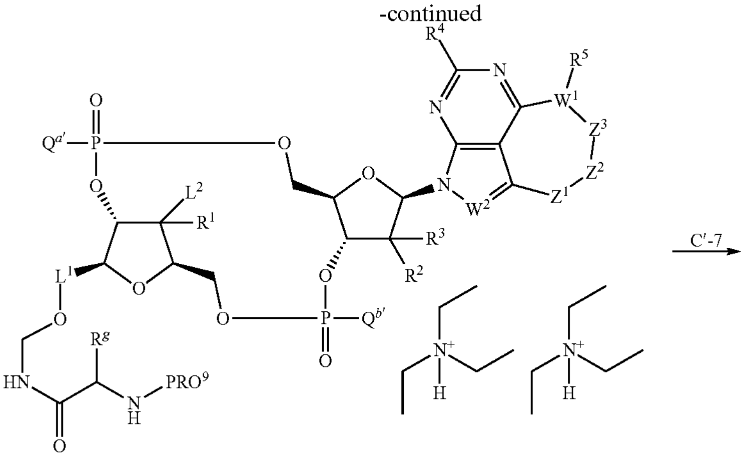
(8c')
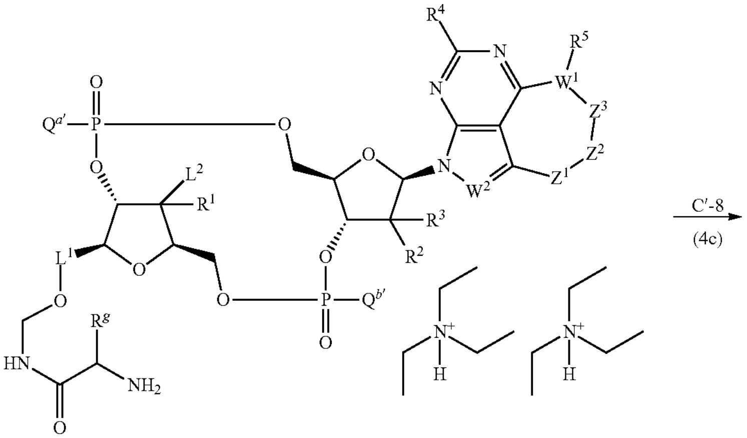
(9c')
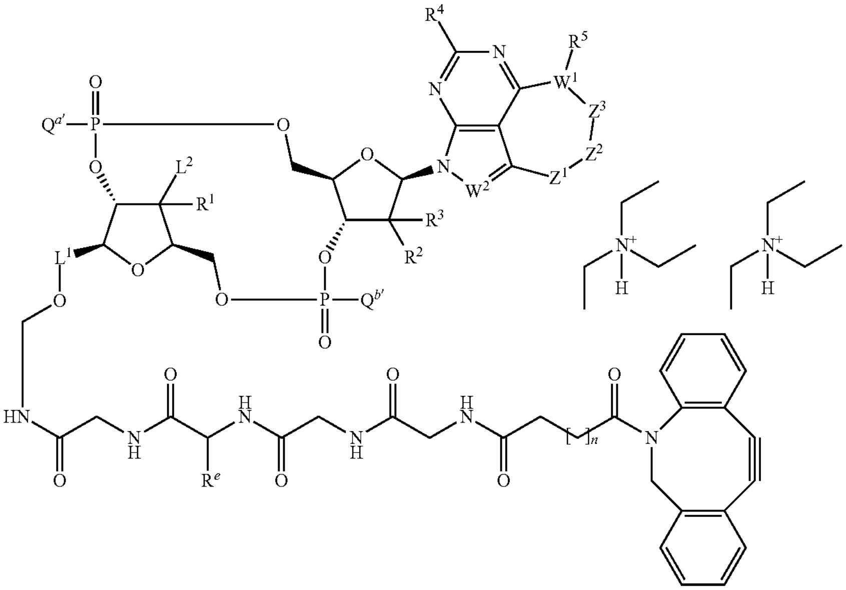
(3')

(Step C'-1)

This step is a step of producing a compound of formula (2c') by using a known organic chemistry-based technique to subject a compound of formula (1c') to hydrolysis and cyanoethyl group removal sequentially. The compound (2c') was obtained according to the procedure described in step A-1 of Method A.

(Step C'-2)

This step is a step of producing a compound of formula (3c') by using a known organic chemistry-based technique to remove a hydroxy group-protecting group from the compound of formula (2c'). The compound (3c') was obtained according to the procedure described in step A-2 of Method A.

(Step C'-3)

This step is a step of producing a compound of formula (5c') by using a known organic chemistry-based technique to subject the compound of formula (3c') to a coupling reaction with a compound of formula (4c') and then subject the resulting coupling product to sulfidation or oxidation in a sequential manner. The compound (5c') was obtained according to the procedure described in step A-3 of Method A or step A''-3 of Method A''.

(Step C'-4)

This step is a step of producing a compound of formula (6c') by using a known organic chemistry-based technique to remove a hydroxy group-protecting group from the compound of formula (5c'). The compound (6c') was obtained according to the procedure described in step A-4 of Method A.

(Step C'-5)

This step is a step of producing a compound of formula (7c') by using a known organic chemistry-based technique to subject the compound of formula (6c') to cyclization and sulfurization or oxidation sequentially. The compound (7c') was obtained according to the procedure described in step A-5 of Method A or step A'-5 of Method A'.

(Step C'-6)

This step is a step of producing a compound of formula (8c') by using a known organic chemistry-based technique to simultaneously remove a cyanoethyl group and all the acyl-based protecting groups from the compound of formula (7c'). The compound (8c') was obtained according to the procedure described in step A-6 of Method A.

(Step C'-7)

This step is a step of producing a compound of formula (9c') by using a known organic chemistry-based technique to simultaneously remove all the silyl-based protecting groups from the compound of formula (8c'). In the case where $PRO^9$ was a 2-(trimethylsilyl)ethoxycarbonyl group, the 2-(trimethylsilyl)ethoxycarbonyl group was removed by treating the compound (8c') with a tetrahydrofuran solution of tetrabutylammonium fluoride at a temperature of 5° C. to 100° C., preferably from 35° C. to 60° C. For each mole of compound (8c'), excess moles and preferably 10 to 30 moles of tetrabutylammonium fluoride was used. The reaction time is from 1 h to 48 h and preferably from 4 h to 24 h. The reaction mixture was diluted with buffer solution, and the organic solvent component was then distilled off under reduced pressure as necessary. The residue was purified by preparative HPLC [e.g., buffer solution/acetonitrile, buffer solution/methanol], C18 silica gel column chromatography [e.g., buffer solution/acetonitrile, buffer solution/methanol], or a combination of these procedures to obtain the compound (9c').

(Step C'-8)

This step is a step of producing a compound of formula (3') by using a known organic chemistry-based technique to subject the compound of formula (9c') to condensation with the compound of formula (4c). The compound (3') was obtained according to the procedure described in step B-4 of Method B.

Method D: To Produce Glycan-Remodeled Antibody

A glycan-remodeled antibody can be produced by the method illustrated in the following scheme in accordance with the procedure described in, for instance, WO2018/003983.

[Formula 88]

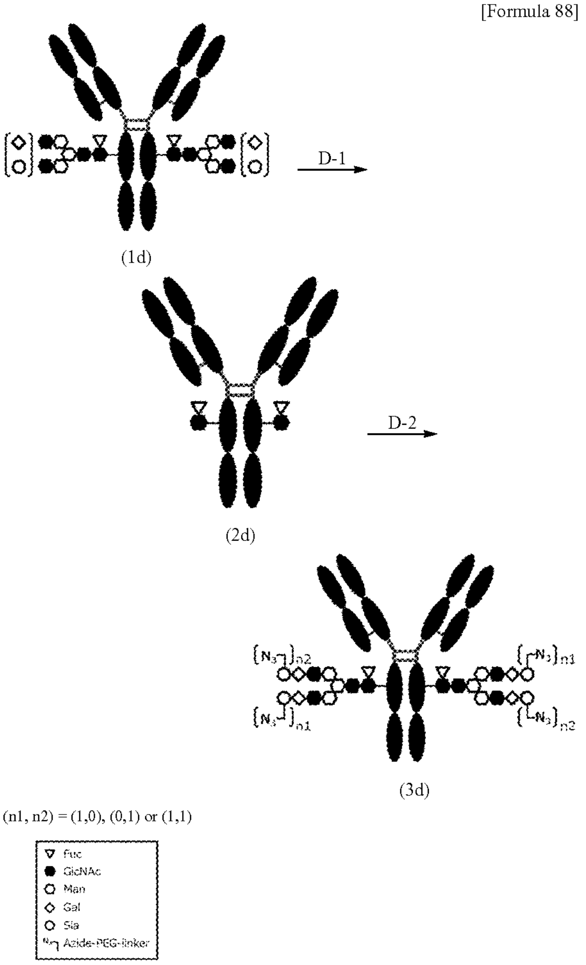

(1d)

(2d)

(3d)

(n1, n2) = (1,0), (0,1) or (1,1)

(Step D-1)

This step is a step of producing a glycan-cleaved antibody by using a known enzymatic reaction to hydrolyze and cleave a glycosidic linkage between GlcNAcβ1-4GlcNAc of the chitobiose structure at the reducing terminal of the N-linked glycan (N297-linked glycan) attached to asparagine at 297-position of the amino acid sequence of an antibody. The hydrolysis reaction of the glycosidic linkage between GlcNAc(31 and 4GlcNAc at the reducing terminal of the chitobiose structure of a desired antibody (1d) (10 mg/mL) was carried out using a hydrolase such as wild-type EndoS enzyme in a buffer solution (e.g., a phosphate buffer) at a temperature of 0° C. to 40° C. The reaction time is from 10 min to 72 h and preferably from 1 h to 6 h. The amount of wild-type EndoS enzyme used was from 0.1 mg to 10 mg and preferably from 0.1 mg to 3 mg per 100 mg of the antibody (1d). After completion of the reaction, the antibody was purified by affinity chromatography (HiTrap rProtein A FF (5 ml) (produced by GE Healthcare)) and/or hydroxyapatite column (Bio-Scale Mini CHT Type I cartridge (5 ml) (produced by BIO-RAD)) to obtain a (Fucα1, 6)GlcNAc antibody (2d).

(Step D-2)

This step is a step of producing a glycan-remodeled antibody (3d) by using a known enzymatic reaction to link the (Fucα1, 6)GlcNAc antibody (2d) obtained in step D-1 with an SG- or MSG (MSG1, MSG2)-type glycan oxazoline moiety having an azide group-containing PEG linker (hereinafter referred to as an "azido-glycan oxazoline moiety").

The transglucosylation reaction was carried out by reacting the antibody (2d) with the azido-glycan oxazoline moiety in the presence of glycosyltransferase (e.g., EndoS (D233Q/Q303L)) in a buffer solution (e.g., a phosphate buffer) at a temperature of 0° C. to 40° C. The reaction time is from 10 min to 72 h and preferably from 1 h to 6 h. The amount of the EndoS enzyme (D233Q/Q303L) used was from 1 mg to 10 mg and preferably from 1 mg to 3 mg per 100 mg of the antibody; and 2 equivalents to excess equivalents and preferably 4 equivalents to 20 equivalents of the azido-glycan oxazoline moiety was used. After completion of the reaction, the antibody was purified by affinity chromatography (HiTrap rProtein A FF (5 ml) (produced by GE Healthcare)) and hydroxyapatite column (Bio-Scale Mini CHT Type I cartridge (5 ml) (produced by BIO-RAD)) to obtain the glycan-remodeled antibody (3d).

In the above preparation of the glycan-remodeled antibody, concentration of the antibody aqueous solution, concentration measurement, and buffer exchange may be carried out according to the following common operations A to C.

Note that the SG-type azido-glycan oxazoline moiety was synthesized in accordance with the procedure described in WO2018/003983. As an example, how to synthesize $[N_3\text{-}PEG(3)]_2$-SG(10)-Ox (compounds 1-10 described in WO2018/003983) is illustrated in the following scheme.

[Formula 89]

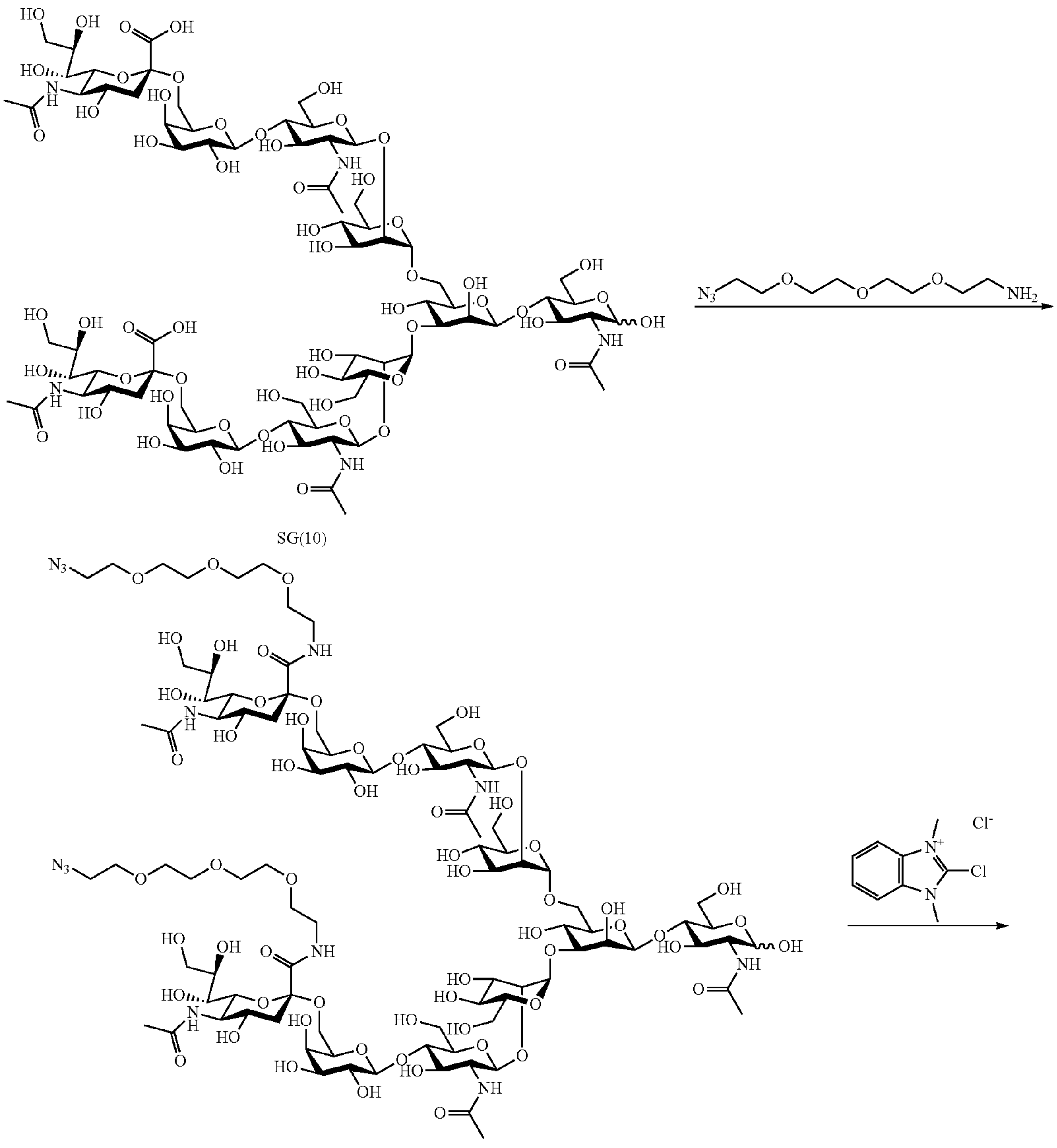

SG(10)

$[N_3\text{-}PEG(3)]_2$-SG (10)

-continued
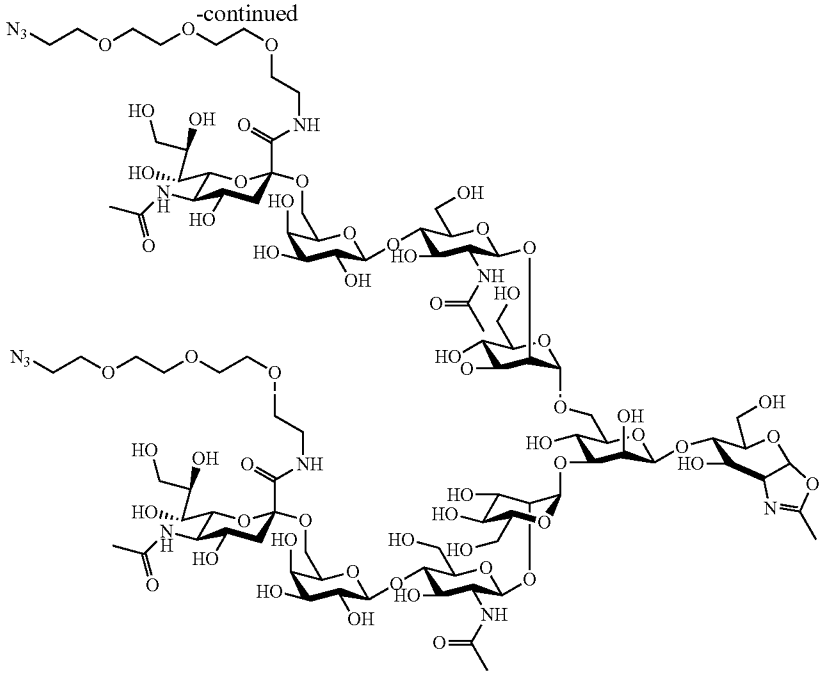
[$N_3$-PEG(3)]$_2$-SG (10) Ox
The MSG-type azido-glycan oxazoline moiety was also synthesized in accordance with the procedure described in WO2018/003983. As an example, how to synthesize [$N_3$-PEG(3)]$_2$-MSG1(9)-Ox (compounds 1-11 described in WO2018/003983) is illustrated in the following scheme.

[Formula 90]
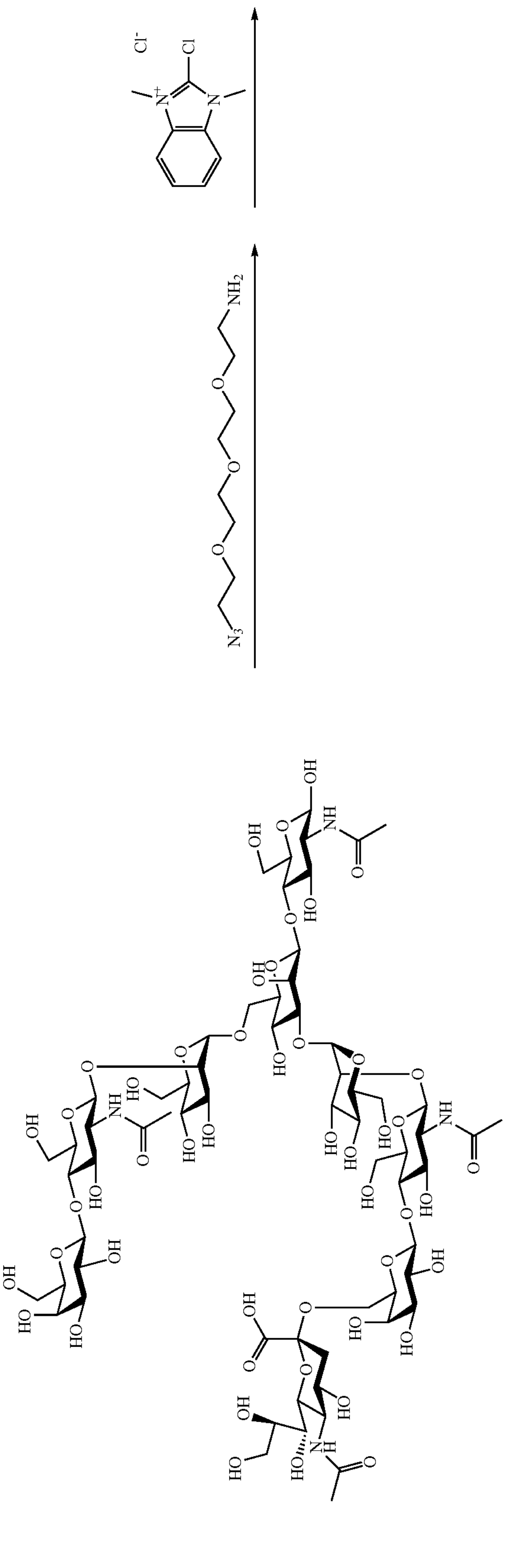
MSG1(9)

-continued
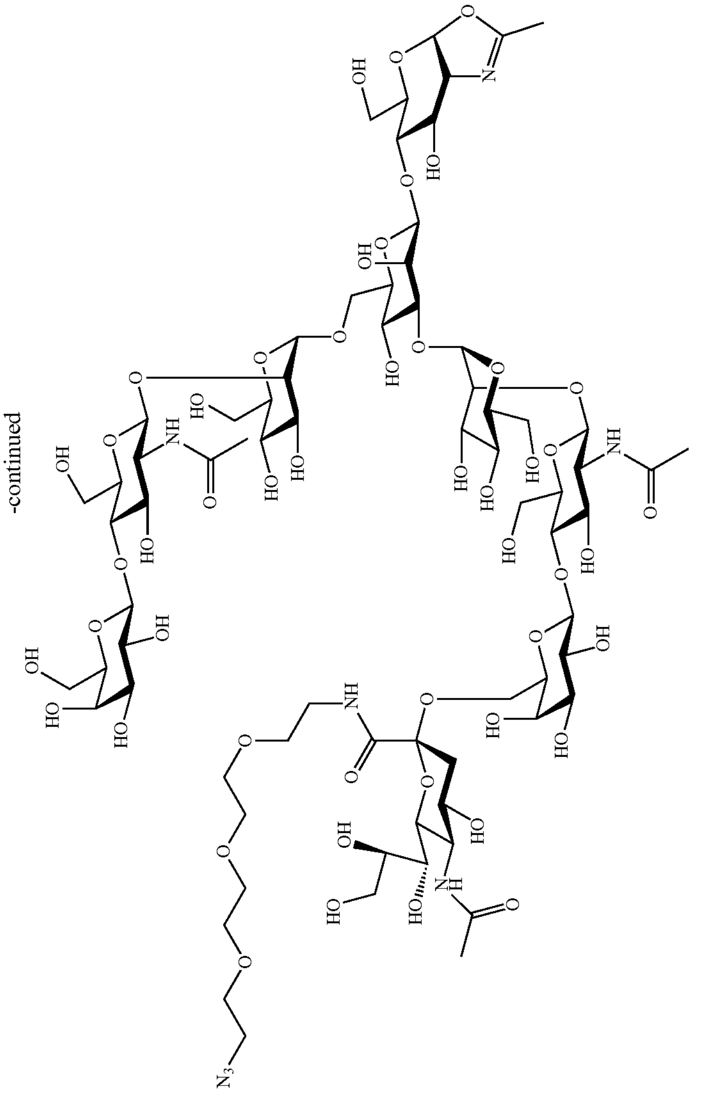
$[N_3$-PEG(3)]-MSG1(9)Ox

Method E: To Conjugate Antibody and Drug (Glycan Conjugation 1)

[Formula 91]
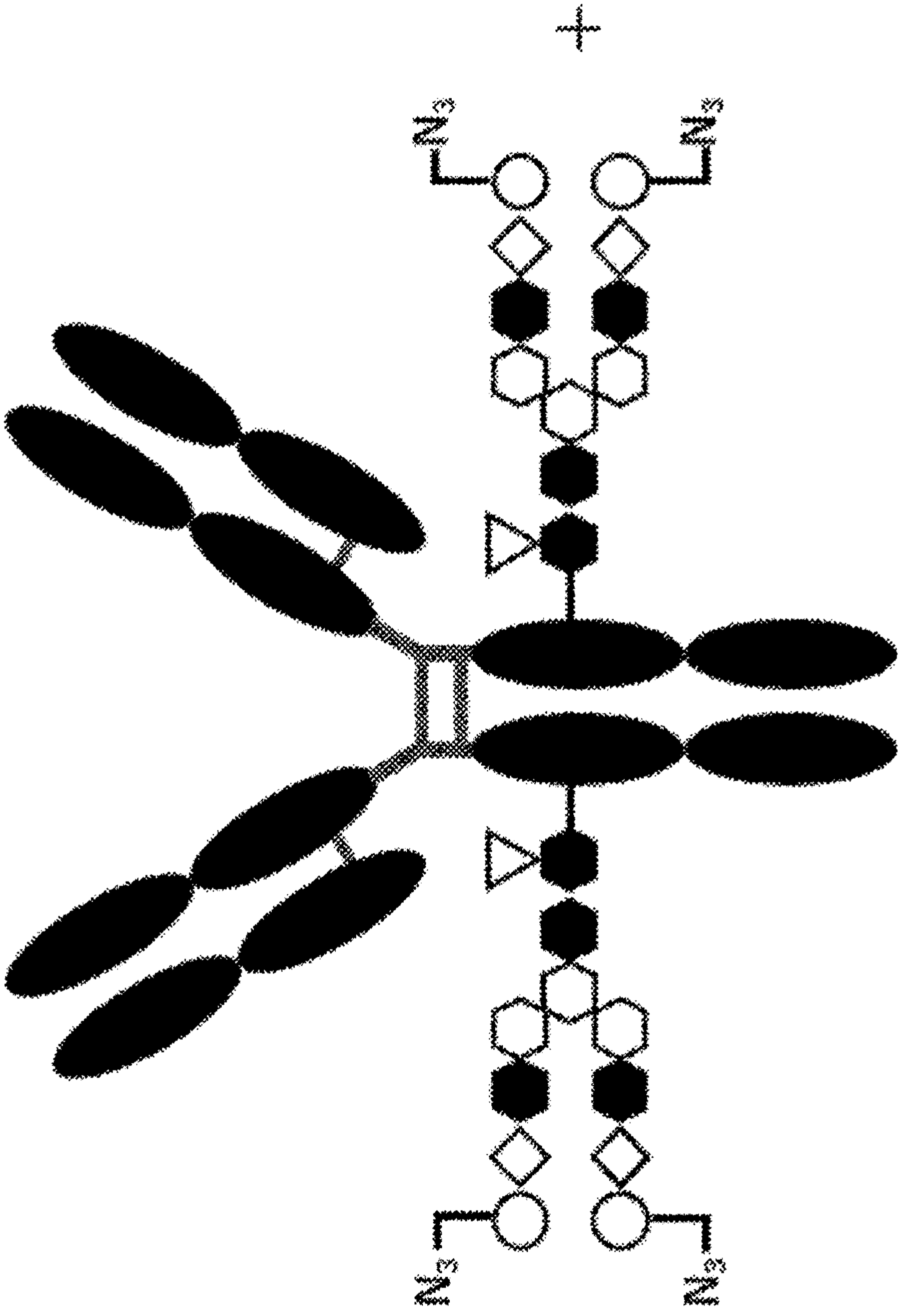
(3d)

-continued
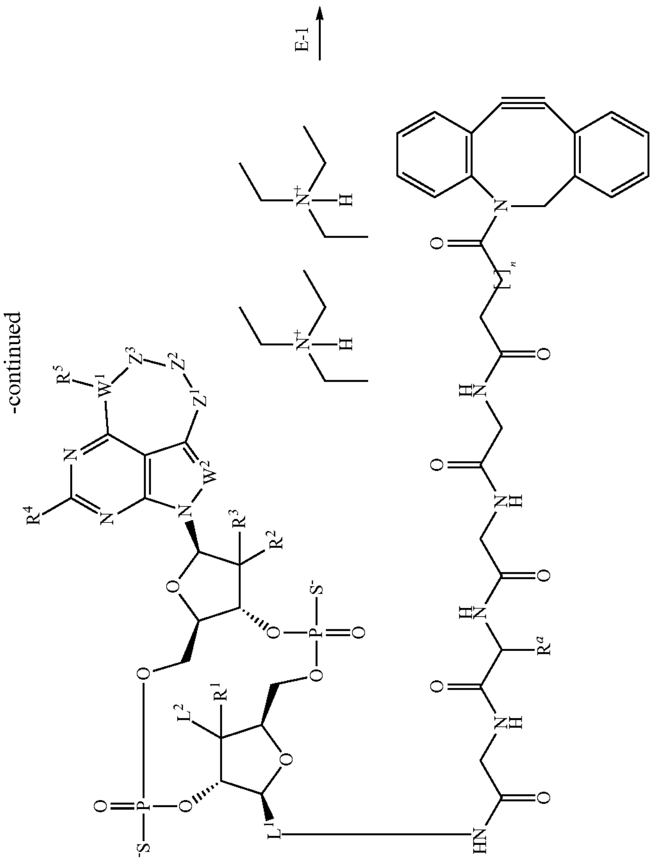
(2)

-continued
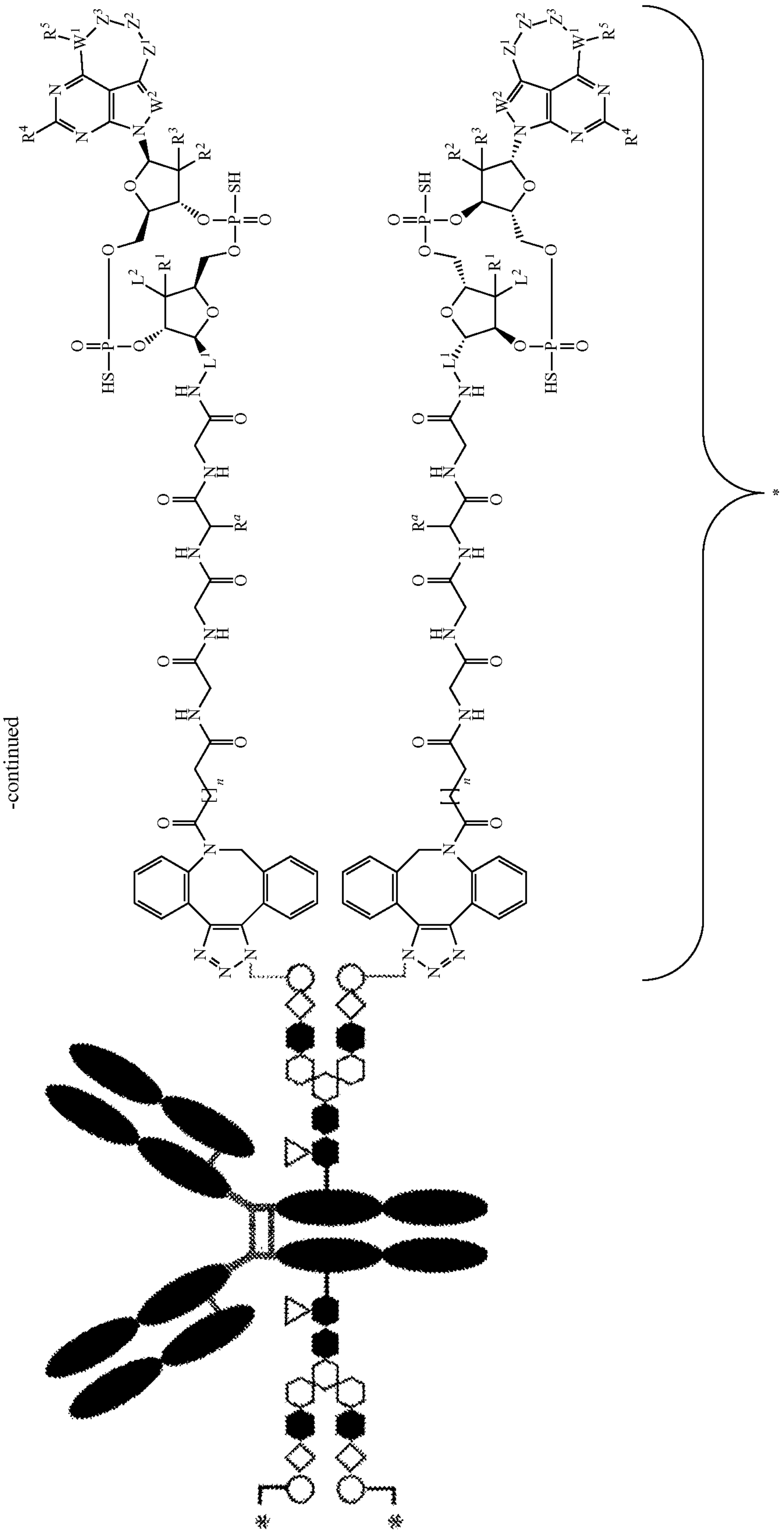

Wherein, the two asterisks (*) on the left side of the antibody-drug conjugate (1e) each indicate a drug-linker portion represented by the asterisk on the right side.

This synthetic scheme is a method for producing an antibody-drug conjugate (1e) by using a SPAAC (strain-promoted azide-alkyne cycloaddition: J. Am. Chem. Soc. 2004, 126, 15046-15047) reaction to conjugate the glycan-remodeled antibody (3d) obtained in step D-2 of Method D with the conjugation precursor (2) obtained in step B-4 of Method B.

(Step E-1)

The SPAAC reaction was carried out by mixing the glycan-remodeled antibody (3d)-containing buffer solution (e.g., phosphate buffer, acetate buffer, borate buffer) with a solution in which the conjugation precursor (2) had been dissolved in an appropriate solvent (dimethyl sulfoxide, N,N-dimethylformamide, N,N-dimethylacetamide, N-methylpyrrolidone, propylene glycol, or a mixture of these solvents). For each mole of the glycan-remodeled antibody (3d), 2 moles to excess moles and preferably 4 moles to 30 moles of the conjugation precursor (2) is used; and the percentage of the organic solvent is preferably from 1% to 200% (v/v) based on the antibody buffer solution. The reaction temperature is from 0° C. to 37° C. and preferably from 15° C. to 25° C. The reaction time is from 1 h to 150 h and preferably from 6 h to 72 h. The pH of the reaction mixture is preferably from 5 to 9. The reaction mixture was subjected to purification by the method described in common operation D to give the antibody-drug conjugate (1e).

Method E': To Conjugate Antibody and Drug (Cysteine Conjugation)

An antibody-drug conjugate with cysteine conjugation according to the present invention can be produced by the procedure described in, for instance, WO2014/057687 while using the desired antibody prepared according to, for instance, Reference Example 3 and the conjugation precursor (2') having a maleimide group as obtained in step B-8 of Method B'.

Method E": To Conjugate Antibody and Drug (Glycan Conjugation 2)

The conjugation precursor (2) was switched, in Method E, to the conjugation precursor (3') obtained in step C'-8 of Method C' to obtain an antibody-drug conjugate (1e") represented by the following formula:

[Formula 92]
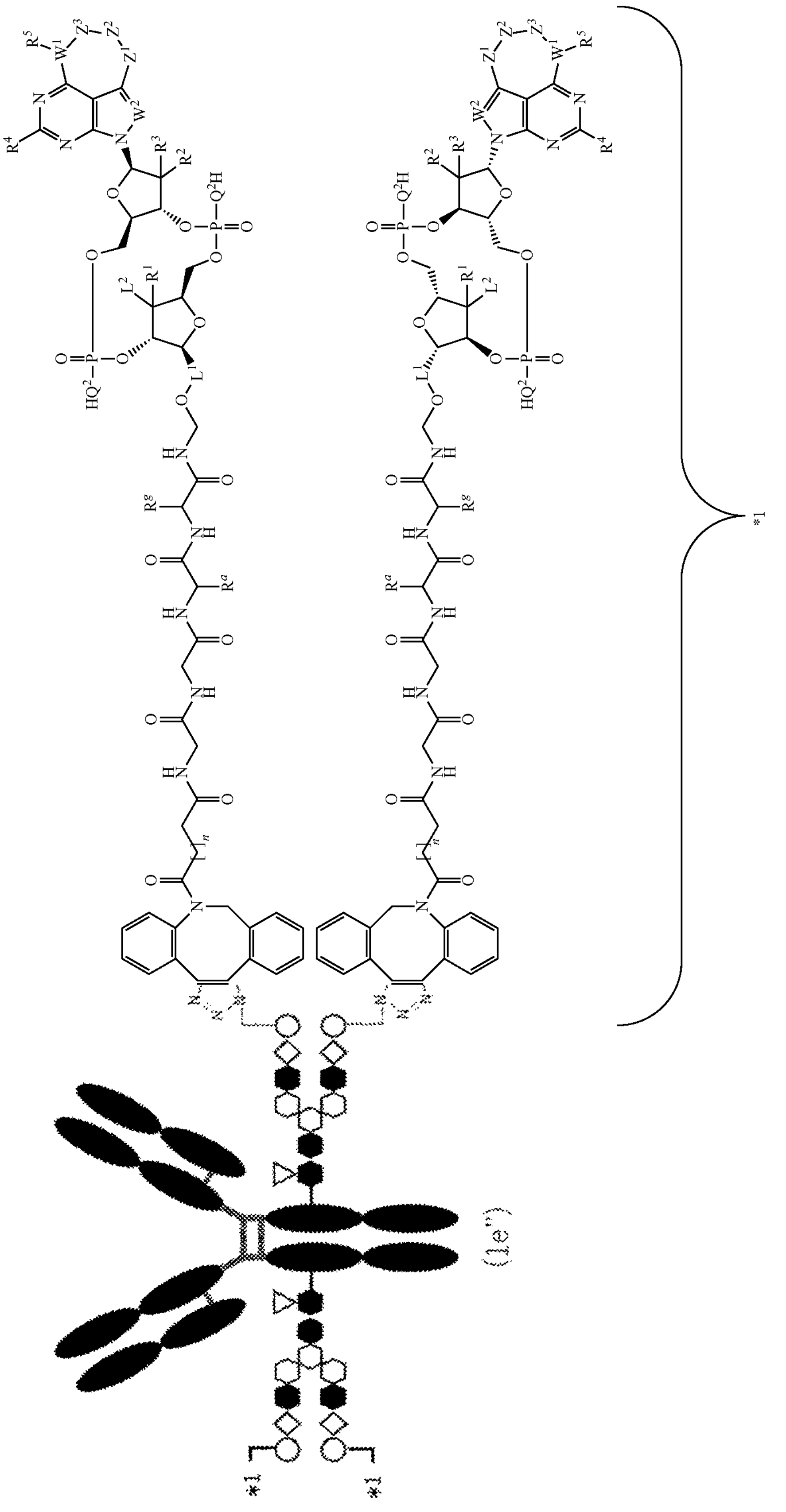
(1e'')

wherein the two asterisks (*[1]) on the left side of the antibody-drug conjugate (1e") indicate a drug-linker portion represented by the asterisk on the right side.

According to the below-described common operations D to G, antibody-drug conjugate can be identified from each other through buffer exchange, purification, measurement of antibody concentration, and measurement of the average number of drugs conjugated per antibody molecule.

Common operation A: To Concentrate Antibody Aqueous Solution

An antibody or antibody-drug conjugate solution was placed in an Amicon (registered trademark) Ultra centrifugal filter device (50,000 NMWL, Merck Millipore, Ltd.) and centrifuged (at 2000 G to 4000 G for 5 to 20 min) using a centrifuge (Allegra X-15R, Beckman Coulter, Inc.). In this way, the antibody or antibody-drug conjugate solution was concentrated.

Common operation B: To Measure Antibody Concentration

The antibody concentration was measured using a UV meter (Nanodrop 1000, Thermo Fisher Scientific, Inc.) in accordance with the method specified by the manufacturer. At that time, the absorbance coefficients at 280 nm (1.3 $mLmg^{-1}$ $cm^{-1}$ to 1.8 $mLmg^{-1}$ $cm^{-1}$) were different for each antibody.

Common operation C: To Exchange Buffer for Antibody

A buffer solution (e.g., phosphate buffered saline (pH 6.0), phosphate buffer (pH 6.0)) was added to the antibody aqueous solution, and the solution was concentrated according to the method described in common operation A. This operation was repeated several times, and the antibody concentration was then measured according to the method described in common operation B. A buffer solution (e.g., phosphate buffered saline (pH 6.0), phosphate buffer (pH 6.0)) was added, if appropriate, to the antibody buffer solution to prepare the antibody buffer solution at a desired concentration (e.g., about 10 mg/mL).

Common operation D: To Purify Antibody-Drug Conjugate (Gel Filtration Chromatography)

Each NAP column (NAP-5, NAP-10, or NAP-25 (produced by GE Healthcare)) was equilibrated with acetate buffer (10 mM acetate buffer, 5% sorbitol, pH 5.5; herein referred to as ABS) or another suitable buffer solution. The antibody-drug conjugate reaction mixture was charged into this NAP column. A buffer solution at a volume specified by the manufacturer was allowed to flow down. Then, the antibody fractions were collected. The fractions were recharged into the NAP column. Subsequently, a buffer solution at a volume specified by the manufacturer was allowed to flow down, and the antibody fractions were then collected. By repeating this operation a total of 2 to 3 times to yield an antibody-drug conjugate from which an unbound drug-linker, dimethylsulfoxide, and propyleneglycol had been removed. As necessary, the concentration of the antibody-drug conjugate solution was adjusted using common operations A and C.

Common operation E: To Measure Antibody Concentration and Average Number of Drugs Conjugated Per Antibody Molecule in Antibody-Drug Conjugate (UV Method).

The concentration of drug conjugated in the antibody-drug conjugate can be calculated by using a spectrophotometer (UV/VIS Spectrometer Lambda 25, PerkinElmer, Inc.) to measure absorbance of the aqueous solution of the antibody-drug conjugate at two wavelengths, 280 nm and 250 nm, and then performing the following calculation. The total absorbance at a certain wavelength is equal to the sum of each absorbance of all the absorption chemical species (each absorbance can be added). Therefore, it is assumed that there is no change in the molar extinction coefficients of the antibody and the drug between before and after the antibody and the drug are conjugated. In this case, the antibody concentration or the drug concentration in the antibody-drug conjugate can be expressed using the following expressions:

$$A_{280}=A_{D,280}+A_{A,280}=\varepsilon_{D,280}C_D+\varepsilon_{A,280}C_A \quad \text{Expression (I);}$$

and $$A_{250}=A_{D,250}+A_{A,250}=\varepsilon_{D,250}C_D+\varepsilon_{A,250}C_A \quad \text{Expression (II).}$$

Wherein, $A_{280}$ represents absorbance at 280 nm of antibody-drug conjugate aqueous solution; $A_{250}$ represents absorbance at 250 nm of the antibody-drug conjugate aqueous solution; $A_{A,280}$ represents absorbance at 280 nm of antibody; $A_{A,250}$ represents absorbance at 250 nm of the antibody; $A_{D,280}$ represents absorbance at 280 nm of conjugate precursor; $A_{D,250}$ represents absorbance at 250 nm of the conjugate precursor; $\varepsilon_{A,280}$ represents the molar extinction coefficient at 280 nm of the antibody; $\varepsilon_{A,250}$ represents the molar extinction coefficient at 250 nm of the antibody; $\varepsilon_{D,280}$ represents the molar extinction coefficients at 280 nm of the conjugate precursor; $\varepsilon_{D,250}$ represents the molar extinction coefficients at 250 nm of the conjugate precursor; $C_A$ represents the concentration of the antibody in the antibody-drug conjugate; and $C_D$ represents the concentration of the drug in the antibody-drug conjugate. Wherein, each of values provided beforehand (estimates based on calculation or measured value) for $\varepsilon_{A,280}$, $\varepsilon_{A,250}$, $\varepsilon_{D,280}$, and $\varepsilon_{D,250}$ is used. For instance, $\varepsilon_{A,280}$ may be estimated from the amino acid sequence of the antibody by using a known calculation process (Protein Science, 1995, vol. 4, 2411-2423). The value $\varepsilon_{A,250}$ used was calculated from the values measured obtained from UV measurement of the antibody and the value estimated for $\varepsilon_{A,280}$. In the Examples, the molar extinction coefficients of anti-TROP2 antibody 1 were $\varepsilon_{A,280}=223400$ and $\varepsilon_{A,250}=63482$. The molar extinction coefficients of anti-TROP2 antibody 2 were $\varepsilon_{A,280}=223400$ and $\varepsilon_{A,250}=69027$ or 71411. The molar extinction coefficients of anti-CD70 antibody 1 were $\varepsilon_{A,280}=226380$ and $\varepsilon_{A,250}=73432$. The molar extinction coefficients of anti-CD70 antibody 2 were $\varepsilon_{A,280}=212400$ and $\varepsilon_{A,250}=72355$. The molar extinction coefficients of anti-EGFR antibody 1 were $\varepsilon_{A,280}=203460$ and $\varepsilon_{A,250}=62692$. The molar extinction coefficients of anti-EGFR antibody 2 were $\varepsilon_{A,28}0=217440$ and $\varepsilon_{A,250}=75731$. Meanwhile, $\varepsilon_{D,280}$ and $\varepsilon_{D,250}$ are obtained by measuring the absorbance of a solution in which the conjugate precursor has been dissolved to a certain molar concentration, and applying Lambert-Beer's law (absorbance=molar concentration×molar extinction coefficient×cell's optical path length). The molar extinction coefficients of the conjugate precursor in the Examples were obtained by UV measurement on a case-by-case basis. $A_{280}$ and $A_{250}$ of the antibody-drug conjugate aqueous solution may be measured; these values may be assigned to Expressions (I) and (II) to solve the simultaneous expressions; and $C_A$ and $C_D$ can thus be calculated. Further, by dividing $C_D$ by $C_A$, the average number of drugs conjugated per antibody molecule may be calculated.

Common operation F: To Measure Antibody Concentration and Average Number of Drugs Conjugated Per Antibody Molecule in Antibody-Drug Conjugate (Reverse-Phase High Performance Liquid Chromatography Method: RP-HPLC)

The antibody concentration and the average number of drugs conjugated per antibody molecule in the antibody-drug conjugate can be calculated by the above-described common operation E as well as high performance liquid chromatography analysis using the following methods.

[F-1. To Prepare Samples for HPLC Analysis (To Reduce Antibody-Drug Conjugate)

A solution of an antibody-drug conjugate solution (about 1 mg/mL; 60 μL) was mixed with an aqueous solution of dithiothreitol (DTT) (100 mM; 15 L). The mixture was incubated at 37° C. for 30 min to cleave each disulfide bond between the L and H chains of the antibody-drug conjugate. The reaction mixture was used directly for HPLC analysis.

[F-2. HPLC Analysis]

Representative analysis conditions are as follows.

HPLC system: Agilent 1290 HPLC system (Agilent Technologies)

Detector: UV spectrophotometer (measurement wavelength: 280 nm)

Column: Acquity BEH Phenyl (2.1×50 mm, 1.7 μm; produced by Waters)

Column temperature: 75° C.

Flow rate: 0.8 mL/min

Sample injection volume: 10 L

Mobile phase A: 0.1% trifluoroacetic acid (TFA), 15% isopropyl alcohol solution

Mobile phase B: 0.075% TFA, 15% isopropyl alcohol acetonitrile solution

Gradient program (mobile phase B): 14%-36% (0 min-15 min), 36%-80% (15-17 min), 80%-14% (17 min-17.1 min), 14%-14% (17.1 min-23 min)

[F-3. Data Analysis]

[F-3-1] In the case of glycan conjugation in the SPAAC reaction, the drug-conjugated H-chain (H-chain having one drug conjugated: H1, H-chain having two drugs conjugated: H2) is more hydrophobic than the drug-free L-chain (L0) and H-chain (H0) of the antibody. The hydrophobicity increases in proportion to the number of drugs conjugated, and the retention time increases accordingly. Accordingly, in principle, L0, H0, H1, and H2 are eluted in this order. By comparing the retention time between L0 and H0, the detection peak can be assigned to any of L0, H0, H1, and H2. In the case of cysteine conjugation, the drug-conjugated L-chain (L chain having one drug conjugated: L1) and the drug-conjugated H-chain (H-chain having one drug conjugated: H1, H-chain having two drugs conjugated: H2, H-chain having three drugs conjugated: H3) are more hydrophobic in proportion to the number of drugs conjugated. Also, the retention time increases. Accordingly, in principle, L0, L1, H0, H1, H2, and H3 are eluted in this order. By comparing the retention time between L0 and H0, the detection peak can be assigned to any of L0, L1, H0, H1, H2, and H3.

[F-3-2] In the case of glycan conjugation in the SPAAC reaction, the peak area was corrected according to the following expression while using the molar extinction coefficients of the H chain and the drug-linker in response to the number of drug-linkers conjugated, because each drug-linker absorbs UV light. In the case of cysteine conjugation, where the drug is also conjugated to the L-chain, the peak area was corrected likewise for the L-chain.

[Expression 1]

$$\text{Corrected } H\text{-chain peak area } (HPA_i) = \text{Peak area} \times \frac{\text{Molar extinction coefficient of } H\text{-chain}}{\text{Molar extinction coefficient of } H\text{-chain} + \text{Number of drugs conjugated} \times \text{Molar extinction coefficient of drug-linker}}$$

Wherein, for the molar extinction coefficients (280 nm) of the L chain and H chain in each antibody, values estimated from the known calculation method described in common operation E were used. For the anti-TROP2 antibody 1 or anti-TROP2 antibody 2, 27702 was used as the molar extinction coefficient of the L chain and 83998 was used as the molar extinction coefficient of the H chain. In the case of the anti-CD70 antibody 1, 30222 was used as the molar extinction coefficient of the L chain and 82968 was used as the molar extinction coefficient of the H chain. In the case of the anti-CD70 antibody 2, 30222 was used as the molar extinction coefficient of the L chain and 75978 was used as the molar extinction coefficient of the H chain. In the case of the anti-EGFR antibody 1, 23232 was used as the molar extinction coefficient of the L chain and 78498 was used as the molar extinction coefficient of the H chain. In the case of the anti-EGFR antibody 2, 30222 was used as the molar extinction coefficient of the L chain and 78498 was used as the molar extinction coefficient of the H chain. The molar extinction coefficient (at 280 nm) of the drug-linker was a value measured for the conjugation precursor in the case of glycan conjugation in the SPAAC reaction. In the case of cysteine conjugation, the conjugation precursor was reacted with mercaptoethanol or N-acetylcysteine, and the value measured for the compound, in which the maleimide group had been converted to a succinimide thioether, was used.

[F-3-3] The peak area ratio (%) of each chain based on the total of corrected peak areas was calculated according to the following expression.

[Expression 2]

$$H\text{-chain peak area ratio } (\%\ HPA_i) = \frac{HPA_i}{HPA_0 + HPA_1 + HPA_2} \times 100$$

[F-3-4] The average number of drugs conjugated per antibody molecule in an antibody-drug conjugate (DAR) was calculated according to the following expression.

[Expression 3]

$$\text{Average number of drugs conjugated } (DAR) = \frac{0 \times \%\ HPA_0 + 1 \times \%\ HPA_1 + 2 \times \%\ HPA_2}{100} \times 2$$

[F-3-5] The antibody concentration in the antibody-drug conjugate was calculated according to the following expression.

[Expression 4]

$$\text{Antibody concentration } (C_A)[\text{mg/mL}] = \frac{\text{Absorbance of antibody-drug conjugate} \times \text{Dilution factor} \times \text{Molecular weight of antibody}}{\text{Molar extinction coefficient of antibody} + \text{Average number of drugs conjugated} \times \text{Molar extinction coefficient of drug-linker}}$$

Wherein, for the absorbance (280 nm) of the antibody-drug conjugate, values measured from the antibody-drug conjugate aqueous solution were used. The dilution factor indicates how many times the antibody-drug conjugate aqueous solution has been diluted for absorbance measurement, and is usually 4. For the molar extinction coefficient (280 nm) of the antibody, values estimated from the known calculation method described in common operation E were used. For the average number of drugs conjugated, values obtained in [F-3-4] were used. For the molar extinction coefficient (280 nm) of the drug-linker, values measured for the conjugation precursor in the case of glycan conjugation in the SPAAC reaction were used. In the case of cysteine conjugation, the conjugation precursor was reacted with mercaptoethanol or N-acetylcysteine, and the value measured for the compound, in which the maleimide group had been converted to a succinimide thioether, was used.

Common operation G: To Measure Antibody Concentration and Average Number of Drugs Conjugated Per Antibody Molecule in Antibody-Drug Conjugate (Hydrophobic Interaction-High Performance Liquid Chromatography Method: HI-HPLC).

The antibody concentration and the average number of drugs conjugated per antibody molecule in the antibody-drug conjugate can be calculated by the above-described common operations E and F as well as high performance liquid chromatography analysis using the following methods.

[G-1. To Prepare Samples for HPLC Analysis]

The antibody-drug conjugate solution (approximately 1 mg/mL, 60 μL) was used directly for HPLC analysis.

[G-2. HPLC Analysis]

Representative analysis conditions are the following two different conditions.

HPLC system: SHIMADZU CBM-20A (Shimadzu Corporation)

Detector: UV spectrophotometer (measurement wavelength: 280 nm)

Column: TSK-gel Butyl-NPR (4.6×100 mm, 2.5 μm; produced by TOSOH)

Column temperature: Constant temperature at or near 25° C.

Mobile phase A: 25 mM phosphate buffer solution containing 1.5 M ammonium sulfate (pH=7.0)

Mobile phase B: 25 mM phosphate buffer solution (pH=7.0)/isopropyl alcohol mixture (3:1)

Flow rate: 0.8 mL/min

Sample injection volume: 15 μL

Gradient program (mobile phase B): 10%-15% (0 min-5 min), 15%-65% (5 min-20 min) or HPLC system: SHIMADZU CBM-20A (Shimadzu Corporation)

Detector: UV spectrophotometer (measurement wavelength: 280 nm)

Column: PolyPROPYL A (4.6×100 mm, 3 μm, 1500 Å; produced by PolyLC)

Column temperature: Constant temperature at or near 40° C.

Mobile phase A: 20 mM phosphate buffer solution containing 1.5 M ammonium sulfate (pH=7.4)

Mobile phase B: 20 mM phosphate buffer solution (pH=7.4)

Flow rate: 0.8 mL/min

Sample injection volume: 15 μL

Gradient program (mobile phase B): 40%-80% (0 min-20 min)

[G-3. Data Analysis]

[G-3-1] The hydrophobicity increases in proportion to the number of drugs conjugated per antibody, and the retention time increases accordingly. Thus, in the case of glycan conjugation in the SPAAC reaction, in principle, DAR=0, DAR=2, and DAR=4 are eluted in this order. By comparing the retention time of DAR=0, the detection peak can be assigned to either DAR=2 or DAR=4. The peak representing DAR=1 or DAR=3 can also be detected depending on the kind of antibody and drug-linker. The DAR at the detection peak may be estimated by measuring the mass spectrum after the peak is fractionated by HI-HPLC.

[G-3-2] The peak area was corrected according to the following expression while using the molar extinction coefficients of the antibody and the drug-linker in response to the number of drug-linkers conjugated, because each drug-linker absorbs UV light.

[Expression 5]

$$\text{Corrected antibody peak area } (WPA_i) = \text{Peak area} \times \frac{\text{Molar extinction coefficient of antibody}}{\text{Molar extinction coefficient of antibody} + \text{Number of drugs conjugated} \times \text{Molar extinction coefficient of drug-linker}}$$

Wherein, for the molar extinction coefficient (280 nm) of the antibody, values estimated from the known calculation method described in common operation E were used. For the molar extinction coefficient (280 nm) of the drug-linker, values measured for the conjugation precursor were used.

[G-3-3] The antibody peak area ratio (%) based on the total of corrected peak areas was calculated according to the following expression.

[Expression 6]

$$\text{Antibody peak area ratio } (\%WPA_i) = \frac{WPA_i}{WPA_0 + WPA_1 + WPA_2 + WPA_3 + WPA_4} \times 100$$

[G-3-4] The average number of drugs conjugated per antibody molecule in an antibody-drug conjugate was calculated according to the following expression.

[Expression 7]

$$\text{Average number of drugs conjugated } (DAR) = \frac{0 \times \%\ WPA_0 + 1 \times \%\ WPA_1 + 2 \times \%\ WPA_2 + 3 \times \%\ WPA_3 + 4 \times \%\ WPA_4}{100}$$

[G-3-5] The antibody concentration in the antibody-drug conjugate was calculated according to the expression described in [F-3-5]. At that time, for the average number of drugs conjugated, values obtained in [G-3-4] were used.

The antibody-drug conjugate or its production intermediate may contain stereoisomers, optical isomers caused by asymmetric carbon atoms, geometric isomers, tautomers, or optical isomers (e.g., d-, 1-, or atrop-isomers). However, all of these isomers, optical isomers, and mixtures of them are included in the invention.

The number of drugs conjugated per antibody molecule is an important factor having influence on efficacy and safety for the antibody-drug conjugate of the present invention. The antibody-drug conjugate is produced under reaction conditions (e.g., the amounts of starting materials or reagents to be reacted) specified so that the number of drugs conjugated can be constant. However, unlike the chemical reaction of small molecule compounds, a mixture with different numbers of drugs conjugated is usually obtained. It is possible to determine the average number of drugs conjugated (DAR), namely the averaged value for the number of drugs conjugated per antibody molecule. The number of cyclic dinucleotide derivatives conjugated to the antibody molecule is controllable. 1 to 10 cyclic dinucleotide derivatives conjugated may be conjugated as the average number of drugs conjugated per antibody. The number is preferably from 1 to 8 and more preferably from 1 to 5.

In an antibody-drug conjugate of the present invention, if the antibody Ab bonds to L through a remodeled glycan of the antibody Ab, $m^2$, which indicates the number of drugs conjugated per antibody molecule in the antibody-drug conjugate, is an integer of 1 or 2. In the case where the glycan is N297 glycan and the glycan is N297-(Fuc)SG, $m^2$ is 2, and DAR is in the range of 3 to 5 (preferably in the range of 3.2 to 4.8, and more preferably in the range of 3.5 to 4.2). In the case where the N297 glycan is N297-(Fuc) MSG1, N297-(Fuc)MSG2, or a mixture of N297-(Fuc) MSG1 and N297-(Fuc)MSG2, $m^2$ is 1, and DAR is in the range of 1 to 3 (preferably in the range of 1.0 to 2.5, and more preferably in the range of 1.2 to 2.2).

Note that a person skilled in the art can design, from the description of the Examples in the present application, a reaction in which the necessary number of drugs can be conjugated to the antibody. Thus, it is possible to obtain an antibody in which the number of cyclic dinucleotide derivatives conjugated is controlled.

Note that an antibody-drug conjugate or production intermediate of the present invention may be left in the air or recrystallized. This may cause moisture absorption, moisture adsorption, or a hydrate. Such compounds and salts containing water are also included in the present invention.

The antibody-drug conjugate or production intermediate in the present invention may be converted into a pharmaceutically acceptable salt, as desired, if having a basic group such as an amino group. Examples of such salts may include hydrogen halide salts such as hydrochlorides and hydroiodides; inorganic acid salts such as nitrates, perchlorates, sulfates, and phosphates; lower alkanesulfonates such as methanesulfonates, trifluoromethanesulfonates, and ethanesulfonates; arylsufonates such as benzenesulfonates and p-toluenesulfonates; organic acid salts such as formates, acetates, malates, fumarates, succinates, citrates, tartrates, oxalates, and maleates; and amino acid salts such as ornithinates, glutamates, and aspartates.

The antibody-drug conjugate of the present invention contains a phosphate group and/or a thiophosphate group in its structure, so that a base addition salt can be generally formed. In addition, if the production intermediate has an acidic group such as a carboxy group, it is generally possible to form a base addition salt. Examples of pharmaceutical acceptable salts may include alkali metal salts such as sodium salts, potassium salts, and lithium salts; alkali earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamates, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The antibody-drug conjugate and production intermediate in the present invention may exist as a hydrate, for example, by absorbing moisture in the air. The solvate in the present invention is not limited to a particular solvate and may be any pharmaceutically acceptable solvate, and specifically hydrates, ethanol solvates, 2-propanol solvates, and so on are preferred. Additionally, the antibody-drug conjugate and production intermediate in the present invention may be in an N-oxide form if a nitrogen atom is present therein, and these solvates and N-oxide forms are included in the scope of the present invention. In addition, the antibody-drug conjugate and production intermediate in the present invention may be in an N-oxide form if a nitrogen atom is present therein, and these solvates and N-oxide forms are included in the scope of the present invention.

The present invention also includes compounds labeled with various radioactive or nonradioactive isotopes. The antibody-drug conjugate and production intermediate in the present invention may contain one or more constituent atoms in which atomic isotopes are present at a non-natural ratio. Examples of atomic isotopes may include deuterium (2H), tritium (3H), iodine-125 (125I), and carbon-14 (14C). The compound in the present invention may be radiolabeled with a radioactive isotope such as tritium (3H), iodine-125 (125I), or carbon-14 (14C). The radiolabeled compound is useful as a therapeutic or prophylactic agent, a reagent for research such as an assay reagent, and a diagnostic agent such as a diagnostic agent for in vivo imaging. Isotopic variants of the antibody-drug conjugate of the present invention are all included in the scope of the present invention, regardless of whether they are radioactive or not.

<4. Medicine>

The antibody-drug conjugate of the present invention exhibits anti-tumor immunity or cytotoxicity against cancer cells, and thus can be used as a medicine, especially as a therapeutic and/or prophylactic agent against cancer, or as an anti-tumor agent.

Examples of cancers to which the antibody-drug conjugate of the present invention is applicable may include lung cancer (e.g., non-small cell lung cancer, small cell lung cancer), kidney cancer, urothelial cancer, colorectal cancer, prostate cancer, glioblastoma multiforme, ovarian cancer (e.g., superficial epithelial tumor, stromal tumor, germ cell tumor), pancreatic cancer, breast cancer, melanoma, liver cancer, bladder cancer, gastric cancer, esophageal cancer, endometrial cancer, testicular cancer (seminoma, non-seminoma), cervical cancer, placental choriocarcinoma, brain tumor, head and neck cancer, thyroid cancer, mesothelioma, Gastrointestinal Stromal Tumor (GIST), gallbladder cancer, bile duct cancer, adrenal cancer, pharyngeal cancer, tongue cancer, auditory organ cancer, thymus cancer, small intestine cancer, squamous-cell carcinoma, leukemia, malignant lymphoma, plasmacytoma, myeloma, or sarcoma. However, the antibody-drug conjugate is not limited to the above cancer cells as long as cancer cells of treatment subject are expressing protein recognizable for the antibody in the antibody-drug conjugate.

The antibody-drug conjugate of the present invention can be preferably administered to mammals, and are more preferably administered to humans.

Substances used in a pharmaceutical composition containing the antibody-drug conjugate of the present invention may be suitably applied after selected from formulation additives or the like that are generally used in the field in view of the dose or concentration for administration.

The antibody-drug conjugate of the present invention may be administered as a pharmaceutical composition containing one or more pharmaceutically applicable components. For example, the pharmaceutical composition typically contains one or more pharmaceutical carriers (e.g., sterilized liquid (including water and oil (petroleum oil and oil of animal origin, plant origin, or synthetic origin (such as peanut oil, soybean oil, mineral oil, and sesame oil)))). Water is a more typical carrier when the pharmaceutical composition above is intravenously administered. Saline solution, an aqueous dextrose solution, and an aqueous glycerol solution can be also used as a liquid carrier, in particular, for an injection solution. Suitable pharmaceutical vehicles are known in the art. If desired, the composition above may also contain a trace amount of a moisturizing agent, an emulsifying agent, or a pH buffering agent. Examples of suitable pharmaceutical carriers are disclosed in "Remington's Pharmaceutical Sciences" by E. W. Martin. The formulations correspond to the administration mode.

Various delivery systems are known and they may be used for administering the antibody-drug conjugate of the present invention. Examples of the administration route include, but not limited to, intradermal, intramuscular, intraperitoneal, intravenous, and subcutaneous routes. The administration may be made by injection or bolus injection, for example. According to a specific preferred embodiment, the administration of the above antibody-drug conjugate is done by injection. Parenteral administration is a preferred administration route.

According to a representative embodiment, the pharmaceutical composition containing the antibody-drug conjugate is prescribed, as a pharmaceutical composition suitable for intravenous administration to humans, according to conventional procedures. The composition for intravenous administration is typically a solution in a sterile and isotonic aqueous buffer. If necessary, the medicine may contain a solubilizing agent and a local anesthetic to alleviate pain at an injection site (e.g., lignocaine). Generally, the ingredients above are provided either individually as a dried lyophilized powder or an anhydrous concentrate contained in each container which is obtained by sealing in an ampoule or a sachet with indication of the amount of the active agent, or as a mixture in a unit dosage form. When the pharmaceutical composition is to be administered by injection, it may be administered from an injection bottle containing water or saline of sterile pharmaceutical grade. When the pharmaceutical composition is administered by injection, an ampoule of sterile water or saline for injection may be provided so that the aforementioned ingredients are admixed with each other before administration. The pharmaceutical composition may be provided as a solution.

The pharmaceutical composition of the present invention may be a pharmaceutical composition containing only the antibody-drug conjugate of the present invention, or a pharmaceutical composition containing the antibody-drug conjugate of the present invention and other cancer treating agents. The antibody-drug conjugate of the present invention may be administered with or in combination with other cancer treating agents, and thereby the anti-tumor effect may be enhanced. Other anti-cancer agents used for such purpose may be administered to an individual simultaneously with, separately from, or subsequently to the antibody-drug conjugate, and may be administered while varying the administration interval for each. Examples of such cancer treating agents may include antimetabolites, alkylating agents, microtubule inhibitors, and other chemotherapeutic agents (e.g., abraxane, carboplatin, cisplatin, gemcitabine, irinotecan (CPT-11), paclitaxel, docetaxel, pemetrexed, vinblastine, or agents described in International Publication No. WO 2003/038043), hormone regulators (e.g., LH-RH analogs (e.g., leuprorelin, goserelin, estramustine), estrogen antagonists (e.g., tamoxifen, raloxifene)), aromatase inhibitors (e.g., anastrozole, letrozole, exemestane), kinase inhibitors, PARP inhibitors, bone destruction inhibitors, osteogenesis promoters, metastasis inhibitors, molecular target drugs (e.g., an anti-EGFR antibody, an anti-VEGF antibody, an anti-VEGFR antibody), immune checkpoint inhibitors (e.g., an anti-PD-1 antibody (e.g., nivolumab, pembrolizumab), an anti-PD-L1 antibody (e.g., atezolizumab, avelumab, durvalumab), an anti-PD-L2 antibody, an anti-CTLA4 antibody (e.g., ipilimumab), an anti-A2aR antibody, an A2a receptor antagonist, an anti-LAG3 antibody, an anti-TIM3 antibody), anti-regulatory T-cell drugs (e.g., an anti-CTLA4 antibody, an anti-CD25 antibody, an anti-GITR antibody, an anti-GARP antibody, an anti-TIGIT antibody, an anti-CCR8 antibody), immune activators (e.g., an anti-4-1BB antibody, an anti-OX40 antibody, an anti-CD40 antibody, an anti-CD3 antibody, an anti-CD28 antibody, an IL-2 analog, cytokines, an TLR agonist), immunomodulators (e.g., an anti-CD47 antibody, an anti-SIRPα antibody, inhibitory myeloid modulators), antibody medicines with ADCC (Antibody Dependent Cellular Cytotoxicity) activity, ADCP (Antibody Dependent Cellular Phagocytosis) activity, or complement activity, BiTE (Bi-specific T-cell engagers), antibody-drug-conjugates (ADCs) (e.g., a drug conjugate containing Deruxtecan, DM1, Pyrrolobenzodiazepine, MMAF, etc. (an anti-HER2-ADC, an anti-TROP2-ADC, an anti-HER3-ADC, etc.)), ADCs in combination with photodynamic therapy, as well as anti-tumor vaccines, anti-tumor cell therapy (e.g., CAR-T, TCR-T, dendritic cells, NK cells), anti-tumor bacterial treatment, or anti-tumor viral treatment. However, the cancer treating agents are not limited as long as the agents have anti-tumor activity. In addition, the antibody-drug conjugate of the present invention can be administered together with another antibody-drug conjugate of the present invention. This can enhance anti-tumor effects. Besides, the antibody-drug conjugate of the present invention can enhance anti-tumor effects not only by the drug alone, but also by use in combination with anti-tumor effect-exerting treatment (e.g., radiation, heavy particle radiation, surgery, bone marrow transplantation). The treatment is not limited as long as it has the anti-tumor effects.

The pharmaceutical composition can be formulated into a lyophilization formulation or a liquid formulation as a formulation having the selected composition and required purity. When formulated as a lyophilization formulation, it may be a formulation containing suitable formulation additives that are used in the art. Also, for a liquid formulation, it may be formulated as a liquid formulation containing various formulation additives that are used in the art.

The composition and concentration of the pharmaceutical composition may vary depending on the administration method. However, the antibody-drug conjugate contained in the pharmaceutical composition of the present invention can exhibit a pharmaceutical effect even at a small dosage when the antibody-drug conjugate has a higher affinity for an antigen, that is, a higher affinity (lower Kd value) in terms of the dissociation constant (Kd value) for the antigen. Thus, for determining the dosage of the antibody-drug conjugate, the dosage may be set in view of the situation relating to the affinity of the antibody-drug conjugate with the antigen. When the antibody-drug conjugate of the present invention is administered to a human, for example, about 0.001 to 100 mg/kg can be administered once or administered in several portions with intervals of 1 to 180 days.

Hereinbelow, the present invention will be described with reference to Examples. However, the invention is not limited to them.

EXAMPLES

In the following Examples, the room temperature is from 15° C. to 35° C. Dehydrated acetonitrile used was acetonitrile (dehydrated) -super- commercially available from KANTO CHEMICAL CO., INC., or acetonitrile (super dehydrated) commercially available from Wako Pure Chemical Industries, Ltd. Pyridine used was pyridine (dehydrated) -super-commercially available from KANTO CHEMICAL CO., INC. Silica gel chromatography was performed using Biotage SNAP Ultra (produced by Biotage), Chromatorex Q-Pack SI (produced by FUJI SILYSIA CHEMICAL LTD.), or Purif-Pack-Ex SI (produced by Shoko Science). DIOL silica gel column chromatography was carried out using Chromatorex Q-pack DIOL (produced by FUJI SILYSIA CHEMICAL LTD.). C18 silica gel column chromatography was carried out using Biotage SNAP Ultra C18 (produced by Biotage). Elution in column chromatography was carried out by thin layer chromatography (TLC) under observation. The 0.1% triethylamine used as the eluting solvent means that 0.1% triethylamine is contained in the total volume of the eluting solvent. Preparative HPLC was carried out using, for instance, a SHIMADZU SPD-M10A HPLC system (Shimadzu Corporation). The preparative column used was Kinetex (5 μm, C18, 100 Å, 250×30.0 mm; produced by Phenomenex) or Kinetex (5 μm, C18, 100 Å, 250×21.2 mm; produced by Phenomenex).

The following instruments were used to measure various spectral data. $^{1}H$-NMR spectra were measured using JEOL ECS-400 (400 MHz), Varian 400-MR (400 MHz), or Varian Unity Inova 500 (500 MHz). $^{31}P$-NMR spectra were measured using JEOL ECS-400 (160 MHz). Mass spectra were measured using an Agilent 6130 Quadrupole LC/MS system (Agilent Technologies). LC/MS measurements were carried out under the following conditions [column: Develosil Combi-RP, 5 μm, 50×2.0 mm (Nomura Chemical Co., Ltd.); mobile phase: 0.1% formic acid acetonitrile solution/0.1% formic acid solution; 0.1% formic acid acetonitrile solution: 2%-100% (0 min-5 min or 0 min-10 min)].

Example 1: To Synthesize CDN6

(5R,7R,8R,12aR,14R,15R,15aS,16R)-15,16-dihydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione

[Formula 93]

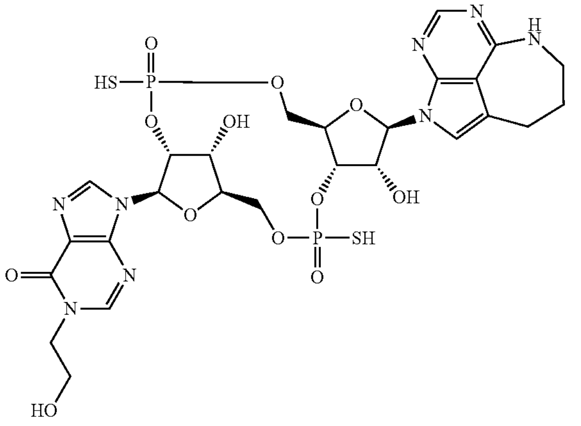

6a (Diastereomer 1)
6b (Diastereomer 2)

[Formula 94]

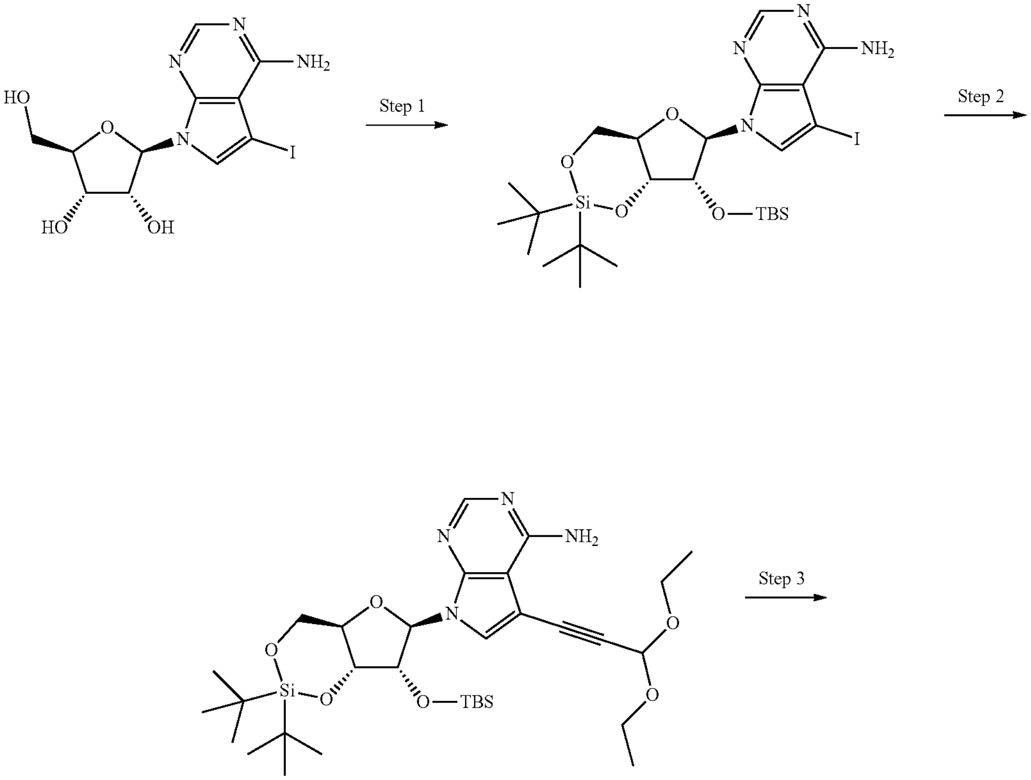

-continued
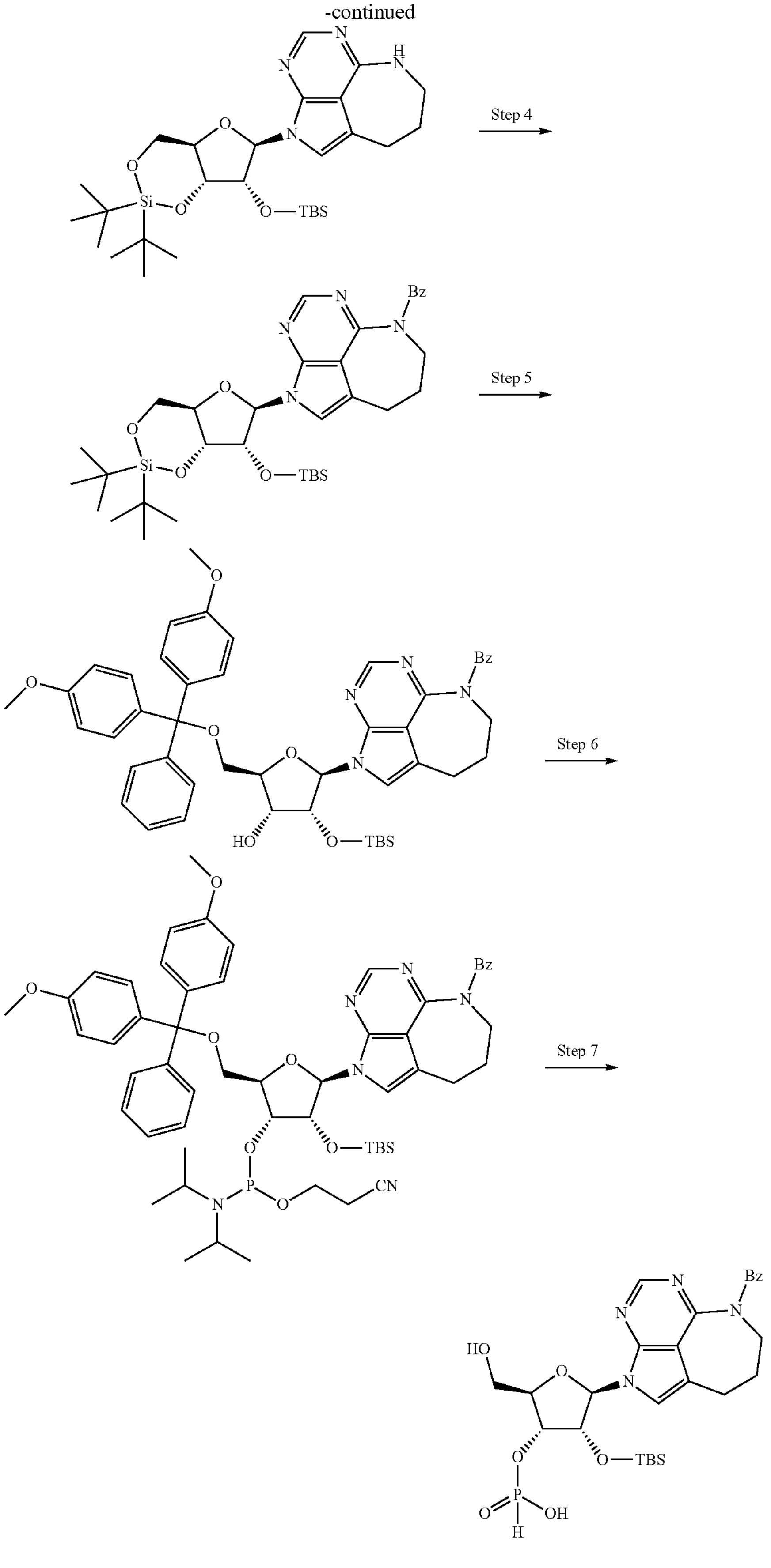

-continued
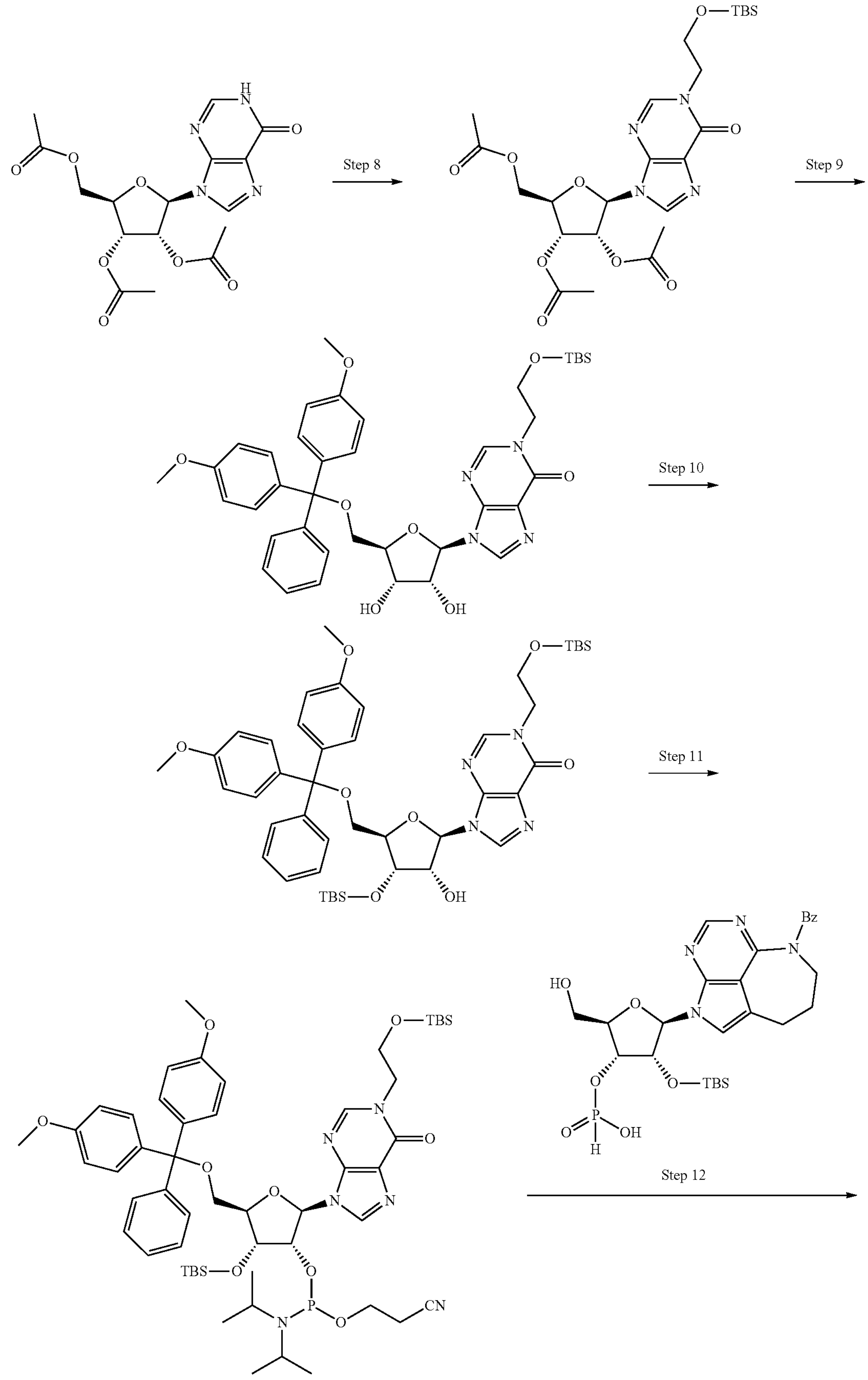

-continued
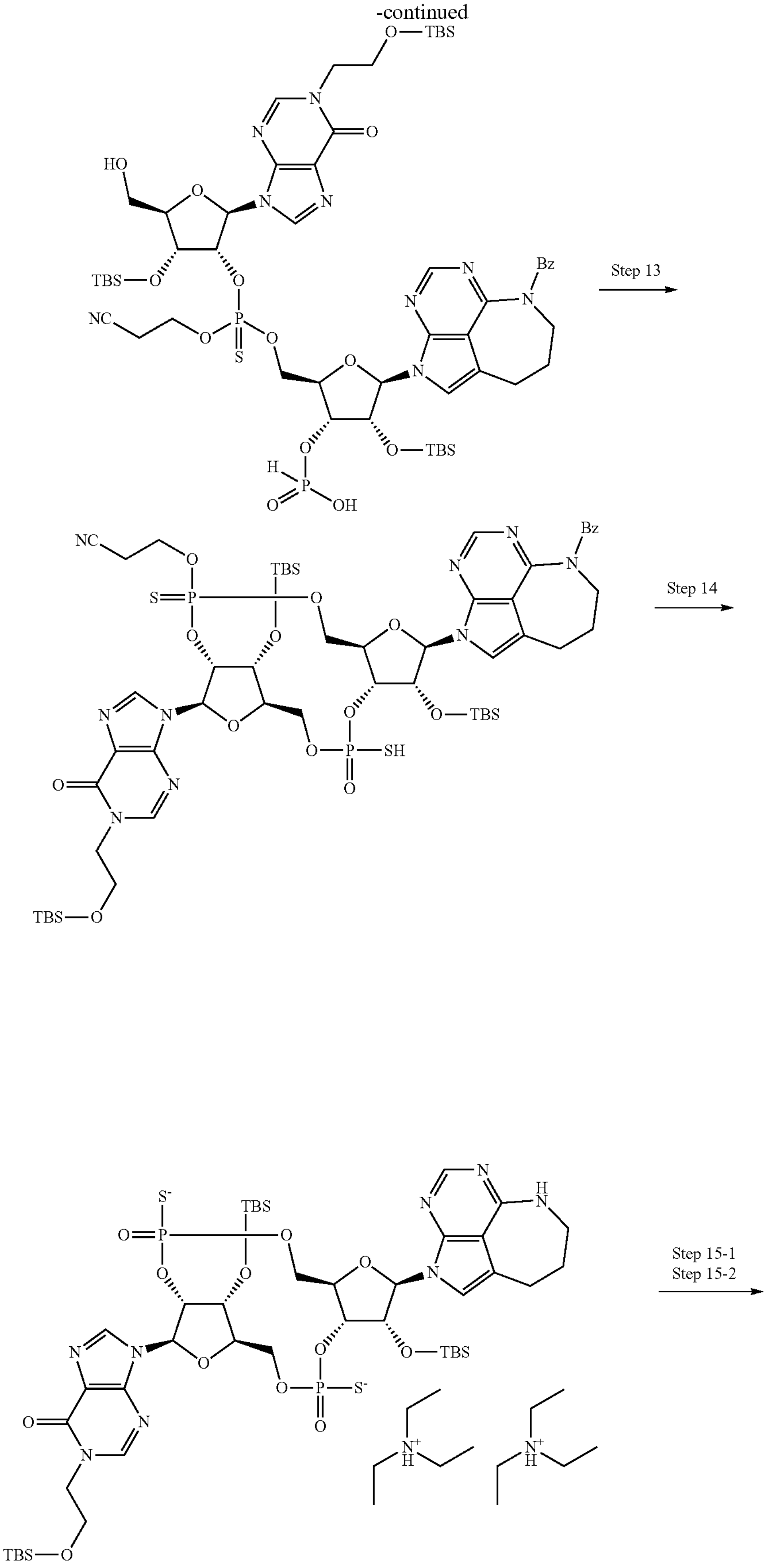

-continued

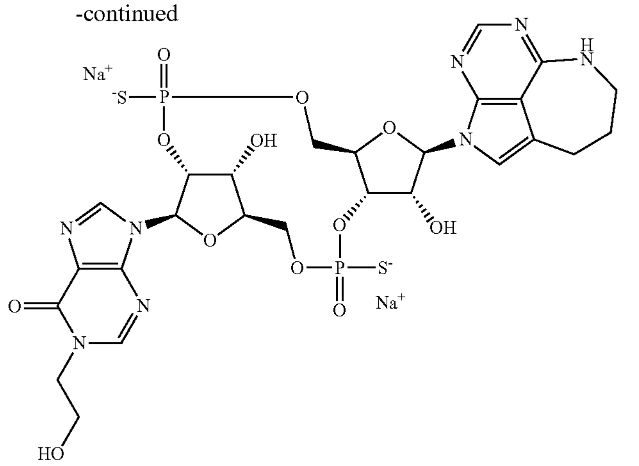

Synthetic Scheme

Step 1

7-{2-O-[tert-butyl(dimethyl)silyl]-3, 5-O-(di-tert-butylsilyliden)-β-D-ribofuranosyl}-5-iodo-7H-pyrrolo[2,3-d]pyrimidin-4-amine To a solution of 5-iodotubercidin (1.0 g), as known in the literature (Tetrahedron 2007, 63, 9850-9861), in N,N-dimethylformamide (10 mL) was added slowly dropwise at 0° C. di-tert-butylsilyl bis(trifluoromethanesulfonate) (1.24 mL). The mixture was then stirred at the same temperature for 30 min. Imidazole (868 mg) was added at 0° C., and the temperature was raised to room temperature, and the mixture was then stirred for 30 min. Next, tert-butyldimethylchlorosilane was added at room temperature, and the mixture was stirred at the same temperature overnight. The reaction was stopped by adding saturated aqueous sodium bicarbonate to the reaction mixture, and the resulting solution was then extracted with ethyl acetate. The organic layer was washed with brine and dried over anhydrous sodium sulfate. The drying agent was filtered off, and the filtrate was concentrated under reduced pressure. The residue was purified by silica gel column chromatography [hexane/ethyl acetate] to give the titled compound (910 mg).

MS (ESI) m/z: 647 $(M+H)^+$.

$^1$H-NMR ($CDCl_3$) δ: 8.25 (1H, s), 7.03 (1H, s), 6.10 (1H, s), 5.63 (2H, brs), 4.49-4.44 (2H, m), 4.26 (1H, dd, J=9.7, 4.8 Hz), 4.17 (1H, m), 4.00 (1H, t, J=9.7 Hz), 1.09 (9H, s), 1.04 (9H, s), 0.91 (9H, s), 0.13 (3H, s), 0.11 (3H, s).

Step 2

7-{2-O-[tert-butyl(dimethyl)silyl]-3, 5-O-(di-tert-butylsilyliden)-β-D-ribofuranosyl}-5-(3,3-diethoxy-prop-1-yn-1-yl)-7H-pyrrolo[2,3-d]pyrimidin-4-amine To a mixed solution of the compound (910 mg) obtained in step 1 in N,N-dimethylformamide (3.0 mL)-tetrahydrofuran (9.0 mL) were added propargylaldehyde dimethyl acetal (1.01 mL), triethylamine (0.392 mL), tetrakis(triphenylphosphine)palladium (0) (163 mg), and copper (I) iodide (53.6 mg) in this order, and the mixture was stirred at 40° C. for 18 h. To the reaction mixture were added saturated aqueous sodium bicarbonate and ethyl acetate. Then, the mixture was extracted with ethyl acetate. The organic layer was washed with brine and dried over anhydrous sodium sulfate. The drying agent was filtered off, and the filtrate was concentrated under reduced pressure. The residue was purified by silica gel column chromatography [hexane/ethyl acetate] to give the titled compound (878 mg).

MS (ESI) m/z: 647 $(M+H)^+$.

$^1$H-NMR ($CDCl_3$) δ: 8.27 (1H, s), 7.17 (1H, s), 6.09 (1H, s), 5.56 (2H, brs), 5.50 (1H, s), 4.48 (1H, dd, J=9.1, 4.9 Hz), 4.42 (1H, d, J=4.9 Hz), 4.25 (1H, dd, J=9.4, 4.6 Hz), 4.17 (1H, m), 4.00 (1H, t, J=9.7 Hz), 3.85-3.77 (2H, m), 3.66 (2H, m), 1.28 (6H, t, J=7.3 Hz), 1.08 (9H, s), 1.04 (9H, s), 0.91 (9H, s), 0.13 (3H, s), 0.11 (3H, s).

Step 3

2-{2-O-[tert-butyl(dimethyl)silyl]-3, 5-O-(di-tert-butylsilyliden)-β-D-ribofuranosyl}-6,7,8,9-tetrahydro-2H-2,3, 5,6-tetraazabenzo[cd]azulene To a solution of the compound (878 mg) obtained in step 2 in ethanol (8.8 mL) was added 10% palladium carbon (M) wet (500 mg), and the mixture was stirred for 9 h at room temperature under a hydrogen atmosphere. After the catalyst was filtered off, washing with dichloromethane was conducted. The filtrate was then concentrated under reduced pressure. To a solution of the residue in acetic acid (8.8 mL) was added 10% palladium carbon (M) wet (500 mg), and the mixture was stirred for 2 days at 40° C. under a hydrogen atmosphere. After the catalyst was filtered off, washing with dichloromethane was conducted. The filtrate was then concentrated under reduced pressure. The residue was purified by silica gel column chromatography [hexane/ethyl acetate/0.1% triethylamine] to give the titled compound (603 mg).

MS (ESI) m/z: 561 $(M+H)^+$.

$^1$H-NMR ($CDCl_3$) δ: 8.47 (1H, brs), 8.07 (1H, s), 6.70 (1H, s), 6.14 (1H, s), 4.47-4.43 (2H, m), 4.29 (1H, dd, J=9.1, 4.8 Hz), 4.15 (1H, m), 3.99 (1H, t, J=9.7 Hz), 3.55 (2H, m), 2.89 (2H, t, J=5.4 Hz), 2.04 (2H, m), 1.09 (9H, s), 1.04 (9H, s), 0.90 (9H, s), 0.10 (3H, s), 0.10 (3H, s).

Step 4

6-benzoyl-2-{2-O-[tert-butyl(dimethyl)silyl]-3,5-O-(di-tert-butylsilyliden)-β-D-ribofuranosyl}-6,7,8,9-tetrahydro-2H-2,3, 5,6-tetraazabenzo[cd]azulene To a solution of the compound (2.17 g) obtained in step 3 in dichloromethane (21.7 mL) were added at room temperature pyridine (1.56 mL), N,N-dimethylaminopyridine (94.5 mg), and benzoyl chloride (0.898 mL) in this order, and the mixture was stirred at 50° C. for 15 h. The reaction was stopped by adding saturated aqueous sodium bicarbonate to the reaction mixture. After extraction with dichloromethane, the organic layer was dried over anhydrous sodium sulfate. The drying agent was filtered off, and the filtrate was concentrated under reduced pressure. The residue was purified by silica gel column chromatography [hexane/ethyl acetate/0.1% triethylamine] to give the titled compound (1.91 g).

MS (ESI) m/z: 665 $(M+H)^+$.

$^1$H-NMR ($CDCl_3$) δ: 8.08 (1H, s), 7.37-7.33 (3H, m), 7.23 (2H, t, J=7.6 Hz), 6.97 (1H, s), 6.21 (1H, s), 4.50-4.46 (2H, m), 4.37-4.30 (2H, m), 4.28-4.09 (2H, m), 4.02 (1H, t, J=10.0 Hz), 3.03 (2H, t, J=6.3 Hz), 2.29-2.17 (2H, m), 1.10 (9H, s), 1.05 (9H, s), 0.90 (9H, s), 0.10 (6H, s).

Step 5

6-benzoyl-2-{5-O-[bis(4-methoxyphenyl)(phenyl)methyl]-2-O-[tert-butyl(dimethyl)silyl]-β-D-ribofuranosyl}-6,7,8,9-tetrahydro-2H-2,3,5,6-tetraazabenzo[cd]azulene To a solution of the compound (1.91 g) obtained in step 4 in dichloromethane (15 mL) was added a mixture of hydrogen fluoride-pyridine (0.30 mL) and pyridine (1.88 mL) as prepared at 0° C., and the mixture was stirred at 0° C. for 2 h. The reaction was stopped by adding saturated aqueous sodium bicarbonate to the reaction mixture. The reaction mixture was extracted with dichloromethane, and the organic layer was then dried over anhydrous sodium sulfate. The drying agent was filtered off, and the filtrate was concentrated under reduced pressure. The residue was dissolved in pyridine (15 mL), 4,4'-dimethoxytrityl chloride (1.17 g) was added, and the mixture was stirred at 0° C. for 12 h. Methanol was added and the mixture was stirred for 30 min. The reaction was then stopped by adding saturated aqueous sodium bicarbonate. The reaction mixture was extracted with dichloromethane, and the organic layer was dried over anhydrous sodium sulfate. The drying agent was filtered off, and the filtrate was concentrated under reduced pressure. The residue was purified by silica gel column chromatography [hexane/ethyl acetate/0.1% triethylamine] to give the titled compound (1.98 g).

MS (ESI) m/z: 827 $(M+H)^+$.

$^1$H-NMR ($CDCl_3$) δ: 8.07 (1H, s), 7.47 (2H, m), 7.37-7.19 (13H, m), 6.84 (4H, m), 6.37 (1H, d, J=5.5 Hz), 4.75 (1H, t, J=5.2 Hz), 4.38-4.20 (4H, m), 3.80 (6H, s), 3.53 (1H, dd, J=10.7, 2.8 Hz), 3.40 (1H, dd, J=11.0, 3.1 Hz), 2.83 (1H, d, J=3.7 Hz), 2.78 (2H, t, J=6.4 Hz), 2.17 (2H, m), 0.81 (9H, s), -0.03 (3H, s), -0.21 (3H, s).

Step 6

6-benzoyl-2-(5-O-[bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-6,7,8,9-tetrahydro-2H-2,3, 5,6-tetraazabenzo[cd]azulene To a solution of the compound (1.98 g) obtained in step 5 in dichloromethane (23.9 mL) were added N,N-diisopropylethylamine (1.02 mL) and 2-cyanoethyl N,N-diisopropylchlorophosphoramidite (1.07 mL), and the mixture was stirred for 15 h at room temperature. The reaction was stopped by adding saturated aqueous sodium bicarbonate to the reaction mixture. The reaction mixture was extracted with dichloromethane, and the organic layer was then dried over anhydrous sodium sulfate. The drying agent was filtered off, and the filtrate was concentrated under reduced pressure. The residue was purified by silica gel column chromatography [hexane/ethyl acetate] to give the titled compound (2.06 g) as a mixture of diastereomers at the phosphorus atom (diastereomer ratio=7:3).

MS (ESI) m/z: 1027 $(M+H)^+$.

$^1$H-NMR ($CDCl_3$) δ: 8.06 (0.3H, s), 8.04 (0.7H, s), 7.50-7.16 (15H, m), 6.85-6.79 (4H, m), 6.35 (0.7H, d, J=6.7 Hz), 6.31 (0.3H, d, J=6.1 Hz), 4.84 (0.7H, dd, J=7.0, 4.6 Hz), 4.78 (0.3H, t, J=5.8 Hz), 4.43-4.17 (4H, m), 4.04-3.85 (1.3H, m), 3.80-3.76 (6H, m), 3.69-3.43 (3H, m), 3.50 (0.7H, dd, J=10.6, 3.3 Hz), 3.33-3.26 (1H, m), 2.87-2.76 (2H, m), 2.74-2.60 (1.4H, m), 2.31 (0.6H, t, J=6.7 Hz), 2.23-2.11 (2H, m), 1.21-1.13 (7.8H, m), 1.04 (4.2H, d, J=6.7 Hz), 0.73 (2.7H, s), 0.72 (6.3H, s), -0.03 (0.9H, s), -0.06 (2.1H, s), -0.24 (3H, s).

Step 7

6-benzoyl-2-{2-O-[tert-butyl(dimethyl)silyl]-3-O-[hydroxy(oxo)-$\lambda^5$-phosphanyl]-P-D-ribofuranosyl}-6,7,8,9-tetrahydro-2H-2,3, 5,6-tetraazabenzo[cd]azulene To a solution of the compound (935 mg) obtained in step 6 in acetonitrile (4.55 mL) were added water (33 μL) and trifluoroacetic acid pyridine salt (229 mg), and the mixture was stirred at room temperature for 15 min. Next, tert-butylamine (4.55 mL) was added to the reaction mixture, and the mixture was stirred at room temperature for 15 min. The reaction mixture was concentrated under reduced pressure, ant then the residue was azeotroped twice with acetonitrile (5 mL). Water (0.164 mL) was added to a dichloromethane solution (11.4 mL) of the residue. Subsequently, a dichloromethane solution (11.4 mL) of dichloroacetic acid (0.651 mL) was added, and the mixture was stirred at room temperature for 15 min. After stopping the reaction by adding pyridine (1.25 mL), and the reaction mixture was concentrated under reduced pressure. The residue was azeotroped three times with dehydrated acetonitrile (10 mL) while the last time, about 5 mL of acetonitrile was left. The resulting acetonitrile solution of the titled compound was used directly in step 12 below.

Step 8

2',3',5'-tri-O-acetyl-1-(2-{[tert-butyl(dimethyl)silyl]oxy}ethyl)inosine

To a suspension of commercially available (Ark Pharm) 2',3',5'-tri-O-acetyl inosine (10.0 g) in tetrahydrofuran (100 mL) were added 2-{[tert-butyl(dimethyl)silyl]oxy}ethan-1-ol (5.37 g) and triphenylphosphine (7.69 g). Next, dipropan-2-yl (E)-diazene-1,2-dicarboxylate (6.10 mL) was added, and the mixture was stirred for 6 h at room temperature. The reaction mixture was concentrated under reduced pressure, and then the residue was purified by silica gel column chromatography [hexane/ethyl acetate/dichloromethane] to give a mixture (10.6 g) of the titled compound and triphenylphosphine oxide.

MS (ESI) m/z: 553 $(M+H)^+$.

$^1$H-NMR ($CDCl_3$) δ: 8.05 (1H, s), 7.92 (1H, s), 6.12 (1H, d, J=5.4 Hz), 5.86 (1H, t, J=5.4 Hz), 5.59 (1H, dd, J=5.4, 4.2 Hz), 4.47-4.41 (2H, m), 4.38-4.31 (1H, m), 4.22-4.17 (2H, m), 3.89 (2H, t, J=4.8 Hz), 2.15 (3H, s), 2.14 (3H, s), 2.08 (3H, s), 0.83 (9H, s), -0.06 (3H, s), -0.06 (3H, s).

Step 9

5'-O-[bis(4-methoxyphenyl)(phenyl)methyl]-1-(2-{[tert-butyl(dimethyl)silyl]oxy}ethyl)inosine To a mixed solution of the compound (10.6 g) obtained in step 8 in tetrahydrofuran (30 mL)-methanol (30 mL) was added potassium carbonate (150 mg), and the mixture was stirred for 3 h at room temperature. Acetic acid (125 μL) was added to the reaction mixture, the mixture was concentrated under reduced pressure, and then the residue was then azeotroped with pyridine. To a pyridine solution (60 mL) of the residue was added at 0° C. 4,4'-dimethoxytrityl chloride (6.50 g). The mixture was stirred for 30 min and then stored in a refrigerator overnight. Methanol (2 mL) was added to the reaction mixture, and the mixture was stirred for 30 min and then concentrated under reduced pressure. The residue was purified by silica gel column chromatography [hexane/ethyl acetate/methanol/0.1% triethylamine] to give a mixture (7.21 g) of the titled compound and triphenylphosphine oxide.

MS (ESI) m/z: 729 $(M+H)^+$.

$^1$H-NMR ($CDCl_3$) δ: 8.01 (1H, s), 7.97 (1H, s), 7.35-7.30 (2H, m), 7.25-7.17 (7H, m), 6.81-6.76 (4H, m), 5.95 (1H, d, J=5.4 Hz), 5.13 (1H, brs), 4.68-4.61 (1H, m), 4.43-4.36 (2H, m), 4.31-4.23 (1H, m), 4.15-4.08 (1H, m), 3.89 (2H, t, J=4.5 Hz), 3.77 (6H, s), 3.42 (1H, dd, J=10.3, 3.6 Hz), 3.34 (1H, dd, J=10.3, 3.6 Hz), 3.10 (1H, brs), 0.83 (9H, s), -0.06 (3H, s), -0.07 (3H, s).

Step 10

5'-O-[bis(4-methoxyphenyl)(phenyl)methyl]-3'-O-[tert-butyl(dimethyl)silyl]-1-(2-{[tert-butyl(dimethyl)silyl]oxy}ethyl)inosine To a solution of the compound (7.21 g) obtained in step 9 in dichloromethane (36 mL) were added imidazole (1.41 g) and tert-butyl(chloro)dimethylsilane (1.49 g), and the mixture was stirred at room temperature for 16 h. The reaction mixture was admixed with saturated aqueous sodium bicarbonate, and the mixture was extracted with dichloromethane. The organic layer was dried over anhydrous sodium sulfate, the drying agent was filtered off, and the filtrate was concentrated under reduced pressure. The residue was purified by silica gel column chromatography [hexane/ethyl acetate/0.1% triethylamine] to give the titled compound (2.17 g) and a regioisomer of the titled compound, namely 5'-O-[bis(4-methoxyphenyl)(phenyl)methyl]-2'-O-[tert-butyl(dimethyl)silyl]-1-(2-{[tert-butyl(dimethyl)silyl]oxy}ethyl)inosine (2.55 g).

MS (ESI) m/z: 843 $(M+H)^+$.

$^1$H-NMR ($CDCl_3$) δ: 7.99 (1H, s), 7.97 (1H, s), 7.43-7.39 (2H, m), 7.33-7.19 (7H, m), 6.83-6.77 (4H, m), 5.96 (1H, d, J=4.2 Hz), 4.56-4.50 (2H, m), 4.33-4.25 (1H, m), 4.19-4.02 (2H, m), 3.89 (2H, t, J=4.8 Hz), 3.78 (6H, s), 3.45 (1H, dd, J=10.9, 4.2 Hz), 3.27 (1H, dd, J=10.9, 4.2 Hz), 3.03 (1H, d, J=6.0 Hz), 0.88 (9H, s), 0.82 (9H, s), 0.07 (3H, s), -0.01 (3H, s), -0.07 (3H, s), -0.07 (3H, s).

Regioisomer (2'-O-TBS isomer)

MS (ESI) m/z: 843 $(M+H)^+$.

$^1$H-NMR ($CDCl_3$) δ: 7.98 (1H, s), 7.94 (1H, s), 7.46-7.42 (2H, m), 7.35-7.20 (7H, m), 6.85-6.79 (4H, m), 5.99 (1H, d, J=5.4 Hz), 4.83 (1H, t, J=5.1 Hz), 4.33-4.29 (1H, m), 4.27-4.24 (1H, m), 4.24-4.12 (2H, m), 3.90 (2H, t, J=4.5 Hz), 3.79 (3H, s), 3.78 (3H, s), 3.48 (1H, dd, J=10.3, 3.0 Hz), 3.40 (1H, dd, J=10.3, 3.0 Hz), 2.71 (1H, d, J=3.6 Hz), 0.86 (9H, s), 0.83 (9H, s), 0.01 (3H, s), -0.07 (3H, s), -0.07 (3H, s), -0.11 (3H, s).

Step 11

5'-O-[bis(4-methoxyphenyl)(phenyl)methyl]-3'-O-[tert-butyl(dimethyl)silyl]-1-(2-{[tert-butyl(dimethyl)silyl]oxy}ethyl)-2'-O-{(2-cyanoethoxy)[di(propan-2-yl)amino]phosphanyl} inosine To a solution of the compound (2.17 g) obtained in step 10 in dichloromethane (25.7 mL) were added 4,5-dicyanoimidazole (334 mg) and 2-cyanoethyl N,N,N',N'-tetraisopropylphosphorodiamidite (0.980 mL), and the mixture was stirred for 16 h at room temperature. The reaction was stopped by adding saturated aqueous sodium bicarbonate to the reaction mixture. The reaction mixture was extracted with dichloromethane, and the organic layer was then dried over anhydrous sodium sulfate. The drying agent was filtered off, and the filtrate was concentrated under reduced pressure. The residue was purified by DIOL silica gel column chromatography [hexane/ethyl acetate] to give the titled compound (2.65 g) as a mixture of diastereomers at the phosphorus atom.

MS (ESI) m/z: 1043 $(M+H)^+$.

$^1$H-NMR ($CDCl_3$) δ: 8.03 (0.53H, s), 8.01 (0.47H, s), 7.97 (0.53H, s), 7.93 (0.47H, s), 7.45-7.41 (2H, m), 7.35-7.19 (7H, m), 6.83-6.78 (4H, m), 6.17 (0.53H, d, J=4.2 Hz), 6.05 (0.47H, d, J=4.2 Hz), 4.87-4.80 (0.47H, m), 4.64-4.58 (0.53H, m), 4.46-4.40 (1H, m), 4.30-4.05 (3H, m), 3.92-3.87 (2H, m), 3.78 (6H, s), 3.86-3.40 (5H, m), 3.33-3.24 (1H, m), 2.54 (0.94H, t, J=6.0 Hz), 2.43 (1.06H, t, J=6.7 Hz), 1.16-1.09 (9H, m), 1.01-0.97 (3H, m), 0.83 (4.23H, s), 0.83 (4.77H, s), 0.82 (9H, s), 0.07 (1.41H, s), 0.04 (1.59H, s), -0.02 (3H, s), -0.07 (1.41H, s), -0.08 (1.59H, s), -0.08 (3H, s).

Step 12

The compound (950 mg) obtained in step 11 was azeotroped three times with dehydrated acetonitrile (5 mL), while the last time, about 3 mL of acetonitrile was left, and Molecular Sieves 3 Å, 1/16 (5 pellets) was then added. This acetonitrile solution was added to the acetonitrile solution prepared in step 7, and the mixture was stirred for 20 min at room temperature under a nitrogen atmosphere. N,N-dimethyl-N'-(3-sulfaniliden-3H-1,2,4-dithiazol-5-yl)methane imidamide (206 mg) was added to the reaction mixture. The resulting reaction mixture was stirred at room temperature for 30 min, and then concentrated under reduced pressure. To a solution of the residue in dichloromethane (13.0 mL) were added water (0.164 mL) and then a solution of dichloroacetic acid (0.822 mL) in dichloromethane (13.0 mL), and the mixture was stirred for 15 min at room temperature. The reaction was stopped by adding pyridine (9.01 mL), and the resulting reaction mixture was then concentrated under reduced pressure. The crude product obtained was used directly in the next reaction.

Step 13

3-({(5R,7R,8R,12aR,14R,15R,15aR,16R)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}--7-[1-(2-{[tert-butyl(dimethyl)silyl]oxy}ethyl)-6-oxo-1,6-dihydro-9H-purin-9-yl]-2-oxo-2-sulfanyl-10-sulfanilidenoctahydro-2H,1OH,12H-5,8-methano-2λ$^5$,10λ$^5$-furo[3,2-1][1,3,6,9,11,2,10]pentaoxadiphosphacyclotetradecin-10-yl}oxy)propanenitrile A solution of the crude product obtained in step 12 in pyridine (27.1 mL) was concentrated to about 20 mL. Next, 2-chloro-5,5-dimethyl-1,3,2$\lambda^5$-dioxaphosphinan-2-one (622 mg) was added and the mixture was stirred for 30 min at room temperature. To the reaction mixture were added water (0.57 mL) and 3H-1,2-benzodithiol-3-one (230 mg), and the mixture was stirred at room temperature for 15 min. The reaction mixture was poured into an aqueous solution (130 mL) of sodium bicarbonate (3.60 g). The mixture was stirred at room temperature for 30 min, and then extracted with ethyl acetate. The organic layer was dried over anhydrous sodium sulfate, the drying agent was filtered off, and the filtrate was concentrated under reduced pressure. The residue was purified by silica gel column chromatography [hexane/ethyl acetate/methanol] to give the titled compound (494 mg) as a mixture of diastereomers at the phosphorus atom.

MS (ESI) m/z: 1274 $(M+H)^+$.

Step 14 bis(N,N-diethylethanaminium) (5R,7R,8R,12aR,14R,15R,15aR,16R)-15,16-bis{[tert-butyl(dimethyl)silyl]oxy}-7-[1-(2-{[tert-butyl(dimethyl)silyl]oxy}ethyl)-6-oxo-1,6-dihydro-9H-purin-9-yl]-2,10-dioxo-14-(6,7,8,9-tetrahydro-2H-2,3, 5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

To a solution of the compound (494 mg) obtained in step 13 in methanol (5 mL) was added 28% aqueous ammonia (5 mL), and the mixture was stirred for 15 h at room temperature. The reaction mixture was concentrated. Subsequently, the residue was purified by C18 silica gel column chromatography [10 mM aqueous triethylammonium acetate/acetonitrile] to give diastereomer 1 (88.5 mg: containing impurities) and diastereomer 2 (70.7 mg: containing impurities) of the titled compound.

Diastereomer 1 (less polar)

MS (ESI) m/z: 1003 $(M-C_6H_{15}Si+2H)^+$.

Diastereomer 2 (more polar)

MS (ESI) m/z: 1003 $(M-C_6H_{15}Si+2H)^+$.

Step 15-1 disodium(5R,7R,8R,12aR,14R,15R,15aS,16R)-15,16-dihydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

To the compound (diastereomer 1) (88.5 mg: containing impurities) obtained in step 14 was added triethylamine trihydrofluoride (2.0 mL), and the mixture was stirred at 45° C. for 3 h. The reaction mixture was admixed at room temperature with an ice-cold mixture of 1 M aqueous triethylammonium bicarbonate (10 mL) and triethylamine (2 mL). The reaction mixture was concentrated under reduced pressure. Subsequently, the product was purified by C18 silica gel column chromatography [10 mM aqueous triethylammonium acetate/acetonitrile] and preparative HPLC [10 mM aqueous triethylammonium acetate/acetonitrile; acetonitrile: 5%-30% (0 min-40 min)]. The resulting compound (triethylamine salt) was converted to a sodium salt by the following procedure.

[Conversion to Sodium Salt]

BT AG (registered trademark) 50W-X2 Resin (biotechnology grade, 100-200 mesh, hydrogen form) (500 mg) was suspended in pure water and packed into an empty column. After pure water in excess was allowed to flow down, 1M aqueous sodium hydroxide (5 mL) and pure water (10 mL) were allowed to flow down in this order. The compound obtained above was dissolved in pure water (5 mL) and charged to the column. The solution, which had been allowed to flow down, was collected, and the column was further eluted with pure water (10 mL). Fractions containing the target product were combined and lyophilized to give the titled compound (25.7 mg).

MS (ESI) m/z: 775 $(M+H)^+$.

$^1$H-NMR ($CD_3OD$) δ: 8.63 (1H, s), 8.22 (1H, s), 8.02 (1H, s), 7.11 (1H, s), 6.30-6.24 (2H, m), 5.46-5.37 (1H, m), 5.23-5.15 (1H, m), 4.83-4.79 (1H, m), 4.78-4.74 (1H, m), 4.53-4.42 (2H, m), 4.35-4.16 (3H, m), 4.16-3.97 (3H, m), 3.83-3.78 (2H, m), 3.52-3.47 (2H, m), 2.88-2.81 (2H, m), 2.03-1.95 (2H, m).

$^{31}$P-NMR ($CD_3OD$) δ: 57.8 (s), 54.4 (s).

Step 15-2 disodium(5R,7R,8R,12aR,14R,15R,15aS,16R)-15,16-dihydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

The compound (diastereomer 2) (70.7 mg: containing impurities) obtained in step 14 was used to carry out the reaction in substantially the same manner as in step 15-1. The reaction mixture was then subjected to purification using the following [Purification Conditions] to give the titled compound as a triethylamine salt.

[Purification Conditions]: C18 silica gel column chromatography [10 mM aqueous triethylammonium acetate/acetonitrile]; preparative HPLC [10 mM aqueous triethylammonium acetate/acetonitrile; acetonitrile: 5%-25% (0 min-40 min)]; and preparative HPLC [10 mM aqueous triethylammonium acetate/methanol; methanol: 15%-70% (0 min-40 min)].

The obtained triethylamine salt was subjected to salt exchange in substantially the same manner as described above in step 15-1 [Conversion to Sodium Salt] to give the titled compound (17.8 mg).

MS (ESI) m/z: 775 $(M+H)^+$.

$^1$H-NMR ($CD_3OD$) δ: 8.72 (1H, s), 8.23 (1H, s), 8.02 (1H, s), 7.11 (1H, s), 6.30 (2H, dd, J=13.6, 7.6 Hz), 5.48-5.39 (2H, m), 4.78 (1H, dd, J=6.7, 4.2 Hz), 4.51-4.28 (5H, m), 4.26-4.13 (2H, m), 4.06-4.00 (1H, m), 3.93-3.86 (1H, m), 3.85-3.80 (2H, m), 3.52-3.47 (2H, m), 2.94-2.88 (2H, m), 2.05-1.97 (2H, m).

$^{31}$P-NMR ($CD_3OD$) δ: 62.9 (s), 60.0 (s).

Example 2: To Synthesize CDN34
(5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl) octahydro-2H,1OH,12H-5,8-methano-2λ[5],10λ[5]-furo [3,2-1][1,3,6,9,11,2,10] pentaoxadiphosphacyclotetradecine-2,10-dione
[Formula 95]
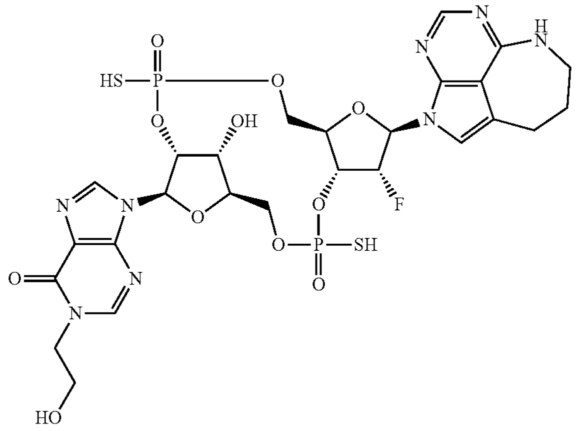
34
34a (Diastereomer 1)
34b (Diastereomer 2)
Synthetic Scheme
[Formula 96]
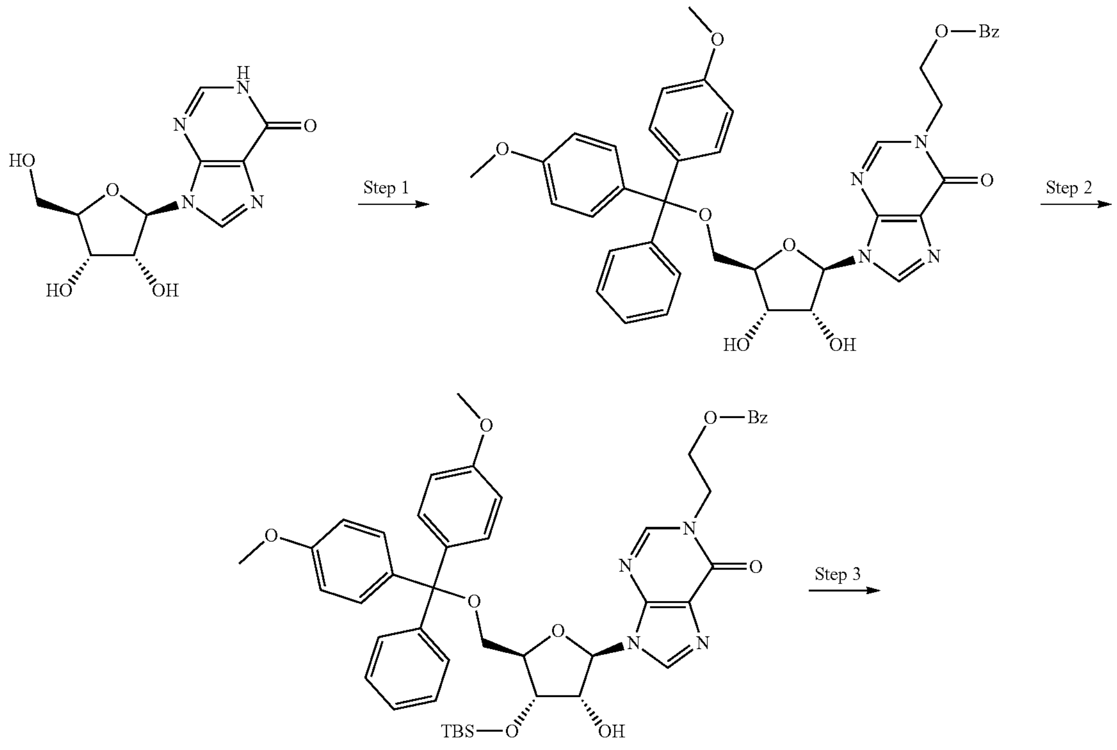

-continued
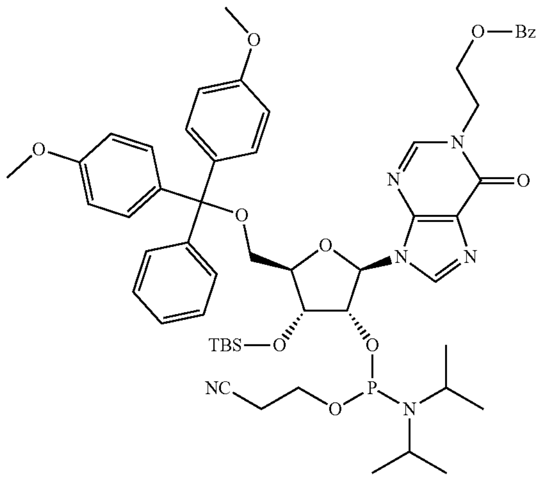
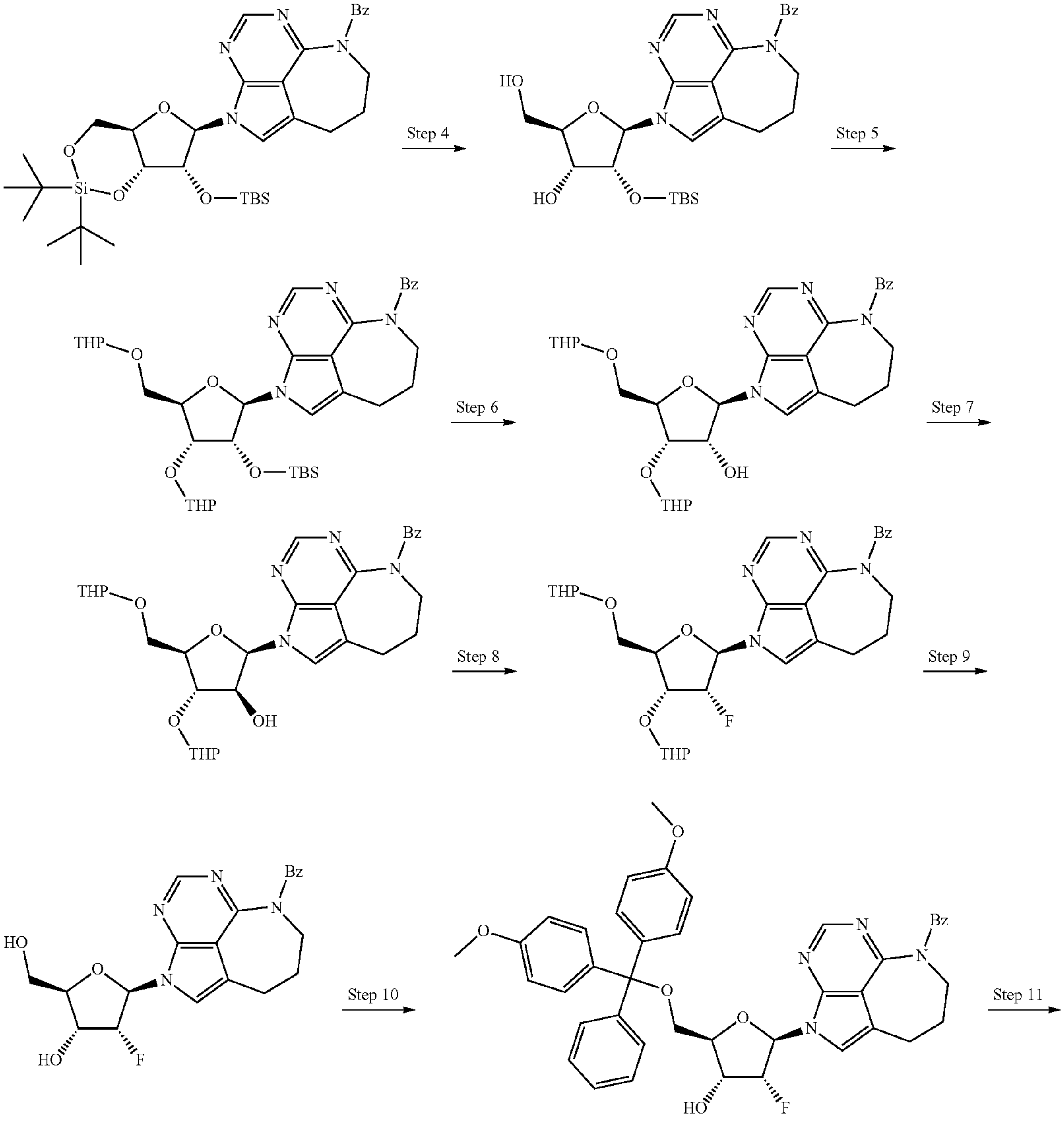

-continued
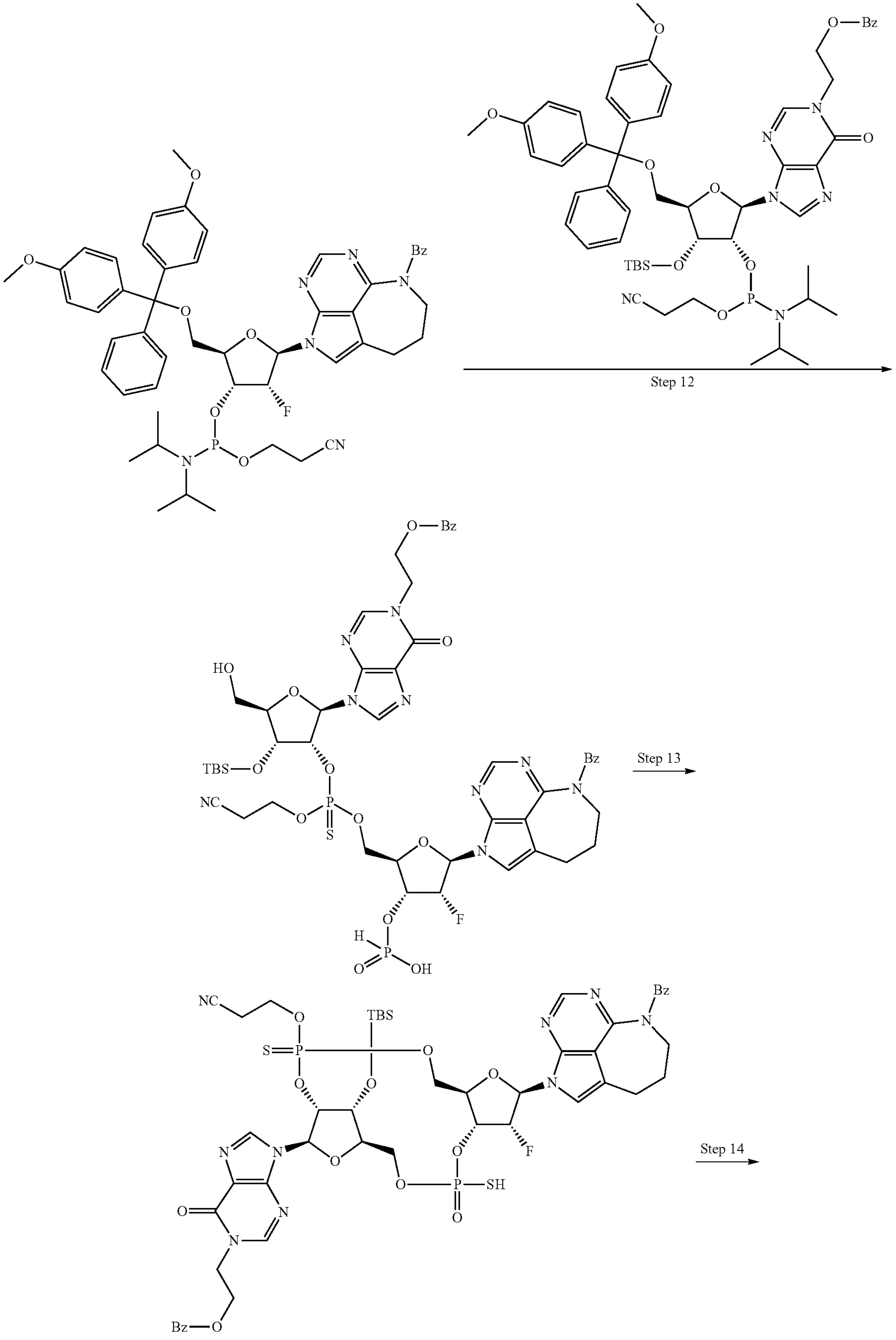

-continued

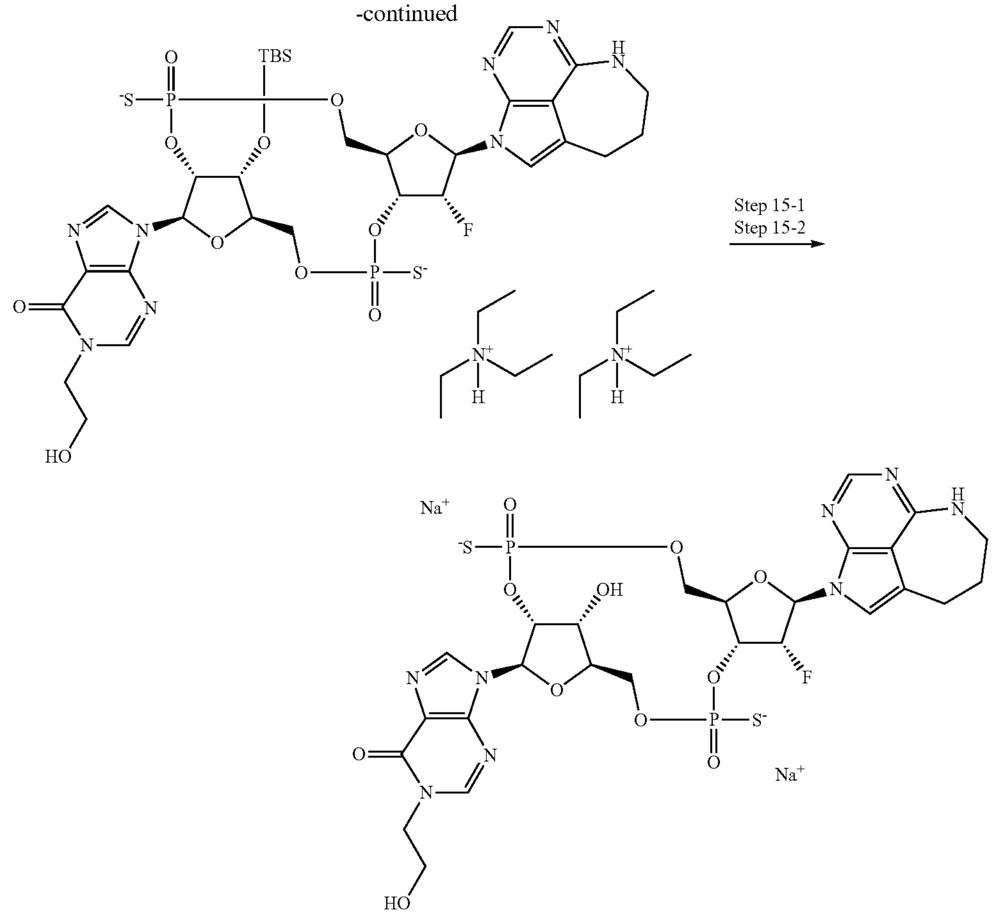

Step 1

1-[2-(benzoyloxy)ethyl]-5'-O-[bis(4-methoxyphenyl)(phenyl)methyl]inosine

To a solution of commercially available (TOKYO CHEMICAL INDUSTRY CO., LTD.) inosine (10.0 g) in pyridine (50 mL) and N,N-dimethylacetamide (50 mL) was added 4,4'-dimethoxytrityl chloride (15.2 g) at 0° C., and the mixture was stirred at 4° C. for 64 h. Methanol (2 mL) was added to the reaction mixture, and the mixture was stirred for 10 min and then concentrated to about 50 mL. To the residue were added 2-bromoethylbenzoate (7.02 mL) and 2,3,4,6,7,8,9,10-octahydropyrimido[1,2-α]azepine (13.9 mL), and the mixture was stirred at room temperature for 1 day. To the reaction mixture were added saturated aqueous sodium bicarbonate and water. Then, the mixture was extracted with ethyl acetate. The organic layer was washed with brine and dried over anhydrous sodium sulfate. The drying agent was filtered off, and the filtrate was concentrated under reduced pressure. The residue was purified by silica gel column chromatography [hexane/ethyl acetate/methanol/0.1% triethylamine] to give the titled compound (15.2 g).

MS (ESI) m/z: 719 $(M+H)^+$.

$^1$H-NMR ($CDCl_3$) δ: 8.00 (1H, s), 7.98 (1H, s), 7.98-7.94 (2H, m), 7.62-7.15 (12H, m), 6.80-6.75 (4H, m), 5.95 (1H, d, J=5.4 Hz), 4.82-4.79 (1H, m), 4.72-4.64 (3H, m), 4.55-4.34 (5H, m), 3.77 (6H, s), 3.43 (1H, dd, J=10.6, 3.9 Hz), 3.34 (1H, dd, J=10.6, 3.6 Hz).

Step 2

1-[2-(benzoyloxy)ethyl]-5'-O-[bis(4-methoxyphenyl)(phenyl)methyl]-3'-O-[tert-butyl(dimethyl)silyl]inosine By using the compound (3.01 g) obtained in step 1, the synthesis was carried out in substantially the same manner as in step 10 of Example 1 to give the titled compound (1.20 g) and a regioisomer of the titled compound, namely 1-[2-(benzoyloxy)ethyl]-5'-O-[bis(4-methoxyphenyl)(phenyl)methyl]-2'-O-[tert-butyl(dimethyl)silyl]inosine (1.22 g).

MS (ESI) m/z: 833 $(M+H)^+$.

$^1$H-NMR ($CDCl_3$) δ: 8.03 (1H, s), 7.98-7.96 (1H, m), 7.96 (1H, s), 7.96-7.94 (1H, m), 7.59-7.52 (1H, m), 7.44-7.38 (4H, m), 7.32-7.15 (7H, m), 6.83-6.77 (4H, m), 5.94 (1H, d, J=4.8 Hz), 4.69-4.63 (2H, m), 4.59-4.35 (4H, m), 4.16 (1H, dd, J=3.8, 1.9 Hz), 3.77 (6H, d, J=1.8 Hz), 3.47 (1H, dd, J=10.9, 3.0 Hz), 3.27 (1H, dd, J=10.9, 4.2 Hz), 3.00 (1H, d, J=6.7 Hz), 0.87 (9H, s), 0.06 (3H, s), -0.01 (3H, s).

(2'-O-TBS isomer)

MS (ESI) m/z: 833 $(M+H)^+$.

$^1$H-NMR ($CDCl_3$) δ: 8.01 (1H, s), 7.97-7.93 (2H, m), 7.91 (1H, s), 7.59-7.53 (1H, m), 7.45-7.38 (4H, m), 7.35-7.17 (7H, m), 6.83-6.77 (4H, m), 5.97 (1H, d, J=6.0 Hz), 4.84 (1H, t, J=5.4 Hz), 4.71-4.60 (2H, m), 4.52-4.37 (2H, m), 4.33-4.28 (1H, m), 4.28-4.24 (1H, m), 3.78 (3H, s), 3.77 (3H, s), 3.47 (1H, dd, J=10.9, 3.0 Hz), 3.38 (1H, dd, J=10.9, 3.6 Hz), 2.71 (1H, d, J=3.0 Hz), 0.80 (9H, s), -0.03 (3H, s), -0.19 (3H, s).

Step 3

1-[2-(benzoyloxy)ethyl]-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}inosine By using the compound (1.20 g) obtained in step 2, the synthesis was carried out in substantially the same manner as in step 11 of Example 1 to give the titled compound (1.41 g) as a mixture of diastereomers (diastereomer ratio=0.55:0.45) at the phosphorus atom.

MS (ESI) m/z: 1033 $(M+H)^+$.

$^1$H-NMR ($CDCl_3$) δ: 8.05 (0.45H, s), 8.04 (0.55H, s), 7.99-7.95 (2H, m), 7.95 (0.55H, s), 7.92 (0.45H, s), 7.59-7.53 (1H, m), 7.45-7.39 (4H, m), 7.35-7.10 (7H, m), 6.83-6.78 (4H, m), 6.15 (0.55H, d, J=5.4 Hz), 6.08 (0.45H, d, J=6.0 Hz), 4.86-4.49 (3H, m), 4.49-4.35 (3H, m), 4.25-4.10 (1H, m), 3.78 (6H, s), 3.72-3.41 (5H, m), 3.35-3.25 (1H, m), 2.47 (1H, t, J=6.7 Hz), 2.32 (1H, t, J=6.3 Hz), 1.33-1.24 (6H, m), 1.13-1.03 (6H, m), 0.84 (4.05H, s), 0.84 (4.95H, s), 0.08 (1.35H, s), 0.05 (1.65H, s), 0.00 (1.35H, s), -0.01 (1.65H, s).

Step 4

6-benzoyl-2-{2-O-[tert-butyl(dimethyl)silyl]-β-D-ribofuranosyl}-6,7,8,9-tetrahydro-2H-2,3, 5,6-tetraazabenzo[cd]azulene To a mixed solution of the compound (35.80 g) obtained in step 4 of Example 1 in dichloromethane (322 mL)-pyridine (35 mL) was added a solution of hydrogen fluoride-pyridine (6.33 g) in dichloromethane (36 mL) under ice-cold conditions over 5 min, and the mixture was stirred at the same temperature for 3 h. The reaction was stopped by adding saturated aqueous sodium bicarbonate (268 mL) and brine (143 mL) in this order to the reaction mixture, and the resulting solution was then extracted with ethyl acetate. The organic layer was dried over anhydrous sodium sulfate, the drying agent was filtered off, and the filtrate was then concentrated under reduced pressure. Hexane/ethyl acetate (1:1) (108 mL) was added to the residue to form a slurry, and the slurry was stirred at 50° C. for 30 min. After that, hexane (161 mL) was added, and the mixture was stirred for additional 2 h. The precipitated solid was filtered off and washed with hexane/ethyl acetate (4:1) (143 mL) to yield the titled compound (26.81 g).

MS (ESI) m/z: 525 $(M+H)^+$.

$^1$H-NMR (DMSO-$d_6$) δ: 7.98 (1H, s), 7.65 (1H, s), 7.39 (1H, m), 7.26-7.20 (4H, m), 6.19 (1H, d, J=6.5 Hz), 5.15 (1H, t, J=5.6 Hz), 5.00 (1H, d, J=4.8 Hz) 4.48 (1H, t, J=5.6 Hz), 4.27 (1H, m), 4.11-4.02 (2H, m), 3.97 (1H, m), 3.67-3.57 (2H, m), 2.99 (2H, m), 2.23-2.07 (2H, m), 0.68 (9H, s), -0.11 (3H, s), -0.26 (3H, s).

Step 5

6-benzoyl-2-{2-O-[tert-butyl(dimethyl)silyl]-3,5-bis-O-(oxan-2-yl)-β-D-ribofuranosyl}-6,7,8,9-tetrahydro-2H-2,3, 5,6-tetraazabenzo[cd]azulene To a solution of the compound (19.93 g) obtained in step 4 and 3,4-dihydro-2H-pyran (35 mL) in N,N-dimethylformamide (200 mL) was added p-toluenesulfonic acid -monohydrate (7.25 g) under ice-cold conditions, and the mixture was stirred for 3 h at room temperature. The reaction was stopped by adding saturated aqueous sodium bicarbonate to the reaction mixture under ice-cold conditions, and the resulting solution was then extracted with ethyl acetate. The organic layer was washed with water and brine in this order, and dried over anhydrous sodium sulfate. The drying agent was filtered off, and the filtrate was concentrated under reduced pressure. The residue was purified by silica gel column chromatography [hexane/ethyl acetate] to give the titled compound (24.73 g).

$^1$H-NMR ($CDCl_3$) δ: 8.10-8.07 (1H, m), 7.59-7.35 (1H, m), 7.35-7.27 (3H, m), 7.25-7.17 (2H, m), 6.44-6.36 (1H, m), 4.90-3.36 (13H, m), 3.06-2.96 (2H, m), 2.31-2.15 (2H, m), 2.01-1.43 (12H, m), 0.84-0.73 (9H, m), 0.04- (−0.35) (6H, m).

Step 6

6-benzoyl-2-[3,5-bis-O-(oxan-2-yl)-β-D-ribofuranosyl]-6,7,8,9-tetrahydro-2H-2,3,5,6-tetraazabenzo[cd]azulene To a solution of the compound (24.73 g) obtained in step 5 and acetic acid (3.1 mL) in tetrahydrofuran (250 mL) was added a tetrahydrofuran solution of tetrabutylammonium fluoride (about 1 M, 55 mL) under ice-cold conditions, and the mixture was stirred overnight at room temperature. The reaction mixture was concentrated under reduced pressure, and ethyl acetate was added to the residue, followed by washing with water and brine in this order. The organic layer was dried over anhydrous sodium sulfate, the drying agent was filtered off, and the filtrate was then concentrated under reduced pressure. The residue was purified by silica gel column chromatography [hexane/ethyl acetate] to give the titled compound (18.74 g).

$^1$H-NMR ($CDCl_3$) δ: 8.12-8.09 (1H, m), 7.49-7.30 (4H, m), 7.28-7.20 (2H, m), 6.41-6.30 (1H, m), 4.83-4.18 (7H, m), 4.12-3.50 (7H, m), 3.06-2.97 (2H, m), 2.31-2.17 (2H, m), 1.96-1.47 (12H, m).

Step 7

6-benzoyl-2-[3,5-bis-O-(oxan-2-yl)-β-D-arabinofuranosyl]-6,7,8,9-tetrahydro-2H-2,3,5,6-tetraazabenzo[cd]azulene To a solution of the compound (18.74 g) obtained in step 6 and pyridine (13.1 mL) in dichloromethane (300 mL) was added dropwise trifluoromethanesulfonate anhydride (11 mL) under ice-cold conditions, and the mixture was stirred for 10 min. The reaction was stopped by adding brine to the reaction mixture. After extraction with dichloromethane, the organic layer was dried over anhydrous sodium sulfate. The drying agent was filtered off, and the filtrate was concentrated under reduced pressure. The residue was dissolved in tetrahydrofuran (300 mL). A solution of tetrabutylammonium nitrite (28.34 g) in tetrahydrofuran (150 mL) was added dropwise under ice-cold conditions, and the mixture was stirred overnight at room temperature. The reaction mixture was concentrated under reduced pressure, and ethyl acetate was added to the residue, followed by washing with water and brine in this order. The organic layer was dried over anhydrous sodium sulfate, the drying agent was filtered off, and the filtrate was then concentrated under reduced pressure. The residue was purified by silica gel column chromatography [hexane/ethyl acetate] to give the titled compound (10.46 g).

$^1$H-NMR ($CDCl_3$) δ: 8.13-8.06 (1H, m), 7.63-7.30 (4H, m), 7.29-7.18 (2H, m), 6.79-6.55 (1H, m), 4.93-3.45 (14H, m), 3.11-2.95 (2H, m), 2.32-2.14 (2H, m), 1.98-1.44 (12H, m).

Step 8

6-benzoyl-2-[2-deoxy-2-fluoro-3,5-bis-O-(oxan-2-yl)-β-D-ribofuranosyl]-6,7,8,9-tetrahydro-2H-2,3,5,6-tetraazabenzo[cd]azulene To a solution of the compound (10.46 g) obtained in step 7 and pyridine (7.3 mL) in dichloromethane (200 mL) was added dropwise trifluoromethanesulfonate anhydride (6.1 mL) under ice-cold conditions, and the mixture was stirred for 10 min. The reaction was stopped by adding brine to the reaction mixture. After extraction with dichloromethane, the organic layer was dried over anhydrous sodium sulfate. The drying agent was filtered off, and the filtrate was concentrated under reduced pressure. The residue was dissolved in tetrahydrofuran (200 mL). A tetrahydrofuran solution of tetrabutylammonium fluoride (about 1 M, 150 mL) was added under ice-cold conditions, and the mixture was stirred at the same temperature for 3 h. The reaction mixture was admixed with saturated aqueous ammonium chloride and was extracted with ethyl acetate. The organic layer was washed with brine and dried over anhydrous sodium sulfate. Subsequently, the drying agent was filtered off, and the filtrate was then concentrated under reduced pressure. The residue was purified by silica gel column chromatography [hexane/ethyl acetate] to give the titled compound (7.65 g).

$^1$H-NMR ($CDCl_3$) δ: 8.13-8.08 (1H, m), 7.53-7.31 (4H, m), 7.26-7.22 (2H, m), 6.68-6.53 (1H, m), 5.42-5.08 (1H, m), 4.93-4.18 (6H, m), 4.10-3.76 (3H, m), 3.71-3.47 (3H, m), 3.06-2.96 (2H, m), 2.29-2.18 (2H, m), 1.96-1.47 (12H, m).

Step 9

6-benzoyl-2-(2-deoxy-2-fluoro-β-D-ribofuranosyl)-6,7,8,9-tetrahydro-2H-2,3,5,6-tetraazabenzo[cd]azulene To a solution of the compound (7.65 g) obtained in step 8 in ethanol (150 mL) was added pyridinium p-toluenesulfonate (6.62 g), and the mixture was stirred at 50° C. for 3 h. The reaction mixture was concentrated under reduced pressure, and ethyl acetate was added to the residue, followed by washing with saturated aqueous sodium bicarbonate and brine in this order. The organic layer was dried over anhydrous sodium sulfate, the drying agent was filtered off, and the filtrate was then concentrated under reduced pressure. The residue was purified by silica gel column chromatography [hexane/ethyl acetate] to give the titled compound (3.55 g).

$^1$H-NMR ($CDCl_3$) δ: 8.05 (1H, s), 7.41-7.35 (3H, m), 7.30-7.24 (2H, m), 7.06 (1H, s), 6.07-6.00 (2H, m), 5.85 (1H, ddd, J=52.8, 6.7, 4.7 Hz), 4.66 (1H, d, J=3.9 Hz), 4.42-4.31 (2H, m), 4.20 (1H, m), 3.93 (1H, dd, J=12.9, 1.6 Hz), 3.74 (1H, td, J=12.3, 1.6 Hz), 3.12-2.96 (2H, m), 2.51 (1H, s), 2.33-2.15 (2H, m).

Step 10

6-benzoyl-2-{5-O-[bis(4-methoxyphenyl)(phenyl)methyl]-2-deoxy-2-fluoro-β-D-ribofuranosyl}-6,7,8,9-tetrahydro-2H-2,3, 5,6-tetraazabenzo[cd]azulene To a solution of the compound (3.55 g) obtained in step 9 in dehydrated pyridine (50 mL) was added 4,4'-dimethoxytrityl chloride (4.43 g), and the mixture was stirred for 2 h at room temperature under a nitrogen atmosphere. Methanol (1 mL) was added to the reaction mixture, and the mixture was stirred for about 10 min and then concentrated under reduced pressure. The residue was purified by silica gel column chromatography [hexane/ethyl acetate/0.1% triethylamine] to give the titled compound (5.77 g).

$^1$H-NMR ($CDCl_3$) δ: 8.09 (1H, s), 7.45-7.41 (2H, m), 7.36-7.17 (13H, m), 6.85-6.79 (4H, m), 6.53 (1H, dd, J=17.2, 2.3 Hz), 5.40 (1H, ddd, J=53.2, 4.8, 2.3 Hz), 4.83-4.72 (1H, m), 4.32-4.21 (2H, m), 4.19-4.14 (1H, m), 3.79 (3H, s), 3.79 (3H, s), 3.59 (1H, dd, J=11.0, 2.7 Hz), 3.45 (1H, dd, J=11.0, 3.5 Hz), 2.79 (2H, t, J=6.3 Hz), 2.45 (1H, s), 2.24-2.11 (2H, m).

Step 11

6-benzoyl-2-(5-O-[bis(4-methoxyphenyl)(phenyl)methyl]-3-O-{(2-cyanoethoxy)[di(propan-2-yl)amino]phosphanyl}-2-deoxy-2-fluoro-β-D-ribofuranosyl)-6,7,8,9-tetrahydro-2H-2,3, 5,6-tetraazabenzo[cd]azulene By using the compound (5.77 g) obtained in step 10, the reaction was carried out in substantially the same manner as in step 6 of Example 1 to give the titled compound (5.95 g) as a mixture of diastereomers (diastereomer ratio=1:1) at the phosphorus atom.

$^1$H-NMR ($CDCl_3$) δ: 8.10 (0.5H, s), 8.09 (0.5H, s), 7.45-7.12 (15H, m), 6.84-6.75 (4H, m), 6.57-6.46 (1H, m), 5.61-5.33 (1H, m), 5.07-4.83 (1H, m), 4.34-4.18 (3H, m), 3.93-3.72 (7H, m), 3.69-3.49 (4H, m), 3.38-3.27 (1H, m), 2.87-2.68 (2H, m), 2.61 (1H, td, J=6.3, 1.6 Hz), 2.40 (1H, td, J=6.4, 2.1 Hz), 2.21-2.12 (2H, m), 1.21-1.13 (9H, m), 1.03 (3H, d, J=6.7 Hz).

Step 12

By using the compound (1.02 g) obtained in step 11, the reaction was carried out in substantially the same manner as in step 7 of Example 1 to give an acetonitrile solution of 6-benzoyl-2-{2-deoxy-2-fluoro-3-O-[hydroxy(oxo)-$\lambda^5$-phosphanyl]-β-D-ribofuranosyl}-6,7,8,9-tetrahydro-2H-2,3, 5,6-tetraazabenzo[cd]azulene. By using the resulting acetonitrile solution and the compound (1.15 g) obtained in step 3, the reaction was carried out in substantially the same manner as in step 12 of Example 1. The resulting crude product was used directly in the next reaction.

Step 13

2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanilidenoctahydro-2H,1OH,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl benzoate By using the crude product obtained in step 12, the reaction was carried out in substantially the same manner as in step 13 of Example 1 to give the titled compound (818 mg; containing impurities) as a mixture of diastereomers at the phosphorus atom.

MS (ESI) m/z: 1152 $(M+H)^+$.

Step 14 bis(N,N-diethylethanaminium) (5R,7R,8R,12aR,14R,15R,15aR,16R)-16-{[tert-butyl(dimethyl)silyl]oxy}-15-fluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

By using the compound (818 mg) obtained in step 13, the reaction was carried out in substantially the same manner as in step 14 of Example 1 to give diastereomer 1 (107 mg; containing impurities) and diastereomer 2 (101 mg; containing impurities) of the titled compound.

Diastereomer 1 (less polar)

MS (ESI) m/z: 891 $(M+H)^+$.

Diastereomer 2 (more polar)

MS (ESI) m/z: 891 $(M+H)^+$.

Step 15-1

Disodium(5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate) (Diastereomer 1)

By using the compound (diastereomer 1) (107 mg; containing impurities) obtained in step 14, the reaction was carried out in substantially the same manner as in step 15-1 of Example 1. The reaction mixture was then subjected to purification using the following [Purification Conditions] to give the titled compound as a triethylamine salt.

[Purification Conditions]C18 silica gel column chromatography [10 mM aqueous triethylammonium acetate/acetonitrile] and preparative HPLC [10 mM aqueous triethylammonium acetate/acetonitrile; acetonitrile: 5%-30% (0 min-30 min)].

The obtained triethylamine salt was subjected to salt exchange in substantially the same manner as described above in step 15-1 [Conversion to Sodium Salt] of Example 1 to give the titled compound (29.1 mg).

MS (ESI) m/z: 777 $(M+H)^+$.

$^1$H-NMR ($CD_3OD$) δ: 8.58 (1H, m), 8.11 (1H, m), 8.03 (1H, s), 7.11 (1H, s), 6.47 (1H, d, J=17.5 Hz), 6.26 (1H, d, J=8.5 Hz), 5.53-5.36 (2H, m), 5.29-5.17 (1H, m), 4.77 (1H, d, J=4.2 Hz), 4.54-4.46 (1H, m), 4.44-4.38 (1H, m), 4.35-4.32 (1H, m), 4.30-4.25 (2H, m), 4.25-4.16 (1H, m), 4.06-3.99 (1H, m), 3.96-3.85 (1H, m), 3.82-3.71 (2H, m), 3.54-3.42 (2H, m), 2.77-2.68 (1H, m), 2.66-2.55 (1H, m), 2.02-1.81 (2H, m).

$^{31}$P-NMR ($CD_3OD$) δ: 57.5 (s), 53.0 (s).

Step 15-2

Disodium(5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)

By using the compound (diastereomer 2) (101 mg; containing impurities) obtained in step 14, the reaction was carried out in substantially the same manner as in step 15-1 of Example 1. The reaction mixture was then subjected to purification using the following [Purification Conditions] to give the titled compound as a triethylamine salt.

[Purification Conditions]C18 silica gel column chromatography [10 mM aqueous triethylammonium acetate/acetonitrile] and preparative HPLC [10 mM aqueous triethylammonium acetate/acetonitrile; acetonitrile: 5%-20% (0 min-30 min)].

The obtained triethylamine salt was subjected to salt exchange in substantially the same manner as described above in step 15-1 [Conversion to Sodium Salt] of Example 1 to give the titled compound (11.2 mg).

MS (ESI) m/z: 777 $(M+H)^+$.

$^1$H-NMR ($CD_3OD$) δ: 8.61 (1H, m), 8.16 (1H, m), 8.02 (1H, m), 7.36 (1H, s), 6.49 (1H, dd, J=16.0, 2.1 Hz), 6.28 (1H, d, J=8.5 Hz), 5.56-5.33 (3H, m), 4.58-4.49 (2H, m), 4.45-4.37 (2H, m), 4.31-4.27 (1H, m), 4.25-4.16 (1H, m), 4.10-3.98 (3H, m), 3.80 (2H, t, J=5.1 Hz), 3.48 (2H, dd, J=6.7, 3.6 Hz), 2.90-2.72 (2H, m), 2.00-1.90 (2H, m).

$^{31}$P-NMR ($CD_3OD$) δ: 59.5 (s), 57.7 (s).

Example 3: To Synthesize CDN49

(5R,7R,8R,12aR,14R,15R,15aR,16R)-7-[1-(2-aminoethyl)-6-oxo-1,6-dihydro-9H-purin-9-yl]-14-(8,9-dihydro-6-thia-2,3,5-triazabenzo[cd]azulen-2(7H)-yl)-15-fluoro-16-hydroxy-2,10-bis(sulfanyl)octahydro-2H,10H,12H-5,8-methano-2λ$^5$,10λ$^5$-furo[3,2-l][1,3,6,9,11,2,10]pentaoxadiphosphacyclotetradecine-2,10-dione

[Formula 97]

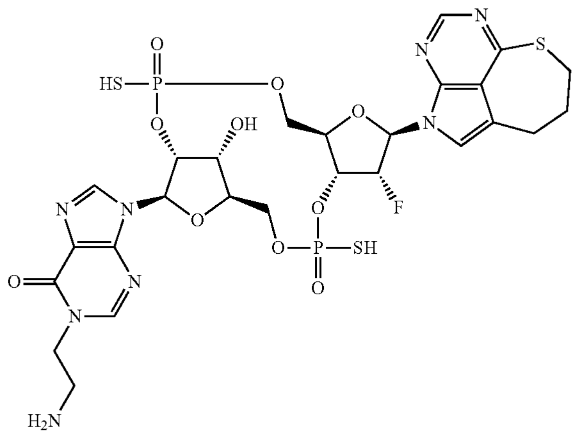

49
49a (Diastereomer 1)
49b (Diastereomer 2)

Synthetic Scheme
[Formula 98]
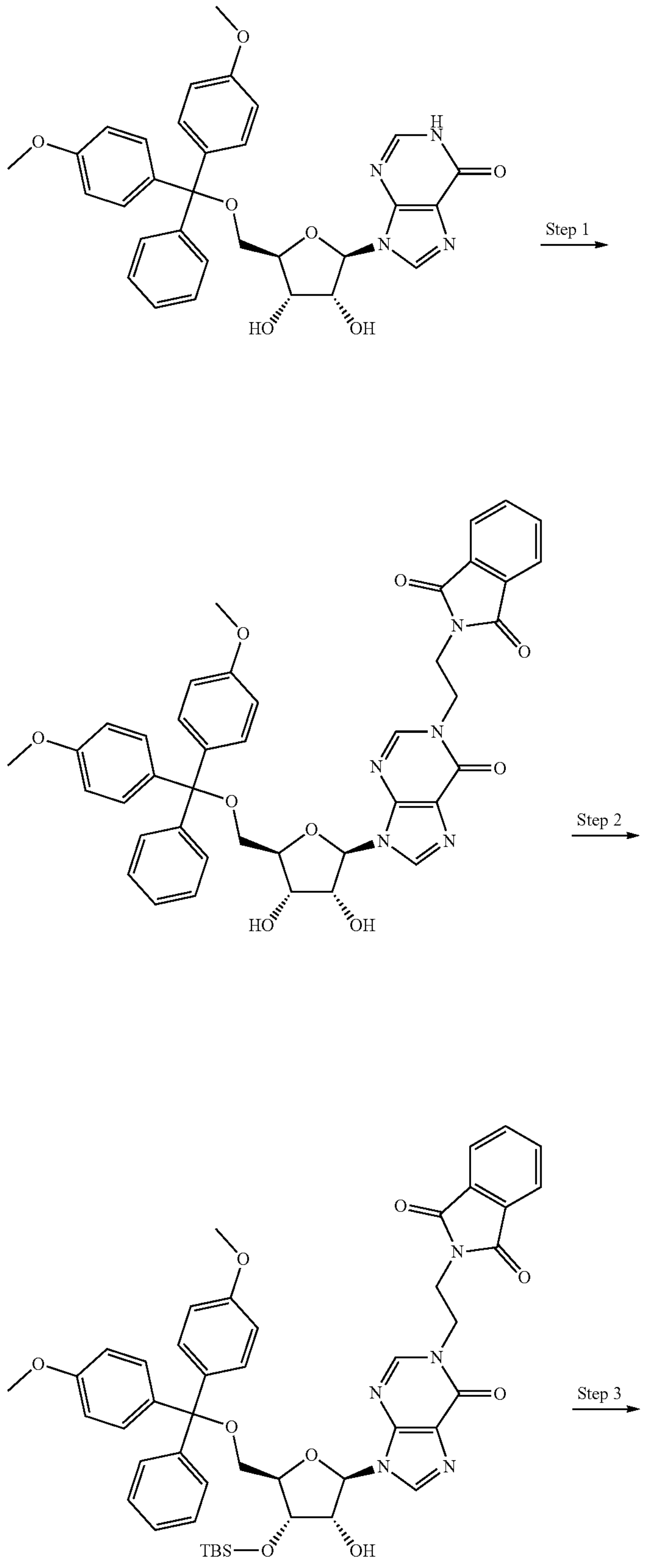

-continued
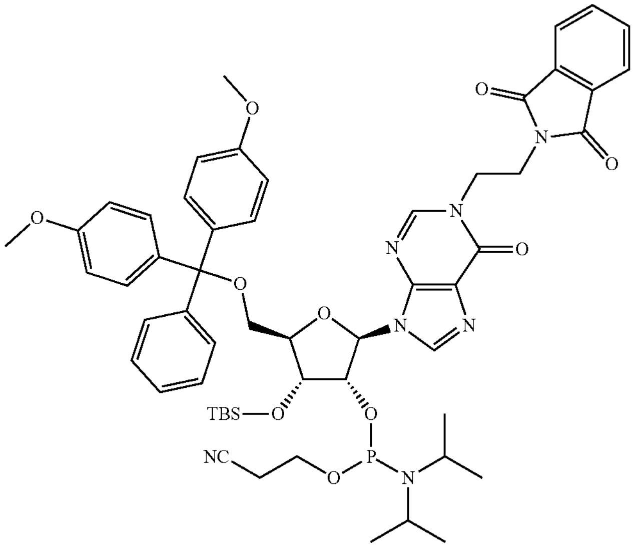
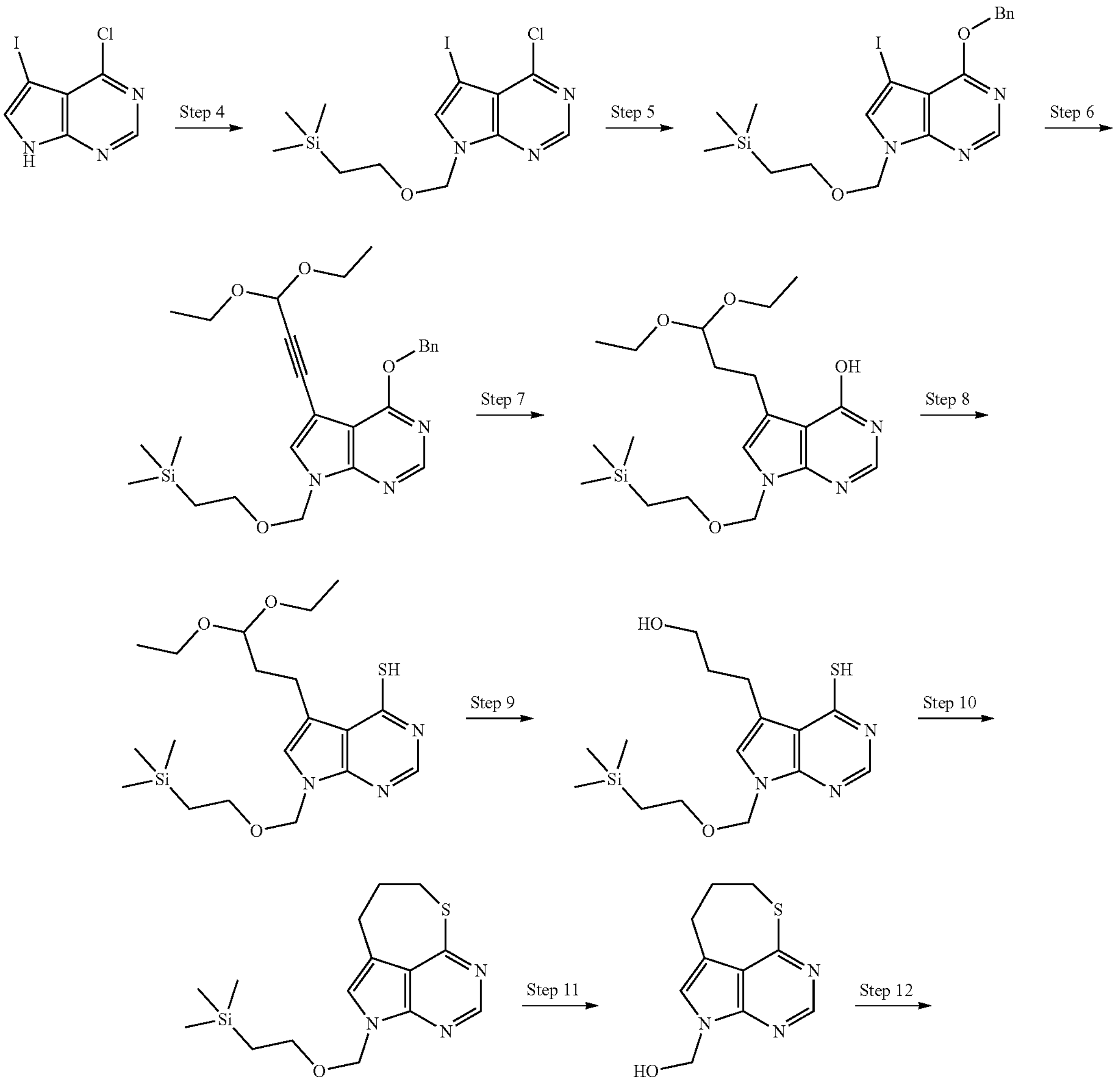

-continued
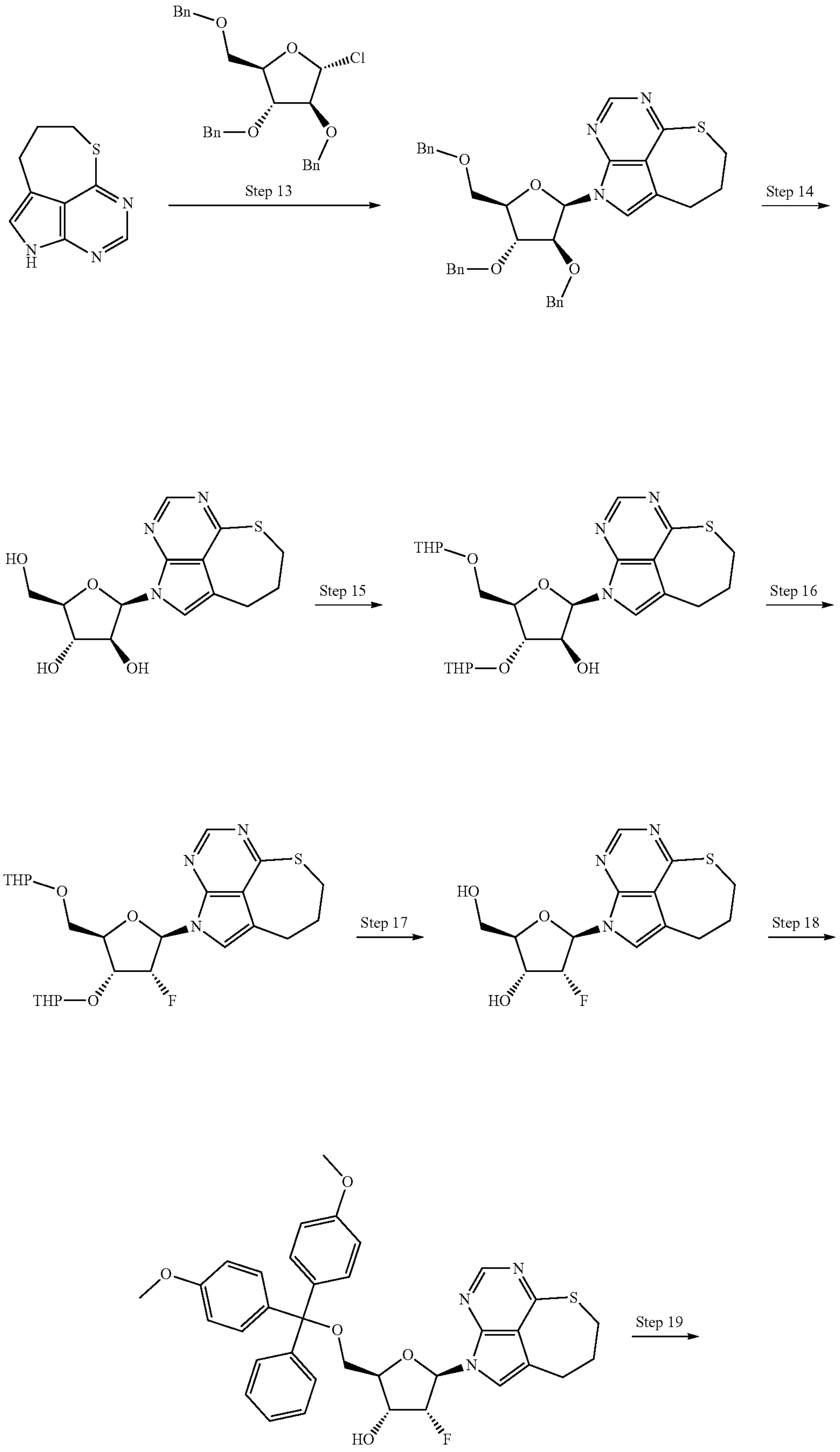

-continued
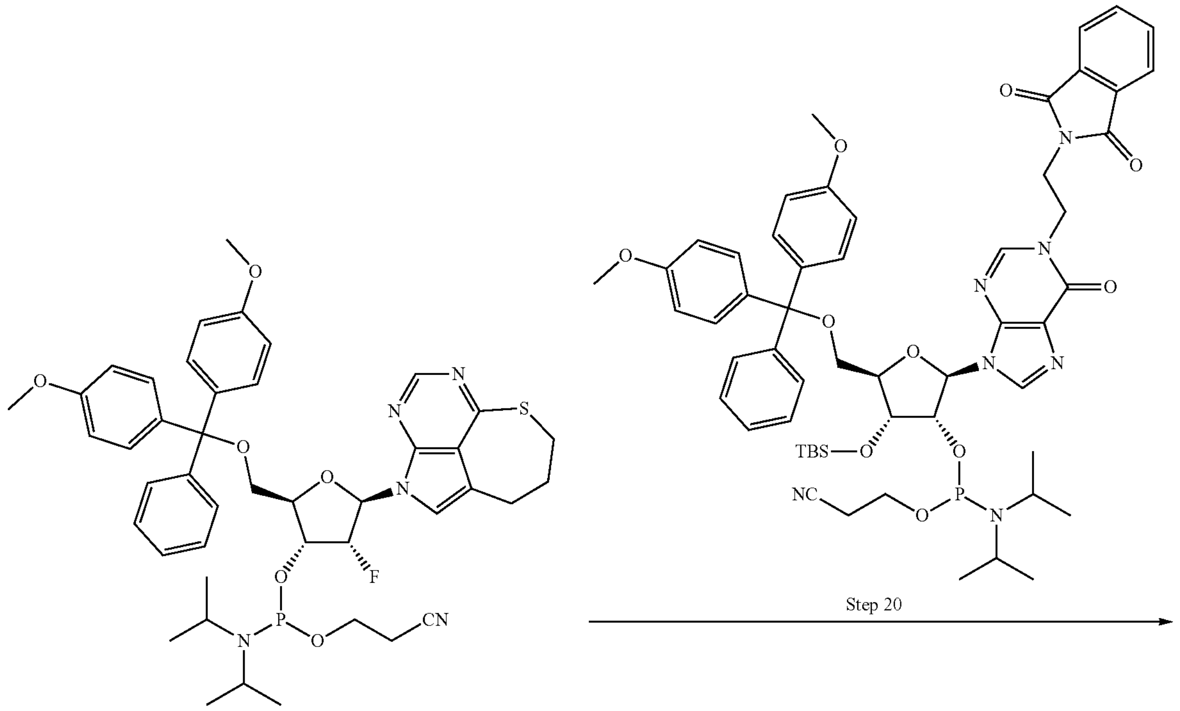
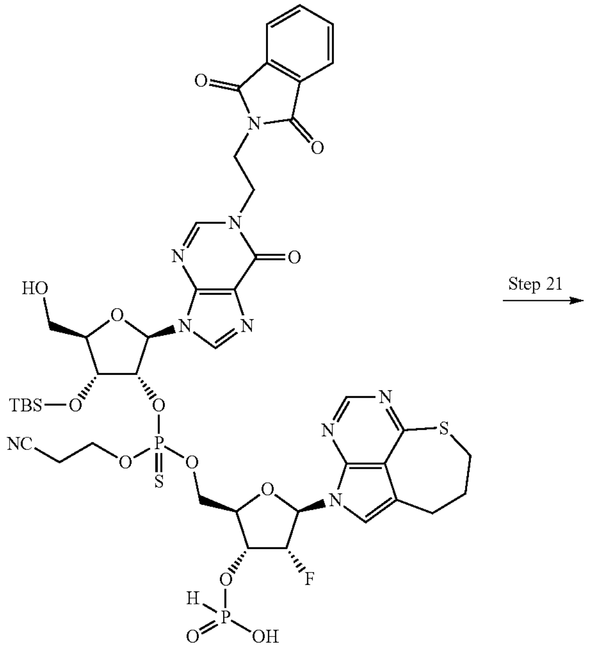

-continued

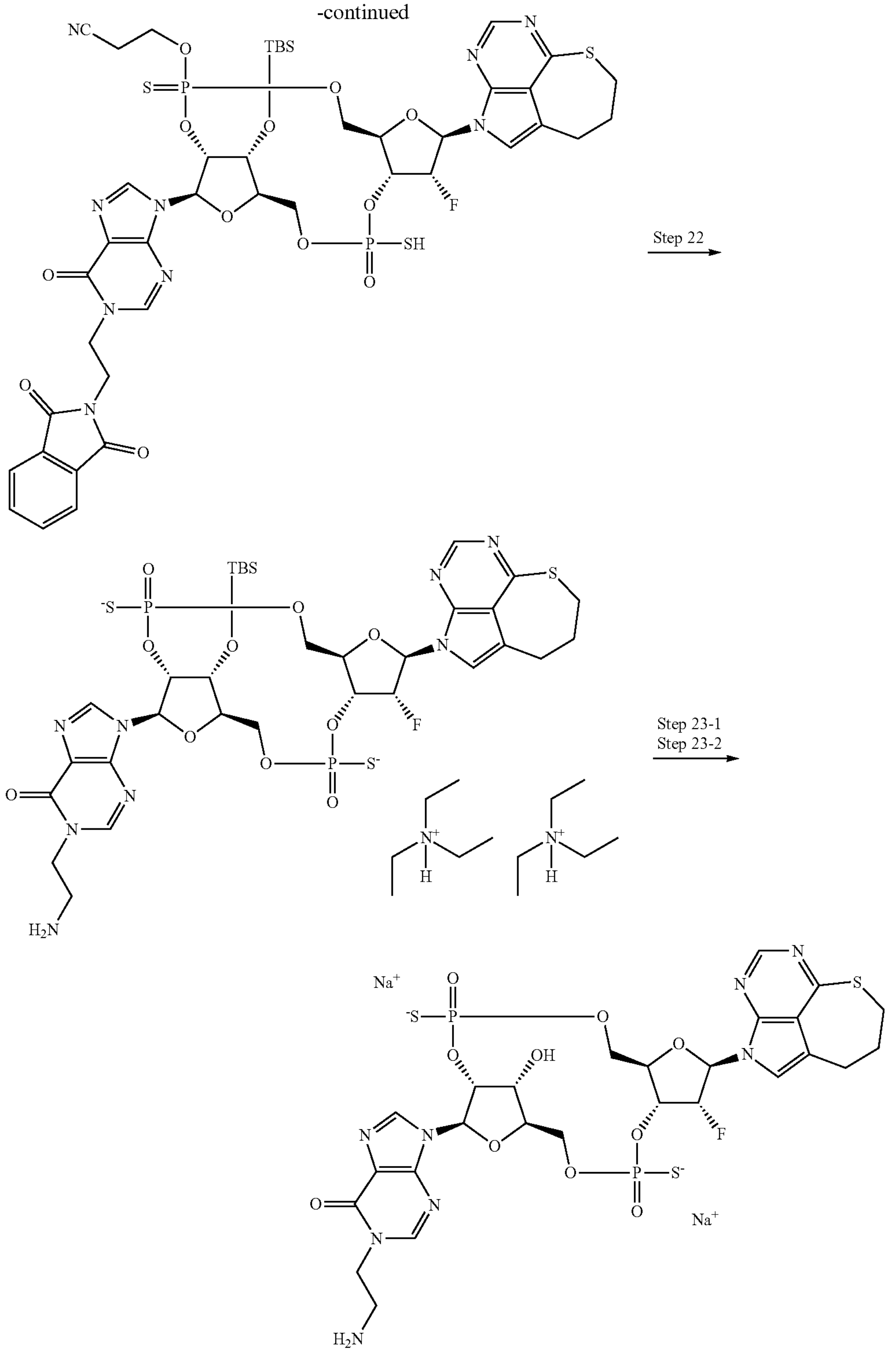

Step 1

5'-O-[bis(4-methoxyphenyl)(phenyl)methyl]-1-[2-(1,3-dioxo-1,3-dihydro-2H-isoindol-2-yl)ethyl]inosine To a suspension of commercially available (Aamdis Chemical) 5'-O-[bis(4-methoxyphenyl)(phenyl)methyl]inosine (13.0 g) in N,N-dimethylacetamide (60 mL) were added N-(2-bromoethyl)phthalimide (7.02 g) and 1,8-diazabicyclo[5.4.0]-7-undecene (4.1 mL), and the mixture was stirred overnight at room temperature. N-(2-bromoethyl) phthalimide (1.75 g) and 1,8-diazabicyclo[5.4.0]-7-undecene (1.1 mL) were further added, and the mixture was stirred for another 1 day. The reaction was stopped by adding water to the reaction mixture, and the mixture was extracted with dichloromethane. The organic layer was dried over anhydrous sodium sulfate, the drying agent was filtered off, and the filtrate was then concentrated under reduced pressure. The residue was purified by silica gel column chromatography [ethyl acetate/methanol] to give the titled compound (12.4 g).

$^1$H-NMR ($CDCl_3$) δ: 7.83 (1H, s), 7.76-7.67 (4H, m), 7.64 (1H, s), 7.35-7.33 (2H, m), 7.25-7.11 (7H, m), 6.74-6.70 (4H, m), 5.93 (1H, d, J=5.1 Hz), 5.68 (1H, d, J=3.9 Hz), 4.71 (1H, q, J=4.8 Hz), 4.43 (1H, m), 4.37-4.18 (3H, m), 4.10-4.06 (2H, m), 3.730 (3H, s), 3.728 (3H, s), 3.51 (1H, m), 3.36 (1H, dd, J=10.6, 3.9 Hz), 3.32 (1H, dd, J=11.0, 5.5 Hz).

Step 2

5'-O-[bis(4-methoxyphenyl)(phenyl)methyl]-3'-O-[tert-butyl(dimethyl)silyl]-1-[2-(1,3-dioxo-1,3-dihydro-2H-isoindol-2-yl)ethyl]inosine By using the compound (12.4 g) obtained in step 1, the reaction was carried out in substantially the same manner as in step 10 of Example 1 to give the titled compound (4.18 g) and a regioisomer of the titled compound, namely 5'-O-[bis(4-methoxyphenyl)(phenyl)methyl]-2'-O-[tert-butyl(dimethyl)silyl]-1-[2-(1,3-dioxo-1,3-dihydro-2H-isoindol-2-yl)ethyl]inosine (6.31 g).

$^1$H-NMR ($CDCl_3$) δ: 8.00 (1H, s), 7.82-7.77 (2H, m), 7.74 (1H, s), 7.72-7.67 (2H, m), 7.41-7.39 (2H, m), 7.32-7.19 (7H, m), 6.83-6.78 (4H, m), 5.90 (1H, d, J=5.1 Hz), 4.53-4.41 (3H, m), 4.32-4.25 (1H, m), 4.19-4.11 (3H, m), 3.79 (3H, s), 3.78 (3H, s), 3.46 (1H, dd, J=10.6, 3.1 Hz), 3.24 (1H, dd, J=10.8, 4.1 Hz), 2.98 (1H, d, J=6.7 Hz), 0.85 (9H, s), 0.04 (3H, s), -0.03 (3H, s).

Regioisomer (2'-O-TBS isomer)

$^1$H-NMR ($CDCl_3$) δ: 7.97 (1H, s), 7.82-7.78 (2H, m), 7.73-7.69 (2H, m), 7.66 (1H, s), 7.44-7.41 (2H, m), 7.33-7.18 (7H, m), 6.81 (4H, d, J=7.8 Hz), 5.91 (1H, d, J=5.9 Hz), 4.82 (1H, t, J=5.5 Hz), 4.43 (1H, m), 4.34-4.23 (3H, m), 4.18-4.08 (2H, m), 3.79 (6H, s), 3.46 (1H, dd, J=10.6, 2.7 Hz), 3.36 (1H, dd, J=10.6, 3.5 Hz), 2.70 (1H, d, J=3.1 Hz), 0.83 (9H, s), -0.04 (3H, s), -0.19 (3H, s).

Step 3

5'-O-[bis(4-methoxyphenyl)(phenyl)methyl]-3'-O-[tert-butyl(dimethyl)silyl]-2'-O-{(2-cyanoethoxy)[di(propane-2-yl)]amino]phosphanyl}-1-[2-(1,3-dioxo-1,3-dihydro-2H-isoindol-2-yl)ethyl]inosine By using the compound (8.89 g) obtained in step 2, the reaction was carried out in substantially the same manner as in step 6 of Example 1 to give the titled compound (9.45 g) as a mixture of diastereomers (diastereomer ratio=1:1) at the phosphorus atom.

$^1$H-NMR ($CDCl_3$) δ: 8.01 (0.5H, s), 8.00 (0.5H, s), 7.82-7.77 (2H, m), 7.74 (0.5H, s), 7.72-7.67 (2.5H, m), 7.42 (2H, d, J=7.8 Hz), 7.33-7.18 (7H, m), 6.81 (4H, d, J=8.6 Hz), 6.10 (0.5H, d, J=5.5 Hz), 6.04 (0.5H, d, J=5.1 Hz), 4.75 (0.5H, m), 4.60 (0.5H, m), 4.49-4.41 (1H, m), 4.38-4.23 (2H, m), 4.22-4.05 (3H, m), 3.79 (6H, s), 3.78-3.65 (1H, m), 3.62-3.39 (4H, m), 3.33-3.23 (1H, m), 2.49 (1H, t, J=6.3 Hz), 2.34 (1H, t, J=6.7 Hz), 1.12-1.08 (9H, m), 0.91 (3H, d, J=7.0 Hz), 0.82 (9H, s), 0.06 (1.5H, s), 0.03 (1.5H, s), -0.03 (3H, s).

Step 4

4-chloro-5-iodo-7-{[2-(trimethylsilyl)ethoxy]methyl}-7H-pyrrolo[2,3-d]pyrimidine To a solution of commercially available (PharmaBlock) 4-chloro-5-iodo-7H-pyrrolo[2,3-d]pyrimidine (73.8 g) in N,N-dimethylformamide (10 mL) was added sodium hydride (containing 45% mineral oil) (13.3 g) under ice-cold conditions, and the mixture was stirred for 40 min while the temperature was raised to room temperature. After re-cooling on ice, [2-(chloromethoxy)ethyl](trimethyl)silane (51.0 mL) was added over 10 min, and the mixture was stirred at the same temperature for 30 min. The reaction was stopped by adding water in a small portion over time (260 mL) to the mostly solidified reaction mixture. The solid was filtered off, washed with water (1500 mL) and hexane (600 mL), and then dried at 40° C. under reduced pressure to yield the titled compound (97.63 g).

MS (ESI) m/z: 410 $(M+H)^+$.

$^1$H-NMR ($CDCl_3$) δ: 8.64 (1H, s), 7.54 (1H, s), 5.61 (2H, s), 3.52 (2H, t, J=8.3 Hz), 0.92 (2H, t, J=8.3 Hz), -0.04 (9H, s).

Step 5

4-(benzyloxy)-5-iodo-7-{[2-(trimethylsilyl)ethoxy]methyl}-7H-pyrrolo[2,3-d]pyrimidine To a solution of benzyl alcohol (27 mL) in N,N-dimethylformamide (170 mL) was added sodium hydride (containing 45% mineral oil) (12 g) under ice-cold conditions, and the mixture was stirred for 40 min while the temperature was raised to room temperature. After re-cooling on ice, a suspension of the compound (97.63 g) obtained in step 4 in N,N-dimethylformamide (360 mL) was added over 40 min, and the mixture was stirred at the same temperature for 35 min. The reaction was stopped by adding a piece of ice and saturated aqueous ammonium chloride to the reaction mixture. The reaction mixture was poured into a two-layer mixture of saturated aqueous ammonium chloride and ethyl acetate, and ethyl acetate:toluene (9:1) was used for extraction. The organic layer was washed twice with water and brine, and dried over anhydrous sodium sulfate. The drying agent was filtered off, and the filtrate was concentrated under reduced pressure. The residue was purified by silica gel column chromatography [hexane/ethyl acetate] to give the titled compound (107.7 g).

MS (ESI) m/z: 482 $(M+H)^+$.

$^1$H-NMR ($CDCl_3$) δ: 8.47 (1H, s), 7.61 (2H, d, J=7.3 Hz), 7.41 (2H, t, J=7.6 Hz), 7.36-7.30 (1H, m), 7.30 (1H, s), 5.65 (2H, s), 5.57 (2H, s), 3.52 (2H, t, J=8.3 Hz), 0.91 (2H, t, J=8.3 Hz), -0.05 (9H, s).

Step 6

4-(benzyloxy)-5-(3,3-diethoxyprop-1-yn-1-yl)-7-{[2-(trimethylsilyl)ethoxy]methyl}-7H-pyrrolo[2,3-d]pyrimidine To a mixed solution of the compound (113.4 g) obtained in step 5 in acetonitrile (1000 mL)-triethylamine (98 mL) were added copper iodide (4.49 g), tetrakistriphenylphosphine palladium (0) (8.17 g), and 3,3-diethoxyprop-1-yn (104 mL) at room temperature under a nitrogen atmosphere, and the mixture was stirred at the same temperature for 4.5 h. The reaction mixture was concentrated under reduced pressure, ethyl acetate and hexane were added to the residue, and the precipitated solid was filtered off. The solid was washed with a mixed solution of ethyl acetate d: hexane (1:1), and the filtrate was then concentrated under reduced pressure. The residue was purified by silica gel column chromatography [hexane/ethyl acetate] to give the titled compound (145.5 g; containing impurities).

MS (ESI) m/z: 482 $(M+H)^+$.

Step 7

5-(3,3-Diethoxypropyl)-7-{[2-(trimethylsilyl)ethoxy]methyl}-7H-pyrrolo[2,3-d]pyrimidin-4-ol To a solution of the compound (145.5 g) obtained in step 6 in ethanol (900 mL) was added 10% palladium carbon catalyst (M) wet (50.2 g), and the mixture was stirred for 5 h at room temperature under a hydrogen atmosphere. Dichloromethane (500 mL) was added to the reaction mixture, the catalyst was filtered off with celite, and the filtrate was then concentrated under reduced pressure. The residue was purified twice by silica gel column chromatography [hexane/ethyl acetate] to give the titled compound (59.6 g).

MS (ESI) m/z: 418 $(M+Na)^+$, 394$[M-H]^-$.

$^1$H-NMR ($CDCl_3$) δ: 11.23 (1H, brs), 7.85 (1H, s), 6.79 (1H, s), 5.47 (2H, s), 4.58 (1H, t, J=5.9 Hz), 3.69 (2H, m), 3.57-3.49 (4H, m), 2.90 (2H, t, J=7.8 Hz), 2.07 (2H, m), 1.23 (6H, t, J=7.1 Hz), 0.91 (2H, t, J=8.1 Hz), -0.04 (9H, s).

Step 8

5-(3,3-Diethoxypropyl)-7-{[2-(trimethylsilyl)ethoxy]methyl}-7H-pyrrolo[2,3-d]pyrimidin-4-thiol To a solution of the compound (59.6 g) obtained in step 7 in dehydrated dichloromethane (300 mL) was added 2,6-lutidine (42 mL) under a nitrogen atmosphere. Trifluoromethanesulfonic anhydride (31 mL) was added dropwise over 20 min at −20° C., and the mixture was stirred at the same temperature for 20 min. N,N-dimethylformamide (500 mL) and sodium hydrogen monosulfide n-hydrate (33.5 g) were added under ice-cold conditions, and the mixture was stirred for 2.5 h after the temperature was raised to room temperature. The reaction mixture was concentrated under reduced pressure, and the low boiling point component was distilled off. The residue was poured into a two-layer mixture of ethyl acetate and ice-cooled saturated aqueous ammonium chloride, and ethyl acetate:toluene (9:1) was used for extraction. The organic layer was washed once with saturated aqueous ammonium chloride and twice with brine, and dried over anhydrous sodium sulfate. The drying agent was filtered off, and the filtrate was concentrated under reduced pressure. The residue was purified by silica gel column chromatography [hexane/ethyl acetate] to give a mixture of the titled compound and 2,6-lutidine. The resulting mixture was poured into a two-layer mixture of ethyl acetate and 1 N hydrochloric acid and ethyl acetate was used twice for extraction. The organic layer was washed three times with brine and dried over anhydrous sodium sulfate. The drying agent was filtered off, and the filtrate was then concentrated under reduced pressure to give the titled compound (57.6 g).

MS (ESI) m/z: 410 $(M-H)^-$.

$^1$H-NMR ($CDCl_3$) δ: 11.69 (1H, brs), 7.90 (1H, s), 6.96 (1H, s), 5.49 (2H, s), 4.61 (1H, t, J=5.9 Hz), 3.71 (2H, m), 3.55 (2H, m), 3.49 (2H, t, J=8.1 Hz), 3.14 (2H, t, J=7.8 Hz), 2.08 (2H, m), 1.23 (6H, t, J=7.1 Hz), 0.90 (2H, t, J=8.3 Hz), -0.04 (9H, s).

Step 9

3-(4-sulfanyl-7-{[2-(trimethylsilyl)ethoxy]methyl}-7H-pyrrolo[2,3-d]pyrimidin-5-yl)propan-1-ol The compound (31.62 g) obtained in step 8 was dissolved in 80% aqueous acetic acid (300 mL), and the mixture was stirred at room temperature for 30 min. After the starting material was found to disappear, the mixture was cooled on ice, and sodium borohydride (1.45 g) was carefully added in small portions. Then, the mixture was stirred at the same temperature for 30 min. Subsequently, sodium triacetoxyborohydride (24.4 g) was added over 15 min, and the mixture was stirred at the same temperature for 1.5 h. The reaction mixture was concentrated under reduced pressure to about one-fifth of its volume. Sodium bicarbonate (solid) was carefully added to the residue for neutralization to some extent, and ethyl acetate was then used for extraction. The organic layer was washed with saturated sodium bicarbonate and brine in this order, and dried over anhydrous sodium sulfate. The drying agent was filtered off, and the filtrate was concentrated under reduced pressure. The residue was purified by silica gel column chromatography [hexane/ethyl acetate] to give the titled compound (17.93 g).

MS (ESI) m/z: 340 $[M+H]^+$.

$^1$H-NMR ($CDCl_3$) δ: 11.92 (1H, brs), 7.95 (1H, s), 7.01 (1H, s), 5.51 (2H, s), 3.70 (2H, t, J=5.9 Hz), 3.50 (2H, t, J=8.1 Hz), 3.23 (2H, t, J=7.3 Hz), 2.33 (1H, brs), 1.99 (2H, m), 0.91 (2H, t, J=8.3 Hz), -0.04 (9H, s).

Step 10

2-{[2-(trimethylsilyl)ethoxy]methyl}-2,7,8,9-tetrahydro-6-thia-2,3,5-triazabenzo[cd]azulene To a solution of the compound (31.31 g) obtained in step 9 in dehydrated tetrahydrofuran (600 mL) were added triphenylphosphine (25.4 g) and diisopropyl azodicarboxylate (21.8 g) at 0° C. under a nitrogen atmosphere, and the mixture was stirred at the same temperature for 1 h. The reaction mixture was concentrated under reduced pressure, and the residue was purified by, in sequence, silica gel column chromatography [dichloromethane/ethyl acetate] and silica gel column chromatography [hexane/ethyl acetate] to give the titled compound (35.93 g: containing impurities).

MS (ESI) m/z: 322 $[M+H]^+$.

$^1$H-NMR ($CDCl_3$) δ: 8.57 (1H, s), 7.08 (1H, s), 5.58 (2H, s), 3.52 (2H, t, J=8.3 Hz), 3.17 (2H, m), 3.06 (2H, t, J=5.6 Hz), 2.36 (2H, m), 0.92 (2H, t, J=8.3 Hz), -0.05 (9H, s).

Step 11

(8,9-dihydro-6-thia-2,3, 5-triazabenzo[cd]azulen-2(7H)-yl)methanol

To a solution of the compound (35.93 g) obtained in step 10 in dichloromethane (150 mL) was added trifluoroacetic acid (150 mL) at room temperature, and the mixture was stirred at the same temperature for 1.5 h. The reaction mixture was concentrated under reduced pressure, and then azeotroped four times with toluene. A mixed solution of dichloromethane and hexane (1:2) was added to the residue, and the precipitated solid was filtered and collected (solid 1). The filtrate was concentrated under reduced pressure. The residue was then purified by silica gel column chromatography [hexane/ethyl acetate --ethyl acetate/methanol] to give a solid 2. The solids 1 and 2 were combined to give the titled compound (20.13 g).

MS (ESI) m/z: 222 $[M+H]^+$.

$^1$H-NMR ($CDCl_3$) δ: 8.60 (1H, s), 7.19 (1H, s), 5.71 (2H, s), 3.21 (2H, m), 3.07 (2H, m), 2.38 (2H, m). (only observable peaks are listed).

Step 12

2,7,8,9-Tetrahydro-6-thia-2,3,5-triazabenzo[cd]azulene

To a suspension of the compound (20.13 g) obtained in step 11 in methanol (250 mL) was added 28% aqueous ammonia (150 mL), and the mixture was stirred at room temperature for 1.5 h. The reaction mixture was concentrated under reduced pressure to about half of its volume. The precipitated solid was filtered off, and washed with ethanol to yield a solid 1. The filtrate was concentrated under reduced pressure, and a solid 2 was then obtained by substantially the same procedure. The filtrate was applied onto silica gel, and purified by silica gel column chromatography [dichloromethane/methanol]. Fractions containing the target product were concentrated under reduced pressure, and washed as a slurry with ethanol and the resulting solid was filtered and collected (solid 3). The solids 1, 2, and 3 were combined to prepare the titled compound (12.36 g).

MS (ESI) m/z: 192 $[M+H]^+$.

$^1$H-NMR ($CDCl_3$) δ: 10.53 (1H, brs), 8.57 (1H, s), 7.10 (1H, s), 3.18 (2H, m), 3.08 (2H, t, J=5.6 Hz), 2.37 (2H, m).

Step 13

2-(2,3, 5-tri-O-benzyl-β-D-arabinofuranosyl)-2,7,8,9-tetrahydro-6-thia-2,3, 5-triazabenzo[cd]azulene To a suspension of the compound (13.47 g) obtained in step 12 in dehydrated acetonitrile (350 mL) were added powdered potassium hydroxide (10.3 g) and tris[2-(2-methoxyethoxy)ethyl]amine (1.13 mL) under a nitrogen atmosphere, and the mixture was stirred at room temperature for 1.5 h. Under ice-cold conditions, a solution of 2,3,5-tri-O-benzyl-α-D-arabinofuranosyl chloride (40.2 g), as in a known literature (J. Med. Chem. 1976, 19, 6, 814-816), in acetonitrile (100 mL) was added little by little, the temperature was raised to room temperature, and the mixture was then stirred for 4 h. The insoluble material was filtered off and washed with acetonitrile. The filtrate was concentrated under reduced pressure. The residue was purified twice by silica gel column chromatography [hexane/ethyl acetate] to give the titled compound (26.19 g).

MS (ESI) m/z: 594 $[M+H]^+$.

$^1$H-NMR ($CDCl_3$) δ: 8.51 (1H, s), 7.37-7.17 (14H, m), 6.86 (2H, m), 6.82 (1H, d, J=4.9 Hz), 4.68 (1H, d, J=11.7 Hz), 4.59 (1H, d, J=11.7 Hz), 4.54 (1H, d, J=13.2 Hz), 4.52 (1H, d, J=11.7 Hz), 4.36-4.33 (2H, m), 4.22 (1H, d, J=11.7 Hz), 4.14-4.08 (2H, m), 3.77 (1H, dd, J=10.7, 3.9 Hz), 3.72 (1H, dd, J=10.5, 4.1 Hz), 3.13 (2H, m), 2.81 (2H, m), 2.27 (2H, m).

Step 14

2-β-D-arabinofuranosyl-2,7,8,9-tetrahydro-6-thia-2,3,5-triazabenzo[cd]azulene

To a solution of the compound (26.19 g) obtained in step 13 in dehydrated dichloromethane (300 mL) was added a dichloromethane solution of boron trichloride (1M, 200 mL) at −78° C. under a nitrogen atmosphere. After the mixture was stirred at the same temperature for 2 h, the temperature was then raised to 0° C., followed by another 4 h stirring. The reaction mixture was re-cooled to −78° C., and a solution of methanol (80 mL) in dichloromethane (160 mL) was added, and the mixture was stirred for 30 min while the temperature was raised to room temperature. The reaction mixture was concentrated under reduced pressure, and then azeotroped twice with ethanol. Ethanol (200 mL) and diethyl ether (100 mL) were added to the residue to form a slurry, and the resulting solid was filtered and collected (solid 1). The filtrate was concentrated under reduced pressure, and the residue was purified by silica gel column chromatography [dichloromethane/methanol]. Fractions containing the target product were concentrated under reduced pressure, and ethanol was added to form a slurry. Then, the resulting solid was filtered and collected (solid 2). The solids 1 and 2 were combined to prepare the titled compound (13.2 g).

MS (ESI) m/z: 324 $[M+H]^+$.

$^1$H-NMR ($CD_3OD$) δ: 8.73 (1H, s), 7.96 (1H, s), 6.70 (1H, d, J=4.9 Hz), 4.32 (1H, t, J=4.6 Hz), 4.25 (1H, t, J=4.6 Hz), 3.97 (1H, m), 3.90 (1H, dd, J=12.0, 3.2 Hz), 3.85 (1H, dd, J=12.0, 4.6 Hz), 3.53 (2H, m), 3.17 (2H, m), 2.43 (2H, m).

Step 15

2-[3,5-bis-O-(oxan-2-yl)-β-D-arabinofuranosyl]-2,7,8,9-tetrahydro-6-thia-2,3, 5-triazabenzo[cd]azulene To a solution of the compound (15.35 g) obtained in step 14 in dehydrated dimethylsulfoxide (160 mL) were added 3,4-dihydro-2H-pyran (17.2 mL) and p-toluenesulfonic acid monohydrate (9.02 g) at 0° C., and the mixture was stirred for 3 h at room temperature. Next, 3,4-dihydro-2H-pyran (8.6 mL) was added, and the mixture was stirred for 45 min. Immediately after that, triethylamine (13 mL) was added to stop the reaction. The reaction mixture was poured into a two-layer mixture of ethyl acetate and saturated aqueous sodium bicarbonate, and ethyl acetate was used for extraction. The organic layer was washed once with water and twice with brine, and dried over anhydrous sodium sulfate. The drying agent was filtered off, and the filtrate was concentrated under reduced pressure. The residue was purified by silica gel column chromatography [hexane/ethyl acetate] to give the titled compound (10.81 g) as a mixture of four diastereomers.

MS (ESI) m/z: 492 $[M+H]^+$.

$^1$H-NMR ($CDCl_3$) δ: 8.548 (0.2H, s), 8.546 (0.3H, s), 8.54 (0.3H, s), 8.53 (0.2H, s), 7.54 (0.2H, s), 7.53 (0.3H, s), 7.51 (0.2H, s), 7.44 (0.3H, s), 6.75 (0.2H, d, J=5.4 Hz), 6.71 (0.2H, d, J=5.9 Hz), 6.57 (0.3H, d, J=5.9 Hz), 6.56 (0.3H, d, J=5.9 Hz), 4.87-4.69 (2H, m), 4.55-3.54 (10H, m), 3.18-3.12 (2H, m), 3.10-2.96 (2H, m), 2.40-2.30 (2H, m), 1.92-1.51 (12H, m).

Step 16

2-[2-deoxy-2-fluoro-3, 5-bis-O-(oxan-2-yl)-β-D-ribofuranosyl]-2,7,8,9-tetrahydro-6-thia-2,3,5-triazabenzo[cd]azulene To a solution of the compound (10.81 g) obtained in step 15 in dehydrated dichloromethane (150 mL) were added pyridine (5.3 mL) and trifluoromethanesulfonate anhydride (5.6 mL) at 0° C. under a nitrogen atmosphere, and the mixture was stirred at the same temperature for 1 h. The reaction was stopped by adding a piece of ice to the reaction mixture. The reaction mixture was poured into a two-layer mixture of ethyl acetate and saturated aqueous sodium bicarbonate, and ethyl acetate was used for extraction. The organic layer was washed twice with brine and dried over anhydrous sodium sulfate. The drying agent was filtered off, and the filtrate was concentrated under reduced pressure, and the crude triflate was then obtained as an amorphous solid. The crude triflate obtained was dissolved in dehydrated tetrahydrofuran (150 mL). A tetrahydrofuran solution of tetrabutylammonium fluoride (about 1 M, 154 mL) was added little by little under ice-cold conditions, and the mixture was stirred overnight at the same temperature. The reaction was stopped by adding saturated aqueous ammonium chloride to the reaction mixture. The reaction mixture was concentrated under reduced pressure to about half of its volume. The residue was poured into a two-layer mixture of ethyl acetate and saturated ammonium chloride, and ethyl acetate was used for extraction. The organic layer was washed once with saturated aqueous ammonium chloride and twice with brine. The aqueous layer was extracted again with ethyl acetate, and the extract was washed with brine. The organic layers were combined and dried over anhydrous sodium sulfate. The drying agent was filtered off, and the filtrate was concentrated under reduced pressure to give a crude titled compound (40.37 g).

MS (ESI) m/z: 494 $[M+H]^+$.

Step 17

2-(2-deoxy-2-fluoro-β-D-ribofuranosyl)-2,7,8,9-tetrahydro-6-thia-2,3,5-triazabenzo[cd]azulene To a solution of the compound (40.37 g) obtained in step 16 in methanol (400 mL) was added p-toluenesulfonic acid-monohydrate (2.09 g), and the mixture was stirred at 60° C. for 4 h. The reaction was stopped by adding triethylamine (16 mL) to the reaction mixture. The reaction mixture was concentrated under reduced pressure. The residue was then purified by silica gel column chromatography [hexane/ethyl acetate --ethyl acetate/methanol]. Fractions containing the target product were concentrated under reduced pressure until a slurry was formed. Then, the resulting solid was filtered and collected. The resulting solid was washed with hexane/ethyl acetate (1:1) to give a solid 1. The filtrate was concentrated under reduced pressure, and the resulting residue was purified by silica gel column chromatography [dichloromethane/methanol] to give a solid 2. The solids 1 and 2 were combined to prepare the titled compound (5.32 g).

MS (ESI) m/z: 326 $[M+H]^+$.

$^1$H-NMR ($CDCl_3$) δ: 8.51 (1H, s), 7.01 (1H, s), 6.00 (1H, dd, J=13.7, 6.3 Hz), 5.95 (1H, dd, J=11.7, 2.0 Hz), 5.87 (1H, ddd, J=52.7, 6.3, 4.9 Hz), 4.69 (1H, m), 4.32 (1H, brs), 3.96 (1H, d, J=12.7 Hz), 3.77 (1H, m), 3.17 (2H, m), 3.04 (2H, m), 2.41-2.31 (3H, m).

Step 18

2-{5-O-[bis(4-methoxyphenyl)(phenyl)methyl]-2-deoxy-2-fluoro-β-D-ribofuranosyl}-2,7,8,9-tetrahydro-6-thia-2,3, 5-triazabenzo[cd]azulene By using the compound (5.32 g) obtained in step 17, the reaction was carried out in substantially the same manner as in step 10 of Example 2 to give the titled compound (10.1 g).

MS (ESI) m/z: 628 $[M+H]^+$.

$^1$H-NMR ($CDCl_3$) δ: 8.54 (1H, s), 7.42 (2H, d, J=7.3 Hz), 7.32-7.21 (8H, m), 6.81 (4H, m), 6.52 (1H, dd, J=17.3, 2.2 Hz), 5.37 (1H, ddd, J=53.3, 4.4, 2.4 Hz), 4.76 (1H, m), 4.16 (1H, m), 3.789 (3H, s), 3.786 (3H, s), 3.59 (1H, dd, J=10.7, 2.4 Hz), 3.44 (1H, dd, J=10.7, 3.4 Hz), 3.12 (2H, m), 2.76 (2H, t, J=5.6 Hz), 2.27 (2H, m), 2.18 (1H, dd, J=7.8, 2.9 Hz).

Step 19

2-(5-O-[bis(4-methoxyphenyl)(phenyl)methyl]-3-O-{(2-cyanoethoxy)[di(propan-2-yl)amino]phosphanyl}-2-deoxy-2-fluoro-β-D-ribofuranosyl)-2,7,8,9-tetrahydro-6-thia-2,3, 5-triazabenzo[cd]azulene By using the compound (10.1 g) obtained in step 18, the reaction was carried out in substantially the same manner as in step 6 of Example 1 to give the titled compound (12.6 g) as a mixture of diastereomers (diastereomer ratio=1:1) at the phosphorus atom.

$^1$H-NMR ($CDCl_3$) δ: 8.53 (1H, s), 7.40 (2H, m), 7.34-7.17 (8H, m), 6.84-6.74 (4H, m), 6.53 (0.5H, dd, J=17.3, 2.2 Hz), 6.48 (0.5H, dd, J=17.6, 1.5 Hz), 5.50-5.31 (1H, m), 4.99 (0.5H, m), 4.85 (0.5H, m), 4.31-4.26 (1H, m), 3.93-3.76 (1H, m), 3.792 (1.5H, s), 3.789 (1.5H, s), 3.779 (1.5H, s), 3.776 (1.5H, s), 3.67-3.51 (4H, m), 3.34-3.30 (1H, m), 3.13-3.10 (2H, m), 2.76-2.69 (2H, m), 2.61 (1H, td, J=6.3, 2.4 Hz), 2.39 (1H, m), 2.28-2.21 (2H, m), 1.19-1.15 (9H, m), 1.03 (3H, d, J=6.8 Hz).

Step 20

By using the compound (1.80 g) obtained in step 19, the reaction was carried out in substantially the same manner as in step 7 of Example 1 to give an acetonitrile solution of 2-{2-deoxy-2-fluoro-3-O-[hydroxy(oxo)-$\lambda^5$-phosphanyl]-β-D-ribofuranosyl}-2,7,8,9-tetrahydro-6-thia-2,3,5-triazabenzo[cd]azulene. By using the resulting acetonitrile solution and the compound (2.30 g) obtained in step 3, the reaction was carried out in substantially the same manner as in step 12 of Example 1. The resulting crude product was used directly in the next reaction.

Step 21

3-{[(5R,7R,8R,12aR,14R,15R,15aR,16R)-16-{[tert-butyl(dimethyl)silyl]oxy}-14-(8,9-dihydro-6-thia-2,3,5-triazabenzo[cd]azulen-2(7H)-yl)-7-{1-[2-(1,3-dioxo-1,3-dihydro-2H-isoindol-2-yl)ethyl]-6-oxo-1,6-dihydro-9H-purin-9-yl}-15-fluoro-2-oxo-2-sulfanyl-10-sulfanilidenoctahydro-2H,1OH,12H-5,8-methano-2$\lambda^5$,10$\lambda^5$-furo[3,2-1][1,3,6,9,11,2,10]pentaoxadiphosphacyclotetradecin-10-yl]oxy}propanenitrile By using the crude product obtained in step 20, the reaction was carried out in substantially the same manner as in step 13 of Example 1 to give the titled compound (1.22 g) as a mixture of diastereomers at the phosphorus atom.

MS (ESI) m/z: 1090 $(M+H)^+$.

Step 22 bis(N,N-diethylethanaminium) (5R,7R,8R,12aR,14R,15R,15aR,16R)-7-[1-(2-aminoethyl)-6-oxo-1,6-dihydro-9H-purin-9-yl]-16-{[tert-butyl(dimethyl)silyl]oxy}-14-(8,9-dihydro-6-thia-2,3,5-triazabenzo[cd]azulen-2(7H)-yl)-15-fluoro-2,10-dioxooctahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

To a mixed solution of the compound (1.22 g) obtained in step 21 in ethanol (10 mL)-tetrahydrofuran (10 mL) was added hydrazine-monohydrate (0.544 mL), and the mixture was stirred at room temperature for 15 h. The reaction mixture was concentrated under reduced pressure. Subsequently, the residue was purified by C18 silica gel column chromatography [10 mM aqueous triethylammonium acetate/acetonitrile] to give diastereomer 1 (108 mg: containing impurities) and diastereomer 2 (111 mg: containing impurities) of the titled compound.

Diastereomer 1 (less polar)

MS (ESI) m/z: 907 $(M+H)^+$.

Diastereomer 2 (more polar)

MS (ESI) m/z: 907 $(M+H)^+$.

Step 23-1

Disodium(5R,7R,8R,12aR,14R,15R,15aR,16R)-7-[1-(2-aminoethyl)-6-oxo-1,6-dihydro-9H-purin-9-yl]-14-(8,9-dihydro-6-thia-2,3, 5-triazabenzo[cd]azulen-2(7H)-yl)-15-fluoro-16-hydroxy-2,10-dioxooctahydro-2H,10H,12H-5,8-methano-2λ$^5$,10λ$^5$-furo[3,2-l][1,3,6,9,11,2,10]pentaoxadiphosphacyclotetradecine-2,10-bis(thiolate) (Diastereomer 1)

By using the compound (diastereomer 1) (108 mg; containing impurities) obtained in step 22, the reaction was carried out in substantially the same manner as in step 15-1 of Example 1. The reaction mixture was then subjected to purification using the following [Purification Conditions] to give the titled compound as a triethylamine salt.

[Purification Conditions]C18 silica gel column chromatography [10 mM aqueous triethylammonium acetate/acetonitrile] and preparative HPLC [10 mM aqueous triethylammonium acetate/acetonitrile-methanol solution (1:1); acetonitrile-methanol solution (1:1): 10%-50% (0 min-40 min)].

The obtained triethylamine salt was subjected to salt exchange in substantially the same manner as described above in step 15-1 [Conversion to Sodium Salt] of Example 1 to give the titled compound (44.4 mg).

MS (ESI) m/z: 793 $(M+H)^+$.

$^1$H-NMR ($CD_3OD$) δ: 8.50 (1H, s), 8.42 (1H, s), 7.92 (1H, s), 7.56 (1H, s), 6.56 (1H, d, J=16.3 Hz), 6.21 (1H, d, J=6.0 Hz), 5.57-5.40 (2H, m), 5.35-5.22 (1H, m), 4.73-4.67 (1H, m), 4.58-4.49 (1H, m), 4.45-4.26 (4H, m), 4.24-4.15 (1H, m), 4.05-3.96 (1H, m), 3.78-3.51 (1H, m), 3.26-3.06 (4H, m), 2.93-2.82 (1H, m), 2.70-2.51 (1H, m), 2.29-2.07 (2H, m).

$^{31}$P-NMR ($CD_3OD$) δ: 57.5 (s), 52.9 (s).

Step 23-2 disodium(5R,7R,8R,12aR,14R,15R,15aR,16R)-7-[1-(2-aminoethyl)-6-oxo-1,6-dihydro-9H-purin-9-yl]-14-(8,9-dihydro-6-thia-2,3, 5-triazabenzo[cd]azulen-2(7H)-yl)-15-fluoro-16-hydroxy-2,10-dioxooctahydro-2H,10H,12H-5,8-methano-2λ$^5$,10λ$^5$-furo[3,2-l][1,3,6,9,11,2,10]pentaoxadiphosphacyclotetradecine-2,10-bis(thiolate) (Diastereomer 2)

By using the compound (diastereomer 2) (111 mg; containing impurities) obtained in step 22, the reaction was carried out in substantially the same manner as in step 15-1 of Example 1. The reaction mixture was then subjected to purification using the following [Purification Conditions] to give the titled compound as a triethylamine salt.

[Purification Conditions]C18 silica gel column chromatography [10 mM aqueous triethylammonium acetate/acetonitrile], preparative HPLC [10 mM aqueous triethylammonium acetate/acetonitrile; acetonitrile: 5%-25% (0 min-40 min)], and preparative HPLC [10 mM aqueous triethylammonium acetate/methanol; methanol:20%-60% (0 min-40 min)].

The obtained triethylamine salt was subjected to salt exchange in substantially the same manner as described above in step 15-1 [Conversion to Sodium Salt] of Example 1 to give the titled compound (40.6 mg).

MS (ESI) m/z: 793 $(M+H)^+$.

$^1$H-NMR ($CD_3OD$) δ: 8.57 (1H, s), 8.41 (1H, s), 8.13 (1H, s), 7.72 (1H, s), 6.59 (1H, dd, J=15.7, 1.8 Hz), 6.26 (1H, d, J=8.5 Hz), 5.61-5.34 (3H, m), 4.57-4.48 (2H, m), 4.48-4.38 (2H, m), 4.38-4.28 (2H, m), 4.08-3.98 (3H, m), 3.29-3.21 (2H, m), 3.20-3.12 (2H, m), 3.02-2.92 (1H, m), 2.92-2.81 (1H, m), 2.29-2.15 (2H, m).

$^{31}$P-NMR ($CD_3OD$) δ: 58.7 (s), 57.8 (s).

Example 4: To Synthesize CDN50

N-(2-{9-[(5R,7R,8R,12aR,14R,15R,15aR,16R)-14-(8,9-dihydro-6-thia-2,3, 5-triazabenzo[cd]azulen-2(7H)-yl)-15-fluoro-16-hydroxy-2,10-dioxo-2,10-bis(sulfanyl)octahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethyl)-2-hydroxyacetamide

[Formula 99]

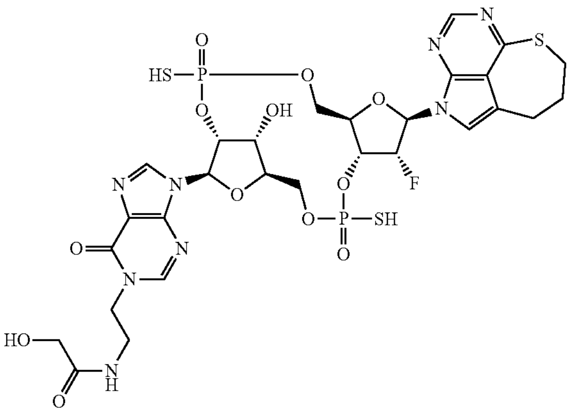

50
50a (Diastereomer 1)
50b (Diastereomer 2)

Synthetic Scheme

[Formula 100]

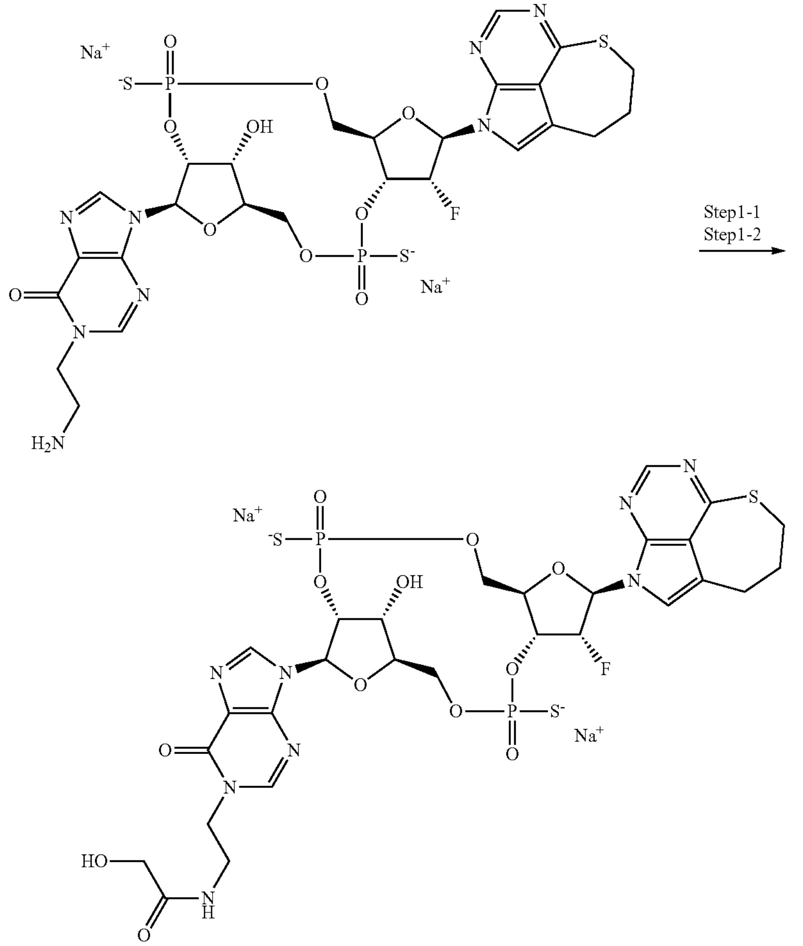

Step 1-1 disodium(5R,7R,8R,12aR,14R,15R,15aR,16R)-14-(8,9-dihydro-6-thia-2,3, 5-triazabenzo[cd]azulen-2(7H)-yl)-15-fluoro-16-hydroxy-7-{1-[2-(2-hydroxyacetamido)ethyl]-6-oxo-1,6-dihydro-9H-purin-9-yl}-2,10-dioxooctahydro-2H,1OH,12H-5,8-methano-2λ$^5$,10λ$^5$-furo[3,2-1][1,3,6,9,11,2,10]pentaoxadiphosphacyclotetradecine-2,10-bis(thiolate) (Diastereomer 1)

To a solution of the compound (20.0 mg) obtained in step 23-1 of Example 3 in N,N-dimethylformamide (0.5 mL) were added triethylamine (17 L) and 1-[(hydroxyacetyl)oxy]pyrrolidin-2,5-dione (10.3 mg), and the mixture was stirred at room temperature for 3 h. The reaction mixture was diluted with 10 mM aqueous triethylammonium acetate. Subsequently, the purification was performed using C18 silica gel column chromatography [10 mM aqueous triethylammonium acetate/acetonitrile] and preparative HPLC [10 mM aqueous triethylammonium acetate/acetonitrile; acetonitrile: 10%-30% (0 min-40 min)]. The obtained compound was subjected to salt exchange in substantially the same manner as described above in step 15-1 [Conversion to Sodium Salt] of Example 1 to give the titled compound (15.6 mg).

MS (ESI) m/z: 851 $(M+H)^+$.

$^1$H-NMR ($CD_3OD$) δ: 8.43 (1H, s), 8.40 (1H, brs), 7.66 (1H, brs), 7.58 (1H, s), 6.53 (1H, d, J=16.3 Hz), 6.14 (1H, d, J=8.5 Hz), 5.73-5.64 (1H, m), 5.59-5.42 (1H, m), 5.42-5.29 (1H, m), 4.80-4.74 (1H, m), 4.53-4.26 (5H, m), 4.21-4.12 (1H, m), 3.99-3.92 (1H, m), 3.83 (2H, s), 3.66-3.56 (1H, m), 3.43-3.26 (2H, m), 3.23-3.06 (2H, m), 2.89-2.79 (1H, m), 2.49-2.33 (1H, m), 2.27-2.15 (1H, m), 2.15-2.02 (1H, m).

$^{31}$P-NMR ($CD_3OD$) δ: 57.0 (s), 52.6 (s).

Step 1-2 disodium(5R,7R,8R,12aR,14R,15R,15aR,16R)-14-(8,9-dihydro-6-thia-2,3,5-triazabenzo[cd]azulen-2(7H)-yl)-15-fluoro-16-hydroxy-7-{1-[2-(2-hydroxyacetamido)ethyl]-6-oxo-1,6-dihydro-9H-purin-9-yl}-2,10-dioxooctahydro-2H,1OH,12H-5,8-methano-2λ$^5$,10λ$^5$-furo[3,2-1][1,3,6,9,11,2,10]pentaoxadiphosphacyclotetradecine-2,10-bis(thiolate) (Diastereomer 2)

By using the compound (10.0 mg) obtained in step 23-2 of Example 3, the reaction was carried out in substantially the same manner as in step 1-1. Subsequently, the purification was performed using C18 silica gel column chromatography [10 mM aqueous triethylammonium acetate/acetonitrile] and preparative HPLC [10 mM aqueous triethylammonium acetate/acetonitrile; acetonitrile: 7%-25% (0 min-40 min)]. The obtained compound was subjected to salt exchange in substantially the same manner as described above in step 15-1 [Conversion to Sodium Salt] of Example 1 to give the titled compound (6.6 mg).

MS (ESI) m/z: 851 $(M+H)^+$.

$^1$H-NMR ($CD_3OD$) δ: 8.46 (1H, s), 8.42 (1H, s), 7.84 (1H, s), 7.78 (1H, s), 6.59 (1H, d, J=15.1 Hz), 6.20 (1H, d, J=7.9 Hz), 5.69-5.38 (3H, m), 4.60-4.50 (2H, m), 4.48-4.38 (2H, m), 4.31-4.20 (2H, m), 4.10-3.93 (2H, m), 3.87 (2H, s), 3.73-3.57 (2H, m), 3.52-3.41 (1H, m), 3.25-3.10 (2H, m), 3.01-2.90 (1H, m), 2.83-2.71 (1H, m), 2.30-2.11 (2H, m).

$^{31}$P-NMR ($CD_3OD$) δ: 58.2 (s), 57.6 (s).

Example 5: To Synthesize Drug-Linker 2

Synthetic Scheme

[Formula 101]

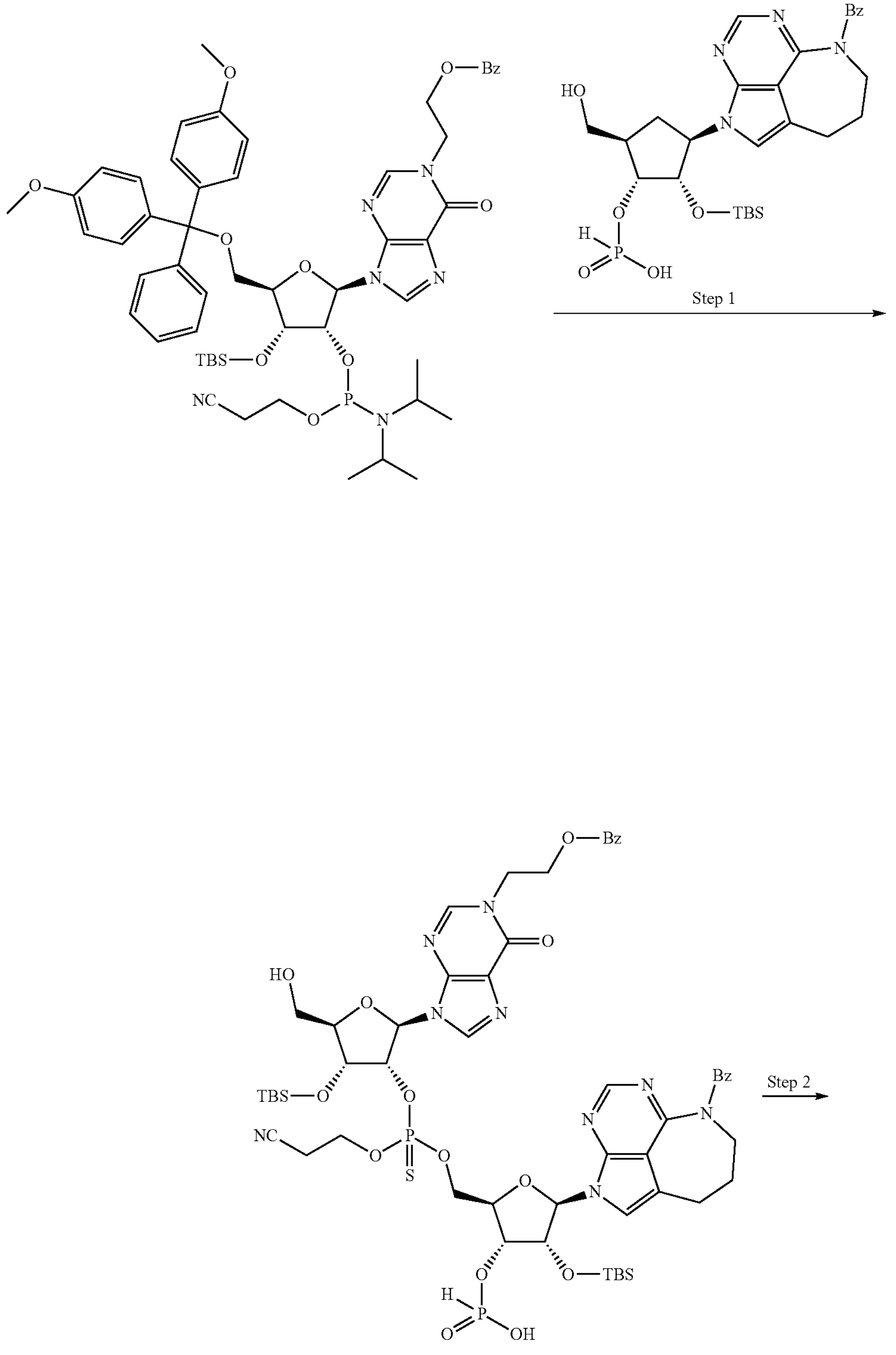

-continued
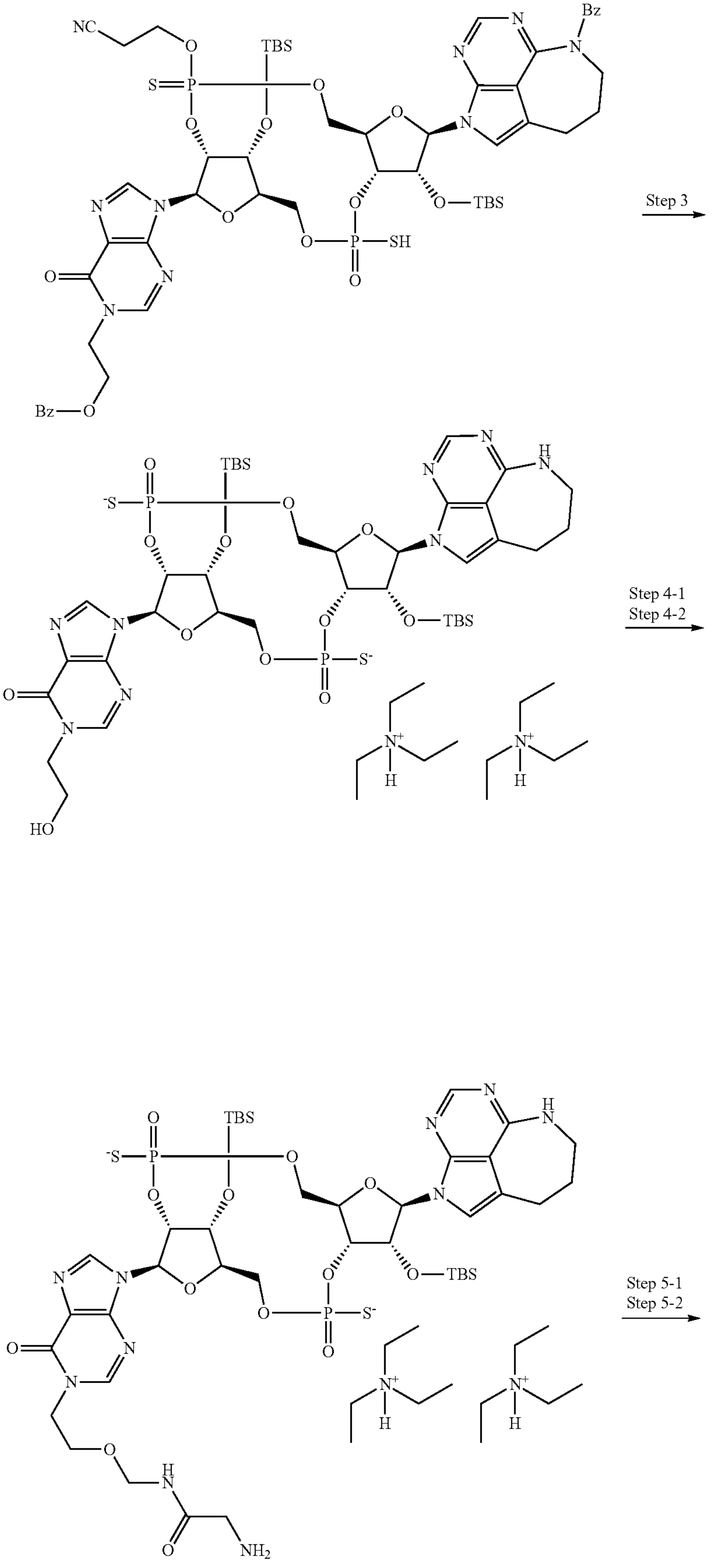

-continued
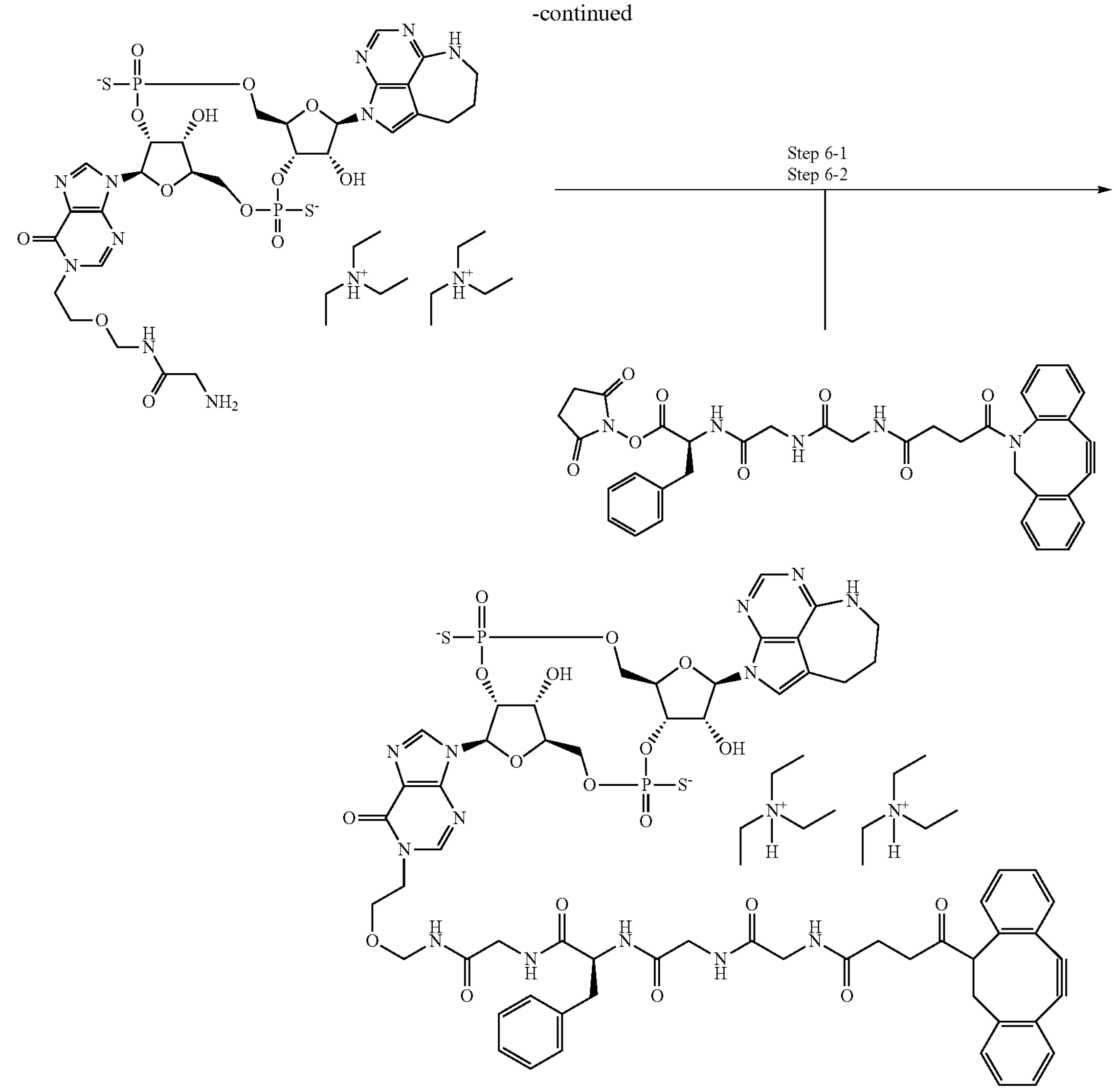
Drug-linker 2a
Drag-linker 2b
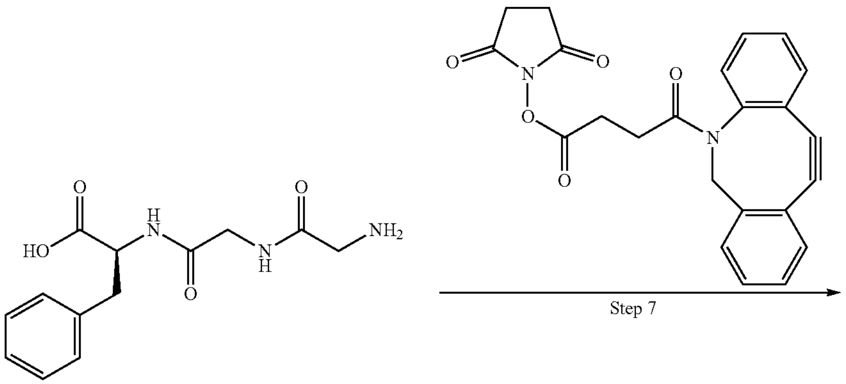

-continued

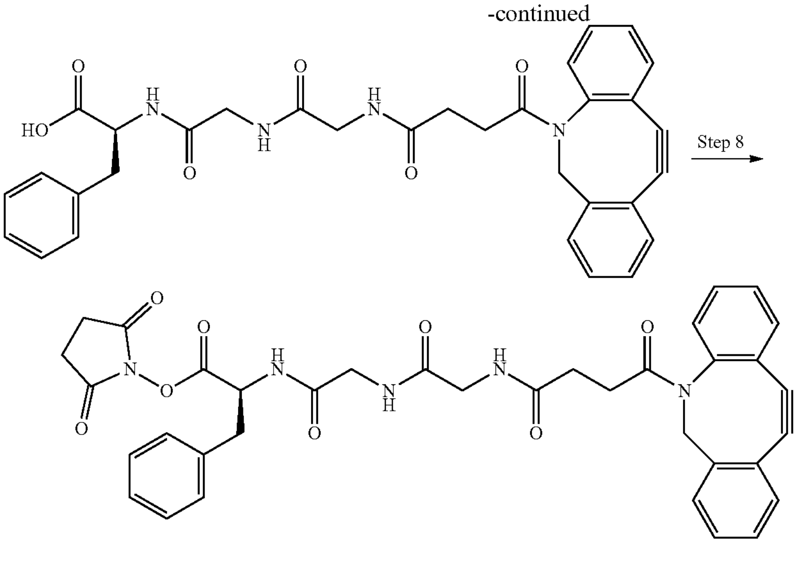

Step 1

The same reaction as in step 7 of Example 1 was carried out at the following scale (starting material: 1.40 g). By using the resulting compound-containing acetonitrile solution and the compound (1.41 g) obtained in step 3 of Example 2, the reaction was carried out in substantially the same manner as in step 12 of Example 1. The crude product obtained was used directly in the next reaction.

Step 2

2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanilidenoctahydro-2H,10OH,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate By using the crude product obtained in step 1, the reaction was carried out in substantially the same manner as in step 13 of Example 1 to give the titled compound (778 mg) as a mixture of diastereomers at the phosphorus atom.

MS (ESI) m/z: 1264 (M+H)$^+$.

Step 3 bis(N,N-diethylethanaminium) (5R,7R,8R,12aR,14R,15R,15aR,16R)-15,16-bis{[tert-butyl(dimethyl)silyl]oxy}-7-[1-(2-hydroxyethyl)-6-oxo-1,6-dihydro-9H-purin-9-yl]-2,10-dioxo-14-(6,7,8,9-tetrahydro-2H-2,3, 5,6-tetraazabenzo[cd]azulen-2-yl)octahydro-2H,1OH,12H-5,8-methano-2λ$^5$,10λ$^5$-furo[3,2-1][1,3,6,9,11,2,10]pentaoxadiphosphacyclotetradecine-2,10-bis(thiolate)

By using the compound (778 mg) obtained in step 2, the reaction was carried out in substantially the same manner as in step 14 of Example 1 to give diastereomer 1 (255 mg) and diastereomer 2 (containing impurities) of the titled compound. The diastereomer 2 was purified again by preparative HPLC [water/0.2% triethylamine-containing acetonitrile; 0.2% triethylamine-containing acetonitrile: 5%-50% (0 min-40 min)] to give the diastereomer 2 (94.6 mg) of the titled compound.

Diastereomer 1 (less polar)

MS (ESI) m/z: 1003 (M+H)$^+$.

$^1$H-NMR ($CD_3OD$) δ: 8.66 (1H, s), 8.21 (1H, s), 8.04 (1H, s), 7.33 (1H, s), 6.27 (1H, d, J=5.1 Hz), 6.25 (1H, d, J=3.6 Hz), 5.39-5.29 (1H, m), 5.18-5.11 (1H, m), 4.85-4.81 (1H, m), 4.79-4.74 (1H, m), 4.71-4.66 (1H, m), 4.50-4.42 (1H, m), 4.36-4.21 (2H, m), 4.09-3.98 (2H, m), 3.85-3.78 (2H, m), 3.78-3.69 (2H, m), 3.55-3.46 (2H, m), 3.17 (12H, q, J=7.3 Hz), 2.98-2.75 (2H, m), 2.05-1.88 (2H, m), 1.28 (18H, t, J=7.3 Hz), 0.98 (9H, s), 0.85 (9H, s), 0.31 (3H, s), 0.27 (3H, s), 0.25 (3H, s), 0.09 (3H, s).

Diastereomer 2 (more polar)

MS (ESI) m/z: 1003 (M+H)$^+$.

$^1$H-NMR ($CD_3OD$) δ: 8.50 (1H, s), 8.22 (1H, s), 8.07 (1H, s), 7.20 (1H, s), 6.33 (1H, d, J=7.3 Hz), 6.26 (1H, d, J=9.1 Hz), 5.59-5.44 (1H, m), 5.38-5.32 (1H, m), 5.21-5.11 (1H, m), 4.99-4.89 (2H, m), 4.68-4.54 (2H, m), 4.25-4.12 (3H, m), 4.09-4.03 (1H, m), 3.90-3.80 (3H, m), 3.59-3.51 (2H, m), 3.20 (12H, q, J=7.3 Hz), 2.96-2.89 (2H, m), 2.07-1.98 (2H, m), 1.30 (18H, t, J=7.3 Hz), 0.99 (9H, s), 0.74 (9H, s), 0.27 (3H, s), 0.27 (3H, s), 0.20 (3H, s), -0.05 (3H, s).

Step 4-1 bis(N,N-diethylethanaminium) (5R,7R,8R,12aR,14R,15R,15aR,16R)-15,16-bis{[tert-butyl(dimethyl)silyl]oxy}-7-(1-{2-[(glycylamino)methoxy]ethyl}-6-oxo-1,6-dihydro-9H-purin-9-yl)-2,10-dioxo-14-(6,7,8,9-tetrahydro-2H-2,3,5,6-tetraazabenzo[cd]azulen-2-yl)octahydro-2H,1OH,12H-5,8-methano-2λ$^5$,10λ$^5$-furo[3,2-1][1,3,6,9,11,2,10]pentaoxadiphosphacyclotetradecine-2,10-bis(thiolate) (Diastereomer 1)

To a solution of the compound (diastereomer 1) (30 mg) obtained in step 3 in tetrahydrofuran (0.5 mL) were added [(N-{[(9H-fluoren-9-yl)methoxy]carbonyl}glycyl)amino]methyl acetate (91.7 mg) and p-toluenesulfonic acid monohydrate (11.8 mg), and the mixture was stirred at room temperature for 6 h. N,N-dimethylformamide (0.5 mL) and 1,8-diazabicyclo[5.4.0]-7-undecene (56 L) were added to the reaction mixture, and the mixture was stirred at room temperature for 3 h. The reaction mixture was admixed with 10 mM aqueous triethylammonium acetate. Subsequently, purification was performed by C18 silica gel column chromatography [10 mM aqueous triethylammonium acetate/acetonitrile] to give the titled compound (25.6 mg) containing the starting materials as impurities.

MS (ESI) m/z: 1089 $(M+H)^+$.

Step 4-2 bis(N,N-diethylethanaminium) (5R,7R,8R,12aR,14R,15R,15aR,16R)-15,16-bis{[tert-butyl(dimethyl)silyl]oxy}-7-(1-{2-[(glycylamino)methoxy]ethyl}-6-oxo-1,6-dihydro-9H-purin-9-yl)-2,10-dioxo-14-(6,7,8,9-tetrahydro-2H-2,3,5,6-tetraazabenzo[cd]azulen-2-yl)octahydro-2H,1OH,12H-5,8-methano-2$\lambda^5$,10$\lambda^5$-furo[3, 2-1][1,3,6,9,11,2,10]pentaoxadiphosphacyclotetradecine-2,10-bis(thiolate) (Diastereomer 2)

By using the compound (diastereomer 2) (84.6 mg) obtained in step 3, the reaction was carried out in substantially the same manner as in step 4-1 to give the titled compound (70.9 mg) containing the starting materials as impurities.

MS (ESI) m/z: 1089 $(M+H)^+$.

Step 5-1 bis(N,N-diethylethanaminium) (5R,7R,8R,12aR,14R,15R,15aS,16R)-7-(1-{2-[(glycylamino)methoxy]ethyl}-6-oxo-1,6-dihydro-9H-purine-9-yl)-15,16-dihydroxy-2,10-dioxo-14-(6,7,8,9-tetrahydro-2H-2,3, 5,6-tetraazabenzo[cd]azulen-2-yl)octahydro-2H,1OH,12H-5,8-methano-2$\lambda^5$,10$\lambda^5$-furo[3,2-1][1,3,6,9,11,2,10]pentaoxadiphosphacyclotetradecine-2,10-bis(thiolate) diastereomer 1

To the compound (25.6 mg) obtained in step 4-1 was added triethylamine trihydrofluoride (2 mL), and the mixture was stirred at 45° C. for 3 h. The reaction mixture was admixed at room temperature with an ice-cold mixture of 1 M aqueous triethylammonium bicarbonate (10 mL) and triethylamine (2 mL). The reaction mixture was concentrated under reduced pressure. Subsequently, purification was performed by C18 silica gel column chromatography (10 mM aqueous triethylammonium acetate/acetonitrile) to give the titled compound (16.6 mg; containing impurities derived from the starting materials in step 7-1).

MS (ESI) m/z: 861 $(M+H)^+$.

Step 5-2 bis(N,N-diethylethanaminium) (5R,7R,8R,12aR,14R,15R,15aS,16R)-7-(1-{2-[(glycylamino)methoxy]ethyl}-6-oxo-1,6-dihydro-9H-purine-9-yl)-15,16-dihydroxy-2,10-dioxo-14-(6,7,8,9-tetrahydro-2H-2,3, 5,6-tetraazabenzo[cd]azulen-2-yl)octahydro-2H,1OH,12H-5,8-methano-2$\lambda^5$,10$\lambda^5$-furo[3,2-1][1,3,6,9,11,2,10]pentaoxadiphosphacyclotetradecine-2,10-bis(thiolate) (Diastereomer 2)

By using the compound (70.9 mg) obtained in step 4-2, the reaction was carried out in substantially the same manner as in step 5-1 to give the titled compound (51.7 mg; containing impurities derived from the starting materials in step 4-2).

MS (ESI) m/z: 861 $(M+H)^+$.

Step 6-1 bis(N,N-diethylethanaminium)N-[4-(11,12-didehydrodibenzo[b,f]azocin-5(6H)-yl)-4-oxobutanoyl]glycylglycyl-L-phenylalanyl-N-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,1OH,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]glycinamide (Drug-Linker 2a: Diastereomer 1)

To a solution of the compound (16.6 mg) obtained in step 5-1 in N,N-dimethylformamide (0.5 mL) were added triethylamine (6 L) and the compound (15.5 mg) obtained in step 8 described below, and the mixture was stirred at room temperature for 3 h. Next, benzylamine (3 μL) was added to the reaction mixture, and the mixture was stirred at room temperature for 1 h. Then, 10 mM aqueous triethylammonium acetate and methanol were added. Subsequently, purification was performed by C18 silica gel column chromatography [10 mM aqueous triethylammonium acetate/acetonitrile] and preparative HPLC [10 mM aqueous triethylammonium acetate/acetonitrile; acetonitrile: 10%-45% (0 min-30 min)] to give the titled compound (5.1 mg)

MS (ESI) m/z: 1409 $(M+H)^+$.

$^1$H-NMR ($CD_3OD$) δ: 8.66-8.60 (1H, m), 8.17 (1H, s), 8.02 (1H, s), 7.65-7.48 (2H, m), 7.43-7.36 (3H, m), 7.31-7.13 (8H, m), 7.11 (1H, s), 6.30-6.21 (2H, m), 5.46-5.37 (1H, m), 5.23-5.16 (1H, m), 5.08-4.99 (1H, m), 4.86-4.81 (1H, m), 4.80-4.75 (1H, m), 4.70-4.40 (7H, m), 4.40-4.20 (3H, m), 4.10-3.97 (3H, m), 3.86-3.58 (8H, m), 3.51-3.43 (3H, m), 3.18 (12H, q, J=7.3 Hz), 3.01-2.93 (1H, m), 2.85-2.72 (3H, m), 2.37-2.15 (2H, m), 2.01-1.93 (2H, m), 1.29 (18H, t, J=7.3 Hz). (only observable peaks are listed).

Step 6-2 bis(N,N-diethylethanaminium)N-[4-(11,12-didehydrodibenzo[b,f]azocin-5(6H)-yl)-4-oxobutanoyl]glycylglycyl-L-phenylalanyl-N-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,1OH,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]glycinamide (Drug-Linker 2b: Diastereomer 2)

By using the compound (51.7 mg) obtained in step 5-2, the reaction was carried out in substantially the same manner as in step 6-1. Then, purification was performed under the following [Purification Conditions] to give the titled compound (33.7 mg).

[Purification Conditions]C18 silica gel column chromatography [10 mM aqueous triethylammonium acetate/acetonitrile] and preparative HPLC [10 mM aqueous triethylammonium acetate/acetonitrile; acetonitrile: 10%-50% (0 min-30 min)].

MS (ESI) m/z: 1409 $(M+H)^+$.

$^1$H-NMR ($CD_3OD$) δ: 8.73 (1H, d, J=6.7 Hz), 8.19 (1H, d, J=3.0 Hz), 8.02 (1H, s), 7.66-7.50 (2H, m), 7.43-7.37 (3H, m), 7.33-7.13 (8H, m), 7.11 (1H, s), 6.33-6.23 (2H, m), 5.51-5.38 (2H, m), 5.04 (1H, t, J=13.6 Hz), 4.83-4.77 (1H, m), 4.64-4.55 (2H, m), 4.52-4.26 (6H, m), 4.25-3.97 (2H, m), 3.93-3.45 (13H, m), 3.19 (12H, q, J=7.3 Hz), 3.17-3.11 (1H, m), 3.02-2.92 (1H, m), 2.91-2.73 (3H, m), 2.40-2.24 (2H, m), 2.07-1.95 (3H, m), 1.30 (18H, t, J=7.3 Hz).

Step 7

N-[4-(11,12-Didehydrodibenzo[b,f]azocin-5(6H)-yl)-4-oxobutanoyl]glycylglycyl-L-phenylalanine To a solution of commercially available (BACHEM) (2S)-2-[[2-[(2-aminoacetyl)amino]acetyl]amino]-3-phenylpropanoic acid (2.86 g) in N,N-dimethylformamide (51.2 mL) were added triethylamine (2.56 mL) and commercially available (Click Chemistry Tools) 1-{[4-(11,12-didehydrodibenzo[b,f]azocin-5(6H)-yl)-4-oxobutanoyl]oxy}pyrrolidin-2,5-dione (3.69 g), and the mixture was stirred at room temperature for 24 h. A solution of citric acid monohydrate (24.0 g) in water (500 mL) was added to the reaction mixture, and the mixture was extracted with ethyl acetate. The organic layer was dried over anhydrous sodium sulfate, the drying agent was filtered off, and the filtrate was then concentrated under reduced pressure. The residue was dissolved in an ethyl acetate/acetonitrile mixed solution, and precipitated using diisopropyl ether, filtered, and collected to give the titled compound (4.30 g).

$^1$H-NMR (DMSO-$d_6$) δ: 12.8 (1H, brs), 8.15-7.95 (3H, m), 7.68-7.17 (13H, m), 5.01 (1H, d, J=14.2 Hz), 4.41-4.37 (1H, m), 3.74-3.57 (5H, m), 3.05-3.01 (1H, m), 2.87 (1H, dd, J=14.2, 9.3 Hz), 2.68-2.59 (1H, m), 2.32-2.25 (1H, m), 2.09-2.03 (1H, m), 1.82-1.76 (1H, m).

Step 8

2,5-dioxopyrrolidin-1-yl-N-[4-(11,12-didehydrodibenzo[b,f]azocin-5(6H)-yl)-4-oxobutanoyl]glycylglycyl-L-phenylalaninate To a solution of the compound (2.10 g) obtained in step 7 in N,N-dimethylformamide (75.9 mL) were added N-hydroxysuccinimide (961 mg) and 1-ethyl-3-(3-dimethylaminopropyl)carbodiimide hydrochloride (1.60 g), and the mixture was stirred at room temperature for 21 h under a nitrogen atmosphere. The reaction mixture was diluted with dichloromethane, washed three times with ice water, and then dried over anhydrous sodium sulfate. The drying agent was filtered off, and the filtrate was concentrated under reduced pressure. Toluene was added to the residue, and the mixture was concentrated again under reduced pressure. The residue was dissolved in acetonitrile and purified by C18 silica gel column chromatography [acetonitrile: 100%]. Fractions containing the target product were concentrated under reduced pressure, and diisopropyl ether was added to the residue to form a slurry. The resulting solid was filtered and collected to give the titled compound (2.59 g).

$^1$H-NMR (DMSO-$d_6$) δ: 8.58-8.51 (1H, m), 8.17-8.00 (2H, m), 7.66-7.20 (13H, m), 5.02-4.98 (1H, m), 4.90-4.85 (1H, m), 3.78-3.57 (5H, m), 3.24-3.19 (1H, m), 3.06-3.00 (1H, m), 2.82 (4H, brs), 2.67-2.58 (1H, m), 2.32-2.23 (1H, m), 2.09-2.02 (1H, m), 1.82-1.75 (1H, m).

Example 6: To Synthesize Drug Linker 17

Synthetic Scheme

[Formula 102]

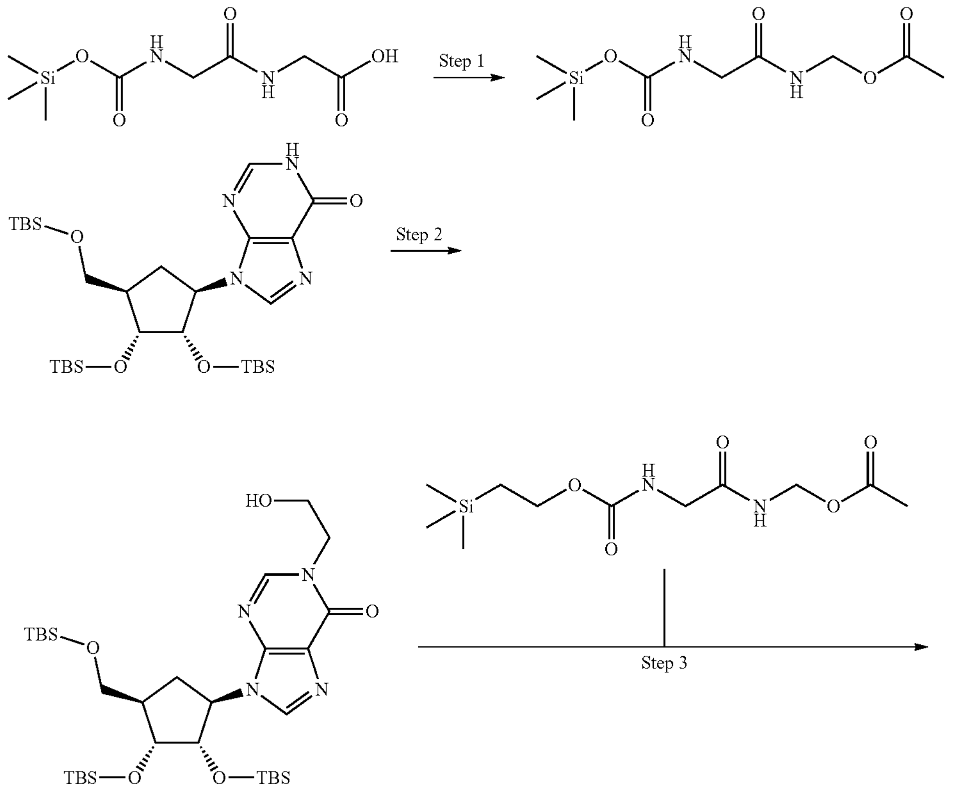

-continued
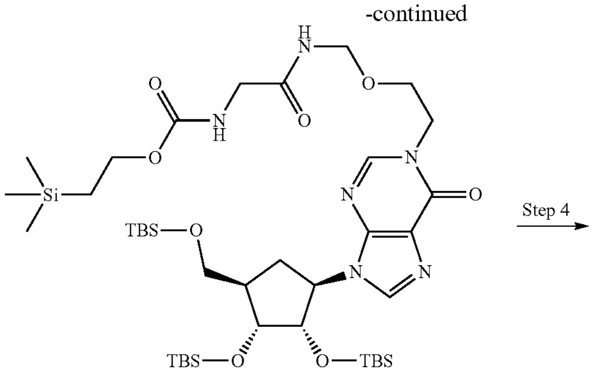
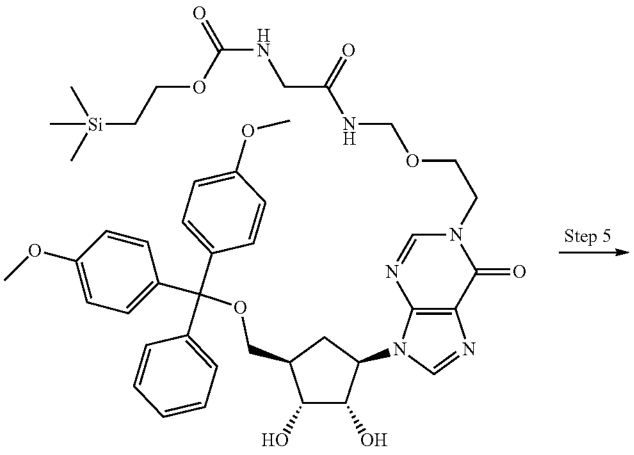
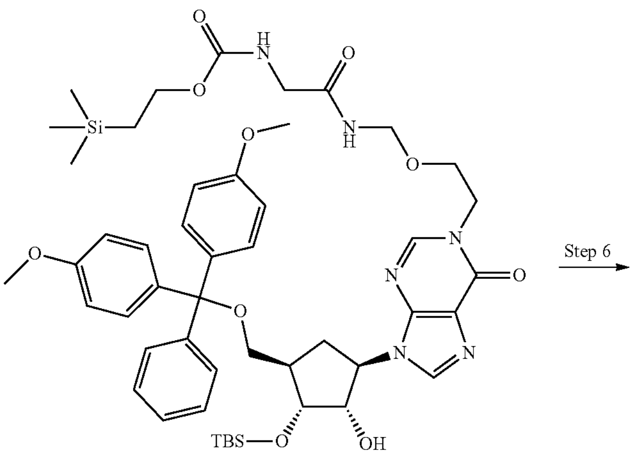

-continued
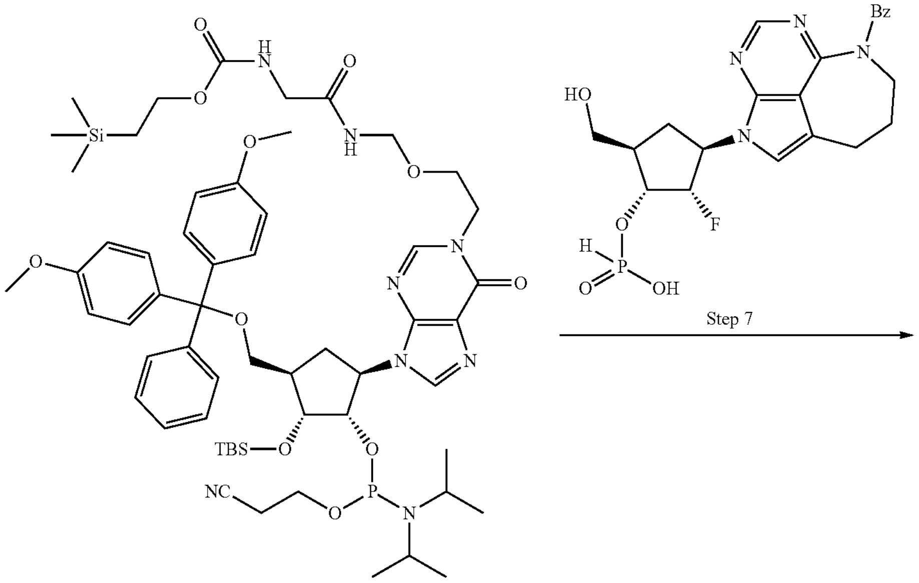
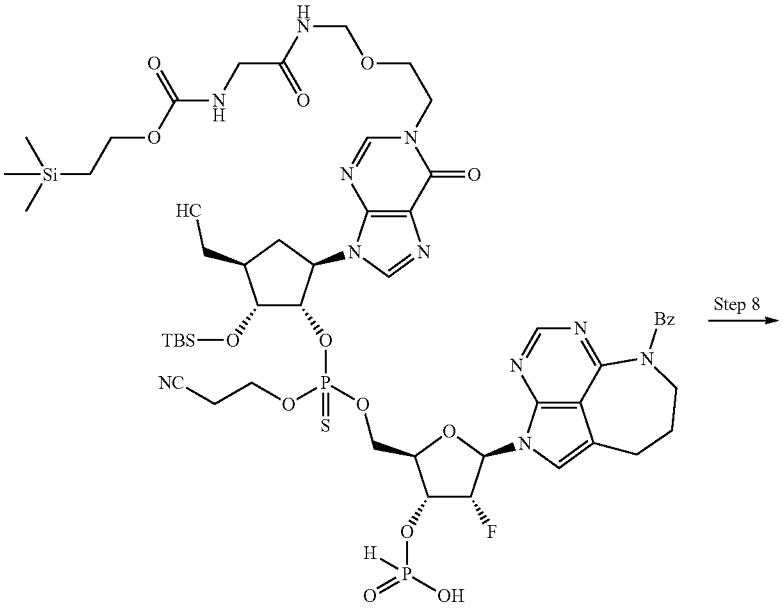

-continued
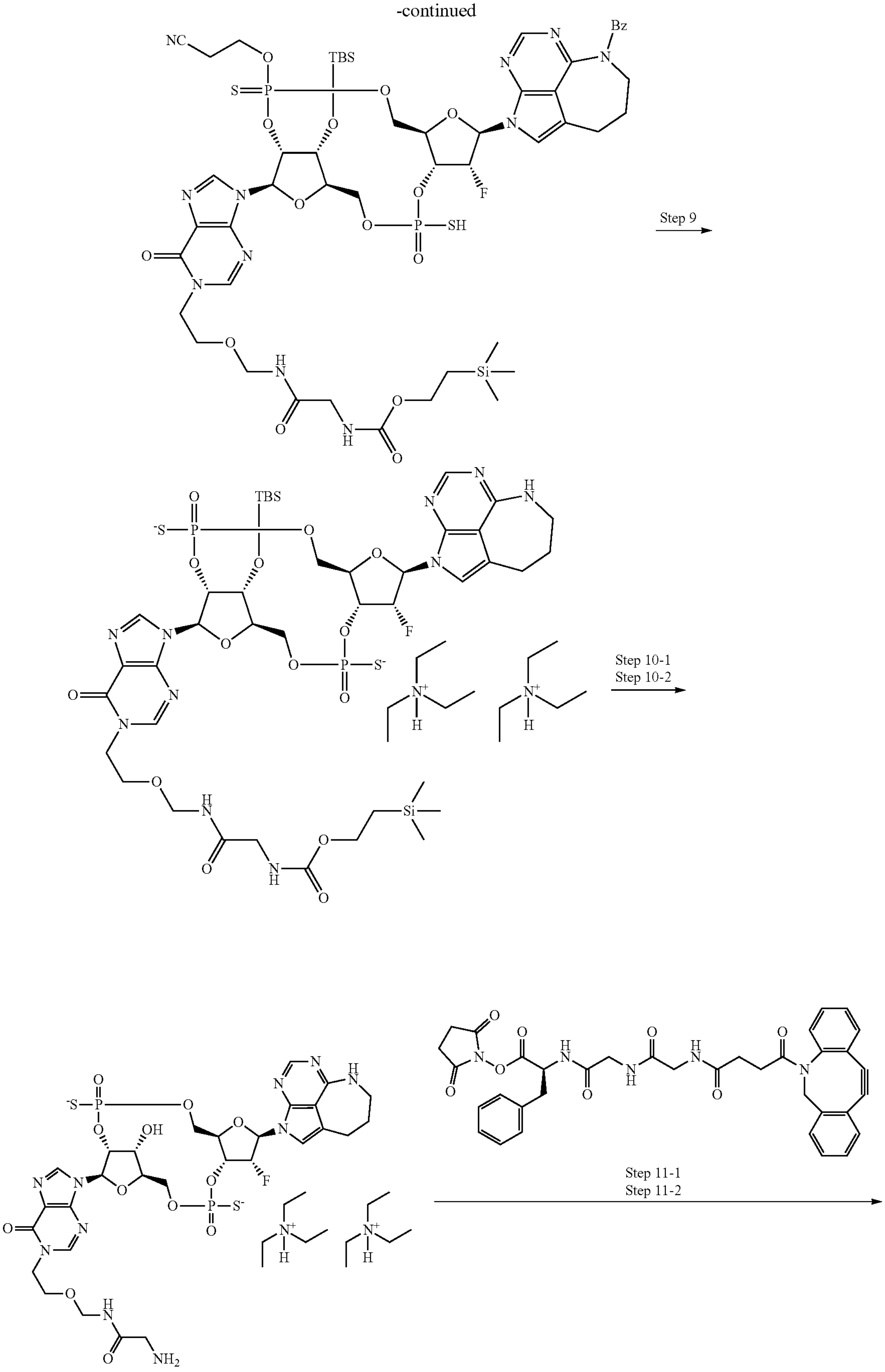

-continued

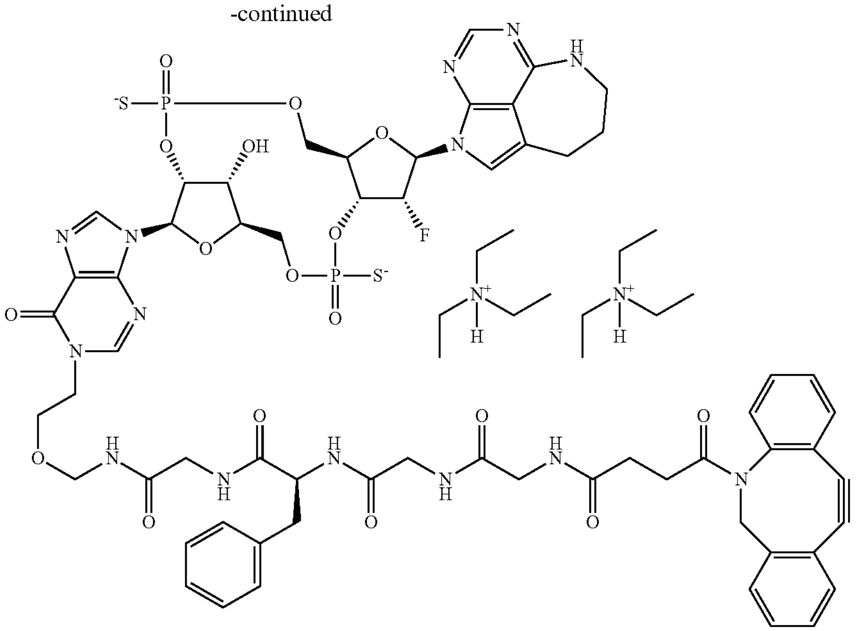

Drug-linker 17a
Drag-linker 17b

Step 1

[(N-{[2-(trimethylsilyl)ethoxy]carbonyl}glycyl)amino]methyl acetate

To a mixed solution of commercially available (SUNDIA) N-{[2-(trimethylsilyl)ethoxy]carbonyl}glycylglycine (9.32 g) in tetrahydrofuran (100 mL)-toluene (33.3 mL) were added pyridine (3.26 mL) and lead tetraacetate (17.9 g) at room temperature, and the mixture was stirred at 65° C. for 3 h. The insoluble material was filtered off, washed with tetrahydrofuran, and the filtrate was concentrated under reduced pressure. The residue was purified by silica gel column chromatography [hexane/ethyl acetate] to give the titled compound (8.24 g).

$^1$H-NMR ($CDCl_3$) δ: 7.14 (1H, brs), 5.27 (2H, d, J=7.3 Hz), 5.20 (1H, brs), 4.22-4.16 (2H, m), 3.88 (2H, d, J=6.0 Hz), 2.08 (3H, s), 1.04-0.97 (2H, m), 0.05 (9H, s).

Step 2

2',3',5'-tris-O-[tert-butyl(dimethyl)silyl]-1-(2-hydroxyethyl)inosine

To a mixed solution of 2',3',5'-tris-O-[tert-butyl(dimethyl)silyl]inosine (31.3 g), known in the literature (Chem. Pharm. Bull. 1987, 35(1), 72-79), in tetrahydrofuran (75 mL)-N,N-dimethylacetamide (75 mL) were added 2-bromoethanol (4.82 mL) and 1,8-diazabicyclo[5.4.0]-7-undecene (7.65 mL), and the mixture was stirred at room temperature for 23 h. The reaction mixture was admixed with water and ethyl acetate, and was extracted with ethyl acetate. The organic layer was washed with brine and dried over anhydrous sodium sulfate. Subsequently, the drying agent was filtered off, and the filtrate was then concentrated under reduced pressure. The residue was purified by silica gel column chromatography [hexane/ethyl acetate] to give the titled compound (29.4 g).

MS (ESI) m/z: 655 $(M+H)^+$.

$^1$H-NMR ($CDCl_3$) δ: 8.16 (1H, s), 7.99 (1H, d, J=2.4 Hz), 5.97 (1H, d, J=4.2 Hz), 4.40-4.25 (3H, m), 4.18-4.06 (3H, m), 4.03-3.92 (2H, m), 3.79 (1H, dd, J=11.5, 2.4 Hz), 3.08-2.83 (1H, brm), 0.96 (9H, s), 0.92 (9H, s), 0.82 (9H, s), 0.15 (3H, s), 0.14 (3H, s), 0.09 (3H, s), 0.08 (3H, s), -0.02 (3H, s), -0.15 (3H, s).

Step 3

2',3',5'-tris-O-[tert-butyl(dimethyl)silyl]-1-(2-{[(N-{[2-(trimethylsilyl)ethoxy]carbonyl]glycyl)amino]methoxy}ethyl)inosine To a solution of the compound (15.6 g) obtained in step 2 in toluene (46.8 mL) were added the compound (10.4 g) obtained in step 1 and pyridine (9.63 mL), and the mixture was stirred at 110° C. for 12 h. The compound (3.46 g) obtained in step 1 was added to the reaction mixture, and the mixture was stirred at 110° C. for 1 day. The reaction mixture was admixed with saturated aqueous sodium bicarbonate and dichloromethane, and was extracted with dichloromethane. The organic layer was dried over anhydrous sodium sulfate, the drying agent was filtered off, and the filtrate was then concentrated under reduced pressure. The residue was purified by silica gel column chromatography [hexane/ethyl acetate] to give the titled compound (20.6 g; containing impurities).

MS (ESI) m/z: 885 $(M+H)^+$.

Step 4

5'-O-[bis(4-methoxyphenyl)(phenyl)methyl]-1-(2-{[(N-{[2-(trimethylsilyl)ethoxy]carbonyl}glycyl)amino]methoxy}ethyl)inosine To a solution of the compound (20.6 g) obtained in step 3 in tetrahydrofuran (50 mL) was added triethylamine trihydrofluoride (10 mL), and the mixture was stirred at room temperature for 17 h. The reaction mixture was admixed gradually under ice-cold conditions with a mixed solution of 1 M triethylammonium bicarbonate solution (50 mL) and triethylamine (10 mL). Then, the reaction mixture was concentrated under reduced pressure. The residue was subjected to crude purification using C18 silica gel column chromatography [water/acetonitrile], and then lyophilized. The resulting crude product was azeotroped with pyridine. The residue-containing pyridine solution (50 mL) was admixed at 0° C. with 4,4'-dimethoxytrityl chloride (4.73 g), and the mixture was stirred at 4° C. for 17 h. Methanol (2 mL) was added to the reaction mixture, and the mixture was stirred at room temperature for 15 min and then concentrated under reduced pressure. The residue was purified by silica gel column chromatography [hexane/ethyl acetate/methanol/0.1% triethylamine] to give the titled compound (9.18 g; containing impurities).

MS (ESI) m/z: 845 $(M+H)^+$.

$^1$H-NMR ($CDCl_3$) δ: 7.94 (1H, s), 7.88 (1H, s), 7.65 (1H, brs), 7.41-7.36 (2H, m), 7.32-7.15 (7H, m), 6.83-6.76 (4H, m), 5.96 (1H, d, J=6.1 Hz), 5.73-5.65 (2H, m), 4.87-4.80 (1H, m), 4.76-4.61 (2H, m), 4.44-4.39 (1H, m), 4.35-4.30 (1H, m), 4.22-4.05 (4H, m), 3.83-3.73 (2H, m), 3.77 (6H, s), 3.72-3.67 (2H, m), 3.48-3.32 (3H, m), 0.99-0.91 (2H, m), 0.02 (9H, s).

Step 5

5'-O-[bis(4-methoxyphenyl)(phenyl)methyl]-3'-O-[tert-butyl(dimethyl)silyl]-1-(2-{[(N-{[2-(trimethylsilyl)ethoxy]carbonyl}glycyl)amino]methoxy}ethyl)inosine By using the compound (5.96 g) obtained in step 4, the reaction was carried out in substantially the same manner as in step 10 of Example 1 to give the titled compound (2.33 g) and a regioisomer of the titled compound, namely 5'-O-[bis(4-methoxyphenyl)(phenyl)methyl]-2'-O-[tert-butyl(dimethyl)silyl]-1-(2-{[(N-{[2-(trimethylsilyl)ethoxy]carbonyl}glycyl)amino]methoxy}ethyl)inosine (2.45 g)

MS (ESI) m/z: 959 $(M+H)^+$.

$^1$H-NMR ($CDCl_3$) δ: 7.99 (1H, s), 7.93 (1H, s), 7.45-7.39 (2H, m), 7.35-7.18 (7H, m), 7.05 (1H, brs), 6.84-6.77 (4H, m), 5.92 (1H, d, J=5.4 Hz), 5.46 (1H, brs), 4.71-4.61 (3H, m), 4.54-4.51 (1H, m), 4.22-4.10 (5H, m), 3.81-3.76 (2H, m), 3.78 (3H, s), 3.78 (3H, s), 3.74 (2H, d, J=6.0 Hz), 3.48 (1H, dd, J=10.9, 4.2 Hz), 3.26 (1H, dd, J=10.9, 4.2 Hz), 3.16 (1H, d, J=6.7 Hz), 1.00-0.93 (2H, m), 0.89 (9H, s), 0.09 (3H, s), 0.02 (9H, s), 0.02 (3H, s).

Regioisomer (2'-O-TBS isomer)

MS (ESI) m/z: 959 $(M+H)^+$.

$^1$H-NMR ($CDCl_3$) δ: 7.99 (1H, s), 7.91 (1H, s), 7.48-7.42 (2H, m), 7.37-7.18 (8H, m), 6.85-6.78 (4H, m), 5.96 (1H, d, J=5.4 Hz), 5.63 (1H, brs), 4.88 (1H, t, J=5.1 Hz), 4.66 (2H, d, J=6.7 Hz), 4.36-4.32 (1H, m), 4.27-4.19 (2H, m), 4.18-4.10 (3H, m), 3.81-3.74 (4H, m), 3.78 (3H, s), 3.78 (3H, s), 3.50 (1H, dd, J=10.9, 3.6 Hz), 3.38 (1H, dd, J=10.9, 3.6 Hz), 2.73 (1H, d, J=4.2 Hz), 0.97-0.90 (2H, m), 0.86 (9H, s), 0.02 (3H, s), 0.01 (9H, s), -0.09 (3H, s).

Step 6

5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}-1-(2-{[(N-{[2-(trimethylsilyl)ethoxy]carbonyl}glycyl)amino]methoxy}ethyl)inosine By using the compound (2.33 g) obtained in step 5, the reaction was carried out in substantially the same manner as in step 11 of Example 1 to give the titled compound (2.72 g) as a mixture of diastereomers (diastereomer ratio=6:4) at the phosphorus atom.

MS (ESI) m/z: 1159 $(M+H)^+$.

$^1$H-NMR ($CDCl_3$) δ: 8.03 (0.4H, s), 8.02 (0.6H, s), 7.95 (0.6H, s), 7.92 (0.4H, s), 7.46-7.40 (2H, m), 7.35-7.17 (7H, m), 6.88 (1H, brs), 6.84-6.78 (4H, m), 6.15 (0.6H, d, J=4.2 Hz), 6.10 (0.4H, d, J=4.8 Hz), 5.34 (1H, brs), 4.86-4.61 (3H, m), 4.48-4.42 (1H, m), 4.29-4.09 (5H, m), 3.83-3.44 (9H, m), 3.79 (3H, s), 3.78 (3H, s), 3.32-3.23 (1H, m), 2.58-2.49 (1H, m), 2.44-2.38 (1H, m), 1.15 (3.6H, d, J=6.7 Hz), 1.11 (6H, d, J=6.7 Hz), 1.04-0.92 (2H, m), 0.97 (2.4H, d, J=6.7 Hz), 0.85 (3.6H, s), 0.84 (5.4H, s), 0.09 (1.2H, s), 0.06 (1.8H, s), 0.03 (9H, s), 0.00 (3H, s).

Step 7

By using the compound (2.15 g) obtained in step 11 of Example 2, the reaction was carried out in substantially the same manner as in step 7 of Example 1 to give an acetonitrile solution of 6-benzoyl-2-{2-deoxy-2-fluoro-3-O-[hydroxy(oxo)-$\lambda^5$-phosphanyl]-β-D-ribofuranosyl}-6,7,8,9-tetrahydro-2H-2,3,5,6-tetraazabenzo[cd]azulene. By using the resulting acetonitrile solution and the compound (2.72 g) obtained in step 6, the reaction was carried out in substantially the same manner as in step 12 of Example 1. The resulting crude product was used directly in the next reaction.

Step 8

2-(trimethylsilyl)ethyl(2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanilidenoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]amino}-2-oxoethyl)carbamate By using the crude product obtained in step 7, the reaction was carried out in substantially the same manner as in step 13 of Example 1 to give the titled compound (1.47 g; containing impurities) as a mixture of diastereomers at the phosphorus atom.

MS (ESI) m/z: 1278 $(M+H)^+$.

Step 9 bis(N,N-diethylethanaminium)(5R,7R,8R,12aR,14R,15R,15aR,16R)-16-{[tert-butyl(dimethyl)silyl]oxy}-15-fluoro-2,10-dioxo-7-[6-oxo-1-(2-{[(N-{[2-(trimethylsilyl)ethoxy]carbonyl}glycyl)amino]methoxy}ethyl)-1,6-dihydro-9H-purin-9-yl]-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

To a mixed solution of the compound (1.47 g) obtained in step 8 in methanol (10 mL)-tetrahydrofuran (10 mL) was added 28% aqueous ammonia (10 mL), and the mixture was stirred at 50° C. for 6 h. The reaction mixture was concentrated under reduced pressure. Subsequently, the residue was purified by C18 silica gel column chromatography [10 mM aqueous triethylammonium acetate/acetonitrile] to give diastereomer 1 (204 mg: containing impurities) and diastereomer 2 (205 mg: containing impurities) of the titled compound.

Diastereomer 1 (less polar)

MS (ESI) m/z: 1121 $(M+H)^+$.

Diastereomer 2 (more polar)

MS (ESI) m/z: 1121 $(M+H)^+$.

Step 10-1 bis(N,N-diethylethanaminium) (5R,7R,8R,12aR, 14R,15R,15aR,16R)-15-fluoro-7-(1-{2-[(glycylamino)methoxy]ethyl}-6-oxo-1,6-dihydro-9H-purine-9-yl)-16-hydroxy-2,10-dioxo-14-(6,7,8,9-tetrahydro-2H-2,3, 5,6-tetraazabenzo[cd]azulen-2-yl)octahydro-2H,10H,12H-5,8-methano-2λ$^5$, 10λ$^5$-furo[3,2-1][1,3,6,9,11,2,10] pentaoxadiphosphacyclotetradecine-2,10-bis (thiolate)

To a solution of the compound (diastereomer 1) (204 mg) obtained in step 9 in tetrahydrofuran (6 mL) was added a tetrahydrofuran solution of tetrabutylammonium fluoride (about 1 M, 3 mL), and the mixture was stirred at room temperature for 33 h. After stored at 4° C. for 3 days, the reaction mixture was admixed with 10 mM aqueous triethylammonium acetate. Subsequently, purification was performed by C18 silica gel column chromatography [10 mM aqueous triethylammonium acetate/acetonitrile] and preparative HPLC [10 mM aqueous triethylammonium acetate/acetonitrile-methanol solution (1:1); acetonitrile-methanol solution (1:1): 10%-50% (0 min-40 min)] to give the titled compound (40.7 mg; containing impurities).

MS (ESI) m/z: 863 $(M+H)^+$.

Step 10-2 bis(N,N-diethylethanaminium) (5R,7R,8R,12aR, 14R,15R,15aR,16R)-15-fluoro-7-(1-{2-[(glycylamino)methoxy]ethyl}-6-oxo-1,6-dihydro-9H-purine-9-yl)-16-hydroxy-2,10-dioxo-14-(6,7,8,9-tetrahydro-2H-2,3, 5,6-tetraazabenzo[cd]azulen-2-yl)octahydro-2H,10H,12H-5,8-methano-2λ$^5$, 10λ$^5$-furo[3,2-1][1,3,6,9,11,2,10] pentaoxadiphosphacyclotetradecine-2,10-bis (thiolate)

By using the compound (diastereomer 2) (205 mg) obtained in step 9, the reaction was carried out in substantially the same manner as in step 10-1. Subsequently, purification was performed by C18 silica gel column chromatography [10 mM aqueous triethylammonium acetate/acetonitrile] and preparative HPLC [10 mM aqueous triethylammonium acetate/acetonitrile-methanol solution (1:1); acetonitrile-methanol solution (1:1): 10%-50% (0 min-40 min)] to give the titled compound (50.8 mg; containing impurities).

MS (ESI) m/z: 863 $(M+H)^+$.

Step 11-1 bis(N,N-diethylethanaminium)N-[4-(11,12-didehydrodibenzo[b,f]azocin-5(6H)-yl)-4-oxobutanoyl] glycylglycyl-L-phenylalanyl-N-[(2-{9-[(5R,7R,8R, 12aR,14R,15R,15aR,16R)-15-fluoro-16-hydroxy-2, 10-dioxo-2,10-disulfide-14-(6,7,8,9-tetrahydro-2H-2,3,5,6-tetraazabenzo[cd]azulen-2-yl)octahydro-2H, 1OH,12H-5,8-methano-2λ$^5$,10λ$^5$-furo[3,2-1][1,3,6,9, 11,2,10]pentaoxadiphosphacyclotetradecin-7-yl]-6-oxo-6,9-dihydro-1H-purin-1-yl}ethoxy)methyl] glycinamide (Drug-Linker 17a: Diastereomer 1)

To a solution of the compound (40.7 mg) obtained in step 10-1 in N,N-dimethylformamide (0.5 mL) were added triethylamine (11 L) and the compound (25.4 mg) obtained in step 8 of Example 5, and the mixture was stirred at room temperature for 2 h. Next, benzylamine (8 μL) was added to the reaction mixture, and the mixture was stirred at room temperature for 1 h. Then, 10 mM aqueous triethylammonium acetate and methanol were added. Subsequently, purification was performed by C18 silica gel column chromatography [10 mM aqueous triethylammonium acetate/acetonitrile], preparative HPLC [10 mM aqueous triethylammonium acetate/acetonitrile; acetonitrile: 20%-45% (0 min-40 min)], and preparative HPLC [10 mM aqueous triethylammonium acetate/methanol; methanol: 40%-90% (0 min-40 min)] to give the titled compound (25.1 mg).

MS (ESI) m/z: 1411 $(M+H)^+$.

$^1$H-NMR ($CD_3OD$) δ: 8.58 (1H, s), 8.09 (1H, s), 8.04 (1H, s), 7.57-7.49 (2H, m), 7.43-7.34 (3H, m), 7.32-7.08 (9H, m), 6.47 (1H, d, J=16.9 Hz), 6.23 (1H, d, J=7.9 Hz), 5.56-5.37 (2H, m), 5.31-5.17 (1H, m), 5.03 (1H, d, J=13.9 Hz), 4.79 (1H, d, J=4.2 Hz), 4.64-4.38 (6H, m), 4.36-4.21 (4H, m), 4.05-3.60 (10H, m), 3.53-3.42 (3H, m), 3.18 (12H, q, J=7.3 Hz), 3.01-2.92 (1H, m), 2.86-2.73 (1H, m), 2.70-2.54 (2H, m), 2.37-2.16 (2H, m), 2.06-1.77 (3H, m), 1.28 (18H, t, J=7.3 Hz).

Step 11-2 bis(N,N-diethylethanaminium)N-[4-(11,12-didehydrodibenzo[b,f]azocin-5(6H)-yl)-4-oxobutanoyl] glycylglycyl-L-phenylalanyl-N-[(2-{9-[(5R,7R,8R, 12aR,14R,15R,15aR,16R)-15-fluoro-16-hydroxy-2, 10-dioxo-2,10-disulfide-14-(6,7,8,9-tetrahydro-2H-2,3,5,6-tetraazabenzo[cd]azulen-2-yl)octahydro-2H, 1OH,12H-5,8-methano-2λ$^5$,10λ$^5$-furo[3,2-1][1,3,6,9, 11,2,10]pentaoxadiphosphacyclotetradecin-7-yl]-6-oxo-6,9-dihydro-1H-purin-1-yl}ethoxy)methyl] glycinamide (Drug-Linker 17b: Diastereomer 2)

By using the compound (50.8 mg) obtained in step 10-2 and the compound (31.7 mg) obtained in step 8 of Example 5, the reaction was carried out in substantially the same manner as in step 11-1. Subsequently, purification was performed by C18 silica gel column chromatography [10 mM aqueous triethylammonium acetate/acetonitrile], preparative HPLC [10 mM aqueous triethylammonium acetate/acetonitrile; acetonitrile: 25%-45% (0 min-40 min)], and preparative HPLC [10 mM aqueous triethylammonium acetate/methanol; methanol: 45%-90% (0 min-40 min)] to give the titled compound (23.4 mg).

MS (ESI) m/z: 1411 $(M+H)^+$.

$^1$H-NMR ($CD_3OD$) δ: 8.67 (1H, s), 8.14 (1H, s), 8.02 (1H, s), 7.67-7.50 (2H, m), 7.43-7.36 (3H, m), 7.34-7.12 (9H, m), 6.48 (1H, d, J=15.1 Hz), 6.26 (1H, t, J=8.8 Hz), 5.60-5.31 (3H, m), 5.09-5.00 (1H, m), 4.61-4.22 (9H, m), 4.11-3.59 (13H, m), 3.50-3.44 (2H, m), 3.18 (12H, q, J=7.3 Hz), 3.04-2.93 (1H, m), 2.87-2.74 (3H, m), 2.39-2.22 (2H, m), 2.06-1.85 (3H, m), 1.28 (18H, t, J=7.3 Hz).
Example 7: To Synthesize Drug-Linker 20
Synthetic Scheme
[Formula 103]
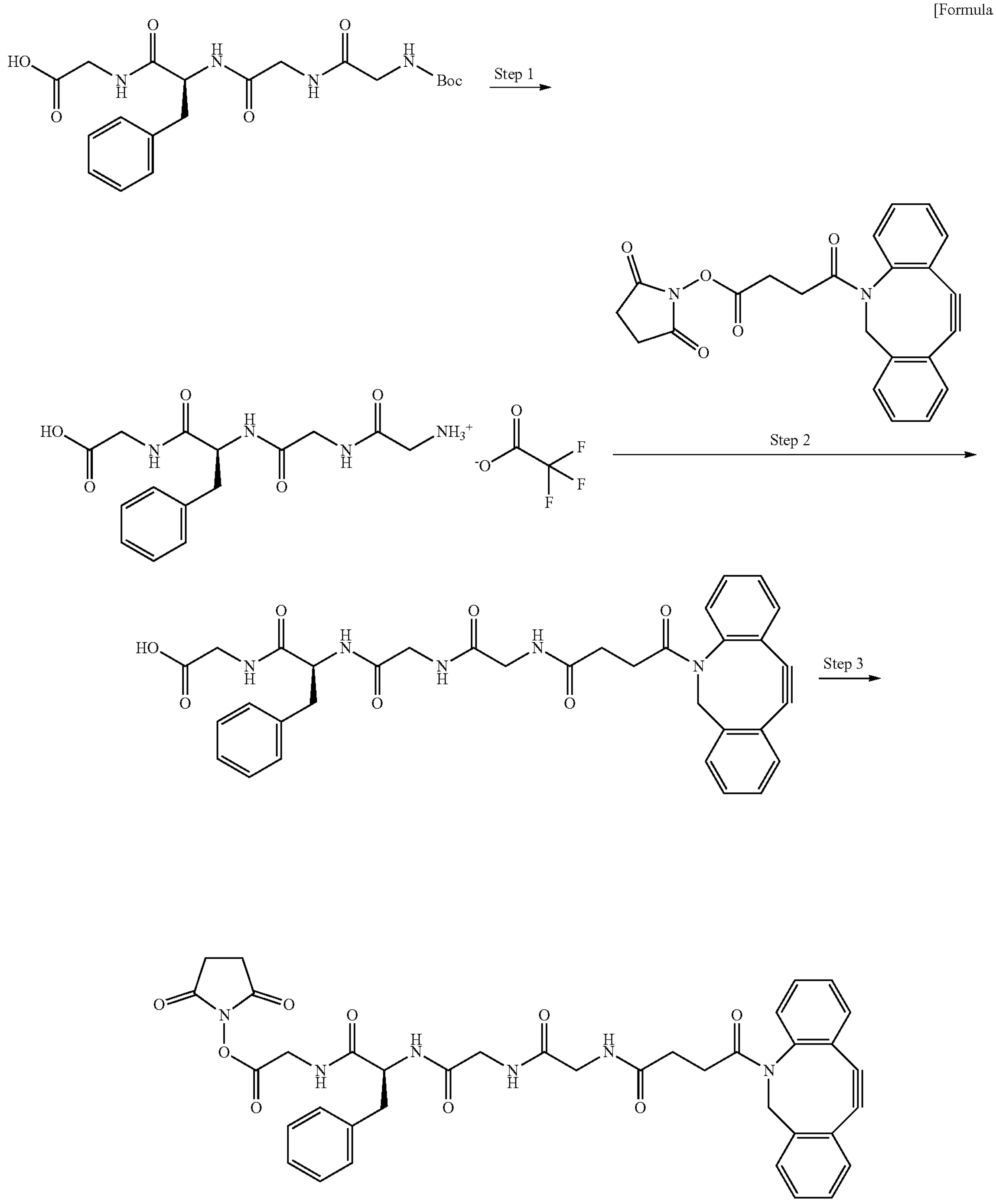

-continued
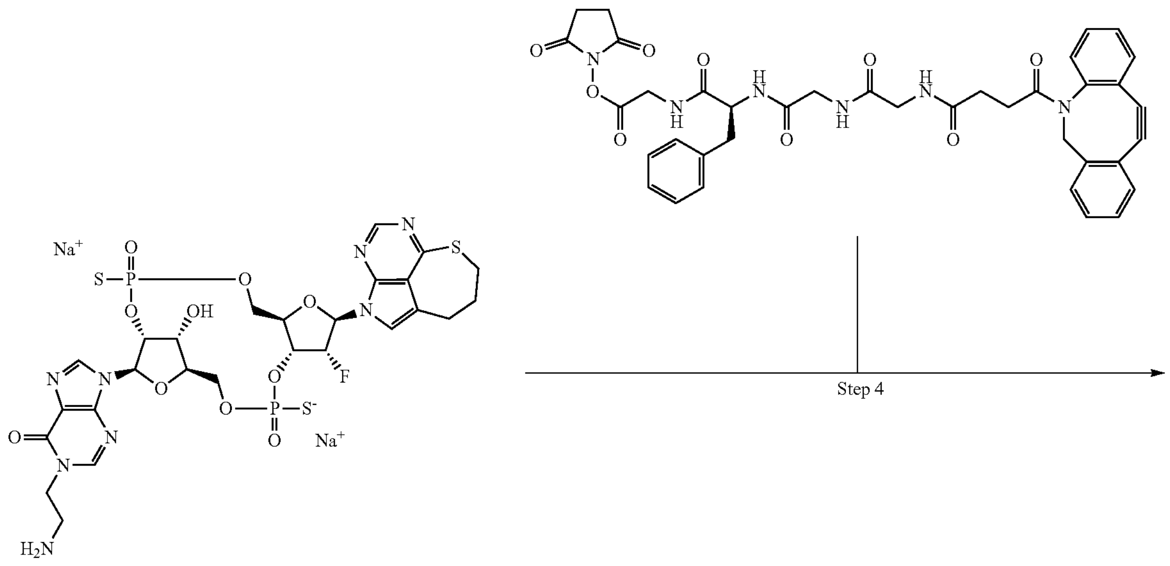
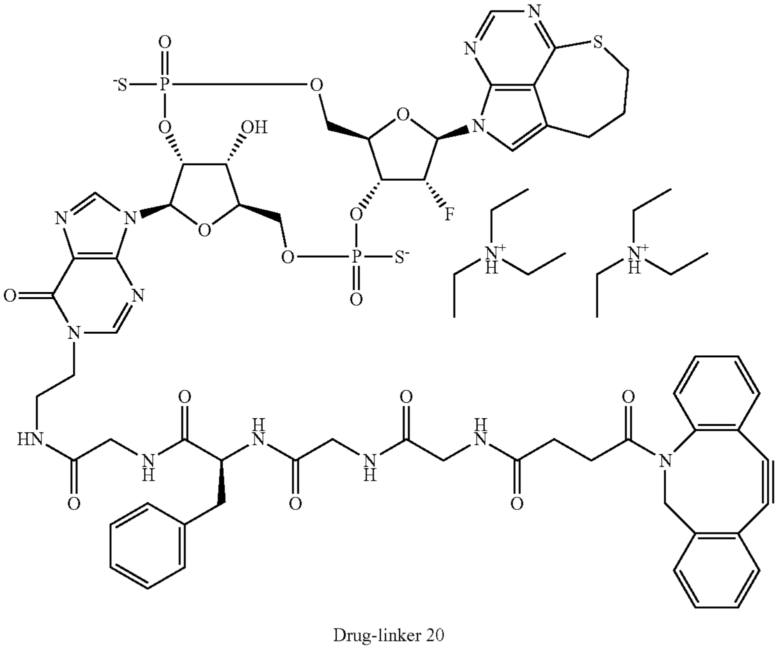
Drug-linker 20

(Step 1)

N-(azaniumylacetyl)glycyl-L-phenylalanylglycine trifluoroacetate

To a solution of commercially available (BACHEM)N-(tert-butoxycarbonyl)glycylglycyl-L-phenylalanylglycine (3.00 g) in dichloromethane (30 mL) was added trifluoroacetic acid (15 mL) at room temperature, and the mixture was stirred at the same temperature for 3 h. The reaction mixture was concentrated under reduced pressure, suspended in toluene, and then re-concentrated under reduced pressure. This concentration procedure was repeated two more times. The residue was made into a slurry with diethyl ether (100 mL), and filtered and collected to obtain the titled compound (3.27 g).

MS (ESI) m/z: 337 $(M+H)^+$.

$^1$H-NMR (DMSO-$d_6$) δ: 12.60 (1H, brs), 8.48 (1H, t, J=5.6 Hz), 8.44 (1H, t, J=5.9 Hz), 8.31 (1H, d, J=8.8 Hz), 7.97 (3H, brs), 7.28-7.16 (5H, m), 4.58 (1H, m), 3.87 (1H, dd, J=16.8, 5.6 Hz), 3.78 (2H, d, J=5.9 Hz), 3.67 (1H, dd, J=17.1, 5.4 Hz), 3.56 (2H, brd, J=4.4 Hz), 3.05 (1H, dd, J=13.7, 3.9 Hz), 2.74 (1H, dd, J=13.7, 10.3 Hz).

Step 2

N-[4-(11,12-didehydrodibenzo[b,f]azocin-5(6H)-yl)-4-oxobutanoyl]glycylglycyl-L-phenylalanylglycine To a solution of the compound (2.09 g) obtained in step 1 in N,N-dimethylformamide (46.4 mL) were added triethylamine (0.804 mL) and 1-{[4-(11,12-didehydrodibenzo[b,f]azocin-5(6H)-yl)-4-oxobutanoyl]oxy}pyrrolidin-2,5-dione (1.87 g), and the mixture was stirred at room temperature for 21 h. The reaction mixture was concentrated under reduced pressure, and the resulting residue was purified by silica gel column chromatography [dichloromethane/methanol]. Diethyl ether was added to the resulting compound-containing dichloromethane solution to form a slurry, and the slurry was filtered and collected to obtain the titled compound (2.10 g).

MS (ESI) m/z: 624 $(M+H)^+$.

$^1$H-NMR (DMSO-$d_6$) δ: 8.20-7.91 (4H, m), 7.68-7.13 (13H, m), 4.98 (1H, dd, J=13.9, 3.2 Hz), 4.51-4.46 (1H, m), 3.73-3.47 (7H, m), 3.00 (1H, dd, J=13.9, 4.1 Hz), 2.73 (1H, t, J=11.7 Hz), 2.67-2.57 (1H, m), 2.29-2.22 (1H, m), 2.06-2.01 (1H, m), 1.80-1.73 (1H, m). (only observable peaks are listed).

Step 3

2,5-dioxopyrrolidin-1-yl-N-[4-(11,12-didehydrodibenzo[b,f]azocin-5(6H)-yl)-4-oxobutanoyl]glycylglycyl-L-phenylalanylglycinate To a solution of the compound (2.10 g) obtained in step 2 in N,N-dimethylformamide (33.7 mL) were added N-hydroxysuccinimide (426 mg) and 1-ethyl-3-(3-dimethylaminopropyl)carbodiimide hydrochloride (710 mg), and the mixture was stirred at room temperature for 16 h under a nitrogen atmosphere. The reaction mixture was diluted with dichloromethane, washed three times with ice water, and then dried over anhydrous sodium sulfate. The drying agent was filtered off, and the filtrate was concentrated under reduced pressure. Ethyl acetate was added to the oily residue and the solid was precipitated. The solvent was distilled off under reduced pressure. Diethyl ether was added to the resulting solid to form a slurry, and the slurry was filtered and collected to obtain the titled compound (2.18 g).

$^1$H-NMR (DMSO-$d_6$) δ: 8.74-8.69 (1H, m), 8.16-8.08 (2H, m), 8.00-7.93 (1H, m), 7.71-7.15 (13H, m), 5.00 (1H, dd, J=13.9, 3.0 Hz), 4.55-4.49 (1H, m), 4.27 (2H, t, J=6.0 Hz), 3.77-3.68 (1H, m), 3.64-3.50 (4H, m), 3.02 (1H, dd, J=13.9, 4.2 Hz), 2.82-2.73 (5H, m), 2.69-2.58 (1H, m), 2.33-2.24 (1H, m), 2.10-2.02 (1H, m), 1.83-1.75 (1H, m).

Step 4 bis(N,N-diethylethanaminium)N-[4-(11,12-didehydrodibenzo[b,f]azocin-5(6H)-yl)-4-oxobutanoyl]glycylglycyl-L-phenylalanyl-N-(2-{9-[(5R,7R,8R,12aR,14R,15R,15aR,16R)-14-(8,9-dihydro-6-thia-2,3,5-triazabenzo[cd]azulen-2(7H)-yl)-15-fluoro-16-hydroxy-2,10-dioxo-2,10-disulfidoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl)glycinamide (Drug-Linker 20)

To a solution of the compound (25.0 mg) obtained in step 23-2 of Example 3 in N,N-dimethylformamide (0.5 mL) were added triethylamine (8 L) and the compound (25.8 mg) obtained in step 3, and the mixture was stirred at room temperature for 2 h. Next, benzylamine (7 μL) was added to the reaction mixture, and the mixture was stirred at room temperature for 1 h. Then, 10 mM aqueous triethylammonium acetate and methanol were added to the reaction mixture. Subsequently, purification was performed by C18 silica gel column chromatography [10 mM aqueous triethylammonium acetate/acetonitrile], preparative HPLC [10 mM aqueous triethylammonium acetate/acetonitrile; acetonitrile: 30%-50% (0 min-40 min)], and preparative HPLC [10 mM aqueous triethylammonium acetate/methanol; methanol: 50%-90% (0 min-40 min)] to give the titled compound (33.1 mg).

MS (ESI) m/z: 1398 $(M+H)^+$.

$^1$H-NMR ($CD_3OD$) δ: 8.58 (1H, brs), 8.39 (1H, d, J=8.5 Hz), 8.00 (1H, brs), 7.71 (1H, brs), 7.64-7.49 (2H, m), 7.44-7.37 (3H, m), 7.32-7.10 (8H, m), 6.59 (1H, d, J=15.1 Hz), 6.23 (1H, d, J=8.5 Hz), 5.65-5.36 (3H, m), 5.03 (1H, dd, J=16.6, 14.2 Hz), 4.57-4.38 (5H, m), 4.30-4.17 (2H, m), 4.07-3.95 (2H, m), 3.94-3.50 (9H, m), 3.50-3.35 (1H, m),, 3.19 (12H, q, J=7.3 Hz), 3.18-3.07 (3H, m), 3.04-2.73 (4H, m), 2.40-2.11 (4H, m), 2.05-1.92 (1H, m), 1.29 (18H, t, J=7.3 Hz).

Example 8: To Synthesize Drug-Linker 21

Synthetic Scheme

[Formula 104]

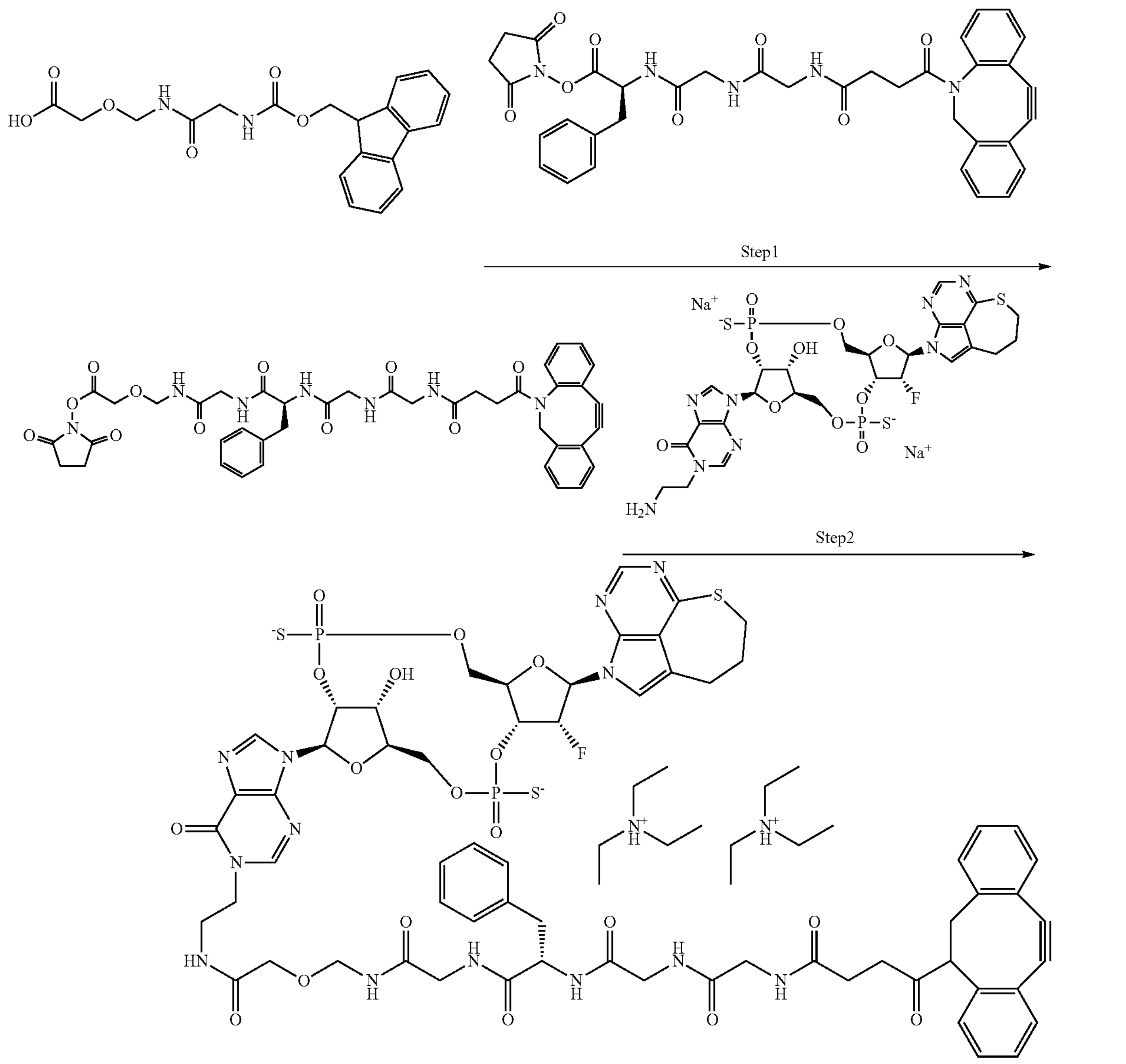

Drug-linker 21

Step 1

N-[4-(11,12-didehydrodibenzo[b,f]azocin-5(6H)-yl)-4-oxobutanoyl]glycylglycyl-L-phenylalanyl-N-({2-[(2,5-dioxopyrrolidin-1-yl)oxy]-2-oxoethoxy}methyl)glycinamide To a solution of {[(N-{[(9H-fluoren-9-yl)methoxy]carbonyl]glycyl)amino]methoxy}acetic acid (955 mg), described in the literature (WO2014/057687), in N,N-dimethylformamide (8.0 mL) was added 1,8-diazabicyclo[5.4.0]-7-undecene (0.74 mL), and the mixture was stirred at room temperature for 1 h (reaction mixture A). To a solution of the compound (938 mg) obtained in step 7 of Example 5 in N,N-dimethylformamide (8.0 mL) were added N-hydroxysuccinimide (229 mg) and 1-ethyl-3-(3-dimethylaminopropyl)carbodiimide hydrochloride (380 mg), and the mixture was stirred at room temperature for 50 min (reaction mixture B). The reaction mixture A was added to the reaction mixture B, and the mixture was stirred at room temperature for 1 h. The reaction mixture was admixed with dichloromethane (50 mL) and 10% aqueous citric acid, (10 mL) and was extracted with dichloromethane. The organic layer was washed with brine and dried over anhydrous sodium sulfate. The drying agent was filtered off, and the filtrate was concentrated under reduced pressure. The residue was purified by silica gel column chromatography [chloroform/lower layer of chloroform/methanol/water=7:3:1]. To a solution of the resulting compound in N,N-dimethylformamide (8.0 mL) were added N-hydroxysuccinimide (229 mg) and 1-ethyl-3-(3-dimethylaminopropyl)carbodiimide hydrochloride (380 mg), and the mixture was stirred at room temperature for 30 min. The reaction mixture was admixed with dichloromethane (100 mL) and water (25 mL), and was extracted with dichloromethane. The organic layer was washed with brine and dried over anhydrous sodium sulfate. The drying agent was filtered off, and the filtrate was concentrated under reduced pressure. The residue was purified by silica gel column chromatography [chloroform/methanol]. Fractions containing the target product were concentrated under reduced pressure, and diethyl ether was added to the residue to form a slurry. The resulting solid was filtered and collected to give the titled compound (412 mg).

$^1$H-NMR (DMSO-$d_6$) δ: 8.72 (1H, m), 8.32 (1H, m), 8.17-7.96 (3H, m), 7.71-7.15 (13H, m), 5.01 (1H, d, J=13.9 Hz), 4.70-4.48 (5H, m), 3.81-3.51 (7H, m), 3.05 (1H, dd, J=14.2, 3.9 Hz), 2.83 (4H, s), 2.80 (1H, m), 2.64 (1H, m), 2.28 (1H, m), 2.07 (1H, m), 1.79 (1H, m).

Step 2 bis(N,N-diethylethanaminium)N-[4-(11,12-didehydrodibenzo[b,f]azocin-5(6H)-yl)-4-oxobutanoyl]glycylglycyl-L-phenylalanyl-N-({2-[(2-{9-[(5R,7R,8R,12aR,14R,15R,15aR,16R)-14-(8,9-dihydro-6-thia-2,3,5-triazabenzo[cd]azulen-2(7H)-yl)-15-fluoro-16-hydroxy-2,10-dioxo-2,10-disulfidoctahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethyl)amino]-2-oxoethoxy}methyl)glycinamide (Drug-Linker 21)

By using the compound (15.0 mg) obtained in step 23-2 of Example 3 and the compound (17.4 mg) obtained in step 1, the reaction was carried out in substantially the same manner as in step 4 of Example 7. Subsequently, purification was performed by C18 silica gel column chromatography [10 mM aqueous triethylammonium acetate/acetonitrile], preparative HPLC [10 mM aqueous triethylammonium acetate/acetonitrile; acetonitrile: 25%-50% (0 min-40 min)], and preparative HPLC [10 mM aqueous triethylammonium acetate/methanol; methanol: 40%-90% (0 min-40 min)] to give the titled compound (21.8 mg).

MS (ESI) m/z: 1485 $(M+H)^+$.

$^1$H-NMR ($CD_3OD$) δ: 8.61 (1H, brs), 8.41-8.34 (1H, m), 8.10-8.05 (1H, m), 7.72-7.37 (6H, m), 7.32-7.12 (8H, m), 6.63-6.50 (1H, m), 6.27-6.22 (1H, m), 5.65-5.31 (3H, m), 5.07-4.94 (1H, m), 4.68-4.20 (10H, m), 4.11-3.53 (14H, m), 3.26-3.08 (2H, m), 3.19 (12H, q, J=7.3 Hz), 3.06-2.67 (4H, m), 2.40-2.11 (4H, m), 2.05-1.88 (1H, m), 1.29 (18H, t, J=7.3 Hz).

Example 9: To Synthesize Glycan-Remodeled Antibody 1

Preparation of Anti-TROP2 Antibody 1-[SG-(N3)$_2$]$_2$

Synthetic Scheme

[Formula 105]

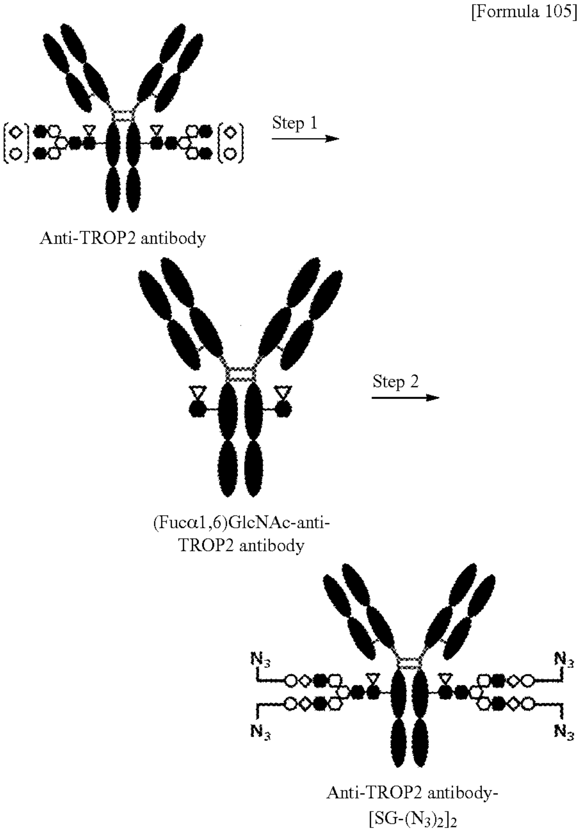

Step 1

Preparation of (Fucα1,6)GlcNAc-Anti-TROP2 Antibody 1

Phosphate-buffered saline (6.0 mL, 16.55 mg/mL, pH 6.0) containing anti-TROP2 antibody 1 prepared according to Reference Example 5 was admixed with wild-type EndoS-containing phosphate-buffered saline (0.064 mL, 7.70 mg/mL, pH 6.0), and the mixture was shaken at 37° C. for 2 h. The progress of the reaction was checked by Experion electrophoresis station (produced by BIO-RAD). After completion of the reaction, purification by affinity chromatography and hydroxyapatite column chromatography were performed according to the following methods.

(1) Purification by Affinity Chromatography

Purification apparatus: AKTA avant 25 (produced by GE Healthcare)

Column: HiTrap rProtein A FF (5 mL) (produced by GE Healthcare)

Flow rate: 5 mL/min (1.25 mL/min at the time of charging)

At the time of column binding, the reaction mixture was added directly to the column, and the binding buffer [20 mM phosphate buffer (pH 6.0)] was made to flow at 1.25 mL/min for 2 CV (column volume), and then flowed at 5 mL/min for 5 CV. At the time of intermediate washing, 15 CV of washing solution [20 mM phosphate buffer (pH 7.0), 0.5 M sodium chloride solution] was flowed. In elution, 6 CV of elution buffer (ImmunoPure IgG Elution buffer; produced by PIERCE) was flowed. The eluate was immediately neutralized with 1M Tris buffer (pH 9.0). Fractions containing the target product were subjected to buffer exchange to 5 mM phosphate buffer and 50 mM 2-morpholinoethanesulfonic acid (MES) solution (pH 6.8) according to the method described in common operation C. The antibody concentration in the resulting buffer solution was measured according to the method described in common operation B, and a crude purified titled antibody solution (12.38 mg/mL, 8 mL) was thus obtained.

(2) Purification by Hydroxyapatite Chromatography

Purification apparatus: AKTA avant 25 (produced by GE Healthcare)

Column: Bio-Scale Mini CHT Type I cartridge (5 mL) (produced by BIO-RAD)

Flow rate: 5 mL/min (1.25 mL/min at the time of charging)

The solution obtained in (1) above was added to the column, and solution A [5 mM phosphate buffer, 50 mM MES solution (pH 6.8)] was made to flow at 1.25 mL/min for 2 CV, and then flowed at 5 mL/min for 3 CV. Subsequently, solution A and solution B [5 mM phosphate buffer, 50 mM MES solution (pH 6.8), 2 M sodium chloride solution] were used for elution. The elution conditions are solution A:solution B=100:0 to 0:100 (5 CV). In addition, 5 CV of washing solution [500 mM phosphate buffer (pH 6.5)] was flowed. Fractions containing the target product were subjected to buffer exchange into 20 mM phosphate buffer (pH 6.0) according to the method described in common operation C. The antibody concentration in the resulting buffer solution was measured according to the method described in common operation B, and a titled antibody solution (12.30 mg/mL, 8 mL) was thus obtained.

Step 2

Preparation of Anti-TROP2 Antibody 1-[SG-(N3)$_2$]$_2$

To 20 mM phosphate buffer solution (12.30 mg/mL, 8 mL, pH 6.0) containing the antibody obtained in step 1 were added [$N_3$-PEG(3)]$_2$-SG(10)Ox (compound 1-10 of WO2018/003983) (22.7 mg) and EndoS (D233Q/Q303L)-containing phosphate-buffered saline (0.339 mL, 5.8 mg/mL, pH 6.0), and the mixture was shaken at 30° C. for 4.5 h. The progress of the reaction was checked by Experion electrophoresis station (produced by BIO-RAD). After completion of the reaction, purification, like in step 1, by affinity chromatography and hydroxyapatite column chromatography were performed. Fractions containing the target product were subjected to buffer exchange to phosphate buffered saline (pH 6.0) according to the method described in common operation C. The antibody concentration in the resulting buffer solution was measured according to the method described in common operation B, and a titled antibody solution (10.24 mg/mL, 9 mL) was thus obtained.

Example 10: To Synthesize Glycan-Remodeled Antibody 2

Preparation of Modified Anti-TROP2 Antibody-[SG-($N_3$)$_2$]$_2$

Synthetic Scheme

[Formula 106]

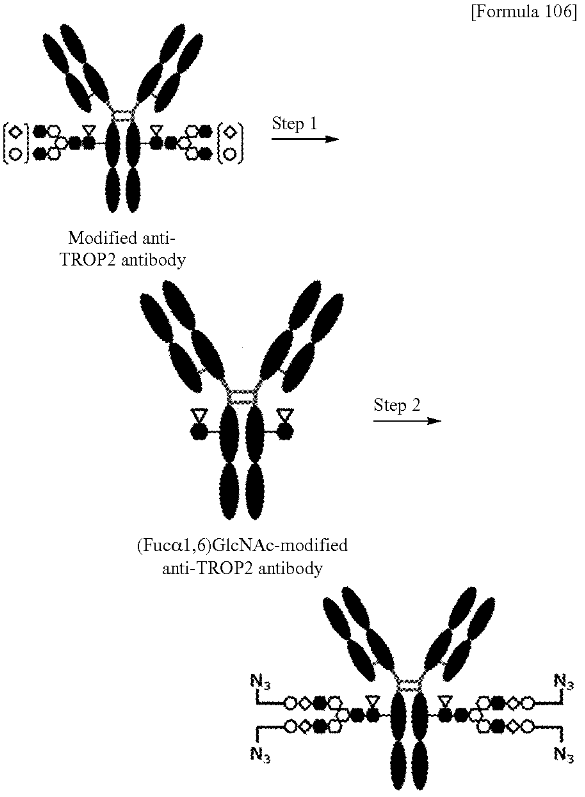

Modified anti-TROP2 antibody-[SG-($N_3$)$_2$]$_2$

Step 1

Preparation of (Fucα1,6)GlcNAc-Modified Anti-TROP2 Antibody

By using phosphate-buffered saline (10 mL, 16.75 mg/mL, pH 6.0) containing the modified anti-TROP2 antibody prepared according to Reference Example 6, substantially the same procedure as in step 1 of Example 9 was repeated. Then, the titled antibody-containing 20 mM phosphate buffer (18.11 mg/mL, 7.5 mL, pH 6.0) was obtained.

Step 2

Preparation of Modified Anti-TROP2 Antibody-[SG-($N_3$)$_2$]$_2$

By using 20 mM phosphate buffer (18.11 mg/mL, 7.5 mL, pH 6.0) containing the antibody obtained in step 1 and [$N_3$-PEG(3)]$_2$-SG(10)Ox (32 mg), substantially the same procedure as in step 2 of Example 9 was repeated. Then, the titled antibody-containing phosphate buffered saline (11.03 mg/mL, 10.5 mL, pH 6.0) was obtained.

Example 11: To Synthesize Glycan-Remodeled Antibody 3

Preparation of Modified Anti-CD70 Antibody 1-[SG-$(N_3)_2$]$_2$

[Formula 107]

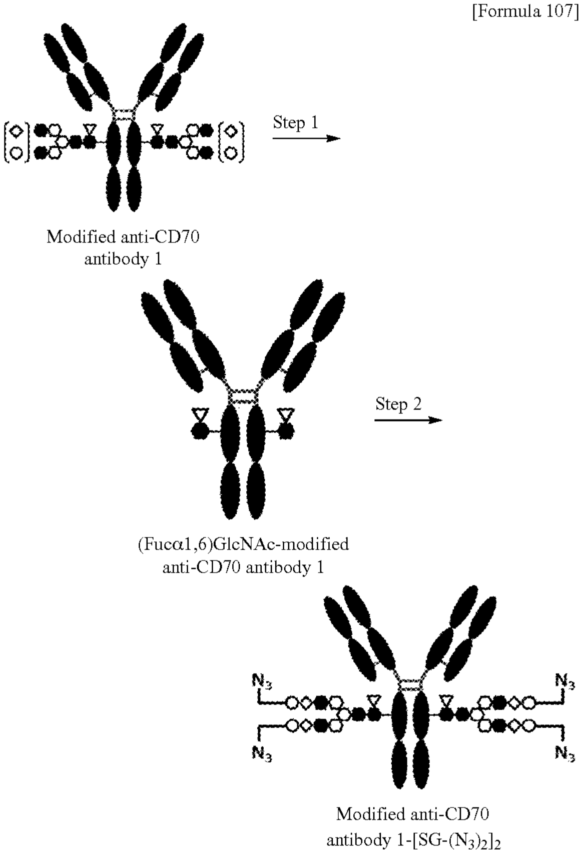

Step 1

Preparation of (Fucα1,6)GlcNAc-Modified Anti-CD70 Antibody 1

By using phosphate-buffered saline (3.0 mL, 16.11 mg/mL, pH 6.0) containing the modified anti-CD70 antibody 1 prepared according to Reference Example 3, substantially the same procedure as in step 1 of Example 9 was repeated. Then, the titled antibody-containing 20 mM phosphate buffer (6.41 mg/mL, 5.5 mL, pH 6.0) was obtained.

[0435](Step 2)

Preparation of Modified Anti-CD70 Antibody 1-[SG-$(N_3)_2$]$_2$

By using 20 mM phosphate buffer (6.41 mg/mL, 5.5 mL, pH 6.0) containing the antibody obtained in step 1 and [$N_3$-PEG(3)]$_2$-SG(10)Ox (10 mg), substantially the same procedure as in step 2 of Example 9 was repeated. Then, the titled antibody-containing phosphate buffered saline (9.24 mg/mL, 3.25 mL, pH 6.0) was obtained.

Example 12: To Synthesize Glycan-Remodeled Antibody 4

Preparation of Modified Anti-CD70 Antibody 2-[SG-$(N_3)_2$]$_2$

Synthetic Scheme

[Formula 108]

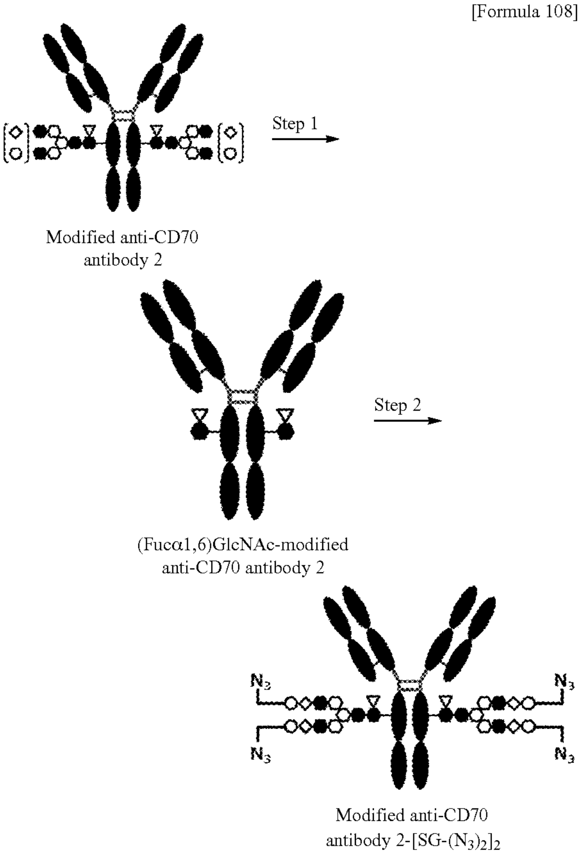

Preparation of (Fucα1,6)GlcNAc-Modified Anti-CD70 Antibody 2

By using phosphate-buffered saline (10.0 mL, 14.00 mg/mL, pH 6.0) containing the modified anti-CD70 antibody 2 prepared according to Reference Example 4, substantially the same procedure as in step 1 of Example 9 was repeated. Then, the titled antibody-containing 20 mM phosphate buffer (18.67 mg/mL, 6 mL, pH 6.0) was obtained.

Step 2

Preparation of Modified Anti-CD70 Antibody 2-[SG-$(N_3)_2$]$_2$

By using 20 mM phosphate buffer (18.67 mg/mL, 6 mL, pH 6.0) containing the antibody obtained in step 1 and [$N_3$-PEG(3)]$_2$-SG(10)Ox (26 mg), substantially the same procedure as in step 2 of Example 9 was repeated. Then, the titled antibody-containing phosphate buffered saline (11.39 mg/mL, 7.5 mL, pH 6.0) was obtained.

Example 13: To Synthesize Glycan-Remodeled Antibody 5

Preparation of Modified Anti-EGFR Antibody 1-[SG-$(N_3)_2$]$_2$

Synthetic Scheme

[Formula 109]

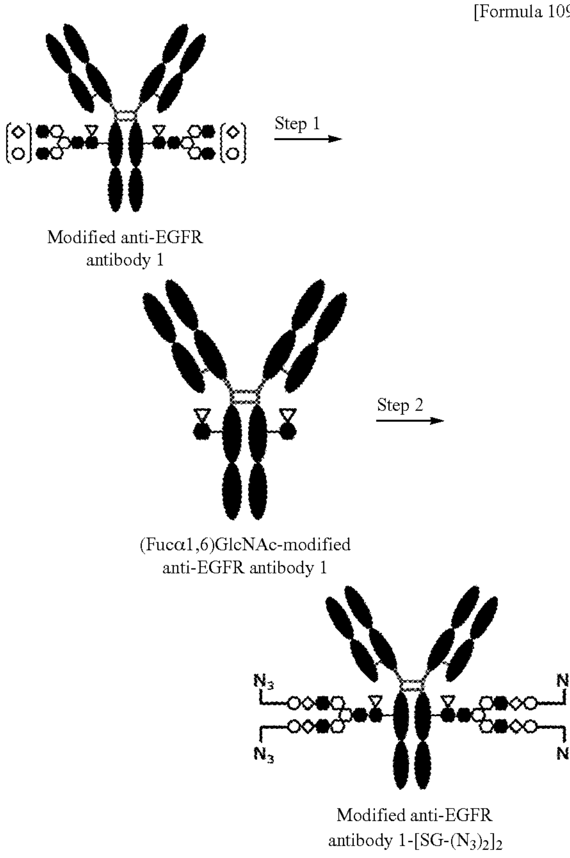

Step 1

Preparation of (Fucα1, 6)GlcNAc-Modified Anti-EGFR Antibody 1

By using phosphate-buffered saline (10.0 mL, 14.00 mg/mL, pH 6.0) containing the modified anti-EGFR antibody 1 prepared according to Reference Example 7, substantially the same procedure as in step 1 of Example 9 was repeated. Then, the titled antibody-containing 20 mM phosphate buffer (16.70 mg/mL, 7.5 mL, pH 6.0) was obtained.

Step 2

Preparation of Modified Anti-EGFR Antibody 1-[SG-$(N_3)_2$]$_2$

By using 20 mM phosphate buffer (16.70 mg/mL, 7.5 mL, pH 6.0) containing the antibody obtained in step 1 and [$N_3$-PEG(3)]$_2$-SG(10)Ox (29 mg), substantially the same procedure as in step 2 of Example 9 was repeated. Then, the titled antibody-containing phosphate buffered saline (10.49 mg/mL, 10 mL, pH 6.0) was obtained.

Example 14: To Synthesize Glycan-Remodeled Antibody 6

Preparation of Modified Anti-EGFR Antibody 2-[SG-$(N_3)_2$]$_2$

Synthetic Scheme

[Formula 110]

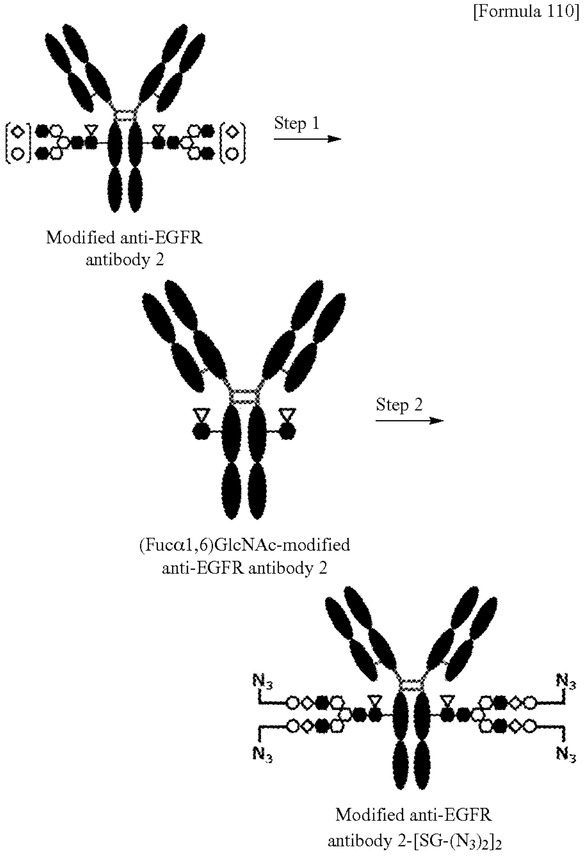

Step 1

Preparation of (Fucα1,6)GlcNAc-Modified Anti-EGFR Antibody 2

By using phosphate-buffered saline (10.0 mL, 14.10 mg/mL, pH 6.0) containing the modified anti-EGFR antibody 2 prepared according to Reference Example 8, substantially the same procedure as in step 1 of Example 9 was repeated. Then, the titled antibody-containing 20 mM phosphate buffer (16.88 mg/mL, 6 mL, pH 6.0) was obtained.

Step 2

Preparation of Modified Anti-EGFR Antibody 2-[SG-$(N_3)_2$]$_2$

By using 20 mM phosphate buffer (16.88 mg/mL, 6 mL, pH 6.0) containing the antibody obtained in step 1 and $[N_3\text{-PEG(3)}]_2$-SG(10)Ox (23 mg), substantially the same procedure as in step 2 of Example 9 was repeated. Then, the titled antibody-containing phosphate buffered saline (8.34 mg/mL, 6.75 mL, pH 6.0) was obtained.

Example 15: To Synthesize Antibody-Drug Conjugate 1 (Synthesis of Anti-TROP2 Antibody 1-CDN Conjugate (1))

Glycan-remodeled antibody 1-containing phosphate-buffered saline (pH 6.0) solution (10.24 mg/mL, 0.500 mL) was diluted with propylene glycol (0.250 mL). The resulting solution was admixed with a mixture of dimethylsulfoxide solution of drug-linker 2b (10 mM, 0.085 mL, 24 equivalents per antibody molecule) and propylene glycol (0.165 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (3.5 mL).

The following results were obtained by analysis according to the methods described in common operations E and G.

Antibody concentration: 0.89 mg/mL

Antibody yield: 3.12 mg (62%)

Average number of drugs conjugated: 3.7

Example 16: To Synthesize Antibody-Drug Conjugate 2 (Synthesis of Anti-TROP2 Antibody 2-CDN Conjugate (1))

Glycan-remodeled antibody 2-containing phosphate-buffered saline (pH 6.0) solution (11.03 mg/mL, 1.00 mL) was diluted with propylene glycol (0.500 mL). The resulting solution was admixed with a mixture of dimethylsulfoxide solution of drug-linker 17a (10 mM, 0.061 mL, 8 equivalents per antibody molecule) and propylene glycol (0.439 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.26 mg/mL

Antibody yield: 8.16 mg (74%)

Average number of drugs conjugated: 3.5

Example 17: To Synthesize Antibody-Drug Conjugate 3 (Synthesis of Anti-TROP2 Antibody 2-CDN Conjugate (2))

Glycan-remodeled antibody 2-containing phosphate-buffered saline (pH 6.0) solution (11.03 mg/mL, 1.00 mL) was diluted with propylene glycol (0.500 mL). The resulting solution was admixed with a mixture of dimethylsulfoxide solution of drug-linker 20 (10 mM, 0.061 mL, 8 equivalents per antibody molecule) and propylene glycol (0.439 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.30 mg/mL

Antibody yield: 8.45 mg (77%)

Average number of drugs conjugated: 3.5

Example 18: To Synthesize Antibody-Drug Conjugate 4 (Synthesis of Anti-TROP2 Antibody 2-CDN Conjugate (3))

Glycan-remodeled antibody 2-containing phosphate-buffered saline (pH 6.0) solution (11.03 mg/mL, 1.00 mL) was diluted with propylene glycol (0.500 mL). The resulting solution was admixed with a mixture of dimethylsulfoxide solution of drug-linker 21 (10 mM, 0.061 mL, 8 equivalents per antibody molecule) and propylene glycol (0.439 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.33 mg/mL

Antibody yield: 8.62 mg (78%)

Average number of drugs conjugated: 3.6

Example 19: To Synthesize Antibody-Drug Conjugate 5 (Synthesis of Anti-CD70 Antibody 1-CDN Conjugate (1))

Glycan-remodeled antibody 3-containing phosphate-buffered saline (pH 6.0) solution (9.24 mg/mL, 1.00 mL) was diluted with propylene glycol (0.500 mL). The resulting solution was admixed with a mixture of dimethylsulfoxide solution of drug-linker 17a (10 mM, 0.051 mL, 8 equivalents per antibody molecule) and propylene glycol (0.449 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.08 mg/mL

Antibody yield: 7.02 mg (76%)

Average number of drugs conjugated: 3.8

Example 20: To Synthesize Antibody-Drug Conjugate 6 (Synthesis of Anti-CD70 Antibody 2-CDN Conjugate (1))

Glycan-remodeled antibody 4-containing phosphate-buffered saline (pH 6.0) solution (11.39 mg/mL, 1.00 mL) was diluted with propylene glycol (0.500 mL). The resulting solution was admixed with a mixture of dimethylsulfoxide solution of drug-linker 17a (10 mM, 0.063 mL, 8 equivalents per antibody molecule) and propylene glycol (0.437 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.33 mg/mL

Antibody yield: 8.65 mg (76%)

Average number of drugs conjugated: 3.7

Example 21: To Synthesize Antibody-Drug Conjugate 7 (Synthesis of Anti-EGFR Antibody 1-CDN Conjugate (1))

Glycan-remodeled antibody 5-containing phosphate-buffered saline (pH 6.0) solution (10.49 mg/mL, 1.00 mL) was diluted with propylene glycol (0.500 mL). The resulting solution was admixed with a mixture of dimethylsulfoxide solution of drug-linker 17a (10 mM, 0.058 mL, 8 equivalents per antibody molecule) and propylene glycol (0.442 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (7.0 mL).

The following results were obtained by analysis according to the methods described in common operations E and G.

Antibody concentration: 0.69 mg/mL

Antibody yield: 4.84 mg (48%)

Average number of drugs conjugated: 3.6

Example 22: To Synthesize Antibody-Drug Conjugate 8 (Synthesis of Anti-EGFR Antibody 2-CDN Conjugate (1))

Glycan-remodeled antibody 6-containing phosphate-buffered saline (pH 6.0) solution (8.34 mg/mL, 1.00 mL) was diluted with propylene glycol (0.500 mL). The resulting solution was admixed with a mixture of dimethylsulfoxide solution of drug-linker 17a (10 mM, 0.055 mL, 9.6 equivalents per antibody molecule) and propylene glycol (0.445 mL), and the reaction was carried out for 2 days at room temperature while using a tube rotator (MTR-103, AS ONE Corporation). The reaction mixture was subjected to purification by the method described in common operation D to give the target antibody-drug conjugate-containing ABS solution (7.0 mL).

The following results were obtained by analysis according to the methods described in common operations E and G.

Antibody concentration: 0.52 mg/mL

Antibody yield: 3.62 mg (43%)

Average number of drugs conjugated: 3.8

Example 23: To Synthesize Glycan-Remodeled Antibody 7 Preparation of Modified Anti-TROP2 Antibody-$[MSG1-(N_3)]_2$ Synthetic Scheme

[Formula 111]

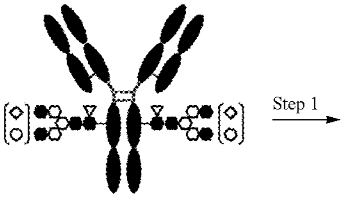

Modified anti-TROP2 antibody

-continued

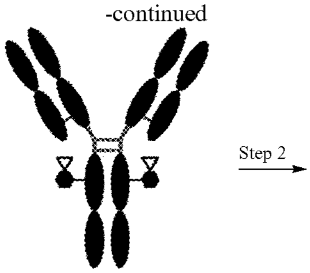

(Fucα1,6)GlcNAc-modified anti-TROP2 antibody

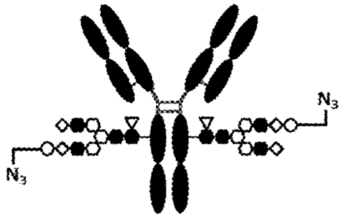

Modified anti-TROP2 antibody-$[MSG1-(N_3)]_2$

Preparation of (Fucα1,6)GlcNAc-Modified Anti-TROP2 Antibody

By using the modified anti-TROP2 antibody-containing phosphate-buffered saline (5 mL, 16.75 mg/mL, pH 6.0), substantially the same procedure as in step 1 of Example 9 was repeated. Then, the titled antibody-containing 20 mM phosphate buffer (9.81 mg/mL, 7.5 mL, pH 6.0) was obtained.

Step 2

Preparation of Modified Anti-TROP2 Antibody-$[MSG1-(N_3)]_2$

By using 20 mM phosphate buffer (9.81 mg/mL, 7.5 mL, pH 6.0) containing the antibody obtained in step 1 and $[N_3$-PEG(3)]-MSG1(9)Ox (compound 1-11 in WO2018/003983) (12 mg), substantially the same procedure as in step 2 of Example 9 was repeated. Then, the titled antibody-containing phosphate buffered saline (13.22 mg/mL, 5 mL, pH 6.0) was obtained.

Example 24: To Synthesize Glycan-Remodeled Antibody 8

Preparation of Modified Anti-CD70 Antibody 2-$[MSG1-(N_3)]_2$

[Formula 112]

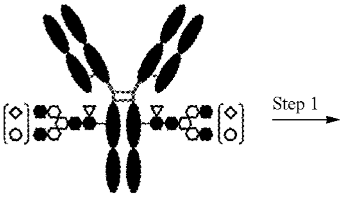

Modified anti-CD70 antibody 2

-continued

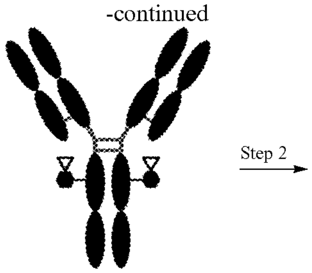

(Fucα1,6)GlcNAc-modified anti-CD70 antibody 2

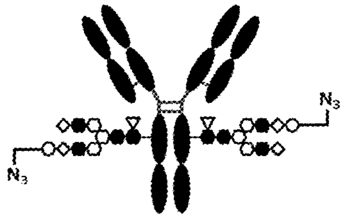

Modified anti-CD70 antibody 2-[MSG1-$(N_3)$]$_2$

Step 1

Preparation of (Fucα1,6)GlcNAc-Modified Anti-CD70 Antibody 2

By using the modified anti-CD70 antibody 2-containing phosphate-buffered saline (1.6 mL, 13.44 mg/mL, pH 6.0), substantially the same procedure as in step 1 of Example 9 was repeated. Then, the titled antibody-containing 20 mM phosphate buffer (8.96 mg/mL, 2 mL, pH 6.0) was obtained.

Step 2

Preparation of Modified Anti-CD70 Antibody 2-[MSG1-$(N_3)$]$_2$

By using 20 mM phosphate buffer (8.96 mg/mL, 2 mL, pH 6.0) containing the antibody obtained in step 1 and [$N_3$-PEG(3)]-MSG1(9)Ox (4 mg), substantially the same procedure as in step 2 of Example 9 was repeated. Then, the titled antibody-containing phosphate buffered saline (12.20 mg/mL, 1.2 mL, pH 6.0) was obtained.

Example 25: To Synthesize Glycan-Remodeled Antibody 9

Preparation of Modified Anti-EGFR Antibody 1-[MSG1-$(N_3)$]$_2$

Synthetic Scheme

[Formula 113]

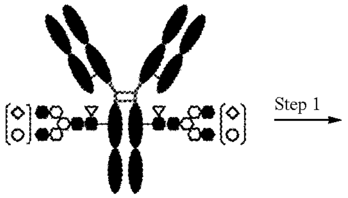

Modified anti-EGFR antibody 1

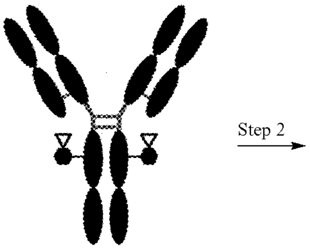

(Fucα1,6)GlcNAc-modified anti-EFGR antibody 1

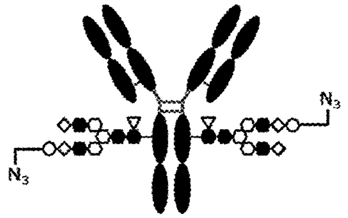

Modified anti-EGFR antibody 1-[MSG1-$(N_3)$]$_2$

Preparation of (Fucα1,6)GlcNAc-Modified Anti-EGFR Antibody 1

By using the modified anti-EGFR antibody 1-containing phosphate-buffered saline (10 mL, 14.00 mg/mL, pH 6.0), substantially the same procedure as in step 1 of Example 9 was repeated. Then, the titled antibody-containing 20 mM phosphate buffer (14.51 mg/mL, 7.5 mL, pH 6.0) was obtained.

Step 2

Preparation of Modified Anti-EGFR Antibody 1-[MSG1-$(N_3)$]$_2$

By using 20 mM phosphate buffer (14.51 mg/mL, 7.5 mL, pH 6.0) containing the antibody obtained in step 1 and [$N_3$-PEG(3)]-MSG1(9)Ox (17.3 mg), substantially the same procedure as in step 2 of Example 9 was repeated. Then, the titled antibody-containing phosphate buffered saline (13.34 mg/mL, 7.5 mL, pH 6.0) was obtained.

Example 26: To Synthesize Antibody-Drug Conjugate 9 (Synthesis of Anti-TROP2 Antibody 2-CDN Conjugate (4))

Glycan-remodeled antibody 7-containing phosphate-buffered saline (pH 6.0) solution (13.22 mg/mL, 1.00 mL) was diluted with propylene glycol (0.500 mL). The resulting solution was admixed with a mixture of dimethylsulfoxide solution of drug-linker 17a (10 mM, 0.073 mL, 8 equivalents per antibody molecule) and propylene glycol (0.427 mL), and the reaction was carried out for 2 days at room temperature while using a tube rotator. The reaction mixture was subjected to purification by the method in common operation D to give the target antibody-drug conjugate-containing ABS solution (6.5 mL).

The following results were obtained by analysis according to the methods described in common operations E and G.

Antibody concentration: 1.36 mg/mL

Antibody yield: 8.83 mg (67%)

Average number of drugs conjugated: 1.9

Example 27: To Synthesize Antibody-Drug Conjugate 10 (Synthesis of Anti-CD70 Antibody 2-CDN Conjugate (2))

Glycan-remodeled antibody 8-containing phosphate-buffered saline (pH 6.0) solution (12.20 mg/mL, 1.20 mL) was diluted with propylene glycol (0.600 mL). The resulting solution was admixed with a mixture of dimethylsulfoxide solution of drug-linker 17a (10 mM, 0.081 mL, 8 equivalents per antibody molecule) and propylene glycol (0.519 mL), and the reaction was carried out for 2 days at room temperature while using a tube rotator. The reaction mixture was subjected to purification by the method described in common operation D to give the target antibody-drug conjugate-containing ABS solution (7 mL).

The following results were obtained by analysis according to the methods described in common operations E and G.

Antibody concentration: 1.46 mg/mL

Antibody yield: 10.25 mg (70%)

Average number of drugs conjugated: 1.9

Example 28: To Synthesize Antibody-Drug Conjugate 11 (Synthesis of Anti-EGFR Antibody 1-CDN Conjugate (2))

Glycan-remodeled antibody 9-containing phosphate-buffered saline (pH 6.0) solution (13.34 mg/mL, 1.00 mL) was diluted with propylene glycol (0.500 mL). The resulting solution was admixed with a mixture of dimethylsulfoxide solution of drug-linker 17a (10 mM, 0.074 mL, 8 equivalents per antibody molecule) and propylene glycol (0.426 mL), and the reaction was carried out for 2 days at room temperature while using a tube rotator. The reaction mixture was subjected to purification by the method described in common operation D to give the target antibody-drug conjugate-containing ABS solution (6.5 mL).

The following results were obtained by analysis according to the methods described in common operations E and G.

Antibody concentration: 1.68 mg/mL

Antibody yield: 10.91 mg (82%)

Average number of drugs conjugated: 1.9

Reference Example 1: To Synthesize ML-RR-CDA-$2Na^+$

The ML-RR-CDA-$2Na^+$ used as a reference compound herein was synthesized according to the procedure described in Patent Literature 3 (WO2014/189805).

Reference Example 2: To Synthesize 2',3'-cGAMP

Here, 2',3'-cGAMP used as a reference compound herein was synthesized enzymatically from ATP and GTP using cGAS. The preparation of cGAS and the enzymatic reaction were carried out by modifying, if appropriate, the procedures described in the literatures (Immunity, 2013, 39, 1019-1031; Cell Rep. 2014, 6, 421-430). Purification was performed by column chromatography using a weakly basic anion exchange resin (DIAION WA10) and a synthetic adsorbent (SEPABEADS SP207SS).

Reference Example 3: To Produce Anti-CD70 Antibody 1

Anti-CD70 antibody 1 was produced with reference to WO2004/073656. The anti-CD70 antibody 1 used in the Examples is an IgG1 isotype with LALA mutation. FIG. 4 shows the light chain amino acid sequence (SEQ ID NO: 1) and the heavy chain amino acid sequence (SEQ ID NO: 2) of anti-CD70 antibody 1 used in the Examples. FIG. 16 shows the amino acid sequence of CDRL1 (SEQ ID NO: 35), the amino acid sequence of CDRL2 (SEQ ID NO: 36), the amino acid sequence of CDRL3 (SEQ ID NO: 37), the amino acid sequence of CDRH1 (SEQ ID NO: 38), the amino acid sequence of CDRH2 (SEQ ID NO: 39), and the amino acid sequence of CDRH3 (SEQ ID NO: 40) of this antibody.

Reference Example 4: To Produce Anti-CD70 Antibody 2

Anti-CD70 antibody 2 was produced with reference to WO2007/038637. The anti-CD70 antibody 2 used in the Examples is an IgG1 isotype with LALA mutation. FIG. 5 shows the light chain amino acid sequence (SEQ ID NO: 3) and the heavy chain amino acid sequence (SEQ ID NO: 4) of anti-CD70 antibody 2 used in the Examples. FIG. 17 shows the amino acid sequence of CDRL1 (SEQ ID NO: 41), the amino acid sequence of CDRL2 (SEQ ID NO: 42), the amino acid sequence of CDRL3 (SEQ ID NO: 43), the amino acid sequence of CDRH1 (SEQ ID NO: 44), the amino acid sequence of CDRH2 (SEQ ID NO: 45), and the amino acid sequence of CDRH3 (SEQ ID NO: 46) of this antibody.

Reference Example 5: To Produce Anti-TROP2 Antibody 1

Anti-TROP2 antibody 1 was produced with reference to WO2015/098099. The anti-TROP2 antibody 1 used in the Examples is an IgG1 isotype. FIG. 6 shows the light chain amino acid sequence (SEQ ID NO: 5) and the heavy chain amino acid sequence (SEQ ID NO: 6) of anti-TROP2 antibody 1 used in the Examples. FIG. 18 shows the amino acid sequence of CDRL1 (SEQ ID NO: 47), the amino acid sequence of CDRL2 (SEQ ID NO: 48), the amino acid sequence of CDRL3 (SEQ ID NO: 49), the amino acid sequence of CDRH1 (SEQ ID NO: 50), the amino acid sequence of CDRH2 (SEQ ID NO: 51), and the amino acid sequence of CDRH3 (SEQ ID NO: 52) of this antibody.

Reference Example 6: To Produce Anti-TROP2 Antibody 2

Anti-TROP2 antibody 1 was produced with reference to WO2015/098099. The anti-TROP2 antibody 1 used in the Examples is an IgG1 isotype. Anti-TROP2 antibody 2 was created by introducing LALA mutation into the anti-TROP2 antibody 1. FIG. 7 shows the light chain amino acid sequence (SEQ ID NO: 7) and the heavy chain amino acid sequence (SEQ ID NO: 8) of anti-TROP2 antibody 2 used in the Examples. FIG. 19 shows the amino acid sequence of CDRL1 (SEQ ID NO: 53), the amino acid sequence of CDRL2 (SEQ ID NO: 54), the amino acid sequence of CDRL3 (SEQ ID NO: 55), the amino acid sequence of CDRH1 (SEQ ID NO: 56), the amino acid sequence of CDRH2 (SEQ ID NO: 57), or the amino acid sequence of CDRH3 (SEQ ID NO: 58) of this antibody.

Reference Example 7: To Produce Anti-EGFR Antibody 1

Anti-EGFR antibody 1 was produced with reference to the Vectibix 100 mg Intravenous Infusion Review Results Report (Mar. 5, 2010, Review and Administration Division, Pharmaceutical and Food Safety Bureau). The anti-EGFR antibody 1 used in the Examples is an IgG1 isotype with LALA mutation. FIG. 8 shows the light chain amino acid sequence (SEQ ID NO: 9) and the heavy chain amino acid sequence (SEQ ID NO: 10) of anti-EGFR antibody 1 used in the Examples. FIG. 20 shows the amino acid sequence of CDRL1 (SEQ ID NO: 59), the amino acid sequence of CDRL2 (SEQ ID NO: 60), the amino acid sequence of CDRL3 (SEQ ID NO: 61), the amino acid sequence of CDRH1 (SEQ ID NO: 62), the amino acid sequence of CDRH2 (SEQ ID NO: 63), and the amino acid sequence of CDRH3 (SEQ ID NO: 64) of this antibody. Each CDR sequence was referred to WO1998/050433.

Reference Example 8: To Produce Anti-EGFR Antibody 2

Anti-EGFR antibody 2 was produced with reference to WO2002/092771. The anti-EGFR antibody 2 used in the Examples is an IgG1 isotype with LALA mutation. FIG. 9 shows the light chain amino acid sequence (SEQ ID NO: 11) and the heavy chain amino acid sequence (SEQ ID NO: 12) of anti-EGFR antibody 2 used in the Examples. FIG. 21 shows the amino acid sequence of CDRL1 (SEQ ID NO: 65), the amino acid sequence of CDRL2 (SEQ ID NO: 66), the amino acid sequence of CDRL3 (SEQ ID NO: 67), the amino acid sequence of CDRH1 (SEQ ID NO: 68), the amino acid sequence of CDRH2 (SEQ ID NO: 69), and the amino acid sequence of CDRH3 (SEQ ID NO: 70) of this antibody.

(Test Example 1) To Evaluate STING Agonist Activity by Using Reporter Cells

<Reporter Gene Assay>

Human STING agonist activity was evaluated using THP1-Dual™ cells (HAQ mutant) (InvivoGen, CA, US), in which activation of the interferon regulatory factor-3 (IRF3) pathway, which is downstream of the STING pathway, could be checked. Mouse STING agonist activity was evaluated using RAW-Dual™ cells (InvivoGen).

The assay was conducted as follows. First, each test compound diluted in PBS was dispensed at 20 μL/well of a transparent 96-well plate (Corning, NY, US). Then, reporter cells suspended in assay buffer (RPMI 1640 medium or DMEM medium containing 10% bovine serum albumin) were added at 180 μL/well ($1\times10^5$ cells/well) to start stimulation. The cells were cultured for 24 h under conditions at 37° C. and 5% $CO_2$, and then centrifuged to collect the supernatant. Next, 6 μL of the collected supernatant was added to a white 384-well plate, and 15 μL of QUANTI-Luc (InvivoGen) solution was added thereto. After well mixing, the luminescence was measured using a plate reader (PerkinElmer, MA, US). The value for the maximum count in cells treated with 1.37 to 100 M ML-RR-CDA-2Na$^+$ (Compound 21 in WO2014/189805) was set to 100% and the count in cells treated with PBS was set to 0%. Then, the concentration of each test compound required to obtain 50% count was calculated as the value for EC50 (μM) by using GraphPad Prism (GraphPad Software, CA, US). Table 1 shows the results of the assay for the human STING agonist activity.

TABLE 1

| Compound No. | THP1-Dual IRF EC50 (μM) |
|---|---|
| 6b (Example 1) | 2.1 |
| 34a (Example 2) | 0.20 |
| 49b (Example 3) | 0.41 |
| 50b (Example 4) | 0.20 |
| ML-RR-CDA•2Na$^+$ | 4.2 |
| 2' 3'-cGAMP | 21.8 |

The results have revealed that each compound used in an antibody-drug conjugate of the present invention has agonist activity against human STING. It has also found that the agonist activity against mouse STING was equivalent to or higher than that of existing CDNs.

(Test Example 2) Protein Thermal Shift Assay Using Recombinant STING C-Terminal Binding Domain Protein (i) To Construct Various Expression Plasmids <Construction of Human TMEM173-Expressing Plasmid>

The plasmid for expressing human STING (sometimes, herein referred to as human TMEM173) in mammalian cells was a human TMEM173 cDNA clone (a plasmid for expressing Accession NM_198282.3, H232 (REF) mutant STING) (GeneCopoeia, MD, US) in which arginine (R) at 232-position was mutated to histidine (H) (herein, referred to as H232 mutant or REF mutant), and was purchased. The human H232 (REF) mutant STING amino acid sequence is provided as SEQ ID NO: 15 and the nucleotide sequence is provided as SEQ ID NO: 16. In addition, the H232 mutant STING expression plasmid was used as a template for site-directed mutagenesis based on the Inverse PCR method. The expression plasmid for each of wild-type STING and mutant STING were constructed. Specifically, two different primers (5'-CGTGCTGGCATCAAGGATCGGGTTTAC-3' (H232R(WT)fwd) (SEQ ID NO: 25) and 5'-GTCACCGGTCTGCTGGGGCAGTTTATC-3'(H232R(WT) rev) (SEQ ID NO: 26)) and a KOD-Plus-Mutagenesis Kit (SMK-101) (TOYOBO) were used to perform PCR. DNA sequencing confirmed the construction of the desired wild-type (R232) STING expression plasmid. The amino acid sequence of human wild-type STING is shown in SEQ ID NO: 13 and the nucleotide sequence is shown in SEQ ID NO: 14.

Next, HAQ (R71H, G230A and R293Q) mutant was generated by substantially the same method as for the wild-type STING expression plasmid. Specifically, the H232 mutant STING expression plasmid was used as a template and two different primers (5'-GCTGACGCTGG-CATCAAGGATCGGGTTTAC-3' (H 232R/G230A fwd) (SEQ ID NO: 27) and 5'-GGTCTGCTGGGGCAGTT-TATCCAGG-3' (H232R/G230A rev) (SEQ ID NO: 28) as well as the Mutagenesis Kit were used to perform PCR. The G230A mutant STING plasmid was obtained by introducing mutations in two sites simultaneously. Further, the G230A mutant STING expression plasmid was used as a template, and two different primers (5'-CACCACATCCACTC CAGGTACCGG-3'(R71H fwd)(SEQ ID NO: 29) and 5'-CAGCTCCTCAGCCAGGCTGCAGAC-3'(R71H rev) (SEQ ID NO: 30)) as well as the Mutagenesis Kit were used to perform PCR. In this way, the R71H/G230A mutant STING expression plasmid was obtained.

Subsequently, the R71H/G230A mutant STING expression plasmid was used as a template, and two different primers (5'-CAGACACTTGAGGACATCCTGGCAG-3' (R 293Q fwd) (SEQ ID NO: 31) and 5'-GCAGAAG AGTTTGGCCTGCTCAA-3'(R293Q rev) (SEQ ID NO: 32)) as well as the Mutagenesis Kit were used to perform PCR. In this way, the HAQ (R71H/G230A/R293Q) mutant expression plasmid was obtained. The amino acid sequence of human HAQ mutant STING is shown in SEQ ID NO: 17 and the nucleotide sequence is shown in SEQ ID NO: 18. The amino acid sequences of human wild-type STING, REF mutant STING, and HAQ mutant STING are shown in FIG. 10.

<To Construct Expression Plasmid for Recombinant STING C-Terminal Binding Domain Protein and Others>

The cDNA for human STING C-terminal binding domain (aa. 139 to 342) protein (UniProt entry Q86WV6) was prepared by PCR from the full-length human TMEM173 cDNA clone-expressing plasmid (wild-type, H232 mutant, and HAQ mutant) while using two different primers (5'-ACCTGTATTTTCAGGGCCTGGCCCCAGCTGAGA TCTCTG-3 '(hST Fw_v2) (SEQ ID NO: 33) and 5'-CAGA ATT CGCAAGCTTTTAAGTAACCTCTTCCTTTTCC TCCTGC-3' (hST Rv_V3) (SEQ ID NO: 34)). Each PCR product was inserted into the *E. coli* expression vector, pET15b, by using an In-Fusion HD Cloning Kit (Takara Bio) such that the N-terminus contained a 6×His tag consisting of six histidine residues, an Avidin tag, and a TEV protease cleavage site. Expression plasmids: pET15b-HisAviTEV-hSTING(139-342) human wild type, pET15b-HisAviTEV hSTING(139-342) human REF mutant, and pET15b-HisAviTEV-hSTING(139-342) human HAQ mutant were constructed.

The cDNA used for expressing mouse STING C-terminal domain (aa. 138-341) protein (UniProt entry Q3TBT3) was an artificially synthesized cDNA (eurofins Genomics) corresponding to amino acids at 138- to 341-positions of the mouse TMEM173 cDNA sequence and was used. The amino acid sequence of mouse STING is shown in SEQ ID NO: 19 and the nucleotide sequence is shown in SEQ ID NO: 20. The synthesized cDNA was inserted into the *E. coli* expression vector, pET15b, by using an In-Fusion HD Cloning Kit such that the N-terminus contained a 6×His tag consisting of six histidine residues, an Avidin tag, and a TEV protease cleavage site. The expression plasmid of pET15b-HisAviTEV-mSTING(138-341) mouse wild type was constructed.

The pCDF_Duet-1 BirA(1-321) expression plasmid was constructed by inserting an artificially synthesized E. co/i BirA (UniProt entry P06709) cDNA into the pCDF_Duet-1 vector.

(ii) How to Prepare STING C-Terminal Binding Domain Protein

Each of prepared expression plasmid pET15b-HisAviTEV-hSTING(139-342) (human wild-type (Hu-WT), human REF mutant (Hu-REF), or human HAQ mutant (Hu-HAQ) STING C-terminal binding domain protein), and expression plasmid pET15b-HisAviTEV-mSTING(138-341) (mouse wild type (Ms-WT) STING C-terminal binding domain protein) was co-transformed with pCDF_Duet-1 BirA(1-321) expression plasmid into Competent *E. coli* Rosetta 2 (DE3) (Merck Millipore, MA, US) to prepare each HisAviTEV-STING expression strain. Each expression strain was added to TB broth containing 100 μg/mL ampicillin, 50 μg/mL streptomycin, and 30 μg/mL kanamycin, and cultured at 37° C. The expression was then induced with 100 μM IPTG, and the cells were further cultured at 16° C.

The culture broth was centrifuged, and the obtained bacteria were suspended in 50 mM HEPES pH8.0, 500 mM NaCl, 20 mM imidazole, 1 mM DTT, 5% (w/v) glycerol, and cOmplete EDTA free, and then frozen and thawed. After the addition of lysozyme and DNase I, the proteins were extracted by sonication, and the supernatant was collected by centrifugation. The resulting supernatant was purified through a HisTrap FF column (GE Healthcare) using an AKTAexpress chromatography system (GE Healthcare, IL, US), made to pass through a Superdex200 16/60 column (GE Healthcare), and eluted with a buffer (20 mM HEPES pH 7.5, 120 mM NaCl, 20% glycerol, 0.8 mM DTT). Fractions containing proteins with the target molecular weight were collected by SEC as His-Avi-TEV-hSTING (139-342) human wild-type protein, HisAviTEV-hSTING (139-342) human REF mutant protein, HisAviTEV-hSTING (139-342) human HAQ mutant protein, or His-Avi-TEV-mSTING(138-341) mouse wild-type protein. The protein concentration was measured using a Nanodrop 2000 (Thermo Fisher Scientific, MA, US), and each protein was frozen and stored at −80° C. until use.

The amino acid sequence of the HisAviTEV-hSTING (139-342) human wild-type protein is set forth in SEQ ID NO: 21, the amino acid sequence of the HisAviTEV-hSTING(139-342) human REF mutant protein is set forth in SEQ ID NO: 22, the amino acid sequence of the HisAviTEV-hSTING(139-342) human HAQ mutant protein is set forth in SEQ ID NO: 23, and the amino acid sequence of the His-Avi-TEV-mSTING(138-341) mouse wild-type protein is set forth in SEQ ID NO: 24.

(iii) STING Binding Assay

The binding of a compound to each STING C-terminal binding domain protein was determined by the protein thermal shift assay, which uses the increase in the thermal denaturation temperature of the protein as an indicator.

Specifically, an assay buffer (20 mM Tris-HCl pH7.5, 120 mM NaCl) was applied to wells of a 384-well real-time PCR plate. Next, 3 μL of each test compound (final concentration 0.5 mM), 3 μL of SYPRO Orange Protein Gel Stain (Thermo Fisher Scientific) (final concentration: 20× concentration), and 6 μL of the STING protein were mixed in each well while using a plate shaker. A real-time PCR system (Thermo Fisher Scientific) was used to increase the temperature from 25° C. to 95° C. at a rate of 0.03° C. per second, and the thermal denaturation temperature of the protein was measured using the fluorescence emitted by SYPRO Orange as an indicator. The measured values were analyzed using Protein Thermal Shift software (Thermo Fisher Scientific) to determine Tm (the midpoint of the unfolding transition) (° C.) as the temperature at which the rate of increase in fluorescence intensity reached its maximum value. The shift of Tm by the test compound was calculated as ΔTm (° C.) by subtracting, from the Tm value of each compound, the Tm value of the well without the compound. The results of the binding assay for each STING protein are shown in Table 2.

TABLE 2

| | Δ Tm (° C.) | | | |
|---|---|---|---|---|
| Compound No. | Hu-WT | Hu-REF | Hu-HAQ | Ms-WT |
| 6b (Example 1) | 8.4 | 3.4 | 11.3 | 12.9 |
| 34a (Example 2) | 14.7 | 8.8 | 18.9 | 20.3 |
| 49b (Example 3) | 12.6 | 6.6 | 16.1 | 19.3 |
| 50b (Example 4) | 12.3 | 6.3 | 15.3 | 7.4 |
| ML-RR-CDA•$2Na^+$ | 7.0 | 2.7 | 12.7 | 15.2 |
| 2' 3'-cGAMP | 13.7 | 4.1 | 24.3 | 25.8 |

The results have revealed that each compound used in an antibody-drug conjugate of the present invention has binding activity toward human wild-type STING or mutant STING, and mouse wild-type STING.

(Test Example 3) HCC Cell Assay

By using the human breast cancer cell line HCC1954 (CRL-2338) cells purchased from the American Type Culture Collection as a strain stably expressing high levels of TROP2 and STING, HCC1954-IFIT1 reporter cells were generated by stably expressing the IFIT1 promoter reporter gene. Specifically, the purchased human IFIT1 (ISG-56) promoter reporter plasmid (GeneCopoeia, HPRM40290-PG04) was transfected into HCC1954 cells using FuGene HD (Promega). The cells were subcultured in medium containing 1.0 g/mL puromycin (Life Technologies) to generate stable expression lines, followed by cloning to obtain a cell line for evaluation. Then, HCC1954-IFIT1 reporter cells suspended in assay buffer (RPMI 1640 medium containing 10% bovine serum albumin) were dispensed at 90 μL/well ($2.5\times10^4$ cells/well) of a 384-well plate. The next day, each test compound was diluted in PBS and 10 μL was added to start stimulation. The cells were cultured for 24 h under conditions at 37° C. and 5% $CO_2$, and then centrifuged to collect the supernatant. Next, 6 μL of the collected supernatant was added to a white 384-well plate, and 15 μL of QUANTI-Luc (InvivoGen) solution was added thereto. After well mixing, the luminescence was measured using a plate reader (PerkinElmer, MA, US).

FIG. 11 shows the results. The vertical axis represents the luminescence count and the horizonal axis represents the concentration of each test compound. The line (white circles) in the graph denotes the anti-TROP2 antibody 2 produced in Reference Example 6; the line (black circles) denotes the anti-TROP2 antibody 2-CDN conjugate (1), in which the anti-TROP2 antibody 2 produced in Reference Example 6 was conjugated with compound 34a of Example 2; the line (black triangles) denotes the anti-TROP2 antibody 2-CDN conjugate (2), in which the anti-TROP2 antibody 2 was conjugated with compound 49b of Example 3; and the line (black squares) denotes the anti-TROP2 antibody 2-CDN conjugate (3), in which the anti-TROP2 antibody 2 was conjugated with compound 50b of Example 4. The anti-TROP2 antibody 2 did not cause an increase in the luminescence count. In contrast, the anti-TROP2 antibody 2-CDN conjugate (1), (2), and (3) caused an increase in the count in a concentration-dependent manner. The above results have demonstrated that any of the anti-TROP2 antibody 2-CDN conjugate (1), (2), and (3) has a potential to activate the human STING pathway.

(Test Example 4) Co-culture Assay System Using CT26.WT or CT26.WT-hCD70 Cell Line and Mouse Bone Marrow-Derived Dendritic Cells CT26.WT (CRL2638), a mouse colon cancer cell line purchased from American Type Culture Collection, was transduced with human CD70 gene (NP_001243) to establish CT26.WT-hCD70 cells. Specifically, a pLVSIN lentiviral vector (Takara Bio), in which the human CD70 gene was inserted, was constructed. Next, *Lenti*-X293T cell line (Takara Bio) was transfected with the vector using a Lentiviral High Titer Packaging Mix (Takara Bio). Then, the supernatant was collected, and the CT26.WT was infected therewith. The cells were maintained in medium supplemented with 10 μg/mL puromycin (Thermo Fisher Scientific).

Mouse bone marrow cells were collected from the femur of 5-week-old female BALB/c mice (BALB/cAnNCrlCrlj) (Charles River, Japan). The mouse bone marrow cells were cultured in the presence of 20 μg/mL murine GM-CSF (PEPROTECH) for 7 days to obtain mouse bone marrow-derived dendritic cells. $1.5\times10^5$ CT26.WT or CT26.WT-hCD70 cell line cells and $1\times10^5$ mouse bone marrow-derived dendritic cells were seeded per well of a 96-well plate. Each test compound was diluted in RPMI medium (Invitrogen), and 200 μL was added. After 20 h of incubation, the cells were washed with FCM buffer (HBSS (Wako), 5% FBS (HyClone), 1 mM EDTA (THERMO FISHER)) and stained with FCM antibodies (anti-mouse CD16/32 (Becton Dickinson), anti-mouse CD45, anti-mouse CD11c, anti-mouse I-A/I-E, and anti-mouse CD86 (all BIOLEGEND)). The cells were washed with FCM buffer again and analyzed using a Fortessa (BD Biosciences). MFI of CD86 in $CD45^+$, $CD11c^+$, and I-A/I-$E^+$ fraction was calculated. Then, the ratio with respect to the test compound-free group was calculated. FIG. 12 shows the results. The DC in the graph shows the results of culturing mouse bone marrow-derived dendritic cells with each test compound; the DC+CT26.WT in the graph shows the results of culturing mouse bone marrow-derived dendritic cells and CT26.WT with each test compound; and the DC+CT26.WT-hCD70 in the graph shows the results of culturing mouse bone marrow-derived dendritic cells and CT26.WT-hCD70 with each test compound. The vertical axis represents the ratio of MFI with respect to the compound-free group, and the horizonal axis represents each test compound. The anti-CD70 antibody 1-CDN(1) in the graph is a compound in which the anti-CD70 antibody 1 from Reference Example 3 was conjugated with compound 34a from Example 2; and the anti-CD70 antibody 2-CDN(1) in the graph is a compound in which the anti-CD70 antibody 2 from Reference Example 4 was conjugated with compound 34a from Example 2. The compound 34a of Example 2 caused an increase in CD86 expression on mouse dendritic cells in all conditions. Neither the anti-CD70 antibody 1 nor the anti-CD70 antibody 2 upregulated CD86 expression in any condition. In contrast, any of the anti-CD70 antibody 1-CDN conjugate (1) and the anti-CD70 antibody 2-CDN conjugate (1) enhanced the expression of CD86 on mouse dendritic cells only when mouse bone marrow-derived dendritic cells were cultured with CT26.WT-hCD70. In conclusion, CD70-dependent activation of dendritic cells was demonstrated in the case of using the anti-CD70 antibody 1-CDN conjugate (1) and the anti-CD70 antibody 2-CDN conjugate (1).

(Test Example 5) Anti-Tumor Test (1)

CT26.WT (CRL2638), a mouse colon cancer cell line purchased from American Type Culture Collection, was transduced with the human TROP2 gene (NP_002344.2) to establish CT26.WT-hTROP2 cells. In detail, a pQCIXN vector (Takara Bio) was digested with BamHI and Eco RI and then treated with T4 DNA polymerase, so that the resulting cleaved ends were blunted. Next, a pQCIXN-DEN vector was prepared by ligation with Gateway reading frame cassette A. The human TROP2 was inserted into the vector using the Gateway system (Thermo Fisher Scientific). The human TROP2-containing pQCXIN-DEN retroviral vector was transfected into EcoPack2-293 cell line (Takara Bio) using Lipofectamine 3000 (Thermo Fisher Scientific). Then, the supernatant was collected, and the CT26.WT was infected therewith. The cells were maintained in medium supplemented with 250 μg/mL geneticin (Thermo Fisher Scientific).

Each antibody or antibody-CDN conjugate was diluted in acetate buffer (10 mM acetate buffer, 5% sorbitol, pH 5.5) (NACALAI TESQUE, INC.).

CT26.WT-hTROP2 cells were suspended in saline. Next, $2.0\times10^6$ cells were transplanted subcutaneously into the right axillary region of each BALB/c mouse (Day 0), and random grouping was conducted after 7 days. The anti-TROP2 antibody 1 or the anti-TROP2 antibody 1-CDN conjugate (1) was administered at a dose of 30 g/animal (equivalent to 1.5 mg/kg), and the anti-TROP2 antibody 2 or the anti-TROP2 antibody 2-CDN conjugate (1) was administered at a dose of 3.0 mg/kg into the tail vein once on Day 7. In addition, the vehicle group was provided in which acetate buffer was administered. The number of mice in each group was 8.

FIG. 13 shows the results of the anti-TROP2 antibody 1 and the anti-TROP2 antibody 1-CDN conjugate (1). In the graph, the line (black squares) denotes the vehicle group; the line (white circles) denotes the anti-TROP2 antibody 1 administration group, which antibody was produced in Reference Example 5; and the line (inverted white triangles) denotes the anti-TROP2 antibody 1-CDN conjugate (1) administration group, in which conjugate the anti-TROP2 antibody 1 was conjugated with compound 6b of Example 1. The vertical axis represents the tumor volume ($mm^3$) and the horizonal axis represents the number of days after tumor implantation. Tumor growth progressed in the vehicle group or the anti-TROP2 antibody 1 administration group. In contrast, the tumor growth was markedly inhibited in the anti-TROP2 antibody 1-CDN conjugate (1) administration group.

FIG. 14 shows the results of the anti-TROP2 antibody 2 and the anti-TROP2 antibody 2-CDN conjugate (1). In the graph, the line (black squares) denotes the vehicle group; the line (white circles) denotes the anti-TROP2 antibody 2 administration group, which antibody was produced in Reference Example 6; and the line (inverted white triangles) denotes the anti-TROP2 antibody 2-CDN conjugate (1) administration group, in which conjugate the anti-TROP2 antibody 2 was conjugated with compound 34a of Example 2. The vertical axis represents the tumor volume ($mm^3$) and the horizonal axis represents the number of days after tumor implantation. The tumor growth progressed in the vehicle group and the anti-TROP2 antibody 2 administration group. In contrast, the tumor growth was markedly inhibited in the anti-TROP2 antibody 2-CDN conjugate (1) administration group.

In conclusion, the intravenous administration of the anti-TROP2 antibody-CDN conjugate has been demonstrated to exert an antibody target-dependent anti-tumor effect in a drug efficacy model in which the anti-TROP2 antibody was ineffective.

(Test Example 6) Anti-Tumor Test (2)

CT26.WT (CRL2638), a mouse colon cancer cell line purchased from American Type Culture Collection, was transduced with the human EGFR gene (NP_005219.2) to establish CT26.WT-hEGFR cells. Specifically, a pLVSIN lentiviral vector (Takara Bio), in which the human EGFR gene was inserted, was constructed. Next, *Lenti*-X293T cell line (Takara Bio) was transfected with the vector using a Lentiviral High Titer Packaging Mix (Takara Bio). Then, the supernatant was collected, and the CT26.WT was infected therewith. The cells were maintained in medium supplemented with 10 μg/mL puromycin (Thermo Fisher Scientific).

CT26.WT-hEGFR cells were suspended in saline. Next, $3\times10^6$ cells were transplanted subcutaneously into the right axillary region of each BALB/c mouse (Day 0), and random grouping was conducted after 12 days. The anti-EGFR antibody 1, the anti-EGFR antibody 2, the anti-EGFR antibody 1-CDN conjugate (1), or the anti-EGFR antibody 2-CDN conjugate (1) was administered at a dose of 1.5 mg/kg into the tail vein once on Day 12. In addition, the vehicle group was provided in which acetate buffer was administered. The number of mice in each group was 8.

FIG. 15 shows the results. In the graph, the line (black squares) denotes the vehicle group; the line (white triangles) denotes the anti-EGFR antibody 1 administration group, which antibody was produced in Reference Example 7; the line (black triangles) denotes the anti-EGFR antibody 1-CDN conjugate (1) administration group; the line (white circles) denotes the anti-EGFR antibody 2 administration group, which antibody was produced in Reference Example 8; and the line (black circles) denotes the anti-EGFR antibody 2-CDN conjugate (1) administration group. The vertical axis represents the tumor volume ($mm^3$) and the horizonal axis represents the number of days after tumor implantation. The tumor growth progressed in the vehicle group. The tumor growth was not inhibited in neither the anti-EGFR antibody 1 administration group nor the anti-EGFR antibody 2 administration group. In contrast, the tumor growth was markedly inhibited in the anti-EGFR antibody 1-CDN conjugate (1) administration group and the anti-EGFR antibody 2-CDN conjugate (1) administration group.

In conclusion, the strong anti-tumor effect of each anti-EGFR antibody-CDN conjugate was demonstrated using a model in which the anti-EGFR antibody did not elicit any anti-tumor effect.

(Test Example 7) Anti-Tumor Test (3)

Each antibody or antibody-CDN conjugate was diluted in acetate buffer (10 mM acetate buffer, 5% sorbitol, pH 5.5) (NACALAI TESQUE, INC.).

Caki-1 (HTB-46) cells, a human renal cancer cell line purchased from American Type Culture Collection, were suspended in Matrigel (CORNING) diluted 50% in saline. Next, $2.5\times10^6$ cells were transplanted subcutaneously into the right axillary region of each BALB/c-nu mouse (Day 0), and random grouping was conducted after 13 days. The anti-CD70 antibody 1, the anti-CD70 antibody 1-CDN conjugate (1), the anti-CD70 antibody 2, or the anti-CD70 antibody 2-CDN conjugate (1) was administered at a dose of 1.5 mg/kg into the tail vein once on Day 13. In addition, the vehicle group was provided in which acetate buffer was administered. The number of mice in each group was 8.

FIG. 22 shows the results. The anti-CD70 antibody 1-CDN conjugate (1) in the graph is a compound in which the anti-CD70 antibody 1 from Reference Example 3 was conjugated with compound 34a from Example 2; and the anti-CD70 antibody 2-CDN conjugate (1) in the graph is a compound in which the anti-CD70 antibody 2 from Reference Example 4 was conjugated with compound 34a from Example 2. In the graph, the line (black squares) denotes the vehicle group; the line (white triangles) denotes the anti-CD70 antibody 1 administration group; the line (inverted white triangles) denotes the anti-CD70 antibody 2 administration group; the line (white diamonds) denotes the anti-CD70 antibody 1-CDN conjugate (1) administration group; and the line (white circles) denotes the anti-CD70 antibody 2-CDN conjugate (1) administration group. The vertical axis represents the tumor volume ($mm^3$) and the horizonal axis represents the number of days after tumor implantation. Tumor growth progressed in the vehicle group, the anti-CD70 antibody 1 administration group, and the anti-CD70 antibody 2 administration group. In contrast, the tumor growth was markedly inhibited in the anti-CD70 antibody 1-CDN conjugate (1) administration group and the anti-CD70 antibody 2-CDN conjugate (1) administration group.

In conclusion, the intravenous administration of any of the anti-CD70 antibody-CDN conjugates has been demonstrated to exert an antibody target-dependent anti-tumor effect in a drug efficacy model in which the anti-CD70 antibody was ineffective.

(Test Example 8) Anti-Tumor Test (4)

Each antibody or antibody-CDN conjugate was diluted in acetate buffer (10 mM acetate buffer, 5% sorbitol, pH 5.5) (NACALAI TESQUE, INC.).

A-498 (HTB-44) cells, a human renal cancer cell line purchased from American Type Culture Collection, were suspended in saline. Next, $3.0\times10^6$ cells were transplanted subcutaneously into the right axillary region of each BALB/c-nu mouse (Day 0), and random grouping was conducted after 20 days. The anti-CD70 antibody 2 or the anti-CD70 antibody 2-CDN conjugate (2) was administered at a dose of 1.0 mg/kg into the tail vein once on Day 20. In addition, the vehicle group was provided in which acetate buffer was administered. The number of mice in each group was 6.

FIG. 23 shows the results. The anti-CD70 antibody 2-CDN conjugate (2) in the graph is an antibody-CDN conjugate using MSG-type glycan-remodeled antibody with an average drug conjugation number of about 2. In the graph, the line (black squares) denotes the vehicle group; the line (white triangles) denotes the anti-CD70 antibody 2 administration group; and the line (inverted white triangles) denotes the anti-CD70 antibody 2-CDN conjugate (2) administration group. The vertical axis represents the tumor volume ($mm^3$) and the horizonal axis represents the number of days after tumor implantation. The tumor growth progressed in the vehicle group. The tumor growth was not inhibited in the anti-CD70 antibody 2 administration group. In contrast, the tumor growth was markedly inhibited in the anti-CD70 antibody 2-CDN conjugate (2) administration group. In conclusion, the anti-CD70 antibody-CDN conjugate has been demonstrated to exert a strong anti-tumor effect in a drug efficacy model in which the anti-CD70 antibody was ineffective.

(Test Example 9) Anti-Tumor Test (5)

CT26.WT (CRL2638), a mouse colon cancer cell line purchased from American Type Culture Collection, was transduced with the human-mouse chimeric EGFR gene (NP_005219.2), in which the epitope region for the anti-EGFR antibody 1 was replaced by a human counterpart, to establish CT26.WT-chimeraEGFR cells. Specifically, a pLVSIN lentiviral vector (Takara Bio), in which the human-mouse chimeric EGFR gene was inserted, was constructed. Next, *Lenti*-X293T cell line (Takara Bio) was transfected with the vector using a Lentiviral High Titer Packaging Mix (Takara Bio). Then, the supernatant was collected, and the CT26.WT was infected therewith. The cells were maintained in medium supplemented with 2 μg/mL puromycin (Thermo Fisher Scientific).

CT26.WT-chimera EGFR cells were suspended in saline. Next, $1\times10^6$ cells were transplanted subcutaneously into the right axillary region of each BALB/c mouse (Day 0), and random grouping was conducted after 7 days. The compound 34a, the anti-EGFR antibody 1, or the anti-EGFR antibody 1-CDN conjugate (2) was administered at a dose of 0.01 mg/kg, 0.98 mg/kg, or 1.0 mg/kg, respectively, into the tail vein once on Day 7. The dose of the compound 34a or the anti-EGFR antibody 1 is equivalent to the dose of each component included in the anti-EGFR antibody 1-CDN conjugate (2). In addition, the vehicle group was provided in which acetate buffer was administered. The number of mice in each group was 8.

FIG. 24 shows the results. The anti-EGFR antibody 1-CDN conjugate (2) in the graph is an antibody-CDN conjugate using MSG-type glycan-remodeled antibody with an average drug conjugation number of about 2. In the graph, the line (black squares) denotes the vehicle group; the line (white triangles) denotes the anti-EGFR antibody 1 administration group; the line (white diamonds) denotes the compound 34a administration group; and the line (white rectangles) denotes the anti-EGFR antibody 1-CDN conjugate (2) administration group. The vertical axis represents the tumor volume ($mm^3$) and the horizonal axis represents the number of days after tumor implantation. The tumor growth progressed in the vehicle group. The tumor growth was not inhibited in neither the compound 34a administration group nor the anti-EGFR antibody 1 administration group. In contrast, the tumor growth was markedly inhibited in the anti-EGFR antibody 1-CDN conjugate (2) administration group.

In conclusion, the strong anti-tumor effect of the anti-EGFR antibody-CDN conjugate has been demonstrated using a model in which the anti-EGFR antibody did not elicit any anti-tumor effect.

INDUSTRIAL APPLICABILITY

The present invention provides an antibody-drug conjugate containing a novel CDN derivative with strong STING agonist activity and potent anti-tumor effects. This antibody-drug conjugate is useful as a therapeutic agent for diseases (e.g., cancer) associated with STING agonist activity.

SEQUENCE LISTING

SEQ ID NO: 1: the amino acid sequence of the light chain of anti-CD70 antibody 1
SEQ ID NO: 2: the amino acid sequence of the heavy chain of anti-CD70 antibody 1
SEQ ID NO: 3: the amino acid sequence of the light chain of anti-CD70 antibody 2
SEQ ID NO: 4: the amino acid sequence of the heavy chain of anti-CD70 antibody 2
SEQ ID NO: 5: the amino acid sequence of the light chain of anti-TROP2 antibody 1
SEQ ID NO: 6: the amino acid sequence of the heavy chain of anti-TROP2 antibody 1
SEQ ID NO: 7: the amino acid sequence of the light chain of anti-TROP2 antibody 2
SEQ ID NO: 8: the amino acid sequence of the heavy chain of anti-TROP2 antibody 2
SEQ ID NO: 9: the amino acid sequence of the light chain of anti-EGFR antibody 1
SEQ ID NO: 10: the amino acid sequence of the heavy chain of anti-EGFR antibody 1
SEQ ID NO: 11: the amino acid sequence of the light chain of anti-EGFR antibody 2
SEQ ID NO: 12: the amino acid sequence of the heavy chain of anti-EGFR antibody 2
SEQ ID NO: 13: the amino acid sequence of human wild-type STING
SEQ ID NO: 14: the nucleotide sequence of human wild-type STING
SEQ ID NO: 15: the amino acid sequence of human H232 (REF) mutant STING
SEQ ID NO: 16: the nucleotide sequence of human H232 (REF) mutant STING
SEQ ID NO: 17: the amino acid sequence of human HAQ mutant STING
SEQ ID NO: 18: the nucleotide sequence of human HAQ mutant STING
SEQ ID NO: 19: the amino acid sequence of mouse STING
SEQ ID NO: 20: the nucleotide sequence of mouse STING
SEQ ID NO: 21: the amino acid sequence of HisAviTEV-hSTING(139-342) human wild-type protein
SEQ ID NO: 22: the amino acid sequence of HisAviTEV-hSTING(139-342) human REF mutant protein
SEQ ID NO: 23: the amino acid sequence of HisAviTEV-hSTING(139-342) human HAQ mutant protein
SEQ ID NO: 24: the amino acid sequence of His-Avi-TEV-mSTING(138-341) mouse wild-type protein
SEQ ID NOs: 25-34: primer sequences
SEQ ID NO: 35: the amino acid sequence of CDRL1 of anti-CD70 antibody 1
SEQ ID NO: 36: the amino acid sequence of CDRL2 of anti-CD70 antibody 1
SEQ ID NO: 37: the amino acid sequence of CDRL3 of anti-CD70 antibody 1
SEQ ID NO: 38: the amino acid sequence of CDRH1 of anti-CD70 antibody 1
SEQ ID NO: 39: the amino acid sequence of CDRH2 of anti-CD70 antibody 1
SEQ ID NO: 40: the amino acid sequence of CDRH3 of anti-CD70 antibody 1
SEQ ID NO: 41: the amino acid sequence of CDRL1 of anti-CD70 antibody 2
SEQ ID NO: 42: the amino acid sequence of CDRL2 of anti-CD70 antibody 2
SEQ ID NO: 43: the amino acid sequence of CDRL3 of anti-CD70 antibody 2
SEQ ID NO: 44: the amino acid sequence of CDRH1 of anti-CD70 antibody 2
SEQ ID NO: 45: the amino acid sequence of CDRH2 of anti-CD70 antibody 2
SEQ ID NO: 46: the amino acid sequence of CDRH3 of anti-CD70 antibody 2
SEQ ID NO: 47: the amino acid sequence of CDRL1 of anti-TROP2 antibody 1
SEQ ID NO: 48: the amino acid sequence of CDRL2 of anti-TROP2 antibody 1
SEQ ID NO: 49: the amino acid sequence of CDRL3 of anti-TROP2 antibody 1
SEQ ID NO: 50: the amino acid sequence of CDRH1 of anti-TROP2 antibody 1
SEQ ID NO: 51: the amino acid sequence of CDRH2 of anti-TROP2 antibody 1
SEQ ID NO: 52: the amino acid sequence of CDRH3 of anti-TROP2 antibody 1
SEQ ID NO: 53: the amino acid sequence of CDRL1 of anti-TROP2 antibody 2
SEQ ID NO: 54: the amino acid sequence of CDRL2 of anti-TROP2 antibody 2
SEQ ID NO: 55: the amino acid sequence of CDRL3 of anti-TROP2 antibody 2
SEQ ID NO: 56: the amino acid sequence of CDRH1 of anti-TROP2 antibody 2
SEQ ID NO: 57: the amino acid sequence of CDRH2 of anti-TROP2 antibody 2
SEQ ID NO: 58: the amino acid sequence of CDRH3 of anti-TROP2 antibody 2
SEQ ID NO: 59: the amino acid sequence of CDRL1 of anti-EGFR antibody 1
SEQ ID NO: 60: the amino acid sequence of CDRL2 of anti-EGFR antibody 1
SEQ ID NO: 61: the amino acid sequence of CDRL3 of anti-EGFR antibody 1
SEQ ID NO: 62: the amino acid sequence of CDRH1 of anti-EGFR antibody 1
SEQ ID NO: 63: the amino acid sequence of CDRH2 of anti-EGFR antibody 1
SEQ ID NO: 64: the amino acid sequence of CDRH3 of anti-EGFR antibody 1
SEQ ID NO: 65: the amino acid sequence of CDRL1 of anti-EGFR antibody 2
SEQ ID NO: 66: the amino acid sequence of CDRL2 of anti-EGFR antibody 2
SEQ ID NO: 67: the amino acid sequence of CDRL3 of anti-EGFR antibody 2
SEQ ID NO: 68: the amino acid sequence of CDRH1 of anti-EGFR antibody 2
SEQ ID NO: 69: the amino acid sequence of CDRH2 of anti-EGFR antibody 2
SEQ ID NO: 70: the amino acid sequence of CDRH3 of anti-EGFR antibody 2

The invention claimed is:

1. An antibody-drug conjugate represented by the following formula (II):

(II)

$$Ab\text{—}[L\text{—}D]_{m^1}$$

wherein $m^1$ ranges from 1 to 10;

Ab represents an antibody or an antigen-binding fragment of the antibody, wherein the antibody optionally has a remodeled glycan, wherein the antibody is an anti-EGFR antibody;

L represents a linker linking Ab and D, wherein

Ab is bound to L through the glycan or remodeled glycan of Ab, and

L is represented by -Lb-La-Lp-Lc-* wherein the asterisk represents bonding to the drug D;

Lp is -GGFG- or -GGPI-:

La represents —C(═O)—$CH_2CH_2$—C(═O)—;

Lb represents the following formula:

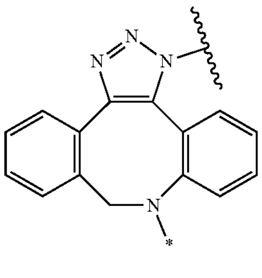

or

-continued

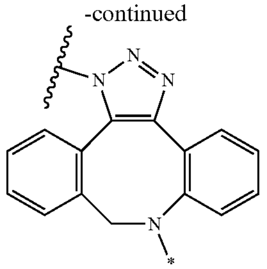

wherein, in the structural formula of Lb shown above, the asterisk represents bonding to La, and the wavy line represents bonding to the glycan or remodeled glycan of Ab; and Lc represents —NH—$CH_2$—;

D represents a compound represented by the following formula (1):

(I)

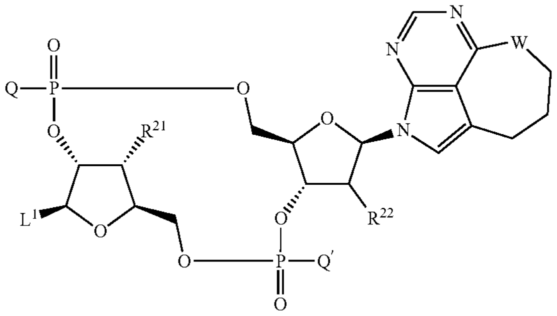

wherein

L bonds to any —$NH_2$ or a hydroxy group included in $L^1$, $L^1$ represents any one group of the formulas selected from the group consisting of:

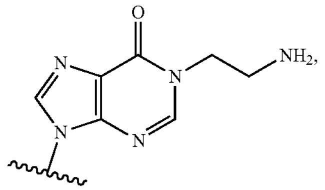

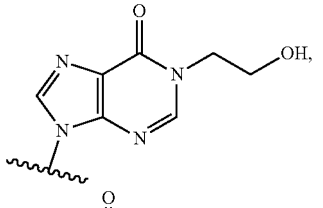

and

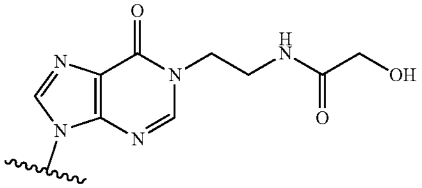

wherein the wavy line represents a position of substitution,

Q and Q' each independently represent a hydroxy group or a thiol group, $R^{21}$ and $R^{22}$ each independently represent a hydroxy group or a fluorine atom, and W represents —NH— or a sulfur atom.

2. The antibody-drug conjugate according to claim 1, wherein D is represented by any one of the following two formulas:

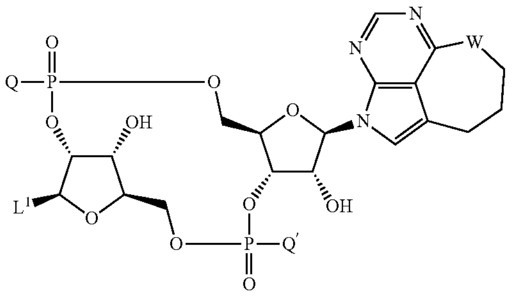

or

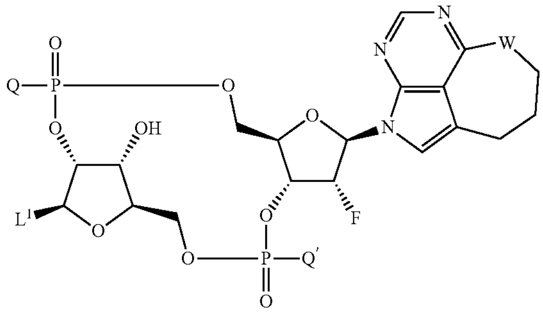

wherein $L^1$, Q, Q', and W are as defined above.

3. The antibody-drug conjugate according to claim 1, wherein D is represented by any one of the following four formulas:

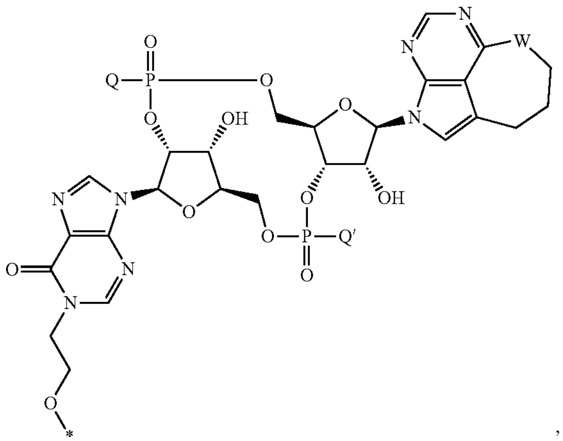

,

-continued
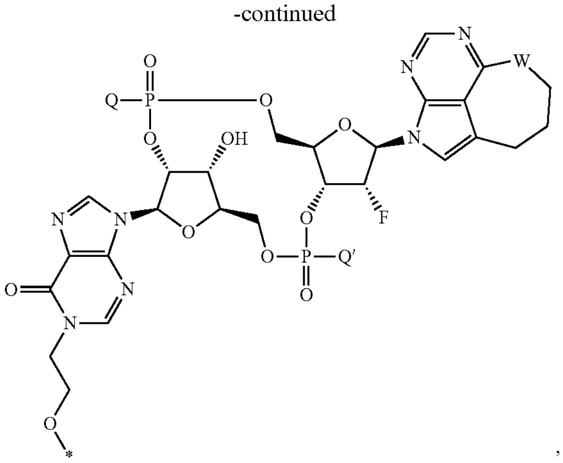
,
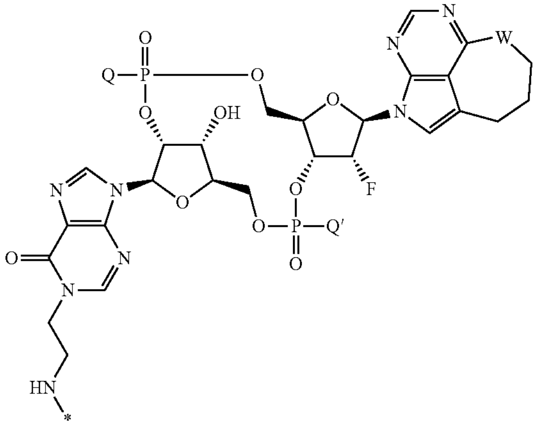
, or
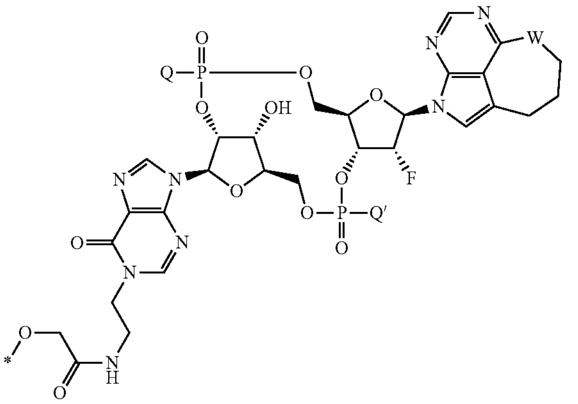
wherein the asterisk represents bonding to L, and Q, Q', and W are as defined above.
4. The antibody-drug conjugate according to claim 1, wherein D is represented by any one of the following three formulas:
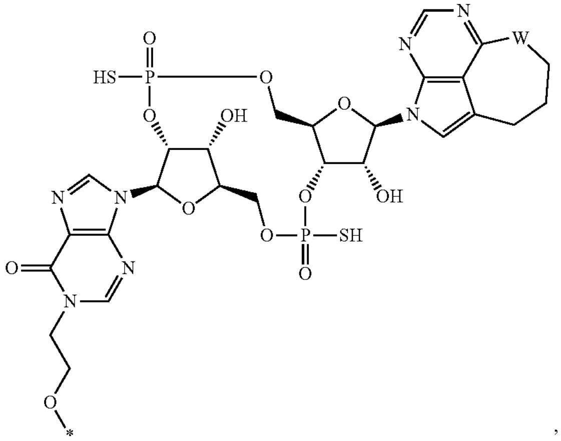
,
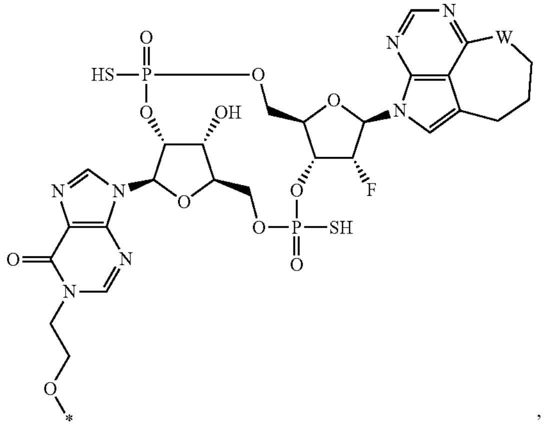
, or
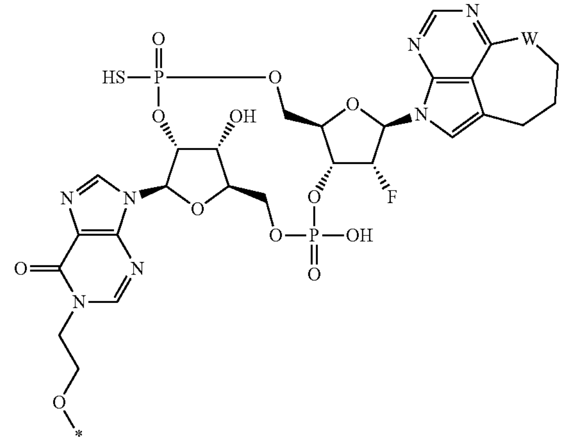
wherein the asterisk represents bonding to L, and W is as defined above.

5. The antibody-drug conjugate according to claim 1, wherein D is represented by any one of the following three formulas:
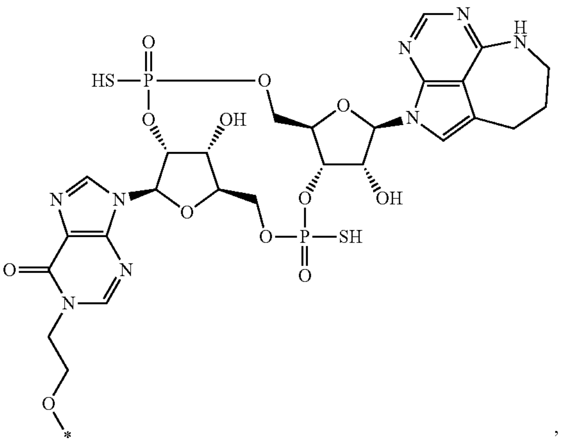
,
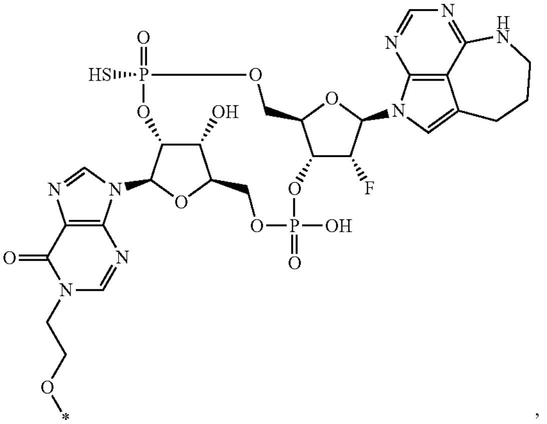
, or
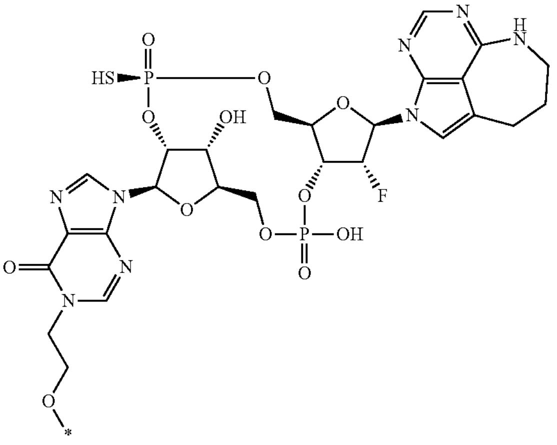
wherein the asterisk represents bonding to L.
6. The antibody-drug conjugate according to claim 1, wherein D is represented by any one of the following four formulas:
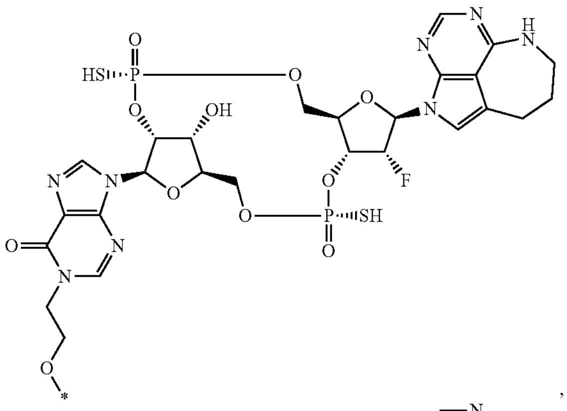
,
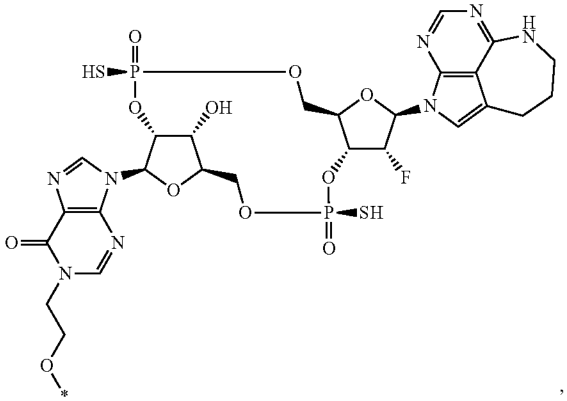
,
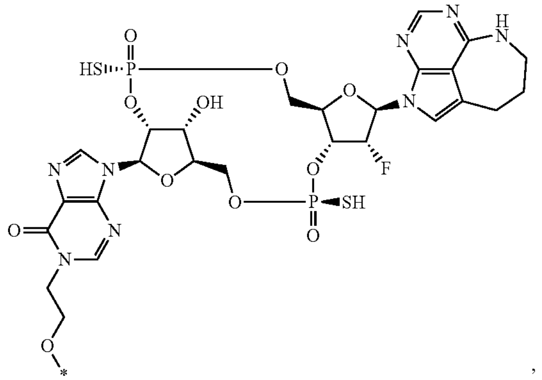
, or
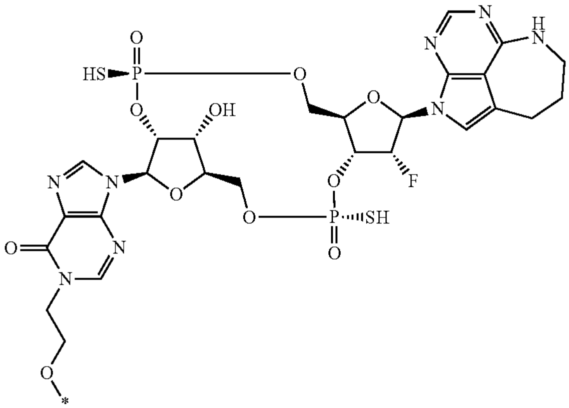
wherein the asterisk represents bonding to L.

7. The antibody-drug conjugate according to claim 4, wherein D is represented by the following formula:

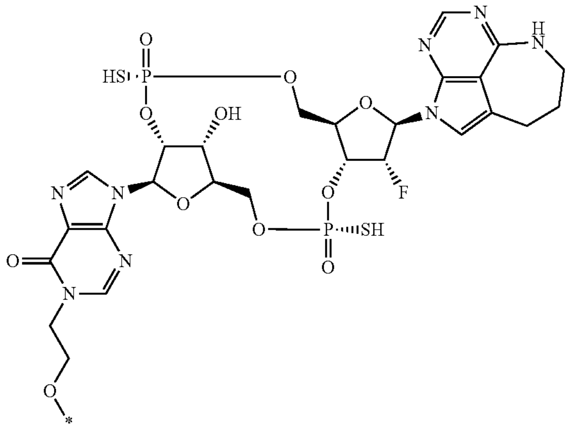 [SMILES: *OCCn1cnc2c(ncn2[C@@H]2O[C@@H]3CO[P@@](=O)(S)O[C@H]4[C@@H](F)[C@H](n5cc6c7c(ncnc75)NCCC6)O[C@@H]4CO[P@@](=O)(S)O[C@@H]2[C@@H]3O)c1=O]

wherein the asterisk represents bonding to L.

8. The antibody-drug conjugate according to claim 1, wherein D is represented by any one of the following two formulas:

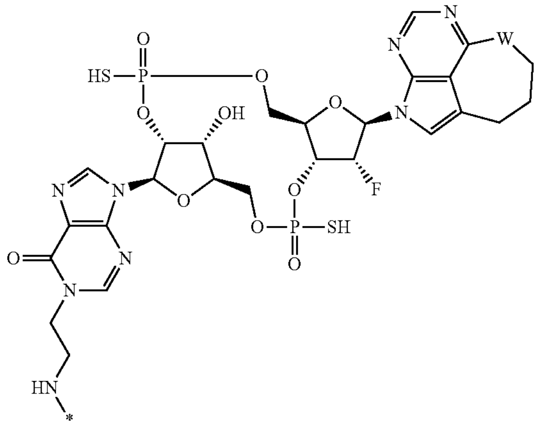

or

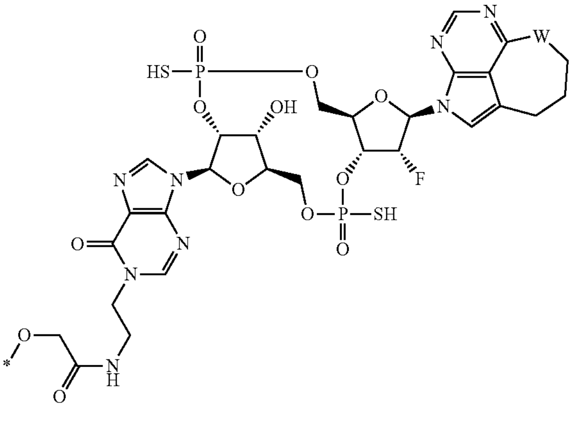

wherein the asterisk represents bonding to L, and W is as defined above.

9. The antibody-drug conjugate according to claim 1, wherein D is represented by any one of the following four formulas:

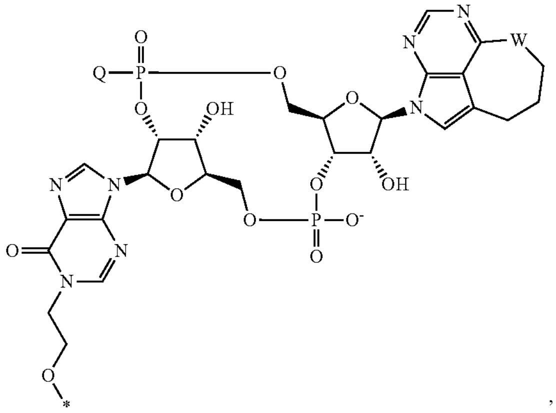

,

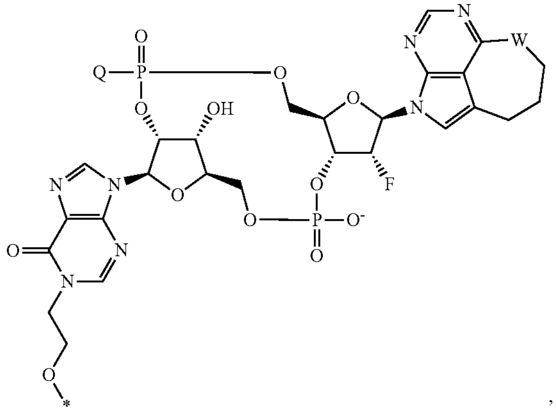

,

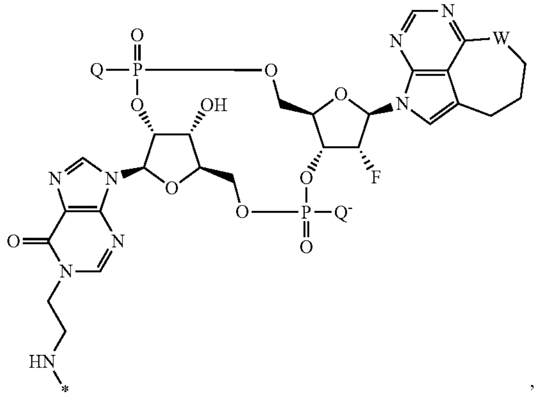

, or

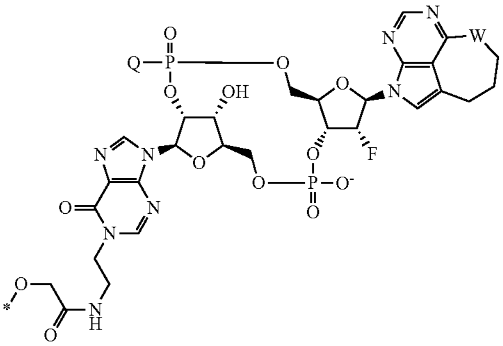

wherein the asterisk represents bonding to L.

10. The antibody-drug conjugate according to claim 1, wherein the average number of the conjugated drug molecules per antibody molecule in the antibody-drug conjugate ranges from 1 to 10.

11. The antibody-drug conjugate according to claim 1, wherein the antibody bonds via a glycan bonding to Asn297 of the antibody (N297 glycan) to L.

12. The antibody-drug conjugate according to claim 11, wherein the N297 glycan is N297-(Fuc)MSG1 or N297-(Fuc)SG having a structure represented by the following formula:

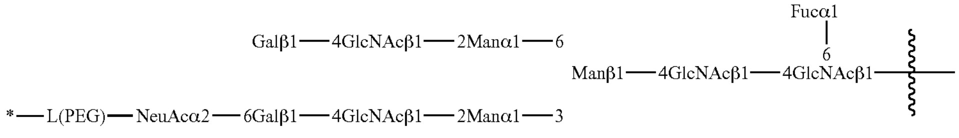

[N297—(Fuc)MSG1]

wherein the wavy line represents bonding to Asn297 of the antibody,

L(PEG) represents $—(CH_2—CH_2O)n^5—CH_2—CH_2—NH—$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ is an integer of 2 to 5;

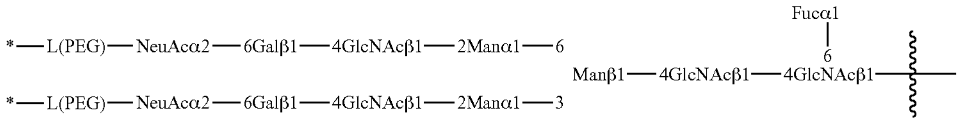

[N297—(Fuc)SG]

wherein the wavy line represents bonding to Asn297 of the antibody,

L(PEG) represents $—(CH_2—CH_2O)n^5—CH_2—CH_2—NH—$, wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, and $n^5$ is an integer of 2 to 5.

13. The antibody-drug conjugate according to claim 11, wherein the antibody-drug conjugate is represented by the following formula:

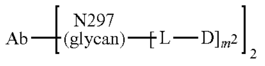

wherein $m^2$ represents an integer of 1 or 2,

L is a linker linking N297 glycan of Ab and D, as defined previously,

Ab represents an anti-EGFR antibody, or an antigen-binding fragment thereof,

N297 glycan of Ab is represented by N297-(Fuc)MSG1 or N297-(Fuc)SG having a structure represented by the following formula:

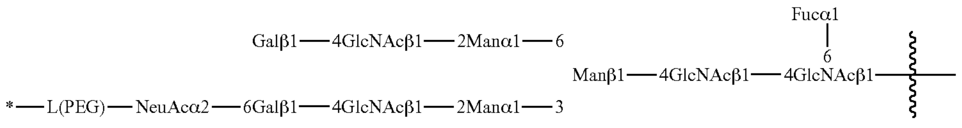

[N297—(Fuc)MSG1]

wherein the wavy line represents bonding to Asn297 of the antibody,

L(PEG) represents $-(CH_2-CH_2O)n^5-CH_2-CH_2-NH-$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on 1,2,3-triazole ring of Lb in the linker L, and $n^5$ represents an integer of 2 to 5;

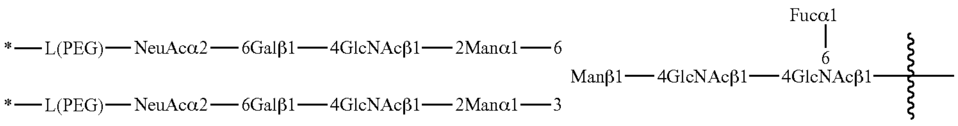

[N297—(Fuc)SG]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on 1,2,3-triazole ring of Lb in the linker L, and $n^5$ represents an integer of 2 to 5, D is represented by any one of the following four formulas:

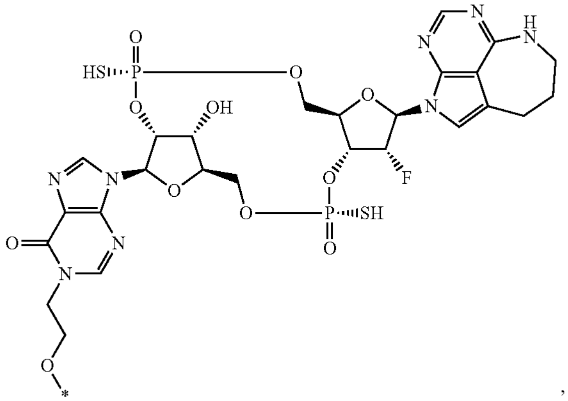

,

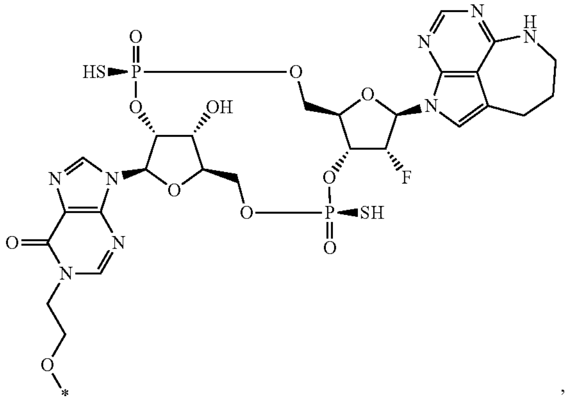

,

-continued

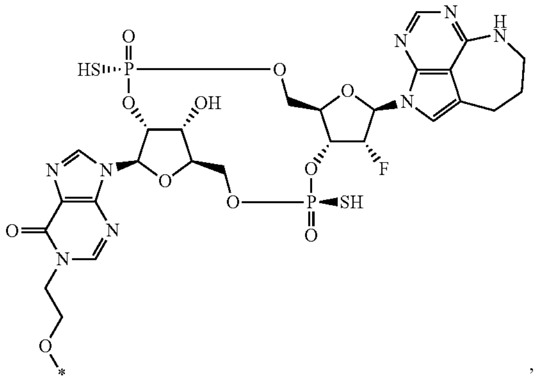

, or

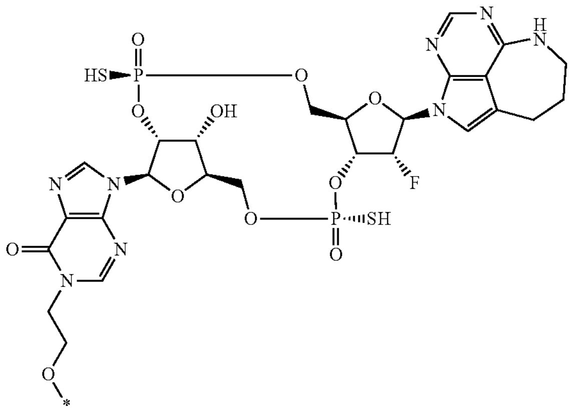

wherein the asterisk represents bonding to L.

14. The antibody-drug conjugate according to claim 13, wherein the antibody-drug conjugate is represented by the following formula selected from
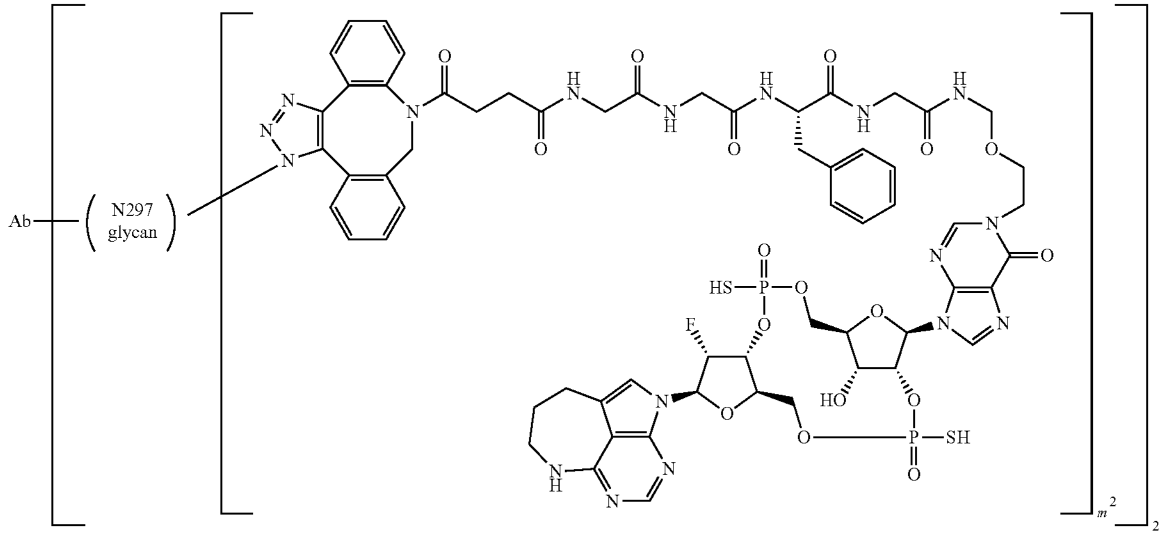
,
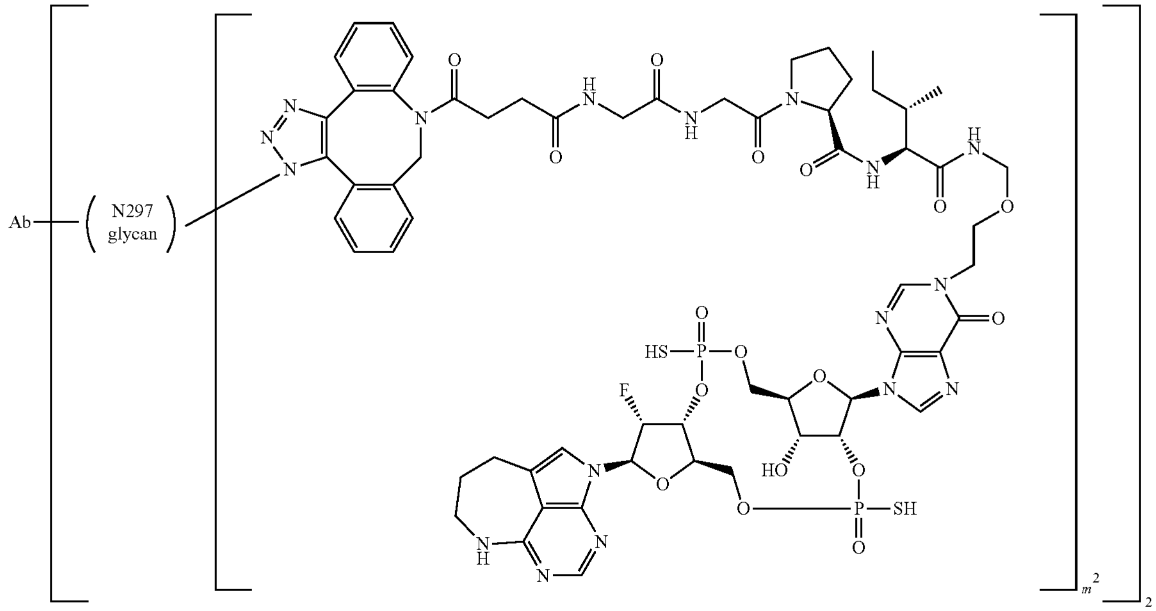
, -continued
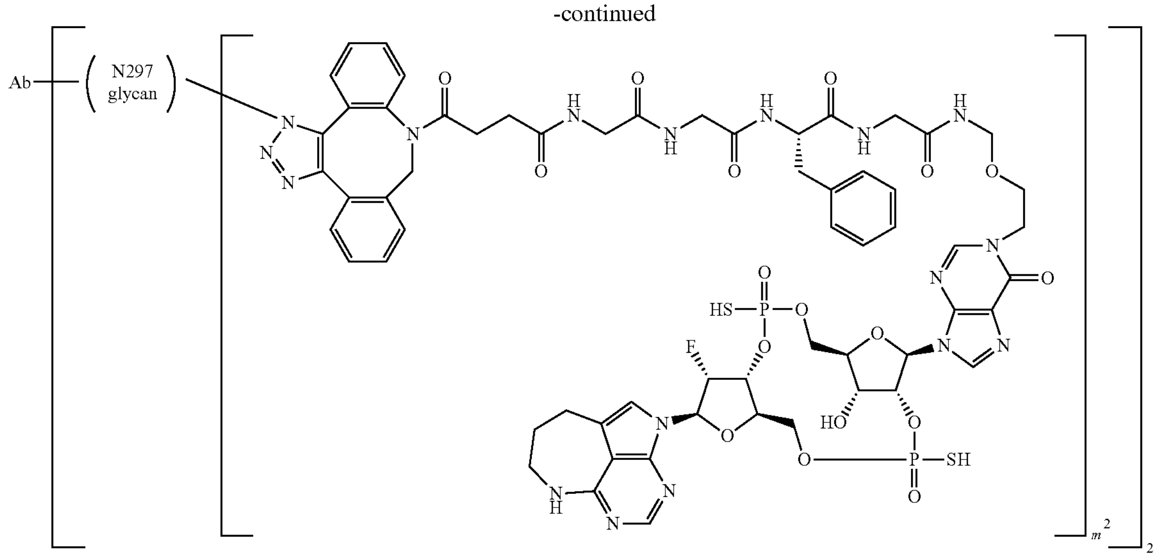
, or
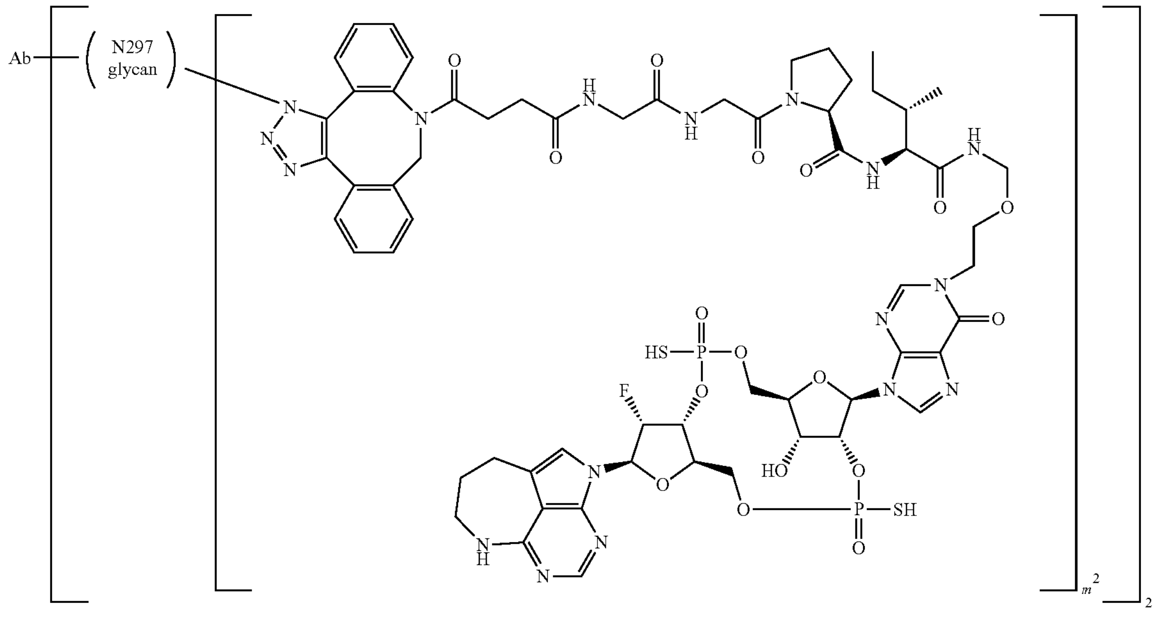
wherein, in each the structural formula shown above, $m^2$ is an integer of 1 or 2,
N297 glycan of Ab is represented by any one of N297-(Fuc)MSG1 or N297-(Fuc)SG having a structure represented by the following formula:
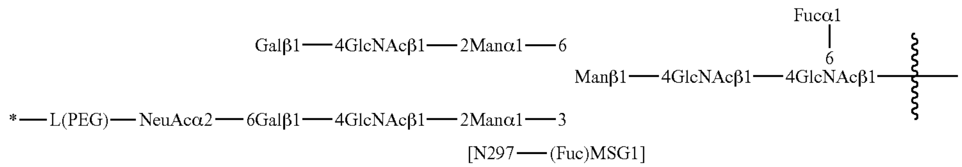
[N297—(Fuc)MSG1]
wherein the wavy line represents bonding to Asn297 of the antibody, L(PEG) represents $-(CH_2-CH_2-O)n^5-CH_2-CH_2-NH-$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on the 1,2,3-triazole ring, and $n^5$ represents an integer of 2 to 5; or

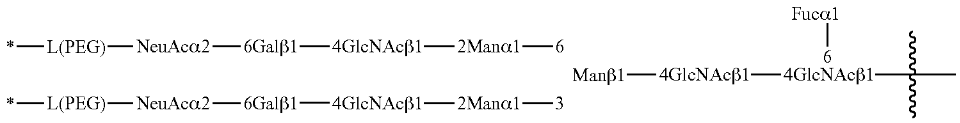

[N297—(Fuc)SG]

wherein the wavy line represents bonding to Asn297 of the antibody,

L(PEG) represents $-(CH_2-CH_2-O)n^5-CH_2-CH_2-NH-$, wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on the 1,2,3-triazole ring, and $n^5$ represents an integer of 2 to 5.

15. The antibody-drug conjugate according to claim 13, wherein the antibody-drug conjugate is represented by the following formula selected from

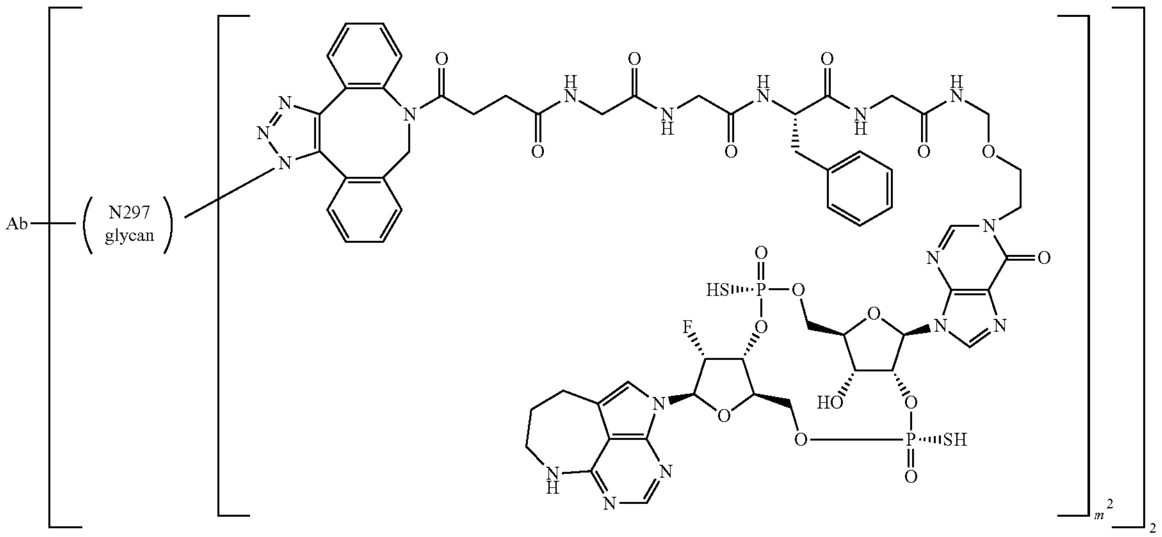

,

-continued
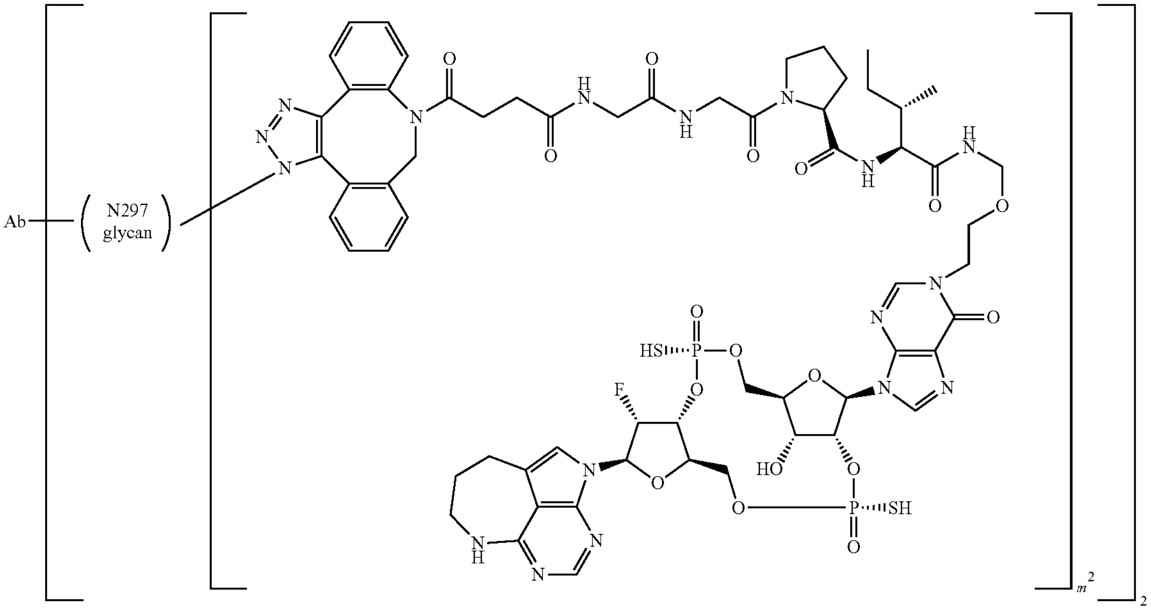
,
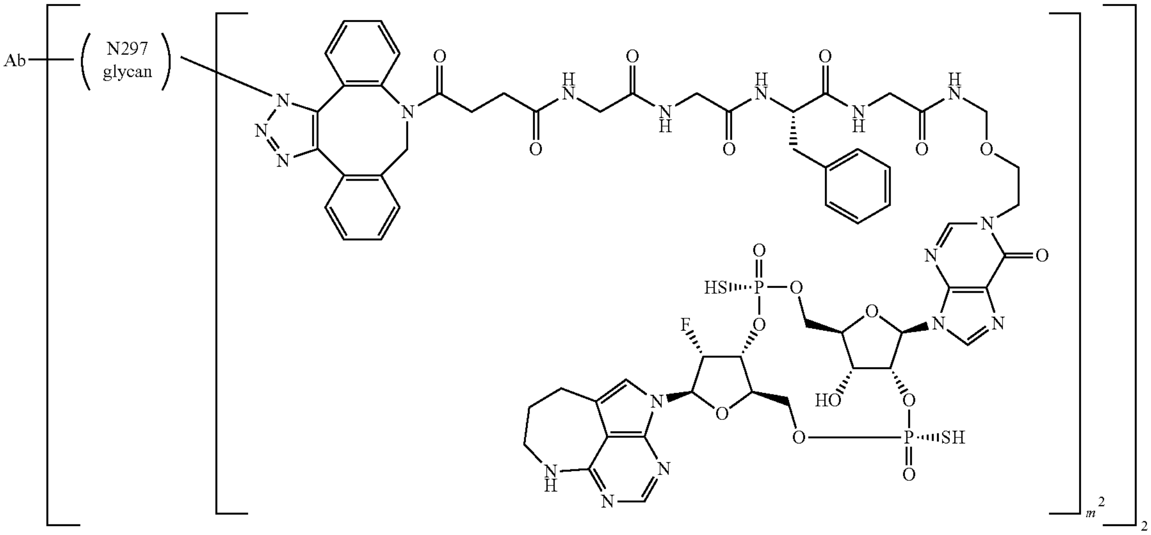
, or

-continued

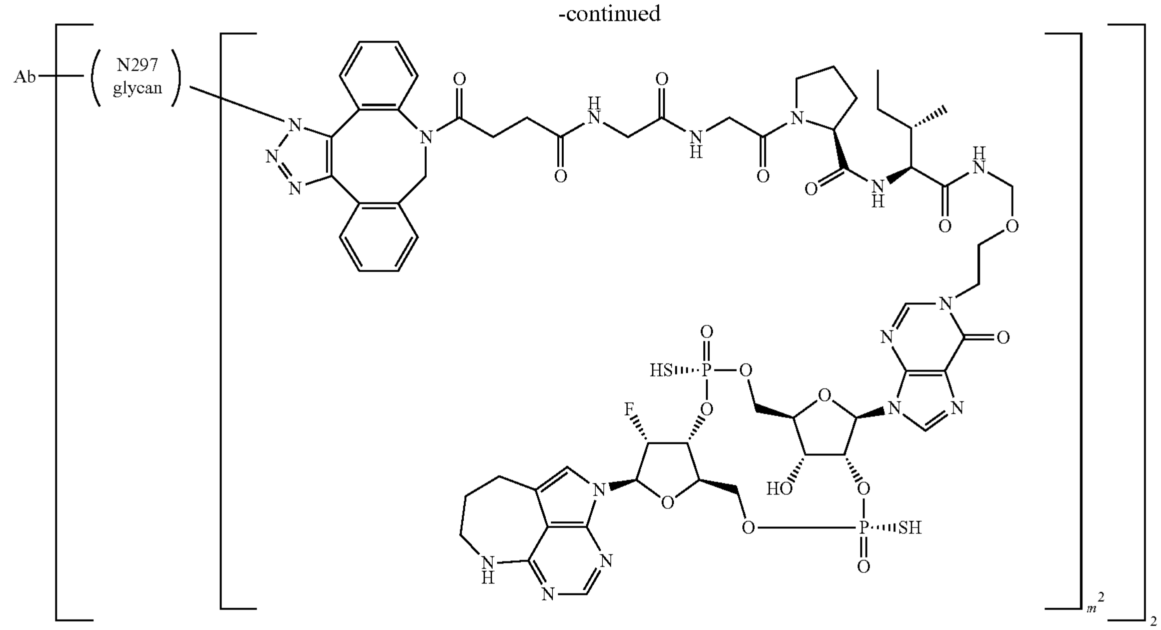

wherein, in each the structural formula shown above, $m^2$ is an integer of 1 or 2, N297 glycan of Ab is represented by any one of N297-(Fuc)MSG1 or N297-(Fuc)SG having a structure represented by the following formula:

wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan,

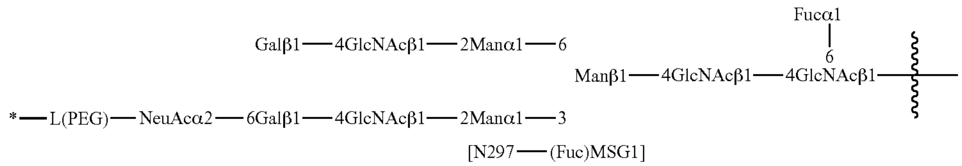

[N297—(Fuc)MSG1]

wherein the wavy line represents bonding to Asn297 of the antibody,

L(PEG) represents $—(CH_2—CH_2—O)n^5—CH_2—CH_2—NH—$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on the 1,2,3-triazole ring, and $n^5$ represents an integer of 2 to 5; or the asterisk represents bonding to a nitrogen atom at 1- or 3-position on the 1,2,3-triazole ring, and $n^5$ represents an integer of 2 to 5.

16. The antibody-drug conjugate according to claim 1, wherein the antibody is an antibody comprising a light chain comprising the amino acid sequence set forth in SEQ ID NO: 9 and a heavy chain comprising the amino acid sequence set forth in SEQ ID NO: 10 or an antibody comprising a light chain comprising the amino acid sequence set forth in SEQ ID NO: 11 and a heavy chain comprising the amino acid sequence set forth in SEQ ID NO: 12.

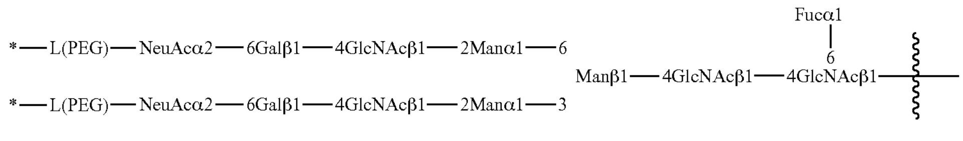

[N297—(Fuc)SG]

wherein the wavy line represents bonding to Asn297 of the antibody,

L(PEG) represents $—(CH_2—CH_2—O)n^5—CH_2—CH_2—NH—$,

17. The antibody-drug conjugate according to claim 1, wherein the antibody is an antibody comprising a light chain comprising a light chain variable region comprising amino acid residues 1 to 108 of SEQ ID NO: 9 and a heavy chain comprising a heavy chain variable region comprising amino acid residues 1 to 119 of SEQ ID NO: 10 or an antibody comprising a light chain comprising a light chain variable region comprising amino acid residues 1 to 108 of SEQ ID NO: 11 and a heavy chain comprising a heavy chain variable region comprising amino acid residues 1 to 116 of SEQ ID NO: 12.

18. The antibody-drug conjugate according to claim 1, wherein the antibody is an antibody comprising a light chain comprising a CDRL1 comprising the amino acid sequence set forth in SEQ ID NO: 59, a CDRL2 comprising the amino acid sequence set forth in SEQ ID NO: 60, and a CDRL3 comprising the amino acid sequence set forth in SEQ ID NO: 61 and a heavy chain comprising a CDRH1 comprising the amino acid sequence set forth in SEQ ID NO: 62, a CDRH2 comprising the amino acid sequence set forth in SEQ ID NO: 63, and a CDRH3 comprising the amino acid sequence set forth in SEQ ID NO: 64 or an antibody comprising a light chain comprising a CDRL1 comprising the amino acid sequence set forth in SEQ ID NO: 65, a CDRL2 comprising the amino acid sequence set forth in SEQ ID NO: 66, and a CDRL3 comprising the amino acid sequence set forth in SEQ ID NO: 67 and a heavy chain comprising a CDRH1 comprising the amino acid sequence set forth in SEQ ID NO: 68, a CDRH2 comprising the amino acid sequence set forth in SEQ ID NO: 69, and a CDRH3 comprising the amino acid sequence set forth in SEQ ID NO: 70.

19. An antibody-drug conjugate represented by the following formula:

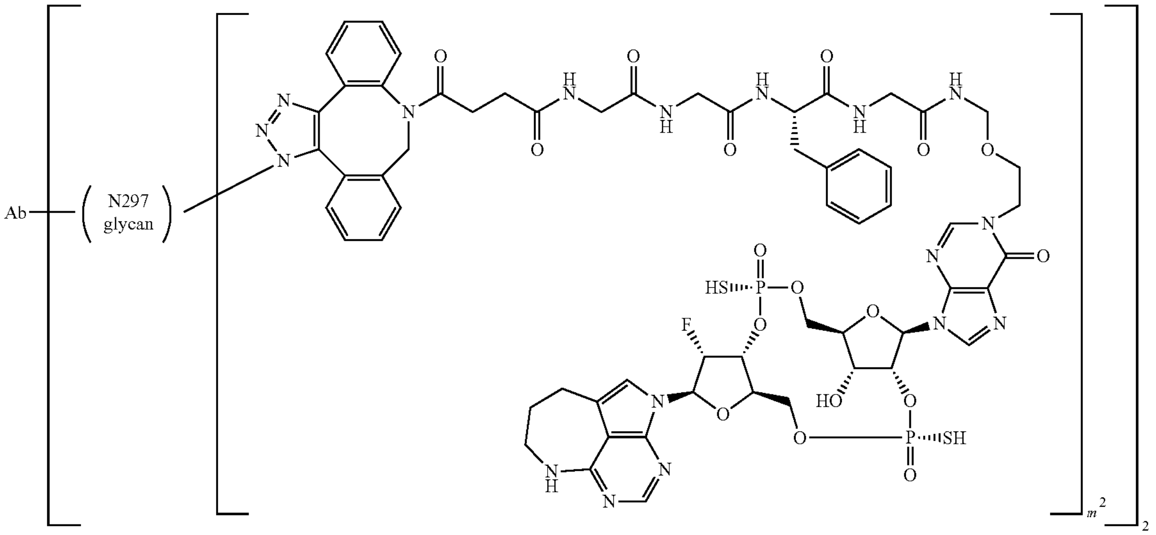

or

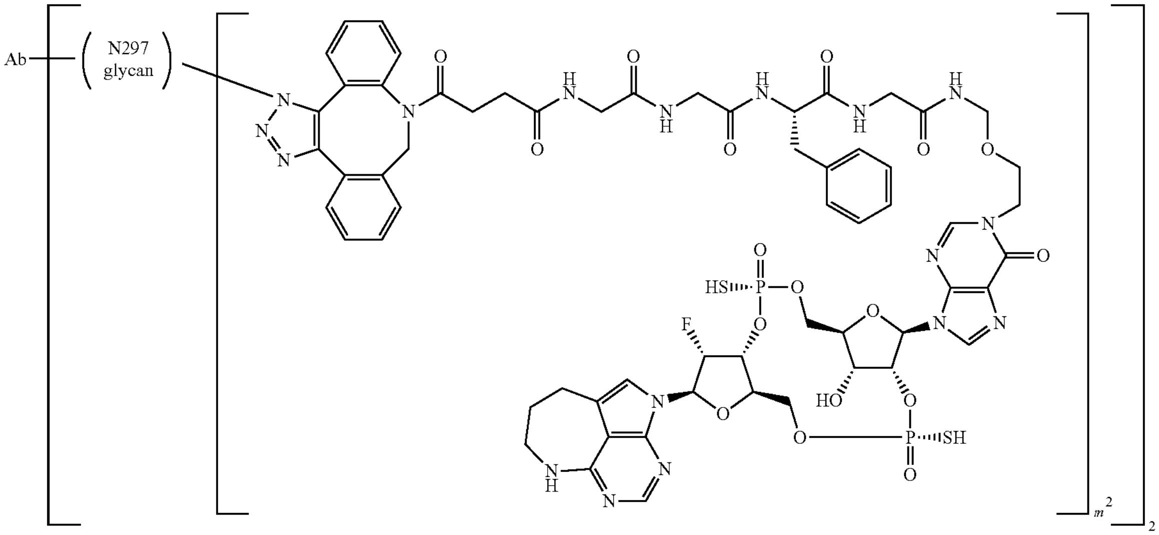

wherein Ab represents any one selected from the group consisting of the following:

an antibody comprising a light chain comprising the amino acid sequence set forth in SEQ ID NO: 9 and a heavy chain comprising the amino acid sequence set forth in SEQ ID NO: 10, and an antibody comprising a light chain comprising the amino acid sequence set forth in SEQ ID NO: 11 and a heavy chain comprising the amino acid sequence set forth in SEQ ID NO: 12 wherein N297 glycan of Ab is represented by the following formula:

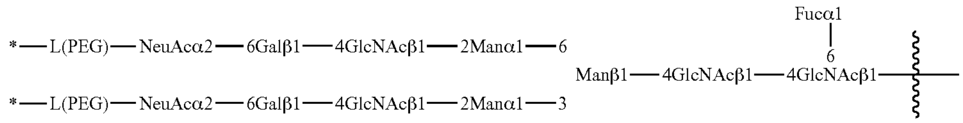

[N297—(Fuc)SG]

wherein the wavy line represents bonding to Asn297 of the antibody,

L(PEG) represents $-(CH_2-CH_2-O)n^5-CH_2-CH_2-NH-$, wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan the asterisk represents bonding to a nitrogen atom at 1- or 3-position on the 1,2,3-triazole ring, $n^5$ is 3, and $m^2$ is 2.

20. An antibody-drug conjugate represented by the following formula:

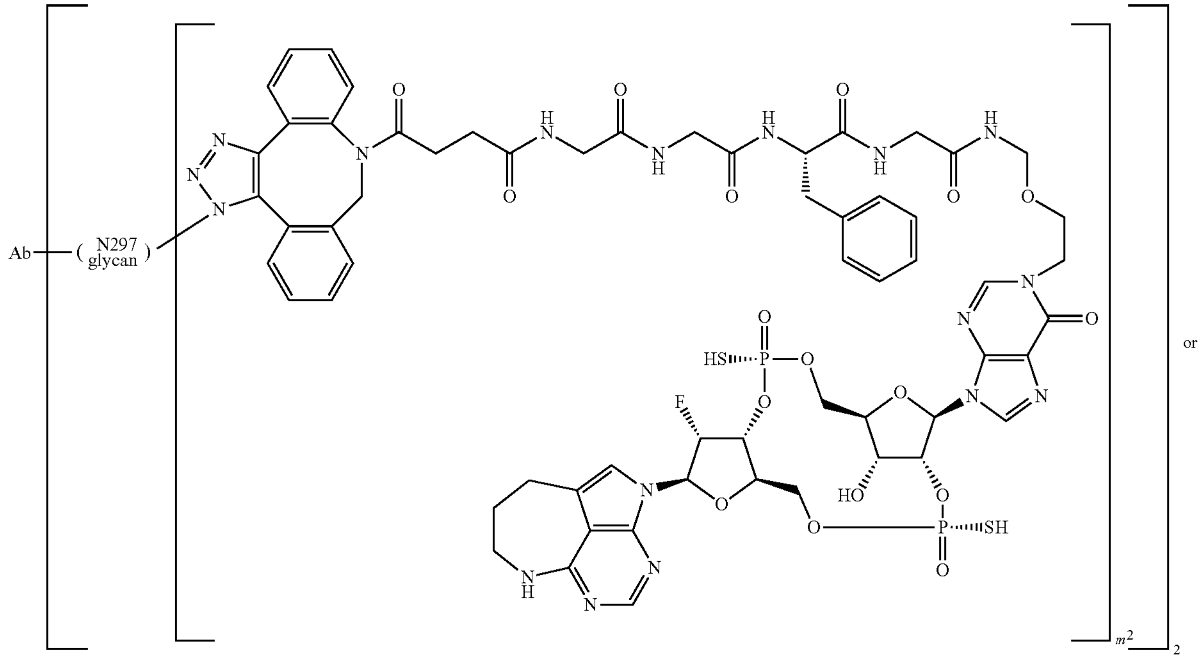

or

-continued

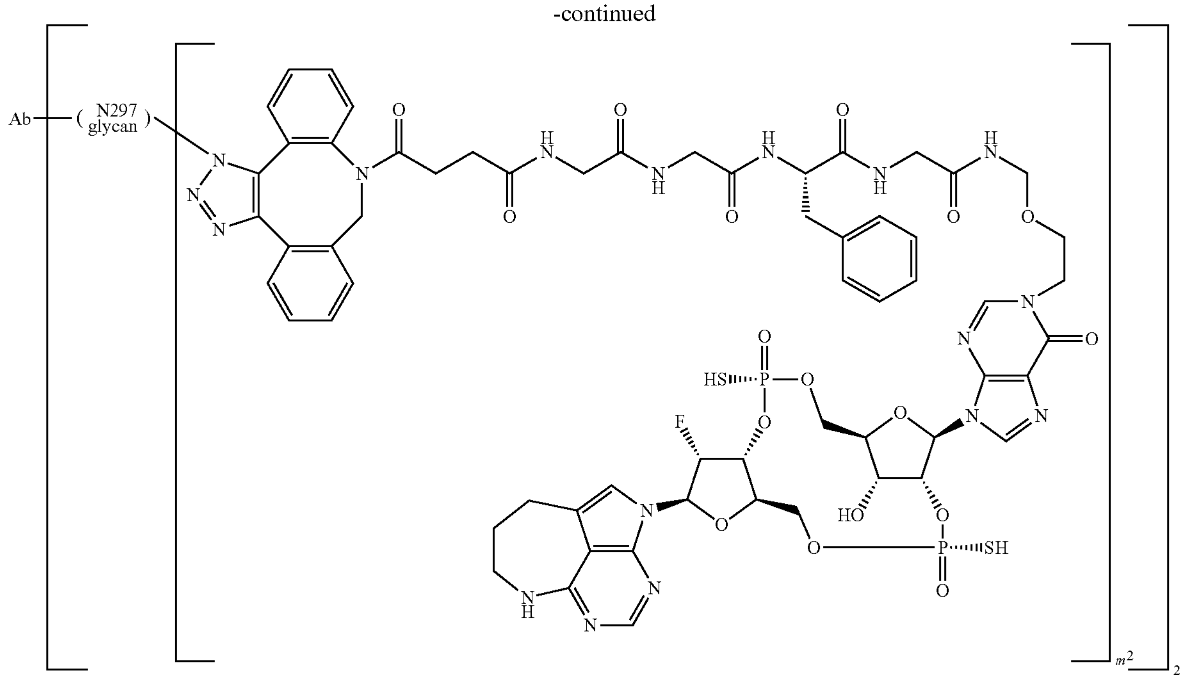

wherein Ab represents any one selected from the group consisting of the following:

an antibody comprising a light chain comprising a light chain variable region comprising of amino acid residues 1 to 108 of SEQ ID NO: 9 and a heavy chain comprising a heavy chain variable region comprising amino acid residues 1 to 119 of SEQ ID NO: 10, and an antibody comprising a light chain comprising a light chain variable region comprising amino acid residues 1 to 108 of SEQ ID NO: 11 and a heavy chain comprising a heavy chain variable region comprising amino acid residues 1 to 116 of SEQ ID NO: 12, wherein N297 glycan of Ab is represented by the following formula:

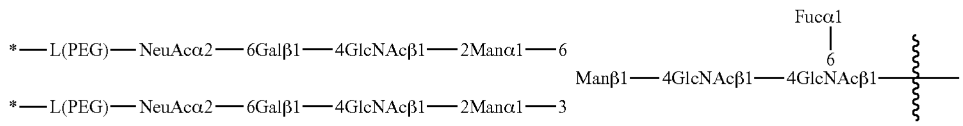

[N297—(Fuc)SG]

wherein the wavy line represents bonding to Asn297 of the antibody,

L(PEG) represents $-(CH_2-CH_2-O)n^5-CH_2-CH_2-NH-$, wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on the 1,2,3-triazole ring, $n^5$ is 3, and $m^2$ is 2.

21. An antibody-drug conjugate represented by the following formula:

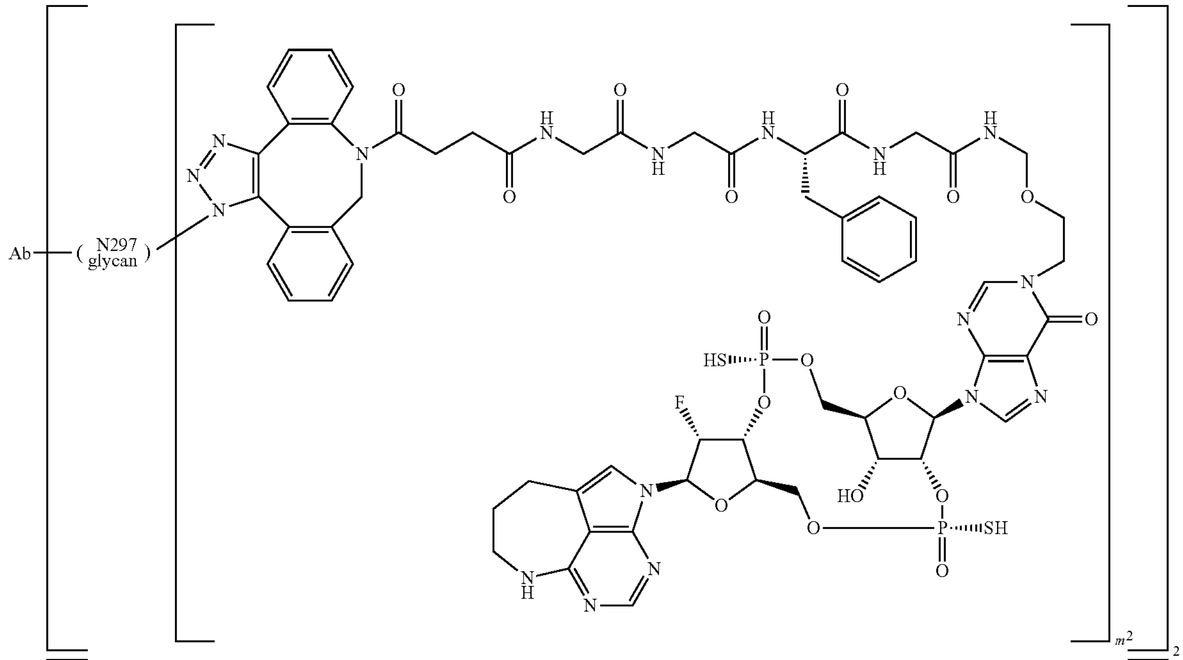

or

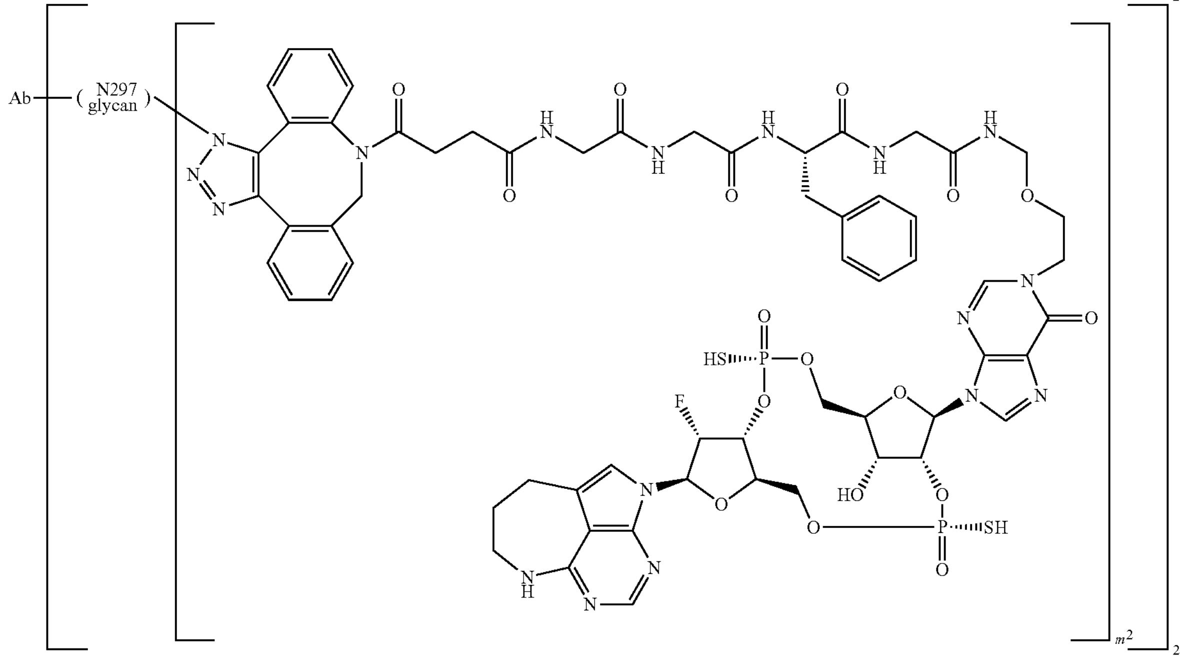

wherein Ab represents any one selected from the group consisting of the following:

an antibody comprising a light chain comprising a CDRL1 comprising the amino acid sequence set forth in SEQ ID NO: 59, a CDRL2 comprising the amino acid sequence set forth in SEQ ID NO: 60, and a CDRL3 comprising the amino acid sequence set forth in SEQ ID NO: 61 and a heavy chain comprising a CDRH1 comprising the amino acid sequence set forth in SEQ ID NO: 62, a CDRH2 comprising the amino acid sequence set forth in SEQ ID NO: 63, and a CDRH3 comprising the amino acid sequence set forth in SEQ ID NO: 64, and an antibody comprising a light chain comprising a CDRL1 comprising the amino acid sequence set forth in SEQ ID NO: 65, a CDRL2 comprising the amino acid sequence set forth in SEQ ID NO: 66, and a CDRL3 comprising the amino acid sequence set forth in SEQ ID NO: 67 and a heavy chain comprising a CDRH1 comprising the amino acid sequence set forth in SEQ ID NO: 68, a CDRH2 comprising the amino acid sequence set forth in SEQ ID NO: 69, and a CDRH3 comprising the amino acid sequence set forth in SEQ ID NO: 70, wherein N297 glycan of Ab is represented by the following formula:

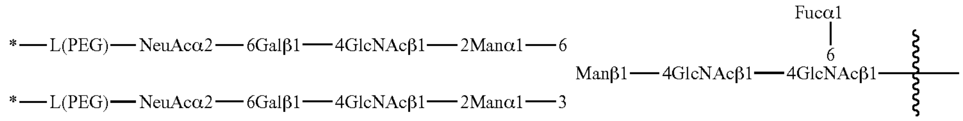

[N297—(Fuc)SG]

wherein the wavy line represents bonding to Asn297 of the antibody,

L(PEG) represents $-(CH_2-CH_2-O)n^5-CH_2-CH_2-NH-$, wherein the amino groups at the right end of the L(PEG) is bound via an amide bond to a carboxyl group at the 2-position on a sialic acid at the non-reducing terminal on each of 1-3 and 1-6 branched chains of β-Man in the N297 glycan, the asterisk represents bonding to a nitrogen atom at 1- or 3-position on the 1,2,3-triazole ring, $n^5$ is 3, and $m^2$ is 2.

22. A pharmaceutical composition comprising the antibody-drug conjugate according to claim 1.

23. The antibody-drug conjugate according to claim 1, wherein the antibody or an antigen-binding fragment of the antibody is a protein produced in host cells by using a gene (a) which is modified by genetical engineering from a gene (b) of the antibody or an antigen-binding fragment of the antibody.

24. The antibody-drug conjugate according to claim 10, wherein the average number of the conjugated drug molecules per antibody molecule in the antibody-drug conjugate ranges from 1 to 5.

25. The antibody-drug conjugate according to claim 24, wherein the average number of the conjugated drug molecules per antibody molecule in the antibody-drug conjugate ranges from 3 to 5.

26. The antibody-drug conjugate according to claim 11, wherein the N297 glycan is a remodeled glycan.

27. The antibody-drug conjugate according to claim 20, wherein Ab represents an antibody comprising a light chain comprising a light chain variable region comprising amino acid residues 1 to 108 of SEQ ID NO: 9 and a heavy chain comprising a heavy chain variable region comprising amino acid residues 1 to 119 of SEQ ID NO: 10.

28. The antibody-drug conjugate according to claim 20, wherein Ab represents an antibody comprising a light chain comprising a light chain variable region comprising amino acid residues 1 to 108 of SEQ ID NO: 11 and a heavy chain comprising a heavy chain variable region comprising amino acid residues 1 to 116 of SEQ ID NO: 12.

29. An antibody-drug conjugate represented by the following formula:

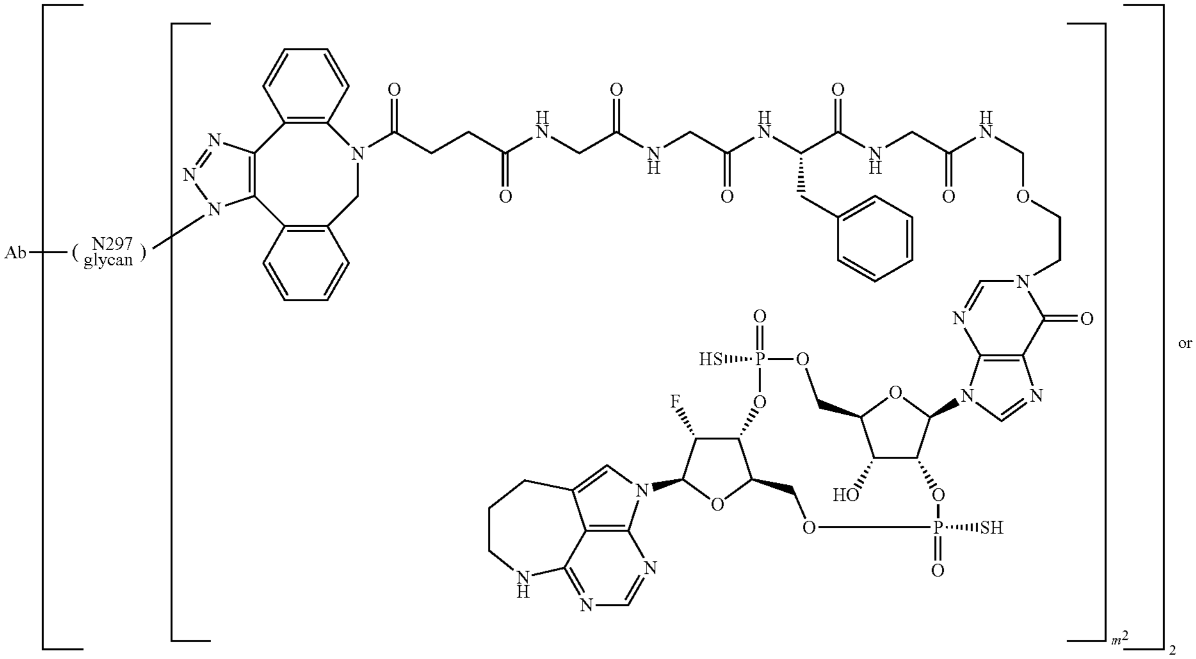

or

-continued

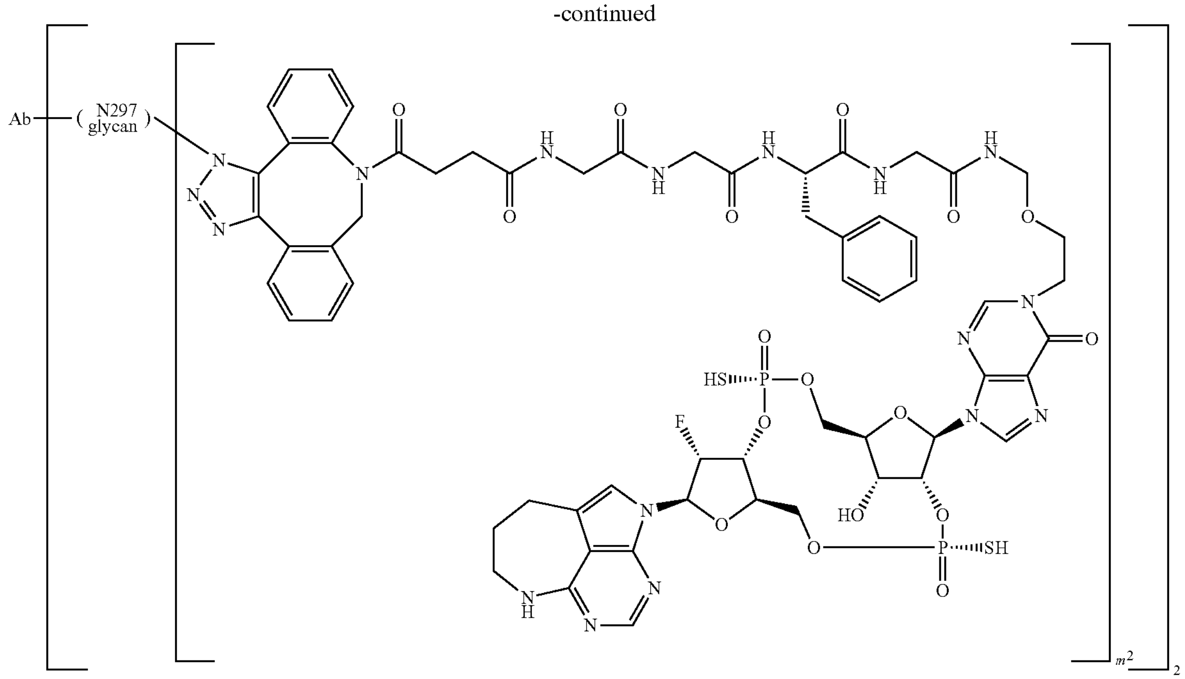

wherein Ab represents any one selected from the group consisting of the following:

an antibody comprising a light chain comprising the amino acid sequence set forth in SEQ ID NO: 9 and a heavy chain comprising the amino acid sequence set forth in SEQ ID NO: 10, and an antibody comprising a light chain comprising the amino acid sequence set forth in SEQ ID NO: 11 and a heavy chain comprising the amino acid sequence set forth in SEQ ID NO: 12, wherein N297 glycan is represented by the following formula:

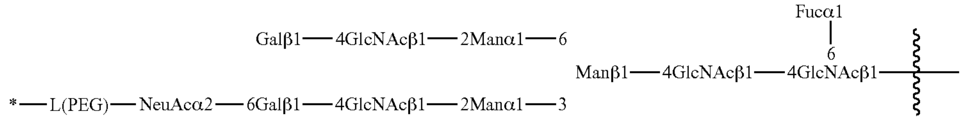

[N297—(Fuc)MSG1]

wherein the wavy line represents bonding to Asn297 of the antibody,

L(PEG) represents —$(CH_2—CH_2—O)n^5—CH_2—CH_2$—NH—, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on the 1,2,3-triazole ring, and $n^5$ is 3, and m2 is 1.

30. An antibody-drug conjugate represented by the following formula:

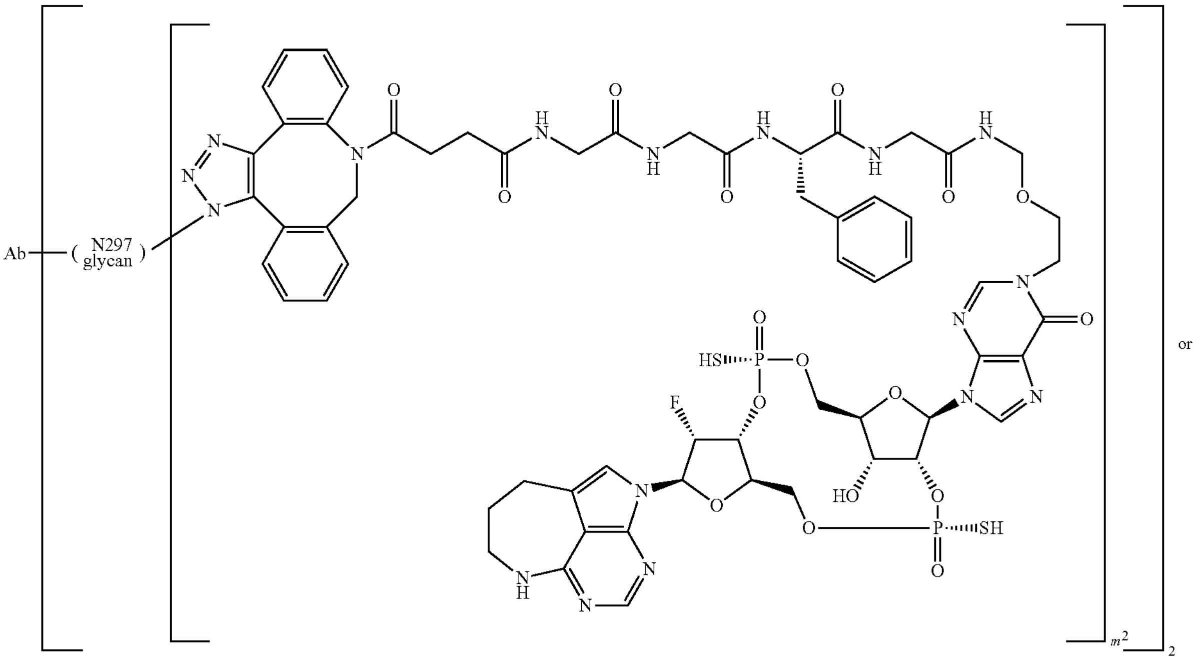

or

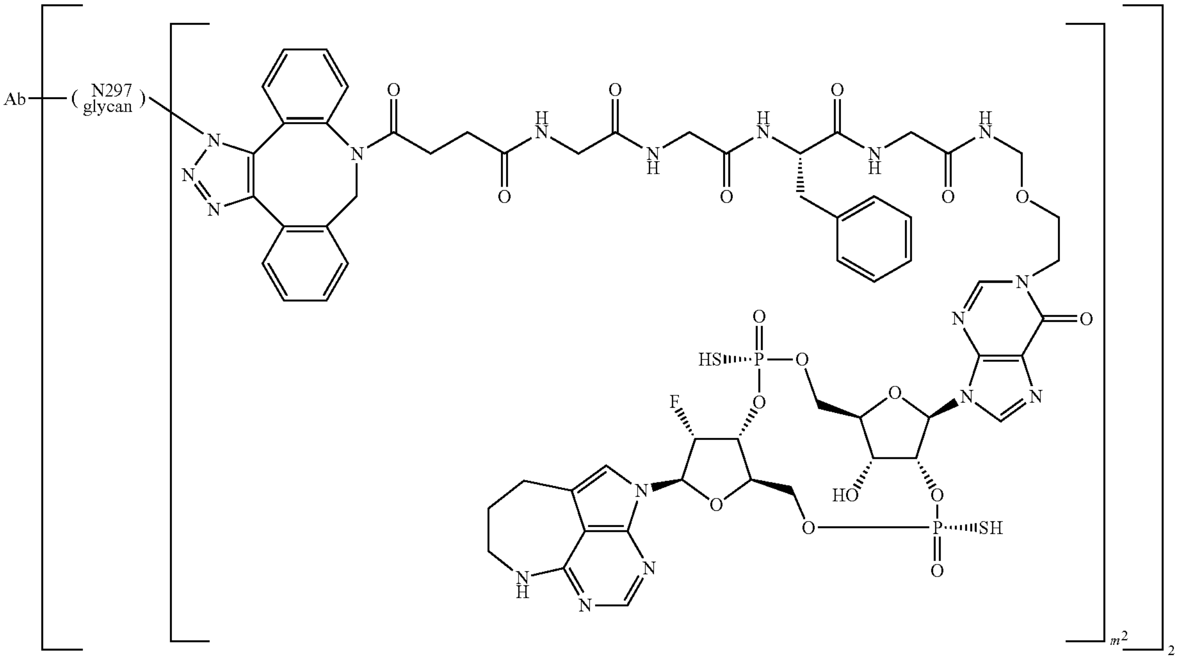

wherein Ab represents any one selected from the group consisting of the following:

an antibody comprising a light chain comprising a light chain variable region comprising amino acid residues 1 to 108 of SEQ ID NO: 9 and a heavy chain comprising a heavy chain variable region comprising amino acid residues 1 to 119 of SEQ ID NO: 10, and an antibody comprising a light chain comprising a light chain variable region comprising amino acid residues 1 to 108 of SEQ ID NO: 11 and a heavy chain comprising a heavy chain variable region comprising amino acid residues 1 to 116 of SEQ ID NO: 12, wherein N297 glycan is represented by the following formula:

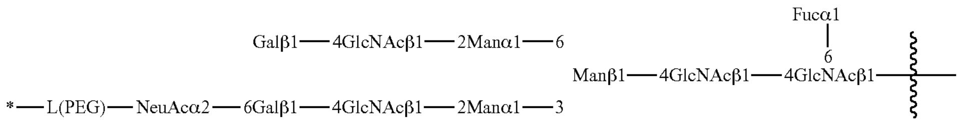

[N297—(Fuc)MSG1]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on the 1,2,3-triazole ring, and $n^5$ is 3, and m2 is 1.

31. The antibody-drug conjugate according to claim 30, wherein Ab represents an antibody comprising a light chain comprising a light chain variable region comprising amino acid residues 1 to 108 of SEQ ID NO: 9 and a heavy chain comprising a heavy chain variable region comprising amino acid residues 1 to 119 of SEQ ID NO: 10.

32. The antibody-drug conjugate according to claim 30, wherein Ab represents an antibody comprising a light chain comprising a light chain variable region comprising amino acid residues 1 to 108 of SEQ ID NO: 11 and a heavy chain comprising a heavy chain variable region comprising amino acid residues 1 to 116 of SEQ ID NO: 12.

33. An antibody-drug conjugate represented by the following formula:

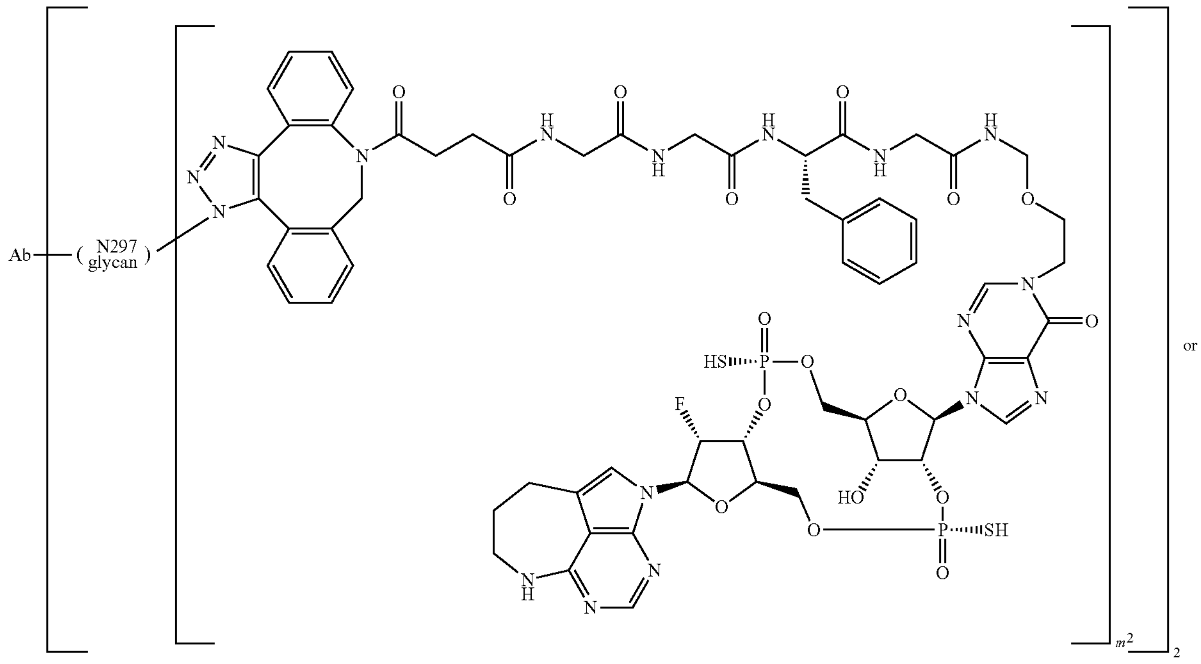

or

-continued

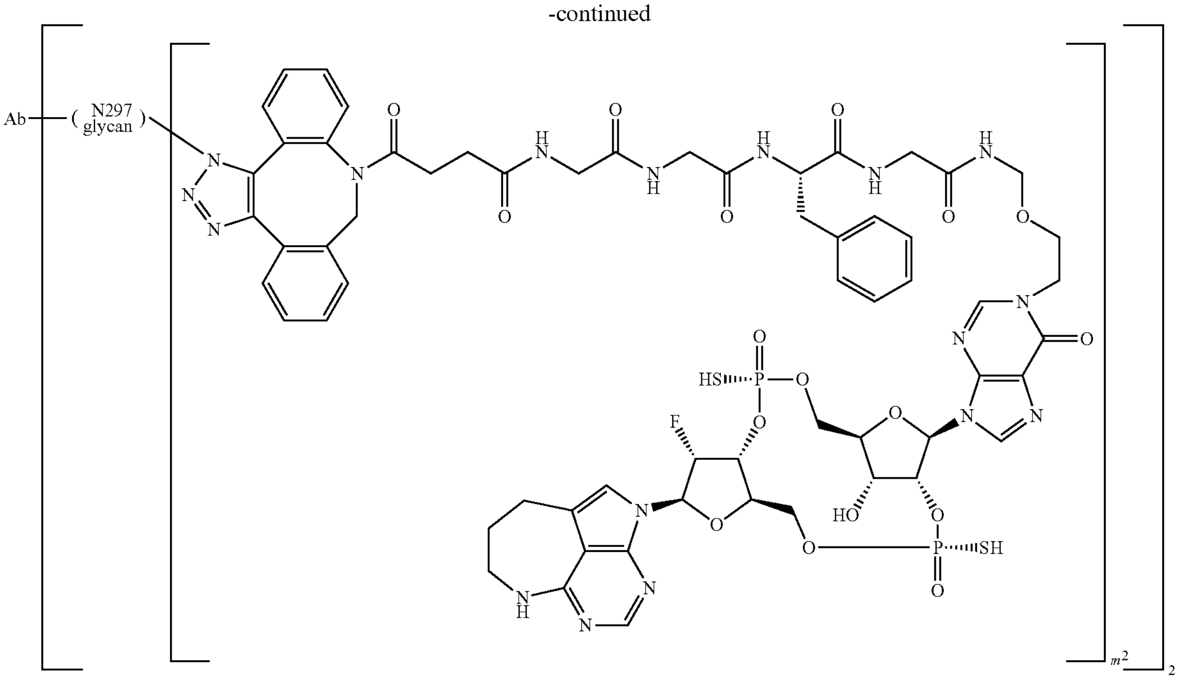

wherein Ab represents any one selected from the group consisting of the following:

an antibody comprising a light chain comprising a CDRL1 comprising the amino acid sequence set forth in SEQ ID NO: 59, a CDRL2 comprising the amino acid sequence set forth in SEQ ID NO: 60, and a CDRL3 comprising the amino acid sequence set forth in SEQ ID NO: 61 and a heavy chain comprising a CDRH1 comprising the amino acid sequence set forth in SEQ ID NO: 62, a CDRH2 comprising the amino acid sequence set forth in SEQ ID NO: 63, and a CDRH3 comprising the amino acid sequence set forth in SEQ ID NO: 64, and an antibody comprising a light chain comprising a CDRL1 comprising the amino acid sequence set forth in SEQ ID NO: 65, a CDRL2 comprising the amino acid sequence set forth in SEQ ID NO: 66, and a CDRL3 comprising the amino acid sequence set forth in SEQ ID NO: 67 and a heavy chain comprising a CDRH1 comprising the amino acid sequence set forth in SEQ ID NO: 68, a CDRH2 comprising the amino acid sequence set forth in SEQ ID NO: 69, and a CDRH3 comprising the amino acid sequence set forth in SEQ ID NO: 70, wherein N297 glycan is represented by the following formula:

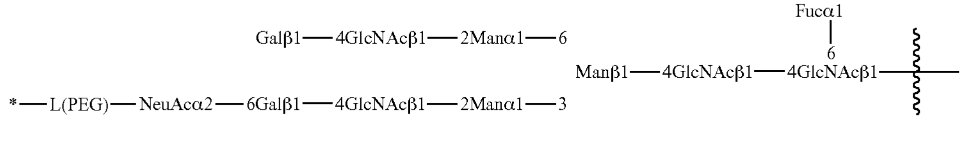

[N297—(Fuc)MSG1]

wherein the wavy line represents bonding to Asn297 of the antibody,

L(PEG) represents $-(CH_2-CH_2-O)n^5-CH_2-CH_2-NH-$, wherein the amino group at the right end of the L(PEG) is bound via an amide bond to a carboxyl group at the 2-position on a sialic acid at the non-reducing terminal of a 1-3 branched chain of β-Man in the N297 glycan, the asterisk represents bonding to a nitrogen atom at 1- or 3-position on the 1,2,3-triazole ring, and $n^5$ is 3, and m2 is 1.

34. The antibody-drug conjugate according to claim 1, wherein one or two amino acids are deleted at a heavy chain carboxyl terminus.

35. The pharmaceutical composition comprising according to claim 22, wherein the average number of the conjugated drug molecules per antibody molecule in the antibody-drug conjugate ranges from 1 to 10.

36. The pharmaceutical composition comprising according to claim 22, wherein the average number of the conjugated drug molecules per antibody molecule in the antibody-drug conjugate ranges from 3 to 5.

37. The antibody-drug conjugate according to claim 16, wherein the antibody is an antibody comprising a light chain consisting of the amino acid sequence set forth in SEQ ID NO: 9 and a heavy chain consisting of the amino acid sequence set forth in SEQ ID NO: 10 or an antibody comprising a light chain consisting of the amino acid sequence set forth in SEQ ID NO: 11 and a heavy chain consisting of the amino acid sequence set forth in SEQ ID NO: 12.

38. The antibody-drug conjugate according to claim 17, wherein the antibody is an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10 or an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

39. The antibody-drug conjugate according to claim 18, wherein the antibody is an antibody comprising a light chain comprising a CDRL1 consisting of the amino acid sequence set forth in SEQ ID NO: 59, a CDRL2 consisting of the amino acid sequence set forth in SEQ ID NO: 60, and a CDRL3 consisting of the amino acid sequence set forth in SEQ ID NO: 61 and a heavy chain comprising a CDRH1 consisting of the amino acid sequence set forth in SEQ ID NO: 62, a CDRH2 consisting of the amino acid sequence set forth in SEQ ID NO: 63, and a CDRH3 consisting of the amino acid sequence set forth in SEQ ID NO: 64; or an antibody comprising a light chain comprising a CDRL1 consisting of the amino acid sequence set forth in SEQ ID NO: 65, a CDRL2 consisting of the amino acid sequence set forth in SEQ ID NO: 66, and a CDRL3 consisting of the amino acid sequence set forth in SEQ ID NO: 67 and a heavy chain comprising a CDRH1 consisting of the amino acid sequence set forth in SEQ ID NO: 68, a CDRH2 consisting of the amino acid sequence set forth in SEQ ID NO: 69, and a CDRH3 consisting of the amino acid sequence set forth in SEQ ID NO: 70.

40. The antibody-drug conjugate according to claim 19, wherein Ab represents any one selected from the group consisting of the following:

an antibody comprising a light chain consisting of the amino acid sequence set forth in SEQ ID NO: 9 and a heavy chain consisting of the amino acid sequence set forth in SEQ ID NO: 10, and an antibody comprising a light chain consisting of the amino acid sequence set forth in SEQ ID NO: 11 and a heavy chain consisting of the amino acid sequence set forth in SEQ ID NO: 12.

41. The antibody-drug conjugate according to claim 20, wherein Ab represents any one selected from the group consisting of the following:

an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10, and an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

42. The antibody-drug conjugate according to claim 21, wherein Ab represents any one selected from the group consisting of the following:

an antibody comprising a light chain comprising a CDRL1 consisting of the amino acid sequence set forth in SEQ ID NO: 59, a CDRL2 consisting of the amino acid sequence set forth in SEQ ID NO: 60, and a CDRL3 consisting of the amino acid sequence set forth in SEQ ID NO: 61 and a heavy chain comprising a CDRH1 consisting of the amino acid sequence set forth in SEQ ID NO: 62, a CDRH2 consisting of the amino acid sequence set forth in SEQ ID NO: 63, and a CDRH3 consisting of the amino acid sequence set forth in SEQ ID NO: 64; or an antibody comprising a light chain comprising a CDRL1 consisting of the amino acid sequence set forth in SEQ ID NO: 65, a CDRL2 consisting of the amino acid sequence set forth in SEQ ID NO: 66, and a CDRL3 consisting of the amino acid sequence set forth in SEQ ID NO: 67 and a heavy chain comprising a CDRH1 consisting of the amino acid sequence set forth in SEQ ID NO: 68, a CDRH2 consisting of the amino acid sequence set forth in SEQ ID NO: 69, and a CDRH3 consisting of the amino acid sequence set forth in SEQ ID NO: 70.

43. The antibody-drug conjugate according to claim 41, wherein Ab represents an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10.

44. The antibody-drug conjugate according to claim 41, wherein Ab represents an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

45. The antibody-drug conjugate according to claim 29, wherein Ab represents any one selected from the group consisting of the following:

an antibody comprising a light chain consisting of the amino acid sequence set forth in SEQ ID NO: 9 and a heavy chain consisting of the amino acid sequence set forth in SEQ ID NO: 10, and an antibody comprising a light chain consisting of the amino acid sequence set forth in SEQ ID NO: 11 and a heavy chain consisting of the amino acid sequence set forth in SEQ ID NO: 12.

46. The antibody-drug conjugate according to claim 30, wherein Ab represents any one selected from the group consisting of the following:

an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10, and an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

47. The antibody-drug conjugate according to claim 46, wherein Ab represents an antibody comprising a light chain comprising a light chain variable region consisting of amino acid residues 1 to 108 of SEQ ID NO: 9 and a heavy chain comprising a heavy chain variable region consisting of amino acid residues 1 to 119 of SEQ ID NO: 10.

48. The antibody-drug conjugate according to claim 46, wherein Ab represents an antibody comprising a light chain comprising a light chain variable region consisting of amino acid residues 1 to 108 of SEQ ID NO: 11 and a heavy chain comprising a heavy chain variable region consisting of amino acid residues 1 to 116 of SEQ ID NO: 12.

49. The antibody-drug conjugate according to claim 33, wherein Ab represents any one selected from the group consisting of the following:

an antibody comprising a light chain comprising a CDRL1 consisting of the amino acid sequence set forth in SEQ ID NO: 59, a CDRL2 consisting of the amino acid sequence set forth in SEQ ID NO: 60, and a CDRL3 consisting of the amino acid sequence set forth in SEQ ID NO: 61 and a heavy chain comprising a CDRH1 consisting of the amino acid sequence set forth in SEQ ID NO: 62, a CDRH2 consisting of the amino acid sequence set forth in SEQ ID NO: 63, and a CDRH3 consisting of the amino acid sequence set forth in SEQ ID NO: 64; or an antibody comprising a light chain comprising a CDRL1 consisting of the amino acid sequence set forth in SEQ ID NO: 65, a CDRL2 consisting of the amino acid sequence set forth in SEQ ID NO: 66, and a CDRL3 consisting of the amino acid sequence set forth in SEQ ID NO: 67 and a heavy chain comprising a CDRH1 consisting of the amino acid sequence set forth in SEQ ID NO: 68, a CDRH2 consisting of the amino acid sequence set forth in SEQ ID NO: 69, and a CDRH3 consisting of the amino acid sequence set forth in SEQ ID NO: 70.

* * * * *